US008058416B2

(12) United States Patent
Prendergast et al.

(10) Patent No.: US 8,058,416 B2
(45) Date of Patent: Nov. 15, 2011

(54) NUCLEIC ACID MOLECULES ENCODING INDOLEAMINE 2,3-DIOXYGENASE-2

(75) Inventors: George C. Prendergast, Penn Valley, PA (US); Richard Metz, Pennington, NJ (US)

(73) Assignee: Lankenau Institute for Medical Research, Wynnewood, PA (US)

( * ) Notice: Subject to any disclaimer, the term of this patent is extended or adjusted under 35 U.S.C. 154(b) by 333 days.

(21) Appl. No.: 12/273,296

(22) Filed: Nov. 18, 2008

(65) Prior Publication Data

US 2009/0158451 A1 Jun. 18, 2009

Related U.S. Application Data

(63) Continuation-in-part of application No. PCT/US2007/069271, filed on May 18, 2007.

(60) Provisional application No. 60/801,255, filed on May 18, 2006, provisional application No. 60/886,815, filed on Jan. 26, 2007, provisional application No. 60/914,472, filed on Apr. 27, 2007.

(51) Int. Cl.
*C07H 21/02* (2006.01)
*C07H 21/04* (2006.01)

(52) U.S. Cl. ........................................................ 536/23.1

(58) Field of Classification Search .................. 536/23.1
See application file for complete search history.

(56) References Cited

FOREIGN PATENT DOCUMENTS

| | | |
|---|---|---|
| EP | 1 447 413 A | 8/2004 |
| WO | 02/057303 | 7/2002 |

OTHER PUBLICATIONS

Ota (Nature Genetics, 2004, vol. 36, p. 40-45).*

Sequence search results 2010, reference 2, which is Ota.*

Gajewski, T. F., et al. "Immune Suppression in the Tumor Microenvironment." Journal of Immunology, 29(3): 233-240 (May/Jun. 2006)[Abstract].

Gajewski, T.F., et al. "Immune suppression in the tumor microenvironment." J Immunother. May-Jun. 2006;29 (3):233-40.

Database EMBL "*Homo sapiens* cDNA FLJ35183 fis, clone PLACE6015460, weakly similar to Indoleamine 2,3-Dioxygenase (EC 1.13.11.42)." retrieved from EBI accession No. EMBL:AK092502 (Feb. 27, 2006)[Online].

Cady, S.G., et al. "1-Methyl-DL-tryptophan, β-(3-Benzofuranyl)-DL-alanine (the Oxygen analog of Tryptophan), and β-[3-Benzo(b)theinyl]-DL-alanine (the Sulfur Analog of Tryptophan) Are Competitive Inhibitors for Indoleamine 2,3-Dioxygenase." Archives of Biochemistry and Biophysics, 291(2):326-333 (Dec. 1, 1991).

Ball, H.J., et al. "Characterization of an indoleamine 2,3-dioxygenase-like protein found in humans and mice." Gene, 396:203-217 (May 31, 2007).

Metz, R., et al. "Novel Tryptophan Catabolic Enzyme IDO2 Is the Preferred Biochemical Target of the Antitumor Indoleamine 2,3-Dioxygenase Inhibitory Compound D-1-Methyl-Tryptophan." Cancer Research, 67(15):7082-7087 (Aug. 1, 2007).

Databse Geneseq. "Full length human cDNA useful for treating neurological disease Seq 1917." retrieved from EBI accession No. GSN:ADR08411 (Nov. 4, 2004)[Online].

* cited by examiner

*Primary Examiner* — Michael C. Wilson
(74) *Attorney, Agent, or Firm* — Dann, Dorfman, Herrell & Skillman; Robert C. Netter, Jr.

(57) ABSTRACT

The nucleotide and amino acid sequences of indoleamine 2,3-dioxygenase-2 (IDO2) and methods of use thereof are provided.

5 Claims, 123 Drawing Sheets

```
MLHFHYYDTSNKIMEPHRPNVKTAVPLSLESYHISEEYGFLLPDSLKELP    50
DHYRPWMEIANKLPQLIDAHQLQAHVDKMPLLSCQFLKGHREQRLAHLVL   100
SFLTMGYVWQEGEAQPAEVLPRNLALPFVEVSRNLGLPPILVHSDLVLTN   150
WTKKDPDGNLEIGNLETIISFPGGESLHGFILVTALVEKEAVPGIKALVQ   200
ATNAILQPNQEALLQALQRLRLSIQDITKTLGQMHDYVDPDIFYAGIRIF   250
LSGWKDNPAMPAGLMYEGVSQEPLKYSGGSAAQSTVLHAFDEFLGIRHSK   300
ESGDFLYRMRDYMPPSHKAFIEDIHSAPSLRDYILSSGQDHLLTAYNQCV   350
QALAELRSYHITMVTKYLITAAAKAKHGKPNHLPGPPQALKDRGTGGTAV   400
MSFLKSVRDKTLESILHPRG                                 420
```

Figure 1A

```
MEPHRPNVKTAVPLSLESYHISEEYGFLLPDSLKELPDHYRPWMEIANKL    50
PQLIDAHQLQAHVDKMPLLSCQFLKGHREQRLAHLVLSFLTMGYVWQEGE   100
AQPAEVLPRNLALPFVEVSRNLGLPPILVHSDLVLTNWTKKDPDGFLEIG   150
NLETIISFPGGESLHGFILVTALVEKEAVPGIKALVQATNAILQPNQEAL   200
LQALQRLRLSIQDITKTLGQMHDYVDPDIFYAGIRIFLSGWKDNPAMPAG   250
LMYEGVSQEPLKYSGGSAAQSTVLHAFDEFLGIRHSKESGDFLYRMRDYM   300
PPSHKAFIEDIHSAPSLRDYILSSGQDHLLTAYNQCVQALAELRSYHITM   350
VTKYLITAAAKAKHGKPNHLPGPPQALKDRGTGGTAVMSFLKSVRDKTLE   400
SILHP                                                405
```

Figure 1B

```
MTLEVPLSLGRYHISEEYGFLLPNPLEALPDHYKPWMEIALRLPHLIENR    50
QLRAHVYRMPLLDCRFLKSYREQRLAHMALAAITMGFVWQEGEGQPQKVL   100
PRSLAIPFVEVSRNLGLPPILVHSDLVLTNWTKRNPEGPLEISNLETIIS   150
FPGGESLRGFILVTVLVEKAAVPGLKALVQGMEAIRQHSQDTLLEALQQL   200
RLSIQDITRALAQMHDYVDPDIFYSVIRIFLSGWKDNPAMPVGLVYEGAA   250
TEPLKYSGGSAAQSSVLHAFDEFLGIEHCKESVGFLHRMRDYMPPSHKAF   300
LEDLHVAPSLRDYILASGPGDCLMAYNQCVEALGELRSYHINVVARYIIS   350
AATRARSRGLTNPSPHALEDRGTGGTAMLSFLKSVREKTMEALLCPGA     398
```

Figure 2A

```
MEPQSQSMTLEVPLSLGRYHISEEYGFLLPNPLEALPDHYKPWMEIALRL    50
PHLIENRQLRAHVYRMPLLDCRFLKSYREQRLAHMALAAITMGFVWQEGE   100
GQPQKVLPRSLAIPFVEVSRNLGLPPILVHSDLVLTNWTKRNPEGPLEIS   150
NLETIISFPGGESLRGFILVTVLVEKAAVPGLKALVQGMEAIRQHSQDTL   200
LEALQQLRLSIQDITRALAQMHDYVDPDIFYSVIRIFLSGWKDNPAMPVG   250
LVYEGAATEPLKYSGGSAAQSSVLHAFDEFLGIEHCKESVGFLHRMRDYM   300
PPSHKAFLEDLHVAPSLRDYILASGPGDCLMAYNQCVEALGELRSYHINV   350
VARYIISAATRARSRGLTNPSPHALEDRGTGGTAMLSFLKSVREKTMEAL   400
LCP                                                  403
```

Figure 2B

```
ESYHISEEYGFLLPDSLKELPDHYRPWMEIANKLPQLIDAHQLQAHVDKMPLLSCQFLKG  89
+ ### ## ## ##+  + ### #  ## ##  ## ##++ ##+  #+#+ +##   #
KEYHIDEEVGFALPNPQENLPDFYNDWMFIAKHLPDLIESGQLRERVEKLNMLSIDHLTD  72

HREQRLAHLVLSFLTMGYVWQEGEAQPAEVLPRNLALPFVEVSRNLGLPPILVHSDLVLT  149
#+ #### ###  +## ### +#     +#####+#+#+ ++#+ # ######++# ##
HKSQRLARLVLGCITMAYVWGKGHGDVRKVLPRNIAVPYCQLSKKLELPPILVYADCVLA  132

NWTKKDPDGFLEIGNLETIISFPGGESLHGFILVTALVEKEAVPGIKALVQATNAILQPN  209
## ####+  #   #++ + ##  #+   ## ##+ ###  #   ## +      #+
NWKKKDPNKPLTYENMDVLFSFRDGDCSKGFFLVSLLVEIAAASAIKVIPTVFKAMQMQE  192

QEALLQALQRLRLSIQDITKTLGQMHDYVDPDIFYAGIRIFLSGWKDNPAMPAGLMYEGV  269
++ ##+##  +   ++   +   #+##+#+#  #++ +##+##### ## +  ##+###
RDTLLKALLEIASCLEKALQVFHQIHDHVNPKAFFSVLRIYLSGWKGNPQLSDGLVYEGF  252

SQEPLKYSGGSAAQSTVLHAFDEFLGIRHSKESG---DFLYRMRDYMPPSHKAFIEDIHS  326
 ++# +++#### ##+#   ##  ###+ +   #    ##  ## ####+#+ #+  + #
WEDPKEFAGGSAGQSSVFQCFDVLLGIQQTAGGGHAAQFLQDMRRYMPPAHRNFLCSLES  312

APSLRDYILSSGQDHLLTAYNQCVQALAELRSYHITMVTKYLITAAAKAKHGKPNHLPGP  386
 ##+#+++## #   #  ##+ ##+##  #####+ +####++  #  ++  # #
NPSVREFVLSKGDAGLREAYDACVKALVSLRSYHLQIVTKYILIPA--SQQPKENKTSED  370

PQALKDRGTGGTAVMSFLKSVRDKTLESIL  416
#  #+ +##### +#+###+##  # +#+#
PSKLEAKGTGGTDLMNFLKTVRSTTEKSLL  400
```

Figure 3A

```
MAHAMENSWTISKEYHIDEEVGFALPNPQENLPDFYNDWMFIAKHLPDLI   50
ESGQLRERVEKLNMLSIDHLTDHKSQRLARLVLGCITMAYVWGKGHGDVR  100
KVLPRNIAVPYCQLSKKLELPPILVYADCVLANWKKKDPNKPLTYENMDV  150
LFSFRDGDCSKGFFLVSLLVEIAAASAIKVIPTVFKAMQMQERDTLLKAL  200
LEIASCLEKALQVFHQIHDHVNPKAFFSVLRIYLSGWKGNPQLSDGLVYE  250
GFWEDPKEFAGGSAGQSSVFQCFDVLLGIQQTAGGGHAAQFLQDMRRYMP  300
PAHRNFLCSLESNPSVREFVLSKGDAGLREAYDACVKALVSLRSYHLQIV  350
TKYILIPASQQPKENKTSEDPSKLEAKGTGGTDLMNFLKTVRSTTEKSLL  400
KEG                                                 403
```

Figure 3B

```
Mouse  1    MEPQSQSMTLEVPLSLGRYHISEEYGFLLPNPLEALPDHYKPWMEIALRLPHLIENRQLR  60
            MEP   ++   VPLSL  YHISEEYGFLLP+ L+ LPDHY+PWMEIA +LP LI+  QL+
Human  1    MEPHRPNVKTAVPLSLESYHISEEYGFLLPDSLKELPDHYRPWMEIANKLPQLIDAHQLQ  60

Mouse  61   AHVYRMPLLDCRFLKSYREQRLAHMALAAITMGFVWQEGEGQPQKVLPRSLAIPFVEVSR  120
            AHV +MPLL C+FLK +REQRLAH+ L+ +TMG+VWQEGE QP +VLPR+LA+PFVEVSR
Human  61   AHVDKMPLLSCQFLKGHREQRLAHLVLSFLTMGYVWQEGEAQPAEVLPRNLALPFVEVSR  120

Mouse  121  NLGLPPILVHSDLVLTNWTKRNPEGPLEISNLETIISFPGGESLRGFILVTVLVEKAAVP  180
            NLGLPPILVHSDLVLTNWTK++P+G LEI NLETIISFPGGESL GFILVT LVEK AVP
Human  121  NLGLPPILVHSDLVLTNWTKKDPDGFLEIGNLETIISFPGGESLHGFILVTALVEKEAVP  180

Mouse  181  GLKALVQGMEAIRQHSQDTLLEALQQLRLSIQDITRALAQMHDYVDPDIFYSVIRIFLSG  240
            G+KALVQ   AI Q +Q+ LL+ALQ+LRLSIQDIT+ L QMHDYVDPDIFY+ IRIFLSG
Human  181  GIKALVQATNAILQPNQEALLQALQRLRLSIQDITKTLGQMHDYVDPDIFYAGIRIFLSG  240

Mouse  241  WKDNPAMPVGLVYEGAATEPLKYSGGSAAQSSVLHAFDEFLGIEHCKESVGFLHRMRDYM  300
            WKDNPAMP GL+YEG + EPLKYSGGSAAQS+VLHAFDEFLGI H KES  FL+RMRDYM
Human  241  WKDNPAMPAGLMYEGVSQEPLKYSGGSAAQSTVLHAFDEFLGIRHSKESGDFLYRMRDYM  300

Mouse  301  PPSHKAFLEDLHVAPSLRDYILASGPGDCLMAYNQCVEALGELRSYHINVVARYIISAAT  360
            PPSHKAF+ED+H APSLRDYIL+SG    L AYNQCV+AL ELRSYHI +V +Y+I+AA
Human  301  PPSHKAFIEDIHSAPSLRDYILSSGQDHLLTAYNQCVQALAELRSYHITMVTKYLITAAA  360

Mouse  361  RA---RSRGLTNPSPHALEDRGTGGTAMLSFLKSVREKTMEALLCP  403
            +A   +   L  P P AL+DRGTGGTA++SFLKSVR+KT+E++L P
Human  361  KAKHGKPNHLPGP-PQALKDRGTGGTAVMSFLKSVRDKTLESILHP  405
```

Figure 3C

```
1    ATG GAG CCT CAA AGT CAG AGC ATG ACG CTG GAG GTG CCG  IDO2
      M   E   P   Q   S   Q   S   M   T   L   E   V   P
      M   A   L   S   K   I   S   P   T   E   G   S   R
1    ATG GCA CTC AGT AAA ATA TCT CCT ACA GAA GGT TCT AGA  MU IDO

40   TTG TCC TTG GGG AGA TAC CAC ATT TCT GAG GAA TAT GGC
      L   S   L   G   R   Y   H   I   S   E   E   Y   G
                          +   H   I       E   +       G
      R   I   L   E   D   H   H   I   D   E   D   V   G
40   AGG ATC CTT GAA GAC CAC CAC ATA GAT GAA GAT GTG GGC

79   TTT CTC CTT CCA AAT CCT CTG GAA GCA CTT CCA GAT CAT
      F   L   L   P   N   P   L   E   A   L   P   D   H
      F       L   P   +   P   L           L   P   D
      F   A   L   P   H   P   L   V   E   L   P   D   A
79   TTT GCT CTA CCA CAT CCA CTG GTG GAG CTG CCC GAC GCA

118  TAC AAG CCT TGG ATG GAA ATT GCC CTC AGA CTT CCT CAC
      Y   K   P   W   M   E   I   A   L   R   L   P   H
      Y       P   W   +       +   A           L   P
      Y   S   P   W   V   L   V   A   R   N   L   P   V
118  TAC AGC CCC TGG GTC CTT GTG GCT AGA AAT CTG CCT GTG

157  TTA ATC GAG AAC CGC CAG CTC CGA GCT CAC GTG TAC AGG
      L   I   E   N   R   Q   L   R   A   H   V   Y   R
      L   I   E   N       Q   L   R           V       +
      L   I   E   N   G   Q   L   R   E   E   V   E   K
157  CTG ATT GAG AAC GGG CAG CTT CGA GAA GAA GTT GAA AAG

196  ATG CCT CTC CTG GAC TGC AGA TTC CTA AAG AGT TAC CGT
      M   P   L   L   D   C   R   F   L   K   S   Y   R
      +   P       L                   L   +       +   R
      L   P   T   L   S   T   D   G   L   R   G   H   R
196  CTG CCC ACA CTG AGC ACG GAC GGA CTG AGA GGA CAC AGG

235  GAG CAG CGC CTG GCA CAC ATG GCG CTG GCC GCT ATC ACC
      E   Q   R   L   A   H   M   A   L   A   A   I   T
          Q   R   L   A   H   +   A   L           I   T
      L   Q   R   L   A   H   L   A   L   G   Y   I   T
235  TTA CAG CGC CTG GCA CAC CTG GCC CTG GGG TAC ATC ACC

274  ATG GGA TTC GTC TGG CAG GAG GGG GAA GGC CAA CCC CAA
      M   G   F   V   W   Q   E   G   E   G   Q   P   Q
      M       +   V   W           G   +               +
      M   A   Y   V   W   N   R   G   D   D   D   V   R
274  ATG GCG TAT GTG TGG AAC CGA GGG GAT GAC GAT GTT CGA

313  AAG GTG CTG CCA AGA TCT CTT GCC ATT CCT TTT GTT GAG
      K   V   L   P   R   S   L   A   I   P   F   V   E
      K   V   L   P   R   +   +   A   +   P   +       E
      K   V   L   P   R   N   I   A   V   P   Y   C   E
313  AAG GTG CTG CCC CGC AAT ATT GCT GTT CCC TAC TGC GAG
```

Figure 3D

```
352  GTA TCC AGG AAC TTG GGA CTC CCG CCT ATC CTG GTC CAC
      V   S   R   N   L   G   L   P   P   I   L   V   H
      +   S   -   -   L   G   L   P   P   I   L   -   +
      L   S   E   K   L   G   L   P   P   I   L   S   Y
352  CTC TCA GAG AAG TTG GGC CTG CCT CCT ATT CTG TCT TAT

391  TCT GAC CTG GTG CTG ACA AAC TGG ACC AAA AGG AAC CCA
      S   D   L   V   L   T   N   W   T   K   R   N   P
      +   D   -   V   L   -   N   W   -   K   +   +   P
      A   D   C   V   L   A   N   W   K   K   K   D   P
391  GCA GAC TGT GTC CTG GCA AAC TGG AAG AAA AAG GAC CCC

430  GAA GGA CCG TTG GAA ATC AGT AAC CTG GAA ACC ATC ATC
      E   G   P   L   E   I   S   N   L   E   T   I   I
      -   G   P   +   -   -   -   N   +   +   -   +   -
      N   G   P   M   T   Y   E   N   M   D   I   L   F
430  AAT GGG CCC ATG ACA TAC GAG AAC ATG GAC ATT CTG TTC

469  TCA TTT CCG GGG GGA GAG AGC CTG CGG GGC TTC ATC CTA
      S   F   P   G   G   E   S   L   R   G   F   I   L
      S   F   P   G   G   +   -   -   +   G   F   -   L
      S   F   P   G   G   D   C   D   K   G   F   F   L
469  TCA TTT CCT GGT GGG GAC TGC GAC AAG GGC TTC TTC CTC

508  GTG ACA GTC TTG GTG GAG AAG GCA GCA GTG CCC GGC CTT
      V   T   V   L   V   E   K   A   A   V   P   G   L
      V   +   +   L   V   E   -   A   A   -   P   -   +
      V   S   L   L   V   E   I   A   A   S   P   A   I
508  GTC TCT CTA TTG GTG GAA ATC GCA GCT TCT CCT GCA ATC

547  AAG GCC CTG GTT CAG GGA ATG GAG GCC ATT CGG CAA CAC
      K   A   L   V   Q   G   M   E   A   I   R   Q   H
      K   A   +   -   -   -   -   -   A   +   -   +   -
      K   A   I   P   T   V   S   S   A   V   E   R   Q
547  AAA GCA ATC CCC ACT GTA TCC AGT GCA GTA GAG CGT CAA

586  AGT CAG GAC ACC CTG CTA GAA GCC CTG CAG CAG CTG AGA
      S   Q   D   T   L   L   E   A   L   Q   Q   L   R
      -   -   -   -   L   -   +   A   L   -   -   +   -
      D   L   K   A   L   E   K   A   L   H   D   I   A
586  GAC CTG AAA GCA TTG GAA AAG GCA CTG CAC GAC ATA GCT

625  CTC TCC ATC CAG GAT ATC ACC AGA GCC TTG GCC CAA ATG
      L   S   I   Q   D   I   T   R   A   L   A   Q   M
      -   S   +   +   -   -   -   -   -   -   -   +   M
      T   S   L   E   K   A   K   E   I   F   K   R   M
625  ACC AGT CTG GAG AAA GCC AAG GAA ATT TTT AAG AGG ATG

664  CAT GAT TAT GTG GAC CCA GAC ATA TTT TAC TCG GTC ATC
      H   D   Y   V   D   P   D   I   F   Y   S   V   I
      -   D   +   V   D   P   D   -   F   +   -   V   +
      R   D   F   V   D   P   D   T   F   F   H   V   L
664  CGT GAC TTT GTG GAC CCA GAC ACG TTT TTC CAC GTT CTC

703  CGG ATC TTC CTC TCT GGG TGG AAG GAC AAT CCA GCC ATG
      R   I   F   L   S   G   W   K   D   N   P   A   M
      R   I   +   L   S   G   W   K   -   +   -   -   +
      R   I   Y   L   S   G   W   K   C   S   S   K   L
703  CGC ATA TAT CTG TCT GGC TGG AAA TGC AGC TCC AAG CTG
```

Figure 3E

```
742  CCT GTG GGG CTG GTC TAT GAA GGT GTT GCC ACA GAG CCT
      P   V   G   L   V   Y   E   G   VA  A   T   E   P
      P   -   G   L   +   Y   E   G   V   -   -   -   P
      P   E   G   L   L   Y   E   G   V   W   D   T   P
742  CCA GAA GGT CTG CTG TAT GAG GGG GTC TGG GAC ACC CCA

781  CTG AAG TAC TCT GGA GGA AGT GCA GCC CAG AGC TCC GTG
      L   K   Y   S   G   G   S   A   A   Q   S   S   V
      -   -   +   S   G   G   S   A   -   Q   S   S   +
      K   M   F   S   G   G   S   A   G   Q   S   S   I
781  AAA ATG TTT TCA GGG GGC AGT GCA GGC CAG AGC AGC ATC

820  CTT CAT GCC TTC GAT GAG TTC CTG GGC ATT GAG CAT ---
      L   H   A   F   D   E   F   L   G   I   E   H
      -   -   +   -   D   -   -   L   G   I   +   H   -
      F   Q   S   L   D   V   L   L   G   I   K   H   E
820  TTC CAG AGT CTT GAT GTC CTT CTG GGA ATA AAA CAC GAG

859  --- TGC AAG GAA AGT --- GTT GGC TTT CTA CAC AGA ATG AGG GAC TAC
      -   C   K   E   S       V   G   F   L   H   R   M   R   D   Y
      -   -   K   E   S   -   -   -   F   L   -   -   M   R   +   Y
      A   G   K   E   S   P   A   E   F   L   Q   E   M   R   E   Y
859  GCT GGC AAA GAA TCT CCT GCA GAA TTC CTC CAG GAA ATG AGA GAG TAC

898  ATG CCG CCT TCC CAT AAG GCT TTC CTG GAA GAT CTC CAC
      M   P   P   S   H   K   A   F   L   E   D   L   H
      M   P   P   +   H   +   -   F   L   -   -   L   -
      M   P   P   A   H   R   N   F   L   F   F   L   E
898  ATG CCT CCA GCC CAC CGG AAC TTC CTT TTC TTC TTA GAG

937  GTA GCT CCT TCT CTG AGA GAC TAC ATA CTG GCC TCT GGT
      V   A   P   S   L   R   D   Y   I   L   A   S   G
      -   A   P   -   +   R   +   +   +   +   +   -   -
      S   A   P   P   V   R   E   F   V   I   S   R   H
937  TCA GCT CCC CCA GTC CGT GAG TTT GTC ATT TCA AGA CAC

976  CCT GGG GAC TGC CTG ATG GCC TAT AAC CAG TGT GTG GAG
      P   G   D   C   L   M   A   Y   N   Q   C   V   E
      -   -   D   -   -   -   A   Y   N   +   C   V   -
      N   E   D   L   T   K   A   Y   N   E   C   V   N
976  AAT GAA GAC TTG ACG AAA GCT TAT AAC GAG TGT GTG AAT

1015 GCC CTG GGA GAG CTG CGC AGT TAC CAC ATC AAT GTC GTG
      A   L   G   E   L   R   S   Y   H   I   N   V   V
      -   L   -   -   +   R   -   +   H   +   -   +   V
      G   L   V   S   V   R   K   F   H   L   A   I   V
1015 GGT CTG GTC TCT GTG AGA AAG TTC CAC CTC GCA ATA GTA

1054 GCC AGA TAC ATT ATC TCC GCT GCC ACC AGG GCC AGG AGC
      A   R   Y   I   I   S   A   A   T   R   A   R   S
      -   -   Y   I   +   -   -   +   -   +   -   -   +
      D   T   Y   I   M   K   P   S   K   K   K   P   T
1054 GAT ACT TAC ATT ATG AAA CCT TCG AAG AAG AAG CCC ACT
```

Figure 3F

```
1093  AGG GGG CTA ACT AAT CCC TCA CCC CAT GCC TTG GAA GAC
       R   G   L   T   N   P   S   P   H   A   L   E   D
       -   G   -   -   +   -   -   P   -   -   +   E   -
       D   G   D   K   S   E   E   P   S   N   V   E   S
1093  GAT GGC GAC AAG TCG GAA GAG CCC TCA AAT GTG GAA AGC

1132  AGG GGC ACT GGG GGT ACT GCC ATG CTG AGC TTC TTG AAG
       R   G   T   G   G   T   A   M   L   S   F   L   K
       R   G   T   G   G   T   -   -   +   +   F   L   +
       R   G   T   G   G   T   N   P   M   T   F   L   R
1132  AGA GGG ACT GGG GGT ACG AAT CCC ATG ACT TTC CTA AGG

1171  AGT GTC AGG GAG AAG ACC ATG GAG GCC CTC CTG TGT CCT
       S   V   R   E   K   T   M   E   A   L   L   C   P
       S   V   +   +   -   T   -   +   A   L   L
       S   V   K   D   T   T   E   K   A   L   L   S   W
1171  AGT GTG AAA GAT ACA ACC GAG AAA GCT CTT CTG AGT TGG

1210  GGT GCT TAG
       G   A   -
       P   -
1210  CCT TAG
```

Figure 3G

```
agtccagatgatagttaagaaagcagtaagaatacagagagtccacaatg    50
agatgaaaatgcactgccagttgaaacatcctcctacactggagctttat   100
aaatatttaaagacaaggattggattagatttgacattagaaatgtacc   150
ataatacagaaggcaatggacacctaaagaacagaatgaaaaccttctta   200
ggaaatgaagcttgacacttcacccaccaggccaccacaagaATGTTGCA   250
TTTTCATTATTATGATACTTCAAACAAAATAATGGAGCCCCACAGACCGA   300
ATGTGAAGACAGCAGTGCCATTGTCTTTGGAAAGCTATCACATATCTGAA   350
GAGTATGGCTTTCTTCTTCCAGATTCTCTGAAAGAACTTCCAGATCATTA   400
TAGGCCTTGGATGGAAATTGCCAACAAACTTCCTCAATTGATTGATGCTC   450
ACCAGCTTCAAGCTCATGTGGACAAGATGCCCCTGCTGAGCTGCCAGTTC   500
CTGAAGGGTCACCGGGAGCAGCGCCTGGCCCACCTGGTCCTGAGCTTCCT   550
CACCATGGGTTATGTCTGGCAGGAAGGAGAGGCGCAGCCTGCAGAGGTCC   600
TGCCAAGGAATCTTGCCCTTCCATTTGTCGAAGTCTCCAGGAACTTGGGG   650
CTCCCTCCTATCCTGGTCCACTCAGACTTGGTGCTGACGAACTGGACCAA   700
AAAAGATCCAGACGGGAACCTGGAGACCATCATCTCATTTCCTGGGGGAG   750
AGAGCCTGCATGGTTTTATACTGGTGACTGCTTTGGTAGAGAAAGAAGCA   800
GTGCCTGGGATAAAGGCTCTTGTTCAGGCCACGAATGCTATCTTGCAGCC   850
CAACCAGGAGGCCCTGCTCCAAGCCCTGCAGCGACTGAGACTGTCTATTC   900
AGGACATCACCAAAACCTTAGGACAGATGCATGATTATGTAGATCCAGAC   950
ATATTTTATGCAGGCATCCGGATCTTTCTCTCTGGATGGAAAGACAACCC  1000
AGCAATGCCTGCAGGGCTGATGTATGAAGGAGTTTCCCAAGAGCCCCTGA  1050
AATACTCCGGCGGGAGTGCAGCTCAGAGCACAGTGCTTCATGCCTTTGAT  1100
GAGTTCTTAGGCATTCGTCATAGCAAGGAAAGTGGTGACTTTCTGTACAG  1150
AATGAGGGATTACATGCCTCCTTCCCATAAGGCCTTCATAGAAGACATCC  1200
ACTCAGCACCTTCCCTGAGGGACTACATCCTGTCATCTGGACAGGACCAC  1250
TTGCTGACAGCTTATAACCAGTGTGTGCAGGCCCTGGCAGAGCTGCGGAG  1300
CTATCACATCACCATGGTCACCAAATACCTCATCACAGCTGCAGCCAAGG  1350
CAAAGCATGGGAAGCCAAACCATCTCCCAGGGCCTCCTCAGGCTTTAAAA  1400
GACAGGGGCACAGGTGGAACCGCAGTTATGAGCTTTCTTAAGAGTGTCAG  1450
GGATAAGACCTTGGAGTCAATCCTTCACCCACGTGGTtgagaggctgccc  1500
tctccccagcaatgcagagcccccatggagggcaggtgggcctggagaat  1550
gagggtcagggttctgcctgggatcatccaggaaggatctcagccctatt  1600
catgtttctgctctacagagcactatattctccttgttgagagctgttgg  1650
cttcacaaaggagagttgatgtggccaagcctttccctccctacctgatc  1700
actgcttaacggcatgtataatggatacttcctcatgcagaacccccaga  1750
ggagtgactgtatgccattctctttgccaagtaatagaaaaccaatctaa  1800
atgtcaaaaatcagataaaattgcctggggatacattacttgttgatttt  1850
cttaaaaaacaaattcacttaacaattcattaagttcatactgagcactg  1900
cctccaagattaaaaccaggatttctgtggtcccagaccagccctcttct  1950
ccctgaatgtgttgagttggtggcaggaggttggaaatgctccagtggag  2000
atgggaagatagaggatgctgacaataaggacttggaagtcactagtgtg  2050
aaaatgagcagttaatgatatgggaacggatgagactttccacgtggtac  2100
ctagatttgcaaattctattgtaatgcctttattttagaagaattattc  2150
tctcttcttactctgaaaatctgtatttgtaaaatgaatgaatggatcct  2200
atataagtaaataagaaaactgggaataagtagtaaatcaatgtgtttag  2250
tgtgcaaataaatgtaaatgcttttattg                       2279
```

Figure 4A

```
cgcacaagtacaaccacacagaagacacagctggaaagctccctggcctg   50
ggcattcctctggggcagagacctcacgcgaaaatatggagcctcaaagt  100
cagagcATGACGCTGGAGGTGCCGTTGTCCTTGGGGAGATACCACATTTC  150
TGAGGAATATGGCTTTCTCCTTCCAAATCCTCTGGAAGCACTTCCAGATC  200
ATTACAAGCCTTGGATGGAAATTGCCCTCAGACTTCCTCACTTAATCGAG  250
AACCGCCAGCTCCGAGCTCACGTGTACAGGATGCCTCTCCTGGACTGCAG  300
ATTCCTAAAGAGTTACCGTGAGCAGCGCCTGGCACACATGGCGCTGGCCG  350
CTATCACCATGGGATTCGTCTGGCAGGAGGGGGAAGGCCAACCCCAAAAG  400
GTGCTGCCAAGATCTCTTGCCATTCCTTTTGTTGAGGTATCCAGGAACTT  450
GGGACTCCCGCCTATCCTGGTCCACTCTGACCTGGTGCTGACAAACTGGA  500
CCAAAAGGAACCCAGAAGGACCGTTGGAAATCAGTAACCTGGAAACCATC  550
ATCTCATTTCCGGGGGGAGAGAGCCTGCGGGGCTTCATCCTAGTGACAGT  600
CTTGGTGGAGAAGGCAGCAGTGCCCGGCCTTAAGGCCCTGGTTCAGGGAA  650
TGGAGGCCATTCGGCAACACAGTCAGGACACCCTGCTAGAAGCCCTGCAG  700
CAGCTGAGACTCTCCATCCAGGATATCACCAGAGCCTTGGCCCAAATGCA  750
TGATTATGTGGACCCAGACATATTTTACTCGGTCATCCGGATCTTCCTCT  800
CTGGGTGGAAGGACAATCCAGCCATGCCTGTGGGGCTGGTCTATGAAGGT  850
GCTGCCACAGAGCCTCTGAAGTACTCTGGAGGAAGTGCAGCCCAGAGCTC  900
CGTGCTTCATGCCTTCGATGAGTTCCTGGGCATTGAGCATTGCAAGGAAA  950
GTGTTGGCTTTCTACACAGAATGAGGGACTACATGCCGCCTTCCCATAAG 1000
GCTTTCCTGGAAGATCTCCACGTAGCTCCTTCTCTGAGAGACTACATACT 1050
GGCCTCTGGTCCTGGGGACTGCCTGATGGCCTATAACCAGTGTGTGGAGG 1100
CCCTGGGAGAGCTGCGCAGTTACCACATCAATGTCGTGGCCAGATACATT 1150
ATCTCCGCTGCCACCAGGGCCAGGAGCAGGGGGCTAACTAATCCCTCACC 1200
CCATGCCTTGGAAGACAGGGGCACTGGGGGTACTGCCATGCTGAGCTTCT 1250
TGAAGAGTGTCAGGGAGAAGACCATGGAGGCCCTCCTGTGTCCTGGTGCT 1300
tagcagtcatgtcctgcaccctaacacttagatgttctcatcctgcatcc 1350
cagcgttagaggttcacatcctgcatcctagtgcttagctgttcttgtgc 1400
tatatcccagcgcttagcagtcatgtcctgcatcctagtgcttagcattt 1450
tatatccagcattttagtgcttagagattcacatcctgcatcctagagct 1500
tagcattttatatccagcatccttgtgcgtatcagctatgttttgtatcc 1550
tgcttagcagttaacatcctgcatcctagtacttatctgttctcatcctg 1600
catcctagagcttagcagtcaggtcccgtgggagcaagaaccagggtctg 1650
agctctgtctgagcccaagcatggctttactgctttgttaattgtggctc 1700
ccacctccaccccaccccagccagtttgcttgctagaagcctttctgcac 1750
tgcctaatccccctgcctcacagcagagagctgcagccatgacctcctca 1800
ttcagtattaggtggacaagtcggagatacccaaactcaattttaaaaga 1850
atcaagttgcttttggggcatgttacttcatcttttcttaccctgggcct 1900
cttcccttcttccctacctccctcgtcccttagtctttcacccctctctc 1950
tttctccttttgtcaccctccccctcccctgcttactctcttttcccttc 2000
cccccctctcctcatccctccttcctttcttccttcccttttttgtctgtga 2050
agcaccaggtctgatgggcctcaaactgtgatcttcctgtctcaccccttc 2100
aaaggttatgtgtatgtgacgtgtgtgtgtgtgtgtgtgtgtgtgtgtgt 2150
gtgtgtgttcgtttcttttgtttttccctagtggagatgacacccaaaga 2200
tttgcacataccaggcaattgctccaccacctgactacagtcccagctct 2250
ctgtattcctgaaggaaagtcttgatgagttgcctaggctggtattgagc 2300
tctttagcccaggcaggccttagtctgagtagctgggatgtacagggatg 2350
agccactgagccatgctgctgctgctaacgatgatgacgatgatgatgat 2400
gaagattatgataactacagtcactgcaataatgacggcaaagataatga 2450
aaaaaaaaaaaaaa                                     2464
```

Figure 4B

```
ATGGAGCCCCACAGACCGAATGTGAAGACAGCAGTGCCATTGTCTTTGGA     50
AAGCTATCACATATCTGAAGAGTATGGCTTTCTTCTTCCAGATTCTCTGA    100
AAGAACTTCCAGATCATTATAGGCCTTGGATGGAAATTGCCAACAAACTT    150
CCTCAATTGATTGATGCTCACCAGCTTCAAGCTCATGTGGACAAGATGCC    200
CCTGCTGAGCTGCCAGTTCCTGAAGGGTCACCGGGAGCAGCGCCTGGCCC    250
ACCTGGTCCTGAGCTTCCTCACCATGGGTTATGTCTGGCAGGAAGGAGAG    300
GCGCAGCCTGCAGAGGTCCTGCCAAGGAATCTTGCCCTTCCATTTGTCGA    350
AGTCTCCAGGAACTTGGGGCTCCCTCCTATCCTGGTCCACTCAGACTTGG    400
TGCTGACGAACTGGACCAAAAAAGATCCAGACGGGTTCCTGGAAATTGGG    450
AACCTGGAGACCATCATCTCATTTCCTGGGGGAGAGAGCCTGCATGGTTT    500
TATACTGGTGACTGCTTTGGTAGAGAAAGAAGCAGTGCCTGGGATAAAGG    550
CTCTTGTTCAGGCCACGAATGCTATCTTGCAGCCCAACCAGGAGGCCCTG    600
CTCCAAGCCCTGCAGCGACTGAGACTGTCTATTCAGGACATCACCAAAAC    650
CTTAGGACAGATGCATGATTATGTAGATCCAGACATATTTTATGCAGGCA    700
TCCGGATCTTTCTCTCTGGGTGGAAAGACAACCCAGCAATGCCTGCAGGG    750
CTGATGTATGAAGGAGTTTCCCAAGAGCCCCTGAAATACTCCGGCGGGAG    800
TGCAGCTCAGAGCACAGTGCTTCATGCCTTTGATGAGTTCTTAGGCATTC    850
GTCATAGCAAGGAAAGTGGTGACTTTCTGTACAGAATGAGGGATTACATG    900
CCTCCTTCCCATAAGGCCTTCATAGAAGACATCCACTCAGCACCTTCCCT    950
GAGGGACTACATCCTGTCATCTGGACAGGACCACTTGCTGACAGCTTATA   1000
ACCAGTGTGTGCAGGCCCTGGCAGAGCTGCGGAGCTATCACATCACCATG   1050
GTCACCAAATACCTCATCACAGCTGCAGCCAAGGCAAAGCATGGGAAGCC   1100
AAACCATCTCCCAGGGCCTCCTCAGGCTTTAAAAGACAGGGGCACAGGTG   1150
GAACCGCAGTTATGAGCTTTCTTAAGAGTGTCAGGGATAAGACCTTGGAG   1200
TCAATCCTTCACCCACGTGGTTAGGAT                          1227
```

Figure 4C

```
ATGGAGCCTCAAAGTCAGAGCATGACGCTGGAGGTGCCGTTGTCCTTGGG    50
GAGATACCACATTTCTGAGGAATATGGCTTTCTCCTTCCAAATCCTCTGG   100
AAGCACTTCCAGATCATTACAAGCCTTGGATGGAAATTGCCCTCAGACTT   150
CCTCACTTAATCGAGAACCGCCAGCTCCGAGCTCACGTGTACAGGATGCC   200
TCTCCTGGACTGCAGATTCCTAAAGAGTTACCGTGAGCAGCGCCTGGCAC   250
ACATGGCGCTGGCCGCTATCACCATGGGATTCGTCTGGCAGGAGGGGGAA   300
GGCCAACCCCAAAAGGTGCTGCCAAGATCTCTTGCCATTCCTTTTGTTGA   350
GGTATCCAGGAACTTGGGACTCCCGCCTATCCTGGTCCACTCTGACCTGG   400
TGCTGACAAACTGGACCAAAAGGAACCCAGAAGGACCGTTGGAAATCAGT   450
AACCTGGAAACCATCATCTCATTTCCGGGGGGAGAGAGCCTGCGGGGCTT   500
CATCCTAGTGACAGTCTTGGTGGAGAAGGCAGCAGTGCCCGGCCTTAAGG   550
CCCTGGTTCAGGGAATGGAGGCCATTCGGCAACACAGTCAGGACACCCTG   600
CTAGAAGCCCTGCAGCAGCTGAGACTCTCCATCCAGGATATCACCAGAGC   650
CTTGGCCCAAATGCATGATTATGTGGACCCAGACATATTTTACTCGGTCA   700
TCCGGATCTTCCTCTCTGGGTGGAAGGACAATCCAGCCATGCCTGTGGGG   750
CTGGTCTATGAAGGTGTTGCCACAGAGCCTCTGAAGTACTCTGGAGGAAG   800
TGCAGCCCAGAGCTCCGTGCTTCATGCCTTCGATGAGTTCCTGGGCATTG   850
AGCATTGCAAGGAAAGTGTTGGCTTTCTACACAGAATGAGGGACTACATG   900
CCGCCTTCCCATAAGGCTTTCCTGGAAGATCTCCACGTAGCTCCTTCTCT   950
GAGAGACTACATACTGGCCTCTGGTCCTGGGGACTGCCTGATGGCCTATA  1000
ACCAGTGTGTGGAGGCCCTGGGAGAGCTGCGCAGTTACCACATCAATGTC  1050
GTGGCCAGATACATTATCTCCGCTGCCACCAGGGCCAGGAGCAGGGGGCT  1100
AACTAATCCCTCACCCCATGCCTTGGAAGACAGGGGCACTGGGGGTACTG  1150
CCATGCTGAGCTTCTTGAAGAGTGTCAGGGAGAAGACCATGGAGGCCCTC  1200
CTGTGTCCTGGTGCTTAG                                  1218
```

Figure 4D

```
TAGTTAGAAG GCAGCTCGTT TCCAGACAGA TCATGCCGGG CCAGCACAGT TCCACGAGGA
GCGATTTTTT TGGATGGGGG AAGAAAGTGA AGAAGAGGAG AAAGAGGAAA AGGGGGTGAA
GGGTCGCGGT CTCAGTCTTT TATTTGTGCC ATGACATAGA TGCCAGGTAA TGAATGATGA
ATGATGCGCA CAGGTGAAGC ATAGGCCTGC CTGGAGTGTA TGGTGGTTGC CATGGCAACA
GACCCAAGAG GGTCCTTGTC GCTTAGGGAT GATGTCATAG CTGGATTCCG AGGCTGGTTG
TAAAGCAGTT TCTGATGCTA ACAATACATA TATATGTAAT GATAACAAAG AAAAAGAGGC
CATGAATTTG AAAGGAAGGA AAGAAGTTAG GAAGGAAGGA AGGAAGGAAG GAAGGAAGGA
AGGAAGGAAG GAAGGAAGGA AGGAAGGAAG GAAGGAAAGA AGATGGGAAT TTGGAGAGAT
GAAAGGGAAG AATGATATAA ATACATTTTA ATTTCAGCAA ATAAATACAT TTTCAAAGAT
AAAAAGCCAA TAAAGAGAAA CCCTGTCTCG AAAAAACAAC AACAAACCAA AAACAAACAA
ACAAACAAGC CAATAAAACT GACTCCTAGT TTAGTCATTT TGATACACTG TCAGAATCCC
TCAGGAACCA AACTCATGTT GAGTATGGAT CTGCACAGCC ATAGCTGAGA GTTAAGTTCG
TGTCTCCCAC TTTGTCCCTG GATTTAACAG CCCCTTTCTC ATACTTTATG AATGAGAAGG
GAAAGGGGGT GGGGGCTTCT CTTGGAGTCA GCATTTTAAT TCCTAATCTT CATTGTTGAC
TTACTACTTG GCTTTCTTTC AGAATAAATT TGCGGCCATC CTGGAGTTCA ACCTCAGGGC
AAGGTTCTCC CCTACCGCTG AAGCACCGCA CAAGTACAAC CACACAGAAG ACACAGCTGG
AAAGCTCCCT GGCCTGGGCA TTCCTCTGGG GCAGAGACCT CACGCGAAAA TATGGAGCCT
                                                       >>......>
CAAAGTCAGA GCATGACGCT GGAGGTGCCG TTGTCCTTGG GGAGATACCA CATTTCTGAG
>.........................exon 1  ..........................>
GAATATGGCT TTCTCCTTCC AAATCCTCTG GTAAGGATTG GCTTGTCCTG GTCAGCACAT
>..........exon1  ...........>>
GTGTCTGGAT TGTTAGTCTT TACCTTATGT GGTTATTGGA AGGTTCGGTA TAAGTCACCA
GCTGGAGGAA GAGTGGGAAT ACAGTCCTGT GAGTCCCGGA AGAGCAGAGG CAACTGCTAC
TGGGGACAGC ACAAAGCCAG TGGTCCCCTC CCCCCAGCCC CCAAAGTTTC CTTAAATCTA
TGGTAGTTAG CACTGACTAA TCAGAAGCAA AGGTGCTATC AGAGAGGAGA GACTGGATGG
AGACATGCCC TAAGGACAAT TAGAACCCTA TAACTACAGC AAAGAGTGGA CATGCACACA
ACCACATGGT GTGACACAGA ATAATGGAGT GGCCCCACTG TATATCCACT CTGCTTTGGA
GACAGGTTCG CCATGCATCC CAGACCTAAG CAGCCAAAGG GCTTAGCCTT CTGTGTTGAT
GCAAACCAGT TTATCTTACT TGCTGGTGAC AGCAGAGATA ATGGGAGACC TGCAATGTTT
TTAGAGCCAG TAAGAAGATT AGATGTTATC GGGAATTTCC GATACTCGTG AGGAATGTTG
GAAAACAAGC AGGCCTGACT TTCAGTCCAA CTGCACAGCA GTCTCTAGTA TACCTGCTCT

                                NgoMIV
                                ------
                                 NaeI
                                ------
TGTTAAGTGT AGTCTGGGCT TGGGAGACAT ATGCCGGCAA AGTGCTAGTG GCAAAGCCCA
TGCTTTTGGC ATCTTTTAAA AACTGACCGT ACCTAAGGGA GGGTGAAGGC CACTGAGTTA
AAAGTCCAGG GACCCGATGT TGCAGTCGCG GTAACTGCTG ATCAGCACCA ACTCACCTAG
TTCCTCTCTT ACTTGTGATT AAAAATATCA GGGTCTCAAA CACCTATCAC AGTGAGACTC
TTGTTGTTTT GAAACAGAGA ATATTGATTT ATGTAGCCCA GGCTGGCCAC TTGCCTCCAC
TTCCTTACTG CTGGGACCAT AGCTGAACTC CCACAGCAGA TCCTTTTGTG TTGAACGGTA
CTGGAGGGAT CTAATTGAAG AGAACTAAGT TCTCCACAGA AAGATGTCAG CTACGACATC
GGTCATAGAC ATCTGCAAGC TGTCCAGGTT AGGGGTTAGT CATTAGAACC AGGGCCAGAT
CTCACAGCTT GAATCAAGCC AGGCCTTCCT GCTGCTCTCT CACGGACAGT TAGGAAGCAG
ACTGTACTCT GACATGATAG CTTGCAGCCG ACGGCTCCCG GCTCCTCTGT GCTCCTTGTC
ACGCAGGCCC TGCTATAAAC TAAAGTGTCT GACATGACTT CCTGGTGCCT CGTAAAGTTA
TTAAAAGTCA GATTTCTCCT TTGTTCTCGG AATTGGTTCG AGAGCCCTCA GGGGATTTGC
TGAGGGTGTG TGTGTGTGTG TGTGTGTGTG TGTGTGTGTG TGTATTCTAA GAGTGCTTCC
CTAAAAGGGT CCTCTGTACT GTCAACGGAT CTTTCATAGT CTCTCTCTCC CTGTCTCCCT
GTCTCTCTGT CTTTCTGTCT CTCTGTCTCT CTCTGTTTCT GTCTTTCTGT CTCTGTCTGT
CTGTCTGTCT GTCTATCTCT GTGTGTGTGT GTGTATTTTG AAGGTAGGAG GATCTGAGCC
TGAACTACAC ACAGCTAGAT CCTGTGACTC TGTCTCAAAA CAGAGACACA ATCAAACTCT
CAACTAATCG AAACACCACA AGGCACACTC CATTCTGGGT GTGTGGTCTC AGTCCAGCGT
ATTCCCATCC TTCCAAGTTT ACAGGAGAGG AAGGGCTGAT GGCAGATACA CCCTTGTCAT
TACTGGGCAT GTGTCCTGAG TTTGGAAAGA GAACACTGCC AAGCAGGGGA ACGAATATCA
GGGCAGGCCA TAGCTCTGGG GCTTTCTGGG CTGCTTTCCT CTTTGTAAAT ACTGGGACCA
```

Figure 10A

GGCAGACATA CAGATAAGAC ACAATAGCAA CATCAAGTTT CCCCCCTATT TGTTAGAAAG
GTTCTATGGT ATGGTGTGAT GGATGGGTAC CCCTTAAAAG AGGTCCCTAG TGCTGTTCAC
ACAGAAAGGA AATATTCCCT GTCCCACCCA GCTACTCATT TATAGCCCAG TAATTTCAAT
ATGATTCTTT CTGTTTCAAT TTTCTTTCAT TCAAGTGATG GTTTTCAATG TCTTTTTTGT
TAAAGGAAGA GGAAGAAACC TTGACTAGGA TCAGGTCCTG GCTGCTCCAA AGGTCAAGAC
AGACTCAGTT CGACTTCACT GGACAAACAG TCCTGCAACT TTACACTGGT TGGGAAAGAA
CAGTGGGTTT GGCCCAGTCC AGTGCCCTAG GGCATAGCCA AGACCTGTTC TTCTTGGGCC
AAGGGCAAGT GGTAGGTGGC AGACCTTCCC CATCTCTTTC AGAAAGTCTC ACTTAAGAAA
ACCTAGCTGG CTAGCAAGTT CAAGGGTATA AATTACCCTA TCCAGCTGTT TCTATCAATT
CAAAGACTTC CAATTTTTAG TGTCTCTATG GAACTTTGCT CCTCGAATCT GTAAAAATAC
CACAAGAATT CTTTGCTAAG ACATCTGTCC TCTGTGTATA TTTGGGAGGA CAAGACATCT
TTTTCAGATG AAGAATGTGA GGAAATCAGT TTGCAGGAGA GGAGGCAGTT AAGAGGAGGC
AGCAAGAGGC TGGCCTGCAG CAGAGCTATG ACCCCAAGTG CCAGGCCCAC TCTGAAAATT
GATTTAACAC CCTTCCTAAA CACAATGTGA CTGCTACTTG AGTCATTTCC TCTCACAGCA
CTAAGGGCAG GGCAGGTTAG AGCAGTGGGT CCTGGGCTGT GGGGTGAGAC CTTTAGGGGA
GTTTCAACAA ACAATCCAGA TGCCAGAGCC CCACCCTGTT TATTCAGACT CTAGACCCAA
GAGCTGTACG CTGGGAAGGC CAGATAGGGA GAACAAGCCA GAGAATGCCA GACAGGGAGC
ACAAGCCAGC AAAGTCAGCC GTGAAGGTGC CACGGCCAAT AGAGACTCCT AAGTGCGAAA
ATAAATAAAC TGATGACATG CCCACTCCAT GCTTAAGGGG AAAGTAGATC AGAGAGGGAG
AGAGAGAGAG AGAGAGAGAG GCACCCAGAG GCAGAGGCCT CTGGACGATT CCGTAGTAGA
TAGAGAAAGC AGACTGAAGA TGGCCACCAG ACTGGACATG GCCAAGGCTA CCTGGGAGGA
AAGGAAGAAC AACAGAAGTC AGAGAATAGA GAAAACCTAG TGAGAGAAGC AGGAAGGGGT
TGGGGGGGTG GATGGAGAGA AGTTAGCAAT GACAGCAGGG TTCTAAGAAG AAAGAGTTGG
GGAGGGGAGA TCCTGTGAGC TGGAGGGAGT GGAGTGAGTG GAGGGGAAGA GCTGAGAAGG
GACAGATGCT AGCAGGGGCT TTGAGATGTA CAGCAGGTAC TTGTGATAGG TGACTGGAGG
CCACTGGTGA CCACATGTCC CTTCTGCAAG AGGTAAGGGA AAACATTCCT TTAGGTAGAG
GGAAACCAGT GTCACAAGTC CCTGAGGAAA GCTGGCTTTT TATCTAACCC CCAGAAATCC
TCCTGTAGTC CAGGTGAAGC TCATTTCTGG ACATACAGAC TGCCTTTTGG AGTTTGGGGA
ACTGGAGTTT CCTTTGGACC TGACAGTCAG GAGACGTTGC ACATGTAACG TAGGGGTAGA
CACAAGACTG ACAGGAATGG CAATGAGAGA GGACAACCTC CAGGGAAAAA CCAACATGTC
CCTTCTCATT CAGAAATTCT AAGCACTTGG TTGAAGCATT GGGCCACAGC TGGAGAGAAG
ACCGGATAGG AAATTAATTG CCACGGACAT CTGTATTTTT CAGATAAGAC AAAAAGGAAG
AGGTCTAACA TTGTCCTGAA ATATGAGGTT GCCACTGATG ATCTCTGGAC ACATCAGACT
AGTCAGATAG GGGACTTGAA ACACAATGAA TCCAGAGTCT GTAGTAGAGA CAAAGAGGCC
AGATTGCAAA ATGGTTAATC TTGATCAAGG CTGGAAAATG TGTATGGAAA TAAGAGAGAC
TGTAATATCT TAAGAATGGG GTTTGTCCTT GTGCCAGTAT TAAAGAACAA CAACAAAAAA
AAAAAAAAAA GAAAAAGAAA AAGAAAGAAA GAAAGAAAGA GAGAAAGAAA GAAAGAGAAA
AAGAAAAATG GAGGAAAGTC ATGGGGAAAC AGGTAATCAG GCTTGAATTA AAAAAATAAA
AAAATAAAAT AAAAAGTTAA AGGACTTGAC TAGTCCCAGG TTTCTGCACA GATGAATTAA
AAAATGAAAA GAAAAGAAAA GAAAAGAAAA GAAAAGAAAG GGAAAAAAAG AAAAAAAGAA
AGGAAAAAAA AAGGAAAGAG AAAAACAAAA GACAGGAAAA GAAGGGAGGA AGGAAGAAGA
GAAAGAAAGA AAGACAGACA GAAAGAGAGA GAGAAAGGAA GGAAGAAAGG AAGAGAGAAA
GAAAGAAAGA AAGAAAGAAA GAAAGAAAGA AAGAAAGGAA GGAAGGAGGA AGGAAGGAAG
GAAAGAAAGA AAAGAAAAGA AAAGAAAAGA AAAGAAAAGA AAAGAAATGA AAAGAAAAGA
AAAGAAAAGA AAAGAAAAGA AAAGAAAAGA AAAGAAAAGA AAAGAGAGGA AGGAAGACAG
AGGAAAGGGC CTGGCTGCTT GTAGGTACTG TAGCCCGGGA GATCATAGCC AGAGGCAAGG
ACAGCTAGGG AAATCCAGAG TGGTCATGAC CGTGAACCAC TTGAGGAGAG GGAAGAGAAA
AGGGCAGCCC AGCCCCCAGG CTAGAGAAGT TTAGGGTTGG GGCAGGGTTT GTCAGCCAGT
GGGTCTTTGT AACTCCCGAG AACTTGTAGG CGGCTTTGAT ATGCTAAGTA GGCACCTCAG
CCTTTCCTCT TGGGTTTGAA ACCCAGAAGG CCTCAGCAAG TGGGACAAGC CAAGCCCAAC
TTGGAAAGCA GAGTTTTAAA GGGTGAAACA ACCAACCAAA AAGGTTCACT CTCTTCTAGC
AAGACGCTTA TGCTGCAAAG AGACTTAAGA CAATCCGGGA GCAAGGACAG GACACACGCT
GAGGATGGGA TGCTAAATCA GCCCTGGAAA ATACGTGTCT AATACAGGAG GCTCTCGCCC
AAGATCTATT GGTTTCCTAG CACAGCCGTA AAATGGCTAG CTATTTTAGA ACAGTAACCA
GTTCTCTGAA CTCCATGCCA GCCTGTCCCC AAGTTTCCAG CCCTCTGCTT CAAACACTTC
TTCCAACCCT TCCACCCTCA ATTTCCCAAC AGTCTTCTTA AACAATTCCT TCTCCCCATT
CTCCCAAGAC TAGCCACTCC AAACGGTAAC AACCATATCT TCCATACCAA CTGCCTTCTC
TTCTCCCTCT GCTAGCCCAA TCCCCCCTCC TTCCCTGACT CAGCTGGCTC TTTTATACTC
TATCCAGTTC CTAGTCATCC AAGAAGCAAC CAATGCTTAG GGTCATAGGG TCAAGCCTTT

Figure 10B

```
GTAACAGCTA AAAGTTCTTA AAGAGGCCAG TTGACTCGCA ACTGGAGACC CTTTATTACT
TATTTATTTT TATGTCTATG AGTACACTGT AGCTGTCTTC AGACACACAC CAGAAAAGGG
CATCAGATCC CATTACAGGG TTGTGAGCCA CCATGTGGTT GCTGGGAATT GAACTCAGGA
CCTATGGAAG AGCAATCAGG GCTCTTAACC CCGCCGAGCT CATCTGGAGA CCCTTTAAAG
GGCCAGGAGC CCAAGATAAA TCACATTACA GTTACATATG ACCCAAACTC AGGTGAGCTA
GACCAGTGAA GACTTAGACT GATTTCTGGA ATTAAGGCAC TGGGCCTGCA GCACTTCCCT
CCAAAGCCTG CAGTGCAGAA TCTGCCCAGG CCTTTCCCAG GCTCCGGTAG CTTCAACAGC
TTCCTGGCTA CTAGCTCCTG GCATCTTTCC ACCCCTTCCT TATATGGCCT TCTGCTGCTC
AGTGTCTTCT CCCCTGATGC CTTTTCTTCT TCTTTTCTTA CAAGGATGCT GCTCATTGGT
TTTTAAGACC CAAGCTAATC CCAGATAATC TCATCAGTAA AGAGCCCTCT CCAAATAGTA
TCACATACTT AGTTCCTAAG GGGACAACTT ATTTGTGTTC TAAGACTTGG GGCAAAGTAT
GAGCAGATGG TGCAATCTTA GGAATGCTGA CTGAAAGAAC TGTCTTGTCC CTAGATTCCC
AAACCTGATC TGTCAGGAAT GAATGGGGGA AAAAAGCCCA GGACAATGAC AGGCAAGAGT
GTAAAATATC AGTGGTCGCC AAGGGGCTTC GGGACATAAA TTCAGTGAGT GAGTGCATTC
TTACCACGTA TGAAGACCAT GCCAAACACA GACATAAATA ACGAAAATTA AAGATTAAAA
GTAAATAAAT TGGCCAGATG TCATGGCAAA TGCCTGCATT CCTAGCAACT AGCAGAAGCA
GGAAGGTATC AAGTTCTAGG CCTGCCTGTA ACACTGAACA CATATGAGAC CAGCCTGAGA
TATGTAGACA AACAAAACAA AACAAAACGA AAGACCATTG ATCAATCAAT AACATAAACG
TTCAGGAAAC ACAGGCCACA CAATCAGGGA GGCTTTGCCT TTGTTTAGGG GCTGGGTTTT
TTTTTATATT TTCCTTTCCT TGTTCTTCTT CTTGTTTGTT TGCTTTTTGT TTGTTTGTTT
GCTTGCTTGC TTGCTTTTGT TTTTTCAAGA CAGGGTTTCT CCGTGTAGGC ATCTCTGGCT
ATCCTGGAAC TCATTCTGTA GATAAGGCTG TCTTTGAACT CAGAGATCTG CTTGCCTCTG
CCTTCTTAAG GCCGGGACTA AAGGTGTGCA CAGTCACTGC CACCTACCTG CTGTTTCTTT
ATCCCCTGCA TTAGTCACCC TCCCACACCC GCCAGAGCTC TGGGATAGAG ACTCTGTGTT
AGGGAATGGA GCCTACAGCT TCCATCAGGT GCTATGTTTT AATTCACATT TTCTATTCCT
CTTTTCTCAT TTGTCTGGGG TGATTCTTTT GGACAAAAAA AAATGTTATC TTTTATAATT
ACTAATTAGG ATACAAACGT TAAAATATAT CTATAATGTA CTCTTGTATA TCATTCATAA
TACCTATTTC GTATTATACT TCCTTATAGT ATATAGCATA TTTTGATAAC AAGGTCACGA
GGTCCCAGGC CTGGAACCAA CTTTTTCCTA TGTAATTGGT TGAAGTTACT GACACCGTAG
TAGACTTAGC CCTCTGGAAA CAGCCTTTGG CAATGAATTT GACTCTGTTT CAGACAACCA
TCACTTTCCT GGAAACGGCC TCTGGCCCAT TCATTACATA TTTCTTGCCC ATCTGTGACA
CGCTCTGGGT ACAATCAGCA TGACTCACTA AGAGGGTGTT CCCGTTTGCT TCTGGTTTCT
GTGAGAAAAC AAACAAAAGC AACTCTGGGA GGCAAGGGTT TATTCAGATT ATAAGTCCCT
GTCACAGTCA ATCGCTGAGG GATGCCAGGT CAAGAGCTCA AGCAGGGCCC TGGATGCAGG
AAGCAGAAAT CAGAGAAATG ATGCTCTGTG GCTTCCTCTC AATTCACACC TCCCGGGACC
ACCTGCCTAG GGATGGCCCC ACCCATAGTG GGCTGGACCT CCCTCCATCA ATCACTAATC
AAGAAAACAC CCCACAGATT TGTCTACAGG CCGATCTGGT AGAGACAATT TCTCAGTGAA
GGCTCCTTCT GACTTAATGT CAAGTTGGCA AAAACTAACA GGCACAGATG GGAACCAGTC
ATAACAGTGC TCTGTACAGT TCTCCCATTG CTCTTTAGAA TGGTCTCACA TGGCCTCTCA
CAATGCTCAC ACAGCTTCTC CTGGGAATTT AATGCCCCTT GCTTCAACTT CTCTTTGCTG
TGCCATGATG CTAGCCTTTC CTATGTCCAA TCCCCCACCC ACATCCACTG AGGTTCTTGT
AGACTAGAAC CTTCCACATG AGACAGACTA CCTTAACCCT TGTCTTAGGG GTAGGCTGGC
AGGGTTACTA TTTCTATAAA ACATACTTTC AATTCCATTT TAACGTTTCA TATGTATTAT
ATATATTTAT ATTATCAATG TAGTGATGCT AAATAGACAA ACAGATGACT TAAGTCTTAA
TGATGATCCT ATAAGAATTC CTAAAATATA TCTGTGGTTA TTAAGCTCTT TTATAGTGGG
ACAGCCATTA AGTCCTTTTC TAATTGTCAA AACTGCAATG AGAACTCTGC CAGTCTCCCA
AGTGTCTCTA GTTAATTGCT ATTAGATCGT AACCAGACTT TCTCCTACTC AGAGCACATT
CCAAGCGGTT GTAAGACAAT CAGTCAAAGT TTATAAAAAG GGACAATTTA TATATATCCT
GCTAGGACAG AAGATAAAAT ATTGGCTGGT TTTGTCGATA CTAAGCTTCA CTAATAACTT
AGTTATGGTT TGAACCCTTC AGTGAACAGG GTGATGGATG TTGAGCAGGA TTTTTACTCC
TCATGGATAT GCATGTAAAC TTTCTCTGTT GTAAACTTAT ATATCAATTT ATGATTTGAT
TTTTGTGTGT GAACTTGTGA TGAACTTTGT AACATGTGAT CATTCTGAAA GATGTATAAG
TACTAAGGAC AAAGAGATGA GAGGCAGATA GAGTTGAATC CCCCCCCCCC CCCCCCAAGA
ATCAATCATT TCCCTTCCTA GAATTTTTGC TCCTGTAGAG AATTTTTCAC TTTCCCCACT
TAGGATCTTT CTGCCTTTCC CCTTAGTTAG CTTTCGTAGG AAACTTTTTA CAACTTAGTA

                         BstBI
                        -------
ATAAATGCTA TAATCATTTT TCGAAGTGTC CCCTTTTCTT CCTGTGACTT CCGACTAGCA
```

Figure 10C

```
GGCCGAAAGT TAGAGTGGAA CAGCTTCTGC TGAGATAGTG CGAAGGCTAT CTACTTTATC
CTTTGCTGTT TGAGGAAGAT GTGCTAAGTG CCAGAGACTG CAGTTTCTGG CCTCCGAGGA
ACACAGAAGG CAGGTCAGCT ACAGTAGCAT CGAGAAGAAC CCAACAAGAA AGAAGAGCTC
CATGCCAGGG CTGGCAGCAT TCCTATGTTT TATGTAATAT TTACTGCTGA GCAGGGGATA
ATATCTGACA TCATATGTTA CTTATACATT TTTGTTGATT AAAAACTATA ATAATCATCC
CTTCTCAGCA CCCACAGAAA ACCAAGGCAT GTGGATCTCT GTGAGCTTGG GGCCAGCCTG
GTTCACATGG TGAGTTCCAG GTCAGCTGGT GTTACATAAC ATGACCTTGT CTCAAAAATA
TAATAATAAT AACAATAATA ATACAATATT ATATATTTTA TAATAAATAA TAACAATCAC
TAGTATTAAA ATAAAAATAA AAGAAAATAT AAAATCATGC TTGTTAAATA TTGCTTTATA
GGACATTATT TGACTGTCTT TTAACCTGGC AAATACCCAT CAGCATTCTT TCTCAAAACT
CAGTACCACT CGAGGCCTCC TTGACCCACT GTCTCGGTTA TTCAGCACTA ATGATCTAAG
TGTATTTTTG GCACACAGTT CATATTGTAG ACAGCACTTT GTAATTTTTT TCTTTTATGT
TTACTTTTTT TTTTTAACTT GGATAAATAA GTATAGGCCA GGACATTTAT CTGTAAAAAG
AAAGGATGTG TATTGGAAAG TTTCTATGAG CTTTGTGTCA GAAGGGGTTT GGCCTGGCCA
CTGACCACAT GTGCTAGGGA GGGAGAGTTA ACCTCCCCTC TCCCCATGGG GAGCCTTAGC
TGTTTATTCT GTTGCTGTGG TAAGATGTCC TGGTAAGCAA CAGAGGCAGG GAGGGAGGGG
TTTGTTTGGG TTCACAGTTC AGCAGAAGCC ACAGGTGGCC TGACCTTAAG GCATCTGGCC
TTGTCGCACC CACACCCAGA GCCACGGGGA TCTTAGCTGC CGTTCTCATC GTTCCATAGT
CTAGGGTCTA GGCCCATGTA ATGATGCCAC CCACAGCCAT CCTAACTAGA CAAACAACCA
CTCAGAGCTG TGCCCAGAGG CTCACCTCTC AGTCATTCCA GACCCCGTTA AACAGACGGC
CAGTACTAAC TGTTACACTT TCTGTATTTC AGTGTGGGAA GAACAAAAGA GAAGCCTCAT
GGCACAAACA CCCACCGATT AAGACAAGCA TCAGCATGAA GACTAGAAAC AATATTAAAC
AATATTAAAA GTGACTTTGG GAAGAGGGGA AATTTTTAAG TATGATTTAA GACCAGAAAA
CGAGTGAGAT GTGGTTTGTT TCATTATTCC ATTAGGAACA GCTATTTAAA ATACACATAA
AGGACACCAT ACCTGGGATA TATACTGGGT TTTAGTCTGG ACTAAAGGAT GACACTTGGT
TTTTAAACAA AGGAAAAATT GAGTGACTAA AGCTTATGAA AATTGAACTT GCAGAAATCT
AAAAATTTAA ATCTAGAATA GTAACAAATT GATATCATCA ATTCGGGAGT TACATAGATC
ACCTAACAAA CCACATTGGG ACCTCCTAAG TGTTATCATT TTAGACAAGA GGGTAAGAAT
CGGGGTACTC TTTCGTCTAC TTTAGAGAGT TCATGCTTTT TTGAATGCCC TGTTAGCAAT
GTTGATCCAG AAGACTACAT CATCTTCTTC TTTATGAATT GGGAAGCCAG CAACAAAGCA
ACTGAGTAGC AAAGGCTTAT TCTTGGCTAA GAATAGGAGA CATGAGAAAC AAACTCACAA
GTTCACTCCG CGATCTGTTG TGGTTATAGG CATAGGATCA AGGAGTTGAG TGGGAAGGAG
AGGCTAGTAA TCAGGGGACA TATTGTTACT GGGAGACATG TTCAAGTATT TCCTAAGACT
AGGTGGAGAT TTCCCAGGAA ATCCATCAAT ATATCTTTTT CAACTATTTT AAAAACTTCA
CTCATTTATT TTAGTATGTG TGTGAAAAAG AGACAGAGAT ATATAGAGAG AGAAAGGGGG
AGGGAGGGAG AAGGAGACGG GGAAAGAAAG ACAGGGAGAT AGAGAGACAG AGAAAAAAGA
CAGAGGGAGG AATGGGTAGA GGGAAAGGGA GAGAGAGAAG AGGGTCAGAG AGAGGGGGGG
AGAGAGAGAA AGAAAAGGGG GGGAGGGGAA AAGGGAGAGA GAAATAGAGA CAGAGAGGGA
GGGAGGGAAA GAAGAAGGAA AGGGGGAGGG GGAGGGGGAG AGAGAGAAAG ACACACACAC
ACACACACAC ACACACACAC ACACACACAC ACACACGGGG GTGGGGGGAG AGAGAATGCT
GATGTCATAG TGTGCCACTG GAGATCAGTG GACAACTGTC TCAGGAACTA GTTCTCTCCT
GCCACCTTGT GGGATGCAGG ATGACCTTAG ATCCTACCTG CTGGCTAGCC TACCTTTCCC
ATCTTTTATG GATCTTTCTT GTCAGAAACG AATGACTGTG ATGTTACTGA GGTTGGTTGG
CATGGAGCAT GCAATGTAGG TGTTATATTG TGAAGGTAGA GGTGTTTAGC AGTCACTCCG
GCACTTATCT GAGACCCAAA TAATTCTGGC CAACCTACCT GAAGAGCAAC CTCTGGCCTA
TACTATCTTG TTATAAAAGG AAATCAGATT AAAGCCAGGA AGACATTCTC TAGGCTAACT
AGGAAGACTT CTCTCTCCTG CCCTCTACAC TGAAACATTC CTCTTTAAAA AAATTATGTG
TCTTTGGAAT TATTATTATT AGTATTAGTA GTAGTATTTT GGTTGCTATT GTTGCACATG
TTAAGCAATG AGCTAACATT TCCCATCATG CCTACCATCA TATAAATGTT AGGTTTGAGT
TCGGGGCTAA GCAGACCACA TTTCCATGTC ATCTTACAGG TACTTGCAGG CCCACCATAG
AACAGTTGTA GAACTCTGAC AAACTTCCAG AGCTCCGCTG AACTTCAGAA AATACTGAAT
CCCAGAGGTC CCACAAGTCT CTATCCTCCT CTCTGCAGAA CCCTCAGAGC TGATTCTGGG
CTTCCTGGTG CTACACGGAA ATATAAAACA ACCCGTCTGA ATGTATCAGA CAAATTCCCT
AGATAACCAG ACGGTAGAGA GCAATGGCTA AGTCACATCC CCCAGGGATG GGGGAACCTC

        PacI
       ---------
ACTAATTAAT TAAATGGTAA ATGTGGTAGG TACATGTACG AACTGACATC AAAGAAGATG
CATGCTGTCT AACCAGAAAC TTGCCTGGTG CTACTGTCTC TAGTATGATA AATTTAAATC
```

Figure 10D

```
TGACAGTTAG GAGTAACCAA TATAATTCTG TACTTTCTTC AGTCTCTAGA GCAGAGACTC
TCAACCTGTG GTTTGAGACC CCCTTTGGAG CTTGCATATC AGAGATTTTG CATAGCCAAT
ATTTACACTA TTATTTGTAA CTTGTAACAA CTTTACAGTT ATGAAGTAGC AACAAAATAA
CTTTATGGTT GCGGGGGGGG GGGGGTCACC ACAACATGAG GAACTGTATT AAAGAGTTGC
ACACGGTATT AGGAAGGGTG AGACCCCGTG CTATAGAGGA AAGGCTGGAA AGTCAAATGG
TTTTTACATG AGTTGTAGTG CTGCCTAAGA GGAGTGTTTA GCAATCTTCT GGGTAAGACT
CAAAGAGACC CAGAAGCCTA GCAATACCCG TGGTAGAGGT GTCACCTCCT ACTCAAATGG
GTTGTAAAAC ACCTTTCAAA CTGCTCTCCT CTCTTCTGGA TTACTGGCAA GCCTTGGTCC
CTGTCTGTGG TTGTCAGACT CAGGCTGTGT CAATCACTTA GCGGATGGAT AACTGGCTAC
AGAGCTCCAC CAGAAGGTCA GCTTCCGTAT GTCTGGGGTG AGGACCAGGA GCCTGTGGGT
TGAATCGTTC CCAAGGGATA AAAGTACTGT GGACGCTGAG TGCACTCGGA TGCTTTGTGG
TTGCGTTTGT CTGTTGAGCT TACAGCAGTC CATGCATGAG ACATTGGAAA CAAAGAGCTG
CAGCCTTCCT CTGGGATCTA AGGGGAAAGA ATAGACTGCA GCCTAGAGTC TTGGTTCTCA
GAAATGAACT GTTTAAGGTT TCTCACGTAA GCTAGGAAGG CAGAGCCCAG CTAGGTTTCA
TTTAATTATG ATGGGATTCC TTATTTAGGT ACCAAAGAAG GAAAAGGCTC CTCTGGTGAT
GGTTAGTGAC AGCTTCTTTT CTGGGTCCCA GCCAATCAAG GGGGCATCTG AGTTCTACAG
ACTTTAAGTG CGTGATTTTT CTATTTCAAA GTAAACACGA GATATTCTAG CCCAGCATTT
GAGTCACTAT GTTCAAATAT ATTCTAAAAT GCCCAGATCA CACCAGCGAG ATTAAGTAAG
TTGGCAGTTC ACAGATACAT CAACATGAAT CTATCTTTCT TTCTTTCTTT CTTTCTTTCT
TTCTTTCTTT CTTTCTTTCT TTCTTTCTTT CATTCATTAT CTATTTATCT GCCTACCTAT
CATCTATCTA CCTACCTAGC TATCTAGCTA TGTCTATCTT CCAGTCCGTA AATCTATCTC
TGTGCATCTA TCTATCTATC TATCTATCTA TCTATCTATC TATCTATCTA TCTATCTATC
TATCTATCTT TCATTATCTA TTTATCTGTC TACCTATCAT CTATCTACCT ACCTAGCTAT
CTAGCTATGT CTATCTTCCA GTCTGTAAAT CTATCTCTGT GCATCTATCT ATCTATCTAT
CTATCTATCT CTATCATTTA TCAACCATCT TTCTATCCAT CATCCATCTC TCTCTCTCTC
ATATCTCTCT CATATATATA CATATGCATA TGTATACGAG ATCCTTTCTC CTGAGGAAGG
AGTCAAGATT CACAGTCCTA GGCAAGTGCT GTACTCCTGG GCAATAGGGC AGCCTTTGCT
TTTATTCTTA GTCTTTCTCT TGATGCCAAC CAAATGCGTA TCAGCTTCAA TTCTGCTCTC
TTCAGCTGTG TACCTGCAGC TGTTTCCTGG AGAAAATGAC ACCATCAACC ATTTCTCTCC
AGGACAAAGG CTGGGTGGGC TGGGAGGGGT GCGGGTGGAG TGAGTGCAGG ACAGGAGACC
AAAGGCTGAA CCAGATGACG GTCTTGCCCA GAACGCCTCC ACCCGTCCAG AACTACAGCC
GCTGCTCCCC ATGCAGTTTG ACTCTGAAAG TATAACAACG TAAAAACAGA ATTCTAGGCC
TTTAGGCCCA GGCTTGAGAA TGTGGCCTTT GTAAAGGTAT GCTAATCATA AAAGAGATAG
CGACATTCCT CTACCCACCC GCTTCCTGGG TTCAAAGAGT GCTCATTCAA AGAAAGTCAC
CCTGAGGATT ACCAGAACCT GCAATGCAAA TGTGCTATTG TTAGAGGCTC TTAGAAGCTG
TCTTGAGAGT TAACACTTAC CAGGTATTCC TTGTGACTCT TGTAACTTTA CACTTCCTTG
TGACTCTTAA CTGGTATCTT TGGTATCTTC CAACAATGCC CTCCCCACTT CCTTGAGTTT
CGGTTTCTTC CTTTAAATAC CCCCTTACCC AGCTACTCGG GGTGCCACGG TCCTCTACCC

                                   Eco  III
                                   -------
CTGCGTGGTG TATGACCATG GGCCCGAGAG CGCTTTTGAA TAAAAATCCT CTTGCAATTT
GCAGCAAGAC CCGTTTCTTG TGGGTGATTT TGGGGTGTCG CCTCTCCTGA GTCAGAACGT
GGGGGAGCCC TCACATTGTG GGTCTTTCAA CTCGAGGCTT CCAGTTCGTC CTGAGTTACT
TTAGAGTCAA AGAAAGAAAA GGGAAGATTA AATGAAGTTC AAAACCTCCA CAGCGTATGG
CAAGATGTTG GAAATACTAG GGATGCAAGT CAACCAGGAG TTTTAGCCCA GAATCACAGG
AGATCTAGAT GTTCATGACC CCGACCCCCA CCCCCTAAAC CCAACTTCCA CCCCCACCCC
CGCCACCCCA ACAGCAACAA GAAGTGACAC GTGGGTCTCC TGTTGATCTC TGCCTCTCCA
GAGCTGGACT TTCAAGTGTC CTGGCTTATT ACTGTCCCTC TGTGTTGTCA CATTTGCTCA
GGGTCAGCTC TCCTCTCCTC TTCCCGGTTC TTAGCATAAC GCTTATTCCT CTCTGTAGTC
TCACAGCCTG ATCTTTACCC CCAGTGAGCT GAGAAACTGG ATCCATGGGA AGCTAAGCCC

                                              BsrBI
                                             -------
CTCACTTCTG CATCTGCCAG GATGCATCTC CTTCTCCGCT CCTCTTCTTC CTCATGCCTT
GCTGCCTCTG TGTCCCCCGC CCCCCTCTTC TTCCCAGTGT TCCTCTTCCA GCAGCAGACC
ATGAACTCCA TACTGCTCTT ATCCCTAGAA GACCTCTGTA AAAGCAGGTT CCCTTTCATT
GATGTCTCTC CTAAAAAGTC CATCACATCG CCCCACACTT CCCCAGCACA GGACCATTTG
```

Figure 10E

```
GACTTAGCTT CCAAGATCCT GTTCTCAGTT TCAATAGCAA AGGTGTAGAG AAACTGGCAT
GAACCTCTTT GTGTTGCTTT GTCTCTAAGG GATGGCCTTC TTTTAACTCT TGCCTTGGAC

                                                      BbeI
                                                     -------
                                                      KasI
                                                     -------
                                                      EheI
                                                     -------
                                                      NarI
                                                     -------
TGGGCTCAGT GGGCCCTCCT CAATCCGTGC GAATCAGAGG ACAGATGGGC GCCGTAGAGT
CGGCGAGTGA CAAACAGAAA CGGCGGCGAG TGTGTAGAAT CTGAGTGTAT TTTTACAAAG
TGAACACCAG TCTTATATAG TACAGAAAAT AAAGGGATAG GATGTCACAG CAGGCAAAGT
ACATTGAAGT TACCTGACAC AAAACAAAGT AATGACTTCA AAAGGACTTT CAGGAACCAG
GTAATAGTTA CAGTAAAGAT AAAACAGCTC TGCTTAGGGT CAGCTAAGGA CAGGTAAGGA
TTTCACACCC TACTCACAAT TTGTGCTACT CCTTTGAACC TTGTGAAAGC TAGCACCAGG
GAGTTCTGCT CTAGCAGACC TTCTCATGAA TAATGCAATA CCACAAACCC CCTATTTCCT
AGGACTTGAT AAATTCTTTC ATGAGTATAA CTTGGCTGTT CTTTTAAGTA TCTGTGGGGA
AGCTCCATTT GTCAGAAGAA TTCACCAACT TGCTTCTAAT ATGCAATGTA GCCTGCTATA
CCTGGCTGTA CAAGATTCCT GTCTCAGTGG GATTCTCTAA CTCTTTCATG GTAAACCCAC
CTATTAGCTA GGCCATGGTG TATTCCCTTG TTTGGGTTAG ACTTGGCTAC TGTCCTAAGT
CCTAAGTAAT CACCCTGCAG ACCAGCCCTG AGCTATTCTA GCTCTGTTCT TTGTAATGCC
TAATTAGTTT CACCATTTCT ACTAGAAGTA AATTTGAATG TTACTGAATA GGTAACATTC
TCACTGAATT TCTACTGAAT TCCAAGCTCG TCGGCTTCAA GAATTTTCTA GGACGTTGGA
ACACTGGTGG AGGCTTACCT ATGTTAAAAT TCAACCTTTA AAGGCACTTA TAATAAAACA
ATACTAAAAG AGAGCATGTG CATCCATATA CCAGACTAAC ACGGGGATAG GGTATGAGTA
TACAGGTTAT GAGAATGCCA AGGTTCTAGG AGGTTGAGTT TCCTTGAAAC TCTTTGCCTC
CATGAGTGCT TCCAGGCCTC TCGGCCTGTC AAGCAGACTT CACTGGAGTG GGTATAGCAA

         ClaI
        -------
ACTCTGTATC GATGCCCTTG ATCTTCTGAT TATTGCCTTT CATAAAATTA TCTTACATTT
TGACTGCCAT ATGGTCTTTC TCTATGGCTC ATTGAACCCC GAGAGTGTTC TTTTTATCTG
TGCCAGTGGA GTCAGTTCCT GTGCCTACCT TGTAAATATC CCCAGTGTGC TAATCTAGGC
TTTCCTTGGT GTTTCGGTTT GCATAACCTT AAGAAGCACT GGCCACACTC TGTGCTTTCT
CTTTTAGTGA CTTCTGAGTC ACACTTCTTG GCACATCATT TGAATTTCTA CAGAAGTGGA
AGCTGAATTG ATTGAGAACT AGCTTTTTGC CTACTCTGAT CTCTACTTGC ATTTCCTGTA
TGTGCTCTGA CCCATTGCAT GGCTGCTCTG TTCATAAACA CGGTCATGGT TTTCACCCCA
TTTCTTCATA ACTCAGAGGC CCTATGGGCT CCATCCATGT TTTGTGTACA ATTTTTTATT
TTTTTATTTT ATTTTATTTT GGTTTTTCGA GACAGGGTTT CTCTGTGTAG TCCTGGCTGT
CCTGGAACTC ACTCTGTAGA CCAGGCTGGC CTCCAACTCA GAAATCTGCC TGCCTCTGCC

                            BssHII
                            ------
TCCCAAGTGC TGGGATTAAA GGCGCGCTTG ACCACCGCCC TGCTTCCTGT ACATTTTCTG
AAAGGCCAAA TCACCTTCTT TTGCAACGCA TACAGCTTTC CGCTGAGATC GCCCAGGTCT
GTTGCTTGTT TTCAGAAGCT GACACAGACA ATGGGAGTGG AGGAGTTTCA GTACAAGTCG

                                                  MunI
                                                 ------
ATTCATAGAG ATAGATGCAG CCTAACTGGG CAGCCCAAGC CTTCAATTGC AGCTATGCTG
GAGGCTGAAG CAGGGGGACC TCAAGGTCAA CGGCAGCCTG AGAAACTCAC AGAGACTGTC
TCAAAATAAA AAATATATAT ATAAAATAAA ACTATACACT TGACTCTTAT CTACAATGTA
GTACGTGGGA GGAGGCTGAG GTCGAAGACT GTGAGTTTGA TCAGCCTGGG CTACATAGCA
AACATCTGCC TCAAAAGACT GGAAATACAA AACTAAAAGT GAAGAAAAGA GAAGCCACGT
TCAGACTTCA AAACCAGGCT CCATTGTCAT GTTTCTGGGA CTATTCCCTA TCCATTCCCA
GAGTAGACTG ACAGAATTAG CCCCCACCCC TTCTCGAGCG TCTCAAGCCC ACACCTGAGC
ATAGAGCATG TGATTTACAT GGGGATCCAT TTTTCCTCCA CTTCTCCCCT CCCGTGTTAT
```

Figure 10F

```
ATGATCGGAG CCTAAGGTCT GTAACCTTGT CAGCTGCGTG TCCGTGTGGC TAGTCTAGCC
TAAGGCCAGG CTTGCCGGAA GTTCTCTTGG CACACCTGGG TTGACTTGAC TTCTCCTGAA
GAGCATTCCA AAGCTGCTCT CTGTAAAATT CTCAGCTGTT TCTATTTGAA ATGCAGGAAG
                                                            >>.>
CACTTCCAGA TCATTACAAG CCTTGGATGG AAATTGCCCT CAGACTTCCT CACTTAATCG
>..........................Exon 2 ............................>
AGAACCGCCA GCTCCGAGCT CACGTGTACA GGGTACGTCG ATTTGTTCTT TGCTTCATGC
>............Exon 2 ............>>
TCCTCCTCTC CCCACCCGTT CCGTCTCCAT ATCCCTTTCC TTCTCAGCTC TCTGGGAGTG
AAACGGTTGA CCTGGCAGTG GGAACCGACT GTCACCACTG AGGCTTTCAG CAAACCTGTC
TTCCTTAGTG CGCACAAACA GCACCTGAGA TGTGTCAAGT CCTCATCGTG TTTGTGCAAA
AGACGATGAT AGATGAGACT TGAAAATAAA TTCTGGGGAA ACGAGGAAGA CACACATTGG
AGATTGGTGG GAGCCGCTTG GCCTGCTTCT GTAAAAGCCT GCCTGTCAGG CAGAGTCAAG
CCAGGGGCTG AATGTTCTGT TAATCTCGGA GGAAGGAACA CGGAGGAATA GAGGCCTCTG

                   BsaBI
                -----------
GATGAGTACA GATATCAGAT ATACATCAGC CGCTGTCTCT GCTGGCTTGT GACTTTGCTT
CCCGTGATAC TACAGAGTAT ATAAAGCCTT AGAGAATTAA ACTCAAGGCT GCTGCAGCAC
TGACTGGATA GCCTTCCCGG TTTTTAAGCT TTGTTTCTGA GTCTTCTTTT CCATCTCTCC
TACAATCCTC ACTCACCCCT CAGAAGACCT GTTCAACTTT GTACTGGCAG GACCGGCAGG
GGAGATGCTC AGTGGACTTG TCCCAAGTCA CGTGGTCACT GCTCTGCTTC CTCTGGGCAG
GTACCTTGAC CTTAGTGTGT TACATACTAG TCAGATCAAA TGTCTTTCTG ATTTTTAAAC
TCAGAGTCAG TCTTGGCTAT GTAGAAGAAG TGAAATCCAT AGACACCACA TTAGAATCTG

                      BtrI
                     ------
CATGCACCTA AGTATATGAC GCACGTCTGT GACAGAGCGA GCAATTTCCC TCCAAAAGGA
ATAAGAAAAA TATGACCCCC ACAGAAGACA TTCTTCCATT CAGGAATTTT ATAGTAAGTG
TGAAACGGAG AGTTGGCCTC AGAATCTTGC TTCCTTCTTT GAGAAATGGA TGAAGTTCTC
ATTTAATGGT TGTGAGCATC AATGGCTTTT GTAAGGACCC TCCCCCTCCT CATCTTCATC
TGTCACAAGC ACACCACAAG ATGTCAGATG TTCAAGCAAG GCGCTCCACC CTCCAGGACC
TTCTTTGCTG ATGCTTAATG TCCAATTATG AGTTGATTTT TAAAAATATT CATTGAATGA
TCCTTATAGC ATATTCAGAA ATCAGGACAG GCAGCTGGCC TTGGTAATAC TCTAGATAAC
CCCCCCTCTG AACCCCCCAC TGAGGCTGAA GACCATGTAA GAAAGTGCAA CTAAAGGAGT
TAATTGTTGC ACAAAACTCA CACAAAGCCT CACAAAGGTA GTTTGTACAC GCTGTTGACA
CATTACACTA ACAAAAACAT CGAGGGGAAA AAAGATGGGA AACAGTAGAA GATAATAATT
AATGGTGACC TATGGCCTAC ACACACACAC ACACACACAC ACACACACAC ACACACACAC
ACACACACAT GCACACATCA CCACACACGT GTGTATGCAT ATGCTCACAC ATGTACAAAC
ATATATCACC ACATATGTGA CACACACATA CACACTCATA TCACCACACA CATGTGTACA
CACATGCACA CACACACATC ACCACACACA TATGCATACA TAGGAACATA TAGTACACAC
ATATCACCAC ATAGATGGCA CACACACACT CACATACCAT CACATATATG CATGCATATA
GACATGCACA CACATGCCCC CCCACACAAA CACACATATA TGTACAAAAC CTATAGTGAA
CACACTACCC TGAGTCAAGC TATGAGTTTT AAGAACATAC ATACTGTCCC CCAAAACTCG
TCACAAGGTG TTTTGTCCTC AAAGGGAAAG CTCCTCTCTA TCTAACTGAT GTCTAGAACC
CACAAATATG TTAGTTGTGT ACCAGAGGGG ACGGCGGGTG GTTAGTTAGT AGAGGGTCTC
CCACAAACCC ATGTGTCTGT CTTCATCCAC CATCTTTTAC ACTGATGAAT GAGTTACTAG
CCAGTAACTC ATGCAGTGAG GCAAAGCAGT TATGATGGTT CTGGGTGACA AGCAAGTGAA
GAGTATTGGT GAGGATACTA AGCACGCGCA TGCACTTTGC TACAACTAGT CTGTCATGTG
AACTGCCATC TCACAGAAAC ATTCATACAA AAAAAAGTGC AGATGAATAT GCAAAGCTGT
TTGCTGTAGC CACTTTCATA GCAACGGTAA ATACAATGTA ACAGAAATAC AATGTAACAG
AAGACAGGAG AGCAGAAGGA GAAGCCCATG AATCTCCATT CACAAATATA TCTGTTACAT
AAATGAAAAG GGACAGATAT TAAGTGGTCA CGTAGGCACC TGCCTGTATC CTTCCGCCAC

                                                 NruI
                                                ------
GCTACACATC TTTGCTCTGT AGTTTACTGA GCATTAGGAA GTTCGCGACA GTATCTATAT
GCAGAATTAT TGAACCTCTA CTTCAACAAC ATGTGCATGT GAGCTTAATA TTTATAGATG
ATAGAGGTAG AAATAGACAT ATTTACTATC TGACAGAGTC CTAACATGTA GCCCAGGATG
```

Figure 10G

GCTTTGAATT AGACATCTTC CTATCTCCGC CTCCAGAGTG CTGGTATCAG TCTTCATAAA
GACTTCTATA TGAAAACAAA TGTCCTGTTT TCTATGTATT CGCCTTCGTG TCAAACTATA
CTTTTCAAGA AGTTCAAGAA GTGATGTCCA CAAGAACCTG ATGTGTGTCA GAAACACTCA
GCTCCCCAGT GAAGTTGGCA GGAGGGCTCG CCTGGTTCAG AGAAGCCTTG CGTGCTCCCT
GAGTTCTGAG AGGAGAGTAT CGAGGTTAAT TCTCCCAGGT TAAATACGCA ATCAAATAAT
GTCAGGGAGA TGACGGGTGT GTGTCGTCCT CCCAGACCAT CTGTGACTGT TTGAGTAAGC
AAAAGGATTG ACTAAAAAGC TATCATTTCC TTTTCAGTCC CTACAGTCAC TTTTGAATCA
CAGGTATGTT TAGGAGGTGA GGCCAACAAT CCTGAAATGT GCAGGGACTC TCCAGAAAGC
AGTCATCATC CCCTGGACCT CGTTCCTTTA CACCGAGGCG TCCTGGCTTG TAGGTGGCCT
TCTTCAACAA CTGAGGGGTG ACAAGGACAA AGCCTGAGAA GACACAGCCT AGATTGTGAA
GACTTTGAAA GATTTTTATA CTGACTGCAT GCTAAAATAT CTTTTATACG TTGACTCAAC
AAAGTACATT ATCAGAACTA ATTTTACTTC TTGTTTGCCT TAAAAAAAAA AAAGTGGCTG
CTGAAA

GTATACGAGA TCCTTTCTCC TGAGGAAGGA GTCAAGATTC ACAGTCCTAG GCAAGTGCTG
TACTCCTGGG CAATAGGGCA GCCTTTGCTT TTATTCTTAG TCTTTCTCTT GATGCCAACC
AAATGCGTAT CAGCTTCAAT TCTGCTCTCT TCAGCTGTGT ACCTGCAGCT GTTTCCTGGA
GAAAATGACA CCATCAACCA TTTCTCTCCA GGACAAAGGC TGGGTGGGCT GGGAGGGGTG
CGGGTGGAGT GAGTGCAGGA CAGGAGACCA AAGGCTGAAC CAGATGACGG TCTTGCCCAG
AACGCCTCCA CCCGTCCAGA ACTACAGCCG CTGCTCCCCA TGCAGTTTGA CTCTGAAAGT
ATAACAACGT AAAAACAGAA TTCTAGGCCT TTAGGCCCAG GCTTGAGAAT GTGGCCTTTG
TAAAGGTATG CTAATCATAA AAGAGATAGC GACATTCCTC TACCCACCCG CTTCCTGGGT
TCAAAGAGTG CTCATTCAAA GAAAGTCACC CTGAGGATTA CCAGAACCTG CAATGCAAAT
GTGCTATTGT TAGAGGCTCT TAGAAGCTGT CTTGAGAGTT AACACTTACC AGGTATTCCT
TGTGACTCTT GTAACTTTAC ACTTCCTTGT GACTCTTAAC TGGTATCTTT GGTATCTTCC
AACAATGCCC TCCCCACTTC CTTGAGTTTC GGTTTCTTCC TTTAAATACC CCCTTACCCA
GCTACTCGGG GTGCCACGGT CCTCTACCCC TGCGTGGTGT ATGACCATGG GCCCGAGAGC
GCTTTTGAAT AAAAATCCTC TTGCAATTTG CAGCAAGACC CGTTTCTTGT GGGTGATTTT
GGGGTGTCGC CTCTCCTGAG TCAGAACGTG GGGGAGCCCT CACATTGTGG GTCTTTCAAC
TCGAGGCTTC CAGTTCGTCC TGAGTTACTT TAGAGTCAAA GAAAGAAAAG GGAAGATTAA
ATGAAGTTCA AAACCTCCAC AGCGTATGGC AAGATGTTGG AAATACTAGG GATGCAAGTC
AACCAGGAGT TTTAGCCCAG AATCACAGGA GATCTAGATG TTCATGACCC CGACCCCCAC
CCCCTAAACC CAACTTCCAC CCCCACCCCC GCCACCCCAA CAGCAACAAG AAGTGACACG
TGGGTCTCCT GTTGATCTCT GCCTCTCCAG AGCTGGACTT TCAAGTGTCC TGGCTTATTA
CTGTCCCTCT GTGTTGTCAC ATTTGCTCAG GGTCAGCTCT CCTCTCCTCT TCCCGGTTCT
TAGCATAACG CTTATTCCTC TCTGTAGTCT CACAGCCTGA TCTTTACCCC CAGTGAGCTG
AGAAACTGGA TCCATGGGAA GCTAAGCCCC TCACTTCTGC ATCTGCCAGG ATGCATCTCC
TTCTCCGCTC CTCTTCTTCC TCATGCCTTG CTGCCTCTGT GTCCCCCGCC CCCCTCTTCT
TCCCAGTGTT CCTCTTCCAG CAGCAGACCA TGAACTCCAT ACTGCTCTTA TCCCTAGAAG
ACCTCTGTAA AAGCAGGTTC CCTTTCATTG ATGTCTCTCC TAAAAAGTCC ATCACATCGC
CCCACACTTC CCCAGCACAG GACCATTTGG ACTTAGCTTC CAAGATCCTG TTCTCAGTTT
CAATAGCAAA GGTGTAGAGA AACTGGCATG AACCTCTTTG TGTTGCTTTG TCTCTAAGGG
ATGGCCTTCT TTTAACTCTT GCCTTGGACT GGGCTCAGTG GGCCCTCCTC AATCCGTGCG
AATCAGAGGA CAGATGGGCG CCGTAGAGTC GGCGAGTGAC AAACAGAAAC GGCGGCGAGT
GTGTAGAATC TGAGTGTATT TTTACAAAGT GAACACCAGT CTTATATAGT ACAGAAAATA
AAGGGATAGG ATGTCACAGC AGGCAAAGTA CATTGAAGTT ACCTGACACA AAACAAAGTA
ATGACTTCAA AAGGACTTTC AGGAACCAGG TAATAGTTAC AGTAAAGATA AAACAGCTCT
GCTTAGGGTC AGCTAAGGAC AGGTAAGGAT TTCACACCCT ACTCACAATT TGTGCTACTC
CTTTGAACCT TGTGAAAGCT AGCACCAGGG AGTTCTGCTC TAGCAGACCT TCTCATGAAT
AATGCAATAC CACAAACCCC CTATTTCCTA GGACTTGATA AATTCTTTCA TGAGTATAAC
TTGGCTGTTC TTTTAAGTAT CTGTGGGGAA GCTCCATTTG TCAGAAGAAT TCACCAACTT
GCTTCTAATA TGCAATGTAG CCTGCTATAC CTGGCTGTAC AAGATTCCTG TCTCAGTGGG
ATTCTCTAAC TCTTTCATGG TAAACCCACC TATTAGCTAG GCCATGGTGT ATTCCCTTGT
TTGGGTTAGA CTTGGCTACT GTCCTAAGTC CTAAGTAATC ACCCTGCAGA CCAGCCCTGA
GCTATTCTAG CTCTGTTCTT TGTAATGCCT AATTAGTTTC ACCATTTCTA CTAGAAGTAA
ATTTGAATGT TACTGAATAG GTAACATTCT CACTGAATTT CTACTGAATT CCAAGCTCGT
CGGCTTCAAG AATTTTCTAG GACGTTGGAA CACTGGTGGA GGCTTACCTA TGTTAAAATT
CAACCTTTAA AGGCACTTAT AATAAAACAA TACTAAAAGA GAGCATGTGC ATCCATATAC

Figure 10H

```
CAGACTAACA CGGGGATAGG GTATGAGTAT ACAGGTTATG AGAATGCCAA GGTTCTAGGA
GGTTGAGTTT CCTTGAAACT CTTTGCCTCC ATGAGTGCTT CCAGGCCTCT CGGCCTGTCA

                                            ClaI
                                           -------
AGCAGACTTC ACTGGAGTGG GTATAGCAAA CTCTGTATCG ATGCCCTTGA TCTTCTGATT
ATTGCCTTTC ATAAAATTAT CTTACATTTT GACTGCCATA TGGTCTTTCT CTATGGCTCA
TTGAACCCCG AGAGTGTTCT TTTTATCTGT GCCAGTGGAG TCAGTTCCTG TGCCTACCTT
GTAAATATCC CCAGTGTGCT AATCTAGGCT TTCCTTGGTG TTTCGGTTTG CATAACCTTA
AGAAGCACTG GCCACACTCT GTGCTTTCTC TTTTAGTGAC TTCTGAGTCA CACTTCTTGG
CACATCATTT GAATTTCTAC AGAAGTGGAA GCTGAATTGA TTGAGAACTA GCTTTTTGCC
TACTCTGATC TCTACTTGCA TTTCCTGTAT GTGCTCTGAC CCATTGCATG GCTGCTCTGT
TCATAAACAC GGTCATGGTT TTCACCCCAT TTCTTCATAA CTCAGAGGCC CTATGGGCTC
CATCCATGTT TTGTGTACAA TTTTTTATTT TTTTATTTTA TTTTATTTTG GTTTTTCGAG
ACAGGGTTTC TCTGTGTAGT CCTGGCTGTC CTGGAACTCA CTCTGTAGAC CAGGCTGGCC
TCCAACTCAG AAATCTGCCT GCCTCTGCCT CCCAAGTGCT GGGATTAAAG GCGCGCTTGA
CCACCGCCCT GCTTCCTGTA CATTTTCTGA AAGGCCAAAT CACCTTCTTT TGCAACGCAT
ACAGCTTTCC GCTGAGATCG CCCAGGTCTG TTGCTTGTTT TCAGAAGCTG ACACAGACAA
TGGGAGTGGA GGAGTTTCAG TACAAGTCGA TTCATAGAGA TAGATGCAGC CTAACTGGGC
AGCCCAAGCC TTCAATTGCA GCTATGCTGG AGGCTGAAGC AGGGGGACCT CAAGGTCAAC
GGCAGCCTGA GAAACTCACA GAGACTGTCT CAAAATAAAA AATATATATA TAAAATAAAA
CTATACACTT GACTCTTATC TACAATGTAG TACGTGGGAG GAGGCTGAGG TCGAAGACTG
TGAGTTTGAT CAGCCTGGGC TACATAGCAA ACATCTGCCT CAAAAGACTG GAAATACAAA
ACTAAAAGTG AAGAAAAGAG AAGCCACGTT CAGACTTCAA AACCAGGCTC CATTGTCATG
TTTCTGGGAC TATTCCCTAT CCATTCCCAG AGTAGACTGA CAGAATTAGC CCCCACCCCT
TCTCGAGCGT CTCAAGCCCA CACCTGAGCA TAGAGCATGT GATTTACATG GGGATCCATT
TTTCCTCCAC TTCTCCCCTC CCGTGTTATA TGATCGGAGC CTAAGGTCTG TAACCTTGTC
AGCTGCGTGT CCGTGTGGCT AGTCTAGCCT AAGGCCAGGC TTGCCGGAAG TTCTCTTGGC
ACACCTGGGT TGACTTGACT TCTCCTGAAG AGCATTCCAA AGCTGCTCTC TGTAAAATTC
TCAGCTGTTT CTATTTGAAA TGCAGGAAGC ACTTCCAGAT CATTACAAGC CTTGGATGGA
AATTGCCCTC AGACTTCCTC ACTTAATCGA GAACCGCCAG CTCCGAGCTC ACGTGTACAG
GGTACGTCGA TTTGTTCTTT GCTTCATGCT CCTCCTCTCC CCACCCGTTC CGTCTCCATA
TCCCTTTCCT TCTCAGCTCT CTGGGAGTGA AACGGTTGAC CTGGCAGTGG GAACCGACTG
TCACCACTGA GGCTTTCAGC AAACCTGTCT TCCTTAGTGC GCACAAACAG CACCTGAGAT
GTGTCAAGTC CTCATCGTGT TTGTGCAAAA GACGATGATA GATGAGACTT GAAAATAAAT
TCTGGGGAAA CGAGGAAGAC ACACATTGGA GATTGGTGGG AGCCGCTTGG CCTGCTTCTG
TAAAAGCCTG CCTGTCAGGC AGAGTCAAGC CAGGGGCTGA ATGTTCTGTT AATCTCGGAG
GAAGGAACAC GGAGGAATAG AGGCCTCTGG ATGAGTACAG ATATCAGATA TACATCAGCC
GCTGTCTCTG CTGGCTTGTG ACTTTGCTTC CCGTGATACT ACAGAGTATA TAAAGCCTTA
GAGAATTAAA CTCAAGGCTG CTGCAGCACT GACTGGATAG CCTTCCCGGT TTTTAAGCTT
TGTTTCTGAG TCTTCTTTTC CATCTCTCCT ACAATCCTCA CTCACCCCTC AGAAGACCTG
TTCAACTTTG TACTGGCAGG ACCGGCAGGG GAGATGCTCA GTGGACTTGT CCCAAGTCAC
GTGGTCACTG CTCTGCTTCC TCTGGGCAGG TACCTTGACC TTAGTGTGTT ACATACTAGT
CAGATCAAAT GTCTTTCTGA TTTTTAAACT CAGAGTCAGT CTTGGCTATG TAGAAGAAGT
GAAATCCATA GACACCACAT TAGAATCTGC ATGCACCTAA GTATATGACG CACGTCTGTG
ACAGAGCGAG CAATTTCCCT CCAAAAGGAA TAAGAAAAAT ATGACCCCCA CAGAAGACAT
TCTTCCATTC AGGAATTTTA TAGTAAGTGT GAAACGGAGA GTTGGCCTCA GAATCTTGCT
TCCTTCTTTG AGAAATGGAT GAAGTTCTCA TTTAATGGTT GTGAGCATCA ATGGCTTTTG
TAAGGACCCT CCCCCTCCTC ATCTTCATCT GTCACAAGCA CACCACAAGA TGTCAGATGT
TCAAGCAAGG CGCTCCACCC TCCAGGACCT TCTTTGCTGA TGCTTAATGT CCAATTATGA
GTTGATTTTT AAAAATATTC ATTGAATGAT CCTTATAGCA TATTCAGAAA TCAGGACAGG
CAGCTGGCCT TGGTAATACT CTAGATAACC CCCCCTCTGA ACCCCCCACT GAGGCTGAAG
ACCATGTAAG AAAGTGCAAC TAAAGGAGTT AATTGTTGCA CAAAACTCAC ACAAAGCCTC
ACAAAGGTAG TTTGTACACG CTGTTGACAC ATTACACTAA CAAAAACATC GAGGGGAAAA
AAGATGGGAA ACAGTAGAAG ATAATAATTA ATGGTGACCT ATGGCCTACA CACACACACA
CACACACACA CACACACACA CACACACACA CACACACATG CACACATCAC CACACACGTG
TGTATGCATA TGCTCACACA TGTACAAACA TATATCACCA CATATGTGAC ACACACATAC
ACACTCATAT CACCACACAC ATGTGTACAC ACATGCACAC ACACACATCA CCACACACAT
ATGCATACAT AGGAACATAT AGTACACACA TATCACCACA TAGATGGCAC ACACACACTC
```

Figure 10I

```
ACATACCATC ACATATATGC ATGCATATAG ACATGCACAC ACATGCCCCC CCACACAAAC
ACACATATAT GTACAAAACC TATAGTGAAC ACACTACCCT GAGTCAAGCT ATGAGTTTTA
AGAACATACA TACTGTCCCC CAAAACTCGT CACAAGGTGT TTTGTCCTCA AAGGGAAAGC
TCCTCTCTAT CTAACTGATG TCTAGAACCC ACAAATATGT TAGTTGTGTA CCAGAGGGGA
CGGCGGGTGG TTAGTTAGTA GAGGGTCTCC CACAAACCCA TGTGTCTGTC TTCATCCACC
ATCTTTTACA CTGATGAATG AGTTACTAGC CAGTAACTCA TGCAGTGAGG CAAAGCAGTT
ATGATGGTTC TGGGTGACAA GCAAGTGAAG AGTATTGGTG AGGATACTAA GCACGCGCAT
GCACTTTGCT ACAACTAGTC TGTCATGTGA ACTGCCATCT CACAGAAACA TTCATACAAA
AAAAAGTGCA GATGAATATG CAAAGCTGTT TGCTGTAGCC ACTTTCATAG CAACGGTAAA
TACAATGTAA CAGAAATACA ATGTAACAGA AGACAGGAGA GCAGAAGGAG AAGCCCATGA
ATCTCCATTC ACAAATATAT CTGTTACATA AATGAAAAGG GACAGATATT AAGTGGTCAC
GTAGGCACCT GCCTGTATCC TTCCGCCACG CTACACATCT TTGCTCTGTA GTTTACTGAG

               NruI
               ------
CATTAGGAAG TTCGCGACAG TATCTATATG CAGAATTATT GAACCTCTAC TTCAACAACA
TGTGCATGTG AGCTTAATAT TTATAGATGA TAGAGGTAGA AATAGACATA TTTACTATCT
GACAGAGTCC TAACATGTAG CCCAGGATGG CTTTGAATTA GACATCTTCC TATCTCCGCC
TCCAGAGTGC TGGTATCAGT CTTCATAAAG ACTTCTATAT GAAAACAAAT GTCCTGTTTT
CTATGTATTC GCCTTCGTGT CAAACTATAC TTTTCAAGAA GTTCAAGAAG TGATGTCCAC
AAGAACCTGA TGTGTGTCAG AAACACTCAG CTCCCCAGTG AAGTTGGCAG GAGGGCTCGC
CTGGTTCAGA GAAGCCTTGC GTGCTCCCTG AGTTCTGAGA GGAGAGTATC GAGGTTAATT
CTCCCAGGTT AAATACGCAA TCAAATAATG TCAGGGAGAT GACGGGTGTG TGTCGTCCTC
CCAGACCATC TGTGACTGTT TGAGTAAGCA AAAGGATTGA CTAAAAAGCT ATCATTTCCT
TTTCAGTCCC TACAGTCACT TTTGAATCAC AGGTATGTTT AGGAGGTGAG GCCAACAATC
CTGAAATGTG CAGGGACTCT CCAGAAAGCA GTCATCATCC CCTGGACCTC GTTCCTTTAC
ACCGAGGCGT CCTGGCTTGT AGGTGGCCTT CTTCAACAAC TGAGGGGTGA CAAGGACAAA
GCCTGAGAAG ACACAGCCTA GATTGTGAAG ACTTTGAAAG ATTTTTATAC TGACTGCATG
CTAAAATATC TTTTATACGT TGACTCAACA AAGTACATTA TCAGAACTAA TTTTACTTCT
TGTTTGCCTT AAAAAAAAAA AAGTGGCTGC TGAAAATTTT CAAAGAAAAC CCGTGACTCA
TTGCATGATT CTCGTGATCG GGGCTGTGGT CAATCCGCAC GCAGAACTGC TTCAATCCTT
CTTGATTCTG TGACCTCCGA GACGAAAATT CCTCTTTGGT TCCCGCAGGG GTGTTTAGCC
TCAAATTTCA AGTCATCCTC TTCCCCCTAG CGGCCGGAGG AGGAAGGGCT CTGCATACCC
CAGCCCGCCC CTAGGAAGCC AATGTCCCCA GCGTTTTACA AGTGGCGCAT GCCCTCTGAG
GCAAGCCTGC GGAGCAAAGG GAGTGAAGTG GTGGCGAGAG CTGAAGAGAT GAGCAATGAG
CCGGTGGCAG CCAGGCAGGA CAGGGAAGCT GGCGTGGTCG GATTGTGTAC TGATGCTGTT
TTTCAGGGTG GCCCTTTCCG TGTCACCAGG AGCTGTGGTT TCCAATGGGG ATGAAGTGGG
GACAGAGCTG GGTGGAAAGC CCCGCCACCT CATCTGGCTG GGCTGTGGTT GTTTGAGCAT
CAGAGCAAGC TTTATATCCA GCCGATCCAT GGTTTTTGTG GGGGACTTTA CATCCCTAAC
CTCACTGGGT CTCGCTGCGT TCAAAATTTT AATACAGTTA CAGGGTTCGA GAAGCTGAGG
GCTTCCAGGT ATTACATATC TATTAATGCT GCTGTGCGGG CTTGGAGGGA AGAACTTATC
TCGCCCTCAA TGCTTACTCT GTGATCCTCA AAGCAATAGA TGGAGACCAG TGTATGGCAC
AAACTGGGCA CATCCTAGGC CATGGACCCC AGGACCTGGC ACCTCCTCTA CTGCATTCCT
CTAAGAGCTG GTTTAAGTGG GTGTGCATGA AGCTAATAGC TGCAATAGCT GTGGGACCCT
CAAGTCACGG GTCCTGGTCC TGGTCCTCCA CCGTTGTTTT TTGTTTTTTG GTTTTTGTTT
TTGTTTTTTG TTTTTTGTTT TTTTTTTTTG GCTTTGTTTT GTTTTGTTTT GTTTTGTTTT
GTTTTGTTTT GTTTTTTCAG CTGCTAATCC TTTTAATCTC TTGACTAGAT GCCTCTCCTG
                                                  >>...EX 3 ...>
GACTGCAGAT TCCTAAAGAG TTACCGTGAG CAGCGCCTGG CACACATGGC GCTGGCCGCT
>..........................EX 3 ...........................>
ATCACCATGG GATTCGTCTG GCAGGAGGGG GAAGGCCAAC CCCAAAAGGT GAGGAGCAAG
>.....................EX3  ......................>>
GAGAAATCAG GCTCTGCTGA GGTCCCTGCA CCTGGAATTA CGACACCAGC TCCAGGTTCC
GTTGCCTAGT TTCCAAAAAT CAGCGGAAGG CAAGAAAAGA GGGTTAGATT TTTTTTTTCC
ATTTTTCTTT TCTTTTCTTT TTCTTTTTTT TTTTCTTTTG CTACGGAGCT GATTTTCTTT
TAGACTAATG TCCACTTTCA AAGACTCCAG CCATTCCAAT AATATGTGAG GAGCTTCCTT
AGGCCCCAAG GACTCAGAAA ACACCCTGCA GAATTTTATA CTTCTAAATA CATTGGTTAT
TATGACTTTC ATAATTACCC CATTGTACAG ACATCTGGGG ATCTGTCCCA AGCTCAAGGC
CTTTGTCCCA GAGCAGCCTG GGACAGTTGG GGAAAGCCAG TTTCTGAGTC CACTGAAGTA
```

Figure 10J

```
GCCATCCTTC TCCAGTACAA CTTGGACACT TCCTTATTTC CTTATTCTGC CCAGCTGATT
GCTGCTTTAG TTTATTAACC CTTTGTCTAA CTCCCTCCAA TAACTTTCTA GTTTCAGTCT
GTCCCTCAGA GCACAAACCC TTTCTTCTCT ACCCCTGGAG GAAACTAATA TTTCTTTTGA
GTCATGGTCT TACAAAGCAG CCCCAAACCA GTCTAGAACC TGCTCTCTTG TCCAAGTTGT
TCTCCAACCT GTGATCTTCT TGCCCCGGCC TTCCAAATGC TGGCATTGCA GTCACTCCAG
GCACGTGACA CCCTGTGCAG TTATGCTCCC AGTCAGTGTT GGGATGGAAT CCAGGACCTG
TGTGTGCCGA GTGAATACTT TATCACTCAA CAGGACCTCC GTTTTCTCTT CCTTTCCCCT
AAGTTTCTCT TTCCCAGAAA TCAAGGTGTT GACATCATTC CAGAATGCGT GAGAAGCCCG
AGGTGTGCTT CAAGGGCTCA TCTTACCCAC AGAGAAACAC TTGAGACCAA GAAGCAAGGA
CAGCACAGAG CTCCTGTTCC TTCAGACTCT AACACGATAC CATATTGTAT CTCATCTAAA
GGACTCGAGT GTCTAGGGTC TGCTGTTGGA AAGTTTAAAA CCCAGGCCAG TGTGACAGAA
CCTCCTGATG AGTTCTGCTG CATAGGCCCC CTAAACCAAT CTCCTGAATT ATGAGTTAGA
GAGGAGGAAG CAATGTCCAG CCCCCAAGGC CATCCCAGGC TCATCACCCC TCATTTTGGA
AGTCTTCCCT GACCTTCCCA GTGGAAGTGT CTGACTCACA TCTTCCCATT CTCCCCAGCC
CTGACTTCTG TGGATGCTTG GCAGAGCTCT ACGCCCTGTA AGCTGTAACT GTTCTCTACC
TAAAGCACAC CTCTTCCCTA ACTCGGAGGA AGAAAGAATG GCAGACACAG ATCTTTAGAC
TCTTCAGTCC TGGGCTGGGG AGACGACTCA GTGGGTAAAT TGGGAGCAAG CAGGCCGAGA
CACTGAAGCT AAGATTCCCA CAACCAGTGA GAAAACTGGC ACAGGCAGCA GGGAGCAAGA
GAGACCCTGT CTCAAACATG GTGGAAGGTG TCAACTGGAG TCCACACATT CCCCTTGGCA
TGAATGTGCC TACATTTACG TCTGTCTGTC TGTCTGTCTG TCTGTCTCTC TGTGTCTCTC
TCACACACAC ACACAAACAG ACAGAGAGAG ACAGAGACAG GGAGAAATTT CTATTTTAGA
AGGAAAATGA TTGGGGGGAG GGGAACATAA AAATGTTCTT TTGTTGTTGT TGTTTGTTTG
TTTGTTTGTT TGTTTTTACA CCTCTACCAG TTTGGCCTTT CCATGGCCGG GACCTCATGG
ACCTGAGCAT CTGCTCTGGA CTGTGGACAG ATAGAGATCT GTACTCAAGG GACACCCCAA
ACGTTAGTGG GTGAAAGGGT AGGGCTATGG ACAGGGGCTT TGCAACCTGA AGGGTCCTTG
GGGCGTGAGC GAGAAGCTTG TGTTTCAGTG GAGTCCTGAA CGGGTGTTAG GAGGTTGATG
TCATACCCCA GGTCGGAACC CTAGCAAATC ATGTTAAGAG TCAGAAGAGA CAAAGGACGG
TCAAGGGGGG GGGGGTCTGT CATTGAGTGA CTACCTGACG TTATGGGGCT TGACTCATGA
GGTGACACAA ACATCAGTTC TGCAAGCTGA AATTCTCTGT CCTCTTTATC CTTTCTGGGG
TGCGCTCTCT ATCTCTCTGT CTCTGTCTCT GTCTGTCTGT CTGTCTGTCT GTCTGTCTGT
CTTTCTCCTA TCCCCCCCTC TCTCACACAC ACATATACAC ACCTCTGTTT TTTTTTATCT
ATGTACATCT TTACTTCTAT TTTGCATCAT GTGCATCTAG CCTTGTATCT ATATATAGAT
CATATATATT ATTTATAATC TATCATCCAT CTAGAAAGCA CTTTACCTTG ATAGTTCTTA
GTCTTTGATT TACATTAAAC ATTTTGGTGA AATAATTCTC TTTCTCCTTT TCTCCTCCTT
CTCCTCCTCC TTCTTTCTCC TCCTCTTCCT TCTCCTCCTT TTTCTCCTGT CTCCTCTTCT
TCCTCCTCTT CCTCCTCCTC CTCTTTCTCC TGTCTCCTCT TCTTCCTCCT CTTCCTGGTA
CAGTTTCCAG AGGTTCTGTT TATCATGTGC ACAGTGTATT CCATCTCTGG GTTTTGCATC
TCTTGAAATG TGTTCTCATA ACCAGCATTC TCACCGGGTC TCTCCCATGA AGCATGTGTA
GGGTATAGGT GTGGAACATT CAGAGAATTC GTGCTTGGTC TCCAGGTCGC TTATCACAGG
CAACCGTGAT GATTTTCTCT GCCAGTAGAA TATACTAATT GTCTGGATTC CTGTCCTAAA
GGTGCTGCCA AGATCTCTTG CCATTCCTTT TGTTGAGGTA TCCAGGAACT TGGGACTCCC
 >>.........................eX4  ..........................>
GCCTATCCTG GTCCACTCTG ACCTGGTGCT GACAAACTGG ACCAAAAGGA ACCCAGAAGG
>.........................eX 4 ..........................>>
GTAAGGAGGG AAAGGATTCC TTCAGTTAGC AGCAGATTGA GAAAAGACTC AGGACTTGAA
CTGTCTTCGC AGAAAAGACT CAGGGTCTTA GGGCTGTTTT ATAGTGAGCT GTGTGCTCCC
ATTCATTTAA TTTAGGGTTC CAATAAAAGG GAATGCACAC ATTTAAACCT GAGACATTTC
TTCTTCCTGG GCTCTCAGGC ACACTGGCTT GCTGCTTCCA GTGCCCATCT GGATCTCTTA
ATCAGACTGT CAGCCTCCAG CTGTAATAAT GACACTGGGC TGTTTTTTCT CAGCATGTTC
TGTGTTCCAT TCAAGTCAGG TTAGGATGGG GTGTCTGGAG GTGATCTCTA TGGTTCTGAA
TAAATGATTT CACGTGGGTG GAATTCTGAT TCACACCATC TATTCTGTCT AGTTTACACC
ATTCCACACT TGTCCCGGGC ACAAAAGCAT CTGTTTATTG ACTTTTCAAC AAACAACCAA

                                                 SalI
                                                ------
TCCATGGAAA CTTCATTTTC ACAGTTGAAT CTGTCTCAGG CGGTCGACGC AAGGCAGCAT
TTACTTTTGT TATAAATTAA AACAGCAAAC AAGAAGTCCA GGCTGGACAT AAAGGGACCT
TTCTTGGCAT GCTGGTTGTA GGTAGCCATG CAGTGCTGAA AGAGATGGTT GAGATCTGCT
GTGGACCCTT TCAAGAGACC CTTCCTTTTA AGAACTGGGG AGGGCTCCTC TTATCTACAG
```

Figure 10K

```
TCTGCTGAGC CTTAGAACTT CATGCTTTCT GGGATGATGA TGTCATATGA CGATGATGTC
ATATGATAAT GTTACATGAT GTCATACGAT GTTGATGTTG TATGGTGATG CTATATGATG
AATGGTATCA TGATGGCATC ATATGTTGAT GATAAGCTTG TTTGTGACTG GGGACTGAAT
GAACCTTCAC CTGTGAGGCA GGAGCTCCAC CCCTGTTTTC TATCCCCAGC CCTCTCTTCA
GCGTTTATTT AGATACAGTT TCTCTCACAA TGCCAAAGCT GACCTGAAAT TCACACTGTA
GCATAAGCAG TCCCTGACTT GGTGATCCTT AGACCTCCTC AGCCCCTTGA CTATCTGCCA
CTAACAGCAT GCACAACCAG GCCTGACTTG GTCTTTGACC AATTATACAG CAACGAAAAA
CTGATCTGCA TTGAAAGCTA CTAAATCTAA CTTAGAATTG GAGTAGGTGA GATGATAAAT
ATGTGCGCCT GGACTATTGT GAAGCTGGGT TTGTGATTCA AGGGAAATTG GGAGATGAAG
TCTTAAGGGA GGTGACAGGG TTGAAAACAA CCCCAGGAAA TGAATGTCCC ATCAAGTGAG
GTACAGCACC CAGAGATGCA AATGCAAGCC TGGAGCTCCC CCACCGTATT TCTTCTGAGC
CATCATCTTC CTGAGTCTTT TAAGATGTCT ACCCAGGGCT TATTAAGTGC TTTGAAGAAA
TGAAAGAAAT AGAAGCAACA CCCCCCCCCA CCTCCACCCC CACCACCCAA ACAGTTCAGT
ATTGAGACAA AGTAGCTCTT AACACAAGTC AAAGAACAAC ATAAACAGTA TCTTCAGAAC
TCCAGGGGGA ACAGCAGGGA AAGCATGGTG CCTGACCAGA CGCTGATGTA AGGCCACTCC
TAACAGGTGG GTAGGATTAG AGTAACTGAA GTGGGGTCTG CACCGAGAGG CAGCTAGAGA
GAGGCAAGCA AGAATGTGTA CATACACAGA CACACGACAC GGGCTGTCAA GTGAGATCTG
GTTTCTGCTG TCACCCAGTG GCTCACTGTC CATCCTAGGT GGGTCCTGAT CCGTACATGT
GCCAGGGCAT TGCAGATGAG TGTGGGAGCC TGGGTACCCG GGACCTCAAG AATTATATCT
GGTTACTAAC TAAGTTGTTT TCTTTTTTTT TTTCTTTTTC TCTTTGTTAT CACCAATAAC
TATTATGCGA CCAGACCGTT GGAAATCAGG TAAGATGTGC CTTTAGAACC ACCCACTGTT
                     >>.....Ex5 .....>>
ACCTTTAAAG GCTTGTGATA AAGCAAGAGG GTGGCATGGT CAGCTGTATG GATGGAATAG

                                 BstBI
                                -------
CATCAGCTGT CTATGAACTC CTGAAAATTC GAAGTGCATT AAAAAGTCAA TAGTCCAAGC
AGTAGCTCTG ATGGAGGTTA GCTTCTAGGG GTGCAGGGAT TAATTTTTCT TAACCACATT
TTCCTGTATG TCCATGATTT AAAAAAAAAG TGTAGTGTAA GAAAAGAAAC CGTGGCTCTG
TGAAAACTGG CAGAGATTTC TTATTTCTGA AGAACATCAG CAAAAGGCCA GAAACAGGCA
GGTCACAGTG ACAGAAGGGT CCCTTTGTAA TCCCTTCTTA CCTGATGGGC TGGAGCCCTT
GTGAGTAGGT GTGGTCTATA GTCATAGGCT CCACCTTCCC CGGGGAGCAG AGCTAGCAGA
GGAGCCAGAG TCACATCCTG CGCTCTCTCT CTCTCTCTCT CTCACACACA CACACACACA
CACACACACA CACACACACA CACACACCCT CCTCAGCTCT GTGGAGCATA CAGGTGGATG
GCAAATATTC CCCAGGCTAA CACCTCTGCT GGACCGAGGA GATGTGTGAC TCACCTCCGC
TTTGCTGTTT TGAGGTTTGA GGCTGGGCTT TGCTTATGTT TGAGATGCTG GGGACAACGC
AGATGTGTGC AGATACTCAT CTGGGTTCTG TATCAGGTCA GATTTGGCTC TGATGGGAAG
ACAGGACAGC AGCAGGTTGA TTAGAAATGA CCTCCCTCCT CCTCCTCCTC CTCTTCTTCT
TCTTCTTCTT CTTCTTCTTC TTCTTCTTCT TCTTCTTCTT CTTCTTCTTC TTCTTCTTCT
TCTTCTTCTT CTTCTTCTTC TTCTTCTTCT TCTTCTTCTT CTTCTTCCAC ACATTATATT
CTATCCACAG TTTCTCCTCC CCTACTCCTC CCAGTCCTCC TCTCACTTCT CCTTTCCCTA
GATCTACTCC TACTTTTCCA AAAAAAAAAA AAAAAAAAAG CAAGCCTCCT GGAGCTATCC
TCCAAACCTG CCCTGACATA GTTACAAACA GCAGCCCCTC ATTTCAAGGC TTGATGAGGC
AACCCACTAG GAGGACAAGG ATCCAAAGAG CAGGCAAGAG TCAGAGACAC TCTTCCACTC
CCACTATTCG GAGTTCCACA GGAACACGAA ACTACACACA ACCACAACAT ATGAGCAGAC
GGCGTAGGTC ACGCCGATGC AGGTTCTGTG ATTGTCACTT CAGTCTCTGT GAGCCCCCAT
GAGGTCGGCT TGTTTTTGAT TCCGTGGGCT GTGTTCTCCT GGCGTTCTCA ACCCCTCTGA
CTACTGTAGT CTGTCCTGCC CCTCTTCTGT AGCGTTCCTG GAGCTCCACC TACTGTTTGG
ATGTGGTAAT GACAGGCTTC CGGCCGCGGT TCTGTGGCAG CAATTCATCC TTGGGTTAGA
ACTCTAGTCA GGCACGCAGG CACACACCCA TAATGGTCAT AGTTCTCAGG TCATAGGAAT
TTGGCTCTAA CTGATCTGAT TTTCTTCTTT TCTTGGTCTC TTCCTCCAGT AACCTGGAAA
                                                      >>..Ex 6 ...>
CCATCATCTC ATTTCCGGGG GGAGAGAGCC TGCGGGGCTT CATCCTAGTG ACAGTCTTGG
>............................Ex6  .............................>
TGGAGAAGGC AGCAGTGCCC GGCCTTAAGG TATCTTCTTA CTCACCCGGC CCTCTCCCTA
>...........Ex 6 ............>>
TGGTGGTTTT CCCCACGTGG ACAGACAGAG GCCTCCTCCT CCTAGGGTTG ACGATGAAGA
GACATATCTG AGTTCTAGCC TGTGGTGTCA GTGCCCTTTT AGCCTGGAGT GAACCGACTT
CTCCGTCTAC ACCCAGGTAC CACACGCTGA GTGCAACAGA CACCCACTGC GCTAGCTGTT
```

Figure 10L

```
CCACTTCATG GACCTGCAGA AGCTAGAGAC TCAGAGGTCA AAAAGAAAAA GACTGTTTTA
TGGAAAGGCA GATAAAGGCA TATCCATGCA TATCTGTAGG GATGCCAGAG TAGAAACGAC
TGTGATATGG GAAACCCAGA AGGAATGAGA AAGCACTTGT GTTGAGGCTC TTGATGTCAC
AATTTACGCT CCAGAGATAT TCCAGTAGTG TGGGCTACTC CGTGGCGATC TGCATCCCGC
GGGGGTTTTA ATAAAAAAAG TTACTTCGTA GCACCTCAAC TGAGAACGTG GATCTTATTC
CTAGGCCCTG GTTCAGGGAA TGGAGGCCAT TCGGCAACAC AGTCAGGACA CCCTGCTAGA
     >>.........................Ex 7 .........................>
AGCCCTGCAG CAGCTGAGAC TCTCCATCCA GGATATCACC AGAGCCTTGG CCCAAATGCA
>...........................Ex7  ............................>
TGGTAAGATA CTGGAGCAGC GTCTCCAGTG GCCTGGACTT GGGCAGGTCC TACGTGGATG
>
ATGGTGGTCC ATCTCTCCAC AAGATGGCGC TAGTGTTCTA TATTTAGCGT AAAGCGTCCC
AGTCAGAGAA TTGTTTTTTT TTTTTTTTTT CCAGTCGGCA GAAATATTTT TTTTAGAATC
GTTCTTTATA GTTTCGTGTG GTTGGGGTAG CTTCCCTTCT CCAGGGTCCA GATACGACTT
TGGCATGCTG ATCTCTTAAC GAAGCCTGGG AGATTGGATG GGCCACAAGG GGGAATGTTG
GTTATACAGG TTAGGCTTGC TGGCGGGCAG GGCTGTCCCG TGGGGGCGTC TGTAAGGCCC
TCAAGAGTCA TTTGCTTTTC CTCTCTGACC ATGTTACAAA TCCAGAAAGA CCCTCATGAT
CCGCTGAAGG AGGTCCAAGG ACCCGGAGAG CTCCCCAATT AGACTCCTTC CAAGCCATCT
GATCCTGAGA CAAATTTCTC TATGTGATGA CTTTTTTTCA AGGTTTTAGA ACTAGCTGTA
TTCACACACG TGGCGAAGGA GAAGGACACG TGTCCACACT TTTCAAAGAT GGCAACAGTA
TCCTCCACAC CATCCCATGA AGCCCTTAGT GTGGGCACGC CCTCCTCGCG TCTCCGGATG
GAGGATATGT CCTAGCCTCT GAAATACTTG CAGTCAAAAT AGGGCACTAG TGAGGACAGT
TTAGTCCAGT GTTCAGTGAG TTTTCATCCC CAGTGCTGAG ACGCCATGGG AAGGGCAGTG
TTCCTGGCAC ACAAGCAGGC TGACAACAGC CTATCAGACA AGGACACACA GCTAAGGGGC
TAAGGGCTGT CCGATGATCC TTACTCAGTG TGGCACTGAG GAGCGGAAAC AGGTCGCCAC
CACCTTGCCT CTATGCAGGC ACCTTGCCAG CAGTACAGAG TCAGCAAGGG GAGGCGCTTG
CCATACTATA ACAGTTACCA TAAAAGAGAG ATCATGTTTA AAAACAAAAT CAAACGCTGG
AAGGCATAGG CAGGGGGTCG TGCGTGTCCT TGGCACGGAG TCTGGTCTGC ATGGGCTGCT
TTTGTGTGTG ATTCGGAGAG CGTGGCTGGG TGGATTCCCT CCACTCCCAA ACCCCCAACT
AGATTTTACC AATAACCAAT CACTGTGTTT AGAGCCCAGC TTCAGCAAGC ATCCTGGGTT
TCCCTCAGGA CATCCTTCCT TCCTTCCCAG GCATGTAGGG TCCATAAAAA TGCCTTTTGT
GGACATCGGA GGCCCACTGC GCTGCAAGCC AAGTCCCCAG GCCTTTGCCC AGCCTAACAT
AGTTGTACAA ATAAGGTTTG TTTAATGCCA TTTGCAAGCA AAAATTCTCC ACTGAAATAT
GGTCCCAGGA CTGTTCGTTA GCTCTTACGT AAGAAATGAT TCAGGAAGAA CAGGTTGGAA
ATATAATCCC CCATACTTTC TTCTGAAGTT TTCATCTTTT ATACTTAAGT TCTTAACTCA
TCTATTATCA TCTGCATGTG CTATGAGATA GCAAATGAAT TCAATCTCCC TCCTGCAGGT
AACGTCCACA TGGTCTCTCC TTAGATTTGG TTAAAGGAGC AGGTTTTCTG CAGTGGCCTC
TGCTCTTTCC CTTTGGGTGT GTCTCTCTGC TCTGGGTGCC CTTAGTCTCT TCTTCCTTTT
CTCTGGAAAG TTCCCTCCCT GGTTTTCTTC TTCAGGGGCC TGGCTGTCTC TCGGGAGCCT
TAGCAGGAAC CACAAAAAGA AACACAGAAA CCAAACCCTC AAATGGGGAC TTAGTTCAAG
CTGCATTAAG TATGGATTCT GATATTATAC GTGCAATTTC TATCACGGAA GGAAAACAGG
CCAAGGGACT AGAAGCAGCA TAAAATATTA GTCTGCATTT CCTGATGACT TCTTCTAACT
CATTTGTCAC GGTTGCTGGG TGGTCTTTAT CTGTCACATG CTGTCTTGAC ACAAGGACCC
CTCTCTGGTA TACACCTTCA TTGGCTACCC AGTTTCCCTG TGTGAGAATT CAGCATCTGC
ATTTTCATGC GCAGGGTTCC TTGAGTTTCT TCCAAAGGAA GGCAGATGCC TAAATTCTGT
TTTATCAACA GTTATTTGCA TTCTTGTGTG TGGCAAACAT ATCTTTTTAT TTAGTTACTT
CTGCGCTGTT TGTTTCTACC TTATAGAATG AAGCAGGTAT TTAAACGTTA ACTTGGAATC
CAGCCCTTTG GTAAACTACA TTCTTATTGA TTACAGCAGT AATTTACAGG GTTAGCTGGG
TTTCTATGCA GAGATCTTGT TGCTGAGACG TATGCTTAGG TTCATCATTA ATTATCTTTT
TCTTAAAAAT AATTTTCCCT CACATAATAT ATCCTTCCCC TTTTCTCCCC TCAGTTTCTG
CCCACCTTCC CTCCCACCCA GATCCACCAC CTTCTGTGTT ACACTGGAAA ACCAACAGGC
TTCTAAGGGG TAATAATAAA ATAAAGTAAG AGAAAACAAA AACTATCATG TTAAGTTGGA
CAAGACAAAC AAACAGATGG AAAGGAGCCT GGGAAAAGGC ACATGCACAC ACACACACAC
ACACACACAC ACACACACAC ACACCAAGAG ACAAAAAGTC AGCTGTAAGT GCACATGCAT
CCACACACTC AGGATACCAC AAAACACTAA ACCAGAAATC ATAGCATATA TACAAAGGAC
CTGTAGGGTA AAAAAAAAAA AAAAAAAAAA AAAAAAAAGT GTGTGTGTGT GTGTGTGTGT
GTGTGTGTGT GTGTGATAGA GAGAGAGAGA GAGAGATGGG GGGAGGGAGA GGGAGAGGGA
GAGGGGGAGG GAGGAGAAGG AGAGGGAGAG GAAGAGAGGG AGGAGAGGGA GAGAGAGGGA
GAGAGGGAGA GGGGGAGGGA GGAGAGGAAG AGAGGGAGAG AGGGAGAGGG AGGAGAGAGA
```

Figure 10M

```
GGGAGAGAGG GAGAGGGGGA GGGAGGAGAA GGAGAGAGAG AGGGAGGAGA GGAGGGAGGG
GGAGGGGAGG GGGAGGGGAG GGGGAGGGGA GGGGGAGGGG GAGGGGAGGA GAAACAGACA
GAGAGAGACA GACACAGAGA TATGAGACAG AGAGACAGAT CCTGTCTAGA GCGCTGGCGA
GTTTTATGTG AACTCAGCAC ATATAGATCA TCTAAGAGGA GAGCTCCTCA GTGCAGAAGA
GGCCCTCATA GGGCAGGGCT GTGCTCAAGC CTGTGGGGCA TTTTCTCAAT TAGTGATTGA
TGGGGAGGAC CCAGCCCATC GTGAGTGGAG CCACCCCTGG GCTGGTGGTC CAGGTTTCTA
TAAGAGAGCA GGCTGAGCAA CCTATGAGGA TCAAGCCAGT AAGCAGCGTC CCTCCACGGT
CTCTGCATCA GCTCCTGCCT CCAGGTGCCA TCCCTGTTGG CGTTCCTGTC CTGAGTTCCC
TTGATTAGGA AGCACGGTGT GGAAGCATAC GATGGATAAA TGCTTTGTTC CTCAAGTTGC
TTGGGTCAGG TTGGTTTTTC ACAGTGATAG CAACCGTAAC CAAGACAACA TGTGAAGTAA
AATAAAAGAT AAAAATAAGA TACACTCTTG AAAATGGAGG GGGTAGGAGT CCCTGTTGTG
ACATTATGAG AGACTGAACC TCCAAAGACG CCATTTTGTT TGACTTCTGC TGCAGTCTAG
TACTGGACAT GCAGCCTGCC CTAAGAGGTG GGGACCAGGA GGGGAAGCAG TGATCGGGAT
GTAAAATGAA TGAATGAATG AGTGAATGAA TGAATGAATG AATGAGGAAA AGAGTATTTT
GTTTTCCCAG TGAGACTTCC TTAGAGAAAA CTAAATTTTT GTTTTCAAGT AGCTGTCACT
TGGAGGCAGC ATCTGGGTGA GGGGTGAGTG CTGTGTCCAC TTCTCCTCTC AGCTGTGACC
CTGTGTGGTG CAGACCAGTG AAGGCCCTGT GCATGCTGTG ACTTCGTTGA CCTTGGTGAT
TGAAAAGGCC TTGTTTTCTT GGTGTCCTTC ACCCCCCCCC CTCCGCCCAA CTCTTAATTT
CTGTTTTCTC TACCATATGG TTCTCTGAGC ACTGAGGGGT GGGGGTTGAT GGAAACATCA
AAGACCATTT ATAACTGAGT GTTCCGAGGT CTCTCACTCT CTGCACACTG TCTGGCTGTG
GGTCTCTGCG TTTGTTTCCT ATCTGCTGCA GGAGGAAGCC TGTCCGATGG TGACGGAGCA
AGGCGCTGAT CTCTGAGAAC AGCAGAACAT CATCAAGAGT CATTGTGTTG CGTTTTGTTT
TTTGTTTTTG TTTTTGTTTT TGTTTTAAAG TCAATATTAT TTAGTTTCCC CCCTAGGTCC
CTGGGCTATC TAGTTTCAGC ATGTTGGTCA CCCAATCAAT TTCGGGCATG AATTCCATTG
TGTGGAGTGG GACTTAAGTC AAATCAGACG TAGCTTAGAT GCTTCTATAA ACTTTGTACA
ACTGCACTAG CATATCTTGC AAACAGGATA CCATTGTAGA ACAAAGGGTC TGTAACTGGC
TATACACACA CACACACACA CACACACACA CACACACACA CACACATATA TATTATATTA
TATATTATAT ATTAATTATA TATTTATGAA TCACTTTTGA AATATCTACC GAATATATTT
TATATTTTCA TGTAAATTCT ATTGTATCTA TCAACATGAT CACTTGGCTT TACCTTTAAT
TCATTAAGTT GTGTAAAATA GTAATGCATA CACATCCCAC TTCCTATGCA AAGGGCTGGA
TACTGTACTT AACAATCTGG AGAAGAAGCA AACATCAAAG TCTAGGGGAG GTCCCAGAAA
ACAGGCTAGC TCAGGGGACA CAGTCGCACT GGTGAAGACC ACCCTGGGGA GTCACACCCT
AGAAGGGAGA GTGTAACCAT ACTAAGGAAT CACACTTGAG GAGAGGTGAG ACTACCCTGG
GGAGTCACAC CTGAGAAGAG AGGGTGTGAC CACCCTAGGG AGTCAGGAAG TCACACTGGT
GAAGAGTGGG GGTGTGGGAT GACCACACTG AGGAGTCACA CTTGAGGAAG GGGGGTGGCC
ACACTGAGGA GTGTCTGAAA GCATTGAGAC TGTACATCTC AGGTTATCAG GGCTTCAGAG
AAAACAGACA GGGAGAAGAG ACAAGAACTG GATTCTGTGC GCAAAGGGGG AAAAGCAAGC
AGATGTGAAG GGTGTGCTGT TAGAGTTTAT CTAAAGATGT TTCTTTCAGA AATAAAGAGA
TATAAGCTTT AATTTGGATG AAATAAATGT GGTCTAATTT CCCAGAATGT AGAGGAACTC
ACTAATGTAG CAAGATTGGC CTTTCAAAGC AGACCAAAGA CATTGAGAAT TAAGATAGCT
ATGATGGCGT GCTTCCTTAG GTGGAAGTCC TATATGGAAT CCCATACTCC CCAAATGTGA
CTGGTCGGTG CAGCTTGGGG CTAACAGCTC TGTTGACCTG TGGTGACCCC TGGAAAGCCC
TGTGGGATAG AGGAACTCCT GGATGTCAGT CATTTGCTCT GCCTCTCTTG TGAAAGCAGT
GGTCTCTGTT TTTCTTCCTT CTCTCGGCTT TTCATATTCT CTTGCATATC CTGTTTATTT
GAAATGTTTC TTAAAGGATG CTCATAGTCT CTCACTGGTG GTGGTGAAGT ACAAAACCCT
GCTGCACAGC AAACAGAGGG GGCCAGCATA CGGAACGGAT TAACAGCCCT ATGAGAGCCC
ACACGCTCTT CAAGAGAACA TTCCATCTGT ATTTGCTGCT GCCATTCTGG GATCTGCATA
CATCAGATAG GAGTGGGAAG CCCTGGGAAA ACAGCAGGGT CCAAGGCACA TGTGGCCAAT
TGCTTTTTGC CCATGGTAAA GTTCACATTT GATTGCTTTC CAGATTATGT GGACCCAGAC
                                             >>......Ex 8 ......>
ATATTTTACT CGGTCATCCG GATCTTCCTC TCTGGGTAAG TACAGCTTAA TTGGTTTCCT
>>>
GCTTGAGACC TGTAGAGTTC CCCAGATTTG TGCGAGGATA GACAGACAGA AGCTTCCTAA
AGTAAGAAGT ATAGCAAGTG ACTCAAGCTG GCAAAGTCAC CACCTGGGTC CACTCTAGGA
GGCTGGACCC CAAAATGATC AGAAGGAAAA AGGTTCCAAC AAAGCTGGGA ACTTAAATCC
AAAAGGGGCA AAAGGGGCTG TCTTCAGCCA CCAGAGGGAG ACCATGGACC CTCTGAGAAC
CCCAACGTGA TGACAGGGGC AAAAATTAAA GATGGGAGAG AGAGTGGGCA GGGAGAATGT
GGGGAGGAGA TGGAAGGGAG GGTAGAGGAG AGAAAGGCTG GAAAATGATA GCTACTTCTT
TGTCCCTTGA CCTTTGAGGA CATAGCATTC AGGGGACCCA TCAGGAGACA AGAGTCCAGG
```

Figure 10N

```
CTGTCACCTG ACAGAACCAT CAATGCCTTG ATCTTAGACT CCCTCTCCTT CGGAGTTGTG
AGAAATACAG TATGATTGAT CATATTCAGC TTGAAGTATT TTGCTATGGT GGTAGCAGGT
ACCCTTGATT TGTCTCACGG CTATACACTT CTCTGTCTGT CTGCCTACCT CGCATGCCCC
CTGCTCCATC AAGCACATGT CTTCACCCAG TTATTTCTAC CTTGACAAGC TTTAACCAGG
TTGCCATCCA ATTCACCAAC CAACAGAGCC GATTCACTTT TGAACGTTTG TGTCTTGTTG
ACTTGGAGGT GCCGGTGATG TTATCAGAAG CATCCAAGCT GTGCCTGGAG ACAGCAAGAG
ACAGACCAGA TGCCGAATCT ATTACCATTA CTGCCAAGTC CCATTGGGAG AAAAACTAAA
GTGTGCATTC GTGCATGTGT GCGTGTACGT GTGTGTCTAG AACTGAAAAT TTTATTTCCT
TGCAAGTATC AGACTAGAGT TTTCCTGGCC TGCTAGGTCC TCTGTTGCCT CTCCCCACCA
TGTCCCCAAT TTGACTCCTG ACACAGCACT GGCACTTGGC ATTTTTCTAG AATTACACAT
TTTCCTGACT TTTCTCTTGA CTACCGCCAG AGGAAATTTC TCTTAAAGGG GCTCCTGTGG
CTGTGCTCAA TCTAGTCGGA TGAGTCAGGG AAATTCCCAC ATTAAAGCTA AACTGATCAG
TGGCCTTAAT CCCATCTGAA AAGTCCTCCT GCCCTGTCCT GTAATAAATA TATCATGGTG
ACCGGAACAG CTCATAGTAT TAAGAGTCCT AGGAATTCGG TTGGGAACCT TGGGGAGCTA
TTTTTAGAAT CCTACCCTCC AGTGTCTTTC AAAGGAATCA TTTCTACTTC CTCTTGGCAG
AGACTTGATA AGAACCAGAA GGGGACTTTG TTTGCATCGA CATAAGTTCC GGGCAATGAC
ACTTTTTATC TGGTATTTGG CATAAAGGCC ATCCCTCCAC TTCAAATGCT GAGACTGTTT
ACTGTGCCGC TAAGTGGCTG TACAAGATCC TAAATGTAGC TGTAGTTTCA ACAAACATCT
GGATTGTTGG GAGTTTCCAG TAGACTTCTC TTTAAAATGT CAGCCTCGCT ATTCTGCATC
TATCCCGAGT TTCTCATTTG CTTCTTTAAA ACACAGTTTT ATTTAAGAGT GGATGTCCTG
TGGAAATGAG ATGTATTCCC TCCAGTTCCC AGCCTGCCAC AGGTCTCAGA GAGGCCAGGA
ACGGGGGGCC CAGGTTGCTC TGCAGGGAAA CATCGCCTCA TTTTGTTGTC TGCCTTAACT
TCCTCTTTCC TTGGGATTGC TAGAAATACA CCAGGAGCAG GTCTAAAAAT AACCTTACCG
TAGAGGCCAG AATTTAAAAT GGCCCCATCC CTTTACAAAT GGCAGCTCAG CCCTACGTGG
AGAAAGAGGC AGTTGTGTCT CCCAGTGCTG CTGGGGATGG GGTGTAAAAA CAGACCCAAG
TTCATCATCT GACCTCAGAG CTGGTGTTTT CTGCATCACC TTCAGCATGG CTGGCTTTGG

                                            AatII
                                            ------
CGAAGGCACT CCAGCGAGTG CTGAAAGGAC ATTGCCTGAT GACGTCCTTG GCATTTGTCA
TATCTGATAG ATCCCTTAAG CACTGGTTGT GCCGTACTGA CTGAAAAGCT CTTTTCTCCT
TCCTTCCTTC CTTCCTTCCT TCCTTCCTTC CTTCCTTCCT TCCTTCCAAT AAATCCATAG
TGAGGGCCTA CCACATCCTA GACACCACTG TATGTGCTGG AAACAGCAGT AAAGAAAAGC
AGTCACGTGG TCCTTGTGGA GCCTGTGACT TCAGGATGGG GAGAAGGTAT TGACAAAGCA
AACCGAATCA AAGCAAACAT CCAACAGTAT GTGTTACAAC TAGAGGCTGC ATGAAGCAAT
GCCGGGTAGG ATGCGGGCTG CTAGGGAGGG ACCACTGGGT GTGGTGGCTC AGGTATCTTG
TTTACTGATA TCTAGAAATA CCACATCCCC AGTGATATGG GAACAGATGT CACAGGCAAT
GGAGTGCTCT CAGAAGAAGA TTCCTGTTGT AAGAGGAGGG AACAGTTCCT GTGACAGGAG
GAGGGAGCAG ACATGAAGAA TAGACTTAGA TGTATGTGAG AAGGAGGATG CCTGCCATTG
TGGAGGACTC TCAGTGTGGG CAGTGCTGCC TTCCTTTCTG AGTGGCACAG TCCTGTTTGG
GGCTGCAGGT TGTCAGTACC CCTCCTGAGT GGGGTAGGGT GGCAGAGAAC AAGATTACAA
AGAAAGCATC AGAGGTGGAC CCAAGGGGAA GATGCCGAGA TGGAGATGAA TGTCAACCAT
CTTGAAGATG AGGGGAGAGG TGGAGAGTAT ACAGCCTGTG GGTCCTGACG CCTGTCACAG
AGAAACAGAA ACATGTGCGT GCCCTTGGCC GCTCTGGACA CAGATTGCAG CCCATGTGCT
GGTGTGGACC AGGTCCATTA TCCACACCGT CGTCATGTCT GCAACATCAC TTGCTCATAA
AATACCATTC TACAGTTTCT CTAGCCCCGA ACTCTTATAT TTGTTTTTGG GTTGTTCACA
GGCCTCTTTG GATTCCATTC AAATCCTCGA ACAGGTGCAA GAAGCAGATT CCCCTACAGA
CTAGGGGAAC TGAGGGTCAG AAAGGCTGTG CACTGTAGCT GAGAGATGAG AGTGGCAGCA
GGCATTCTTA GCCTCCAGGG TTGCTAGAAC AATAAATAGC TGGTGCTTAC CGAATGTCTA
ATGTGCTCCA GACACCTGGC AAATAGTATT TGAGTCGGAT CTTACAATGA CCCATAAGCT
AAGTATGAAT GTCAATGCCA AACATAGCTC TTATCTCAAA GGAATAAGAG TTAGTTTATT
CTTTGGCCAA ATATTAATGC CCAGAAACAC AGATTCCAGT TGTCCCAAAT TAACATGTTC
CACTGGGGAA ATGAAGGAGT TTTCATAGCT CAAGGGCAAA GCAAGTTACC AATCAAGGGG
TTTTTTGAGA ACACTGGTGG GGGCCCCAGG CAGGCAAGTT ACAGCAAACA AGAACTCTGT
ACATAGTCAC ATGCAGACGG GTAGTGGAAG CCTGTTGTCT ACTAGGTCAA TACATTCCAA
ACCATCAAAG ATACTGGGTC AGGCAGGACG GAGTTAAAGA TAGCCCATTG TCGTTTGACT
CTGGATCTTC AAACTTTCCA ACTCTCCACG ATCAATCAGT TTTGTAGAAT CTTTAACATA
GGCATGGCTT CCCCCTCCCT CCTCCCACAC ACCCCAGCGC CACCTGGAAC TTCAGTTTAT
ACTAACACTA CTCAGACAAG GGAGCCAAGG CTCTGAGAGG TCCCATGTGC TAACCCAGGG
```

Figure 100

```
CTAGCAACCA ATGCACAGTA GAGCTTAGAT TCTGTATCTG CCCAGAATAG AGACCTTGTC
CCACAGTTTG TGTGACGCTC CCTTCTACCT GTGTATCCTT TCTTCTTCTT TCTTATGCTG
TATCTCTTTT CTGAACATGA CTTCCTCAGT TGGTTACCAT TGAAATTCAC TAATCGGTTG
ACTTTAAACA GCCACCAAAT CTGGCAACCT GGCCACTTGC TGTGTTGGCA GCCTCAGAGC
AGAGTCTGGG GAAAGGTCTA GGATGCAGGT GGGGGGAGCT AGCCTGAACA CAAGGCTTGG
ATTGACAGGG AGCAGAAACA GCCATGTAAA CCTGCTACTT GCCCTGTCAA CCAGGGGCTG
GTTTGCTTGC TGGCAAAAGA GGTCAATGTG CTTCTTGGCG AAGGTAGACA TCTATGGGAT
AAAGAAAAGT AGACTGCAAC TTAGAGATGC ATGTGTGTGT GTGTGTGTGT GTGTGTGTGT
GTGTGTGTGT TCCTGGAATG CTGGGGGTCT GGGAACTTAG CTCAAGTCTT TGATTCTTTA
GGAAAGAAGG TAAAAATTGC CTGGTCCTAT CTACTGTCAA GTGGTCGGGG TGAGAGAGTG
AGTGTATGCT CGTGTATGTA TGTGAGCACT GCAGGTGTCT GCATGGTGTG CCATGGTGCT
CCACTGGGCT TCATGCTGTG CTCCCCTAGG CTTCAGTCAA GTCAAGACTA GGTCAAGTCA
TGGAGGGTAA ACAGAAGAGA GAGAGAGCAG AAAATGAGGG ACACAGGAAG GGTAGAGGGG
GAAAGAGAGG GTTGTGAAGC TCACGCGTGA TCAGGAGCCC CAGGCTTTCT TCTTCCAGCC
GCCCATAGGC TCTGGTGCCC ACAACATTGG TTACAACCCC GCTCTCCATC ATCATGCTTG
TCATCACTGC TGTGACAAAC CGCTTAATAA TGGTTCTCAC GGAACATTAA AAGCCAAGCC
AAGTTTAACA CCTCGAACAT TTCCAAGTGT TATGGGGAAT AACAGTTAAG TGTCTGGGTG
TGCTTGTGTG TAATTGGGAA TCTGTAGTGG TGGGGTTACC AGTGTCAGGC CACAGTGTTT
GTGATGAGCA GAGGGGTCGG GGTCTTTCTC AGATCCCTTA TCTTGTCCTG TCAATGGTGG
TGATGTAATA GGTGCACGCC TGTGACAGAG CTGTTTAAAG CATTGTAAGA CCAATGAGTA
AAGTTCCTAC CCTTGCTTCT CCTTTAAGTG AGGCAGAAAA AGGCTCCACC ATGACGTGGT
GTAAAGATGA AGTCAATCTA ATACTTCCTT GGATACTCTA GCAAGCTTCA TTCACACTTT
TTATTTCTTC CTCTTCCTCT TCCTCTTCCT CTTCCTCTTC CTCTTCCTCT TCCCCTCCTC
CTCTTCCTCC TCCTCTTCCT CCTCCTCTTC CTCCTCCTCC TCTTCCTCCT TCTCCTCTTC
CTCCTCCCCC TCCCCTTCCC CTGTGCTCCT CATTATTATT ATTATTGCTC CTGTCTAGGT
                                                           >>>
GGAAGGACAA TCCAGCCATG CCTGTGGGGC TGGTCTATGA AGGTGTTGCC ACAGAGCCTC
>...........................Ex 9 ............................>
TGAAGTACTC TGGAGGAAGT GCAGCCCAGA GCTCCGTGCT TCATGCCTTC GATGAGTTCC
>...........................Ex 9 ............................>
TGGGCATTGA GCATTGCAAG GAAAGTGGTG AGCAGCAGTC TGATCTCACC TATGCTTTGA
>..........Ex 9 ..........>>
TGGGACAGCG AGGTAGACTA GGGAGACATC TCTAGCAACT GATAAAGACG GGTGTAAATG
AAAATGTCCT GAAGTTTATC CTTGCCTAAG CCAGCAGGCA GCTGTGTGCA TGTGCCCTCT
CTTACACTGA GTTAGTCAGT ATTGGGGCAT CGGATCTTAT TAGGGTCTTC CAACAGTCCT
GTGACCTGGG TTGTTCACTG TCCTGTTGGC TGGGGTCTTT TATCCGCAGA TTCCCCTTTC
TACAATGAGG TGATAATGTC ACATTGAAAG GCCAGTCTGG AGCAGCAAGT GATAGTGCTG
AACTTCTCTG CTAAAGCCTT TCCCATGAAA TGGCCCAGCC TCCCACTGAA TCTATGTGGA
CCAGGCGAGG GAGCCCATCG CTTTGAAGCC TTTAAAATAG TTGTTATTGA TTTTTCTGGC
AGCATAGAGC TATCCTTTAA TGACTACCAA AAAAAAAAAT ATTGCTACCA AACTTTAATT
TGGATCAGAA CCAAAAAGAA TTAAAACTCT CTGGCACGAA CCTGTTCTCT GGAACAGTCA
GGGTTGTTTC TGGGTTTCAG CATTTGATTT TAGTCACTGA CTCTCAACAA CCAACCAACC
AAACAAACAA ACAAACAACC AAACAACCAA ACAACAACAA CAAAACCTAA CCCAAACAAC
AACAGTTAAA GGTGTAATGG TTTTCAAGAA AACACTGAGT TTTCAGTGTT TCGGCTTCTC
TGGGTTTTTA CTAAAATACC TGCTTACCAA TGTCGTCTCT ACGTGCACAG TAACTTCCAT
TTCCTGCCCC CCTGCCCGCC CCCCATTTAT AAGTATCTAG CAAACAGAAT TCACCAGAGT
GTTCTGTGTT TGTGTGTGTG CGTGTAGACT CGTCTCTTAG TCCTCAGCAG GGAATACCAC
ATCAGTCATA CACACGGAGC AGTAGATTTC TGTCCAACTT TATTATCTGA GAGATGTTTG
CTTCTTTTTC TCCCCTGTGT CTCCTGTCAA CAACCAGAAA TGAACATTTG AGCATTTGGC
AGCTATAACA AAAGCCCGAC AAGGCTGAGG GAGAGCCCTA TCAAGCATTT CTGGTACCTG
AGTGTTTGGA ACAGTGGGCA AACCCTCCCA AATGTCTGCC TCGAGCTAAC GTATTTCTCC
CGGCTGTTTC TTTCAGTTGG CTTTCTACAC AGAATGAGGG ACTACATGCC GCCTTCCCAT
                >>...................Ex 10  ......................>
AAGGCTTTCC TGGAAGATCT CCACGTAGCT CCTTCTCTGA GAGACTACAT ACTGGCCTCT
>...........................Ex 10  ............................>
GGTCCTGGGG ACTGCCTGAT GGCCTATAAC CAGTGTGTGG AGGCCCTGGG AGAGCTGCGC
>...........................Ex 10  ............................>
AGTTACCACA TCAATGTCGT GGCCAGATAC ATTATCTCCG CTGCCACCAG GGCCAGGAGC
>...........................Ex 10  ............................>
```

Figure 10P

```
AGGGGGCTAA CTAATCCCTC ACCCCATGCC TTGGAAGACA GGGGCACTGG GGGTACTGCC
>............................Ex 10  ............................>
ATGCTGAGCT TCTTGAAGAG TGTCAGGGAG AAGACCATGG AGGCCCTCCT GTGTCCTGGT
>............................Ex 10  ............................>
GCTTAGCAGT CATGTCCTGC ACCCTAACAC TTAGATGTTC TCATCCTGCA TCCCAGCGTT
>...>>
AGAGGTTCAC ATCCTGCATC CTAGTGCTTA GCTGTTCTTG TGCTATATCC CAGCGCTTAG
CAGTCATGTC CTGCATCCTA GTGCTTAGCA TTTTATATCC AGCATCTTAG TGCTTAGAGA
TTCACATCCT GCATCCTAGA GCTTAGCATT TTATATCCAG CATCCTTGTG CGTATCAGCT
ATGTTTTGTA TCCTGCTTAG CAGTTAACAT CCTGCATCCT AGTACTTATC TGTTCTCATC
CTGCATCCTA GAGCTTAGCA GTCAGGTCCC GTGGGAGCAA GAACCAGGGT CTGAGCTCTG
TCTGAGCCCA AGCATGGCTT TACTGCTTTG TTAATTGTGG CTCCCACCTC CACCCCACCC
CAGCCAGTTT GCTTGCTAGA AGCCTTTCTG CACTGCCTAA TCCCCCTGCC TCACAGCAGA
GAGCTGCAGC CATGACCTCC TCATTCAGTA TTAGGTGGAC AAGTCGGAGA TACCCAAACT
CAATTTTAAA AGAATCAAGT TGCTTTTGGG GCATGTTACT TCATCTTTTC TTACCCTGGG
CCTCTTCCCT TCTTCCCTAC CTCCCTCGTC CCTTAGTCTT TCACCCCTCT CTCTTTCTCC
TTTTGTCACC CTCCCCCTCC CCTGCTTACT CTCTTTTCCC TTCCCCCCTC TCCTCATCCC
TCCTTCCTTT CTTCCTTCCC TTTTTGTCTG TGAAGCACCA GGTCTGATGG GCCTCAAACT
GTGATCTTCC TGTCTCACCC TTCAAAGGTT ATGTGTATGT GACGTGTGTG TGTGTGTGTG
TGTGTGTGTG TGTGTGTGTG TGTTCGTTTC TTTTGTTTTT CCCTAGTGGA GATGACACCC
AAAGATTTGC ACATACCAGG CAATTGCTCC ACCACCTGAC TACAGTCCCA GCTCTCTGTA
TTCCTGAAGG AAAGTCTTGA TGAGTTGCCT AGGCTGGTAT TGAGCTCTTT AGCCCAGGCA
GGCCTTAGTC TGAGTAGCTG GGATGTACAG GGATGAGCCA CTGAGCCATG CTGCTGCTGC
TAACGATGAT GACGATGATG ATGATGAAGA TTATGATAAC TACAGTCACT GCAATAATGA
```

Figure 10Q

```
CCAAAAGTTG TTTGGTAGGA GAGGGTTGAG GCTGGGAGAG GTGGCTCATG CCTGTAATCC
CAGCACTTTG GGAGGCCAAG GTGGGTGGAT CTCCTGAGGT CAGGAGTTCC AGACCAGCCT
GGTCAACATG GTGAAACCCC ATCTCTACTA AAAATACAAA AAATTGGCGT GGTGGTGGGT
GCCTACAATC CCAATTACTT GGGAGACTGA GGCAGGATAA TCGCTCGAAC CTGGGAGGCA
GAGGTTGCAG TGAGCAGAGA TCGCGCCACT GCACTCAAGC CTAACCAACA GGGGCAAAAC
TCTAGGACTA GAGCTAAGGT ATCAAAAAAA AAAAAAAAAA AAAAAAGAAG TAGAGTGTTT
AATTAAATAA TTTGTTCTTG CTGTAAAATG TAAAGTAGAT ATTCCTCTTC AAAGACTTTC
CTCCCCGTCT AATTAGGAAT AAATAGTAAC TTCTCTTAGA AGCAAAATTT ATTCAAAGAC
CTGTGCTAAC ATTCTTAAAT ATCTGCTAGC CACAATAAGG AAATCAATGT ACTTTATGTT
CTTAGCTCCC ACAATTTAGC CTAAATATTT TCCCTGGCAT GTTTATACTG GTCTAAGCAA
GCATTAGGTC ATAGCCTGTT CCTCTTCCTT ATTTAAAAGT GTTTTTACCT TTCTCAGCGT
TCCACAAGTT ACTTCCTCCT TCCTTTGTTC TCCTCTACCT GTGCCTCTTT TAAAAAGTTC
TAAGTTGCTA GCCAATTGGG ACAAATACAG AATGTAAGGT CCCATTCCAG CCAACGGAAA
CTGGACACAG CAGTAGGGTG GATGTGTCAG GTTATAAATG ACCCTGTCTC CTTTGTTTGG
TGTACTCTAG TGGCAAAACT GCTGGCAAGT GTACCTTTTC TGCAGGAAGT AAAAATGGCC
TTACTAAATA AATTAAATTT ATGTTCAAGT GCTATTTCTT TTTTTTTTTT TTTCGAGATG
GAATTTCACT TTTGTTGCCC AGCCTGGAGT GCAATGGCGC GATCTCGGCT CACTGCAACC
TCCACCTCCC AGGTTCAAGC AATTCTCCTG CCTCAGCCTC CCGAGTAGCT GGGATTACAG
GCATGCGCCA CCACGCTCGG CTAATTTTGT ATTTTTAGTA GAGATGGGGT TTCTCCATGA
TGAGGCTGGT CTCAAACTCC TGACCTCAGG TGATCCGCCT GCCTTGGCCT TCCAAAGTGC
CTTGGCCTTC CAAAGTGGCG TGAGCCACTG CGCCCAGCCT CGAGTGCTAT TTCTTTACGG
CACGGAAGAA CAAACATTTC AAACAATGCT ATTACCAAGT TTGTTAGTAT TTATTATCTC
ATTTGCTAAA CCTAAAAAAT ATATATCCTT CTTTAACGTG ATCGAATATT TCAAAAAGTT
ATTGTGTTGT TTCTTAAAAT AAATCAATCA TAATCCTAGA CTATGTTACT CAAACTACAT
ACAACACCTT CTGAGCTTCT GGCAGGCCCT TCCTCCCCTC CCTGCTCACC ACAGATCACT
GGAATAATTG TCTGCATGTA ACTTCTAATT TTGAAGTGGT TGTGGTTTAT CAAACCTGGA
ACATGGCACT TCCAAGTACA TGAGCTAAGG TCACAGTAAG ACTCAAGCCC CTTCAACAGA
ATACCTGGAA TTTCTCTGTT AAAGATTTTC TCCTTTACCT GACTACATGT TTGTAATGCA
GATCCCTCCA GGAGCGCTTA CTTATAAACT GTCCTGGATC ACTAACGCGA CATTTTGATG
TAAATTAGTT TATCTTGACG TGCTAATGGT AGAAAAAAAG AGAACATGAG GAAACTTGGG
TGCTTTCAGG GCTGGTAGGA AGGATTAAAT CTTTGCGGCA ATTTCTGAGA AGGGGAAGGA
AACCTTGCTA ACAATTTTGA TAGTTTACTC CATTTGGCTG GAGTAACTCT GATCCATTTG

                         KpnI
                        -------
TCAAATTCAC GATGGAGCAG GTACCTGTTA GGGTACAGGT TTGATAAACC ACAACCACAG
GTCTATTTCA TTTCTCCTTT TCCAAAGTGG AACAAATTTG TCTCTGGGGT TAAAACTGCT
TTTCTCATAT TGGTGTGTAA GAGAAAATGA GGGAATTTCT TTGAGTTTGT TTGGTTTGTC
TGTTTGTTTA AGCAGCATTT TTTAAATAAT TTACTCAGCC CTGTCTCAGA GAAAGTCCAT
GATGATCTGG AATTCAACCT CAGGGAAAAG TTCTCTCCTG TGCCTGAGAC ACTGCGCAAC
TAACTGGAAC CGAAGGATGG AACCTGGGTG TTTAATTTAT TAGGAACAAT TGATTCTTCA
GTGACACTTT CCATGCAGAT ACTTCAAACA AAATAATGGA GCCCCACAGA CCGAATGTGA
                                        >>.........Exon1  .........>
AGACAGCAGT GCCATTGTCT TTGGAAAGCT ATCACATATC TGAAGAGTAT GGCTTTCTTC
>..........................Exon 1 ............................>
TTCCAGATTC TCTGGTAAGG ATAGAGCCTT GGTAAGGATA GGTCAGAATA TGTTTCTTGA
>....Exon 1 ....>>
GATGTTGGTT GGTTTGTTTT TTAAAAATGT ATGTGATTAT TAAGAGACCA ATATAAATAT
CAAGTTGTTT ACCTGAGAAA GATGCTACAA AGAGCATAGA TTATCATTAC TATCAAAAGA
GAAGTGACAG ATACCACAGA GAACAGGTCA AATGGAACAT TTTTTGTTTC AGTTTCTTTT
GACTAGATTG TCAGGCCAGA GAAATTATAA GCAAACCTGT AGTTATCAAG AAAAAGCATG
AACTTAAATA TAAATAAAGA ACAAATACAG AGCCTCAGCA CCTGGAACAT GGCACTTCCA
AGTACATGAG CTAAGGTCAC AGTAAGACTC AAGCCCCTTC AACAGAGTAC CTGGAATTTC
TCTGTTAAAG ATTTTCTCCT TTGCATGACT ACATGTTTGT AATGCAGATC CCCCCAGGAG
CGCTTACTTA TAAACTGTCC TGGATCACTA TCGCGACATT TTGATGTAAA TTAGTTTATC
TTGACTTGCT AATGGTAGAA AAAAAGAGAA CATGAGGAAA CTTGGGTGCT TTCAGGGCTG
GTAGGAAGGA TTAAATCTTT GTGGCAATTT CTGAGAAGGG GAAGGAAACC TTGCTAACAA
ACAATACCTC TTTCTTAATT CTACTTAGGG CTCAAATTGT AATGCAAATC TTTTTCATCA
```

Figure 11A

```
TTTAGCCCTT ATAAACACTG TTTTTCTCAT CTGGTGTGGT CCAAGGCCTA GAACATTAAA
ACTATCAAAG CTTTTACAGA CCATCAGGTG TCATCCCCCT CTTTCTACAT CTGAGCTAGC

                                                        SpeI
                                                       ------
TGAAATCCAG AGGAAATGAC TTGCTGAAAG TCATGAGTGG CAAAAGCAGA ACTAGTTCTG
CTTATAACTC TTGACTTTTA GTTATTATTA TTATTAATTA TTATTATTAC ATCCTAAATG
AGGGCCAAGG CCACTCAGTT AAAAATCGTG GGGTCCAGGC CAGGTGCAGT GGCTCACGCC
TATAATCCCA GCACTTTTGG GAGGCCAAGG CAGGTGGATC ACTTGAGGTT CAGGAGTTCA
AGACCAGGTT GATCAACATG GTGAAACCCC GTCTCTACTA AAAATACAAA AATTGGCCAG
GCGTGGTGGC ACATGCCTGT AGTTCCAGCT ATTGGGGAGG CTGAGGCAGG AGAATCCTTG
AACCCAGGAG GGGGAGGTTG CAATGAGTGG AGATCATGCT GTTGGGAATG AAGTTTTTGG
TGTCACAGAA AAAGAATGAA CATGGGAACA AATGATCTCT CAGCAAAAGG ACCTTTACTT
TCTGCAGAAA GGGTGCTACT CAATAGCTGT CCAGCCACGA GAGCACACCA AACAAAGGAG
ACAGAGTTAT TTATAACCTG ACGCATCTAC CCTACTGCTG TGTCCAGCTT CCATTGGCTG
GAATAGGACC TCACATTTTA CACTTTACCC AATCGGCTAT TAGTTTAAAA CTTTTTTAAT
TGGATAAGGG AACAGAACAA AGAAAGAAAA GCAAGTTGCC CAGGGATAGT TAAGGAAACA
TCTCCATATA AGGAATGGCA TGCACTATGG GCTGGGGCTT TTCTAGTTCT GTACAGACAT
GCCGGAGCAA GCTACGACAG CTGATTTGGA CAGCCACTAA TAGTGGCTAG CAATCTTATA
GTAAGAAATT GTGACTTTTT ATAATCTTTG AAGAACTTTC CCATTTCTGA CAGTGCCACT
GCACTCCAGC CTGGGCAACA AGAGCGAAAC TCGTCTCAAA ACAAAACAAA ACAAAACAAA
ACAAAACAAA ACAGCTCTCT ACTCTTGGAA GCAGCAGAGT TTTTATCTTC ATTTATATCA
CTCCGGTAAC ACTCAGAAGT AGACAAGCCT CAGGGTAGGT ATTCAGTAAA AGCCCACTGA
ATTCCACACT ATTCTTTAAT CATAGTTAAA TGGCAAATTA GGCTGGAGGG TGGGGGTGGA
ACCTCTCCAA AATTACTGCA ATGACTGCAA CATCGGACCC CAAGATTTTT TTTTTTTTTT
CTGAGATAGA ATCTCTTTCT ATCGCCCAGG CTGGAGTGCA GTGGCACTGT GAGAAATGGG

                                             AhdI
                                          ------------
AATGGACCGG ACTGTTTCCT CTGACACTGC CACTAGGTTG ACCAAGTGTC CCTATTTGTT
AGGTACTGGA TGGACGCCTG ACATGCAAGA CTCTCAGTGC TAAATCAGGA AAGTGCTGGG
ACAATTCGGA TGAGTCGGTC ACGCTAAGTT GCACTTAATA GCTCTTGTGA CTTTGACTGA
ATTACAAACA TCCCCTGACC CTCAATTTTC ACATTTACTG GATGGAGATC TGGTGCCACC
TCCACTAGAT TGCTATGGAG AATGAATGTG AAAGCATTTT CATAAATCCA GTGTAAGGAC
CAGAAGCCAG TCTTCTGACC TTGAGCCAGT GCTTGTTAAA AACTCCACTC TATACATCTA
ACCCAATTCA GGAATATCCT GCCTAGTTCC AAAGGAAGAA AAGACCAAAT TGCTCTTATT
GGGATTAAAT GCGTACACTG AGCTGAGGAA AAACAGTATT ACAAATGAGC TAAACATGAC
GTAGATCCAC AGTTGTAGAA TTCCCCTCTT TGTTCTTTCC TCTTTCATAA CTACGGAAAC
AGATGAGAAA CATTTACGGC ATCAGGTTCT TGTGATGCTC CCTGCCTGAT ATGCTATGGT
TTTGTTAATG GAATGTCCAT TCCTGAGCTT ATGCAGAAAA AAGTCCCTTG GGAAAGTGGT
TTTACTGTGT TATGTTCATT TTCCCCATAG TTCTCAAAAT GTACTTCCTT GTTTCAGTTT
TAATTTTCTT TCATTGGTGT GACCATTTTC AACTGCTCCC TTTCTGGGAA GAGGTAGCAG
ACGGACATTT TCATCAAAAT CTGCCCCAGG TTGCTTCACA GATAAGGAGG GACCCAGCCA
CTAAAATCAC CAGGCAGAGT GTTGCAAGAG TAGATAGAGA ATCACAATTG GCTGCCCTGC
TCAAGGGGAC ACCAGATCTT ACTTTCGTTT AGTTGAAAGG CAAGCGTCAG AGTCGGGAGG
CTGTACCTTC ATGTCCAGTG GCCTCACAGA AGTTCCTTCA GTATCTCTTT TAGATGAAAC
TCTTTTAGAA GTTCCTTCAG TATCTCTTTT GGTTTCTCAC TATAGATAGT TACTTGAACA
TGTCTGAAGA AAACGTGGTC AAGACAGTGA ATAAAAAAAA TTCTGGTTTT GGGAAGCAGT
CTGACTTAGT TTCAAATATT CTATCCCACT GTTTCTGTCA ATGTTCAAAC CTTTCCAAGC
TCCAACATTT ATTGTGGAAA ATGTGTGCCT CACCAACTCA TGCAAATAAA TGTTTCATGT
GCCCTACGTG TGTAGAGGGG GCATGGATGT GTGTTTTTGG AGGGAGGGCT AATTTTTCTT
TAGACATGGA GAATACGAGG AAATTAGCTT GGCATCAAGA AGGTTACAGC AGGAGACAAG
AGTGAAGAGA ACTGAGAGAG CCCGGAAATG AGGCTCTGGA GTTCAGATTT TTTTTTTTTT
GAGATGGCGT CTTGTACCCC AGGTTGGAGT GCAATGGCAA AATCTCAGCT CACTGCAACC
TCCGCCTCCC GGGTTCAAGC GATTCTCCTG CCTCAGCCTC CTGAGTAGCT GGGATTACAG
GCATGAGCCA CCATGCCTGG CTAATTCTGT AGTTTTAGTA CAGATGGGGT TTCTCCATGT
TGGTCAGGCT GGTCTCAAAC TCCCAACCTC AGGTGATCCA CCCTCCTTGG CCTCCCAAAG
TTCAAGGATT ACAGCCATGA ACCACTGCGC CTGGCCTAAT TTTTGTATTT TTAGTAGAGA
CAGGGTTTCA CCATGTTGGT CAGGCTGGTC TTGAACTCCT GACCTCGTGA TCTGCCCACC
```

Figure 11B

TCAGCCTCAT GAAGTGCTGG GATTACAGGC ATGAGCCACA GGGCCAGGCC TGGAGTTCAG
ATTTAACACA TCCTGTAAAT GACATGATGC ATCTGATATT TGAAGAGTTT TCCTCAAAGA
ATGTTACATG CAAGGTGGTT TAGAGTTGTT GTTTCCGGCT ATATAGCAAA AGTACTTGGG
GAGTTTTAAA AAATACTGAT GCCGAAGCTC CACCTAGAAT AGTTCATTCA GAATCTCTAG
CATAATTGAC CTCAGTACTT GAAATATGAT TATTATAAAT GTTAGTCAAC TGCTTTTTTA
GGCTCTATGA CTGATAGAAA TCTTTCACTT TTATATCATC TCCAGTTAAT GAGTCCCATA
AATTGAAATC TAGTGTTTAA ATTTTTACTT CATATTTATT TTTACTGATT GTTTTATTAT
TATTATTTTT GAGACAGAGT CCGCTTTGTC GCCCAGGCTA GAGTGCAGTG ACGCCATCTC
GGCTCCCTGC AACCTCCGCC TCCTGGGTTC AAACGATTCT CCTGCCTCAG CCTCCTGAGT
AGCTGGGATT ACAGGAGCCC ACCACCAACC ACACCCAGCT AATTTTTGTA TTTTTAGTAG
ACGGGGTTTC GCCATGTTGG CCAGGCTGGT CTCGAACCCC TGACCTCAAG TGATCCACCC
GCCTCGGCCC TCTGTCTCAA AACAAAAACA AAAACAATAA CAAAACTTTT CTCTTCTACC
CGAGATGTTT AAGTTTAAAT CACACCATTT GTACAAAAAT TCCCTGTCTT GTCCTTAAAA
ATAATTTGTA ATCACTAGCT AGTTTTGAGA TCGATTGCCA TCTAACCGAA TGCCATTTGT
TCTCTCTCTC TAGTTTCAAC TTAATAACCC TTTCTGCATT TTCTATTCTT TCAAAATTTT
TCCGGCCATT TTATTGTTTC TATTTAGTGA AAATTTATTC ACTGGTTTCT ATGCCTAAGG
GCATTTAGGA AGTTGCTTAG GATACAGACG TGATAAAAAG ACCAGTGTAA AAACTCTCCA
CTCCTAGACA TTATATTCTA GTCCTCATCT CCTGTCATTT AAGTCCTCAG TGATTCTATG
CACTTTTGCT TTTGGTTTGG GCAGATGCTC TGAGTTTAAT GTTTCTCTGA GATGAGGACC
CCCTATTCAA CTCACAAATC CCATAAGGAG GCCTCTGTGC CTTTGCTGGT GCCCCAGACA
GGGTGCTGAT GCTTACTTAT CTTCAAGATT GTGAAGTCAG ATTTAATAGT ATAGTCGTTT
GCCAGAGCTG CTGTAACAGT AGCCACAAAC AGTTGGGCTT AAAATACCAC AAACAGGAGG
GCTTAAATCA CAGAAGTTGA TTTTCTCACA GTTCTTGAGG CAGGAAGTCC AAGATCAAGG
TGTCGTGGAG TTGGTTTCTT CTGATGTCTT GCTCCTTGGC TTGTAGATGG CCTCCTTATT
ATTGTGTCCT CACATGGTCT TTTCTCCACT ATGCACAAAT TCCCTATGTC TCTCTCTCTT
TTTTTTTTTT TTTTTTTTTT TTGAGACAGA GTTGCACTCT GTCACCCAGG CTGGAGTGCA
GTGGTGCAAT CTCGGCTCAC TGCAACCTTT GCCTCCCGGG TTCAAGCAAT TCTCCTGCCT
CAGTCTCCTG AATAGCTGGT ATTACAGGTG CGCACCACAA AGCCCAGCTA ATTTTTTGTA
TTTTTAGTAG AGATAGGGTT TCGCTATTTT GGTCAGGTTG GTTTTGAACT CCTGGCCTCA
AGTGATCCGC GCACCTCGGC CTCTCAAAGT GCTAGGATTA CAGGCATAAG CTACTGTGCC
CAGTCTCCCC CTGTCTCTTT GTGTCCAAAT TTCCTCTTCT TTAGGGACAC CAATCAGATT
AAATTGGACC CACCCTAAAG GCCTCATTTC AATGTACCTC CTTCAAGGGC CTATCTCCAA
ATACAGTTAT ATTTTTAGGT ACTAGGGCTA GGGCTTCAGC ATAGGAATTT GGGGGAGACA
CAATTTAGCA CATAGCAGAA AATATAAGGC CAGGAAAAAA TATTCTGGCA TGCTAGATGG
ACTCATTAAC AAATATTAAC CAATATAAAC CAATTAACAA ATATTTCTTT AATATTTGCC
TTTTTTTTTT TTTTTTTTTG AAACAGAGTT TCACTCTTGT TGCCTAGGCT GGAGTGCAGT
GGCACGTTCT TGGCTCACTG AAACCTCTGC CTCCTGGGTT CAAGTGATTC TCCTGCCTCA
TCCTCCCAAG TAGCTGGGAT TACAGGTGCG GGCCATCACA CCCGGCTTAT TTTTTGTATT
TTTAGTAGAG ATGGGGTTTC ACTATGTTGG CCAGGCTGGT CTCGAACTTC TGACCTCAGG
TGATCCACCT GCCTTGGCAT CTGAAAATGC TGGGGTTACA GGTTGCCTGG TGATTTTTAA
GAGGAATGAC TGAGCTCTCA TGCCAGGTGG GGGGAGGGGA CAGAGAAAGT TGAATACTCT
GACGATAGCC ATGATCCATA GCTCTGAAGC TTAGACTCGA ATCTACCCAT CCCGCAAGGA
AGAAAACAAA GAAATAAAAA AGAAGAAAAG AAATCTCCCA ATGTCAGGTC CCACCCTCTT
TAGAAGTAAT TTCAGCAAAA CTTTGTTGCT ATTTTGGCAT GTCCTCTACT GTAGTAGCTT
GTCAAAATAC TGTCCCCAAA CGTTTTCTAT ATTTCTAGAT TTTACTGTTT AATGTATAAT
AATAATGTTC TAACATTAAA ACGTAACCAT AGCAATGCTC CGACTCACTT GATCTTTAAA
TATATTGTTG AACTCAATTT TGTGACATCT TCAGAATTGT CTTTTTGTAT TCATAAATAG
CAACAGTGGA TAGTTGCCTT GGTTAGTGTT ATTATTTCAA GGATTAATCT TTAGGTTACG
TTTTCTTCAT AAGATGCATT AGATGACTTT TTTTTTTTTT TTTTTGAGAC AGAGTCTTGC
TCTGTTGCTC AGACTGGAGT GCAGTGGTGC AGTCTCAGCT CACTGCAATC TCCACCTCCT
GGCTCAAGAG AGTCTCTCGA CTCAGCCTCC TGAGTAGCTG GGATTACAGG CACGCACCAC
CATGCCTGGC TAATTTTTGT ATCCTTTTTA GTAAAGACGG GATTTCCCCA TGTTGGCCAG
GCTGATCTCC AACTCCTGAC CTCAAGTGAT CCATCTGGCT TGGCCTCCCA AAGTGCTGGG
ATTACAGGCA TGAGCCACCA CACGCAGCCA ATTAGATGCC TTCTCATGCT TTTCTGTGTT
GTGAAACAGA TCATCTATCC GTTGATATAG CATAGCTCTT CAGACTACAG ACATTTTAGG
CTATAAGTTT TGAATTACAT TTTCTATTCC CTTTATGCTT CTTGTTCTAG TTAGGTTTTT
TATTTCTAAA TAAAAATATG AATTTTTGCA ATTTCCCAAA TGCGAACTCA ACTGAAATTT
TCAAGTGTAT TAGCAAAATT TATTCATAGC AGCCTCTTAC ATTTCATTAA GAATTGATTT
TTTCTTATTC CCTGTTGAAG TTTGTTTATA AAATATAGTA ATAGTAATAA CTATATAGAA

Figure 11C

AGTGTTCACT TTGTAGTAGG CCCTATGTTA ACTTTAACTA CACTTTTTAA ATCTAAGCCT
CATAGTAGTC TTGGATGGAT GCGGTGGCTC ACGCCTGTAA CCCCAGCACT TTGGGAGGCT
GAGGCGGGTG GATCACGATG TCAGGAGTTC AAGACCAGCC TGGCCAACAT GGTGACACTG
TCTCTACTAA AAAGACAAAA ATCAGCCGGA CGTGGTGGTA TACACCTGTA GTCCCAGCTA
TTTGGGATGC TGAGTCAGGA GAATTGCTTG AACCCAGGTG GTGGAGGTTG CAGTGAACCG
AGATCACACA AGTGCACTCT AGCCTGGATG ACAGAGTGAG ACTCCATCTC AAAAAAAAAA
AAAAAAAAAA AAAGAGATCA ATAAATAAAA TAAATAAATA ATCCTCACAA TAGTCTTCAC
CATTTGCAAA TGATCCATTT GACAATAAAT GAATTCAGCA CTATCATGGA AATATATTTC
CAAGCTGACC AGTTTTCTCC ATTTCCACCC CACTTCAATC CACCTTCATG TAGCCCTAGG
ACTATTGTCT CCTCCCCTTG TTTCCTTATT TCCATTCCTG TTCAGCTGTA ACACATTCTG
TTCATAGCAG TCAAGTGATG CTTACAAATG GAAATCAGGC TAGAGGTGGT AGTTCACACC
TATAATTCCA GCATTTTGGG AGGCTGAGGC AGGAGGATCA CATGAGGCCA GGAGTTTGAG
ACCAGCCTGG GCAACATAGC GAGACCCCAT CTCTACAAAA ATAAAAAAGA ATTAGCTGTG
CATGATCCTA TGTGCCTGTG TTCCAGCTAC TTGGGAGGCT GAGGTGGGAA GATTGCTTGA
CCCAGGGAGT TTGAGGCTGC AATAAGCTAT ATTTGTACCA CTACACTCCA GTGTGGGTGA
CAGAGTGAGA TCCTGTCTCT AAAAAACGTA AAATGAAAAT AAAACCTTGA TAGTTTGCTC
TTTAAAACTC TTCCTACAGG GCCCCTGTGA TGCTCACCTG TCTCTAGAAG GGCATGTAAT
AGCTCTTTCT CCTTCACTTT ACTTTGATGC AATGTCAGAA CAGCTTCTTT CCATCAAAAC
TTAAACCTTT GATTTCATTT AAAATCATCT GCTTCAAATT CTAATCTTTC TGATAGTTTA
GGTTCTAATT TTTCTGATGT TAATATTGTC ACCCAAGTTT CCTGTTCATA TTTACCTGGT
TTATTTTATT TTTATTTTTA TTTATGTATT TGAGATGGAG TCTAGCTCTG TCACCCAGGC
TGGAGTGCAG TGGTGCGATC TCAGCTCACT GCAACCTTCG CCTCCTGGGT TCACGCCATT
CTCCTGCCTC AGCCTCCCGA GTAGCTGGGA TTACAGGGAC CCGCCACCAT GCCCGGCTCA
TTTTTTGTAT TTCTACTAGA GACGTGGTTT CACCGTGTTA GCCAGGATGG TCTTGATCTC
CTGACCTCGT GATCTGCCCG CATCGGCCTC CTAGAGTGCT GGGATTACAG GCGTGAGCCA
CCGCGCCCAG ACTTTATTTT ATTTTTTGAG ACGAAGTCTT GCTCTCTTCC CCAGGCTGGA
GTGCAGTGGC TTGATCTCAG CTCACTGCAA CCTCTGCCTC CCAGGTTCAG GCGATTCTCC
CGCCTCTGCC TCCCAGGTTC AGGCGATTCT CCCGCCTCAG CCTCCCGAAC AGCTGGGGTT
ACAGATGCCT GCTACCACAC CCAGCTAATT TTTTTCTTTT TTTGGAGACA GTCTCACTCT
GTCGCCCAGG CTGGAGTGCA CTGGCGTGAT CTCAGCTCAC TGCAACCTCC GCCTCCTGGG
TTCAAGCGAT TCTCCTGCAT CAACCTCCTA AGTAGCTGGG ATTACAGACG TCTGCCACCA
CATCAAACTA ATTTTTGTAT TTTTAGTAGC TGAGATTATA GGCTCGTGTC ACCACGCCTG
GCTAATTTTT GTATTTTTAG TAGAGACGGG GTTTCACCAT GATGGCCAGG CTCGTCTTGA
ACCTCTGACC TCAAGTGATC TGCCCATCTC AGCCTCCCAA AGTGCTGGGA TTACAGGTGT
GAGCCACTGG GCCTGGCACC TGGTTTATTT TTGTGCATGC TTTTATTTTT AATTTTCCTA
TGCTACTTTC TTAGCCAAAA TTTATACTTA ATCTAATCAA GCATTAATCT AACAAAGAGT
TTAGTGTTCA TATAAAATAC AGTTTTACAA ATCTGTTTTT CTTTAAATTA TAAATTTGTT
AAGAAAATTA TCCAAAGAAT GATCCAGAAA CAAAAGAATG GCTGTGTGTC TTTTCAATAT
CATCCTGGAG CATTGTCTCA ACCATCTCAC TTTACGGTGA CTAAAACATC TAGAGGTTTT
CCCTTTGTTT TCTGTACTTC TTAGTATTGA TTAATACTGT TGTGCTACTT CAGTCTGAAG
TTCCATGTTA ATCTGTAGAT TTTTTTTTTT TTTTTTGAGA CAGTGTCTCG CTCTGTCGCC
CAGGCTGGAG TGCAGTGGTG CGATTGGCTC ACTGCAAGCT CTGCCTCCCA GGTTCAGGCC
ATTCTCCTGC CTTAGCCTCC CGAGTAGCTG GGACTACAGG TGCCCGCCAC CACGCTGGGC
TAATTTTTTC TATTTTTTTT TTTAGGAGAG ACGGGGTTTC ACCGTGTTAG CCAGGATGGT
CTTGATCTCC TGACTTCGTG ATCTGCCTAC CTTGGCCTCC CAAAGTGCTG GGATTACAGG
CGTGAGCCAC TGTGCCCGGC TGTTAATTTG TAGATTTTTA TACAGAAAAG CAGCAAAATA
TTTCTGTTGA GTAGAAAATA TAACTCCAAT GCTTATGACT GTATTCCTTA TAGGACACTA
ACTCATTATG TGTCTAACCT AGCAATTTTA TGTCAACACT ATTTTCTCAA ACCTCTATAA
ACTTTGGCTG GGCACAGTGG GTCACACCTG TAATCTTAGC ACTTTGAGAG GCTGAGGCAG
GTGGATCACC TTAGGTCAGG AGTTCAAGAC AAGGCTGGCC AACATGGCAA AACCCCATCT
CTACTAAAGA TACAAAAAAT TAGCCAGGCA TGGTGACATG CCCCTGTAAT CCCAGCTACT
CAGGAGGCTG AGGCAGGAGA ATCTCTTGAA CTCAGGAGGT GGAGCCAAGA TCATGCCACT
GCATTCCAGC CTGAGCAATA GGGTGAAACT GTGCCTCAAA ATGAATAAAT AAAATAAATA
AATAAGTCAG AGATTGTGAA TAGGATGTTG GATATACCCA AGTTATGAAT TAATTAGGAG
CTTGAACCCA GGAGGCAGAG GTTGCAGTGA GCTGAGATCG CACCACTGCA CTTTAGCCTG
AGCGATAGAG TGAAACTGTG TCTCAATCAA TCAATCAATC AGAGATTGTG AGTAGGATGT
TGGATGTACC CAAGTTATGA ATTAATTAGG AGCTTGAACC CAGGTTTGTC TCAGATCCTC
AGGGACTGAA GACTTCCAAG TGAATTATGG GTAATGTATA GGTCTATACT ACTCCAAATT
TACAGTTTTC AGACTTCCCT GGGTTCTCAT GGACCTTCCA TGTCATTTCT ATGTTTAGGT

Figure 11D

```
TGAGGTCCCT GGTCTTTTCT CCTCTGTAAT TAATTTCACA CCCACCCCTA TCTCAACTCA
CACAACTTGA TCTTCACTCC CATCTGCTAA GAAATTGAGT CCATAAAAAG TGAACTCCTT
TAAACTCTAG ATCTTCTACT GCTGCAAGGA CAGACATTCC ATTCTGGCTC TCTCTCTCCT
CCTTTGCTTC TTCCAGTCCT TTGCTCCTTC TGCATTCTGT TACTCTCCTC TCTCCTTTGT
CTTCAATCTC TCCCTCTTGC AATAGCCAAC TATAAACTGC TCAAGCTTCT CATTCTTAAA
AGATCTCTCT GAAATGCAAA TTCCCTACTG CCTTATGGCT CTCCTTCAAA AGTAATCTAC
ATTTTCTCTA TTTTCTAATT CCTCAACACA CTAACGTTTG AACCCTGCTT CTATGACCCT
GACCTAAATT TCTATTAAAT GTACATAGAT AAACTAATAT ATATTTGTGA CTTCCTAATA
TTGTTTTGTT TTTTAAAGAG GTCAATCTTA CTTTAACTCT GTAATGATGC GGTTGACCTT
CTGATGATTC TCTACTTCTG TGAAATCCTC TACTGTCTTG ACTTTTTAAT TAATTTATTT
TTTTTTGAGA CGGAGTCTCG CTCTGTTGCC CAGGATGGAG TGCAGTGGCA CAATCTCGGC
TCACTGCAAG CTCCACCTCC CGGGTTCATG CCATTCTCCT GCCTCAGCCT CCCGAGTAGC
TGGGACTACA GGTGCCCGCC AACACGCCCA GCTAATTTTT TTGTATTTTT AGTAGAGACG
GGGTTTCACC GTGTTAGCCA GGATGGTCTT GATCTCCTGA CCTCGTGATC TGCCTGCATT
GGCCTCCCAA AGAGTTGGGA TTATAGGCGT GAGCCACCGC ACCTGGCCCT ACTGTCTTGA
CTTTTATAGG GTCATTCTAT TCAAGCTCAT TGAGCGTCTG TCACTATGTT TTTGATCTGT
ATTGCTGGAA TCAGTTCCTC TATCTGCCTT GTGAATATTC TCCATTGTGC TAATCTAGGC
      >>.........................Exon?.........................>
TTCTCCTTTC ATTTTTCATA TTCCCTCACA TGGCTTTATA CACTCTTGTG GTTTTAACCA
>>
CAATATAGGG TTTTTACTGT AGTTATGCTT TCAAATTGTA TACTTCTTTT TTTTTTTTTT
TTTTGAAATG GAGTGTTACT CTGTTACTCC AGTCTGGAGT GCAGTGGTAC GATCTTGGCT
CACTGCAACT TTCGCCTCCC AGGTTCAAGC GATTCTCCTA CATCAGCCTC CCGAGTAGCT
GGGATTACAG GCATGTGCCA ACACGCCTGC CTAATTTTTT ATTTTTAGTA GAGACAGGAT
TTCACCATGT TGGTCAAGCC CGTCACAAAC TCCTGACCTT AGGTGATCCG CCCTCCTCGG
CCTCCCCAAG TGCTGAAATT ACAGGTATGA GCCATCGTGC CCAGCCCCAA TTGTATGTTT
CTAATATGAC TTTTCTCCTG AACTTTAAAC TGTGTATCCA ACTTCTCAGC ACAGTCATAT
CTTTTGATTC CACAGGTAAT TTAATGTCAA TATATTTAAA AATGAATTTA CCACCTTTAT
CCCCACTCTT TGACTTTCAC CTGCATTTCT GTTTCAATTC TTGTTTCCAT CCATTCATTT
GCTCACCTAA TTCATAAACA TGGAAATCAT CCTCAATTCC TCTTCTTCTT AGCCCAAAAA
TTCAATTGTG CAGGTTATGC ACTGAGAAAA AGAGCCTCAG GTTAGGGGGA TAAATCAGAG
ATTGGTGAAC TTTTTCTGAA GGGCCAAATA CTAACTGCTT TAAGCTTGCT TACCATATGG
TTTATGTTGC AACTACCAAC TCTCCTGCTG TAATGTAAAA GCAACCATAG ATAGCATGTA
AACAAATGAG ACAGGCTGGG TGCCAATGAA AATTCACGAA AATTAATGTA GTTTACTGTC
CCTTGGGTGA GAGTTGGGGG TCACTGAAAT TCGGACTATG TCTTACTTGG CTAAACCACA
GGCCTAGAGT GGGCCATAAA TGGAGCTATT GGGCTAGTGA TTTTCTTGCC TTAAGCCCCC
AGCCCCAAAT TTAATAATCA CATCATTTTA ATTTCATTTT CCAAGTGTAT CTTTAATATA
TGGCTTCTCC TTTCCAAATT CACTGTCATT ACCTAAGTTT AGTCCTTGAA CAATATTTTA
AAGGCTTCCT TATCTGACTT TATATCTTAA AGTCCTACAA ATTTATCTTC CTAAAATTCA
AATCAAACCA TGTCACCAAC TTACAGAAAG GGAAAATTCA TATATTCTAC ACACAGCACA
TTTCATGTAA CTTTCTAGGC TCATCTTTCA TCATCCTTTT GATGCAGGAT TTTCTGCTCC
TCAGCTCAGC GAAATCCAGG ATCTTGTCTC ATGACCAGGA AGAATTAGGC AGGTGGACAT
AGTGAAGGGT GAGGATGACG GAATTTATTA AGCAAAAGGG GAGTTCTCTG CAAAGAGAGG
GGTTTCACCA GCAGTCTCCC ACCTCACAAT GGAGCACCAG GACTTTCACA CACAAACTGA
AAAGGCTAGG CTCCTCCCCA GCATAAGGCA TGAATTCCTG GTGGTTCCAC CAGTTTTCCT
ACTATGCATG TGGGTGTGCC CAAGCAAACC ATAGGTAGTA TCAGAAAAGG CAACATTTGA
TTGGTTAAAA GGCATTATTC ACCCAAGCAA ACCATAGGTA GTATCAGAAA AGGCAACATT
TGATTGGTTA AAAGGCATTA TTCAGAAAGA ATCAATCGGG AAAGGGTGAG CCAATAGGGG
AAGTTCTCCC TCTGGGTCAC GGGTTTCATC TGGGACCAGG AGTCTGGCCT TTCAGCCTTT
AGACTGTTTT AGGCTTGAAG GTGGGTTTCA CAGGGACCCT TCCCTATCTG CCTAGGCATC
TGTCTGCCTC CTGCCTCTAT CACTTTCTCT TGAGTTTTAT ATTTTAGCAA CACTGAGTCA
TCTTTGTCCC AGGAAGCACC TACATCTGTT TATCTGCTGT CCCCTCTACC TTTACTACCT
TCCCTTCTTC ACATTTATAC CCAGAAAAGT CACTTCCCCT CCAAAAATTG GGATCAACTG
TCATATTTTT ATGAATATTT CACTTTAATT CCTCACAACA GCTGACAGAA TTAACTACTT
CCTCTTCTTT GCAAGTTATT TGGCTCACAC AGATATCAGT AATTAAACAT ATTTTACTGC
ATTGGCATAT ATCTGACTAA TGTGTTTTTC TCCCGTACTA GGCAATATGC TCCTTAGTCA
TCTGTGTATC TGAGGTGAGC ACAGGGCCTA ACTAGCATAT GGTGCATTCT CAATGTTCGT
TCAACTGCAT TGACTTGAAT TCCCCTGAAG ACTGAAATGT GAAAATAGCT ACTCTCGGAA
GCCCCTTTCC AGAGAGGTCT AAAATATTTA CATGTTTCTA TTTTAAATGC AGAAAGAACT
```

Figure 11E

```
                                                                    >>..>
TCCAGATCAT TATAGGCCTT GGATGGAAAT TGCCAACAAA CTTCCTCAAT TGATTGATGC
>...........................exon 2 ............................>
TCACCAGCTT CAAGCTCATG TGGACAAGGT ATTCTTCTCT TCACCCCCTC ATCACATTCT
>..............exon 2...............>>
GTTTTCATCA TCATACCACT TTTCTTTCTT AGCCTTGTGG AAGTGTGTCA ATTGTCCTGG
GAAACTGTTC ATTACCATTG AACTTATCAG CAAAGCTATA TCTTCCTTCC TGAAAAACAG
AATGACCCCT TCGTAATCTG ATACATGTGT TTTCCTAAGG TTTTCAGAGC CAGCACAAAA
CAATGCCTGA CACATGCCAA TAACTCACCA AATGTTTGTT TAAAGAAGAA TCTGGGTGGG
AATGATAAAC TAACTAATGG ACAAGGTATC GCCTAAGAAG GTCAGCTTGG AAATTCTCAG
GTTCCTCATT CCATGTACGT ACTCAAGGCT CTGTTGTTAC TGAGGGGGTC TAACTTGATT
TTGTCCTAGG TGTTATAGAA TAGTTAAATG GAGGGAATTT CTGAATTATA AAATTGGCCA
TGGGTTCTAC AAAACATCCA ATAAGCCTGT AAATTCCACA AAAGTGTTGA TTAGGCTGAT
ACAAAGGTAA TTGCAGTTTT TGCCATTACT TTTAATGACA AAAACCACAA ACACTTTTGT
ACCAACCTAA TAGCTATGTA ACCCTGAAAA AGTTACTCAA CTCTGTAATC CCATTTCCTT
ATTTATAAAA TGAGAGAAAC TCTGGTCTCA CAGTATTGTT ATGGGAAGTA AATCACTTTC
AAAGTGGCCC TTTTGTAGTT CTTGTCCTAT AATAGCATTC AGTATACATT CATTACTTCT
CTGTAGTCTC TTCTCCATCT GTCCTAATCT ATCAGTTTGG AGTACCACAT AATTGCGGAA
GTCCATGAAA AGTTTTCCGC TCTCCAAAAT TTCCCTTTGC TGATGGATAA TATTTAATGT
CTAGAATTAC AAATTCTTTT TAAAATACTC ATTGAATGTT TGCTTTGTGC AAAGCACTAG
AACCTTGTAA AAGATGAGTA AGGGACTGGC TTCAATGTCT GTGAAGATAG CAAACTAAAC
AGAGTAATTT CTTTGCCTGA TAGATAAAAT GTTGTGTTGA CATGACCAAA GAAATCCAAA
AATAAGAAAA AAACTATCTG TAAACACAGA AAAATAGAGA AAAGTTCCAA TGATGGAATA
AAAATTTAAA GGATTTTTTT GAACGTATTA AGCAAATCAT GTATAAAATC CAGAAATAAG
TTTACAGGAC CCATGTCAAG GATTTAACCA AAGCAGAGGG AGATCCCCAT GAGTCCCCTT
TTCCCATCTC AGAATAGCAG AGAAGAGAAG CAAGGGAAGC CTGGAACAGT TGGCAAGAGG
GCAGGTTAGA ATTCAGTTTG TGAATTATGA GGTCGTCTGC CGTAGGCATT TACCAGGCTT
TATTTGATTT AACTGCCATA AAGGAAGAGA AGGACTTGTT AAATTGGGGC TCCTCTTAGC
ACAGCATTGA AACCAGTCCC TATTCCTTCT TGGCCTTTTG GCTAAAATTG AGTGTGAAAT
CTATCACCTA ACATTTGTAC TGGGTTTAGG CTGGGTGTGG TGGCTCACGC CTGTAATCCT
AGCACTTTGG GAGGCCAAGG CTGGCGGATT GCCTGAGCTC AGGAGTTCGA GACCAGCCTG
AGAAACATGG TGAAACCATG TCTCTACTAA AAATAGAAAA AATTAGCAGG GTATGGTGGC
ACATGCCTGT AGTCCCAGCT ATTTGGGAGG CTGGGGCAGA AGAATCACTT GAACCCAGGA
GACAGAGGTT GCAGTTAGCT GAGATCACAC CACTGAACTC TAGCCTGGGC CACAGAGTGA
GACTCTGTCT CAAAAAACAA AACAAAACAA ACAAACAAAT ATATATATAT TAAAATACAA
ATTTTTACTG GGTTTAATAG TGTCTTCCTA GAAGTCATGT TCATGCATAA TCTGTGAAAG
TGGTCTTATT TGGAAATAGG GTGTGTACAG TTGTATTCGA GTTAAGCTGA GGTGATACTG
GATTAAATTG TATATGATGA GTGTCCTTAT AAGAAGAGGA AAAATTAAAC ACAGGAACAT
AGACTCAAGG GAAAACATCA CGTGAAGATG GAGGTAGAAT TGGAATGATG CATTGACAAG
CCAAGATGTG CCAAGGATTG CTGGCAGTCA CCAGGAGTTA GGAGACAGGC ATGGAACAGA
ATGGAACAAA TTCTCCCTCA GAGGCTCCAG AAGAAATCAA CCCTATTGAT ACCTTAATTT
GGGACTTCTA TCTTCCATAA CTGTGGCAGA GTACATTTCT GCTATTTTAA GTCATGATGT
TTGTGGTCAT TAGTTATGGC AGCGCATAAA ACTAACACAA CACTCTTGGT CTCTATCGCT
TCTTTTTTTT TTTTTTTTTT TTGAGACAGA GTCTCACTCT GTCTCCCAGG CTGGAATGCA
GTGGTGCAAT CTTGGCTCAC TGCAACCTCC AGCTCCCAGG TTCAAGCAAT TCTCCTGCCT
CAGCCTCCTG AGTAGCTGGG ACTACAGGCA CCCGCCACCA TGCCCATGTA ATTTTTGTAT
TTGTAGTAGA GACGGGGTTT CACCATATTG GCCAGGCTGG TCTCGAACTC CTAACCTTGT
GATCCACCAG CCTCAGCCTC CCAAAGCCCT GGGATTACAG GCCTGAGCCA CCATGCACGG
CCTCTATCCC TACTCTTAAT TGCCTGGAAA ATACCTAACA AATGAAGGCC AGTTTTTAGA
CTTTACCACC AAAGGCTGAA ATTGAAACAG GAATTGTTTG TGAGAAGCAA ACACAATAGT
TTCGAGAGAC TGAATCAGTT AGCAATTTCC TGTGAGAGGC AAATGTAATA GTTTCTAGAA
CCACAGATGG AGCTATAACA AAAACATGTG TTCTCTGGAT CCTTTACTTG CTACAGACAA
CACAATAAGT GAATTTACAG CTTTGATCTT ACAGTGCACC TAAGCCAACC ACCTTGTCTT
AGAATGTCTC AACATACCTA TCTGTATCTT GAAACAAAAT ATATTAATTG CCTTAGACCC
ATTCACTCAC ATTTCCTAGG AAGACATGAT CAGAGGGAGC TATGCAAGAA GAAATCCAGC
AGAACTCTGG AAATACAATA AGAAAATCCA TATTAGACAC TAATCTTAAT AAAACTAACC
TTCGTTCATG AATTTGAATA GACAAAATTA CCAAATAATA TGGAAAAAAT GGGCAACTCA
AAAAGAAGAG GGTAGCCCAC TTGGCATTCA GGACCAATGG CCTCCAATAA ATAAGATGAT
ATTAGTGCTT TAAATATTTT ATTTAGTGTA TCCAGTATAT TGCCTTCCTA AATTAAGTGA
```

Figure 11F

AAGCTGATAT ATAAAAAGAA CTATTAGAAA TAAAAAACCA CACACATCCC AGAACTCCTC
AATATAAACC TAACAAATTC AGTAAAACAT TGATTGCAAA AAATATATAT AGTGACTTAG
GGACTTCCTT GATAAATTTC ATAAAGCATA AAGAAAAATC AAAGAGTGCA AACCATCAGA
AAAATACAAA TATATAAAAA AGAGAAATAC AGGTGATCCA AATTCCTTTT AATGGAATCC
CATAAGCAGA TGGGTGGAGG AAAAGTAAAA CTTCCAACAT ATAAGCACAA AATTTTTAGA
CCTTAAGAAA TATTTGAGTT TTTTATATCA GAAAGACAGT GTTGGGGTGA GGGTTGGGGG
GCACATGTAA ATACTCAGAT AAAATTGTGA ATTTTCTAGG GTAAAGAAAT CTGCATATTC
ATAGAAAACA AAAATGAAAA ATAGTTTATT TACAGAGTAA ATACATACGA CTGTTTACCT
GTAATGCTAA ATATTAAAAG ACAGTTTCTT TTCTTTTTTT TGAGACAGAG TTTCACTCTT
GTCGCCCAGG CTGGAGTGCA GTGGTGCTAT ATCGACTCAC TGCAACCTCT GCCTCTGGGT
TCAAGCAATT GTCCTGCCTC AGCTTCCCGA GTAGCTGGGA TTACAGGCAC CCGCCACCAC
ACCCAGCTCA TTTTTGTATT TTTATTAGAG ACGGGGTTTC ACCATGTTGG CCAGGCTGGT
CTCAAACTCC TGACCTCAGG TGATCCACCC GCCTTGGCCT CCCAAAGTGC TGGGATTACA
GGCGTGAGCC ACCGTGCTGG CCTAAAAGAC AATTTCATAC CTATTTGTAT GGCTAATTTT
TTAAAAATCT GGCCATATCA AAATACTGAA GAGGACGTAT AGCAATAGAG ACTTTCATTC
ATTGCTGGTT GAAATGCAAA ATGGTACAGC CAGTTTGAAA ACTAGCTTGG CAGATTCTTA
TAAAATGAAA CATAGATTTA CCATGCAACT CAGCAATGGC ATTCCTAAGC ATTTATCCAA
GTAAATGGAA AATGTATGTT CCCAGAAAAA AAATCCATAT ATGAATGTTT ATAACAGCTT
TATTCATAAT CACCAAAAAA AAAAAAAAAT CTGGAAGAAA ACAGGATATC CTTCAACCGG
GGAATGAATA AACCAAATTA TAATAATTGT AAATTGTGGG ATGGATAGTG GAATAGTATT
CAGCGATACA AATGATTGAG CAATTAATTT GTGCAATGAC AGGGATGAAC CTTAAATACA
TTTACCTAAA TGAAAGATGT CAGGCCTATA TTGTATGATT CTTTTCAAAT GACTTTTTAG
AAAGGGCAAA ACTAGAAGGA TTAAATATAG CTTTATGGTT ACTAGAGACA GGTAAGGAGT
GGGTAGTTGA CTGCAAAGGT AATATATAGG GGAATGTTTA GCATGATGAA ACTGTTTTAT
ATGGCACTCA GGTGATGGAT ATATGGCTCT AGGCACTGAA AAACCCATGG AATTGTATGT
CACAAAGAAT GGACTTTCAT GTATGCAAAT TTTAAAAAAT AAACCAGAAA ATTGGGAGAA
TACTAGGATG GAATGCAGAC TGTGATAAAT AAAACTAACT GGACTCTCAG CAAACTAACA
CAGGAACAGA ACACCAAACA CCGCATGTTC TTACTTATAA GTGGGAGTTG AACAATGAGA
ACACAAGGAC ACAGAGAGGG GAACATCACA CACCGGGGCC TGTTGTGGGG TGGGGGGCTA
GGGGAGGGAG AGCATTAGGA CAAATACCTA AAGCATGAGG GGCTTAAAAC CTAGATGATG
GGTTGACAGG CGCAGCAAAC CACCATGGCA CATGTATACA TATGTAACAA ACCAGCACAT
TCTGCACATG TATCCCAGAA CTTAAAGCAA ATTTTTAAAA AAGTAAAAAA AAAAAAAACA
AACAACAACA CCTAACTGGA CTACAAATGC ACTATATAAC TTCGATGAAG AGAGTGGGGA
GTAGGGAAAG GAACGGACTT AAATTACTCC AGAAAATAGT GTTGTGTTGT GACTAGAATC
TATAAGGCTT ACGGTAAATG AAACTTTACA GGATCACTAT ACTCTAATTG GTAAATCAGT
TTTTCATGGG GTGCGGGTGA ACAGTTGTGA AACTGCTTTA CATGTAGTCA TACCTTTGCA
TTTTGCAGAT ATTTCAATTT TTACAAATTG AAGATTCGTA GCAACCTTGC ATCAAGCAAG
TCTGTCAACC CCATTTTTCC AATAGTGTGT ACGCATTTGG TGTCTGTGTG TCATATTTTG
ATAATTATAA CAATAGTTAA AACTTTTTCT TTACTATTAC ATCTGTTACA GTGATCTGTG
ATCAGTGATC TTTAATGTTA CTATCATAAT CGTTTTGAAG GTGCCATAAA CTGTGCCCCT
ATAAGTCCTG AAACTTAATT GATAAATGTA TGTGTTCTGA CTGCTCCACT GACCAGCCAT
TGCCCCATCT CTCTCCCCCT CCTCAGGCCT CCTGATTTCC TGAGACATAA TAATATTGAA
ATTAGGCCAA TTAATAATCC TACAATGGCC TCTAAGTGTT CAAGTGAAAG GAGTTGCATG
TCTCTCACTT TAAAAATCTA AAACTAGAGG CTGGTCATGG TGGCTCAGGC CTCTAATCCC
AGCACTTTGG GAAGCCAAGG CGGGGAGATC ACCTGAGTTC AGGACTTCGA GACCAGCCTG
GCCAACATGG CGAAACTCTG TCTTGACTAA AAATGCAAAA ATTAGCCAGG CATGGTGGTG
CACACCTGTA ATCCTAGCTA CTCAGGAGAC TGAGGCAGAA CAATCGTTTG AACCCTGGAA
ATGGAGGTTG CAGTGAGCCT AGATTGTGCG ATTGCACTCC AGCCAGGGCA ACAAGAGTAA
AACTCCTTCT CAAAAAAAAA AAAAAAAATA TCTAAAGCTA GAAATGATTA AGCTTGGTGA
GAAAGTCATG TCAAAACCAG ATAGGCTTAA AGCTGGGCCT CTTTTGCCAA ACAGCCAAGC
TGGGAGTGCA AAGGAAAAGC TTTTGAAGAA AATTAAAAGT GCTACTCCAG TGAACATACG
AATGATAAGA AAGCAAAAGA GCCTTATTGC TGGTATAGAG GAAGTTTGAG TATTTTGGAT
AGAAGATCAA ACCAGCCACA ACTTCCCTTA AACCAAAGCC TAATTCAAAG AAAGGCCCTA
ATTCTCTTCA ATTCTACAAA GTCTGAGAGG GCTGAAGAAG CTGTAGTAAA AAAGTTTTAA
ACCAGCAGAA TCTGGTTCAT GAAGTATGAG GCTAGAAGCC ATCTCCACAA CATAAAAGTG
CAAGGTGAAG CAGCAAGTGC TGATGGAGAA GCTGCAGCTA ATTATCCAGA AGATCCAGCT
AAAATCATCA ATGAAGGTGG CTACATTTAT TTTTTATTTT TGTTATTTAT TAATTTATTT
ATTTTGAGAC AAAGTCTTGC TCTGTCCCCC AGGCTGGAGT GTGGTGGCAT GATGTTGGCT
CACTGCAACC TCCACCTCCT AGGTTCAAGC AATTCTCCTG CCTCAGCCTT CCCAGTACCT

Figure 11G

```
GGGATTACAG GCATCTGCCA CAACGCCTGA CTAATTTTTG TATCTTTGGT AGAGACGGGG
TTTCACCACA TTGGCCAGGC TGGTCTTGAA CTCCTGACCT CAGGTGATCC ACCCGCCTTG
GCCTCCCAAA GAGCTGGATT ACAGGCATGA GCCACCACGC CTGGCCAGTG GCTACATTTA
AAAATAGGTG TTCAATGCAG ACAAAACCAT CTTTTATTGG AAGAAGATTC CAACCAGGAC
TTTTTTTTTT TTTTTTTTTT TGAGACAGAG TCTCACTCTG TCGCCAGGCT GGAGTGCAGT
GATGCGATCT CAGCTCACTG CAATCTCTGC CTCCCGGGTT CAAGTGTTTC CCCTGCCTCA
GCCTCCTGAG TAGCTGGGAC TACAGGCACG TGCCACCATG CCCAGCTAAT TTTTGCAGTT
TTAGTAGAGA CGGGGTTTCA CCATGTTGGC CAAGATGGTC TCTATCTCTG ACCTCGTGAT
CCACCCCCCT TGGCCTCCCA AAGTGCTGGG ATTACAGGTG TGAGCCACTG CGCCCGGCCC
AGGACTTTCA TAGTTAGAAA AAAGTCAATG CCTAGCTTGA AAGGACAGGC TGACTCTCTT
GTTAGGGGCT AGTGCAGCTG GTGACTTTAA GTTGAAGCCA GTGCTCATTT ACCATTCCTG
AAATCTTAGG GCCCTTACCA GCTATGCTAA ATCTACTCTG CCTGTGCTCT GTAAACGGAC
AATAAGGCCT GGATGATGGC ATATCTATTT ACAGCATGCT TTACTGAATA CTTTAAGCTC
ACTGTTGCGA CCTACTGCTC AGAAAAAAAT ATTCCTTTCA AAATATTACT GCTTATTAAC
AATGCCTCTG GTCACCCAAG AGCTCTACTG GAGATATACA GGAAATAAAT GTTGTTTTCA
TGTCTGCTAA CACATTTGTT CTGCAACCTA TGGATCAAGG GGTCATTTTG GCTTTCAAGT
CTTATTATTT AAGAACTATA CTTTGTAAGG CTATTCCTGA CACAGATAAT GATCCCTCTG
AAGAATCTGG GCAAAGTCAA ATGGAAACCT GGAAAGGATT CACTATTCTA GATACTATTA
AAAGCATTCA TGATTCATGG AGGACGTCAA AATAAAAACA TTAATAGGAG TTTGCAAGAA
GTCAACCCTC ATGGATGACT TTGAGGGGTT CAAGACTTGA GCAGAGGAAG TCACTGGAGA
TGTCGCAGAA ATAGTATGAG AACTAAAATT AGAAGTGGAA TCTGATTTTA TAACTGAGTT
GCTGCAATCT TACGATTGAA CTTTTCTTTT CTTTTTTTTT TGAG

ATGCCCCTGC TGAGCTGCCA GTTCCTGAAG GGTCACCGGG AGCAGCGCCT GGCCCACCTG
>>..........................EXON3 ...........................>
GTCCTGAGCT TCCTCACCAT GGGTTATGTC TGGCAGGAAG GAGAGGCGCA GCCTGCAGAG
>..........................EXON 3 ...........................>>
GTGAGGGCCA GAGAGCAGCT TCTCCTGTTA CCCGGCAGGT TACCTGCGCC TGGAGTAACG
TGCTCCCTGC TTGGTGCTAC CCTGTTTTCC TGGAAAATGG GTACTTTCTT CTTCTCGATG
GGCATCAGTT TAAGCAACGA TGAAGGGCTC ATTTATTATT TATTATTATT ATTTTTTTAT
TTTATTTTGA GCCAGTCTCA CTCTGTCACT CAGGCTGGAG GGCAGTGGGG TGATCTTGGC
TCACTGCAAC CTCCCCTTCC AGGTTCAAGC AATTCTCCTG CCTCAGCCTT TCTTGTAGCT
GAGACTACAG GCACCCACCA CCACACCTGG CTAATTTTTG TATTTTTAGT AGAGATGGGT
TTCACCATGT TGCCCAGGCT GGTCTCGAAC TCTTGACCTC AGGTAATCTG CCTGCCTGGG
CTTCCCACAG TGCTGGGATT ATAGGCGTGA GCCACTGCGT TCAGCCTGAA GGGCCATTTA
AATGAAGGAT TTTTTTATTT TAATTTTTCT GACTAAGAGC TAATTTGTTT TTTAAACTGG
TAGCTATTTC TTCCTTTTAT AAGCTTTTGA ATGTTTGTTT GTTTGTTTTT GGCACTCTCT
TCCAAGAATG TTTGAAGACC TGCATTTGAA GGCAGATTGC CTTTTTGCTT TAAAACAGGG
TTGCACCATG TTGCCCAGGC TGGAGTGCAG TGGTGCAATC ATAGCTCACT GCAGCCTCAA
CTCCTCCCAG GCTCAAGCAA CCCTCCCACC TCAGCCTCCT GAGAAGCTGG GGCTACCAGC
ATGTACCGCC ACACCCAGCT AATGTTAAAA ATTTTTTGTA GAGATGAGGG TCTTGCTGTT
TTGCCCAGGC TGATCTTAAA CTCCTGGCCT CAAGTGATCC TCCTGCCTTT GCCTCCTGTG
CTGGGATTAC AGGCGTGAGC CACCATGCCG GGCCTGAAGA CAGACTCTGA GAATTCATAA

                                                      SapI
                                                    ---------
AAACCTCACA GCATTTTGTA CTCTTATGTA TATAAATTAT CTAGGTTGCT CTTCATAATC

                        Cfr I
                        ------
CTGTAAAGTA ACAAGAGCCA TACCGGCCCA TTTTACAACT GAAAAGCACA GACACTTATT
TCCTTAATCA AGGTCAGACA GCAAATTAGT GGAAAAGCCA AGGCCAGAAC CCAGGTCTTC

     SpeI
    -------
TGATTTTACT AGTGCAGCCT TCTTTCCCCA GGGGACACAT TGACATTTAC AACACTCATC
TTTATTTTTT TTTTAATACT GCTTTCTATC CAGCCAATTA TTAGTCTGTC TTTTAATAAT
TCATCCAAAT CTCTTCTGAA TCATTGCATA ACTTTGTACA GTTTCCACCC ACAGTGTCTT
```

Figure 11H

```
TTACTTTTAT TTTTGGAAGT AACTGTTTTT AAAAGTTACT GTTATTTTTA AAAGTGTGCC
TTCCCCAGAA ATCAGGGAGT TACCCATGTC CTAGAACTCC ACGGTGAAGA GAACAGCCTG
TGCCCATCGT GTTTGCCTGA TTGATCCTAC CTCTTGTCTC TCGGGGAAAC ACAGGAGACT
CAGGGAAGAG GAAAAGTGTA GAGTCATTGC AGCCTTGTTA TTTGTCAATG CATCTCTTTT
CTTTTTCTTT TTCTTTTTTT GATACAGAGT TTCACTCTTG TCGCCCAGGC TAGAGTGCAG
TGGCGTGATC TCGGCTCACT GCAACCTCGG CTTCCTGGGT CCAAGGGATT CTCCTGACTC
AGTCTCCTGA GTAGCTGGGA TTACAGGCAC CTGCCGCCAC GGCCAGCTAA TTTTTTTTGT
ATTTTTAGTA GAGACGGGTT TCACCACGTT GGCCAGGCTG ATCTCGAACT CCTGACCTCA
GGTGATCCAC CCACCTGAGC CTCCCAAAGT GCTGTGATTA CAGGCATGGG CCCCAGCACC
CGGCCAGTGC ATTGCATTTT TTTTTTTTTT TTCGAGACGG AGTCTCACTC TGTCACCCAG

                                             EciI
                                            -------
GCTGGAGTGC AGTGGCACGA TCTTGGCTCA CTGCAAGCTC CGCCTCCCAG GTTCACGCCA

                                           NarI
                                          -------
                                           KasI
                                          -------
                                           EheI
                                          -------
                                           BsaHI
                                          -------
                                           BbeI
                                          -------
GTCTCCTATC TCAGCCTCCC AAGTAACTGG GACTACAGGC GCCCACCACA ACGCCTGGCT
AATTTTTATA TTTTTAGTAA AGACGGCGTT TCACCATGTT AGCCAGGATG GTCTCGATCT
CTTGACCTCG TGATCTGCCC GCCTTCGCCT CCCAAAGTGC TGGGATTACA GGCGTGAGCC
ACCGTGCCCG GCGTGCATTT TTAAAAGTGT GTCTGATGCT GAAAAGTTTG AAGTCTAGGC
ACGTCCCAGT GGGTCCTCTT TATACCATCC CCTCTGCAAA CCATTATCCT AAATTGGGGT
TTGGGGGAGA GAAGAGTGAC AGTGGAAAGA AGTCTCCACC TCCCAGCTGT GCCCTGGTAG

      SanDI
     --------
TTCCAGGGGA CCCGGAGGCT CCCCACACCC ACCACCCCGC CTCAGATCAC CTTTCACTTT
CTTTGTTTCT CCTCCCTTGA CTTTTCAGCT CAGAAAGTAC CTGGCTCTCC AATGCCTTCT
GAGGAAAGTT TACCCGAGGT TCACATTGCA AGACTCATTA AAGCTCTTTA GTGTTTTCCA
CCCGAGAAAA AATTCAAGGG AAAAATGAAG ACAAAAGCAG GGCATTCTTA ATGGATATTT

  AflII
  ------
TATCTTAAGG AGAAATGAAA ATGGAGATGG AAGAGGGGGC ACAAGGATGG GGTTTGAATC
TAGACTCGTT CAGCCTTTAC CTCCGATAGA GAACCTCATA CAGCTTTTCT GGACTTCTGG
CTGATAAAGA GCCGTGGAGG GTTCCTTGGA TAAAAAAGGT TGAAGGGGGT CTGTCCTGTG
GTGGCTTACT TGAAGGTATT ACTGGGTTTG ACTTATGGAG TAAGAGACGG AGTCAGTTTC
CCCACAGGCT GAGGCAGTCT GTCCTCATGC TTTTCTAGGG CACTGTGGTC TCCCAGGCTC
ATACCTAGGT GCACACACAG GTTTCTGCAT CTAGCTTTGT ATCTCTATGA GTCGGTCAAT

                                                          NheI
                                                         -------
CAATAAATCT ATCTATCATC TGTCTACTGA TCTATCATCT ATCTATCTAG CTAGCTATCA
TCTCTCTATC ATCTATCTAT GTATCTATCA TCTCTCTCTA TATATGTGTG TATATATATA
TATATATGTA TATATATATT TCTATCCTTC CATCTACTTA CCTATCTATC AAAATTTTTT
TCCGTTGATA ATATTCTCGG GCCCCAGTTT ATGTTTAATT GTTTTGGTAA TGCCTTTCTT
TGCACAGTCA GTTTACAGAG GTTATTTTAT ATTCTATATG TATGTGTGGT CCAGCGTTGT
AATTTTCACA TATATTGCAC CGTGTACTCA TAAGCAGTAT TTCCACTGGG TCATTAACAG
AAAGATATGT GTGCGGCATA TGAATGTGCA TCACTCAGGT AATTCAAGCT TGGTTCCCAG
ATCATTTCTG TACCACAGGA TTGCCGAAAT AAAAGACAAC CATGGTTATT TCCTCTGCTG
CAAGCTTTCT AGAATATGCT ATTTGTCTGG ATTTATATCT GAAAGGTCCT GCCAAGGAAT
```

Figure 11I

```
                                                   >>...EXON4  ...>
CTTGCCCTTC CATTTGTCGA AGTCTCCAGG AACTTGGGGC TCCCTCCTAT CCTGGTCCAC
>..........................EXON4   ...........................>
TCAGACTTGG TGCTGACGAA CTGGACCAAA AAAGATCCAG ACGGGTAAGG AAGGAAGAGA
>..................EXON 4  ..................>>
ATGCTTTGAA TTTCCATAAC TTTCCCCCAG GAAACACCCA GGCTTTTTTT TATAATTAGG
GAAGTTCATA TTTATGGTCT GCCGTATGGT TCCAAAGAAG GGGTGAGCTT GACCAAAAAT
TCAAAATATCA CAGGCCCCAG AAGTTTCCTC TTAATCCATT CTGAACACAT TGGCTCAGAC

   DrdI
------------
CATTTTGTCT TGTTTGTTTC CACATGACGT GTGAATTTCT CAACCTGACC TTCAAGCTCC
TGCAAAATCA GCTTTTATTT GTTCTTTCTC TTCAAACTGT TTATTCCCTA AGATGCCCTC
CATTCATATC AGGTTAAAAC CAGTTGGCTT TGATAAGTAA TCATTATATA ATGATCAGAA
GAGAATGATT ATGGATGAAT TCAGAGCAGA TGCTCCAGGT GGGTTGGATT GAGAATTTGA
TTAATAATTC CATCTATTCC ACCAAAGTCA CATCATTCCT TTGACAGTTG GGCTGGGAAT
AGGGGCATTT GTCTACAGAA GGAATAGCAT GAGATTTTAA CAAACAAGAA ATTCAACAAA
CAGAATTAGA CAGATGATCT GAGATGTTAA ATTTTCCTTT CACCTTAATT TTTGCAGCCA
AATTTATTTC AGCTCTAGAT GAAAGAGACA GCACTTTCTT TTGTGGCTGA CTACAACAGC
TGAAGATTCA CTGAGGTTTG ATATGAGGAA GAACTTCCTC AGCCATGGGA TTGCCAGAGG
CGATGATGGG AATCTACTTA AAAGGGTTAC ATATTTAGTA GACAGCCTAG ATTTTAAGAC

                Eco  I
                ------
                BsiEI
                ------
TAATTTATGT GCCCCGGCCG GGCCCGGTGG CTCACCCCTG TAATCCCGGC ACTTTGGGAG
GCTGAGGCAG GTGGATCATC TGAGGTCAGG AGTTGAAGAC CAGCCTGGCC AACATGGTGA
AACCCCGTCT CTACTAAAAA TACAAAAAAA TTAGCCGGGC ATGGTGGCAC ATACCTGTAA
TGCCAGCTGC TCGGGAGGCT GAGGCAGGAG AATTGCTTGA ACGAAGGAAG TAGAGGTTGC
AGTGAGCGAA ATCATGCCAT TGCACTCCAG CCTAGGTGAC AAACTCTGTC TCAAAAGAAA
AAAAAATTAT GTGCCCCATT GGAAGAAGTG AGATTCGGCC ATCTCATCTC TCTCGGGAGC
TCTGAGCCCT GGAGTTTTAT GTTTTCTGCA ATTATGAATT GTGATCCTTG ATTAATTATG
CTTTAATAAT AAAATGGGTG ACTACTGAAA GCTGCTGAAT CTGGGTAAGA ATTTGGATGA
AAAAAATAAT ATATGTGCGT AATTTATTCT GTTCAAGGTA CTGAATATTG AATAAGCTGG
ATTTATTACT CAAAGAGAAA GACAGAATAA GAGAAGGTTG AAGGGAAAAA TGACTGTACT
AGAATGGTAG TCAAAAATGC AACAACAGGC AGGTGCAGCG GCTCATGCCT ATAATCCCAG
CACATTGGGA GGCCCAGGTG GGCAGGTCAC CTGAGATCAG GAGTTTGAGA CCAGCGTGGC

   SfiI
-------------
CAACATGGCC AAACCCCCTC TCTACTAAAA ATACAAAAAT TAGCCAGGTG TGGCAGTGGG
TGCCTGCAAT CCCAGCTACT CAGGAGGCTG AGGCAGGAGA ATCACTTGAA CCTGGGAGGC
AGAGGTTGCA GTAAGCTGAG ACTGCACCAC TGCACTCCAG CCTGGGTGAC AGAGTGAGAT
CCTATCTCAA AAACAAACAA AACAAAACAA AACAATAACA AAAAAGCTAT TAATAGCTTC
CTAGGGAGTA AGAGTGAAGG GCTAGTTTAA TTCCAGAGAT GCGGACACAG TCCTGGGTCT
CACCAATTAT TCTGCTTGGT AATTACCTTT TGAAGCCTTT TAATATGCCT AACACAGAGC
TAAGTGCTAT GAAGAAATGA AAGAAATAGA AGCAAAGTAC TCCCCATGTG GTTAAATAAC

                 PshAI
              -----------
AAGACACTAC ATGACAAATG TCAAAGAGTG ACTCAAACAA TATGTCCTTT AGAATTTCAG
AGAAATGACA TCAATGCAGG CTTTACAAGT CAGTAAAAAT CTTGGTGATG AGGCAGAACT
TGATGTAAGG CAAATCCTAA AAGTTGAGTA GGAATCAACT AGCTAGAATA AAATGTGGGG
TTGTGGTAAA TACAAAAATG TAAGATGAGT GAAATAACTT ATTTATTTAT TTATTTATTT
TCAGAGACGG AGTCTCCCTC TGTCTCCCAG GCTGGAGTGC AGTGGCATGA TCTCGGCTCA
CTGCAACCTC TGCCTCCTGG GTTTGAGCAA TTCTCCTGCC TCAGCCTCCT GAGTAGCTGG
GATTGCAGGC ACCTACCACC ACACCCGACT AATTTTTGTA TTTTTAGAGA GATGGGGTTT
TACCACGTTG GCCAGTCTGG TATCGAATCC TCGACCTCAT AATCCACCTG CCTCAGCCTT
```

Figure 11J

```
CCAAAGTGCT AGGATTACAG GCATGAGCCA CTGTGCCCAG CCTAATAATA TATTAAGATG
GCCACAGGCC AAATATTCTG GGGCTGGAAT GTGAGTGGAA ATGTCGCTCA CCCTTTATCA
CATAGCACCC CATAGTCCAG CCACAACTTG CAGAATTCAA AGTAAGTGTG GATGTGTGTG
TGCCTGCAGT GCCTTGCACA CAAGTGTGCA TGCCTGTGGA CATGTGACCC TAGAAGTTAT
TAATATATCT GGTTTACAAA CTGAATTGTT CTTTTATTTT TTTTCTCTCT TGGTGGTCAT
CAATAACTGA AATTGGGCTA GATTCCTGGA AATTGGGTAA GTTCTCAGAA ATCATTTACG
                        >>...Exon 5 ...>>
CACTTTAGAA TCCAGGCCAA ATTTAAAATC TTACAATAAA ACAAAGAACA AAGCATGCTA
AATTATATGT ATAATATAAT ATCAACCATA TAAAATGCAT AAAAAATATA CTAGAAGGAA
ATGTGCCTAA AATTCACAGT CTAAAATTTA ACAGTGATTG CCTCTTCCTT GTATAGATAA
GGGATTTTTT TTTACTGTAT TTTCCAGTCT GTACATAATA AAACAAGTAA TGTGCAATGC
AAACAAAACA AAATGAAACT TTATCAAATT TCAGTAACTC CTTGAAGTTT AATTTTTTTT
TTGAGACTGA GTCTTAGTCT GTTGCCCAGG TTGGAGTGCA GTGGTGTGAT CTCGGCTCAC
TGCAACCTCT GCCTCTGGGT TCAAGGGATT CTCCTGCCTC AGCCTCCCGA GTACCTGAGA
TTACAGGCAC CCACCACCAC ACCTGGCTAA TTTTTGTATT TTTAGTTGAG ACAGCGTTTC
ACTATATTGG CCAGGCAGGT CTTGAACTCC TGACCTCAGG TGATCCACCC GCCTTGGCCT
CCCAAAGTGC TGGGATTGCA GGCGTGAGCC ACTGCACCCA GTTGAAGTTT AATAGTGTGA
AAAAAATATT TCTCATCTCA CTATATCTTC TATGGGAGGC CAGATTGCAG ATTGTCTACA
GAAAAATCCC TTCAAAAGAC CTTGTTATTA CATAGACTGG AGCTCATGGG GCAGGTCTGG
TCCACACATC CTTAGGCTCC GCTTCTCCTG GAAAACAAAA ATAGCCTCTG ATCCAGTGTT
GCCTCTCCCA TCACCAAACC TCAGCTTCTA TCGCCAAACT CATCAAATAA GAGTGTCCAG
TAGAAAAACT GGGCAGATGG GGGCACAGAA GGTGAAGACA TCATTTCCCA AGCTAATGTT
GCTGCTGGAA CAATGTAAGT CTTGACTTTG TCTTGGTTTG GTTTGGTTTG ACATTGGTTT
GTTTTTCATC TTTGTCTCAT GCTTAAAATG TGAAGGGCAA ATATGATCCT TAGAGTTAAG
GTTTTAGGTT TTGTAGATGT TTTACTCCAT TTAAATGACA GCAGATCATT TAGAAATGAT
TCCTCTGTAA CAGCCTTCCA GATCCCATTC GATTGTACAG CATTGAGATA GATAGATAGA
TAGATAGATA GATAGATAGA TAGATAGATA GACGGAATTT GGCCCTGTGT TCCCACCCAT

                                          BamHI
                                         -------
ATCTCATGTC AAATTGTAAC CCCCACATGT CAGGAGAGGG ATCCAGTGGG AGGTGACAGG
ATCATGGGGT TGGATTTCCC CAATGCTATT CTCATGATAG TGAGTTCTCA CAATATCTCA
TTATTATTAT TATTATTATT ATTATTGCAA CAGAGTCTCA CTCTATCTCC CAGGCTGGAG
TGCAGTGGTG TCATCTCGGC TCTCTGCAAC CTCTTGCCTC AGTCTCTTGC GTAGCTGGGA
TTACAGGCAT GCCCCGCCAT GCCCAGCTAA TTTTTGTATT TTTAGTAGAG ACGGAGTTTC
ACCATGTTGG CCAGGCTGAT CTCGAACTCC TGACCTCAGG TAATCTGCCT ACCTCGCTCT
CCCAAAGTGC TGGAATTACA GGCGTGAGCC ACTGTGCCTG GCCAGTTCTC ACAAGATCTG
ATGGTTTAAA AGTGTGGCAC TTCCCCCACC TCCTGCCGCC ATGTAAGATG CTTGCTTACC

                                StuI
                               -------
CTTCCACCAT GATTGAAAAG TTTCATGAGG CCTCCTAGCC ATGCTTCCTG GTAAGCCTAA
GGATCTCTGA GTCAATTACA CCTCGTTTCT TTATAAATTA CCCAGTCTCA GGTATTTCTT
TATAGCAGTG TAAGAATGAA CTAATACACA CATAAACAGA TTAGAGGCAG CACTGGCCTG
AGTTGTGAAA CTCTTCCCAG CCTGGTCCTG CGATTAGCTG GCTATATGAC CTTGGACAAG
CTGCTTTGCT TCTCTGGGCC ATGGTTTCAT ACCTGCAAAA AAAAGAGCAT GGACTTGGCT
GTTGCCTGGG TCTCTCTAGC CCTGTGGAGA ATCAGCTACA TCTCTTACTA GGAACTTCTC
ATTCAGCCAG TTATTCCACT GCGGAGATGG TCCAGGACCA TTAGGGCCAT GCTAGACATT
GGGAGGCTGC CTGTCAGGTG AACATGAAAT TGAACTTATC TGTTCTCTTT CCTCCCTGAA
TGTTGCTGAA GGTAGATGCC CATCCTCAGG GCTGTCTTAC GGAGAGGAGA AAGTTGTGCA
GTGATTCCAC CCTGCAGTTA TCTAACTCGG CAGGGAACTC TGGGCAGTGA GTACTCACGG

                                       EcoNI
                                    ------------
TACAGTCTCC ACACCTCTAA TCATGTGCTC CTCTCCTTCC CAAGGAACCT GGAGACCATC
                                             >>....EXON 6 .....>
ATCTCATTTC CTGGGGGAGA GAGCCTGCAT GGTTTTATAC TGGTGACTGC TTTGGTAGAG
>..........................EXON 6 ............................>
```

Figure 11K

AAAGAAGCAG TGCCTGGGAT AAAGGTATCT TCTCACTTGA TAGCACCTTT TCTTTTTAAA
>........EXON6 .........>>

DraIII
---------
TGAGCTTGAG CTTTACTTCC CACTCAGTGC CTTTCCTGCA GTGGATTTCT CAACACAAAT
GAACATAGAC CTTGTCCTGC TTAGTTCAAG TCTGAGAGAA GAGATCTAAG CTCTAGGCCA

AhdI
------------
CCATATTTGC TCCCTTTTCT CAATTCCTAT AAAACTCGGA ATGGACCTTT TGTCCATTCA
ACAAACAGGC ATTGGTTTGG GCAATGGGAA ATTGGATCGA ACAAGACAGA CATTTTCCCA

BciVI
------
GCCCTGACAG AAGCTTATGA TGGATACAGT GGATGAAGAT GGATTAACGT GGATTACAGG
TGTGAGCCAC TGCACCGGGC CTCAAACTGG AAATTCTTCA GGAGTCAGAC AGGTATCAGG
AAGGCTGGAT AGAAGACAAA AGACAGTGAT GCAGCTTGTG ATCAACTACA GCGTTAATGC
CTTGCCTAAA AATATTTCAG TTAGATTTCT GCCTTCGCTC TGTCGCTCAG GCCAGAGTGC
AATGGCGTGG TTTTAGCTCA CTGCAATCTC CACCTCCCAG GTTCAAGCAA TTCTCCTCCC
TCAGCCTCCT AAGTAGTGCA CGCCACCACG CCTGGCTAAT TTTTGTATTT TTAGTAGAGA
CAGGGTTTCA CCATGTTGGT CAGGCTGGCC TCGAACTCCT GACCTCGTGA TCTGCTTGCC
TCAGCCTCCC AAAGTGCTGG GATTACAGGT GTGAGCCACC CTGCCCAGCC AACACTACCT
CCCTTGATAA GCATATGTTG AGCACCTACT GGTCCTCAAT AGGGTGACCC ATTTCTGCTA

Eco III
-------
TATTATAGCG CTTTCTTTCT CTCTCAGTAG TTAAACTCCA TGGTTACTTT AGTTCTCATC
CATGTGTTTA GTCCATTAGA AGATACAGAG TCAAATATCG GCCTTCCAAG TGTAGTTCAG
ATGAAGTAGA GACTCAAGGA AGACAAGGA

AGTCTTCCCA GCAGAGGGGA TTCTAGAGCT GGGGGCTCTG TAGAATCTGT CTGTGTATTA
GTCCATTTTC ACACTGTTAT AAACATACTA CCTGAGACTG GGTAATTTAT AAAGGAAAGA
AGTTTAATTG ACTCATAGTT CTGCATGGAT GGGGAGGCCT CAGGAAACTT ACAGCCATGG
AGGAAAGTGA AGGGGAAGCA AGAACCTCTT CACGAGGCAG CAGGAGAGAG AGCAAAGGGG
GGAGCTGCCA AACACTTTTA TACAATCAGA TTTTGTGAAA ACTCTCCCTC GTATCATGAG
AACAGTATGG GAGAGCCCAC CCCCATAATT CAATCACCTC CCACCAGGTC CCTCCATCAG
CCTGTGGGGA TTACCATCCA AGATGAGATT TGGGTGGGGA CACAGATTTC AACACAGATT
TAAATCTGAC TTTATATGAG AGCTTCGGAG CAAGGATGCC CCAGTTGGAG ATGCAGTAGA
ACTGATCATA ACGTGACAAA TCCGAGAGAA GAAGAGTAAA ATAATAGTAC TCAGGCCCTT
GGGAGGTGCA AGAAGTAACA GCCAGATGAA ATTCCAGAAA CACTTACCTA GGGGTCTGTC
TGGGAGGTCC CCAGGGAGCT TCTGGCTGTC AGGCCAACCC CACAGTGGAT CTAGCTTAGG
ACGTTCCCAG GAAGCTCTGA CAAACTGTCC GGTCCTCCCC TGGGTTCCAA CAGTATGAGG
CTTACTCTGC CTGCATGGAC TTTAAGGGAG TGCTAATAAG TTGTGTACAT GCATCTCATC
CCTAGGCTCT TGTTCAGGCC ACGAATGCTA TCTTGCAGCC CAACCAGGAG GCCCTGCTCC
>>.........................EXON 7 ..........................>
AAGCCCTGCA GCGACTGAGA CTGTCTATTC AGGACATCAC CAAAACCTTA GGACAGATGC
>..........................EXON7 ............................>
ATGGTAAGAT GCTTCCGAAG CTCCTGAAGG ATCCCCCAGG GGTCCTGGGC TCTGCTTAGG
>>>
GGAAGAGGGC CTGGGGACCA GGCATGTCCT GAAGGGGGTG ATAATACATT CATCCACCAG
ATGACGCTGG TGGACTATCT TTGTTTTAGG TTAAACACAT ATTATCTTGG AGAGCTATTG
TCACAGCTTT GTATTCTCCC TCTCCTTTAT ATTCTCCCGT GATTAAGATG GTTTCCCTTC
TGCAGTGGCC AGATATTTCT TAGGCATGTT GAGGTCTTGC CTGAAGCTTG AGAGGAGGGG
ATGGGATGCA CAGTAATGTT GGTCGCGCGT GCCCCATCCT GCAGTGTTAG GTACTGCAGA
GCAGGTTGTC TACACTCTGT AATGCCCCTT TTATTCTAAC CCCCTGTGTT GGTTCCTGAG
ATGTCTGACC TTGGTTTTAA GCCTTGTCTA ATGGATGGCC TGTATTCCCT TTCTGTAGCT
AGGGCAGGCT GATTTGTCAA AGGTAGGAAA GTTGTCAGAA TCAAAATGGA GTCACTTGTG
TTGAATAAAA ATTTTTAAAC CTTGACAAAT AGAGCTGGGG AAGGCTACAA AGAGAGAGCT

Figure 11L

```
CCCGTGTATA AATGCCTGAT AACAAAATCT TTTCCAAAGG ACTGAAAAAA TCACCACCTT
GCACAAAGGC CATCACAACC TTACATACAC AAAAAAATAC TTACACAACG ACATCTGCCC
AGCAACTGCC TTTCCAACAT TGGCCTTGTG CCACCCTTTT TATTGATGCT CATAGCCAAG
GTTAATGATC TCAAAACAGT TACATAATTG TCCTCATTTT TCCTTTAAAA ACCTTTGTCT
TCCTTTATCT TTCTGAATAC CCACATGGTT TATTATGGCA CATGTATTCC CATTGCAATG
CCCTATTCCA GAATAAATAT CAGTTTCCAT TAGGGAGCCT CTCCCTGTTA ATCTGCTTAA

                                        AgeI
                                      -------
CACAGGCATG GTCAGTTACG GGGCCCAACC TTCCTGGACC GGTTACATCT TATTCTGGTT
ACTGCATTCA GTTTCCAACA TCTGGGAGGC TCTTCAAATT CTTCTCTCAG AGGAATCTGA
AGAATGTATG TGTTTAGGAG GATGTGAGAG AGGGGTGTGG TTTCTTAACA AGAGAATATC
AGAGTCTAAG TATCATTTTC CCTGAATCTT GCTTCCCTGC AGGAAAGAAA GATTCTGGGA
AAAGAGAGTG TTTACAAGAA GCAGGACTGG AGGGAGGGAG AAAGACGCTA GGTACTGCCA
AGCTTTATTA TCTTGTATTA AAAAAGTAAA TATAATTTGT CATCCCAGCC TCTCAGCACT
AGTAGAAATC TATCTGAAGT CACAGGATTA GGTATTATCC ACTTCCTGGT TTTATAGTTT
ATATTTGTAT TTTCTCTATT TCCTTGAATT TTAATTTTAA AGCCCTCATG ATCACATCAG
TAGGTCTTCT GCCAAACAGC TCCCTTAAGT TGTATGGTGG CTTTGCCAAG CTGAAATGAG
ATGAGATGTG TTTTAGCTTT GCCAAGAAAG CCTGAGTCCA TCACTTAGGA TAGCAAGGCT
ATTAGGGAGA TAGTGCAGGT GTCTTCAGAT CACATGGATG AGCAAAAGGA AGCAATTTTG
GAAGATTATG AGAAACCTTC CAACAGGTCC CAGTGTACAT AGCAGTAAGA TGGTGCATGC
AGTGTCTAAC TGTCACAGGC TTTCCTAGGG CTCACTTTCA GACTCACTTC TTTTTTTTTT
TTTTTTTTTT TGTGAGATGG AGTCTCACTC TGTCACTCAG GCTGGAGTGC AGTGGCACGA
TCTTGGCTCA CTGCAAGCTC TGCCTCCCGG GTTCAAGCGA TTCTCTTGCC TCAGTCTCCC
TAGTAGCTGG GATTATAGGC ATGCACCACC ATGCCCAGCT AATTTTTGTA TTTTTAGTAG
AGATGGGGTT TCGCCATGTT GGCCAGGCTG GTCTCGAACT CCTGACCTCA GGTGATCTGC
CTACCTTGGC CTCCCAAAGT GCTGGGATTA CAGCCGTGAG CCACTGCGCC CAGCTCAGAC
TCACTTTTTA GGCCCAGGCC AACCTGCTGT GTTCTCCTGC TCAGCTTCTG CAGGAGGTCT
CATCGTCTAA GGAGGTCCCA GGGCTACCGC CCTTGTTTTC TCAAAAGGCA CATTTTCCCA
CACAGACATA ATTTCGTTTC AGTGTTTTAC TCCTAGTCAC ATTCATCTAT ATGGACAAAT

                                                     BssHII
                                                    -------
AGCTGAATGG ATTGGACTGT GTTTTCTAAA GATGGCCCCA TGCCATCCTG CGCGCTCCTC
CACAGCGTGG CCTGGGCATT CCTTTCGACC AGGGGTGGAC TCTGTGCCCC TACTTGTGAT
GTACGTGTTG CCAATAGAAT GTAGTATAGG GGATAGCACA GACTTCTGAG GCAAGACTAG
AAGAGGTGAT GCAGGTTTAA CCTTGTGTCC TGAGCCACTA GGTAAAAAGT CCACCTACCC
TGAGATCACT CTGCTGTGCA AACGACACAG GCAAACCACA TCAAAGAGCC ATGTGGGTTC
TCCAGTTGGC TTCTGCCCAG GAGTGAAGGT GCCCTCAGAT GGTTCTAGGC TCCCATCCCA
ACTTATGTCC TGTCTTGAAG TCTTCCCAAC TGAGGCACCA GCCACTGTGG AGCAGAGTCA
AGCCATTGCC ATCTTGTTCT GCCCAGATTC CCCATCAACA GAATATAGTG GTTTTTTCAC
ACCTCTATGT TTGGAGTGGT TTCTATGCAG CAATAGTAAC CACAAGAAAT AAAGTTATAA
AAATAGTAAC AAACACTAGA AACTGCAAGA TTTAAGGAAT CACCTGAATG CTCCAGTCAT
TGTCTCTGGT TTGTAATGAT AAACTTTCTT CTGCGTGATA AATAGAGCTT GGCTGGACTT
TTTCCCTCTG CTTCCATTCC CCAAAATGGA GCGTACCAAA CAATTGCTTC TTTCAGAGCC
CAGCTTTAGC AAGAGTCATG AGCTCTAATC CCTTCATCCA TAAATACTTC CTTTCCAGGC
ACGTAGAGCC CTTCACACTC AGGGCTGAGT AGAAAATGCC TGTTGCAGAC TGCAGTGGCG

                       KpnI
                      ------
                      Acc  I
                      ------
TTTTGGAGAG CCACCCTCCT GGTACCTGAG TCACTAGTCC TTTGCCCAGC TTTTCTCAGT

     Eco  III
     -------
TTTGTAAAGC GCTCACTTCT GAGTGGAAGA CAGAACCAGC CCGGTCTATT TTCATAATCT
GCCCCCATAA GGCAGAAGTC CACACGGTAC TGGAAACATA ACCATATCTA TGTCAGTCTG
CCACTGCCTG CCGCCTGTCA ACCGTGCGTG TCTGCATCCA GTCCTTCTTT GGAGCTGCTT
```

Figure 11M

```
TCCAGCGACT CAGCCAGATC TGAGCTTTCT GACTCATTGG AAGGTTAAAC TATTTTCAGA
CTTTCAAGTG TTGAGATTAT TAAGACATGT GTTTTTTTTT TTCTTCTTTT TTTGGCATGC
TTACTGATCG CCCCTGTTCT CTAGGAAGTA ATGTTCTTCT TGGAAAAGGT GAAGGATATT
TTTCTCCCCA AAAAGCCATG GAAATGTTTG CCTTTATTTA CTTCCAAATT AACAGAATTT
CCAGCTTTTG CTTGACCCAT CGGCGCATTG GCAGCGTTAA GAATTTTTTC TTTTAGCAGT
AATGAGGAGT CGAAGGGTTT CTTCCTAACC ATTTAGTGTA TGCATTTAAA TCAGGTTTCT
TTTTGAGTAA ATTGGGGCTA AGCTGTAGTG TGAACTTCTG CTACTGTTCC TTTCTCATTA
GTTCACTTGA TTTCATGGAA GGAATTTTCC ATCTCAGCCT GTGAACTTAT TTTGTCTAAA
CTCAATTGGA AAGTAATTAA CACTGAGATT CTTCTTTAAT AAATTCTATA TGATAATAAA
ATCATACAAA CATCTCTTTA TTTTTCTTTT TGACCTAGAA AAGATGTTCA CAGGCCAGAC
CTGGTGGCTG AAGCCTGTAA TCCCAGCACA CTGAGAGGAA GAGGCGGGTG GATCACATGA
GGTCAGTCCG AGGGCAGGGT AGCCAACGTG GTGAAACCCC ATCTCTAGTA AAAACACAAA
AATTAGCTGG GCATGGTGGC ACATGCCTGC AATCCCAGCT ACTCAGGAGG CTGAGGCAGG
AGAATCACTT GAACCTGGGA GATGGAAGTT GCAGTGAGCC TAGATCCTGC CACTGCACTC
CAGCCTGGGC GACAGAGTGA GACTCTGTCC CCAAAAAAAT AAATAAATAA AAGATGTTCA
CAATATATTG TTAAGTGAAA AAAGCAGGCT ACATAACTTG CATAATATGA GTGCATTTTA
ATAAAAATAT ACATATTTAG CAAAATAAAA GGACAAATGG TATTTATTAA AATATTTACG
TTGATTATTT CAACACAGAG GATGATAGTT GATTTTGCTT AATTTCTTCC CTCCTTCTTT
TCAATTTGAA TTTTCTATAA TGAAGATTGT TTCTTTTTCT TTCTTTCTTT TTTTTTTTTG

                                              NarI
                                             ------
                                              KasI
                                             ------
                                              EheI
                                             ------
                                              BsaHI
                                             ------
                                              BbeI
                                             ------
AGATGGAGTT TCGCTCTTGT TGCCCAGGCT GGGGTGCGAT GGCGCCATCT CGGTTCACCA
CAACCTCTGC GTCCCAGGTT TAAGTGATTC TTCTGCCTCA GCCTCCCTAG TAGCTGGGAT
TATAGGCGTG TGCCACCACA CCCGGCTGAT TTTGTATTTT TAGTAGAGAC GGGCTTTCTC
CATGTTGGTC AGGCTGGTCT CGAACTCCTG ACCTTAGGTG ATCTGCCCAC CTCAGCCTCC
CAAAGTGCTG GGATTACAGG CATGAGCCAC CGCGCCTGGA CTGATTATTT TTTAAATAGG
GTTAGAAAGT GAGGAAGTTA CTAAACTCCG ATTAGCCCAA ATATGCCCCA GTGGGTCCTT
CTGGCAGAGT AAATGTCTCG GTTCAGCCTG AATCTGGGAA ATTGTTCCTA CGGTTCAGCC
TGAATCTGGG AAATTGTTCC TACCTTATAA ACTGGAGTAT CCTTCAGAAA TGACATTTAC
TCAAACTTCC TTTTAGGCAG ACTGCATAAT AGCAATTTTT AATATTAACC ATTTAAAAAA

              PacI
            --------
AACCTTCAGA TTAATTAACA CCAAAAGAAT AATTGGGAAA ATACAACTCC TCACTTTAAA
AAAGAAACAA CCAAAGTAAA TACTAAAAAA CTATATGATG TTATATTATC TAAGCTTAGT
TTACTGCAAA GATCAAGAGC ACACTACTAG TTGACGGCCT CTATTCACAC TGTTCATAGC
CCTCGCTCGC TTCTCCAGCC ATTCACTCAC TCATGCAAAA GGTCTGTACA CACAATGATG
CCTGATGGTA TAATAGGAAC CTTAACATTT CAATTAAAAG GCAAAATGAG GACACTTACC
ATCAGCCTAT AAAATTATTC TTATTATTCT TCTTCTTCTT CTCCTCCTCC TCCTCCTCTT
CTTCCTTCTT CTTCTTCTTC TTCTTCTCCT TCTCCTTCTC CTTCTCCTTC TCCTTCTCCT
TCTCCTTCTC CTTCTCCTTC TTCTTCTTCC TCTTCTTCTT CTTCTTCTTC TTCTTTTTTT
TTTGAGATGG AGTCTTGCTC TGTTGCCCAG GCTGGAGTGC AGTGGTGTGA TCTCGGCTCA
CTGCAACCTC TGCCTCCCAG GTTCAAGCTA TTCTCCTGCC TCAGCCTCCC AAGTAACTGG
GATTACAGGT GCATGCCACC ACGCCCGGAT AATTTTTTGT ATTTTTACTA GGGATGGGGT
TTCACCATGT TGGCCAGGCT AGTCTCTAAC TCCTGACCTC AAGTGATCCA CCTGCCTCGG
CCTCCCAAAG TGCTGGGTGT GGGCGGCAAG CCACCCAGGT GCCAAGGCAA GAGACAGAGG
GCACGAGCTG TTCCAGTATA ATGAGGAAAA TATATAGAAT AAGAATAGTT ATACTAGAAA
TAGATTATAG ATATGATTAC ATATGAATAT CATTCTTCAT TAGTTTGTAG CACTACTCTT
TATTCCAGTA TTATAATAAT CTTTGTTCTA CAATTATAAC CTAGGAAAAA CCAGGCCATA
```

Figure 11N

```
CAGAGATAGG AGCTAAAGGG ACAGGGTGAG AAGTGACCAG AAGAGTGTGA GCCTTCTGTT
ATGCCCGGAC AGGGCCACTA GAGGGCTCCT TGGTCTAGCG GTAACGCCCG CGTCTGGGAA

                 RsrII
                 --------
GATGCCTGTC ACCTAACGGA CCGTGGTCTA GCGGTAGCGT CAGTGCCTAG AAAAGGCACT
CTTTTTAAAT ATACTTTTTA TTTTTGTTTA ATCTTCCCTG ATTTCCTATA GATCTGAGAT
ATGTCATGCT TATTTTCATT GCTATCTAAA AATCTCAATA AACTTTATAC CTAAGAGTAA

                                              BsiEI
                                              ------
AAAAAAAAAA AAAGAAAAGA AAAGGCGCTC GTTACTTAGC CGACCGGGAA AGGGAGTCTC
CCTTTCCCCG GGGGAGTTAG AGAAGACTCT GCTCCACCAC CTCTTGTGGA GGGCCTGACA
TGAGTCAGGC CTGCCTGCAG TCATCTGGAG GCCTAACCGT CTCCCTGTGA TGCTGTGCTT
CAGCGGTCAC GCTCCTAGTC CTGAACACCT GGCTCCGCCT TTTAGATAGC AGTAGCAGAA
TTAGTGAAAG TACTAAAAGT CTTTGAAATG CAGAAGTAAT GGCGTAAGCT GTCACGTCTC
TCTCTCCGCC TCAGCTGCCA AACAGAGAAG GGTCCCCTGT CCAGTGGACA CGTGACTTGG
GTGACCTTAC CTGTCATTGG AGACGACTCA TACTCCTTAC CCTGCCCCTT GCCTTGTATC
TAATAAATAA CAGCTCAATC TGGCATTTGG GGCCACTACT GGTCTCCGCA TCTTGGTGGT
AGTGGTCCCC CGGGCCCAGC CGTCTTTTAT TCTATCTCTT TGTCTTGTGT CTTTATTTCT
ACCATCTCTT GTCTCCGCAC ACGAGGAGAA AAACCCACAG ACCCTGTAGG GCTGGCCCCT
ACAGCTGGGA ATTACAGGCA TGAGCCACCG CATCCAGCCA GCCTAAAATT CTTCTGAAGG
ATAATAATAT AGTACTTGAA GACACGGTTT GAAAAAAATC ATACTAAATG AAAGGGCACC
ATTTTACAAG CACTAGAACT ACATTAAACT TAAATGAATT CCAACACTCT TAATAATGTA
ACTCAAAAAC AAGTCTAGTG TTAACAAAAG CTCCAATAAC TAAAACTACA TTAACAGGCA
CAATGAACAT TGTAAACGCC GCTAATTGGC ACCAAGTTTA ATAGGGCAGA CAATATTTTC
TTCTGCATTC ACACTTACTC AGTTACACTG TTGAAAAATG CTGCTGCTCA AGCTATGAAT
GCTTTACAAA AGAAATCATT TTAATAAATA CAGTAAATGC TAAAACTCTA GCTAAACTAT
TATGCAAGAT ATACAACCAA GACAAATACA AATTCATAAT ACAAGCAACT TGCATTCAAA
ATGAACTCTA CCACTATATT TTATTAAAAG GGCAGACTTT ATGAATTAAC CCAGCTGCTT
CCTGAATTAC AAAAGTGGCA TGACTCAATA TGAAAATAAG AAACTGTCTA CAAATTTCTG
ACAGTAATAA ATTGTAATAT ACAATACATG CAGGAGTCTT ACGGAAGAAT AAACTCTCCT
AGGAAACAAA AATATTTTAT ACTTTTAAAA TCCAAAGTAA AAAAAAAAGA AATCATTGCC
AGATGCGGTG GCTCATGCCT GTAATCCAAG CACTTTGGGA GGCCAAGGCA GGATCGCTTG
AGCCCAGGAG TTTGAGACCA GCCTGGGCAA CATAGCAAAA CCCCATCTCT ACAAAAAAAT
ACAAAAATTA GATGGTAATG GTGGTGAGCG CCTGTGGTTC CAGCTACCCA GGAGGCTGAG
GTGGGAGGAT GCACCTCAAG GCTGCAATGA GCCAAGGTCA CACCATTGTA CTGAAGCCTG
GGGACAGAGT GAGACCCTGT CTCAATAAGT AAATAAATAA ATATCTTTTA TGAAAAAGAT
TCTCTAGTCA GAATTAACAC CTCAACTAGC CAAACATCAG GAAGTTACAT TACAGCTACT
TAATACACAA AGGGACACAT TTTCACCAGT CGTTGTCTTC TGATATTTCT ATTCCAGAAA
CACACACTCT CACTTCCCTA CACTCCCCAT CCCATCATTT CTTCAGAGCA TGGAAACAGA
ATTTGTTGAA CACCAGAAAT CTCTTGCTAT GGTGGTACAT AAGTCATAAC ATTTGTTGCT
GCCCAGCAGC AGGTATGAAG CCGGCTGGTG ACTGGCTAGC AAATGCCTAT TCTGTAAGCT
CCTCACTTAG CCCATCTGTA GCTCTGACTT CTCCACCAAT TCCCTTCTCT CCTTTCACAG
CCTTTCTGAG TTTCTGAGGG ATAATTTCAG AGGTTCCATA TAACTGTCAA AGCCTATGGT
AGACATGGCA AAGTGAAAAT CCTCTCCACT GGCCATTTCT GTTTCTCTTG GGGGCATCTT
TCACTTGCCT CAGGTGTTAT AAAGCTGATG AACACACGTA CACGTTGTTT AACACTTTCT
TGGGCATTTC CCATTTGAGA TATGGCATGT TTCATTATCC TAGTGACATG TGCAATCAGA
AAATGTATAT TTTGTTCTCT GCAACTTTCT TTTGAAAAAT GTATATTTGA ACAAAATATA
CATTTTTTGT ATCTTCATGA CCATTCATGC TGTCCTCACT GTCATCATGA GGCTCTATAT
AACATAATGA CTCCTCCAGG GCAGTCTTCG GAAATTCCCA GTGCAGAAGC ACGTGTCATA
CAGCAGTCCC CATTCATCTC CAGTGCAGCT CTGGCTGGCT CCCATGTCTG ATCAGCTGTT
TGGTTGGACA GAAAATGACT GCAAGGGAAT CAGTTCCAGT GTGAGCTCTG TTTGCAGAAC
TCAGACTCCC CTCCCTCCCA TGTTAATGCT TTTTTTCTTC TTCTTTTTTT TTTTTTTTTT
TTTTTGACAG AGTCTCATTC TGTCACCCAG GCTGGAGTGC AATGCTATGA TCTCGGCTCA
CTACAACCTG TGCCTCCCCG GTTCAAGCAA TTCTCGTGCC TCAACTTCCC GAGTAGCTGA
GATTACAGGT GCACACCACC ACACCCCACT AATTTTTTTG TATTTTTAGT AGAGACGGGG
TTTTGCCATG TTGCCAAGGC TGGTGTCAAA CTCCTGAGCT CAGGAAATCC ACCTTCCTCA
GCCTCCCAAA GTGCTAGGAT TACAGGCGTG AGCCACCATG CCCAGCCCCA TGTTAATGCT
```

Figure 110

TCTAAAGTTT GCCCTCACTT CTTTAGAAAT TCCTTCAGTA CATCCTTTAA GACTTCCTCT
AGTGAGTGTC TGCTGGTGGT AAACTCTCCC CTCTAAAAGT TGCTTTATTT CTCCTCAATT
CCTGAAGGAT ATTTTTGCTA GCAGCTATAT TCTTTTAGAT GTTGAACATA TCGGTACAAA
AGCTTCTGGT TTCCATGGTT GCTATTGAGA TGTTAGCTGT CGGTTTATCT TTCTCCCCTG
ACTATGTGTA CCTGTTTCTC TGTATCTGTC TACTTTTTGG GTTGCTCAAT TTATTGGCCT
TGGGCTTCAT TCTGCTGCTG CTTTTTTTTT TTTTTTTTTT TTGAGATGGA GTCTTCCTCT
GTTGCCCAGG CTGGAGTGCA GTGGTGCAAT CTTGGCTCAA TGCAACCTCT GCCTCTCGGT
TCAAGCGATT CTCCTGCCTC AGCCTACCGA GTAGCTGGGA TTACAGGCAC CTGCCAACAC
GCCAGGCTAA TTTTTGTATT TTTAGTAGAA ATAGGATTTC ACTATGTTGG CCAGGCTGGT
CTCAAACTCT TGACTTCAGG TGATCCACCC ACCTCAGTCT CCCAAAGTGC TAAGATTACA
GGCCTGAGCC ACCACGCCTG GCCACAATTT TTAAACTTTT TATTTTTACA GGCACCTGCC
AACATGCACA ACTAATTTTT GTATTTTTAG TAGAAACAGG ATTTCACTGT GTTGGCCAGG
CTGGTCTCAA ACTCTTGACC TCAGGTCATC CACCACCTTG GTCTCCCAAA GTGCTAGGAT
TACAGGCGGG AGCCACCATG CCTGGCCAAA ATTGTTAAAC TTTTTATTTT CTTCCTCAAG
AGGATGAGAA GAAAGGTCAA TTGTAAGCTT TAGAAGTCTT GCCCAATAGC CAATCTGAGA
ATATTCTCCG TAAACATTCA CCAGAGGCAG CCAGTGACCA TGGGATACTT TTGGTGAGAG
GAATTGATTG CTGGGGTCAG GAATGGGAGG AAAGCATACT TCTCATTAGA TACCTTGTTG
AACTTCGTAA ATTGTGTGCC AAATGCATGT CTTACCTAGA CTTCATAAAT TAATTTCTTT
AAAAATAATC AAAGACAATT TTTTAAAGAC TTATTTAATT TAAGGTGATT ATAAAACATC
CAGTATACTT TCACTATTAA AAAAGTAAGT ATTCCTGTCT GGGCTTGGTG GATCACACCT
GTAATCCCAG CACTCTGGGA GGCTGAGGTG GTCGGATCAT GAGGTCAAGA GATTGAGACC
ATCCTGGCCA ATATGATGAA ACCATGTCTC TCCTAAAAAT ACAAAAACTA GCTGGGCGTA
GTGGCGTGCC TGTAGTCCTA GTTACTCAGG AAGCTGAGGC AGGAGAATCG CTTGAACCCA
GGAGGCGGAG GTTGCAGTGA ACTGAGATCG TGCCACTGCA CTCCAGTGTG GCAACAGAGT
GAGACTCCAT CTTCAAAAAA AAAAAAAAGT ATTCCTAAAC AGCATATTAT CATGATATAT
TATTTTGTTT TGTAGGGTTT TGAACCTTGT CTAAAAAGAA TTAAAATGTA TAAATTTCTT
CCTGCAATTT CCCTATTTCA CTAAGGGTCA TTCACATTGG TCATATAGAC ATAGCACATT
TTCACCACTA TATAGCAGCA TTTTGTACAA ATAGACTACA ATTTACTTAT TCTGCACTTA
TTTCTGTTTG TTTGTTTTGC TATGAAAAGC AATGTCATTA CATATATTCA TGCCCATAGC
TACAAGTTTA CATATTTCAG GTTTTCTGTA GGGTGGACAC CAGGGAGTTG AATTGTTCAA
CAGGACTTTA CATTCATCTT TAGTTTTATT GGCCAACACC AAATTGTTCT TCACAATGTT
TGAACTAAGT TGAAATTCCA CCTCCCCATC ACATTTAGTT TTGTCAACTT CATTTCTTCA
TTCATTAATT CATTCATTCA GTCTTTTGTT TATTTGTTTA TTGCCAGTCT GATAGGCGTA
TAGTGGTGCT TCATCATGGT TTTACTTTGC ATTTCTCTGA TTTTCTTTTT AAATTTTTAA
AAAATTATTT TTATGTAGAA ACAAGGTCTC GCTACATGGC CCAGGCTGGT CTTGAACTCC
TGGCTTCAAA TGATCCTCCC ACATTGGCCT TTCAAAGTAC CGAGATTGAT TATAGGCGTG
TGCCACTGTG GCCAGCTGAT TTCCCTGATT TCTGATGAGT TAACAATCTC TTCTTTCTCT
CTCTCTCTCT CTGTGTATAC AGGTACTCAC CATTCGTGCC TATTTTCTGT AAAATATGTG
GCTTTCCTCA TTTTTTTTTT TTTTTTTTTT TTTTGAGGCA GAGTCTCGCT CTGTTGCAGG
CTAGAGTGCA GTGGTGCGAT CTTGGCTCAC CACAACCTCC ACTTCCTGGG TTCGAGCAAT
TCTCCTGCCT CAGCCTTCAG AGTAGCTGGG ACTACAGGCG TGCACCACCA TGCCCAGCTA
ATTTTTGTAT TTTTAGTAGA GATTGGGTTT CACTATGTTG GCCAGACTGG TCTCAAACTC
CTGACTTTGT GATCTGCCCA CCTCAGCCTC CCAAAGTGCT GGGATTACAG GAGTGAGCCA
CTGCGCCCAG CCATCTTTCC TCATTTTTAT ACTAATTAGG CTTTTATCTT ACTTGTTTTT
TTTAATGTTT TTTGTACACT CTGAAGGCTG ATTTTTGTTA ATTGTATGTG TTGCATTTTT
TATGGTTTGT CTTATGCCTT TTGAAAGTAA AAGTTCTTAA TTTAAATATA GCCAACCTGT
AAATCATTTG TGAAAGTCTG TGGTTTAAGA GGTCTTGAAT AAGAAATTAT CCCATCATCA
TAAGTCATAA ATACTTTTTT GTTGTTGTTG AGACAGAATC TCATTTTGTT GTCCAGGCTG
GAGTGCAGTG GGTTGATCTC AGCTCACTGC AACCTCTGCC TCCTGGGTTC AGCAATTCTC
CTGCCTCAGC CTCCCAAGTA GCTGTGATAA TAAGCATGTG CCACCACACC AGTCTAATTT
TTGTATTTTT AGTGGAGACA GGATTTCATC ATGTTGGCCA GGCTGGTCTC AAACTCCTGA
CTTCAAGTGA TCCACCTGTC TCAGCCTCCC AAAGTGCTGG GATTATAGGT GTGAACCACC
ATGCCTGGCC CATAAATACA TTTTTATGTA TTTTCTTCTA AAGTTGTTTT GTCTTTCACT
TTTTAGTTTT TAATTCACAT ATAATTACTA CTTGCTACTT ATAATTATCT GTAAGTAGTA
TGAGATGAGA AATAAATTCT ATTTCCCTCC TATGGATAAG CACAAACCTG CAGTATTAGC
ACAGTCTTAT GTCAGATTTT CTAAAATGAA TGGGTGTGTT TTCTAGGCTC TCTGTTCTGT
TTCATTATCT GTCTTTTCCT GCAACGATAT CATCTGCCTT AAAAACTCTA GCCTTGTGGT
ATTCCTCATT TTCAAGCAGA GCAAACCCCG TCACCTTGCT TTTCTCCTCC AGCATCGCTT
GTGCTATCCT GGACTAAGAC CTTCATATAG ACTGTTAGAA TCATCTAGCC AAGTTCCATT

Figure 11P

```
TTAAAAATCT ATGTTGGAGC TGGGCGCGGT GGCTCACGCC TGTAATCCCA GCACTTTGGG
AGGCTGAGGA GGGCAGATCA CTTGAGGTCA GGAGTTGGAG ACCAGCCTGA TGAAACCCCG
TCTCTACTAA AAATACAAAA ATTAGCTGGA CGTTGGGCAC TTGAATTCTA GCTACTCAGG
AGGCTGAGGC AGGAGAATCG CTTGAACCTG GCAGGCGGGG GGTGCAGTGA GCCGCGATCA
TGCCACTGTA CTCCAGCCTG GGTGACAGAG TGAGGCTCCA TCTCCAAAAA TAAATAAATA
AATAAAATAA AATATCTATG TTGGAAATTT TGTACAAATT TTATTAAATG TCTACATTAA
TTTGGAGAAA AATGACTTGA TTTTGATTAT CTATTCAATA TTTCTGTATT ATGAATAAGG
CAAAAAGAGA GGCAGAGAAT AGCATAAAAT AATAACTAAA ATTCCTGGGT AAACCACCTC
AAATCATTTC TTCATATGGC TCAATATTCT TTTGTGACAT GGCCTGAAAT ATATCCAGAC
AGAGAACTCT TCTCTTCAAT ACATTTCTTC TTTTAGGTAT TCATATTGAG TTTTCCTGTC
CATGAACATG GTATAAGAGA GTATATCCCT TCGGGAGGCC AAGGTGGGTG GATCACCTGA
GGTCAGGAGT TTGAGACGAG CCTGGCCAAC ATGGTAAAGT CCCATCTCTA CTAAAAACCC
AAGAATTATC CAGGTGTGGT GACACATGCC TGTAGTCCCA GCTACTCAGG ATGCTGAAGC
AGGAGAATTG CTTGAACCAA GGAGGCGGAG GTTGCAATGA GCCAAGGTCA TGCCATTGCA
CTCCAGCCTG GGTGAAGAGC GAGACTCCAT CTCAAAAAAA AAAAAAAAAA AAAAAAGAAA
ACGAGAATAT ATCCTTTCAT TTACTAGTTT TTCTTCAATT TCTTTCAAGA TAAAGGGCTT
ACCTATCTTC TGCTTTATTC ATAGTTACTT GATATTTTTG TTTCTAATAA ATATGGTGTC
TGTCTATTTA CCTGCCTCTT ACCTGTTCAT TTCCAGTTTC AAAAATGATG TTGATATTTG
AATATTAACC TTAAATCTAG CACCTTGGTA AACACTATTA TTCATTCTAA TAATTATCAG
TAGATTATAT GTGTTTTTTA TTTATAAATC ATATTGTTTG AGTAGCATGC TTTGCTTCTT
CATTTATAAA ATTTACAACT TTTATTTCTT TTTAATAATT TTTTTCTTAT TCTCCTGGCT
AGGACTTCTA ACACAGTATT GAGTGGAAGT GCTGATCCTT GTTTAGTTTC ACATTTGAAA
AAAGATTGCT TTTACTATTT CACTGTTAAG TATAATATGC ACCATAGGCT TTCTGTGGAT
TCCTTTTATC CATTTAAGAA CATCTCTTAT TCCTAATTAG CTGAAGTTTT CTGCATGTTT
GTTTTCATCA TGAGTGGATT TTTTTACATC TATTGAAATC ATTTTACATA GAAGATATTT
CACACCTATT GAAATGGTCA TTTCACTTTT CCTTCTTTAA TATGTTAAGT TGGGCAAAAT
ATTAAAGTAT CACCTGTCAT TCTGCTTCAG CAAAAAGTAG TAGTGTCTTA GCAGTATTGG
TGAAAAGACA GCATCAAATA AAAAAGATGT AGAAGTAGGA CCCAGTAAAA ATCTAGCGCA
TGGGGCATTG TCACATGTAA GCAGACAGAA TGTGACACCA CCAAGGAGCA TCTGAAGGGC
TGGAGGCTGA AGGAAGACAT GAGTCACCCA GGCTCATGGA CACTTCAGAG AAATTAGGGA
GCAGGAAGAA GAAATAGGAT CAAAGACTAC GTATGTTGGT TGGAAAAGGA AGCTGATGGT
ATGGAGATGT TATTATTTAG GTCTCACATA AAAGATGTAG ATAAATAGGT AGATAGGTAG
ATAGATGATA GATAGAGAGA TAGATAGATA AATACATAGA TAGATAGATG ATAAATAGAT
GTTGTTATTT AGGCCTCACA TAAAGATGTA GACAGATTAG ACAGACAGAT GATAGATAGA
TAGATAGATA GATAGATAGA TAGATAGATA GACGATAGAT AGATAGATAG ATAATCTCAG
AAACAGAGAC ACAGTGATCT CAGTAAGATA GGCATATGCC AGGTGACAGA ATTCAGAGGG
GTCCCACTAC GTGAAAACAA TAGAACAACC TTCGAAAAGA AATTTAGTAC AAATAAGAGG
GCAGGCTTCC TTACATACAA GTTAGTAAAC TGGAAGAATC AGTTATCCTC AAACATTGGA
ATAGATCAAA AATAGTTGTT TATATTAATG AAGGTAGCTA AACATGAAGC TAAGTGAACC
TGTCTCTGAC CTAGTGTGGC AATCCCTGGG CAAGGGACAC TTGCTCCGCT CTTGTATCCT
TCACTGAATA TTCAGACTTT CAGTTAAGCA TCGGTGAATT TAGTTTTCAT CTCTTGTGAA
AACCTTGAGA GAGGTAATTC TCTCTGCTTT TCTTCTTTTC CCTTCCTTCA TTTTCTCAAA
CATTGCCTGT TTAAAATACG AAATTTTAAA AGATGGCCTT GTTCTCTTTT TTGTTGTTAT
TATTAAGTAC AGAGAAAGGA AGAACCACAA ATAGCAAAGG GCAACATATG GAATAGTTTA
GAAGTTCCGG GAGCACCCAT GAGGGCAACT GCAGAAGAGA ACATTCTATC CCCCGTTGCT
GCAGCTTTCA TTCCAGGTCT CCATGCATAT CAGATAGGGA AGGAACTCCG GGACAGCAGC
AGGGCCCATG CACATGTAAC CAATTGCTTT CTTTGCCTGT AGTAAAGTTC ACATTTTGAT

                                                AccIII
                                                ------
TGCTTCTCCA GATTATGTAG ATCCAGACAT ATTTTATGCA GGCATCCGGA TCTTTCTCTC
           >>.....................EXON 8 .......................>
TGGGTAAGTA TAGTTCAGTT GTTTTCCTGT GTGAAGTCTC TGTAGCATTG ACTGAATGTA
>>>
TAAGGGGACG AAGAGACAGA AGCTTCCTAG CGTAAGAAAC ATACCAAGTG ACTCTTGCTA
GGGATCCACT CTCAGGTAAA AGAAGTGGGA TACCATCTGC ACAACAAATA ACACTGAGGG
CTAAGTATTT CAGTTAAGAG TGTTTGTTCC TAGGCAGTTC AGATCCATTT ATATTCACTT
TTCTTAGAAT CCTAGCTCAA TGACAGAAGA AGAAAAACAC AGTATGTCAC TCACACAGTT
CTATCACTTA CATCTACTTT TTCTTCTTGT TATTAAGGCA TGTAGAAGGC TGGGGAGTGT
```

Figure 11Q

AGTATAGAGT TGGATAGCAT CGAAGCTTTC TTCTAAAGTT CCTGGAAGAG CTACACTGTG
GTTTGAACGA ATGTGTCCCT CCAAAATTCA TATGTTAAAA CCTAATTGTG ATGGTGAGGT
ATTCGAAGGT GGGTTCTCTG GGAGGTGATT ATGTCTCCTC TGAGAGGAGA AGACAATCCC
CTGAGTGGAA CTAATGCCCT TATAAAGGGG CTGGAGGGAG TTCACTTGGC CCTTTTTGCT
CCTTTTTTCT TCCATTCCTT GTCCCTTCCA CTATGTGAGG ACACGGGAGT TGAGGCATTA
CCTTGGACGT GGAGACCAGG CCCTCACCAG ACACTGAACT TGCCAGCACC TTGATCTTGG
ACTTCCCAGC CTCCAGAACT GTGAGAAATA CATTTCTGTT ATGGGTAGTC CCCAACTCAA
TACAGTTTGA CTTACCATTT TTTGACTTTA TGTTGGTGCA AAAGCATACA TATTCAGTAG
AAACTACTTT GAGTACCCAT ACAACCATTC TGTTTTTCAC ATTTGGTACA GTATTTAATA
AATTCCATAA CATATTCAAC ATGTTGACAT AAATAAGCTT TGCGTTAGGT GATTTTGCCC
AACTGTGGGC TAATGTAAGT GTTCTGAGCA CATTTAAGGG CAGCTAGGCT AAGCTAAGGT
GTTTGGTAGG TCAGATGTAT TAAATGCATT TTTTGTCTTA TGATATTTTC AACTTACATT
GGGTTTATCA GGATGTAACC CACTGTGAAT TAAGGAATAT CTGTATTTAC AAATTACCCA
GTCTAATGTA TTTTGTTGTA GCAACAGGAA CAAACTAAAA CACTACCCCA AACCATTTTT
TTCATATTTT CTGAGTACTC TTCTTTTGTC ACATGGCTTG AAATTTCTTC ACATAGAGAA
CTCTACTATT ATTTTATTTT ATTTTATTTT ATTTTATTTT TTGAGACAGA GTCTTGCTCT
TTTCACCCAG GCTGGAGTGC AGTGGTGCCA TCTTGGCTCA CGGCAACCTC TGCCTCCTGG
ATTCAAACTA CTCTCCTGCC TCAGCCTCCC GAGTAGCTGC GATTACAGGT GGCTGCCACC
AAGCCTGGCT AATTCTTGTA TTTTTAGTAG AGACGGAGTA TTGCCATGTT AGTCAGGCTG
GTCTCGAACT CCTGACCTCA GGTGATCTGC CCACCTTGGC CTCCCAAAAT GTTGGGATTA
CAGGCTTGAG CCACCACGTC TGGCTGATAA CTCTACTTTT AGATACTCTC TTTGCTTAAA
CAAATTAGCC ATTCCTTCCT TGACATGTTT TAATCAGATT GCCTTCCTAT TAACTTCGGA
AATTAAGAGT TTCTGCTATG TTTTTGTTTA ATTTTTAAAC AGTGAAAAAT GAAAGGTGGA
GGCAATGGCT GGATGAGGTG AATATGTCAA ATAGATATCA TCTAGTGGGC CATCTTATTA
ACTAGGAGAC ACCTGAAGTG CTATCAATAG AAATAATCTG AAGCTGTGTC TGGATACAGC
AAGAGACATG CAAATGCTAA AAATCTACTA TATTACATTG GTGCAAGGAC AGAGTAGCAA
CACATACTAA GTATTTTCTC CAGATTGGGT GTGTTTGACG TGTGAAGCAC TTCAAACAGA
GTCCAGCCTG GGAGGGAGTG GGGATGGAAT CCTCCTTGTA GAGGGTACAG AGTGGAAGCA
AGAAGGTTTC CAAGATTGAG AGTAATGGGT GTATGGTTTA TGGGGGAAAG GGAAAACAAA
AAGAAGGGTG CAGAAATGGA GCTGGGAGTG TGTTTTAGTA TTTAGGCTTT CTCTGTATAC
CTTTGATAGG ATTAGAAAAA GAAAAATGGA CCATTTTTAA AAATTTCATG CTACCACATA
GCAGGCTTAT ACTATAGATG CAGAAACAGA CTGGGATTTA GGAAGCACCC CAATTCTGGA
AAATCCCTTT TTGCTTCACA TTGCTCTCTA AATCTGTATG TTTTCCCTTG TTACGTAACA
ATTTACCACA AATTTAGCAG CTTAAAACAA TATGCATTCA TTGTTTCACA ATTCTGTAAG
TCGGAATCAT AGGCAAGCTC AACTGACTTT TCCATTTAGG GTCGCAAAAG GCCGAAGTCA
ATTTATCTAT TGGGCTGGGC TCTTAACTGA AGATCTGGGG AAGAATTCCC TTCAAAACTC
ATTTAGGTTG TTGTCAGAAT TCAGTGTTTT GTGGTTCTAG AACTGAGATC TGTTTCCTTG
TTGGCTGTCA GACAGGAGCT GCTCTCAGCT TCTTGAGGCA TCCAGTATTC CTTATCATGT
GTTTTTTTTT TTCCATCTCA GCACTGGCAC TTTTTTTTTT TTTTTTTTTG AGACAGAGTC
TTGCTTTGTC ACCCAGGCTG GGGTGCAGTG GCACGATCTC GGCTCACCAC AACCTCCATC
TCCCGGGTTC AAGTGATTCT CCTGCCTCAG CCTCCCGAGT AGCTGGGATT ACAGGCACCC
GCCACCAGCC CGGCTGATTT TTGTATTTTT CATAGAGATG TGGTCTCACC ATGTTGGCCA
GGCTGGTCTT GAACTCCTGA CCTCAAGTGA TCCTCCCACT TCAGCCTCCC AAAGTGCTGA
GATTACAGGC ATGAGCCATC ATGCCCAGCC AGCACTGACA ATTCTAATCC TTCTAGCACT
TTGATTCCTT CTCACCTCTC CTTCTGCCTC TAGCCAGAGA AAACTCTCTG ATTTAAAGG
TCTTATGTGA TTAGATTCAG CTTACCTAGG TAATTCAGGA TAACTCCCTA TGTCAAGGTC
AACTGATTAA TAACCTTAAT TACACCTGCA AAGTCCCCTT TGCCATAATA TATCATACTG
ACAGACATGC TATAGCATAA TACTAATAGT TCTAAGAATT ATGATAAGAA TCTTGGAAAA
CCATTTTTAG AATTATACCT ACCACAGTAT CCTTCAAGGG ATAAATTGAT TCTACTTCTT
CTCTATGTCA GAAGCATCTG ATGAGGATGA ACTATATATT CTGAAATCCC CATGATTAGA
TGTGTACTAG AAGGTGATTT TACTTTCATT AAAATAAATT CGGAGTCATT GACACATTTT
ATCTTTGATT TACATAAATG CCTCCGCTCT GTTTCTTACC CTCAAAATAT TTCCCATGTA
GCTAAGTGGC CAGTACCGAA TCCTACATGC ATTAATAAGT GTAGATGGAC AAAAATATCT
GGATTACTGA GAATTCCCAT TAGCATTGTC TAGAAAAATG TAAATTTGCT TTTTTGTTCT
TGATTTATCC TATTTTTGAT TTATTATTTA TATTTATTTA TTTATTTATT TATTTTTAGA
TGGAGGTCTC GCTTTGTCGC CCAGGCTGGA GCGCAATGGC GCAATCTTGG CTCACTGCAA
CCTCTGCCTC CCAGGTTCAA GCTTTCCTCC TGCCTCAGCC TCCCAAGTAG CTGGGACTAC
AGGCACCTGC CACAGTGCCC GGCTAATTTT TGTATTTTCA GTAGAGACAG GGTTTTGCCC
TGTGGGCCAG GCTGTTCTTG AACTCCTGAC CTCAGGTGAT CTGCCCACCT TGGTCCCCCA

Figure 11R

```
AAGTGCTGGG ATTACAGGCA TGAGCCACCA CACCTGGCCT TTTTGCTTAC TTTTTAAAAA
CATTTTTATT TAGGAGAATG GAGATATTTC ATATGTAGAT GACACATATT CATTCCCTTT
AGTTCCCACA CACATTCAAT TTCTTGAGGA AGTTAGCCTT TGCAAAAAAA AAAAAATGAT
CTCATTTTTT TTTCCCCACT AAAACTTCTC ATTTTCTTGG GGTTGCTAGA AAGTTGCTAC
AAGAAAGGCT AAAAATAATT GTGCCTACAG ATATTTGAAA GGAAAATAGT TCCTCTTTTT
TCACAGTAGC AGCTTGGACC TGAGAATGTA TGGGAGCAAT AATTGGGCTG CTCAAAGAAA
CACAATTTCC CTTCCTCAGA CTAGAATTAC CAACCTAGAG AACATGAGTT TTTAAAGTAG
ATGTGCTTCT TTTATCTTTT TGGACTTGTA TGCTGGTGTT TTCTCTGTCA CCTTCACTGT
GGAAATCCTC TTGAGGGTGA GGCACTGAAA GCAGATTGAT TAATGTCTCT TGGCCATTTG
AGACATTGGA TGGCTCTTTT AAGTTGGCCA CGTTCTTTCA AGAACTATGC TTGGGCTACA
TATTCTGGAT ATATAATACA TACTTGTAGG ATGTTATTTT TAAATCATTC ATTTATCACA
TATTTAGTGA GTGCCTACCC CATGTCAGTT CTAGGTGCTG GAAATAGAGC AGTAAAACCA
ACCCTCAACT TGGCCCCTCT GGAGCTTACA TTTCAATGCG GTGGGTGGGG GGATGGACAA
TTAATACACA AGTAAATCTA ATAAAAGCGT CATACAATAT ACATTACAAT GGTAAGCACA
ATGAAGAAAT GGAAAGCTGG ATAGAGAGTA TTAGAGACTG TCGAATGTAG TGGCCAAATT
TTCCTGTTTA TTGTGGTCCA AGAGTGCCAC AGCCCTCTAT GACATTTGAG CAGACACCTG
GAGGAAGTGA GGGAGTGAGC CGCCAAGAAG GAATGGCAAG TGCAATAACC CTGAGGTGGG
AGCGTGTTGG TCGTGGTGGA AGAGCTGCAG GAAGCCAGCA GGGCCGCAAC ACTCAGGGGA
GAATAAGAAA GAGTGAGGTG ACAGTAGAGA CCGGATCATG TAGAGCTTTG TCAGCTTCTT
TTCTGAGTGA GATGGACAAC ACGGACACGT TTTGAAAAGA ATAACAATGT GATCTGCCTT
CAGTTGCAAA TCATCTCTGT ATTGACTGAG TAGGAAATAA ACTCCAAGAA TAAAGACGGA
AACAGGGAAA ATATTTAAGA AGCGATCATT ACAATCCAGG GTGGTGGCTT GTACTAGGGT
ACAAGGGCTA AAGGTGTTGA GAAATGGTCA GATTCTGGAT ATATACTGAA ATCAAAGTTG
ATGGAAAGAT ATGAGTCAAA GATAATTTGC AGGTTTTGGG GTCCTGGTTC ACTGAAAGAA
CAGAGACATC ATTTACTCCA ATGAGGAAGA CTATAGGAGG AACAGGTTTA GCAAAGAAGA
AAGGAAATCA GGAGATCAGT TTGGGGACAC GGTCATATCA AGTAGGCAGT TGGATGTATG
GGTCTGGAAT ATAGGGGAGT GGTCTAGCTA TCAGTGTAAA TAGCTTTTTA CATTTGTAAA
TAGTCAGGAT ATAGGCTTTT CTTTTTCTTT TTGTGAGACA CAGTCTTGCT CTTTCGCCCA
AACTGGAGTG CAATGGCACA ATCTCAGCTC ACTGCAACCT CTGCCTCTGG GTTCAAGCGA
TACTCCTGCC TCAGCCTCCC GAGTAGCTGG GACTACAGGT GTGCACCACC ATACCAGGCT
AATTTTTGTG TTTTTAATGG AAATGGGGTT TCACCATGTT GACCAGGCTG GTGTCAAACT

             ClaI
            ------
CCTGACCTCA ATCGATCTCC CCGCCTGGGC CTCCCAAAGT GCTGGGATTA CAGGCATGAG
CCACCCCATC CAGCTGGGAT ATAGTTGTTT TCTAAATCTA TGAGGCTAGA GAAGACCATT
TGGGAATTGA GAGCAGTGAG CAGTCCACGG ACTGACCCTT TGAGAGTGCA ACATTTAGCA
GTACTCAAGA TGGGAAGGAG CTAGTGAAAA AGCCCCAAAT GACTACATAA GACCATCAAC
CAGATTACAA AGAAAGACCC GAACATGTGT GCCCATATAT CACCCAACAG CAGTTATGTC
TTTCATGTTT CTTCCCCATA AAATGTTGTT CATCAACTTT ATTAGACTAG GGTCTTAACA
TTGGACAAAT CACAAAACCT CTCTGGAGCC TATTTTATTT TTCAACAGCT GTAGGAAGCA
AATACAAATT GGAAATCTAA GGCTCAGAAA GATTTGTACA AAGTTACACA GTAATGAAAG
GGGAGCCGGG ATTCCCACTC ACTCTAAAGA ATATGATAAA ATGGCTAGTA TTCACTGAAT
GCTTAACATG TTCCAGGCCC TGGGCAGGTA TTATTTTAAT TAGTTCTCAC AATAATCCAA
TAAGGGAGAT ACTAATTTAC TCAGATGAGA AAGCTGAGGC TCAGAGAGGT TAATGAACTA
AGCCAAGGCT CACTGTTAAT AAATAGCAAA GGTAAAATTA AATTCCATAT CTGCTTGAGA
TAGAGGCCTT GCTCCTAATA GCTGCAGCCT GTCAGGGCCT GGCAGCAGTA ACCTCTCCTT
TCCTCTTCCC ACCATTCCCC TGCACTGCTT TCTGTACCGC ATCTCTTTTC AGAGTGATGT
TGCCCCAATT GCGGAGGCCA CTGTGCTGTT TATCCAGTGA AAGCTGTAGC ACAGCCAACC
CAAAGCGTCC CCAGTGAAAA CAACCTGGCT CCTTACAGCA CTTCCAGCCT CAGAGCAGTA
TTTGAAAAAT ATCATGAACA GCAAACACAG CAGTCTGTCT GTGGCTTTTA TATGTGTATA
TGGTGTGTGT GTATGTCCCT TCTCTTGAGC AAAATAACTT TTAGAATTAT AGAAAAAAAA

                                   PmeI
                                 ---------
TGTGCAACAT CAATGTGGAT CTGCTGTTTA AACTCATAAC AGAGAAAGTA GCTTGTTTCT
GGCTATAGGA GGAAAAGACG ATATTCCTTA GTAAAAATGG AAATCCACAT ATGGGGTTCT
TGTAAAAATG AAGATAGAAA ATTGCAAGTT TGGGGATCAA GTTCTGGTTC TATCATCCTT
TAACAGTATG ACCCTGGAAC CTTAATTGCT TTGAGTCTTT GTTACTTTAT CTATGAAATG
```

Figure 11S

```
AAGTATTTAA AAAAACTCCA AAAATCTGTC CTGATGTACA CACAAGAGGT CAAATGAGAA
AATGAATGTG AAGATGCTTT ATAAACTATA CAGCATGGTA GGTGCAAATG TGACATGAAC
TTGTTTTGGA CACATTATAA AGTCACCCCC ACAAACTGTG ATTGTTCAAG ACTATGCAAA
GTCAGACACA GGAAAATAAG TAAAACAGAT GGAGGCATAA AGAGGGGGAA CTCAGAGAAA
ACAGTGAAGA ACAGGAATCA GGAAGACAAA GGAGAGGAAA GGTGGGGAGG AGAGGAGAAG
GAAAGGGGGA AGGGAATGGA GGAGAGGAGA ACAGCTGCTT CACAGAGCAT GGCCGGCAGC
CCAGTCCCAG CCTTTCTGCA TGTCCCTGAC TTCAGCCTCT GGCGAGGCAC AGGCTTACTC
TGTGCTTCCT GCTGTTACTC TTCTTATCCA TCCTTATTAT CAATACCTGT GGTCAACAAA
GTATTTGATA AAGGCATCCT CAAAGTCAGG TAACATCTGT ACGTTATAGA TTACAAAGTT
GAGTAATATC CAGAATTGGT AGTTTAACGT GATGACTTCT TAACAATTAT CACTGTTTCA
GGGAAGGGCA AAGGTGTGTG TGTGTGTGTG TTCATCTGTG TGTATCTGTG TATGTAATTG
TGGGTGTTTG TGTATATTTG TGAGGCTCTT TACTTGGCGG AGTTAAAAAG TATCTGCTCA
TCAAGGTTGA GATTAGCAAA GGAAGTGAAG ATTTTTCCAG AGCCCCTAAA ATGTGCCTTT
TGACCAACAC TGAGGACATC TTTATAACTG AGTATGTGCA ATAAATATGT CTTGGGACCT
GTGCCACAAA TTCCTCTCTA AATAGCCTTT ACCTCTCTGG AATAACCCTT TAGATGAGGA
AGAAAAGGGC TGTGATTTTA TAGCTTGTTA TGAAGCTGGA GTGAAGATGA TGCTTCAGTA
CTTACCCTAC AAAGATACCC CCAATCCCTC ACCCTAAAAT TACCATTGAA ATCATGTTCC
CTTTCTCATT CACTCTCAGT TTCCATGTCA GAAAATATAC CATTACCTCC CTGCACCCCT
TTCATCTCTC TCACTTTTCT CTTGCTTAGA TGGAAAGACA ACCCAGCAAT GCCTGCAGGG
                                 >>...........EXON 9 ............>
CTGATGTATG AAGGAGTTTC CCAAGAGCCC CTGAAATACT CCGGCGGGAG TGCAGCTCAG
>..........................EXON 9 ............................>
AGCACAGTGC TTCATGCCTT TGATGAGTTC TTAGGCATTC GTCATAGCAA GGAAAGTGGT
>..........................EXON 9 ...........................>>
AAGTCAGACA TTTTGTTTTC CCTTGAGAGT AGAGGGAGGA AGAGGAGAGG TGTTTTTTTT
TTTTCCAATT GATAAAACCA AATATAAATT AAAATGTCAT GAAGTTTATA CTTCTCTAAG
TCAGCCAAGA AACTGCATGA CTGCCAATGT TTTTGTGTCA AGCCAATTAA TATTGGAATA
TCAGATGTCA GCTTGATCTT GGGTTTTACT TCCAAATCTT AAAATGTTGC TCTGTTTCCA
ACTGTTCACT ATCACTTTGG TTTGGATCTT TAGACACTAG CTTCCTTTTT CTGAAATGGG
GGAGAGATGT GGAGTTTGAA GGCTATGAGT CTGGGCCAGC TGGAAACAGG TCTGGGATCT
TCCAAGAAAG TCCTTCCCCA CAAAATGGTG CAACTTCTAG CCAAATCTAT TTATACCAGC
AGAGGGATCT ATCACCCTGG AAGCTTGAAA TTGTTCATTT TCTTACCTGC CAGGATCAAG
TTAAGTTTTT AACAGTTGCA AAAAGACACT TCATACTATG GAGTTTTCAA GTTGGATTAG
AAGAAAAAGA ATCACCAGAA CTTAGTGTCG TAGATTCAAG TCACTTCTCT AAAACTGTCA
TAATTTTTCA CGGATTTTGG CATTTGGTGA CATTAATGGT TGATTTACTT ACCATGCATA
ATATTAAACC CATAACGAAT TTCCTATAAA TATCTATTGA TTTGATTTTT AAATCACTTG
GCTTCAAGAG GCTATTACTA AAACAGTGAC TCATTCTTTA TCTTTTTTGC CTTCACGGGC
TTTATATAAC TTTCTCCTTT TCTTGTGCTC CCTCCAAAAC AAAGCACTGA GAAAACAAAA
TTCACCAGAG TATTCAGCTA GTCAGTTCAA GGGTTTGTGT TCTACATTTG AAGATATTCC
TTATAGCAGC TACCAACGGG ATACTTTGTT TACATTTGTT GTGTAGTAAA TATTTATATA
TTGGCAAACA AATCTAGTTC CAACTCTGTC ATCTGAGATG TTCTTACTTT GTTTCCTCTT
CTCCATCTCC TGTCAACTGT TAGAAATATA CATTTGAGTA CGTGAAGTCT GCAAACAAAA
GGGCCAAGGT AGATTTGAGT TAGAACACCA GCAACAGTTT CTGGTGCATT CTTGTCTGAA
AAAGCAGAGA AGATTGGGCA CCGTGGGTCA TGCCTGTAAT CCCAAAATTT TGGAAGTCTG
AGGCAGGTGG ATCGCTTGAG CCCAGGAGTT CAAGACAAGC CTGGGCAACA TAGCAAGAAC
CCGTCTCTAC TAAAAGGAAT ACAAAAAAAT ATTAGCTGGG TGTGGTGGCG CACACCTGTA
GTTTCAGCTA CTCAGAAGAC TGAGGTGGGA GGATCACTTG AACTCAGGGG CAGAGGTGGC
AGTAAGCTGA GATCACACCA CTGCACTCCA GCCTGGGCAA CAGAGCAAGA TCTCATCTAG
AGAAAAAAAA AATAAAAAAG AAGAAGAAGC AGACGAGCTC TGCTATATTT CCATGTGGAG
CTATGACGTT ATGCTGTATT GTTTCTTTCA GGTGACTTTC TGTACAGAAT GAGGGATTAC
                                      >>..........EXON10 ..........>
ATGCCTCCTT CCCATAAGGC CTTCATAGAA GACATCCACT CAGCACCTTC CCTGAGGGAC
>..........................EXON 10 ............................>
TACATCCTGT CATCTGGACA GGACCACTTG CTGACAGCTT ATAACCAGTG TGTGCAGGCC
>..........................EXON 10 ............................>
CTGGCAGAGC TGCGGAGCTA TCACATCACC ATGGTCACCA AATACCTCAT CACAGCTGCA
>..........................EXON 10 ............................>
GCCAAGGCAA AGCATGGGAA GCCAAACCAT CTCCCAGGGC CTCCTCAGGC TTTAAAAGAC
>..........................EXON 10 ............................>
```

Figure 11T

```
                                                                    DrdI
                                                                 ---------
---
      AGGGGCACAG GTGGAACCGC AGTTATGAGC TTTCTTAAGA GTGTCAGGGA TAAGACCTTG
      >..........................EXON  ...........................>
      GAGTCAATCC TTCACCCACG TGGTTAG
      >..........EXON  ..........>>
```

Figure 11U

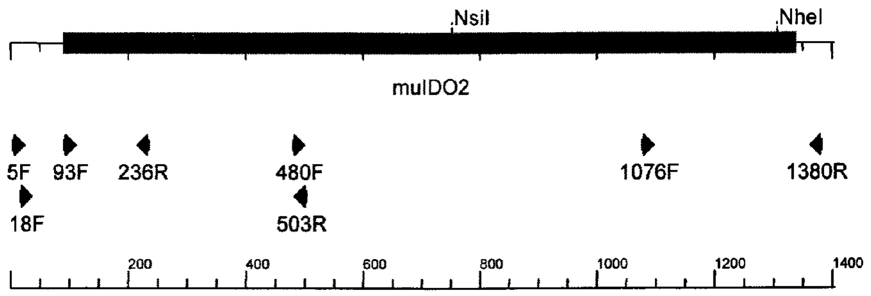

muIDO2 mRNA (1402 bps)

| **Primers** | |
|---|---|
| mF480A | 5′ACTCTGACCTGGTGCTGACAAACT |
| mR1380A | 5′TGCAGGATGTGAACCTCTAACGCT |
| mF93B | 5′TGGAGCCTCAAAGTCAGAGCATGA |
| mR503B | 5′AGTTTGTCAGCACCAGGTCAGAGT |
| mF1076C | 5′TGCCTGATGGCCTATAACCAGTGT |
| mR1380C | 5′TGCAGGATGTGAACCTCTAACGCT |
| mF18D | 5′AACCACACAGAAGACACAGCTGGA |
| mR236DE | 5′TGAGGGCAATTTCCATCCAAGGCT |
| mF5E | 5′ACCGCACAAGTACAACCACACAGA |
| MUIDO-2-L898 | 5′AGCCTTATGGGAAGGCGGCATG |
| MUIDO-2-L430 | 5′ACTGATTTCCAACGGTCCTTC |
| MUIDO-2-L160 | 5′TCGGAGCTGGCGGTTCTCGAT |
| MUIDO-2-U313 | 5′AAGGTGCTGCCAAGATCTC |
| MUIDO-2-U820 | 5′CTTCATGCCTTCGATGAG |

Figure 12A

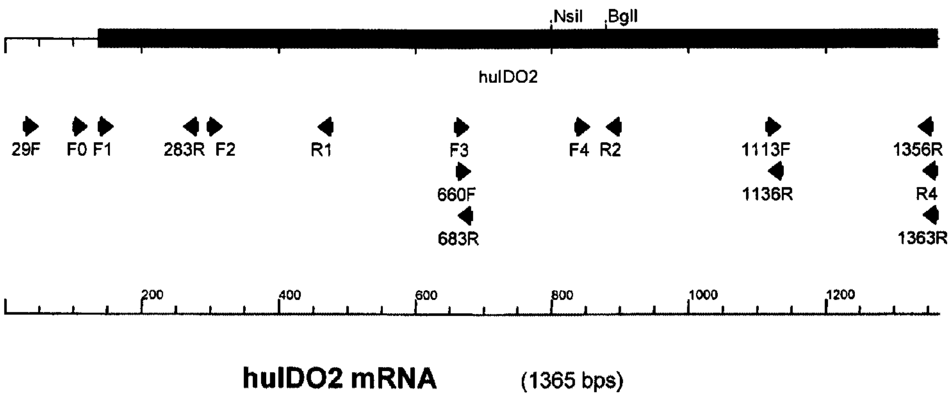

Human IDO2 Primers

| | |
|---|---|
| hF660B | 5′AGAGAAAGAAGCAGTGCCTGGGAT |
| hR1136B | 5′TAAGCTGTCAGCAAGTGGTCCTGT |
| hF29C | 5′TGAGACACTGCGCAACTAACTGGA |
| hR683C | 5′ATCCCAGGCACTGCTTCTTTCTCT |
| hF1113D | 5′ACAGGACCACTTGCTGACAGCTTA |
| hR1356D | 5′ACGTGGGTGAAGGATTGACTCCAA |
| hR283E | 5′TGTTGGCAATTTCCATCCAAGGC |
| hR1363F | 5′AACCACGTGGGTGAAGGATTGACT |
| HUIDO2F0 | TTCAGTGACACTTTCCATGCAG |
| HuIDO2F1 | ATGGAGCCCCACAGACCGAATG |
| HuIDO2R1 | GAAGGGCAAGATTCCTTGGCAG |
| HUIDO2F2 | ATTGATGCTCACCAGCTTCAAG |
| HuIDO2R2 | CTTCATACATCAGCCCTGCAGG |
| HuIDO2F3 | GTAGAGAAAGAAGCAGTGCCTG |
| HuIDO2F4 | GGCATCCGGATCTTTCTCTCTG |
| HuIDO2R4 | CTAACCACGTGGGTGAAGGATTG |

Figure 12B

Mouse IDO1 primers

| | | |
|---|---|---|
| MUIDO-12-U1140 | GGTACTGCCATGCTGAGC | 62 |
| MUIDO-1-L157 | AAGCTGCCCGTTCTCAATCAG | 67 |
| MUIDO-1-L433 | CTCGTATGTCATGGGCCCATTG | 70 |
| MUIDO-1-L900 | GAAGTTCCGGTGGGCTGGAGGC | 75 |
| MUIDO-1-u315 | GGTGCTGCCCCGCAATAATGC | 74 |
| MUIDO-1-U822 | CCAGAGTCTTGATGTCCTTC | 59 |
| MUIDO-1-U1120 | CCTCAAATGTGGAAAGCAGAG | 63 |

Additional cloning primers

| | |
|---|---|
| Ido2 5'KpnATG` | ATCCGGTACCATGGAGCCTCAAAGTCAG |
| Ido2 5' SacI | GTTGAGCTCTCCAGGAACTTGGGA |
| Ido2 5'EcorI | AGTGTTGAATTCCTACAGGAAATGAGG |
| Ido2 5'HinDIII | CTGAAAGCTTATAACCAGTGTGTGGAG |
| Ido2 3'BsrG1 | CATCCTGTACACGTGAGCTCG |
| Ido2 3' SacI | TGGAGAGCTCAACAAAAGGAATGG |
| Ido2 3'EcorI | CTGTAGGAATTCAACACTTTCCTTGCAATG |
| Ido2 3'HinDIII | TATAAGCTTTCAGGCAGTCCCCAG |
| 5'UTR mu 1 | GAAGACACAGCTGGAAAGCTC |
| 5'UTR mu 2 | CCATGCTGACCTCCAGGCTC |

IDO

| | |
|---|---|
| Ido 5'KpnATG | ATCCGGTACCATGGCACTCAGTAAAATA |
| Ido 5'BsrG1 | GAAGTGTACAAGCTGCCCACACTG |
| Ido 5' NsiI | GAGGATGCATGACTTTGTGGAC |
| Ido 3'BsrG1 | AGCTTGTACACTTCTTCTCGAAG |
| Ido 3' NsiI | GTCATGCATCCTCTTAAAAATAAC |

The Universal 3' Primer for pcDNA3,1/-V5his-TOPO

| | |
|---|---|
| TOPO 3' NheI | GTCGCGCTAGCAAACTCAATGGTGATGGTGATG |

Figure 12C

ATGTTGCATTTTCATTATTATG*ATACTTCAAACAAAATAATGGAGCCCCACAG
ACCGAATGTGAAGACAGCAGTGCCATTGTCTTTGGAAAGCTATCACATATCT
GAAGAGTATGGCTTTCTTCTTCCAGATTCTCTG*AAAGAACTTCCAGATCATTA
TAGGCCTTGGATGGAAATTGCCAACAAACTTCCTCAATTGATTGATGCTCACC
AGCTTCAAGCTCATGTGGACAAG*ATGCCCCTGCTGAGCTGCCAGTTCCTGAA
GGGTCACCGGGAGCAGCGCCTGGCCCACCTGGTCCTGAGCTTCCTCACCATG
GGTTATGTCTGGCAGGAAGGAGAGGCGC*AGCCTGCAGAG*GTCCTGCCAAGG
AATCTTGCCCTTCCATTTGTCGAAGTCTCCAGGAACTTGGGGCTCCCTCCTAT
CCTGGTCCACTCAGACTTGGTGCTGACGAACTGGACCAAAAAAGATCCAGAC
GGGTTCCTGGAAATTGGG*AACCTGGAGACCATCATCTCATTTCCTGGGGGAG
AGAGCCTGCATGGTTTTATACTGGTGACTGCTTTGGTAGAGAAAGAAGCAGT
GCCTGGGATAAAG*GCTCTTGTTCAGGCCACGAATGCTATCTTGCAGCCCAAC
CAGGAGGCCCTGCTCCAAGCCCTGCAGCGACTGAGACTGTCTATTCAGGACA
TCACCAAAACCTTAGGACAGATGCAT*GATTATGTAGATCCAGACATATTTTAT
GCAGGCATCCGGATCTTTCTCTCTGGG*TGGAAAGACAACCCAGCAATGCCTG
CAGGGCTGATGTATGAAGGAGTTTCCCAAGAGCCCCTGAAATACTCCGGCGG
GAGTGCAGCTCAGAGCACAGTGCTTCATGCCTTTGATGAGTTCTTAGGCATTC
GTCATAGCAAGGAAAGTGGT*GACTTTCTGTACAGAATGAGGGATTACATGCC
TCCTTCCCATAAGGCCTTCATAGAAGACATCCACTCAGCACCTTCCCTGAGGG
ACTACATCCTGTCATCTGGACAGGACCACTTGCTGACAGCTTATAACCAGTGT
GTGCAGGCCCTGGCAGAGCTGCGGAGCTATCACATCACCATGGTCACCAAAT
ACCTCATCACAGCTGCAGCCAAGGCAAAGCATGGGAAGCCAAACCATCTCCC
AGGGCCTCCTCAGGCTTTAAAAGACAGGGGCACAGGTGGAACCGCAGTTATG
AGCTTTCTTAAGAGTGTCAGGGATAAGACCTTGGAGTCAATCCTTCACCCACG
TGGTTAGGAT

Figure 14

```
<------6665 bases to the end of IDO1 coding region--------------
CCCTGGCCTT GGAAGATGCC CTAGAGACGC TGAGGTGGTT GTACTTTTGC CATAGGAGTG
GCAGCCAGAG AACTGAGCCC AATGAATGCA AAGGCTGGTG CCTGGAAATA TTGTGACTTT
GCCACAGAAA GAAGATGGAG AATTTTAAAG TTGGAAATCT GCCTGGTAAG GGATCATTTG
CTGGTGTCTG CAAAGTTGAG TCCATACACA CTGGTTTGGA AATTTCAGTC CAGATGATAG
                                                 >>..Exon  a...>
TTAAGAAAGC AGTAAGAATA CAGAGAGTCC ACAATGAGAT GAAAATGCAC TGCCAGTTGA
>..........................Exon  1a...........................>
AACATCCTCC TACACTGGAG CTTTATAAAT ATTTTAAAGA CAAGGATTGG ATTAGATTTG
>..........................Exon  1a...........................>
ACATTAGAAA TGTACCATAA TACAGAAGGC AATGGACACC TAAAGAACAG AATGAAAACC
>..........................Exon  1a...........................>
TTCTTAGGAA ATGAAGCTTG ACACTTCACC CACCAGGCCA CCACAAGAAT GTTGCATTTT
                                                    >>.ATG-ORF..>
>..........................Exon  1a...........................>
CATTATTATG GTAAGTACAC TGGTAACTTC TTTTCTAACC TCGTATGCAT AATGTAAACA
>.......>>
>.......>>
TCAAGACTGA CAATTTGGGG CTAGCAACTC AATTGGAAAA TCACTGTTCT CTATTGTAAA
ATTCCTAATT ATGTTTCCCT AGAAATTGCA AAGTGCACAT GTACTTGCAT TTAATGTTTG

   NcoI
  ------
GTCCATGGGC TGAATGCTTT GTGCATTACT TTTCTGGTTG TTGTTGTTGT TGTTGTTGTT
GTTGTTGTTG TTGTTGTTTT GAGACAGAGT CTCACTCTGT TGCCAGGCTG GAGTGCAGTG
GCATGATCTC GGCTCACTGC AACCTCTGCC TCCCAGGTTC AAGCAATTCT TCTGCCACAG
CCTTCCAAGT AACTGGGATT ACAGGCGCTC ACCACCACAC CCTGCTAATT TTTGTACTTT
TAGTAGAGAC GGGGTTTCAC CATGTTGGCC AGGCTGGCCT CAAACTCCTG ACCTCAAGTG
ATCCACCTGC TTTGACCTCC CAAAATGCTG GGATTACAGG CATGAGCCAC CTTGCCCAGC
CTGTGCATTA CTTTTGAGGA CACATTTGAC AATGGCACAG TCAAGAACAC CACATAAAGT
AGTATTGGCA GATTATGAAA TAGCAATTGT TTTGGAAGAC AGCAAAACCT GAAGTATTTT
CAGACATGTA CATTATGAAG TATTATACCT TCTTTAACTA TGTGCAAGTT AAAATCAGTC
ATAACTGAAA ATCAAAAGGG CAATAATGAA CATACTTCAT CCAGAAGAGG TATCCACAAA
ACTTCTGAAA GAGGTCTTAG TATATCCAGG GATGGAGATA TTATTACAAT GTATTATCCA
AATGATGGAA GTTTTCTCTT GCTGATAGAA TGCATCCACC TACTAACATC AGTAAGTACA
GGTTTAACAA TTTACCAGAA ATGTACTGGA GGAAATATGA ATATGCTTCC AGATTTATTC
TACCTAAAGG ATCTGGCTCT ATTTTACAAG GTCATCTATT TTACAAGGTA CTGTAGATGC
ATTTTGATGA AAAAAATTAC CCTGCTATTG ATTTTGAGGT CTGGTATTAT GATAGAGCAA
AAACTATCCA AAAGAGATTT AATTCAAGTC ATTGCAAAAT CTTGGAAAAT GTGTGAGAAA
TCTTACACAT GGAAAGGAGG AAGTAAAGAT GGTAGCTTAA ACATGTGTTC CACTGTGAAC
AATTCTCTGC AAACCCACCC CCAAAAGTCA AGGAGGCTGA CAGGCTGAAG AAAGAGGCTG
TCAAATCTAG TTTCTCAGAA AAAGAAAAAT TAATAGGGAC TTAAGAACAG AAGCCATATA
TCTGCCCTGA GATGAGCTGG TGGATCCTCA CACTGTTACC CCCAGACCCA GGGCTTATAT
ACCACAGGGA AAGACAATTG CAGTAATTTG CTTAACGGCA GGATTTACGG CAAGTACATG
CTCTTAAGAG TAGATTAAGT AGTAACCTTA GAGGCATTCC TAGAACTGGA GTTAATCAGA
AGTCAACACA GTGGATTAGC ATCCAAGATG GAGTTGCTTT AGCCTCCACA AAGAGAAAAT
GAAGATAAAT TTGGTCCATG CTAATTAGGG GGTGTTCCAT TTGTTTGAAA CTGAAATCTA
TAATTTCCAA AGAAGAAAAT AAACGTGGAA GTCGTCCTTC CTTTTTGGTA TGCATAGACA
ATCTGGCAGT GTTAGGCCCC TAAGGCCTTA TCACCTCCTC CTTCTGTGGG TCAAACTTTA
CAGTGAGAGG AAAGACATCT TTTAAAAGAA GAATAATCAT GACTAGTTTA ATCATGACTA
GTTCATCTTC CCTGCAATAG ATACCCATAT TTAACATACC TATTGTACAA AGAATATGAT
TGCACAGCTA CAACTTTGGG ACAAACTCCT TTTCTGCCGC TTTCAATGAT CGTCTTCCAA
AATCAGAACA GCTTTTGAAT TTTATTTTGT GAAAAATGTC GTTTGAGTGA CACAGTAAAC
TCTGTGGAGC TCTGTGGATA CAGTTGAATG ATGGCTCCCA GTTTATCATG CAGGTGGGAT
TATATTCCAA CAGTTATGTT TCACAGAAAG GCAAAAATAAC CAGGTACGGA AAAAATGAAA
AATTTGCAGC TTACATCAAA CAGAAATTGC AGTGTCTTTC ATCTCTTTAA AGTTTTCTAA
TCAAAATTCT AGTTTTCATC AATTAAAACT TTATTTAGGT AGATACATTT AATAAGTAAC
TTTTTGTTGG CTTAAAGGGA ATGAACTTTA TGTAATGTAA CTGTCTATTT CAGGAAGCTT
```

Figure 15A

```
                                                            AhdI
                                                         -----------
TTCTATGAGA ATTTAAAACT ACACCAAAAT ATCTTCTTTT TTTTTTTTTT GAGACAAGGT
GTCACATTGT CTCTCAGGCT GGAGTGCAGT GGTGTGATCC TAGCTCACTG TAGCCTTGAA
TTCCTGGGCT CAACTGATCC TGCTACCTCA ACCCCCCACG TAGCTAGGAC TACAGGCCTG
CACCACCACA TCTGGCTAAT TTTTTATATT TTTGTAGAGA AATGGTCTGG CTACGTTGCC
CAGGCTGGTC CCAAACTCCT GGCCTCAGGT GATCCTCCTG CGTCAACCTC CCAAAGTGTT
GGGATTACAG GTGTGAGCAA ACCTGCCATC TCAAAACATG TGTATTTTAA TGAGACAACA
AAGATCAAGG GAACTTTAGT CCTTACAATG TAATGATCAA AAAAGTGAAA TAGATAATCA

             AccI
            ------
ACATAACATT GCTTGTAGAC CATGCAAACA ATCTTATTGC ATTTGTATAT TTGTAATGAA
CTGTTTTATA ATAACAAAAT GTAAAATGTG TATTTTATTT GTCCTTTTAT TGTTTTCCTA

                                                        SwaI
                                                      ---------
CTTCTTAGAC ATGTTAAGAA CTATGGAAAA AGATATGGGA GTTTGTGAAA ATTTAAATAA
TTCATATTTA TATTACAAGA AACAGATATT AGAATATGTT TGTTTTATAT TTCTTTTGTA
GCAGAATTTT CTAGCCAGGC ATTGTGGCTT ACACCTGTAA TTCCAGCACT TTGGGAGGCT
GAGGTGGGAC AATCACTTAA GCCCAAGAGT TTGAAATCAG TGAGGGCAAC ATAGTGAGAC
TCTATCTCTA CAAAAAATTC TCTATCTATA TCTATATAAA GGAATTTTGT GAGGAAAACT
ATATATTTTG TATATAAATG AATTTTATCA GGAAATATAT CTGTAAATGA ATTTTATAAA
ATATAGCATC ACTTTATCCT TGATTTATTT CATTTAATAA TTATTTTAAA GTAATATACT
AATAAACTCA TTTTAAAAAC TGCTATGACC ATAAAACTAT TAGAGATAAC ATAAGAGAAA
ATCTAGGTGA CCTTGGGTTT GGAGATAACT TTTTATATAT AACACCAAAG GCGCAATCAA
TGAAAAAAAA TGACAAGCTC TATATCACAT ATCAATATTA AAATGTGATC TGTGAAAGGC
ATCGTCAAGA GAACAAAAAG ACAAGCCACA GACTGGGAGA AAATATTTGC AAAAGACATA
TGTGATAAAA GACAATTATC AAAATATACA AATAATTCTT AAAACTCAAA AATAAGAAAA
TGAACAACTC AGTTAAATAA TGGGCAAAAG ATCTCAACAG AAACCCCATC AAAGAAGAAA
CACAGTGGCA AGCATATGAA AATATGATCT ACATCATATG CCATTAGGAA ATTGCAAATT
AAAACAATGA GATACCACTA CATTTCTACA TTGGTGAAAA TTCCAAGTAC TGACAGCACT
CTCAGTGCTG GTGAGGATAT GGTGCAGTAG AAATCCACAC TCATGCCGGG CACAGTGGCT
CATGCCTGTA ATCCCAGCAC TTTGGGAGGC TGAGGCGGGT GGATCACCAG GTCAGGAGTT
TGAGATCAGC CTGACCAACA TGGTGAAACC CCGGCTCTAC TAAAAATACA AAAATTAGCC
CGGTGTGGTG GCGGGCGCCT GCTACTCGGG AGTCTGAGGC AGGAGAATCG CTTGAACCCA
GGAGGTGGAG GTTGCAGTGA GCCGAGATGG CGCCACTGCA CTCTAGCCTG GGCGACAGAG
CAAGACTCCA TCTCAAAAAA AAAAAAAAAA AAAAGAGGCC AGGAGTGGTG GCTCACACCT
GTAATCCCAG CACTTTGGGA GACTGAGGTA GGCGGATCAC TTGAGGTCAG GAGTTGGAGA
CCAGCCTTGC CAACATGACA AAACCCTGTC TCTACTAAAA CCACAAAAAT TAGCCAGGAG
TATTGGCACA TGCCTGTAGT CCCAGTTACT CGGGAGGCTG AGACAGGAGA ATTTCTTGAA
CCCGGGAGGC GGAGGCTGCA GTGAGCCGAT ATCGCACCAC TGTACTCCAG CCTGAACGAC
AGGGCGAGAC TCTGTCTCAA AAAAAAAAAA AAAAAAAAAA AAAAGGAAAG AAAGAAAGAA

                                SnaBI
                               ------
AGAAAAAAGA AAATTCCGTG ATTGCAGTCT TTACGTATTT ATTTGTTATT AAGTACAGTA
AAATAAAGAA GGATAGATGT CATGGAAAAT GTCACGAAAA TAAAAGAGTT AAAAAAAAAA

                                                     DrdI
                                                 -------------
AAAAGTAGGC TGCAATGCCA GATGCCTGAA AAGTTAATCA ACGAAAGGAC TTAAATGTCC
CCATTGAATT TAGGAACAAA GAAGTAATTA ATGAACTGGG CAAAAACACT CAATGTACCA
GCGTTATCGA TTTAGAAACT GAAACTAAGT ATATCTGATG TTGCTTTTAG GAAACAAGTA
AATGAGGTCC TAAAAAGTTA AACTGTGACC ATATTTTCTT TCCTTTTTCT AATTTCTCCT
TGGGCCATTT CCAAAAAGCC CTAATACCCC GACTGATAGA AATGGATACC TTGCTGTGCA
CTGGTACTAC TGTGATTCAT GGAAAGCTGA TCATGCAACC CAAGACGCCA AAATTCCCAG
CCTTACTGTT ACGAAAGAAA GTTTCTAAGC ACAATTGTCT CTAGCCAACT TCCTCTTAGT
AAGAAAGAGG CCAGGCAGGG CTTCATGCAG GGTACAGCCC TGAGTTTCTT ACTGCGTGGT
```

Figure 15B

```
                                                                    BsaWI
                                                                    ------
AAGTTTCTGG GGCTGGGAGT AAAGCAGCGT GACCGAAAGC AGTACAAAGT TCTACCGGAC
ACGCAGATCC CGGTCCTACA AATATGAGGT CCATAATGAG ACTGAGATAT CATTCATCCA
ACAAATATTT ATTGAATACC AAACATTGGG CTTACGGCTA AAGGAAAATA CAAAGTTGTG
TTGGATATGG GTTCTGTTTT CAAGGAGCTT ATAATCTAAT AGGAAAGATG AGGTTACTAC
ATTAGTAGCA ATCAGACCAG ATAGAACTGG AAGTGTGATG TAAATGAGGT ACAGATTGAT
TGTAGAATTT TGCAGAAAGA AAACAATTCT GAAGAAATGT TCATGGAAGT ATTAGCAGTT
GAGATGTATC TTAAAAGATA AGTGGGGTTC CTGTTGGAAA CATTCAAAAC TCTCTCTTCT
AGCTATTTTA AAATACGCAA TATATTATTA ACTATGGTCA CCTTACTGTG CTATAGAACA
CTAGAACTTA TTCCTACTAT CTAACTATAA TTTTGTACCC ACTAACCAAC CTCTCCCTGT
CCCTCCTCCC CCTATTCATC CCACCCTCTG GTAACCACTG TTCTACTCTC TGCTTCCCAA
AACAAAGAAA TGATCACTGT TTCGGTGATG GAGATGTCAA TTACCCTGAT TTGATCATTA
CACATTGCAT ACATGTATAG AAATATCACA TGCAACTCTT AAGTATATAC CATTCTTATG
TACCAAATAC AAATAAAATT GAAAAAAAAA AAAAACTTTG GCTGGGCGCG GTAGGTCATG
CCAGCACTTT GGGAGGCTGA GGCAGGCGGA TCACCTGAGG TCAGGAGTTC CAGACCAGCC
TGGCCAACAT GGTGAAACCC AATCTCTTCT AAAAAATACA AAAATTAGCT TGGTGTGGTG

     PspOMI
     ------
      ApaI
     ------
GCAGGGGCCC GTAATCCCAG CTACTCAGGA GGCTGAGGCA GGAGAAATGC TTGAACCTGG
AAGGCAGAGG CTACAGTGAG CCGAGATCAT GCCACTGCAC TTCAGCCTGG GTGACAAAGC
AAGACTCCAT CTCAAAAAAA AAAAAAAAAA AGCCTCCTGA GTAACTGGGA CTACAGGCAT
GCGACAATAC TCCCGGCTCT CTTTTTAAAA ATGAGAAGTA GAAGTAGTGG TGACTGTCAA
GAAAGTATTT TGGAAAAATA CTATGAATAA CCAGACCAAA GAAACCAAAT ACCAGTTGTT
TCAGGAGCAG TAAATCATTT TTGAGGGCTT GAGCAAAGGT CTTGCTAGAA AGGTGCTTAG
GGGTCAGATT TTGGACATAA TGCCAGGCCA AGAAAATTTG CACTTTATTT CATTAACAAT
GAGGAGCTCT TGAAAGTTTT ATTGGCAGGA CCTAAGATAG TTACAGACCC ACAAGTAACA
TGGGTCTAGA CCTTGGGAAC AAGAAAAGTC AAGATCGAGT ATGCAGACTT GGGAACCGAG
TATAACTAAT GGTTAAGATT AAATAAAAAT ACATAAGAAC ACTGAGATAG AGAAATGGCT
CATTAATGCT GCAAATGTCT GCATGTTTAG GGATGAAATA GAAAAAGAAG TCAGAAAAAT
ACAGTTCAAA CAATAGGAAA GAAAACCAGA AATGCATGAT TCTAAGAAAT GAATGGGTGG
ACATGGTGGC TCACATCTGT AATCCCAGCA CTTTGGGAGG CCGAGGCAGA AGGATAGCTA
CAGCCCAGGA GTTCAAGACC ACCCAGAGCA ACACAGCAAA ACCCCATCTC TACAAAAAAC
AAAAATAAAA ATTAGCCAAG CATGGTGGTA CACACCTGTA GTCCCAGCTA CTCACTCAAC
AGGCTGAGGC AGAAGGATCA CTTGAGCCCA GGAGGTGAAG GATACAGTAA GCTATGATTG
CACCATTGCA CTCCAGCCTG GCTGAGAGAA TGAGAGCTTG TTTCCAAAAA TAAAAAATAA
GAAAGAATTT TTAGAATGAG AGGAAAACAA CATGAAACAT GAGAAAAATA ACATTCCCTG
TTATATGGTA GGTGCTTCGC TTATAGTTTC TCATTAATTC ATCATGTAAT GTCTCTGGGA
TAAACATTAT GGATTTCCTG CAGAAACAGA AGCTCAGAAT TTTATGCCAG GTGTTGAAAG
GCCATGTAGC TAATAGATGA TAGAACACAG ACTCACACTC TGGTAGTCCT GAGTTAACAG
TAGAAAAGTC CTGGGCTGGG CGTGGTGGTT CACGCCTGTA ATCCCAGCAT TTTGGGAGGT
TGAGGCAGGC AGATCACCAG AGGTCAGGAG TTTGAGACCA GCCTGGCCAA CATGACTAAA
GCCTGTCTCT ACCAAAAACCA CAATTACCCA GCGTGGTGGC GGGCACTTAT AGTACCAACT
ACTCAGGAGG CTGAGGCAGA AGAATTGCTT GAACCTGGGA GGTAGAGGTT TCAGTGAGGC
AAGATCAAGC CACGGCACTC CAGCCTGGGT GACAGAATGA GACTCTGTAT AACAAACAAA
CAAACAAAAT CAGTAAGAAA GTCCCAGACT AAGAGGCATC AAATCAGGAT TCTACTCCAA
CTCTGATGCC AGCTTCCAGG AATACACTTG ATAAGTTGTT TCATTCCCAT AAATCTTGGG
TGATTCGTGT TTAATGAGAG CATTGAACTG AATCATTTAT TCTATGACTC AGTTCTAATA
TTTCACAATT CTATGGTTGT ATAATATTAC AGGAAATTCT TGAGAAGGTG CAGAGGGAAT
GGATGAAAAA AACCACATGA CTAACATAAA AAATAATGGG GCCATCTTTT CATTTGAGAT
TGAAGGAAAG AACGAGAGGA CAATTAAACA TGCAGAGTCT GAGAACTTGC ATTTAGGAGG
CATAAGATGC TGAACTGCAA AATTGGTTAG ATATTGGGCT GAAGAGAATT GAGAATTTTT
TAATAATAAA AACTCTTGGC AGGGCGCAGT GGCTCACGCC TGTAATCCCA GCAGTTTGGG
AGGCTGAGGT GGGTGGATCA CTTGAGGTCA GGAGTTTGAG ACCAGCGTGA CTAACGTGGG
GAAACCCCGT CTTTAAGAAA AATGCAAAAA ATATTAGCTG GGTGTGGTGG TACAAGCCTG
```

Figure 15C

```
                                                  PmlI
                                                -------
TAATCCCAGC TACTTGAGAG GCTTAGGCAG GAGGATCACG TGAGCCCAGG AGGTGGAGGT
TGCAGTAAGC CGAGATTGTG CCACTGTACT CCAGTCTGGA TGACAGAGGG ACACTATCTC
AAAAAACAAA CAAACACTCT TAAGAAATTA GGTGTAGAAA GAATGTTCCT CAATACCATA
AAGGCCATAT GTAAGAAACC TATAGCTGGC CGGGCGCGGT GGCTCAAGCC TGTAATCCCA

                                NruI
                              -------
GCACTCTAGG AGGCCGAGGC GGGCAGATCG CGAGGTCAGG AGATCGAGAC CATCCTGGCT
AACACAGTGA AACCCCGTCT CTACTAAAAA TACAAAAAAT TAGCCGGGCG AGGTGGCTGG
TGCCTGTAGT CCCAGCTACT CGGGAGGCTG AGGCAGGAGA ATGGCGTGAA CCCCGGGGGG
CGGAGCCTGC AGTGAGCTGA GATCGCGCCA CTGCACTCCA GCCTGGGCGA CAGCGAGACT
CCATCTCAAA AAAAAAAAAA AAAAAAAAAA GGAAACCTAT AGCTAACATC ATACTGAATG
GTGAACAGTT GAATGCTTTC GTCTAAGAAC TGGAACAAGA CAAGCACGCC AACTCTCACC
ACTCTTACTC AACATAGTAC TTTAAGTCCT AGCCAGAGCA ATCAAACAGG GGAAGTGGAT
AATTGAGAAT GGCTCGAGAG GTGCTGTGGC TCAGTCCTGT TGTCCTGGCA CAGAAGGAGC
TGAGGCCAGG CGTTCAAGAA TGGCTCCTAG ATGTCTCATA AGGAACCATA AATCAAACAA
CTTTCAAAAC TGAAACCTGC GTGAGAACGG TTGCATTAGT TAATCTGGGA GCTTCCTGCT
TTTTTTTAGC TTTCATATTT ATCTTAGAGA AAGGGAGGAA GGAGAGATGT GTATGGATAC
ATAAGCATTC AAATACATTT GTGTATAATC TTATGACCAG AATTCAGGTC CAATGAACAA
AAAGGTAGGG TCTTCGGAAT TTCCCCAGTG AGATCTATGA CCTGAATATT ATTACGCAAG
GATCCACTTT GGGATTACAG GCGTGAACCA CTACACCCAG CCCAGGACTT TCCTGCTGTT
AACTCAGGAC TACCACAATG TGAGTCTCTG TTCTGTAATG CCCAACCTTG TTTTTACTAA
CCCCGCTTTT AGACTCCCCG TTTTCCTTTA ATCACCTAGC CTTGTTTCCA CCTGAATTGA
CTCTCCCTTA GCTAAGAGAG CCAGACAGAC TCCATCTTGG CTCTTTCACT GGCAGCCCCT
TCCTCAAGGA CTTAGCTTGT GCAAGCTGAC TCCCAGCACA TCCAGGAATG CAATTAACTG
GTAAGATACT GTGGCAAGCT ATATCCGCAA TTCACAGGAA TTCGTCTGAT TGATAACGCC
CAAAGCCCCG AGTCTATCAC CTTGTAATAG TCTTAAAGCC CCTGCACCTG GAACTGTTTA
CTTTCCTGTA ACCATTTATC CTTTTAACTT TTTGCCTAAT TTATTTCTGT AAAATTGTTT
TAACTGGACC CCCCTCCCCT TTCTAAACCA AAGTATAAAA GAAAATCTAG TCCCTTCTTT

                                          BsiEI
                                         ------
GGGGCTGAGA GAATTTTGAG CGATAGCCGT CTCTCGGTCG CTGGCTAATA AAGGATTCTT
AATTTGTCTG AAAGTGTGGC GTTTTTCCAA CTCGTTCAGG TACAACAGTT CTAGCATCTA
TTAGCTATGT GGCCTTTCAA CACCTGGCAT AAAATTCTGA ACAATGGCTT GGAAATTAAG
ATACCTTAGC TCTAGTCCTT GCTCTGCTAA TAATTAATAG AGTGAAACTG GACAGGGTTA
TTCACATGTG TGTGCCTCAG TTTACTGTTA ACTGAAGAAT GACAAAGTTC ATAAATTTGA

                                       SbfI
                                     --------
AAAGGAGAGG TTTCTTATAT GGGGTTGCAA CCTGCAGGGT GGCCATGCTA CAGTCTGGGA
AGCATTGCCT CTGGCTGGAA GCCAGAAACA GGCACTTTCA GGGTCAGAAG AATAAGACAG
AGATTTATGC TGAATGGGGT GACCAAATAT ACATATTCAA TAGGCTATAG GAGGAGTTAT
GAATATTTAT GAAAGGAGAA ATGTGTACAT GTGCAATTTG GCTTCATGCC CCTTCATGGG
ACCTACATTC AAAAAATGGC AGCCTTAGCA TGATCTGAGG GAGGATCTTT CAGCCCTCTG
AGGTCAAAAG TGAAGGAGAG GACAGGAAAC CCTCACTGTG TGTTCTCCGT AGGGGCCAGA
ACCACTGCAT GTTTGGTGAA CCTGGCTGGT TGTTATGTTG AAACTGCAAA AGGGAGGGAT
AACAGTCAGG TGCTTGTTTG ATACCAGGGG TAGAGGAGAC TTTCAAAAGG GCTGGTTTCT
GTTTAGCCCT TAGGGAAGAA TGTCTAAAGA GAATTACCTA CAAGGGTATA ACGAGGAGTG
TCTGACATTC CATCTAGTAA TGAACTAGAA CTCAGTTTTC AAGTTAACTC TGGGACCCTC
TTAGCCAAGA AGAGGTCCAT TCAGTTGGTT GAAGAGCTTA GGATTTCATT TATATCTCTC
ATCACTAATC TGCAAAAGCT GGTAGTGAAA CCGCCTTTGC AAAATTATGA CTGAGACAGC
GAAAGAGATC TAACTTAATC GATTCCGTCT TGCTTCTAAC CTCCAAGCTG TCCTTATTCA
TTCCCGGGCA TAGGCTGAAC TAACTCCGGG AGAAGCTTAG TTTATAGTTT TTAGTTTAAA
ACAAAGATAG TAACAGCCCT TTCCCAAAGC AGACCTCCTT CTTGCCTTGG AACTAGACTG
```

Figure 15D

```
                                                                  PvuII
                                                                  ------
                                                                  MspA I
                                                                  ------
CCTTTAGTGG GACTAACATT AGCCACAAGA TTAGAAACTG TGGCTTAGGA GTCATACAGC
TGGAGGCTAC AAGATTCTGA CTCTCCCTAA ACTGCTCCTA AGATCAGTCC TTGAGATATT
TTGCAGACCC TGTACTTGAT GGATCAGGTG GCACCACCCA GATTGATAAA GTGGCTCATC
TGATCTTGTG GCCCCCACCC AGGAACTGAC TCAGCACAAG AAGAGAGCTT TGACTCTCTA

                                                 EcoNI
                                              ------------
TGATTTCATC TCTGACCCGT CAGCACTCCT GGCTCGCTGG CCTCCCTCAG GCCACCAAGT
TGTCCTTAAA AACTCTGCTC CCACTGGGCG GTGGCTCATG CCTGTAATCC CAGCACTTTG
GGAGGCCAAG GCAGGCGGAT CACAAGGTCA GGAGATTGAG ACCATCTGGC TAACATGGTA
AACCCTGTCT CTACTAAAAG TACAAAAAAT TAGCTGGGCA TGGTGGCACG CACCTGTAGT
CCCAGCTACT CGGGAGGCTG AGGCAGGAGA ATCACTTGAA CCTGGGAGGC AGAGGTTACA
GTGAGCCGAG ATCATGCCAC TGCACTCCAG CCTGGGCAAC AGAGTGAGAG ACTTCATCTC

                         BsrBI
                        -------
AAAAAAATAA ATAGATAAAT AACCTCCGCT CCCTGAATGA ATGCTCCCGG AGACTGATTT
GAATCATAAT AAAACTCCAG TCTCCCGCAC AGCCTGCTCT TCATGAATTA CTCTTTCTCT
ATTGCAAATC CCCTGTCTTG ATAAATTGGC TCTGTCTAGA CAGTGGGCAA GGTGACCTCA
CTGGGCAGTT ACAGTAGTAC CCACTTCATA AGTGAAATCA CTTATCTTAG TGGTAGGGTC
CCAAAAGTTG TTTGGTAGGA GAGGGTTGAG GCTGGGAGAG GTGGCTCATG CCTGTAATCC
CAGCACTTTG GGAGGCCAAG GTGGGTGGAT CTCCTGAGGT CAGGAGTTCC AGACCAGCCT
GGTCAACATG GTGAAACCCC ATCTCTACTA AAAATACAAA AAATTGGCGT GGTGGTGGGT
GCCTACAATC CCAATTACTT GGGAGACTGA GGCAGGATAA TCGCTCGAAC CTGGGAGGCA
GAGGTTGCAG TGAGCAGAGA TCGCGCCACT GCACTCAAGC CTAACCAACA GGGGCAAAAC
TCTAGGACTA GAGCTAAGGT ATCAAAAAAA AAAAAAAAAA AAAAAAGAAG TAGAGTGTTT
AATTAAATAA TTTGTTCTTG CTGTAAAATG TAAAGTAGAT ATTCCTCTTC AAAGACTTTC
CTCCCCGTCT AATTAGGAAT AAATAGTAAC TTCTCTTAGA AGCAAAATTT ATTCAAAGAC
CTGTGCTAAC ATTCTTAAAT ATCTGCTAGC CACAATAAGG AAATCAATGT ACTTTATGTT
CTTAGCTCCC ACAATTTAGC CTAAATATTT TCCCTGGCAT GTTTATACTG GTCTAAGCAA
GCATTAGGTC ATAGCCTGTT CCTCTTCCTT ATTTAAAAGT GTTTTTACCT TTCTCAGCGT
TCCACAAGTT ACTTCCTCCT TCCTTTGTTC TCCTCTACCT GTGCCTCTTT TAAAAAGTTC
TAAGTTGCTA GCCAATTGGG ACAAATACAG AATGTAAGGT CCCATTCCAG CCAACGGAAA
CTGGACACAG CAGTAGGGTG GATGTGTCAG GTTATAAATG ACCCTGTCTC CTTTGTTTGG
TGTACTCTAG TGGCAAAACT GCTGGCAAGT GTACCTTTTC TGCAGGAAGT AAAAATGGCC
TTACTAAATA AATTAAATTT ATGTTCAAGT GCTATTTCTT TTTTTTTTTT TTTCGAGATG
GAATTTCACT TTTGTTGCCC AGCCTGGAGT GCAATGGCGC GATCTCGGCT CACTGCAACC
TCCACCTCCC AGGTTCAAGC AATTCTCCTG CCTCAGCCTC CCGAGTAGCT GGGATTACAG
GCATGCGCCA CCACGCTCGG CTAATTTTGT ATTTTTAGTA GAGATGGGGT TTCTCCATGA
TGAGGCTGGT CTCAAACTCC TGACCTCAGG TGATCCGCCT GCCTTGGCCT TCCAAAGTGC
CTTGGCCTTC CAAAGTGGCG TGAGCCACTG CGCCCAGCCT CGAGTGCTAT TTCTTTACGG
CACGGAAGAA CAAACATTTC AAACAATGCT ATTACCAAGT TTGTTAGTAT TTATTATCTC
ATTTGCTAAA CCTAAAAAAT ATATATCCTT CTTTAACGTG ATCGAATATT TCAAAAAGTT
ATTGTGTTGT TTCTTAAAAT AAATCAATCA TAATCCTAGA CTATGTTACT CAAACTACAT
ACAACACCTT CTGAGCTTCT GGCAGGCCCT TCCTCCCCTC CCTGCTCACC ACAGATCACT
GGAATAATTG TCTGCATGTA ACTTCTAATT TTGAAGTGGT TGTGGTTTAT CAAACCTGGA
ACATGGCACT TCCAAGTACA TGAGCTAAGG TCACAGTAAG ACTCAAGCCC CTTCAACAGA
ATACCTGGAA TTTCTCTGTT AAAGATTTTC TCCTTTACCT GACTACATGT TTGTAATGCA
GATCCCTCCA GGAGCGCTTA CTTATAAACT GTCCTGGATC ACTAACGCGA CATTTTGATG
TAAATTAGTT TATCTTGACG TGCTAATGGT AGAAAAAAAG AGAACATGAG GAAACTTGGG
TGCTTTCAGG GCTGGTAGGA AGGATTAAAT CTTTGCGGCA ATTTCTGAGA AGGGGAAGGA
AACCTTGCTA ACAATTTTGA TAGTTTACTC CATTTGGCTG GAGTAACTCT GATCCATTTG
```

Figure 15E

```
                    KpnI
                  -------
TCAAATTCAC GATGGAGCAG GTACCTGTTA GGGTACAGGT TTGATAAACC ACAACCACAG
GTCTATTTCA TTTCTCCTTT TCCAAAGTGG AACAAATTTG TCTCTGGGGT TAAAACTGCT
TTTCTCATAT TGGTGTGTAA GAGAAAATGA GGGAATTTCT TTGAGTTTGT TTGGTTTGTC
TGTTTGTTTA AGCAGCATTT TTTAAATAAT TTACTCAGCC CTGTCTCAGA GAAAGTCCAT
GATGATCTGG AATTCAACCT CAGGGAAAAG TTCTCTCCTG TGCCTGAGAC ACTGCGCAAC
TAACTGGAAC CGAAGGATGG AACCTGGGTG TTTAATTTAT TAGGAACAAT TGATTCTTCA
GTGACACTTT CCATGCAGAT ACTTCAAACA AAATAATGGA GCCCCACAGA CCGAATGTGA
                                   >>.........Exon1  .........>
AGACAGCAGT GCCATTGTCT TTGGAAAGCT ATCACATATC TGAAGAGTAT GGCTTTCTTC
>..........................Exon 1 ............................>
TTCCAGATTC TCTGGTAAGG ATAGAGCCTT GGTAAGGATA GGTCAGAATA TGTTTCTTGA
>....Exon 1 ....>>
GATGTTGGTT GGTTTGTTTT TTAAAAATGT ATGTGATTAT TAAGAGACCA ATATAAATAT
CAAGTTGTTT ACCTGAGAAA GATGCTACAA AGAGCATAGA TTATCATTAC TATCAAAAGA
GAAGTGACAG ATACCACAGA GAACAGGTCA AATGGAACAT TTTTTGTTTC AGTTTCTTTT
GACTAGATTG TCAGGCCAGA GAAATTATAA GCAAACCTGT AGTTATCAAG AAAAAGCATG
AACTTAAATA TAAATAAAGA ACAAATACAG AGCCTCAGCA CCTGGAACAT GGCACTTCCA
AGTACATGAG CTAAGGTCAC AGTAAGACTC AAGCCCCTTC AACAGAGTAC CTGGAATTTC
TCTGTTAAAG ATTTTCTCCT TTGCATGACT ACATGTTTGT AATGCAGATC CCCCCAGGAG
CGCTTACTTA TAAACTGTCC TGGATCACTA TCGCGACATT TTGATGTAAA TTAGTTTATC
TTGACTTGCT AATGGTAGAA AAAAAGAGAA CATGAGGAAA CTTGGGTGCT TTCAGGGCTG
GTAGGAAGGA TTAAATCTTT GTGGCAATTT CTGAGAAGGG GAAGGAAACC TTGCTAACAA
ACAATACCTC TTTCTTAATT CTACTTAGGG CTCAAATTGT AATGCAAATC TTTTTCATCA
TTTAGCCCTT ATAAACACTG TTTTTCTCAT CTGGTGTGGT CCAAGGCCTA GAACATTAAA
ACTATCAAAG CTTTTACAGA CCATCAGGTG TCATCCCCCT CTTTCTACAT CTGAGCTAGC

                                                        SpeI
                                                       ------
TGAAATCCAG AGGAAATGAC TTGCTGAAAG TCATGAGTGG CAAAAGCAGA ACTAGTTCTG
CTTATAACTC TTGACTTTTA GTTATTATTA TTATTAATTA TTATTATTAC ATCCTAAATG
AGGGCCAAGG CCACTCAGTT AAAAATCGTG GGGTCCAGGC CAGGTGCAGT GGCTCACGCC
TATAATCCCA GCACTTTTGG GAGGCCAAGG CAGGTGGATC ACTTGAGGTT CAGGAGTTCA
AGACCAGGTT GATCAACATG GTGAAACCCC GTCTCTACTA AAAATACAAA AATTGGCCAG
GCGTGGTGGC ACATGCCTGT AGTTCCAGCT ATTGGGGAGG CTGAGGCAGG AGAATCCTTG
AACCCAGGAG GGGGAGGTTG CAATGAGTGG AGATCATGCT GTTGGGAATG AAGTTTTTGG
TGTCACAGAA AAAGAATGAA CATGGGAACA AATGATCTCT CAGCAAAAGG ACCTTTACTT
TCTGCAGAAA GGGTGCTACT CAATAGCTGT CCAGCCACGA GAGCACACCA AACAAAGGAG
ACAGAGTTAT TTATAACCTG ACGCATCTAC CCTACTGCTG TGTCCAGCTT CCATTGGCTG
GAATAGGACC TCACATTTTA CACTTTACCC AATCGGCTAT TAGTTTAAAA CTTTTTTAAT
TGGATAAGGG AACAGAACAA AGAAAGAAAA GCAAGTTGCC CAGGGATAGT TAAGGAAACA
TCTCCATATA AGGAATGGCA TGCACTATGG GCTGGGGCTT TTCTAGTTCT GTACAGACAT
GCCGGAGCAA GCTACGACAG CTGATTTGGA CAGCCACTAA TAGTGGCTAG CAATCTTATA
GTAAGAAATT GTGACTTTTT ATAATCTTTG AAGAACTTTC CCATTTCTGA CAGTGCCACT
GCACTCCAGC CTGGGCAACA AGAGCGAAAC TCGTCTCAAA ACAAAACAAA ACAAAACAAA
ACAAAACAAA ACAGCTCTCT ACTCTTGGAA GCAGCAGAGT TTTTATCTTC ATTTATATCA
CTCCGGTAAC ACTCAGAAGT AGACAAGCCT CAGGGTAGGT ATTCAGTAAA AGCCCACTGA
ATTCCACACT ATTCTTTAAT CATAGTTAAA TGGCAAATTA GGCTGGAGGG TGGGGGTGGA
ACCTCTCCAA AATTACTGCA ATGACTGCAA CATCGGACCC CAAGATTTTT TTTTTTTTTT
CTGAGATAGA ATCTCTTTCT ATCGCCCAGG CTGGAGTGCA GTGGCACTGT GAGAAATGGG

                                            AhdI
                                        ------------
AATGGACCGG ACTGTTTCCT CTGACACTGC CACTAGGTTG ACCAAGTGTC CCTATTTGTT
AGGTACTGGA TGGACGCCTG ACATGCAAGA CTCTCAGTGC TAAATCAGGA AAGTGCTGGG
ACAATTCGGA TGAGTCGGTC ACGCTAAGTT GCACTTAATA GCTCTTGTGA CTTTGACTGA
ATTACAAACA TCCCCTGACC CTCAATTTTC ACATTTACTG GATGGAGATC TGGTGCCACC
TCCACTAGAT TGCTATGGAG AATGAATGTG AAAGCATTTT CATAAATCCA GTGTAAGGAC
```

Figure 15F

CAGAAGCCAG TCTTCTGACC TTGAGCCAGT GCTTGTTAAA AACTCCACTC TATACATCTA
ACCCAATTCA GGAATATCCT GCCTAGTTCC AAAGGAAGAA AAGACCAAAT TGCTCTTATT
GGGATTAAAT GCGTACACTG AGCTGAGGAA AAACAGTATT ACAAATGAGC TAAACATGAC
GTAGATCCAC AGTTGTAGAA TTCCCCTCTT TGTTCTTTCC TCTTTCATAA CTACGGAAAC
AGATGAGAAA CATTTACGGC ATCAGGTTCT TGTGATGCTC CCTGCCTGAT ATGCTATGGT
TTTGTTAATG GAATGTCCAT TCCTGAGCTT ATGCAGAAAA AAGTCCCTTG GGAAAGTGGT
TTTACTGTGT TATGTTCATT TTCCCCATAG TTCTCAAAAT GTACTTCCTT GTTTCAGTTT
TAATTTTCTT TCATTGGTGT GACCATTTTC AACTGCTCCC TTTCTGGGAA GAGGTAGCAG
ACGGACATTT TCATCAAAAT CTGCCCCAGG TTGCTTCACA GATAAGGAGG GACCCAGCCA
CTAAAATCAC CAGGCAGAGT GTTGCAAGAG TAGATAGAGA ATCACAATTG GCTGCCCTGC
TCAAGGGGAC ACCAGATCTT ACTTTCGTTT AGTTGAAAGG CAAGCGTCAG AGTCGGGAGG
CTGTACCTTC ATGTCCAGTG GCCTCACAGA AGTTCCTTCA GTATCTCTTT TAGATGAAAC
TCTTTTAGAA GTTCCTTCAG TATCTCTTTT GGTTTCTCAC TATAGATAGT TACTTGAACA
TGTCTGAAGA AAACGTGGTC AAGACAGTGA ATAAAAAAAA TTCTGGTTTT GGGAAGCAGT
CTGACTTAGT TTCAAATATT CTATCCCACT GTTTCTGTCA ATGTTCAAAC CTTTCCAAGC
TCCAACATTT ATTGTGGAAA ATGTGTGCCT CACCAACTCA TGCAAATAAA TGTTTCATGT
GCCCTACGTG TGTAGAGGGG GCATGGATGT GTGTTTTTGG AGGGAGGGCT AATTTTTCTT
TAGACATGGA GAATACGAGG AAATTAGCTT GGCATCAAGA AGGTTACAGC AGGAGACAAG
AGTGAAGAGA ACTGAGAGAG CCCGGAAATG AGGCTCTGGA GTTCAGATTT TTTTTTTTTT
GAGATGGCGT CTTGTACCCC AGGTTGGAGT GCAATGGCAA AATCTCAGCT CACTGCAACC
TCCGCCTCCC GGGTTCAAGC GATTCTCCTG CCTCAGCCTC CTGAGTAGCT GGGATTACAG
GCATGAGCCA CCATGCCTGG CTAATTCTGT AGTTTTAGTA CAGATGGGGT TTCTCCATGT
TGGTCAGGCT GGTCTCAAAC TCCCAACCTC AGGTGATCCA CCCTCCTTGG CCTCCCAAAG
TTCAAGGATT ACAGCCATGA ACCACTGCGC CTGGCCTAAT TTTTGTATTT TTAGTAGAGA
CAGGGTTTCA CCATGTTGGT CAGGCTGGTC TTGAACTCCT GACCTCGTGA TCTGCCCACC
TCAGCCTCAT GAAGTGCTGG GATTACAGGC ATGAGCCACA GGGCCAGGCC TGGAGTTCAG
ATTTAACACA TCCTGTAAAT GACATGATGC ATCTGATATT TGAAGAGTTT TCCTCAAAGA
ATGTTACATG CAAGGTGGTT TAGAGTTGTT GTTTCCGGCT ATATAGCAAA AGTACTTGGG
GAGTTTTAAA AAATACTGAT GCCGAAGCTC CACCTAGAAT AGTTCATTCA GAATCTCTAG
CATAATTGAC CTCAGTACTT GAAATATGAT TATTATAAAT GTTAGTCAAC TGCTTTTTTA
GGCTCTATGA CTGATAGAAA TCTTTCACTT TTATATCATC TCCAGTTAAT GAGTCCCATA
AATTGAAATC TAGTGTTTAA ATTTTTACTT CATATTTATT TTTACTGATT GTTTTATTAT
TATTATTTTT GAGACAGAGT CCGCTTTGTC GCCCAGGCTA GAGTGCAGTG ACGCCATCTC
GGCTCCCTGC AACCTCCGCC TCCTGGGTTC AAACGATTCT CCTGCCTCAG CCTCCTGAGT
AGCTGGGATT ACAGGAGCCC ACCACCAACC ACACCCAGCT AATTTTTGTA TTTTTAGTAG
ACGGGGTTTC GCCATGTTGG CCAGGCTGGT CTCGAACCCC TGACCTCAAG TGATCCACCC
GCCTCGGCCC TCTGTCTCAA AACAAAAACA AAAACAATAA CAAAACTTTT CTCTTCTACC
CGAGATGTTT AAGTTTAAAT CACACCATTT GTACAAAAAT TCCCTGTCTT GTCCTTAAAA
ATAATTTGTA ATCACTAGCT AGTTTTGAGA TCGATTGCCA TCTAACCGAA TGCCATTTGT
TCTCTCTCTC TAGTTTCAAC TTAATAACCC TTTCTGCATT TTCTATTCTT TCAAAATTTT
TCCGGCCATT TTATTGTTTC TATTTAGTGA AAATTTATTC ACTGGTTTCT ATGCCTAAGG
GCATTTAGGA AGTTGCTTAG GATACAGACG TGATAAAAAG ACCAGTGTAA AAACTCTCCA
CTCCTAGACA TTATATTCTA GTCCTCATCT CCTGTCATTT AAGTCCTCAG TGATTCTATG
CACTTTTGCT TTTGGTTTGG GCAGATGCTC TGAGTTTAAT GTTTCTCTGA GATGAGGACC
CCCTATTCAA CTCACAAATC CCATAAGGAG GCCTCTGTGC CTTTGCTGGT GCCCCAGACA
GGGTGCTGAT GCTTACTTAT CTTCAAGATT GTGAAGTCAG ATTTAATAGT ATAGTCGTTT
GCCAGAGCTG CTGTAACAGT AGCCACAAAC AGTTGGGCTT AAAATACCAC AAACAGGAGG
GCTTAAATCA CAGAAGTTGA TTTTCTCACA GTTCTTGAGG CAGGAAGTCC AAGATCAAGG
TGTCGTGGAG TTGGTTTCTT CTGATGTCTT GCTCCTTGGC TTGTAGATGG CCTCCTTATT
ATTGTGTCCT CACATGGTCT TTTCTCCACT ATGCACAAAT TCCCTATGTC TCTCTCTCTT
TTTTTTTTTT TTTTTTTTTT TTGAGACAGA GTTGCACTCT GTCACCCAGG CTGGAGTGCA
GTGGTGCAAT CTCGGCTCAC TGCAACCTTT GCCTCCCGGG TTCAAGCAAT TCTCCTGCCT
CAGTCTCCTG AATAGCTGGT ATTACAGGTG CGCACCACAA AGCCCAGCTA ATTTTTTGTA
TTTTTAGTAG AGATAGGGTT TCGCTATTTT GGTCAGGTTG GTTTTGAACT CCTGGCCTCA
AGTGATCCGC GCACCTCGGC CTCTCAAAGT GCTAGGATTA CAGGCATAAG CTACTGTGCC
CAGTCTCCCC CTGTCTCTTT GTGTCCAAAT TTCCTCTTCT TTAGGGACAC CAATCAGATT
AAATTGGACC CACCCTAAAG GCCTCATTTC AATGTACCTC CTTCAAGGGC CTATCTCCAA
ATACAGTTAT ATTTTTAGGT ACTAGGGCTA GGGCTTCAGC ATAGGAATTT GGGGGAGACA
CAATTTAGCA CATAGCAGAA AATATAAGGC CAGGAAAAAA TATTCTGGCA TGCTAGATGG

Figure 15G

```
ACTCATTAAC AAATATTAAC CAATATAAAC CAATTAACAA ATATTTCTTT AATATTTGCC
TTTTTTTTTT TTTTTTTTTG AAACAGAGTT TCACTCTTGT TGCCTAGGCT GGAGTGCAGT
GGCACGTTCT TGGCTCACTG AAACCTCTGC CTCCTGGGTT CAAGTGATTC TCCTGCCTCA
TCCTCCCAAG TAGCTGGGAT TACAGGTGCG GGCCATCACA CCCGGCTTAT TTTTTGTATT
TTTAGTAGAG ATGGGGTTTC ACTATGTTGG CCAGGCTGGT CTCGAACTTC TGACCTCAGG
TGATCCACCT GCCTTGGCAT CTGAAAATGC TGGGGTTACA GGTTGCCTGG TGATTTTTAA
GAGGAATGAC TGAGCTCTCA TGCCAGGTGG GGGGAGGGGA CAGAGAAAGT TGAATACTCT
GACGATAGCC ATGATCCATA GCTCTGAAGC TTAGACTCGA ATCTACCCAT CCCGCAAGGA
AGAAAACAAA GAAATAAAAA AGAAGAAAAG AAATCTCCCA ATGTCAGGTC CCACCCTCTT
TAGAAGTAAT TTCAGCAAAA CTTTGTTGCT ATTTTGGCAT GTCCTCTACT GTAGTAGCTT
GTCAAAATAC TGTCCCCAAA CGTTTTCTAT ATTTCTAGAT TTTACTGTTT AATGTATAAT
AATAATGTTC TAACATTAAA ACGTAACCAT AGCAATGCTC CGACTCACTT GATCTTTAAA
TATATTGTTG AACTCAATTT TGTGACATCT TCAGAATTGT CTTTTTGTAT TCATAAATAG
CAACAGTGGA TAGTTGCCTT GGTTAGTGTT ATTATTTCAA GGATTAATCT TTAGGTTACG
TTTTCTTCAT AAGATGCATT AGATGACTTT TTTTTTTTTT TTTTTGAGAC AGAGTCTTGC
TCTGTTGCTC AGACTGGAGT GCAGTGGTGC AGTCTCAGCT CACTGCAATC TCCACCTCCT
GGCTCAAGAG AGTCTCTCGA CTCAGCCTCC TGAGTAGCTG GGATTACAGG CACGCACCAC
CATGCCTGGC TAATTTTTGT ATCCTTTTTA GTAAAGACGG GATTTCCCCA TGTTGGCCAG
GCTGATCTCC AACTCCTGAC CTCAAGTGAT CCATCTGGCT TGGCCTCCCA AAGTGCTGGG
ATTACAGGCA TGAGCCACCA CACGCAGCCA ATTAGATGCC TTCTCATGCT TTTCTGTGTT
GTGAAACAGA TCATCTATCC GTTGATATAG CATAGCTCTT CAGACTACAG ACATTTTAGG
CTATAAGTTT TGAATTACAT TTTCTATTCC CTTTATGCTT CTTGTTCTAG TTAGGTTTTT
TATTTCTAAA TAAAAATATG AATTTTTGCA ATTTCCCAAA TGCGAACTCA ACTGAAATTT
TCAAGTGTAT TAGCAAAATT TATTCATAGC AGCCTCTTAC ATTTCATTAA GAATTGATTT
TTTCTTATTC CCTGTTGAAG TTTGTTTATA AAATATAGTA ATAGTAATAA CTATATAGAA
AGTGTTCACT TTGTAGTAGG CCCTATGTTA ACTTTAACTA CACTTTTTAA ATCTAAGCCT
CATAGTAGTC TTGGATGGAT GCGGTGGCTC ACGCCTGTAA CCCCAGCACT TTGGGAGGCT
GAGGCGGGTG GATCACGATG TCAGGAGTTC AAGACCAGCC TGGCCAACAT GGTGACACTG
TCTCTACTAA AAAGACAAAA ATCAGCCGGA CGTGGTGGTA TACACCTGTA GTCCCAGCTA
TTTGGGATGC TGAGTCAGGA GAATTGCTTG AACCCAGGTG GTGGAGGTTG CAGTGAACCG
AGATCACACA AGTGCACTCT AGCCTGGATG ACAGAGTGAG ACTCCATCTC AAAAAAAAAA
AAAAAAAAAA AAAGAGATCA ATAAATAAAA TAAATAAATA ATCCTCACAA TAGTCTTCAC
CATTTGCAAA TGATCCATTT GACAATAAAT GAATTCAGCA CTATCATGGA AATATATTTC
CAAGCTGACC AGTTTTCTCC ATTTCCACCC CACTTCAATC CACCTTCATG TAGCCCTAGG
ACTATTGTCT CCTCCCCTTG TTTCCTTATT TCCATTCCTG TTCAGCTGTA ACACATTCTG
TTCATAGCAG TCAAGTGATG CTTACAAATG GAAATCAGGC TAGAGGTGGT AGTTCACACC
TATAATTCCA GCATTTTGGG AGGCTGAGGC AGGAGGATCA CATGAGGCCA GGAGTTTGAG
ACCAGCCTGG GCAACATAGC GAGACCCCAT CTCTACAAAA ATAAAAAAGA ATTAGCTGTG
CATGATCCTA TGTGCCTGTG TTCCAGCTAC TTGGGAGGCT GAGGTGGGAA GATTGCTTGA
CCCAGGGAGT TTGAGGCTGC AATAAGCTAT ATTTGTACCA CTACACTCCA GTGTGGGTGA
CAGAGTGAGA TCCTGTCTCT AAAAAACGTA AAATGAAAAT AAAACCTTGA TAGTTTGCTC
TTTAAAACTC TTCCTACAGG GCCCCTGTGA TGCTCACCTG TCTCTAGAAG GGCATGTAAT
AGCTCTTTCT CCTTCACTTT ACTTTGATGC AATGTCAGAA CAGCTTCTTT CCATCAAAAC
TTAAACCTTT GATTTCATTT AAAATCATCT GCTTCAAATT CTAATCTTTC TGATAGTTTA
GGTTCTAATT TTTCTGATGT TAATATTGTC ACCCAAGTTT CCTGTTCATA TTTACCTGGT
TTATTTTATT TTTATTTTTA TTTATGTATT TGAGATGGAG TCTAGCTCTG TCACCCAGGC
TGGAGTGCAG TGGTGCGATC TCAGCTCACT GCAACCTTCG CCTCCTGGGT TCACGCCATT
CTCCTGCCTC AGCCTCCCGA GTAGCTGGGA TTACAGGGAC CCGCCACCAT GCCCGGCTCA
TTTTTTGTAT TTCTACTAGA GACGTGGTTT CACCGTGTTA GCCAGGATGG TCTTGATCTC
CTGACCTCGT GATCTGCCCG CATCGGCCTC CTAGAGTGCT GGGATTACAG GCGTGAGCCA
CCGCGCCCAG ACTTTATTTT ATTTTTTGAG ACGAAGTCTT GCTCTCTTCC CCAGGCTGGA
GTGCAGTGGC TTGATCTCAG CTCACTGCAA CCTCTGCCTC CCAGGTTCAG GCGATTCTCC
CGCCTCTGCC TCCCAGGTTC AGGCGATTCT CCCGCCTCAG CCTCCCGAAC AGCTGGGGTT
ACAGATGCCT GCTACCACAC CCAGCTAATT TTTTTCTTTT TTTGGAGACA GTCTCACTCT
GTCGCCCAGG CTGGAGTGCA CTGGCGTGAT CTCAGCTCAC TGCAACCTCC GCCTCCTGGG
TTCAAGCGAT TCTCCTGCAT CAACCTCCTA AGTAGCTGGG ATTACAGACG TCTGCCACCA
CATCAAACTA ATTTTTGTAT TTTTAGTAGC TGAGATTATA GGCTCGTGTC ACCACGCCTG
GCTAATTTTT GTATTTTTAG TAGAGACGGG GTTTCACCAT GATGGCCAGG CTCGTCTTGA
ACCTCTGACC TCAAGTGATC TGCCCATCTC AGCCTCCCAA AGTGCTGGGA TTACAGGTGT
```

Figure 15H

```
GAGCCACTGG GCCTGGCACC TGGTTTATTT TTGTGCATGC TTTTATTTTT AATTTTCCTA
TGCTACTTTC TTAGCCAAAA TTTATACTTA ATCTAATCAA GCATTAATCT AACAAAGAGT
TTAGTGTTCA TATAAAATAC AGTTTTACAA ATCTGTTTTT CTTTAAATTA TAAATTTGTT
AAGAAAATTA TCCAAAGAAT GATCCAGAAA CAAAAGAATG GCTGTGTGTC TTTTCAATAT
CATCCTGGAG CATTGTCTCA ACCATCTCAC TTTACGGTGA CTAAAACATC TAGAGGTTTT
CCCTTTGTTT TCTGTACTTC TTAGTATTGA TTAATACTGT TGTGCTACTT CAGTCTGAAG
TTCCATGTTA ATCTGTAGAT TTTTTTTTTT TTTTTTGAGA CAGTGTCTCG CTCTGTCGCC
CAGGCTGGAG TGCAGTGGTG CGATTGGCTC ACTGCAAGCT CTGCCTCCCA GGTTCAGGCC
ATTCTCCTGC CTTAGCCTCC CGAGTAGCTG GGACTACAGG TGCCCGCCAC CACGCTGGGC
TAATTTTTTC TATTTTTTTT TTTAGGAGAG ACGGGGTTTC ACCGTGTTAG CCAGGATGGT
CTTGATCTCC TGACTTCGTG ATCTGCCTAC CTTGGCCTCC CAAAGTGCTG GGATTACAGG
CGTGAGCCAC TGTGCCCGGC TGTTAATTTG TAGATTTTTA TACAGAAAAG CAGCAAAATA
TTTCTGTTGA GTAGAAAATA TAACTCCAAT GCTTATGACT GTATTCCTTA TAGGACACTA
ACTCATTATG TGTCTAACCT AGCAATTTTA TGTCAACACT ATTTTCTCAA ACCTCTATAA
ACTTTGGCTG GGCACAGTGG GTCACACCTG TAATCTTAGC ACTTTGAGAG GCTGAGGCAG
GTGGATCACC TTAGGTCAGG AGTTCAAGAC AAGGCTGGCC AACATGGCAA AACCCCATCT
CTACTAAAGA TACAAAAAAT TAGCCAGGCA TGGTGACATG CCCCTGTAAT CCCAGCTACT
CAGGAGGCTG AGGCAGGAGA ATCTCTTGAA CTCAGGAGGT GGAGCCAAGA TCATGCCACT
GCATTCCAGC CTGAGCAATA GGGTGAAACT GTGCCTCAAA ATGAATAAAT AAAATAAATA
AATAAGTCAG AGATTGTGAA TAGGATGTTG GATATACCCA AGTTATGAAT TAATTAGGAG
CTTGAACCCA GGAGGCAGAG GTTGCAGTGA GCTGAGATCG CACCACTGCA CTTTAGCCTG
AGCGATAGAG TGAAACTGTG TCTCAATCAA TCAATCAATC AGAGATTGTG AGTAGGATGT
TGGATGTACC CAAGTTATGA ATTAATTAGG AGCTTGAACC CAGGTTTGTC TCAGATCCTC
AGGGACTGAA GACTTCCAAG TGAATTATGG GTAATGTATA GGTCTATACT ACTCCAAATT
TACAGTTTTC AGACTTCCCT GGGTTCTCAT GGACCTTCCA TGTCATTTCT ATGTTTAGGT
TGAGGTCCCT GGTCTTTTCT CCTCTGTAAT TAATTTCACA CCCACCCCTA TCTCAACTCA
CACAACTTGA TCTTCACTCC CATCTGCTAA GAAATTGAGT CCATAAAAAG TGAACTCCTT
TAAACTCTAG ATCTTCTACT GCTGCAAGGA CAGACATTCC ATTCTGGCTC TCTCTCTCCT
CCTTTGCTTC TTCCAGTCCT TTGCTCCTTC TGCATTCTGT TACTCTCCTC TCTCCTTTGT
CTTCAATCTC TCCCTCTTGC AATAGCCAAC TATAAACTGC TCAAGCTTCT CATTCTTAAA
AGATCTCTCT GAAATGCAAA TTCCCTACTG CCTTATGGCT CTCCTTCAAA AGTAATCTAC
ATTTTCTCTA TTTTCTAATT CCTCAACACA CTAACGTTTG AACCCTGCTT CTATGACCCT
GACCTAAATT TCTATTAAAT GTACATAGAT AAACTAATAT ATATTTGTGA CTTCCTAATA
TTGTTTTGTT TTTTAAAGAG GTCAATCTTA CTTTAACTCT GTAATGATGC GGTTGACCTT
CTGATGATTC TCTACTTCTG TGAAATCCTC TACTGTCTTG ACTTTTTAAT TAATTTATTT
TTTTTTGAGA CGGAGTCTCG CTCTGTTGCC CAGGATGGAG TGCAGTGGCA CAATCTCGGC
TCACTGCAAG CTCCACCTCC CGGGTTCATG CCATTCTCCT GCCTCAGCCT CCCGAGTAGC
TGGGACTACA GGTGCCCGCC AACACGCCCA GCTAATTTTT TTGTATTTTT AGTAGAGACG
GGGTTTCACC GTGTTAGCCA GGATGGTCTT GATCTCCTGA CCTCGTGATC TGCCTGCATT
GGCCTCCCAA AGAGTTGGGA TTATAGGCGT GAGCCACCGC ACCTGGCCCT ACTGTCTTGA
CTTTTATAGG GTCATTCTAT TCAAGCTCAT TGAGCGTCTG TCACTATGTT TTTGATCTGT
ATTGCTGGAA TCAGTTCCTC TATCTGCCTT GTGAATATTC TCCATTGTGC TAATCTAGGC
      >>.......................Exon?.........................>
TTCTCCTTTC ATTTTTCATA TTCCCTCACA TGGCTTTATA CACTCTTGTG GTTTTAACCA
>>
CAATATAGGG TTTTTACTGT AGTTATGCTT TCAAATTGTA TACTTCTTTT TTTTTTTTTT
TTTTGAAATG GAGTGTTACT CTGTTACTCC AGTCTGGAGT GCAGTGGTAC GATCTTGGCT
CACTGCAACT TTCGCCTCCC AGGTTCAAGC GATTCTCCTA CATCAGCCTC CCGAGTAGCT
GGGATTACAG GCATGTGCCA ACACGCCTGC CTAATTTTTT ATTTTTAGTA GAGACAGGAT
TTCACCATGT TGGTCAAGCC CGTCACAAAC TCCTGACCTT AGGTGATCCG CCCTCCTCGG
CCTCCCCAAG TGCTGAAATT ACAGGTATGA GCCATCGTGC CCAGCCCCAA TTGTATGTTT
CTAATATGAC TTTTCTCCTG AACTTTAAAC TGTGTATCCA ACTTCTCAGC ACAGTCATAT
CTTTTGATTC CACAGGTAAT TTAATGTCAA TATATTTAAA AATGAATTTA CCACCTTTAT
CCCCACTCTT TGACTTTCAC CTGCATTTCT GTTTCAATTC TTGTTTCCAT CCATTCATTT
GCTCACCTAA TTCATAAACA TGGAAATCAT CCTCAATTCC TCTTCTTCTT AGCCCAAAAA
TTCAATTGTG CAGGTTATGC ACTGAGAAAA AGAGCCTCAG GTTAGGGGGA TAAATCAGAG
ATTGGTGAAC TTTTTCTGAA GGGCCAAATA CTAACTGCTT TAAGCTTGCT TACCATATGG
TTTATGTTGC AACTACCAAC TCTCCTGCTG TAATGTAAAA GCAACCATAG ATAGCATGTA
AACAAATGAG ACAGGCTGGG TGCCAATGAA AATTCACGAA AATTAATGTA GTTTACTGTC
```

Figure 15I

```
CCTTGGGTGA GAGTTGGGGG TCACTGAAAT TCGGACTATG TCTTACTTGG CTAAACCACA
GGCCTAGAGT GGGCCATAAA TGGAGCTATT GGGCTAGTGA TTTTCTTGCC TTAAGCCCCC
AGCCCCAAAT TTAATAATCA CATCATTTTA ATTTCATTTT CCAAGTGTAT CTTTAATATA
TGGCTTCTCC TTTCCAAATT CACTGTCATT ACCTAAGTTT AGTCCTTGAA CAATATTTTA
AAGGCTTCCT TATCTGACTT TATATCTTAA AGTCCTACAA ATTTATCTTC CTAAAATTCA
AATCAAACCA TGTCACCAAC TTACAGAAAG GGAAAATTCA TATATTCTAC ACACAGCACA
TTTCATGTAA CTTTCTAGGC TCATCTTTCA TCATCCTTTT GATGCAGGAT TTTCTGCTCC
TCAGCTCAGC GAAATCCAGG ATCTTGTCTC ATGACCAGGA AGAATTAGGC AGGTGGACAT
AGTGAAGGGT GAGGATGACG GAATTTATTA AGCAAAAGGG GAGTTCTCTG CAAAGAGAGG
GGTTTCACCA GCAGTCTCCC ACCTCACAAT GGAGCACCAG GACTTTCACA CACAAACTGA
AAAGGCTAGG CTCCTCCCCA GCATAAGGCA TGAATTCCTG GTGGTTCCAC CAGTTTTCCT
ACTATGCATG TGGGTGTGCC CAAGCAAACC ATAGGTAGTA TCAGAAAAGG CAACATTTGA
TTGGTTAAAA GGCATTATTC ACCCAAGCAA ACCATAGGTA GTATCAGAAA AGGCAACATT
TGATTGGTTA AAAGGCATTA TTCAGAAAGA ATCAATCGGG AAAGGGTGAG CCAATAGGGG
AAGTTCTCCC TCTGGGTCAC GGGTTTCATC TGGGACCAGG AGTCTGGCCT TTCAGCCTTT
AGACTGTTTT AGGCTTGAAG GTGGGTTTCA CAGGGACCCT TCCCTATCTG CCTAGGCATC
TGTCTGCCTC CTGCCTCTAT CACTTTCTCT TGAGTTTTAT ATTTTAGCAA CACTGAGTCA
TCTTTGTCCC AGGAAGCACC TACATCTGTT TATCTGCTGT CCCCTCTACC TTTACTACCT
TCCCTTCTTC ACATTTATAC CCAGAAAAGT CACTTCCCCT CCAAAAATTG GGATCAACTG
TCATATTTTT ATGAATATTT CACTTTAATT CCTCACAACA GCTGACAGAA TTAACTACTT
CCTCTTCTTT GCAAGTTATT TGGCTCACAC AGATATCAGT AATTAAACAT ATTTTACTGC
ATTGGCATAT ATCTGACTAA TGTGTTTTTC TCCCGTACTA GGCAATATGC TCCTTAGTCA
TCTGTGTATC TGAGGTGAGC ACAGGGCCTA ACTAGCATAT GGTGCATTCT CAATGTTCGT
TCAACTGCAT TGACTTGAAT TCCCCTGAAG ACTGAAATGT GAAAATAGCT ACTCTCGGAA
GCCCCTTTCC AGAGAGGTCT AAAATATTTA CATGTTTCTA TTTTAAATGC AGAAAGAACT
                                                             >>..>
TCCAGATCAT TATAGGCCTT GGATGGAAAT TGCCAACAAA CTTCCTCAAT TGATTGATGC
>..........................exon 2 ............................>
TCACCAGCTT CAAGCTCATG TGGACAAGGT ATTCTTCTCT TCACCCCCTC ATCACATTCT
>..............exon 2..............>>
GTTTTCATCA TCATACCACT TTTCTTTCTT AGCCTTGTGG AAGTGTGTCA ATTGTCCTGG
GAAACTGTTC ATTACCATTG AACTTATCAG CAAAGCTATA TCTTCCTTCC TGAAAAACAG
AATGACCCCT TCGTAATCTG ATACATGTGT TTTCCTAAGG TTTTCAGAGC CAGCACAAAA
CAATGCCTGA CACATGCCAA TAACTCACCA AATGTTTGTT TAAAGAAGAA TCTGGGTGGG
AATGATAAAC TAACTAATGG ACAAGGTATC GCCTAAGAAG GTCAGCTTGG AAATTCTCAG
GTTCCTCATT CCATGTACGT ACTCAAGGCT CTGTTGTTAC TGAGGGGGTC TAACTTGATT
TTGTCCTAGG TGTTATAGAA TAGTTAAATG GAGGGAATTT CTGAATTATA AAATTGGCCA
TGGGTTCTAC AAAACATCCA ATAAGCCTGT AAATTCCACA AAAGTGTTGA TTAGGCTGAT
ACAAAGGTAA TTGCAGTTTT TGCCATTACT TTTAATGACA AAAACCACAA ACACTTTTGT
ACCAACCTAA TAGCTATGTA ACCCTGAAAA AGTTACTCAA CTCTGTAATC CCATTTCCTT
ATTTATAAAA TGAGAGAAAC TCTGGTCTCA CAGTATTGTT ATGGGAAGTA AATCACTTTC
AAAGTGGCCC TTTTGTAGTT CTTGTCCTAT AATAGCATTC AGTATACATT CATTACTTCT
CTGTAGTCTC TTCTCCATCT GTCCTAATCT ATCAGTTTGG AGTACCACAT AATTGCGGAA
GTCCATGAAA AGTTTTCCGC TCTCCAAAAT TTCCCTTTGC TGATGGATAA TATTTAATGT
CTAGAATTAC AAATTCTTTT TAAAATACTC ATTGAATGTT TGCTTTGTGC AAAGCACTAG
AACCTTGTAA AAGATGAGTA AGGGACTGGC TTCAATGTCT GTGAAGATAG CAAACTAAAC
AGAGTAATTT CTTTGCCTGA TAGATAAAAT GTTGTGTTGA CATGACCAAA GAAATCCAAA
AATAAGAAAA AAACTATCTG TAAACACAGA AAAATAGAGA AAAGTTCCAA TGATGGAATA
AAAATTTAAA GGATTTTTTT GAACGTATTA AGCAAATCAT GTATAAAATC CAGAAATAAG
TTTACAGGAC CCATGTCAAG GATTTAACCA AAGCAGAGGG AGATCCCCAT GAGTCCCCTT
TTCCCATCTC AGAATAGCAG AGAAGAGAAG CAAGGGAAGC CTGGAACAGT TGGCAAGAGG
GCAGGTTAGA ATTCAGTTTG TGAATTATGA GGTCGTCTGC CGTAGGCATT TACCAGGCTT
TATTTGATTT AACTGCCATA AAGGAAGAGA AGGACTTGTT AAATTGGGGC TCCTCTTAGC
ACAGCATTGA AACCAGTCCC TATTCCTTCT TGGCCTTTTG GCTAAAATTG AGTGTGAAAT
CTATCACCTA ACATTTGTAC TGGGTTTAGG CTGGGTGTGG TGGCTCACGC CTGTAATCCT
AGCACTTTGG GAGGCCAAGG CTGGCGGATT GCCTGAGCTC AGGAGTTCGA GACCAGCCTG
AGAAACATGG TGAAACCATG TCTCTACTAA AAATAGAAAA AATTAGCAGG GTATGGTGGC
ACATGCCTGT AGTCCCAGCT ATTTGGGAGG CTGGGGCAGA AGAATCACTT GAACCCAGGA
GACAGAGGTT GCAGTTAGCT GAGATCACAC CACTGAACTC TAGCCTGGGC CACAGAGTGA
```

Figure 15J

GACTCTGTCT CAAAAAACAA AACAAAACAA ACAAACAAAT ATATATATAT TAAAATACAA
ATTTTTACTG GGTTTAATAG TGTCTTCCTA GAAGTCATGT TCATGCATAA TCTGTGAAAG
TGGTCTTATT TGGAAATAGG GTGTGTACAG TTGTATTCGA GTTAAGCTGA GGTGATACTG
GATTAAATTG TATATGATGA GTGTCCTTAT AAGAAGAGGA AAAATTAAAC ACAGGAACAT
AGACTCAAGG GAAAACATCA CGTGAAGATG GAGGTAGAAT TGGAATGATG CATTGACAAG
CCAAGATGTG CCAAGGATTG CTGGCAGTCA CCAGGAGTTA GGAGACAGGC ATGGAACAGA
ATGGAACAAA TTCTCCCTCA GAGGCTCCAG AAGAAATCAA CCCTATTGAT ACCTTAATTT
GGGACTTCTA TCTTCCATAA CTGTGGCAGA GTACATTTCT GCTATTTTAA GTCATGATGT
TTGTGGTCAT TAGTTATGGC AGCGCATAAA ACTAACACAA CACTCTTGGT CTCTATCGCT
TCTTTTTTTT TTTTTTTTTT TTGAGACAGA GTCTCACTCT GTCTCCCAGG CTGGAATGCA
GTGGTGCAAT CTTGGCTCAC TGCAACCTCC AGCTCCCAGG TTCAAGCAAT TCTCCTGCCT
CAGCCTCCTG AGTAGCTGGG ACTACAGGCA CCCGCCACCA TGCCCATGTA ATTTTTGTAT
TTGTAGTAGA GACGGGGTTT CACCATATTG GCCAGGCTGG TCTCGAACTC CTAACCTTGT
GATCCACCAG CCTCAGCCTC CCAAAGCCCT GGGATTACAG GCCTGAGCCA CCATGCACGG
CCTCTATCCC TACTCTTAAT TGCCTGGAAA ATACCTAACA AATGAAGGCC AGTTTTTAGA
CTTTACCACC AAAGGCTGAA ATTGAAACAG GAATTGTTTG TGAGAAGCAA ACACAATAGT
TTCGAGAGAC TGAATCAGTT AGCAATTTCC TGTGAGAGGC AAATGTAATA GTTTCTAGAA
CCACAGATGG AGCTATAACA AAAACATGTG TTCTCTGGAT CCTTTACTTG CTACAGACAA
CACAATAAGT GAATTTACAG CTTTGATCTT ACAGTGCACC TAAGCCAACC ACCTTGTCTT
AGAATGTCTC AACATACCTA TCTGTATCTT GAAACAAAAT ATATTAATTG CCTTAGACCC
ATTCACTCAC ATTTCCTAGG AAGACATGAT CAGAGGGAGC TATGCAAGAA GAAATCCAGC
AGAACTCTGG AAATACAATA AGAAAATCCA TATTAGACAC TAATCTTAAT AAAACTAACC
TTCGTTCATG AATTTGAATA GACAAAATTA CCAAATAATA TGGAAAAAAT GGGCAACTCA
AAAAGAAGAG GGTAGCCCAC TTGGCATTCA GGACCAATGG CCTCCAATAA ATAAGATGAT
ATTAGTGCTT TAAATATTTT ATTTAGTGTA TCCAGTATAT TGCCTTCCTA AATTAAGTGA
AAGCTGATAT ATAAAAAGAA CTATTAGAAA TAAAAAACCA CACACATCCC AGAACTCCTC
AATATAAACC TAACAAATTC AGTAAAACAT TGATTGCAAA AAATATATAT AGTGACTTAG
GGACTTCCTT GATAAATTTC ATAAAGCATA AAGAAAAATC AAAGAGTGCA AACCATCAGA
AAAATACAAA TATATAAAAA AGAGAAATAC AGGTGATCCA AATTCCTTTT AATGGAATCC
CATAAGCAGA TGGGTGGAGG AAAAGTAAAA CTTCCAACAT ATAAGCACAA AATTTTTAGA
CCTTAAGAAA TATTTGAGTT TTTTATATCA GAAAGACAGT GTTGGGGTGA GGGTTGGGGG
GCACATGTAA ATACTCAGAT AAAATTGTGA ATTTTCTAGG GTAAAGAAAT CTGCATATTC
ATAGAAAACA AAAATGAAAA ATAGTTTATT TACAGAGTAA ATACATACGA CTGTTTACCT
GTAATGCTAA ATATTAAAAG ACAGTTTCTT TTCTTTTTTT TGAGACAGAG TTTCACTCTT
GTCGCCCAGG CTGGAGTGCA GTGGTGCTAT ATCGACTCAC TGCAACCTCT GCCTCTGGGT
TCAAGCAATT GTCCTGCCTC AGCTTCCCGA GTAGCTGGGA TTACAGGCAC CCGCCACCAC
ACCCAGCTCA TTTTTGTATT TTTATTAGAG ACGGGGTTTC ACCATGTTGG CCAGGCTGGT
CTCAAACTCC TGACCTCAGG TGATCCACCC GCCTTGGCCT CCCAAAGTGC TGGGATTACA
GGCGTGAGCC ACCGTGCTGG CCTAAAAGAC AATTTCATAC CTATTTGTAT GGCTAATTTT
TTAAAAATCT GGCCATATCA AAATACTGAA GAGGACGTAT AGCAATAGAG ACTTTCATTC
ATTGCTGGTT GAAATGCAAA ATGGTACAGC CAGTTTGAAA ACTAGCTTGG CAGATTCTTA
TAAAATGAAA CATAGATTTA CCATGCAACT CAGCAATGGC ATTCCTAAGC ATTTATCCAA
GTAAATGGAA AATGTATGTT CCCAGAAAAA AAATCCATAT ATGAATGTTT ATAACAGCTT
TATTCATAAT CACCAAAAAA AAAAAAAAAT CTGGAAGAAA ACAGGATATC CTTCAACCGG
GGAATGAATA AACCAAATTA TAATAATTGT AAATTGTGGG ATGGATAGTG GAATAGTATT
CAGCGATACA AATGATTGAG CAATTAATTT GTGCAATGAC AGGGATGAAC CTTAAATACA
TTTACCTAAA TGAAAGATGT CAGGCCTATA TTGTATGATT CTTTTCAAAT GACTTTTTAG
AAAGGGCAAA ACTAGAAGGA TTAAATATAG CTTTATGGTT ACTAGAGACA GGTAAGGAGT
GGGTAGTTGA CTGCAAAGGT AATATATAGG GGAATGTTTA GCATGATGAA ACTGTTTTAT
ATGGCACTCA GGTGATGGAT ATATGGCTCT AGGCACTGAA AAACCCATGG AATTGTATGT
CACAAAGAAT GGACTTTCAT GTATGCAAAT TTTAAAAAAT AAACCAGAAA ATTGGGAGAA
TACTAGGATG GAATGCAGAC TGTGATAAAT AAAACTAACT GGACTCTCAG CAAACTAACA
CAGGAACAGA ACACCAAACA CCGCATGTTC TTACTTATAA GTGGGAGTTG AACAATGAGA
ACACAAGGAC ACAGAGAGGG GAACATCACA CACCGGGGCC TGTTGTGGGG TGGGGGGCTA
GGGGAGGGAG AGCATTAGGA CAAATACCTA AAGCATGAGG GGCTTAAAAC CTAGATGATG
GGTTGACAGG CGCAGCAAAC CACCATGGCA CATGTATACA TATGTAACAA ACCAGCACAT
TCTGCACATG TATCCCAGAA CTTAAAGCAA ATTTTTAAAA AAGTAAAAAA AAAAAAAACA
AACAACAACA CCTAACTGGA CTACAAATGC ACTATATAAC TTCGATGAAG AGAGTGGGGA
GTAGGGAAAG GAACGGACTT AAATTACTCC AGAAAATAGT GTTGTGTTGT GACTAGAATC

Figure 15K

TATAAGGCTT ACGGTAAATG AAACTTTACA GGATCACTAT ACTCTAATTG GTAAATCAGT
TTTTCATGGG GTGCGGGTGA ACAGTTGTGA AACTGCTTTA CATGTAGTCA TACCTTTGCA
TTTTGCAGAT ATTTCAATTT TTACAAATTG AAGATTCGTA GCAACCTTGC ATCAAGCAAG
TCTGTCAACC CCATTTTTCC AATAGTGTGT ACGCATTTGG TGTCTGTGTG TCATATTTTG
ATAATTATAA CAATAGTTAA AACTTTTTCT TTACTATTAC ATCTGTTACA GTGATCTGTG
ATCAGTGATC TTTAATGTTA CTATCATAAT CGTTTTGAAG GTGCCATAAA CTGTGCCCCT
ATAAGTCCTG AAACTTAATT GATAAATGTA TGTGTTCTGA CTGCTCCACT GACCAGCCAT
TGCCCCATCT CTCTCCCCCT CCTCAGGCCT CCTGATTTCC TGAGACATAA TAATATTGAA
ATTAGGCCAA TTAATAATCC TACAATGGCC TCTAAGTGTT CAAGTGAAAG GAGTTGCATG
TCTCTCACTT TAAAAATCTA AAACTAGAGG CTGGTCATGG TGGCTCAGGC CTCTAATCCC
AGCACTTTGG GAAGCCAAGG CGGGGAGATC ACCTGAGTTC AGGACTTCGA GACCAGCCTG
GCCAACATGG CGAAACTCTG TCTTGACTAA AAATGCAAAA ATTAGCCAGG CATGGTGGTG
CACACCTGTA ATCCTAGCTA CTCAGGAGAC TGAGGCAGAA CAATCGTTTG AACCCTGGAA
ATGGAGGTTG CAGTGAGCCT AGATTGTGCG ATTGCACTCC AGCCAGGGCA ACAAGAGTAA
AACTCCTTCT CAAAAAAAAA AAAAAAAATA TCTAAAGCTA GAAATGATTA AGCTTGGTGA
GAAAGTCATG TCAAAACCAG ATAGGCTTAA AGCTGGGCCT CTTTTGCCAA ACAGCCAAGC
TGGGAGTGCA AAGGAAAAGC TTTTGAAGAA AATTAAAAGT GCTACTCCAG TGAACATACG
AATGATAAGA AAGCAAAAGA GCCTTATTGC TGGTATAGAG GAAGTTTGAG TATTTTGGAT
AGAAGATCAA ACCAGCCACA ACTTCCCTTA AACCAAAGCC TAATTCAAAG AAAGGCCCTA
ATTCTCTTCA ATTCTACAAA GTCTGAGAGG GCTGAAGAAG CTGTAGTAAA AAAGTTTTAA
ACCAGCAGAA TCTGGTTCAT GAAGTATGAG GCTAGAAGCC ATCTCCACAA CATAAAAGTG
CAAGGTGAAG CAGCAAGTGC TGATGGAGAA GCTGCAGCTA ATTATCCAGA AGATCCAGCT
AAAATCATCA ATGAAGGTGG CTACATTTAT TTTTTATTTT TGTTATTTAT TAATTTATTT
ATTTTGAGAC AAAGTCTTGC TCTGTCCCCC AGGCTGGAGT GTGGTGGCAT GATGTTGGCT
CACTGCAACC TCCACCTCCT AGGTTCAAGC AATTCTCCTG CCTCAGCCTT CCCAGTACCT
GGGATTACAG GCATCTGCCA CAACGCCTGA CTAATTTTTG TATCTTTGGT AGAGACGGGG
TTTCACCACA TTGGCCAGGC TGGTCTTGAA CTCCTGACCT CAGGTGATCC ACCCGCCTTG
GCCTCCCAAA GAGCTGGATT ACAGGCATGA GCCACCACGC CTGGCCAGTG GCTACATTTA
AAAATAGGTG TTCAATGCAG ACAAAACCAT CTTTTATTGG AAGAAGATTC CAACCAGGAC
TTTTTTTTTT TTTTTTTTTT TGAGACAGAG TCTCACTCTG TCGCCAGGCT GGAGTGCAGT
GATGCGATCT CAGCTCACTG CAATCTCTGC CTCCCGGGTT CAAGTGTTTC CCCTGCCTCA
GCCTCCTGAG TAGCTGGGAC TACAGGCACG TGCCACCATG CCCAGCTAAT TTTTGCAGTT
TTAGTAGAGA CGGGGTTTCA CCATGTTGGC CAAGATGGTC TCTATCTCTG ACCTCGTGAT
CCACCCCCCT TGGCCTCCCA AAGTGCTGGG ATTACAGGTG TGAGCCACTG CGCCCGGCCC
AGGACTTTCA TAGTTAGAAA AAAGTCAATG CCTAGCTTGA AAGGACAGGC TGACTCTCTT
GTTAGGGGCT AGTGCAGCTG GTGACTTTAA GTTGAAGCCA GTGCTCATTT ACCATTCCTG
AAATCTTAGG GCCCTTACCA GCTATGCTAA ATCTACTCTG CCTGTGCTCT GTAAACGGAC
AATAAGGCCT GGATGATGGC ATATCTATTT ACAGCATGCT TTACTGAATA CTTTAAGCTC
ACTGTTGCGA CCTACTGCTC AGAAAAAAAT ATTCCTTTCA AAATATTACT GCTTATTAAC
AATGCCTCTG GTCACCCAAG AGCTCTACTG GAGATATACA GGAAATAAAT GTTGTTTTCA
TGTCTGCTAA CACATTTGTT CTGCAACCTA TGGATCAAGG GGTCATTTTG GCTTTCAAGT
CTTATTATTT AAGAACTATA CTTTGTAAGG CTATTCCTGA CACAGATAAT GATCCCTCTG
AAGAATCTGG GCAAAGTCAA ATGGAAACCT GGAAAGGATT CACTATTCTA GATACTATTA
AAAGCATTCA TGATTCATGG AGGACGTCAA AATAAAAACA TTAATAGGAG TTTGCAAGAA
GTCAACCCTC ATGGATGACT TTGAGGGGTT CAAGACTTGA GCAGAGGAAG TCACTGGAGA
TGTCGCAGAA ATAGTATGAG AACTAAAATT AGAAGTGGAA TCTGATTTTA TAACTGAGTT
GCTGCAATCT TACGATTGAA CTTTTCTTTT CTTTTTTTTT TGAG
ATGCCCCTGC TGAGCTGCCA GTTCCTGAAG GGTCACCGGG AGCAGCGCCT GGCCCACCTG
>>..........................EXON3 ..........................>
GTCCTGAGCT TCCTCACCAT GGGTTATGTC TGGCAGGAAG GAGAGGCGCA GCCTGCAGAG
>..........................EXON 3 ..........................>>
GTGAGGGCCA GAGAGCAGCT TCTCCTGTTA CCCGGCAGGT TACCTGCGCC TGGAGTAACG
TGCTCCCTGC TTGGTGCTAC CCTGTTTTCC TGGAAAATGG GTACTTTCTT CTTCTCGATG
GGCATCAGTT TAAGCAACGA TGAAGGGCTC ATTTATTATT TATTATTATT ATTTTTTTAT
TTTATTTTGA GCCAGTCTCA CTCTGTCACT CAGGCTGGAG GGCAGTGGGG TGATCTTGGC
TCACTGCAAC CTCCCCTTCC AGGTTCAAGC AATTCTCCTG CCTCAGCCTT TCTTGTAGCT
GAGACTACAG GCACCCACCA CCACACCTGG CTAATTTTTG TATTTTTAGT AGAGATGGGT
TTCACCATGT TGCCCAGGCT GGTCTCGAAC TCTTGACCTC AGGTAATCTG CCTGCCTGGG
CTTCCCACAG TGCTGGGATT ATAGGCGTGA GCCACTGCGT TCAGCCTGAA GGGCCATTTA

Figure 15L

```
AATGAAGGAT TTTTTTATTT TAATTTTTCT GACTAAGAGC TAATTTGTTT TTTAAACTGG
TAGCTATTTC TTCCTTTTAT AAGCTTTTGA ATGTTTGTTT GTTTGTTTTT GGCACTCTCT
TCCAAGAATG TTTGAAGACC TGCATTTGAA GGCAGATTGC CTTTTTGCTT TAAAACAGGG
TTGCACCATG TTGCCCAGGC TGGAGTGCAG TGGTGCAATC ATAGCTCACT GCAGCCTCAA
CTCCTCCCAG GCTCAAGCAA CCCTCCCACC TCAGCCTCCT GAGAAGCTGG GGCTACCAGC
ATGTACCGCC ACACCCAGCT AATGTTAAAA ATTTTTTGTA GAGATGAGGG TCTTGCTGTT
TTGCCCAGGC TGATCTTAAA CTCCTGGCCT CAAGTGATCC TCCTGCCTTT GCCTCCTGTG
CTGGGATTAC AGGCGTGAGC CACCATGCCG GGCCTGAAGA CAGACTCTGA GAATTCATAA

                                                     SapI
                                                   --------
AAACCTCACA GCATTTTGTA CTCTTATGTA TATAAATTAT CTAGGTTGCT CTTCATAATC

                        Cfr  I
                        ------
CTGTAAAGTA ACAAGAGCCA TACCGGCCCA TTTTACAACT GAAAAGCACA GACACTTATT
TCCTTAATCA AGGTCAGACA GCAAATTAGT GGAAAAGCCA AGGCCAGAAC CCAGGTCTTC

        SpeI
       -------
TGATTTTACT AGTGCAGCCT TCTTTCCCCA GGGGACACAT TGACATTTAC AACACTCATC
TTTATTTTTT TTTTAATACT GCTTTCTATC CAGCCAATTA TTAGTCTGTC TTTTAATAAT
TCATCCAAAT CTCTTCTGAA TCATTGCATA ACTTTGTACA GTTTCCACCC ACAGTGTCTT
TTACTTTTAT TTTTGGAAGT AACTGTTTTT AAAAGTTACT GTTATTTTTA AAAGTGTGCC
TTCCCCAGAA ATCAGGGAGT TACCCATGTC CTAGAACTCC ACGGTGAAGA GAACAGCCTG
TGCCCATCGT GTTTGCCTGA TTGATCCTAC CTCTTGTCTC TCGGGGAAAC ACAGGAGACT
CAGGGAAGAG GAAAAGTGTA GAGTCATTGC AGCCTTGTTA TTTGTCAATG CATCTCTTTT
CTTTTTCTTT TTCTTTTTTT GATACAGAGT TTCACTCTTG TCGCCCAGGC TAGAGTGCAG
TGGCGTGATC TCGGCTCACT GCAACCTCGG CTTCCTGGGT CCAAGGGATT CTCCTGACTC
AGTCTCCTGA GTAGCTGGGA TTACAGGCAC CTGCCGCCAC GGCCAGCTAA TTTTTTTTGT
ATTTTTAGTA GAGACGGGTT TCACCACGTT GGCCAGGCTG ATCTCGAACT CCTGACCTCA
GGTGATCCAC CCACCTGAGC CTCCCAAAGT GCTGTGATTA CAGGCATGGG CCCCAGCACC
CGGCCAGTGC ATTGCATTTT TTTTTTTTTT TTCGAGACGG AGTCTCACTC TGTCACCCAG

                                          EciI
                                         -------
GCTGGAGTGC AGTGGCACGA TCTTGGCTCA CTGCAAGCTC CGCCTCCCAG GTTCACGCCA

                                         NarI
                                        -------
                                         KasI
                                        -------
                                         EheI
                                        -------
                                         BsaHI
                                        -------
                                         BbeI
                                        -------
GTCTCCTATC TCAGCCTCCC AAGTAACTGG GACTACAGGC GCCCACCACA ACGCCTGGCT
AATTTTTATA TTTTTAGTAA AGACGGCGTT TCACCATGTT AGCCAGGATG GTCTCGATCT
CTTGACCTCG TGATCTGCCC GCCTTCGCCT CCCAAAGTGC TGGGATTACA GGCGTGAGCC
ACCGTGCCCG GCGTGCATTT TTAAAAGTGT GTCTGATGCT GAAAAGTTTG AAGTCTAGGC
ACGTCCCAGT GGGTCCTCTT TATACCATCC CCTCTGCAAA CCATTATCCT AAATTGGGGT
TTGGGGGAGA GAAGAGTGAC AGTGGAAAGA AGTCTCCACC TCCCAGCTGT GCCCTGGTAG

       SanDI
      --------
TTCCAGGGGA CCCGGAGGCT CCCCACACCC ACCACCCCGC CTCAGATCAC CTTTCACTTT
CTTTGTTTCT CCTCCCTTGA CTTTTCAGCT CAGAAAGTAC CTGGCTCTCC AATGCCTTCT
```

Figure 15M

```
GAGGAAAGTT TACCCGAGGT TCACATTGCA AGACTCATTA AAGCTCTTTA GTGTTTTCCA
CCCGAGAAAA AATTCAAGGG AAAAATGAAG ACAAAAGCAG GGCATTCTTA ATGGATATTT

   AflII
   ------
TATCTTAAGG AGAAATGAAA ATGGAGATGG AAGAGGGGGC ACAAGGATGG GGTTTGAATC
TAGACTCGTT CAGCCTTTAC CTCCGATAGA GAACCTCATA CAGCTTTTCT GGACTTCTGG
CTGATAAAGA GCCGTGGAGG GTTCCTTGGA TAAAAAAGGT TGAAGGGGGT CTGTCCTGTG
GTGGCTTACT TGAAGGTATT ACTGGGTTTG ACTTATGGAG TAAGAGACGG AGTCAGTTTC
CCCACAGGCT GAGGCAGTCT GTCCTCATGC TTTTCTAGGG CACTGTGGTC TCCCAGGCTC
ATACCTAGGT GCACACACAG GTTTCTGCAT CTAGCTTTGT ATCTCTATGA GTCGGTCAAT

                                                         NheI
                                                        -------
CAATAAATCT ATCTATCATC TGTCTACTGA TCTATCATCT ATCTATCTAG CTAGCTATCA
TCTCTCTATC ATCTATCTAT GTATCTATCA TCTCTCTCTA TATATGTGTG TATATATATA
TATATATGTA TATATATATT TCTATCCTTC CATCTACTTA CCTATCTATC AAAATTTTTT
TCCGTTGATA ATATTCTCGG GCCCCAGTTT ATGTTTAATT GTTTTGGTAA TGCCTTTCTT
TGCACAGTCA GTTTACAGAG GTTATTTTAT ATTCTATATG TATGTGTGGT CCAGCGTTGT
AATTTTCACA TATATTGCAC CGTGTACTCA TAAGCAGTAT TTCCACTGGG TCATTAACAG
AAAGATATGT GTGCGGCATA TGAATGTGCA TCACTCAGGT AATTCAAGCT TGGTTCCCAG
ATCATTTCTG TACCACAGGA TTGCCGAAAT AAAAGACAAC CATGGTTATT TCCTCTGCTG
CAAGCTTTCT AGAATATGCT ATTTGTCTGG ATTTATATCT GAAAGGTCCT GCCAAGGAAT
                                                     >>...EXON4  ...>
CTTGCCCTTC CATTTGTCGA AGTCTCCAGG AACTTGGGGC TCCCTCCTAT CCTGGTCCAC
>...........................EXON4   ...........................>
TCAGACTTGG TGCTGACGAA CTGGACCAAA AAAGATCCAG ACGGGTAAGG AAGGAAGAGA
>..................EXON 4  ..................>>
ATGCTTTGAA TTTCCATAAC TTTCCCCCAG GAAACACCCA GGCTTTTTTT TATAATTAGG
GAAGTTCATA TTTATGGTCT GCCGTATGGT TCCAAAGAAG GGGTGAGCTT GACCAAAAAT
TCAAATATCA CAGGCCCCAG AAGTTTCCTC TTAATCCATT CTGAACACAT TGGCTCAGAC

  DrdI
------------
CATTTTGTCT TGTTTGTTTC CACATGACGT GTGAATTTCT CAACCTGACC TTCAAGCTCC
TGCAAAATCA GCTTTTATTT GTTCTTTCTC TTCAAACTGT TTATTCCCTA AGATGCCCTC
CATTCATATC AGGTTAAAAC CAGTTGGCTT TGATAAGTAA TCATTATATA ATGATCAGAA
GAGAATGATT ATGGATGAAT TCAGAGCAGA TGCTCCAGGT GGGTTGGATT GAGAATTTGA
TTAATAATTC CATCTATTCC ACCAAAGTCA CATCATTCCT TTGACAGTTG GGCTGGAAT
AGGGGCATTT GTCTACAGAA GGAATAGCAT GAGATTTTAA CAAACAAGAA ATTCAACAAA
CAGAATTAGA CAGATGATCT GAGATGTTAA ATTTTCCTTT CACCTTAATT TTTGCAGCCA
AATTTATTTC AGCTCTAGAT GAAAGAGACA GCACTTTCTT TTGTGGCTGA CTACAACAGC
TGAAGATTCA CTGAGGTTTG ATATGAGGAA GAACTTCCTC AGCCATGGGA TTGCCAGAGG
CGATGATGGG AATCTACTTA AAAGGGTTAC ATATTTAGTA GACAGCCTAG ATTTTAAGAC

                Eco  I
                ------
                BsiEI
                ------
TAATTTATGT GCCCCGGCCG GGCCCGGTGG CTCACCCCTG TAATCCCGGC ACTTTGGGAG
GCTGAGGCAG GTGGATCATC TGAGGTCAGG AGTTGAAGAC CAGCCTGGCC AACATGGTGA
AACCCCGTCT CTACTAAAAA TACAAAAAAA TTAGCCGGGC ATGGTGGCAC ATACCTGTAA
TGCCAGCTGC TCGGGAGGCT GAGGCAGGAG AATTGCTTGA ACGAAGGAAG TAGAGGTTGC
AGTGAGCGAA ATCATGCCAT TGCACTCCAG CCTAGGTGAC AAACTCTGTC TCAAAAGAAA
AAAAAATTAT GTGCCCCATT GGAAGAAGTG AGATTCGGCC ATCTCATCTC TCTCGGGAGC
TCTGAGCCCT GGAGTTTTAT GTTTTCTGCA ATTATGAATT GTGATCCTTG ATTAATTATG
CTTTAATAAT AAAATGGGTG ACTACTGAAA GCTGCTGAAT CTGGGTAAGA ATTTGGATGA
AAAAAATAAT ATATGTGCGT AATTTATTCT GTTCAAGGTA CTGAATATTG AATAAGCTGG
ATTTATTACT CAAAGAGAAA GACAGAATAA GAGAAGGTTG AAGGGAAAAA TGACTGTACT
```

Figure 15N

```
AGAATGGTAG TCAAAAATGC AACAACAGGC AGGTGCAGCG GCTCATGCCT ATAATCCCAG
CACATTGGGA GGCCCAGGTG GGCAGGTCAC CTGAGATCAG GAGTTTGAGA CCAGCGTGGC

   SfiI
-------------
CAACATGGCC AAACCCCCTC TCTACTAAAA ATACAAAAAT TAGCCAGGTG TGGCAGTGGG
TGCCTGCAAT CCCAGCTACT CAGGAGGCTG AGGCAGGAGA ATCACTTGAA CCTGGGAGGC
AGAGGTTGCA GTAAGCTGAG ACTGCACCAC TGCACTCCAG CCTGGGTGAC AGAGTGAGAT
CCTATCTCAA AAACAAACAA AACAAAACAA AACAATAACA AAAAAGCTAT TAATAGCTTC
CTAGGGAGTA AGAGTGAAGG GCTAGTTTAA TTCCAGAGAT GCGGACACAG TCCTGGGTCT
CACCAATTAT TCTGCTTGGT AATTACCTTT TGAAGCCTTT TAATATGCCT AACACAGAGC
TAAGTGCTAT GAAGAAATGA AAGAAATAGA AGCAAAGTAC TCCCCATGTG GTTAAATAAC

                 PshAI
               -----------
AAGACACTAC ATGACAAATG TCAAAGAGTG ACTCAAACAA TATGTCCTTT AGAATTTCAG
AGAAATGACA TCAATGCAGG CTTTACAAGT CAGTAAAAAT CTTGGTGATG AGGCAGAACT
TGATGTAAGG CAAATCCTAA AAGTTGAGTA GGAATCAACT AGCTAGAATA AAATGTGGGG
TTGTGGTAAA TACAAAAATG TAAGATGAGT GAAATAACTT ATTTATTTAT TTATTTATTT
TCAGAGACGG AGTCTCCCTC TGTCTCCCAG GCTGGAGTGC AGTGGCATGA TCTCGGCTCA
CTGCAACCTC TGCCTCCTGG GTTTGAGCAA TTCTCCTGCC TCAGCCTCCT GAGTAGCTGG
GATTGCAGGC ACCTACCACC ACACCCGACT AATTTTTGTA TTTTTAGAGA GATGGGGTTT
TACCACGTTG GCCAGTCTGG TATCGAATCC TCGACCTCAT AATCCACCTG CCTCAGCCTT
CCAAAGTGCT AGGATTACAG GCATGAGCCA CTGTGCCCAG CCTAATAATA TATTAAGATG
GCCACAGGCC AAATATTCTG GGGCTGGAAT GTGAGTGGAA ATGTCGCTCA CCCTTTATCA
CATAGCACCC CATAGTCCAG CCACAACTTG CAGAATTCAA AGTAAGTGTG GATGTGTGTG
TGCCTGCAGT GCCTTGCACA CAAGTGTGCA TGCCTGTGGA CATGTGACCC TAGAAGTTAT
TAATATATCT GGTTTACAAA CTGAATTGTT CTTTTATTTT TTTTCTCTCT TGGTGGTCAT
CAATAACTGA AATTGGGCTA GATTCCTGGA AATTGGGTAA GTTCTCAGAA ATCATTTACG
                          >>...Exon 5 ...>>
CACTTTAGAA TCCAGGCCAA ATTTAAAATC TTACAATAAA ACAAAGAACA AAGCATGCTA
AATTATATGT ATAATATAAT ATCAACCATA TAAAATGCAT AAAAAATATA CTAGAAGGAA
ATGTGCCTAA AATTCACAGT CTAAAATTTA ACAGTGATTG CCTCTTCCTT GTATAGATAA
GGGATTTTTT TTTACTGTAT TTTCCAGTCT GTACATAATA AAACAAGTAA TGTGCAATGC
AAACAAAACA AAATGAAACT TTATCAAATT TCAGTAACTC CTTGAAGTTT AATTTTTTTT
TTGAGACTGA GTCTTAGTCT GTTGCCCAGG TTGGAGTGCA GTGGTGTGAT CTCGGCTCAC
TGCAACCTCT GCCTCTGGGT TCAAGGGATT CTCCTGCCTC AGCCTCCCGA GTACCTGAGA
TTACAGGCAC CCACCACCAC ACCTGGCTAA TTTTTGTATT TTTAGTTGAG ACAGCGTTTC
ACTATATTGG CCAGGCAGGT CTTGAACTCC TGACCTCAGG TGATCCACCC GCCTTGGCCT
CCCAAAGTGC TGGGATTGCA GGCGTGAGCC ACTGCACCCA GTTGAAGTTT AATAGTGTGA
AAAAAATATT TCTCATCTCA CTATATCTTC TATGGGAGGC CAGATTGCAG ATTGTCTACA
GAAAAATCCC TTCAAAAGAC CTTGTTATTA CATAGACTGG AGCTCATGGG GCAGGTCTGG
TCCACACATC CTTAGGCTCC GCTTCTCCTG GAAAACAAAA ATAGCCTCTG ATCCAGTGTT
GCCTCTCCCA TCACCAAACC TCAGCTTCTA TCGCCAAACT CATCAAATAA GAGTGTCCAG
TAGAAAAACT GGGCAGATGG GGGCACAGAA GGTGAAGACA TCATTTCCCA AGCTAATGTT
GCTGCTGGAA CAATGTAAGT CTTGACTTTG TCTTGGTTTG GTTTGGTTTG ACATTGGTTT
GTTTTTCATC TTTGTCTCAT GCTTAAAATG TGAAGGGCAA ATATGATCCT TAGAGTTAAG
GTTTTAGGTT TTGTAGATGT TTTACTCCAT TTAAATGACA GCAGATCATT TAGAAATGAT
TCCTCTGTAA CAGCCTTCCA GATCCCATTC GATTGTACAG CATTGAGATA GATAGATAGA
TAGATAGATA GATAGATAGA TAGATAGATA GACGGAATTT GGCCCTGTGT TCCCACCCAT

                                                BamHI
                                               -------
ATCTCATGTC AAATTGTAAC CCCCACATGT CAGGAGAGGG ATCCAGTGGG AGGTGACAGG
ATCATGGGGT TGGATTTCCC CAATGCTATT CTCATGATAG TGAGTTCTCA CAATATCTCA
TTATTATTAT TATTATTATT ATTATTGCAA CAGAGTCTCA CTCTATCTCC CAGGCTGGAG
TGCAGTGGTG TCATCTCGGC TCTCTGCAAC CTCTTGCCTC AGTCTCTTGC GTAGCTGGGA
TTACAGGCAT GCCCCGCCAT GCCCAGCTAA TTTTTGTATT TTTAGTAGAG ACGGAGTTTC
ACCATGTTGG CCAGGCTGAT CTCGAACTCC TGACCTCAGG TAATCTGCCT ACCTCGCTCT
```

Figure 150

```
CCCAAAGTGC TGGAATTACA GGCGTGAGCC ACTGTGCCTG GCCAGTTCTC ACAAGATCTG
ATGGTTTAAA AGTGTGGCAC TTCCCCCACC TCCTGCCGCC ATGTAAGATG CTTGCTTACC

                                StuI
                               -------
CTTCCACCAT GATTGAAAAG TTTCATGAGG CCTCCTAGCC ATGCTTCCTG GTAAGCCTAA
GGATCTCTGA GTCAATTACA CCTCGTTTCT TTATAAATTA CCCAGTCTCA GGTATTTCTT
TATAGCAGTG TAAGAATGAA CTAATACACA CATAAACAGA TTAGAGGCAG CACTGGCCTG
AGTTGTGAAA CTCTTCCCAG CCTGGTCCTG CGATTAGCTG GCTATATGAC CTTGGACAAG
CTGCTTTGCT TCTCTGGGCC ATGGTTTCAT ACCTGCAAAA AAAAGAGCAT GGACTTGGCT
GTTGCCTGGG TCTCTCTAGC CCTGTGGAGA ATCAGCTACA TCTCTTACTA GGAACTTCTC
ATTCAGCCAG TTATTCCACT GCGGAGATGG TCCAGGACCA TTAGGGCCAT GCTAGACATT
GGGAGGCTGC CTGTCAGGTG AACATGAAAT TGAACTTATC TGTTCTCTTT CCTCCCTGAA
TGTTGCTGAA GGTAGATGCC CATCCTCAGG GCTGTCTTAC GGAGAGGAGA AAGTTGTGCA
GTGATTCCAC CCTGCAGTTA TCTAACTCGG CAGGGAACTC TGGGCAGTGA GTACTCACGG

                                            EcoNI
                                         ------------
TACAGTCTCC ACACCTCTAA TCATGTGCTC CTCTCCTTCC CAAGGAACCT GGAGACCATC
                                                   >>....EXON 6 .....>
ATCTCATTTC CTGGGGGAGA GAGCCTGCAT GGTTTTATAC TGGTGACTGC TTTGGTAGAG
>..........................EXON 6 .............................>
AAAGAAGCAG TGCCTGGGAT AAAGGTATCT TCTCACTTGA TAGCACCTTT TCTTTTTAAA
>........EXON6  .........>>

                         DraIII
                        ---------
TGAGCTTGAG CTTTACTTCC CACTCAGTGC CTTTCCTGCA GTGGATTTCT CAACACAAAT
GAACATAGAC CTTGTCCTGC TTAGTTCAAG TCTGAGAGAA GAGATCTAAG CTCTAGGCCA

                                                       AhdI
                                                   ------------
CCATATTTGC TCCCTTTTCT CAATTCCTAT AAAACTCGGA ATGGACCTTT TGTCCATTCA
ACAAACAGGC ATTGGTTTGG GCAATGGGAA ATTGGATCGA ACAAGACAGA CATTTTCCCA

                         BciVI
                         ------
GCCCTGACAG AAGCTTATGA TGGATACAGT GGATGAAGAT GGATTAACGT GGATTACAGG
TGTGAGCCAC TGCACCGGGC CTCAAACTGG AAATTCTTCA GGAGTCAGAC AGGTATCAGG
AAGGCTGGAT AGAAGACAAA AGACAGTGAT GCAGCTTGTG ATCAACTACA GCGTTAATGC
CTTGCCTAAA AATATTTCAG TTAGATTTCT GCCTTCGCTC TGTCGCTCAG GCCAGAGTGC
AATGGCGTGG TTTTAGCTCA CTGCAATCTC CACCTCCCAG GTTCAAGCAA TTCTCCTCCC
TCAGCCTCCT AAGTAGTGCA CGCCACCACG CCTGGCTAAT TTTTGTATTT TTAGTAGAGA
CAGGGTTTCA CCATGTTGGT CAGGCTGGCC TCGAACTCCT GACCTCGTGA TCTGCTTGCC
TCAGCCTCCC AAAGTGCTGG GATTACAGGT GTGAGCCACC CTGCCCAGCC AACACTACCT
CCCTTGATAA GCATATGTTG AGCACCTACT GGTCCTCAAT AGGGTGACCC ATTTCTGCTA

     Eco  III
    -------
TATTATAGCG CTTTCTTTCT CTCTCAGTAG TTAAACTCCA TGGTTACTTT AGTTCTCATC
CATGTGTTTA GTCCATTAGA AGATACAGAG TCAAATATCG GCCTTCCAAG TGTAGTTCAG
ATGAAGTAGA GACTCAAGGA AGACAAGGA
```

Figure 15P

```
AGTCTTCCCA GCAGAGGGGA TTCTAGAGCT GGGGGCTCTG TAGAATCTGT CTGTGTATTA
GTCCATTTTC ACACTGTTAT AAACATACTA CCTGAGACTG GGTAATTTAT AAAGGAAAGA
AGTTTAATTG ACTCATAGTT CTGCATGGAT GGGGAGGCCT CAGGAAACTT ACAGCCATGG
AGGAAAGTGA AGGGGAAGCA AGAACCTCTT CACGAGGCAG CAGGAGAGAG AGCAAAGGGG
GGAGCTGCCA AACACTTTTA TACAATCAGA TTTTGTGAAA ACTCTCCCTC GTATCATGAG
AACAGTATGG GAGAGCCCAC CCCCATAATT CAATCACCTC CCACCAGGTC CCTCCATCAG
CCTGTGGGGA TTACCATCCA AGATGAGATT TGGGTGGGGA CACAGATTTC AACACAGATT
TAAATCTGAC TTTATATGAG AGCTTCGGAG CAAGGATGCC CCAGTTGGAG ATGCAGTAGA
ACTGATCATA ACGTGACAAA TCCGAGAGAA GAAGAGTAAA ATAATAGTAC TCAGGCCCTT
GGGAGGTGCA AGAAGTAACA GCCAGATGAA ATTCCAGAAA CACTTACCTA GGGGTCTGTC
TGGGAGGTCC CCAGGGAGCT TCTGGCTGTC AGGCCAACCC CACAGTGGAT CTAGCTTAGG
ACGTTCCCAG GAAGCTCTGA CAAACTGTCC GGTCCTCCCC TGGGTTCCAA CAGTATGAGG
CTTACTCTGC CTGCATGGAC TTTAAGGGAG TGCTAATAAG TTGTGTACAT GCATCTCATC
CCTAGGCTCT TGTTCAGGCC ACGAATGCTA TCTTGCAGCC CAACCAGGAG GCCCTGCTCC
  >>.........................EXON 7 .........................>
AAGCCCTGCA GCGACTGAGA CTGTCTATTC AGGACATCAC CAAAACCTTA GGACAGATGC
>..........................EXON7  ...........................>
ATGGTAAGAT GCTTCCGAAG CTCCTGAAGG ATCCCCCAGG GGTCCTGGGC TCTGCTTAGG
>>>
GGAAGAGGGC CTGGGGACCA GGCATGTCCT GAAGGGGGTG ATAATACATT CATCCACCAG
ATGACGCTGG TGGACTATCT TTGTTTTAGG TTAAACACAT ATTATCTTGG AGAGCTATTG
TCACAGCTTT GTATTCTCCC TCTCCTTTAT ATTCTCCCGT GATTAAGATG GTTTCCCTTC
TGCAGTGGCC AGATATTTCT TAGGCATGTT GAGGTCTTGC CTGAAGCTTG AGAGGAGGGG
ATGGGATGCA CAGTAATGTT GGTCGCGCGT GCCCCATCCT GCAGTGTTAG GTACTGCAGA
GCAGGTTGTC TACACTCTGT AATGCCCCTT TTATTCTAAC CCCCTGTGTT GGTTCCTGAG
ATGTCTGACC TTGGTTTTAA GCCTTGTCTA ATGGATGGCC TGTATTCCCT TTCTGTAGCT
AGGGCAGGCT GATTTGTCAA AGGTAGGAAA GTTGTCAGAA TCAAAATGGA GTCACTTGTG
TTGAATAAAA ATTTTTAAAC CTTGACAAAT AGAGCTGGGG AAGGCTACAA AGAGAGAGCT
CCCGTGTATA AATGCCTGAT AACAAAATCT TTTCCAAAGG ACTGAAAAAA TCACCACCTT
GCACAAAGGC CATCACAACC TTACATACAC AAAAAAATAC TTACACAACG ACATCTGCCC
AGCAACTGCC TTTCCAACAT TGGCCTTGTG CCACCCTTTT TATTGATGCT CATAGCCAAG
GTTAATGATC TCAAAACAGT TACATAATTG TCCTCATTTT TCCTTTAAAA ACCTTTGTCT
TCCTTTATCT TTCTGAATAC CCACATGGTT TATTATGGCA CATGTATTCC CATTGCAATG
CCCTATTCCA GAATAAATAT CAGTTTCCAT TAGGGAGCCT CTCCCTGTTA ATCTGCTTAA

                                                AgeI
                                               -------
CACAGGCATG GTCAGTTACG GGGCCCAACC TTCCTGGACC GGTTACATCT TATTCTGGTT
ACTGCATTCA GTTTCCAACA TCTGGGAGGC TCTTCAAATT CTTCTCTCAG AGGAATCTGA
AGAATGTATG TGTTTAGGAG GATGTGAGAG AGGGGTGTGG TTTCTTAACA AGAGAATATC
AGAGTCTAAG TATCATTTTC CCTGAATCTT GCTTCCCTGC AGGAAAGAAA GATTCTGGGA
AAAGAGAGTG TTTACAAGAA GCAGGACTGG AGGGAGGGAG AAAGACGCTA GGTACTGCCA
AGCTTTATTA TCTTGTATTA AAAAAGTAAA TATAATTTGT CATCCCAGCC TCTCAGCACT
AGTAGAAATC TATCTGAAGT CACAGGATTA GGTATTATCC ACTTCCTGGT TTTATAGTTT
ATATTTGTAT TTTCTCTATT TCCTTGAATT TTAATTTTAA AGCCCTCATG ATCACATCAG
TAGGTCTTCT GCCAAACAGC TCCCTTAAGT TGTATGGTGG CTTTGCCAAG CTGAAATGAG
ATGAGATGTG TTTTAGCTTT GCCAAGAAAG CCTGAGTCCA TCACTTAGGA TAGCAAGGCT
ATTAGGGAGA TAGTGCAGGT GTCTTCAGAT CACATGGATG AGCAAAAGGA AGCAATTTTG
GAAGATTATG AGAAACCTTC CAACAGGTCC CAGTGTACAT AGCAGTAAGA TGGTGCATGC
AGTGTCTAAC TGTCACAGGC TTTCCTAGGG CTCACTTTCA GACTCACTTC TTTTTTTTTT
TTTTTTTTTT TGTGAGATGG AGTCTCACTC TGTCACTCAG GCTGGAGTGC AGTGGCACGA
TCTTGGCTCA CTGCAAGCTC TGCCTCCCGG GTTCAAGCGA TTCTCTTGCC TCAGTCTCCC
TAGTAGCTGG GATTATAGGC ATGCACCACC ATGCCCAGCT AATTTTTGTA TTTTTAGTAG
AGATGGGGTT TCGCCATGTT GGCCAGGCTG GTCTCGAACT CCTGACCTCA GGTGATCTGC
CTACCTTGGC CTCCCAAAGT GCTGGGATTA CAGCCGTGAG CCACTGCGCC CAGCTCAGAC
TCACTTTTTA GGCCCAGGCC AACCTGCTGT GTTCTCCTGC TCAGCTTCTG CAGGAGGTCT
CATCGTCTAA GGAGGTCCCA GGGCTACCGC CCTTGTTTTC TCAAAAGGCA CATTTTCCCA
CACAGACATA ATTTCGTTTC AGTGTTTTAC TCCTAGTCAC ATTCATCTAT ATGGACAAAT
```

Figure 15Q

```
                                                                  BssHII
                                                                  -------
AGCTGAATGG ATTGGACTGT GTTTTCTAAA GATGGCCCCA TGCCATCCTG CGCGCTCCTC
CACAGCGTGG CCTGGGCATT CCTTTCGACC AGGGGTGGAC TCTGTGCCCC TACTTGTGAT
GTACGTGTTG CCAATAGAAT GTAGTATAGG GGATAGCACA GACTTCTGAG GCAAGACTAG
AAGAGGTGAT GCAGGTTTAA CCTTGTGTCC TGAGCCACTA GGTAAAAAGT CCACCTACCC
TGAGATCACT CTGCTGTGCA AACGACACAG GCAAACCACA TCAAAGAGCC ATGTGGGTTC
TCCAGTTGGC TTCTGCCCAG GAGTGAAGGT GCCCTCAGAT GGTTCTAGGC TCCCATCCCA
ACTTATGTCC TGTCTTGAAG TCTTCCCAAC TGAGGCACCA GCCACTGTGG AGCAGAGTCA
AGCCATTGCC ATCTTGTTCT GCCCAGATTC CCCATCAACA GAATATAGTG GTTTTTTCAC
ACCTCTATGT TTGGAGTGGT TTCTATGCAG CAATAGTAAC CACAAGAAAT AAAGTTATAA
AAATAGTAAC AAACACTAGA AACTGCAAGA TTTAAGGAAT CACCTGAATG CTCCAGTCAT
TGTCTCTGGT TTGTAATGAT AAACTTTCTT CTGCGTGATA AATAGAGCTT GGCTGGACTT
TTTCCCTCTG CTTCCATTCC CCAAAATGGA GCGTACCAAA CAATTGCTTC TTTCAGAGCC
CAGCTTTAGC AAGAGTCATG AGCTCTAATC CCTTCATCCA TAAATACTTC CTTTCCAGGC
ACGTAGAGCC CTTCACACTC AGGGCTGAGT AGAAAATGCC TGTTGCAGAC TGCAGTGGCG

                       KpnI
                      ------
                      Acc  I
                      ------
TTTTGGAGAG CCACCCTCCT GGTACCTGAG TCACTAGTCC TTTGCCCAGC TTTTCTCAGT

     Eco  III
      -------
TTTGTAAAGC GCTCACTTCT GAGTGGAAGA CAGAACCAGC CCGGTCTATT TTCATAATCT
GCCCCCATAA GGCAGAAGTC CACACGGTAC TGGAAACATA ACCATATCTA TGTCAGTCTG
CCACTGCCTG CCGCCTGTCA ACCGTGCGTG TCTGCATCCA GTCCTTCTTT GGAGCTGCTT
TCCAGCGACT CAGCCAGATC TGAGCTTTCT GACTCATTGG AAGGTTAAAC TATTTTCAGA
CTTTCAAGTG TTGAGATTAT TAAGACATGT GTTTTTTTTT TTCTTCTTTT TTTGGCATGC
TTACTGATCG CCCCTGTTCT CTAGGAAGTA ATGTTCTTCT TGGAAAAGGT GAAGGATATT
TTTCTCCCCA AAAAGCCATG GAAATGTTTG CCTTTATTTA CTTCCAAATT AACAGAATTT
CCAGCTTTTG CTTGACCCAT CGGCGCATTG GCAGCGTTAA GAATTTTTTC TTTTAGCAGT
AATGAGGAGT CGAAGGGTTT CTTCCTAACC ATTTAGTGTA TGCATTTAAA TCAGGTTTCT
TTTTGAGTAA ATTGGGGCTA AGCTGTAGTG TGAACTTCTG CTACTGTTCC TTTCTCATTA
GTTCACTTGA TTTCATGGAA GGAATTTTCC ATCTCAGCCT GTGAACTTAT TTTGTCTAAA
CTCAATTGGA AAGTAATTAA CACTGAGATT CTTCTTTAAT AAATTCTATA TGATAATAAA
ATCATACAAA CATCTCTTTA TTTTTCTTTT TGACCTAGAA AAGATGTTCA CAGGCCAGAC
CTGGTGGCTG AAGCCTGTAA TCCCAGCACA CTGAGAGGAA GAGGCGGGTG GATCACATGA
GGTCAGTCCG AGGGCAGGGT AGCCAACGTG GTGAAACCCC ATCTCTAGTA AAAACACAAA
AATTAGCTGG GCATGGTGGC ACATGCCTGC AATCCCAGCT ACTCAGGAGG CTGAGGCAGG
AGAATCACTT GAACCTGGGA GATGGAAGTT GCAGTGAGCC TAGATCCTGC CACTGCACTC
CAGCCTGGGC GACAGAGTGA GACTCTGTCC CCAAAAAAAT AAATAAATAA AAGATGTTCA
CAATATATTG TTAAGTGAAA AAAGCAGGCT ACATAACTTG CATAATATGA GTGCATTTTA
ATAAAAATAT ACATATTTAG CAAAATAAAA GGACAAATGG TATTTATTAA AATATTTACG
TTGATTATTT CAACACAGAG GATGATAGTT GATTTTGCTT AATTTCTTCC CTCCTTCTTT
TCAATTTGAA TTTTCTATAA TGAAGATTGT TTCTTTTTCT TTCTTTCTTT TTTTTTTTTG

                                             NarI
                                            ------
                                             KasI
                                            ------
                                             EheI
                                            ------
                                            BsaHI
                                            ------
                                             BbeI
                                            ------
AGATGGAGTT TCGCTCTTGT TGCCCAGGCT GGGGTGCGAT GGCGCCATCT CGGTTCACCA
```

Figure 15R

```
CAACCTCTGC GTCCCAGGTT TAAGTGATTC TTCTGCCTCA GCCTCCCTAG TAGCTGGGAT
TATAGGCGTG TGCCACCACA CCCGGCTGAT TTTGTATTTT TAGTAGAGAC GGGCTTTCTC
CATGTTGGTC AGGCTGGTCT CGAACTCCTG ACCTTAGGTG ATCTGCCCAC CTCAGCCTCC
CAAAGTGCTG GGATTACAGG CATGAGCCAC CGCGCCTGGA CTGATTATTT TTTAAATAGG
GTTAGAAAGT GAGGAAGTTA CTAAACTCCG ATTAGCCCAA ATATGCCCCA GTGGGTCCTT
CTGGCAGAGT AAATGTCTCG GTTCAGCCTG AATCTGGGAA ATTGTTCCTA CGGTTCAGCC
TGAATCTGGG AAATTGTTCC TACCTTATAA ACTGGAGTAT CCTTCAGAAA TGACATTTAC
TCAAACTTCC TTTTAGGCAG ACTGCATAAT AGCAATTTTT AATATTAACC ATTTAAAAAA

                PacI
           --------
AACCTTCAGA TTAATTAACA CCAAAAGAAT AATTGGGAAA ATACAACTCC TCACTTTAAA
AAAGAAACAA CCAAAGTAAA TACTAAAAAA CTATATGATG TTATATTATC TAAGCTTAGT
TTACTGCAAA GATCAAGAGC ACACTACTAG TTGACGGCCT CTATTCACAC TGTTCATAGC
CCTCGCTCGC TTCTCCAGCC ATTCACTCAC TCATGCAAAA GGTCTGTACA CACAATGATG
CCTGATGGTA TAATAGGAAC CTTAACATTT CAATTAAAAG GCAAAATGAG GACACTTACC
ATCAGCCTAT AAAATTATTC TTATTATTCT TCTTCTTCTT CTCCTCCTCC TCCTCCTCTT
CTTCCTTCTT CTTCTTCTTC TTCTTCTCCT TCTCCTTCTC CTTCTCCTTC TCCTTCTCCT
TCTCCTTCTC CTTCTCCTTC TTCTTCTTCC TCTTCTTCTT CTTCTTCTTC TTCTTTTTTT
TTTGAGATGG AGTCTTGCTC TGTTGCCCAG GCTGGAGTGC AGTGGTGTGA TCTCGGCTCA
CTGCAACCTC TGCCTCCCAG GTTCAAGCTA TTCTCCTGCC TCAGCCTCCC AAGTAACTGG
GATTACAGGT GCATGCCACC ACGCCCGGAT AATTTTTTGT ATTTTTACTA GGGATGGGGT
TTCACCATGT TGGCCAGGCT AGTCTCTAAC TCCTGACCTC AAGTGATCCA CCTGCCTCGG
CCTCCCAAAG TGCTGGGTGT GGGCGGCAAG CCACCCAGGT GCCAAGGCAA GAGACAGAGG
GCACGAGCTG TTCCAGTATA ATGAGGAAAA TATATAGAAT AAGAATAGTT ATACTAGAAA
TAGATTATAG ATATGATTAC ATATGAATAT CATTCTTCAT TAGTTTGTAG CACTACTCTT
TATTCCAGTA TTATAATAAT CTTTGTTCTA CAATTATAAC CTAGGAAAAA CCAGGCCATA
CAGAGATAGG AGCTAAAGGG ACAGGGTGAG AAGTGACCAG AAGAGTGTGA GCCTTCTGTT
ATGCCCGGAC AGGGCCACTA GAGGGCTCCT TGGTCTAGCG GTAACGCCCG CGTCTGGGAA

                      RsrII
                     ---------
GATGCCTGTC ACCTAACGGA CCGTGGTCTA GCGGTAGCGT CAGTGCCTAG AAAAGGCACT
CTTTTTAAAT ATACTTTTTA TTTTTGTTTA ATCTTCCCTG ATTTCCTATA GATCTGAGAT
ATGTCATGCT TATTTTCATT GCTATCTAAA AATCTCAATA AACTTTATAC CTAAGAGTAA

                                            BsiEI
                                            ------
AAAAAAAAAA AAAGAAAAGA AAAGGCGCTC GTTACTTAGC CGACCGGGAA AGGGAGTCTC
CCTTTCCCCG GGGGAGTTAG AGAAGACTCT GCTCCACCAC CTCTTGTGGA GGGCCTGACA
TGAGTCAGGC CTGCCTGCAG TCATCTGGAG GCCTAACCGT CTCCCTGTGA TGCTGTGCTT
CAGCGGTCAC GCTCCTAGTC CTGAACACCT GGCTCCGCCT TTTAGATAGC AGTAGCAGAA
TTAGTGAAAG TACTAAAAGT CTTTGAAATG CAGAAGTAAT GGCGTAAGCT GTCACGTCTC
TCTCTCCGCC TCAGCTGCCA AACAGAGAAG GGTCCCCTGT CCAGTGGACA CGTGACTTGG
GTGACCTTAC CTGTCATTGG AGACGACTCA TACTCCTTAC CCTGCCCCTT GCCTTGTATC
TAATAAATAA CAGCTCAATC TGGCATTTGG GGCCACTACT GGTCTCCGCA TCTTGGTGGT
AGTGGTCCCC CGGGCCCAGC CGTCTTTTAT TCTATCTCTT TGTCTTGTGT CTTTATTTCT
ACCATCTCTT GTCTCCGCAC ACGAGGAGAA AAACCCACAG ACCCTGTAGG GCTGGCCCCT
ACAGCTGGGA ATTACAGGCA TGAGCCACCG CATCCAGCCA GCCTAAAATT CTTCTGAAGG
ATAATAATAT AGTACTTGAA GACACGGTTT GAAAAAAATC ATACTAAATG AAAGGGCACC
ATTTTACAAG CACTAGAACT ACATTAAACT TAAATGAATT CCAACACTCT TAATAATGTA
ACTCAAAAAC AAGTCTAGTG TTAACAAAAG CTCCAATAAC TAAAACTACA TTAACAGGCA
CAATGAACAT TGTAAACGCC GCTAATTGGC ACCAAGTTTA ATAGGGCAGA CAATATTTTC
TTCTGCATTC ACACTTACTC AGTTACACTG TTGAAAAATG CTGCTGCTCA AGCTATGAAT
GCTTTACAAA AGAAATCATT TTAATAAATA CAGTAAATGC TAAAACTCTA GCTAAACTAT
TATGCAAGAT ATACAACCAA GACAAATACA AATTCATAAT ACAAGCAACT TGCATTCAAA
ATGAACTCTA CCACTATATT TTATTAAAAG GGCAGACTTT ATGAATTAAC CCAGCTGCTT
CCTGAATTAC AAAAGTGGCA TGACTCAATA TGAAAATAAG AAACTGTCTA CAAATTTCTG
ACAGTAATAA ATTGTAATAT ACAATACATG CAGGAGTCTT ACGGAAGAAT AAACTCTCCT
```

Figure 15S

AGGAAACAAA AATATTTTAT ACTTTTAAAA TCCAAAGTAA AAAAAAAAGA AATCATTGCC
AGATGCGGTG GCTCATGCCT GTAATCCAAG CACTTTGGGA GGCCAAGGCA GGATCGCTTG
AGCCCAGGAG TTTGAGACCA GCCTGGGCAA CATAGCAAAA CCCCATCTCT ACAAAAAAAT
ACAAAAAATTA GATGGTAATG GTGGTGAGCG CCTGTGGTTC CAGCTACCCA GGAGGCTGAG
GTGGGAGGAT GCACCTCAAG GCTGCAATGA GCCAAGGTCA CACCATTGTA CTGAAGCCTG
GGGACAGAGT GAGACCCTGT CTCAATAAGT AAATAAATAA ATATCTTTTA TGAAAAAGAT
TCTCTAGTCA GAATTAACAC CTCAACTAGC CAAACATCAG GAAGTTACAT TACAGCTACT
TAATACACAA AGGGACACAT TTTCACCAGT CGTTGTCTTC TGATATTTCT ATTCCAGAAA
CACACACTCT CACTTCCCTA CACTCCCCAT CCCATCATTT CTTCAGAGCA TGGAAACAGA
ATTTGTTGAA CACCAGAAAT CTCTTGCTAT GGTGGTACAT AAGTCATAAC ATTTGTTGCT
GCCCAGCAGC AGGTATGAAG CCGGCTGGTG ACTGGCTAGC AAATGCCTAT TCTGTAAGCT
CCTCACTTAG CCCATCTGTA GCTCTGACTT CTCCACCAAT TCCCTTCTCT CCTTTCACAG
CCTTTCTGAG TTTCTGAGGG ATAATTTCAG AGGTTCCATA TAACTGTCAA AGCCTATGGT
AGACATGGCA AAGTGAAAAT CCTCTCCACT GGCCATTTCT GTTTCTCTTG GGGGCATCTT
TCACTTGCCT CAGGTGTTAT AAAGCTGATG AACACACGTA CACGTTGTTT AACACTTTCT
TGGGCATTTC CCATTTGAGA TATGGCATGT TTCATTATCC TAGTGACATG TGCAATCAGA
AAATGTATAT TTTGTTCTCT GCAACTTTCT TTTGAAAAAT GTATATTTGA ACAAAATATA
CATTTTTTGT ATCTTCATGA CCATTCATGC TGTCCTCACT GTCATCATGA GGCTCTATAT
AACATAATGA CTCCTCCAGG GCAGTCTTCG GAAATTCCCA GTGCAGAAGC ACGTGTCATA
CAGCAGTCCC CATTCATCTC CAGTGCAGCT CTGGCTGGCT CCCATGTCTG ATCAGCTGTT
TGGTTGGACA GAAAATGACT GCAAGGGAAT CAGTTCCAGT GTGAGCTCTG TTTGCAGAAC
TCAGACTCCC CTCCCTCCCA TGTTAATGCT TTTTTTCTTC TTCTTTTTTT TTTTTTTTTT
TTTTTGACAG AGTCTCATTC TGTCACCCAG GCTGGAGTGC AATGCTATGA TCTCGGCTCA
CTACAACCTG TGCCTCCCCG GTTCAAGCAA TTCTCGTGCC TCAACTTCCC GAGTAGCTGA
GATTACAGGT GCACACCACC ACACCCCACT AATTTTTTTG TATTTTTAGT AGAGACGGGG
TTTTGCCATG TTGCCAAGGC TGGTGTCAAA CTCCTGAGCT CAGGAAATCC ACCTTCCTCA
GCCTCCCAAA GTGCTAGGAT TACAGGCGTG AGCCACCATG CCCAGCCCCA TGTTAATGCT
TCTAAAGTTT GCCCTCACTT CTTTAGAAAT TCCTTCAGTA CATCCTTTAA GACTTCCTCT
AGTGAGTGTC TGCTGGTGGT AAACTCTCCC CTCTAAAAGT TGCTTTATTT CTCCTCAATT
CCTGAAGGAT ATTTTTGCTA GCAGCTATAT TCTTTTAGAT GTTGAACATA TCGGTACAAA
AGCTTCTGGT TTCCATGGTT GCTATTGAGA TGTTAGCTGT CGGTTTATCT TTCTCCCCTG
ACTATGTGTA CCTGTTTCTC TGTATCTGTC TACTTTTTGG GTTGCTCAAT TTATTGGCCT
TGGGCTTCAT TCTGCTGCTG CTTTTTTTTT TTTTTTTTTT TTGAGATGGA GTCTTCCTCT
GTTGCCCAGG CTGGAGTGCA GTGGTGCAAT CTTGGCTCAA TGCAACCTCT GCCTCTCGGT
TCAAGCGATT CTCCTGCCTC AGCCTACCGA GTAGCTGGGA TTACAGGCAC CTGCCAACAC
GCCAGGCTAA TTTTTGTATT TTTAGTAGAA ATAGGATTTC ACTATGTTGG CCAGGCTGGT
CTCAAACTCT TGACTTCAGG TGATCCACCC ACCTCAGTCT CCCAAAGTGC TAAGATTACA
GGCCTGAGCC ACCACGCCTG GCCACAATTT TTAAACTTTT TATTTTTACA GGCACCTGCC
AACATGCACA ACTAATTTTT GTATTTTTAG TAGAAACAGG ATTTCACTGT GTTGGCCAGG
CTGGTCTCAA ACTCTTGACC TCAGGTCATC CACCACCTTG GTCTCCCAAA GTGCTAGGAT
TACAGGCGGG AGCCACCATG CCTGGCCAAA ATTGTTAAAC TTTTTATTTT CTTCCTCAAG
AGGATGAGAA GAAAGGTCAA TTGTAAGCTT TAGAAGTCTT GCCCAATAGC CAATCTGAGA
ATATTCTCCG TAAACATTCA CCAGAGGCAG CCAGTGACCA TGGGATACTT TTGGTGAGAG
GAATTGATTG CTGGGGTCAG GAATGGGAGG AAAGCATACT TCTCATTAGA TACCTTGTTG
AACTTCGTAA ATTGTGTGCC AAATGCATGT CTTACCTAGA CTTCATAAAT TAATTTCTTT
AAAAATAATC AAAGACAATT TTTTAAAGAC TTATTTAATT TAAGGTGATT ATAAAACATC
CAGTATACTT TCACTATTAA AAAAGTAAGT ATTCCTGTCT GGGCTTGGTG GATCACACCT
GTAATCCCAG CACTCTGGGA GGCTGAGGTG GTCGGATCAT GAGGTCAAGA GATTGAGACC
ATCCTGGCCA ATATGATGAA ACCATGTCTC TCCTAAAAAT ACAAAAACTA GCTGGGCGTA
GTGGCGTGCC TGTAGTCCTA GTTACTCAGG AAGCTGAGGC AGGAGAATCG CTTGAACCCA
GGAGGCGGAG GTTGCAGTGA ACTGAGATCG TGCCACTGCA CTCCAGTGTG GCAACAGAGT
GAGACTCCAT CTTCAAAAAA AAAAAAAAGT ATTCCTAAAC AGCATATTAT CATGATATAT
TATTTTGTTT TGTAGGGTTT TGAACCTTGT CTAAAAAGAA TTAAAATGTA TAAATTTCTT
CCTGCAATTT CCCTATTTCA CTAAGGGTCA TTCACATTGG TCATATAGAC ATAGCACATT
TTCACCACTA TATAGCAGCA TTTTGTACAA ATAGACTACA ATTTACTTAT TCTGCACTTA
TTTCTGTTTG TTTGTTTTGC TATGAAAAGC AATGTCATTA CATATATTCA TGCCCATAGC
TACAAGTTTA CATATTTCAG GTTTTCTGTA GGGTGGACAC CAGGGAGTTG AATTGTTCAA
CAGGACTTTA CATTCATCTT TAGTTTTATT GGCCAACACC AAATTGTTCT TCACAATGTT
TGAACTAAGT TGAAATTCCA CCTCCCCATC ACATTTAGTT TTGTCAACTT CATTTCTTCA

Figure 15T

TTCATTAATT CATTCATTCA GTCTTTTGTT TATTTGTTTA TTGCCAGTCT GATAGGCGTA
TAGTGGTGCT TCATCATGGT TTTACTTTGC ATTTCTCTGA TTTTCTTTTT AAATTTTTAA
AAAATTATTT TTATGTAGAA ACAAGGTCTC GCTACATGGC CCAGGCTGGT CTTGAACTCC
TGGCTTCAAA TGATCCTCCC ACATTGGCCT TTCAAAGTAC CGAGATTGAT TATAGGCGTG
TGCCACTGTG GCCAGCTGAT TTCCCTGATT TCTGATGAGT TAACAATCTC TTCTTTCTCT
CTCTCTCTCT CTGTGTATAC AGGTACTCAC CATTCGTGCC TATTTTCTGT AAAATATGTG
GCTTTCCTCA TTTTTTTTTT TTTTTTTTTT TTTTGAGGCA GAGTCTCGCT CTGTTGCAGG
CTAGAGTGCA GTGGTGCGAT CTTGGCTCAC CACAACCTCC ACTTCCTGGG TTCGAGCAAT
TCTCCTGCCT CAGCCTTCAG AGTAGCTGGG ACTACAGGCG TGCACCACCA TGCCCAGCTA
ATTTTTGTAT TTTTAGTAGA GATTGGGTTT CACTATGTTG GCCAGACTGG TCTCAAACTC
CTGACTTTGT GATCTGCCCA CCTCAGCCTC CCAAAGTGCT GGGATTACAG GAGTGAGCCA
CTGCGCCCAG CCATCTTTCC TCATTTTTAT ACTAATTAGG CTTTTATCTT ACTTGTTTTT
TTTAATGTTT TTTGTACACT CTGAAGGCTG ATTTTTGTTA ATTGTATGTG TTGCATTTTT
TATGGTTTGT CTTATGCCTT TTGAAAGTAA AAGTTCTTAA TTTAAATATA GCCAACCTGT
AAATCATTTG TGAAAGTCTG TGGTTTAAGA GGTCTTGAAT AAGAAATTAT CCCATCATCA
TAAGTCATAA ATACTTTTTT GTTGTTGTTG AGACAGAATC TCATTTTGTT GTCCAGGCTG
GAGTGCAGTG GGTTGATCTC AGCTCACTGC AACCTCTGCC TCCTGGGTTC AGCAATTCTC
CTGCCTCAGC CTCCCAAGTA GCTGTGATAA TAAGCATGTG CCACCACACC AGTCTAATTT
TTGTATTTTT AGTGGAGACA GGATTTCATC ATGTTGGCCA GGCTGGTCTC AAACTCCTGA
CTTCAAGTGA TCCACCTGTC TCAGCCTCCC AAAGTGCTGG GATTATAGGT GTGAACCACC
ATGCCTGGCC CATAAATACA TTTTTATGTA TTTTCTTCTA AAGTTGTTTT GTCTTTCACT
TTTTAGTTTT TAATTCACAT ATAATTACTA CTTGCTACTT ATAATTATCT GTAAGTAGTA
TGAGATGAGA AATAAATTCT ATTTCCCTCC TATGGATAAG CACAAACCTG CAGTATTAGC
ACAGTCTTAT GTCAGATTTT CTAAAATGAA TGGGTGTGTT TTCTAGGCTC TCTGTTCTGT
TTCATTATCT GTCTTTTCCT GCAACGATAT CATCTGCCTT AAAAACTCTA GCCTTGTGGT
ATTCCTCATT TTCAAGCAGA GCAAACCCCG TCACCTTGCT TTTCTCCTCC AGCATCGCTT
GTGCTATCCT GGACTAAGAC CTTCATATAG ACTGTTAGAA TCATCTAGCC AAGTTCCATT
TTAAAAATCT ATGTTGGAGC TGGGCGCGGT GGCTCACGCC TGTAATCCCA GCACTTTGGG
AGGCTGAGGA GGGCAGATCA CTTGAGGTCA GGAGTTGGAG ACCAGCCTGA TGAAACCCCG
TCTCTACTAA AAATACAAAA ATTAGCTGGA CGTTGGGCAC TTGAATTCTA GCTACTCAGG
AGGCTGAGGC AGGAGAATCG CTTGAACCTG GCAGGCGGGG GGTGCAGTGA GCCGCGATCA
TGCCACTGTA CTCCAGCCTG GGTGACAGAG TGAGGCTCCA TCTCCAAAAA TAAATAAATA
AATAAAATAA AATATCTATG TTGGAAATTT TGTACAAATT TTATTAAATG TCTACATTAA
TTTGGAGAAA AATGACTTGA TTTTGATTAT CTATTCAATA TTTCTGTATT ATGAATAAGG
CAAAAAGAGA GGCAGAGAAT AGCATAAAAT AATAACTAAA ATTCCTGGGT AAACCACCTC
AAATCATTTC TTCATATGGC TCAATATTCT TTTGTGACAT GGCCTGAAAT ATATCCAGAC
AGAGAACTCT TCTCTTCAAT ACATTTCTTC TTTTAGGTAT TCATATTGAG TTTTCCTGTC
CATGAACATG GTATAAGAGA GTATATCCCT TCGGGAGGCC AAGGTGGGTG GATCACCTGA
GGTCAGGAGT TTGAGACGAG CCTGGCCAAC ATGGTAAAGT CCCATCTCTA CTAAAAACCC
AAGAATTATC CAGGTGTGGT GACACATGCC TGTAGTCCCA GCTACTCAGG ATGCTGAAGC
AGGAGAATTG CTTGAACCAA GGAGGCGGAG GTTGCAATGA GCCAAGGTCA TGCCATTGCA
CTCCAGCCTG GGTGAAGAGC GAGACTCCAT CTCAAAAAAA AAAAAAAAAA AAAAAAGAAA
ACGAGAATAT ATCCTTTCAT TTACTAGTTT TTCTTCAATT TCTTTCAAGA TAAAGGGCTT
ACCTATCTTC TGCTTTATTC ATAGTTACTT GATATTTTTG TTTCTAATAA ATATGGTGTC
TGTCTATTTA CCTGCCTCTT ACCTGTTCAT TTCCAGTTTC AAAAATGATG TTGATATTTG
AATATTAACC TTAAATCTAG CACCTTGGTA AACACTATTA TTCATTCTAA TAATTATCAG
TAGATTATAT GTGTTTTTTA TTTATAAATC ATATTGTTTG AGTAGCATGC TTTGCTTCTT
CATTTATAAA ATTTACAACT TTTATTTCTT TTTAATAATT TTTTTCTTAT TCTCCTGGCT
AGGACTTCTA ACACAGTATT GAGTGGAAGT GCTGATCCTT GTTTAGTTTC ACATTTGAAA
AAAGATTGCT TTTACTATTT CACTGTTAAG TATAATATGC ACCATAGGCT TTCTGTGGAT
TCCTTTTATC CATTTAAGAA CATCTCTTAT TCCTAATTAG CTGAAGTTTT CTGCATGTTT
GTTTTCATCA TGAGTGGATT TTTTTACATC TATTGAAATC ATTTTACATA GAAGATATTT
CACACCTATT GAAATGGTCA TTTCACTTTT CCTTCTTTAA TATGTTAAGT TGGGCAAAAT
ATTAAAGTAT CACCTGTCAT TCTGCTTCAG CAAAAAGTAG TAGTGTCTTA GCAGTATTGG
TGAAAAGACA GCATCAAATA AAAAAGATGT AGAAGTAGGA CCCAGTAAAA ATCTAGCGCA
TGGGGCATTG TCACATGTAA GCAGACAGAA TGTGACACCA CCAAGGAGCA TCTGAAGGGC
TGGAGGCTGA AGGAAGACAT GAGTCACCCA GGCTCATGGA CACTTCAGAG AAATTAGGGA
GCAGGAAGAA GAAATAGGAT CAAAGACTAC GTATGTTGGT TGGAAAAGGA AGCTGATGGT
ATGGAGATGT TATTATTTAG GTCTCACATA AAAGATGTAG ATAAATAGGT AGATAGGTAG

Figure 15U

```
ATAGATGATA GATAGAGAGA TAGATAGATA AATACATAGA TAGATAGATG ATAAATAGAT
GTTGTTATTT AGGCCTCACA TAAAGATGTA GACAGATTAG ACAGACAGAT GATAGATAGA
TAGATAGATA GATAGATAGA TAGATAGATA GACGATAGAT AGATAGATAG ATAATCTCAG
AAACAGAGAC ACAGTGATCT CAGTAAGATA GGCATATGCC AGGTGACAGA ATTCAGAGGG
GTCCCACTAC GTGAAAACAA TAGAACAACC TTCGAAAAGA AATTTAGTAC AAATAAGAGG
GCAGGCTTCC TTACATACAA GTTAGTAAAC TGGAAGAATC AGTTATCCTC AAACATTGGA
ATAGATCAAA AATAGTTGTT TATATTAATG AAGGTAGCTA AACATGAAGC TAAGTGAACC
TGTCTCTGAC CTAGTGTGGC AATCCCTGGG CAAGGGACAC TTGCTCCGCT CTTGTATCCT
TCACTGAATA TTCAGACTTT CAGTTAAGCA TCGGTGAATT TAGTTTTCAT CTCTTGTGAA
AACCTTGAGA GAGGTAATTC TCTCTGCTTT TCTTCTTTTC CCTTCCTTCA TTTTCTCAAA
CATTGCCTGT TTAAAATACG AAATTTTAAA AGATGGCCTT GTTCTCTTTT TTGTTGTTAT
TATTAAGTAC AGAGAAAGGA AGAACCACAA ATAGCAAAGG GCAACATATG GAATAGTTTA
GAAGTTCCGG GAGCACCCAT GAGGGCAACT GCAGAAGAGA ACATTCTATC CCCCGTTGCT
GCAGCTTTCA TTCCAGGTCT CCATGCATAT CAGATAGGGA AGGAACTCCG GGACAGCAGC
AGGGCCCATG CACATGTAAC CAATTGCTTT CTTTGCCTGT AGTAAAGTTC ACATTTTGAT

                                                AccIII
                                                ------
TGCTTCTCCA GATTATGTAG ATCCAGACAT ATTTTATGCA GGCATCCGGA TCTTTCTCTC
           >>......................EXON 8 .......................>
TGGGTAAGTA TAGTTCAGTT GTTTTCCTGT GTGAAGTCTC TGTAGCATTG ACTGAATGTA
>>>
TAAGGGGACG AAGAGACAGA AGCTTCCTAG CGTAAGAAAC ATACCAAGTG ACTCTTGCTA
GGGATCCACT CTCAGGTAAA AGAAGTGGGA TACCATCTGC ACAACAAATA ACACTGAGGG
CTAAGTATTT CAGTTAAGAG TGTTTGTTCC TAGGCAGTTC AGATCCATTT ATATTCACTT
TTCTTAGAAT CCTAGCTCAA TGACAGAAGA AGAAAAACAC AGTATGTCAC TCACACAGTT
CTATCACTTA CATCTACTTT TTCTTCTTGT TATTAAGGCA TGTAGAAGGC TGGGGAGTGT
AGTATAGAGT TGGATAGCAT CGAAGCTTTC TTCTAAAGTT CCTGGAAGAG CTACACTGTG
GTTTGAACGA ATGTGTCCCT CCAAAATTCA TATGTTAAAA CCTAATTGTG ATGGTGAGGT
ATTCGAAGGT GGGTTCTCTG GGAGGTGATT ATGTCTCCTC TGAGAGGAGA AGACAATCCC
CTGAGTGGAA CTAATGCCCT TATAAAGGGG CTGGAGGGAG TTCACTTGGC CCTTTTTGCT
CCTTTTTTCT TCCATTCCTT GTCCCTTCCA CTATGTGAGG ACACGGGAGT TGAGGCATTA
                      Clone 152 alternative exon 8
                                                A not in mRNA seq
CCTTGGACGT GGAGACCAGG CCCTCACCAG ACACTGAACT TGCCAGCACC TTGATCTTGG

ACTTCCCAGC CTCCAGAACT GTGAGAAATA CATTTCTGTT ATGGGTAGTC CCCAACTCAA
TACAGTTTGA CTTACCATTT TTTGACTTTA TGTTGGTGCA AAAGCATACA TATTCAGTAG
AAACTACTTT GAGTACCCAT ACAACCATTC TGTTTTTCAC ATTTGGTACA GTATTTAATA
AATTCCATAA CATATTCAAC ATGTTGACAT AAATAAGCTT TGCGTTAGGT GATTTTGCCC
AACTGTGGGC TAATGTAAGT GTTCTGAGCA CATTTAAGGG CAGCTAGGCT AAGCTAAGGT
GTTTGGTAGG TCAGATGTAT TAAATGCATT TTTTGTCTTA TGATATTTTC AACTTACATT
GGGTTTATCA GGATGTAACC CACTGTGAAT TAAGGAATAT CTGTATTTAC AAATTACCCA
GTCTAATGTA TTTTGTTGTA GCAACAGGAA CAAACTAAAA CACTACCCCA AACCATTTTT
TTCATATTTT CTGAGTACTC TTCTTTTGTC ACATGGCTTG AAATTTCTTC ACATAGAGAA
CTCTACTATT ATTTTATTTT ATTTTATTTT ATTTTATTTT TTGAGACAGA GTCTTGCTCT
TTTCACCCAG GCTGGAGTGC AGTGGTGCCA TCTTGGCTCA CGGCAACCTC TGCCTCCTGG
ATTCAAACTA CTCTCCTGCC TCAGCCTCCC GAGTAGCTGC GATTACAGGT GGCTGCCACC
AAGCCTGGCT AATTCTTGTA TTTTTAGTAG AGACGGAGTA TTGCCATGTT AGTCAGGCTG
GTCTCGAACT CCTGACCTCA GGTGATCTGC CCACCTTGGC CTCCCAAAAT GTTGGGATTA
CAGGCTTGAG CCACCACGTC TGGCTGATAA CTCTACTTTT AGATACTCTC TTTGCTTAAA
CAAATTAGCC ATTCCTTCCT TGACATGTTT TAATCAGATT GCCTTCCTAT TAACTTCGGA
AATTAAGAGT TTCTGCTATG TTTTTGTTTA ATTTTTAAAC AGTGAAAAAT GAAAGGTGGA
GGCAATGGCT GGATGAGGTG AATATGTCAA ATAGATATCA TCTAGTGGGC CATCTTATTA
ACTAGGAGAC ACCTGAAGTG CTATCAATAG AAATAATCTG AAGCTGTGTC TGGATACAGC
AAGAGACATG CAAATGCTAA AAATCTACTA TATTACATTG GTGCAAGGAC AGAGTAGCAA
CACATACTAA GTATTTTCTC CAGATTGGGT GTGTTTGACG TGTGAAGCAC TTCAAACAGA
GTCCAGCCTG GGAGGGAGTG GGGATGGAAT CCTCCTTGTA GAGGGTACAG AGTGGAAGCA
AGAAGGTTTC CAAGATTGAG AGTAATGGGT GTATGGTTTA TGGGGGAAAG GGAAAACAAA
```

Figure 15V

AAGAAGGGTG CAGAAATGGA GCTGGGAGTG TGTTTTAGTA TTTAGGCTTT CTCTGTATAC
CTTTGATAGG ATTAGAAAAA GAAAAATGGA CCATTTTTAA AAATTTCATG CTACCACATA
GCAGGCTTAT ACTATAGATG CAGAAACAGA CTGGGATTTA GGAAGCACCC CAATTCTGGA
AAATCCCTTT TTGCTTCACA TTGCTCTCTA AATCTGTATG TTTTCCCTTG TTACGTAACA
ATTTACCACA AATTTAGCAG CTTAAAACAA TATGCATTCA TTGTTTCACA ATTCTGTAAG
TCGGAATCAT AGGCAAGCTC AACTGACTTT TCCATTTAGG GTCGCAAAAG GCCGAAGTCA
ATTTATCTAT TGGGCTGGGC TCTTAACTGA AGATCTGGGG AAGAATTCCC TTCAAAACTC
ATTTAGGTTG TTGTCAGAAT TCAGTGTTTT GTGGTTCTAG AACTGAGATC TGTTTCCTTG
TTGGCTGTCA GACAGGAGCT GCTCTCAGCT TCTTGAGGCA TCCAGTATTC CTTATCATGT
GTTTTTTTTT TTCCATCTCA GCACTGGCAC TTTTTTTTTT TTTTTTTTTG AGACAGAGTC
TTGCTTTGTC ACCCAGGCTG GGGTGCAGTG GCACGATCTC GGCTCACCAC AACCTCCATC
TCCCGGGTTC AAGTGATTCT CCTGCCTCAG CCTCCCGAGT AGCTGGGATT ACAGGCACCC
GCCACCAGCC CGGCTGATTT TTGTATTTTT CATAGAGATG TGGTCTCACC ATGTTGGCCA
GGCTGGTCTT GAACTCCTGA CCTCAAGTGA TCCTCCCACT TCAGCCTCCC AAAGTGCTGA
GATTACAGGC ATGAGCCATC ATGCCCAGCC AGCACTGACA ATTCTAATCC TTCTAGCACT
TTGATTCCTT CTCACCTCTC CTTCTGCCTC TAGCCAGAGA AAACTCTCTG ATTTTAAAGG
TCTTATGTGA TTAGATTCAG CTTACCTAGG TAATTCAGGA TAACTCCCTA TGTCAAGGTC
AACTGATTAA TAACCTTAAT TACACCTGCA AAGTCCCCTT TGCCATAATA TATCATACTG
ACAGACATGC TATAGCATAA TACTAATAGT TCTAAGAATT ATGATAAGAA TCTTGGAAAA
CCATTTTTAG AATTATACCT ACCACAGTAT CCTTCAAGGG ATAAATTGAT TCTACTTCTT
CTCTATGTCA GAAGCATCTG ATGAGGATGA ACTATATATT CTGAAATCCC CATGATTAGA
TGTGTACTAG AAGGTGATTT TACTTTCATT AAAATAAATT CGGAGTCATT GACACATTTT
ATCTTTGATT TACATAAATG CCTCCGCTCT GTTTCTTACC CTCAAAATAT TTCCCATGTA
GCTAAGTGGC CAGTACCGAA TCCTACATGC ATTAATAAGT GTAGATGGAC AAAAATATCT
GGATTACTGA GAATTCCCAT TAGCATTGTC TAGAAAAATG TAAATTTGCT TTTTTGTTCT
TGATTTATCC TATTTTTGAT TTATTATTTA TATTTATTTA TTTATTTATT TATTTTTAGA
TGGAGGTCTC GCTTTGTCGC CCAGGCTGGA GCGCAATGGC GCAATCTTGG CTCACTGCAA
CCTCTGCCTC CCAGGTTCAA GCTTTCCTCC TGCCTCAGCC TCCCAAGTAG CTGGGACTAC
AGGCACCTGC CACAGTGCCC GGCTAATTTT TGTATTTTCA GTAGAGACAG GGTTTTGCCC
TGTGGGCCAG GCTGTTCTTG AACTCCTGAC CTCAGGTGAT CTGCCCACCT TGGTCCCCCA
AAGTGCTGGG ATTACAGGCA TGAGCCACCA CACCTGGCCT TTTTGCTTAC TTTTTAAAAA
CATTTTTATT TAGGAGAATG GAGATATTTC ATATGTAGAT GACACATATT CATTCCCTTT
AGTTCCCACA CACATTCAAT TTCTTGAGGA AGTTAGCCTT TGCAAAAAAA AAAAAATGAT
CTCATTTTTT TTTCCCCACT AAAACTTCTC ATTTTCTTGG GGTTGCTAGA AAGTTGCTAC
AAGAAAGGCT AAAAATAATT GTGCCTACAG ATATTTGAAA GGAAAATAGT TCCTCTTTTT
TCACAGTAGC AGCTTGGACC TGAGAATGTA TGGGAGCAAT AATTGGGCTG CTCAAAGAAA
CACAATTTCC CTTCCTCAGA CTAGAATTAC CAACCTAGAG AACATGAGTT TTTAAAGTAG
ATGTGCTTCT TTTATCTTTT TGGACTTGTA TGCTGGTGTT TTCTCTGTCA CCTTCACTGT
GGAAATCCTC TTGAGGGTGA GGCACTGAAA GCAGATTGAT TAATGTCTCT TGGCCATTTG
AGACATTGGA TGGCTCTTTT AAGTTGGCCA CGTTCTTTCA AGAACTATGC TTGGGCTACA
TATTCTGGAT ATATAATACA TACTTGTAGG ATGTTATTTT TAAATCATTC ATTTATCACA
TATTTAGTGA GTGCCTACCC CATGTCAGTT CTAGGTGCTG GAAATAGAGC AGTAAAACCA
ACCCTCAACT TGGCCCCTCT GGAGCTTACA TTTCAATGCG GTGGGTGGGG GGATGGACAA
TTAATACACA AGTAAATCTA ATAAAAGCGT CATACAATAT ACATTACAAT GGTAAGCACA
ATGAAGAAAT GGAAAGCTGG ATAGAGAGTA TTAGAGACTG TCGAATGTAG TGGCCAAATT
TTCCTGTTTA TTGTGGTCCA AGAGTGCCAC AGCCCTCTAT GACATTTGAG CAGACACCTG
GAGGAAGTGA GGGAGTGAGC CGCCAAGAAG GAATGGCAAG TGCAATAACC CTGAGGTGGG
AGCGTGTTGG TCGTGGTGGA AGAGCTGCAG GAAGCCAGCA GGGCCGCAAC ACTCAGGGGA
GAATAAGAAA GAGTGAGGTG ACAGTAGAGA CCGGATCATG TAGAGCTTTG TCAGCTTCTT
TTCTGAGTGA GATGGACAAC ACGGACACGT TTTGAAAAGA ATAACAATGT GATCTGCCTT
CAGTTGCAAA TCATCTCTGT ATTGACTGAG TAGGAAATAA ACTCCAAGAA TAAAGACGGA
AACAGGGAAA ATATTTAAGA AGCGATCATT ACAATCCAGG GTGGTGGCTT GTACTAGGGT
ACAAGGGCTA AAGGTGTTGA GAAATGGTCA GATTCTGGAT ATATACTGAA ATCAAAGTTG
ATGGAAAGAT ATGAGTCAAA GATAATTTGC AGGTTTTGGG GTCCTGGTTC ACTGAAAGAA
CAGAGACATC ATTTACTCCA ATGAGGAAGA CTATAGGAGG AACAGGTTTA GCAAAGAAGA
AAGGAAATCA GGAGATCAGT TTGGGGACAC GGTCATATCA AGTAGGCAGT TGGATGTATG
GGTCTGGAAT ATAGGGGAGT GGTCTAGCTA TCAGTGTAAA TAGCTTTTTA CATTTGTAAA
TAGTCAGGAT ATAGGCTTTT CTTTTTCTTT TTGTGAGACA CAGTCTTGCT CTTTCGCCCA
AACTGGAGTG CAATGGCACA ATCTCAGCTC ACTGCAACCT CTGCCTCTGG GTTCAAGCGA

Figure 15W

```
TACTCCTGCC TCAGCCTCCC GAGTAGCTGG GACTACAGGT GTGCACCACC ATACCAGGCT
AATTTTTGTG TTTTTAATGG AAATGGGGTT TCACCATGTT GACCAGGCTG GTGTCAAACT

               ClaI
              ------
CCTGACCTCA ATCGATCTCC CCGCCTGGGC CTCCCAAAGT GCTGGGATTA CAGGCATGAG
CCACCCCATC CAGCTGGGAT ATAGTTGTTT TCTAAATCTA TGAGGCTAGA GAAGACCATT
TGGGAATTGA GAGCAGTGAG CAGTCCACGG ACTGACCCTT TGAGAGTGCA ACATTTAGCA
GTACTCAAGA TGGGAAGGAG CTAGTGAAAA AGCCCCAAAT GACTACATAA GACCATCAAC
CAGATTACAA AGAAAGACCC GAACATGTGT GCCCATATAT CACCCAACAG CAGTTATGTC
TTTCATGTTT CTTCCCCATA AAATGTTGTT CATCAACTTT ATTAGACTAG GGTCTTAACA
TTGGACAAAT CACAAAACCT CTCTGGAGCC TATTTTATTT TTCAACAGCT GTAGGAAGCA
AATACAAATT GGAAATCTAA GGCTCAGAAA GATTTGTACA AAGTTACACA GTAATGAAAG
GGGAGCCGGG ATTCCCACTC ACTCTAAAGA ATATGATAAA ATGGCTAGTA TTCACTGAAT
GCTTAACATG TTCCAGGCCC TGGGCAGGTA TTATTTTAAT TAGTTCTCAC AATAATCCAA
TAAGGGAGAT ACTAATTTAC TCAGATGAGA AAGCTGAGGC TCAGAGAGGT TAATGAACTA
AGCCAAGGCT CACTGTTAAT AAATAGCAAA GGTAAAATTA AATTCCATAT CTGCTTGAGA
TAGAGGCCTT GCTCCTAATA GCTGCAGCCT GTCAGGGCCT GGCAGCAGTA ACCTCTCCTT
TCCTCTTCCC ACCATTCCCC TGCACTGCTT TCTGTACCGC ATCTCTTTTC AGAGTGATGT
TGCCCCAATT GCGGAGGCCA CTGTGCTGTT TATCCAGTGA AAGCTGTAGC ACAGCCAACC
CAAAGCGTCC CCAGTGAAAA CAACCTGGCT CCTTACAGCA CTTCCAGCCT CAGAGCAGTA
TTTGAAAAAT ATCATGAACA GCAAACACAG CAGTCTGTCT GTGGCTTTTA TATGTGTATA
TGGTGTGTGT GTATGTCCCT TCTCTTGAGC AAAATAACTT TTAGAATTAT AGAAAAAAAA

                                PmeI
                             ----------
TGTGCAACAT CAATGTGGAT CTGCTGTTTA AACTCATAAC AGAGAAAGTA GCTTGTTTCT
GGCTATAGGA GGAAAAGACG ATATTCCTTA GTAAAAATGG AAATCCACAT ATGGGGTTCT
TGTAAAAATG AAGATAGAAA ATTGCAAGTT TGGGGATCAA GTTCTGGTTC TATCATCCTT
TAACAGTATG ACCCTGGAAC CTTAATTGCT TTGAGTCTTT GTTACTTTAT CTATGAAATG
AAGTATTTAA AAAAACTCCA AAAATCTGTC CTGATGTACA CACAAGAGGT CAAATGAGAA
AATGAATGTG AAGATGCTTT ATAAACTATA CAGCATGGTA GGTGCAAATG TGACATGAAC
TTGTTTTGGA CACATTATAA AGTCACCCCC ACAAACTGTG ATTGTTCAAG ACTATGCAAA
GTCAGACACA GGAAAATAAG TAAAACAGAT GGAGGCATAA AGAGGGGGAA CTCAGAGAAA
ACAGTGAAGA ACAGGAATCA GGAAGACAAA GGAGAGGAAA GGTGGGGAGG AGAGGAGAAG
GAAAGGGGGA AGGGAATGGA GGAGAGGAGA ACAGCTGCTT CACAGAGCAT GGCCGGCAGC
CCAGTCCCAG CCTTTCTGCA TGTCCCTGAC TTCAGCCTCT GGCGAGGCAC AGGCTTACTC
TGTGCTTCCT GCTGTTACTC TTCTTATCCA TCCTTATTAT CAATACCTGT GGTCAACAAA
GTATTTGATA AAGGCATCCT CAAAGTCAGG TAACATCTGT ACGTTATAGA TTACAAAGTT
GAGTAATATC CAGAATTGGT AGTTTAACGT GATGACTTCT TAACAATTAT CACTGTTTCA
GGGAAGGGCA AAGGTGTGTG TGTGTGTGTG TTCATCTGTG TGTATCTGTG TATGTAATTG
TGGGTGTTTG TGTATATTTG TGAGGCTCTT TACTTGGCGG AGTTAAAAAG TATCTGCTCA
TCAAGGTTGA GATTAGCAAA GGAAGTGAAG ATTTTTCCAG AGCCCCTAAA ATGTGCCTTT
TGACCAACAC TGAGGACATC TTTATAACTG AGTATGTGCA ATAAATATGT CTTGGGACCT
GTGCCACAAA TTCCTCTCTA AATAGCCTTT ACCTCTCTGG AATAACCCTT TAGATGAGGA
AGAAAAGGGC TGTGATTTTA TAGCTTGTTA TGAAGCTGGA GTGAAGATGA TGCTTCAGTA
CTTACCCTAC AAAGATACCC CCAATCCCTC ACCCTAAAAT TACCATTGAA ATCATGTTCC
CTTTCTCATT CACTCTCAGT TTCCATGTCA GAAAATATAC CATTACCTCC CTGCACCCCT
TTCATCTCTC TCACTTTTCT CTTGCTTAGA TGGAAAGACA ACCCAGCAAT GCCTGCAGGG
                                >>............EXON 9 .............>
CTGATGTATG AAGGAGTTTC CCAAGAGCCC CTGAAATACT CCGGCGGGAG TGCAGCTCAG
>...........................EXON 9 ...........................>
AGCACAGTGC TTCATGCCTT TGATGAGTTC TTAGGCATTC GTCATAGCAA GGAAAGTGGT
>...........................EXON 9 ...........................>>
AAGTCAGACA TTTTGTTTTC CCTTGAGAGT AGAGGGAGGA AGAGGAGAGG TGTTTTTTTT
TTTTCCAATT GATAAAACCA AATATAAATT AAAATGTCAT GAAGTTTATA CTTCTCTAAG
TCAGCCAAGA AACTGCATGA CTGCCAATGT TTTTGTGTCA AGCCAATTAA TATTGGAATA
TCAGATGTCA GCTTGATCTT GGGTTTTACT TCCAAATCTT AAAATGTTGC TCTGTTTCCA
ACTGTTCACT ATCACTTTGG TTTGGATCTT TAGACACTAG CTTCCTTTTT CTGAAATGGG
```

Figure 15X

```
GGAGAGATGT GGAGTTTGAA GGCTATGAGT CTGGGCCAGC TGGAAACAGG TCTGGGATCT
TCCAAGAAAG TCCTTCCCCA CAAAATGGTG CAACTTCTAG CCAAATCTAT TTATACCAGC
AGAGGGATCT ATCACCCTGG AAGCTTGAAA TTGTTCATTT TCTTACCTGC CAGGATCAAG
TTAAGTTTTT AACAGTTGCA AAAAGACACT TCATACTATG GAGTTTTCAA GTTGGATTAG
AAGAAAAAGA ATCACCAGAA CTTAGTGTCG TAGATTCAAG TCACTTCTCT AAAACTGTCA
TAATTTTTCA CGGATTTTGG CATTTGGTGA CATTAATGGT TGATTTACTT ACCATGCATA
ATATTAAACC CATAACGAAT TTCCTATAAA TATCTATTGA TTTGATTTTT AAATCACTTG
GCTTCAAGAG GCTATTACTA AAACAGTGAC TCATTCTTTA TCTTTTTTGC CTTCACGGGC
TTTATATAAC TTTCTCCTTT TCTTGTGCTC CCTCCAAAAC AAAGCACTGA GAAAACAAAA
TTCACCAGAG TATTCAGCTA GTCAGTTCAA GGGTTTGTGT TCTACATTTG AAGATATTCC
TTATAGCAGC TACCAACGGG ATACTTTGTT TACATTTGTT GTGTAGTAAA TATTTATATA
TTGGCAAACA AATCTAGTTC CAACTCTGTC ATCTGAGATG TTCTTACTTT GTTTCCTCTT
CTCCATCTCC TGTCAACTGT TAGAAATATA CATTTGAGTA CGTGAAGTCT GCAAACAAAA
GGGCCAAGGT AGATTTGAGT TAGAACACCA GCAACAGTTT CTGGTGCATT CTTGTCTGAA
AAAGCAGAGA AGATTGGGCA CCGTGGGTCA TGCCTGTAAT CCCAAAATTT TGGAAGTCTG
AGGCAGGTGG ATCGCTTGAG CCCAGGAGTT CAAGACAAGC CTGGGCAACA TAGCAAGAAC
CCGTCTCTAC TAAAAGGAAT ACAAAAAAAT ATTAGCTGGG TGTGGTGGCG CACACCTGTA
GTTTCAGCTA CTCAGAAGAC TGAGGTGGGA GGATCACTTG AACTCAGGGG CAGAGGTGGC
AGTAAGCTGA GATCACACCA CTGCACTCCA GCCTGGGCAA CAGAGCAAGA TCTCATCTAG
AGAAAAAAAA AATAAAAAAG AAGAAGAAGC AGACGAGCTC TGCTATATTT CCATGTGGAG
CTATGACGTT ATGCTGTATT GTTTCTTTCA GGTGACTTTC TGTACAGAAT GAGGGATTAC
                                    >>..........EXON10 ..........>
ATGCCTCCTT CCCATAAGGC CTTCATAGAA GACATCCACT CAGCACCTTC CCTGAGGGAC
>...........................EXON 10 ............................>
TACATCCTGT CATCTGGACA GGACCACTTG CTGACAGCTT ATAACCAGTG TGTGCAGGCC
>...........................EXON 10 ............................>
CTGGCAGAGC TGCGGAGCTA TCACATCACC ATGGTCACCA AATACCTCAT CACAGCTGCA
>...........................EXON 10 ............................>
GCCAAGGCAA AGCATGGGAA GCCAAACCAT CTCCCAGGGC CTCCTCAGGC TTTAAAAGAC
>...........................EXON 10 ............................>

                                                              DrdI
                                                          ------------
AGGGGCACAG GTGGAACCGC AGTTATGAGC TTTCTTAAGA GTGTCAGGGA TAAGACCTTG
>...........................EXON  ............................>
GAGTCAATCC TTCACCCACG TGGTTAG
>..........EXON  ..........>>
```

Figure 15Y

```
wt hu ido2           >#1>         ATGGAGCCCCACAG ACCGAATGTGAAGACAGCAG TGCCATTGTCTTTGGAAAGC
hu ido2 Δ 3/4/6      >#1>     GGCTTATGGAGCCCCACAG ACCGAATGTGAAGACAGCAG TGCCATTGTCTTTGGAAAGC
hu ido2 Δ 8          >#1>     GGCTTATGGAGCCCCACAG ACCGAATGTGAAGACAGCAG TGCCATTGTCTTTGGAAAGC
hu ido2 Δ 6/8        >#1>     GGCTTATGGAGCCCCACAG ACCGAATGTGAAGACAGCAG TGCCATTGTCTTTGGAAAGC
hu ido2 Δ 4/5        >#1>     GGCTTATGGAGCCCCACAG ACCGAATGTGAAGACAGCAG TGCCATTGTCTTTGGAAAGC
hu ido2 R235W        >#1>     GGCTTATGGAGCCCCACAG ACCGAATGTGAAGACAGCAG TGCCATTGTCTTTGGAAAGC
hu ido2        Stop  >#1>        TATGGAGCCCCACAG ACCGAATGTGAAGACAGCAG TGCCATTGTCTTTGGAAAGC
                            ............................................................
                     # 1    CGGCTTATGGAGCCCCACAG ACCGAATGTGAAGACAGCAG TGCCATTGTCTTTGGAAAGC
                                 M  E  P  H  R   P  N  V  K  T  A  V   P  L  S  L  E  S
                            _____________________________Exon 1__________________________

wt hu ido2           #55    TATCACATATCTGAAGAGTA TGGCTTTCTTCTTCCAGATT CTCTGAAAGAACTTCCAGAT
hu ido2 Δ 3/4/6      #60    TATCACATATCTGAAGAGTA TGGCTTTCTTCTTCCAGATT CTCTGAAAGAACTTCCAGAT
hu ido2 Δ 6/8        #60    TATCACATATCTGAAGAGTA TGGCTTTCTTCTTCCAGATT CTCTGAAAGAACTTCCAGAT
hu ido2 Δ 8          #60    TATCACATATCTGAAGAGTA TGGCTTTCTTCTTCCAGATT CTCTGAAAGAACTTCCAGAT
hu ido2 Δ 4/5        #60    TATCACATATCTGAAGAGTA TGGCTTTCTTCTTCCAGATT CTCTGAAAGAACTTCCAGAT
hu ido2 R235W        #60    TATCACATATCTGAAGAGTA TGGCTTTCTTCTTCCAGATT CTCTGAAAGAACTTCCAGAT
hu ido2       Stop   #60    TATCACATATCTGAAGAGTA TGGCTTTCTTCTTCCAGATT CTCTGAAAGAACTTCCAGAT
                            ............................................................
                     #12    TATCACATATCTGAAGAGTA TGGCTTTCTTCTTCCAGATT CTCTGAAAGAACTTCCAGAT
                             Y  H  I  S  E  E  Y   G  F  L  L  P  D   S  L  K  E  L  P  D
                             ___________________________EXON1______________>|<_____Exon 2___

wt hu ido2           #115   CATTATAGGCCTTGGATGGA AATTGCCAACAAACTTCCTC AATTGATTGATGCTCACCAG
hu ido2 Δ 3/4/6      #120   CATTATAGGCCTTGGATGGA AATTGCCAACAAACTTCCTC AATTGATTGATGCTCACCAG
hu ido2 Δ 6/8        #120   CATTATAGGCCTTGGATGGA AATTGCCAACAAACTTCCTC AATTGATTGATGCTCACCAG
hu ido2 Δ 8          #120   CATTATAGGCCTTGGATGGA AATTGCCAACAAACTTCCTC AATTGATTGATGCTCACCAG
hu ido2 Δ 4/5        #120   CATTATAGGCCTTGGATGGA AATTGCCAACAAACTTCCTC AATTGATTGATGCTCACCAG
hu ido2 R235W        #120   CATTATAGGCCTTGGATGGA AATTGCCAACAAACTTCCTC AATTGATTGATGCTCACCAG
hu ido2 Stop         #120   CATTATAGGCCTTGGATGGA AATTGCCAACAAACTTCCTC AATTGATTGATGCTCACCAG
                            ............................................................
                     #72    CATTATAGGCCTTGGATGGA AATTGCCAACAAACTTCCTC AATTGATTGATGCTCACCAG
                             H  Y  R  P  W  M  E   I  A  N  K  L  P   Q  L  I  D  A  H  Q
                            _______________________Exon 2_______________________________
```

Figure 16A

```
wt hu ido2             #175   CTTCAAGCTCATGTGGACAA GATGCCCCTGCTGAGCTGCC AGTTCCTGAAGGGTCACCGG
hu ido2 Δ 3/4/6        #180   CTTCAAGCTCATGTGGACAA G::::::::::::::::::: ::::::::::::::::::::
hu ido2 Δ 6/8          #180   CTTCAAGCTCATGTGGACAA GATGCCCCTGCTGAGCTGCC AGTTCCTGAAGGGTCACCGG
hu ido2 Δ 8            #180   CTTCAAGCTCATGTGGACAA GATGCCCCTGCTGAGCTGCC AGTTCCTGAAGGGTCACCGG
hu ido2 Δ 4/5          #180   CTTCAAGCTCATGTGGACAA GATGCCCCTGCTGAGCTGCC AGTTCCTGAAGGGTCACCGG
234-M13R-pUC.ab1       #180   CTTCAAGCTCATGTGGACAA GATGCCCCTGCTGAGCTGCC AGTTCCTGAAGGGTCACCGG
hu ido2 R235 Stop      #176   CTTCAAGCTCATGTGGACAA GATGCCCCTGCTGAGCTGCC AGTTCCTGAAGGGTCACCGG
                              ............................................................
                       #132   CTTCAAGCTCATGTGGACAA GATGCCCCTGCTGAGCTGCC AGTTCCTGAAGGGTCACCGG
                               L  Q  A  H  V  DK  M  P  L  L  S  C  Q  F  L  K  G  H  R
                              ______Exon 2______>|<_______Exon 3___________________________
                                                                          BstEII

Wt hu ido2             #235   GAGCAGCGCCTGGCCCACCT GGTCCTGAGCTTCCTCACCA TGGGTTATGTCTGGCAGGAA
hu ido2 Δ 3/4/6        #240   :::::::::::::::::::: :::::::::::::::::::: ::::::::::::::::::::
hu ido2 Δ 6/8          #240   GAGCAGCGCCTGGCCCACCT GGTCCTGAGCTTCCTCACCA TGGGTTATGTCTGGCAGGAA
hu ido2 Δ 8            #240   GAGCAGCGCCTGGCCCACCT GGTCCTGAGCTTCCTCACCA TGGGTTATGTCTGGCAGGAA
hu ido2 Δ 4/5          #240   GAGCAGCGCCTGGCCCACCT GGTCCTGAGCTTCCTCACCA TGGGTTATGTCTGGCAGGAA
234-M13R-pUC.ab1       #240   GAGCAGCGCCTGGCCCACCT GGTCCTGAGCTTCCTCACCA TGGGTTATGTCTGGCAGGAA
hu ido2 R235 Stop      #236   GAGCAGCGCCTGGCCCACCT GGTCCTGAGCTTCCTCACCA TGGGTTATGTCTGGCAGGAA
                              ............................................................
                       #192   GAGCAGCGCCTGGCCCACCT GGTCCTGAGCTTCCTCACCA TGGGTTATGTCTGGCAGGAA
                               E  Q  R  L  A  H  L  V  L  S  F  L  T  M  G  Y  V  W  Q  E
                                                 SexAI
                              ______________________________Exon 3_________________________

wt hu ido2             #295   GGAGAGGCGCAGCCTGCAGA GGTCCTGCCAAGGAATCTTG CCCTTCCATTTGTCGAAGTC
hu ido2 Δ 3/4/6        #300   :::::::::::::::::::: :::::::::::::::::::: ::::::::::::::::::::
hu ido2 Δ 6/8          #300   GGAGAGGCGCAGCCTGCAGA GGTCCTGCCAAGGAATCTTG CCCTTCCATTTGTCGAAGTC
hu ido2 Δ 8            #300   GGAGAGGCGCAGCCTGCAGA GGTCCTGCCAAGGAATCTTG CCCTTCCATTTGTCGAAGTC
hu ido2 Δ 4/5          #300   GGAGAGGCGCAGCCTGCAGA G::::::::::::::::::: ::::::::::::::::::::
hu ido2 R235           #296   GGAGAGGCGCAGCCTGCAGA GGTCCTGCCAAGGAATCTTG CCCTTCCATTTGTCGAAGTC
hu ido2 Stop           #296   GGAGAGGCGCAGCCTGCAGA GGTCCTGCCAAGGAATCTTG CCCTTCCATTTGTCGAAGTC
                              ............................................................
                       #252   GGAGAGGCGCAGCCTGCAGA GGTCCTGCCAAGGAATCTTG CCCTTCCATTTGTCGAAGTC
                               G  E  A  Q  P  A  E  V  L  P  R  N  L  A  L  P  F  V  E  V
                              _______Exon 3________>|<_____________Exon 4__________________
```

Figure 16B

```
wt hu ido2             #355   TCCAGGAACTTGGGGCTCCC TCCTATCCTGGTCCACTCAG ACTTGGTGCTGACGAACTGG
hu ido2 Δ 3/4/6        #360   :::::::::::::::::::: :::::::::::::::::::: ::::::::::::::::::::
hu ido2 Δ 6/8          #360   TCCAGGAACTTGGGGCTCCC TCCTATCCTGGTCCACTCAG ACTTGGTGCTGACGAACTGG
hu ido2 Δ 8            #360   TCCAGGAACTTGGGGCTCCC TCCTATCCTGGTCCACTCAG ACTTGGTGCTGACGAACTGG
hu ido2 Δ 4/5          #360   :::::::::::::::::::: :::::::::::::::::::: ::::::::::::::::::::
hu ido2 R235W          #360   TCCAGGAACTTGGGGCTCCC TCCTATCCTGGTCCACTCAG ACTTGGTGCTGACGAACTGG
hu ido2        Stop    #360   TCCAGGAACTTGGGGCTCCC TCCTGTCCTGGTCCACTCAG ACTTGGTGCTGACGAACTGG
                              ..............................................................
                       #312   TCCAGGAACTTGGGGCTCCC TCCTATCCTGGTCCACTCAG ACTTGGTGCTGACGAACTGG
                               S  R  N  L  G  L  P   P  I  L  V  H  S   D  L  V  L  T  N  W
                              ______Bst X I________________Exon 4_____________________________

wt hu ido2             #415   ACCAAAAAAGATCCAGACGG ATTCCTGGAAATTGGGAACC TGGAGACCATCATCTCATTT
hu ido2 Δ 3/4/6        #420   :::::::::::::::::::: ATTCCTGGAAATTG:::::: ::::::::::::::::::::
hu ido2 Δ 6/8          #420   ACCAAAAAAGATCCAGACGG ATTCCTGGAAATTG:::::: ::::::::::::::::::::
hu ido2 Δ 8            #420   ACCAAAAAAGATCCAGACGG ATTCCTGGAAATTGGGAACC TGGAGACCATCATCTCATTT
hu ido2 Δ 4/5          #420   :::::::::::::::::::: ::::::::::::::GGAACC TGGAGACCATCATCTCATTT
hu ido2 R235W          #420   ACCAAAAAAGATCCAGACGG ATTCCTGGAAATTGGGAACC TGGAGACCATCATCTCATTT
hu ido2 Stop           #420   ACCAAAAAAGATCCAGACGG ATTCCTGGAAATTGGGAACC TGGAGACCATCATCTCATTT
                              ..............................................................
                       #372   ACCAAAAAAGATCCAGACGG ATTCCTGGAAATTGGGAACC TGGAGACCATCATCTCATTT
                               T  K  K  D  P  D  G   F  L  E  I  G  N   L  E  T  I  I  S  F
                              __Exon 4____________>|<__Exon 5__>|<____________Exon 6__________

wt hu ido2             #475   CCTGGGGGAGAGAGCCTGCA TGGTTTTATACTGGTGACTG CTTTGGTAGAGAAAGAAGCA
hu ido2 Δ 3/4/6        #480   :::::::::::::::::::: :::::::::::::::::::: ::::::::::::::::::::
hu ido2 Δ 6/8          #480   :::::::::::::::::::: :::::::::::::::::::: ::::::::::::::::::::
hu ido2 Δ 8            #480   CCTGGGGGAGAGAGCCTGCA TGGTTTTATACTGGTGACTG CTTTGGTAGAGAAAGAAGCA
hu ido2 Δ 4/5          #480   CCTGGGGGAGAGAGCCTGCA TGGTTTTATACTGGTGACTG CTTTGGTAGAGAAAGAAGCA
hu ido2 R235W          #480   CCTGGGGGAGAGAGCCTGCA TGGTTTTATACTGGTGACTG CTTTGGTAGAGAAAGAAGCA
hu ido2 Stop           #480   CCTGGGGGAGAGAGCCTGCA TGGTTTTATACTGGTGACTG CTTTGGTAGAGAAAGAAGCA
                              ..............................................................
                       #432   CCTGGGGGAGAGAGCCTGCA TGGTTTTATACTGGTGACTG CTTTGGTAGAGAAAGAAGCA
                               P  G  G  E  S  L  H   G  F  I  L  V  T   A  L  V  E  K  E  A
                              ___________________________________Exon 6_______________________
```

Figure 16C

```
wt hu ido2          #535   GTGCCTGGGATAAAGGCTCT TGTTCAGGCCACGAATGCTA TCTTGCAGCCCAACCAGGAG
hu ido2 Δ 3/4/6     #540   :::::::::::::GGCTCT TGTTCAGGCCACGAATGCTA TCTTGCAGCCCAACCAGGAG
hu ido2 Δ 6/8       #540   :::::::::::::GGCTCT TGTTCAGGCCACGAATGCTA TCTTGCAGCCCAACCAGGAG
hu ido2 Δ 8         #540   GTGCCTGGGATAAAGGCTCT TGTTCAGGCCACGAATGCTA TCTTGCAGCCCAACCAGGAG
hu ido2 Δ 4/5       #540   GTGCCTGGGATAAAGGCTCT TGTTCAGGCCACGAATGCTA TCTTGCAGCCCAACCAGGAG
hu ido2 R235W       #540   GTGCCTGGGATAAAGGCTCT TGTTCAGGCCACGAATGCTA TCTTGCAGCCCAACCAGGAG
hu ido2 Stop        #540   GTGCCTGGGATAAAGGCTCT TGTTCAGGCCACGAATGCTA TCTTGCAGCCCAACCAGGAG
                           ..............................................................
                    #492   GTGCCTGGGATAAAGGCTCT TGTTCAGGCCACGAATGCTA TCTTGCAGCCCAACCAGGAG
                            V  P  G  I  K  A  L   V  Q  A  T  N  A   I  L  Q  P  N  Q  E
                            ___Exon 6___>|<________Exon 7____Bsm I______________________

wt hu ido2          #595   GCCCTGCTCCAAGCCCTGCA GCGACTGAGACTGTCTATTC AGGACATCACCAAAACCTTA
hu ido2 Δ 3/4/6     #600   GCCCTGCTCCAAGCCCTGCA GCGACTGAGACTGTCTATTC AGGACATCACCAAAACCTTA
hu ido2 Δ 6/8       #600   GCCCTGCTCCAAGCCCTGCA GCGACTGAGACTGTCTATTC AGGACATCACCAAAACCTTA
hu ido2 Δ 8         #600   GCCCTGCTCCAAGCCCTGCA GCGACTGAGACTGTCTATTC AGGACATCACCAAAACCTTA
hu ido2 Δ 4/5       #600   GCCCTGCTCCAAGCCCTGCA GCGACTGAGACTGTCTATTC AGGACATCACCAAAACCTTA
hu ido2 R235        #600   GCCCTGCTCCAAGCCCTGCA GCGACTGAGACTGTCTATTC AGGACATCACCAAAACCTTA
hu ido2       Stop  #600   GCCCTGCTCCAAGCCCTGCA GCGACTGAGACTGTCTATTC AGGACATCACCAAAACCTTA
                           ..............................................................
                    #552   GCCCTGCTCCAAGCCCTGCA GCGACTGAGACTGTCTATTC AGGACATCACCAAAACCTTA
                            A  L  L  Q  A  L  Q   R  L  R  L  S  I   Q  D  I  T  K  T  L
                           ___________________________Exon 7____________________________

wt hu ido2          #655   GGACAGATGCATGATTATGT AGATCCAGACATATTTTATG CAGGCATCCGGATCTTTCTC
hu ido2 Δ 3/4/6     #655   GGACAGATGCATGATTATGT AGATCCAGACATATTTTATG CAGGCATCCGGATCTTTCTC
hu ido2 Δ 6/8       #655   GGACAGATGCATG::::::: :::::::::::::::::::: ::::::::::::::::::::
hu ido2 Δ 8         #655   GGACAGATGCATG::::::: :::::::::::::::::::: ::::::::::::::::::::
hu ido2 Δ 4/5       #655   GGACAGATGCATGATTATGT AGATCCAGACATATTTTATG CAGGCATCCGGATCTTTCTC
hu ido2 R235W       #655   GGACAGATGCATGATTATGT AGATCCAGACATATTTTATG CAGGCATCTGGATCTTTCTC
hu ido2       Stop  #655   GGACAGATGCATGATTATGT AGATCCAGACATATTTTATG CAGGCATCCGGATCTTTCTC
Alternative Exon 8                      GACACGG GAGTTGAGGCATTACCTTGG ACGTGGAGACCAGGCCCTCACCAGACACTG
                           ..............................................................
                    #612   GGACAGATGCATGATTATGT AGATCCAGACATATTTTATG CAGGCATCCGGATCTTTCTC
                            G  Q  M  H  D  Y  V   D  P  D  I  F  Y   A  G  I RW I  F  L
                           ____________>|<_______________Exon 8_________________________
```

Figure 16D

```
wt hu ido2          #715               TCTGGATGGAAAGACAACCC AGCAATGCCTGCAGGGCTGA TGTATGAAGGAGTTTCCCAA
hu ido2 Δ 3/4/6     #715               TCTGGATGGAAAGACAACCC AGCAATGCCTGCAGGGCTGA TGTATGAAGGAGTTTCCCAA
hu ido2 Δ 6/8       #715               :::::ATGGAAAGACAACCC AGCAATGCCTGCAGGGCTGA TGTATGAAGGAGTTTCCCAA
hu ido2 Δ 8         #715               :::::ATGGAAAGACAACCC AGCAATGCCTGCAGGGCTGA TGTATGAAGGAGTTTCCCAA
hu ido2 Δ 4/5       #715               TCTGGATGGAAAGACAACCC AGCAATGCCTGCAGGGCTGA TGTATGAAGGAGTTTCCCAA
hu ido2 R235        #715               TCTGGATGGAAAGACAACCC AGCAATGCCTGCAGGGCTGA TGTATGAAGGAGTTTCCCAA
hu ido2       Stop  #715               :::::ATGGAAAGACAACCC AGCAATGCCTGCAGGGCTGA TGTATGAAGGAGTTTCCCAA
Alternative Exon 8                    Exon 8|9 junction
AACTTGCCAGCACCTTGATCTTGGACTTCCCAGC CTCCAGAACTATGGAAAGACAACCC AGCAATGCCTGCAGGGCTGA TGTATGAAGGAGTTTCCCAA
                                       ............................................................
                    #672               TCTGGATGGAAAGACAACCC AGCAATGCCTGCAGGGCTGA TGTATGAAGGAGTTTCCCAA
                                        S  G  W  K  D  N  P   A  M  P  A  G  L  M   Y  E  G  V  S  Q
                                       _Exon8>|<__________Exon 9________________________

wt hu ido2          #775               GAGCCCCTGAAATACTCCGG CGGGAGTGCAGCTCAGAGCA CAGTGCTTCATGCCTTTGAT
hu ido2 Δ 3/4/6     #775               GAGCCCCTGAAATACTCCGG CGGGAGTGCAGCTCAGAGCA CAGTGCTTCATGCCTTTGAT
hu ido2 Δ6/8        #775               GAGCCCCTGAAATACTCCGG CGGGAGTGCAGCTCAGAGCA CAGTGCTTCATGCCTTTGAT
hu ido2 Δ8          #775               GAGCCCCTGAAATACTCCGG CGGGAGTGCAGCTCAGAGCA CAGTGCTTCATGCCTTTGAT
hu ido2 Δ4/5        #775               GAGCCCCTGAAATACTCCGG CGGGAGTGCAGCTCAGAGCA CAGTGCTTCATGCCTTTGAT
hu ido2 R235        #775               GAGCCCCTGAAATACTCCGG CGGGAGTGCAGCTCAGAGCA CAGTGCTTCATGCCTTTGAT
hu ido2       Stop  #775               GAGCCCCTGAAATACTCCGG CGGGAGTGCAGCTCAGAGCA CAGTGCTTCATGCCTTTGAT
                                       ............................................................
                    #732               GAGCCCCTGAAATACTCCGG CGGGAGTGCAGCTCAGAGCA CAGTGCTTCATGCCTTTGAT
                                        E  P  L  K  Y  S  G   G  S  A  A  Q  S  T   V  L  H  A  F  D
                                       ________________Exon 9____________________
wt hu ido2          #835               GAGTTCTTAGGCATTCGTCA TAGCAAGGAAAGTGGTGACT TTCTGTACAGAATGAGGGAT
hu ido2 Δ 3/4/6     #835               GAGTTCTTAGGCATTCGTCA TAGCAAGGAAAGTGGTGACT TTCTGTACAGAATGAGGGAT
hu ido2 Δ 6/8       #835               GAGTTCTTAGGCATTCGTCA TAGCAAGGAAAGTGGTGACT TTCTGTACAGAATGAGGGAT
hu ido2 Δ 8         #835               GAGTTCTTAGGCATTCGTCA TAGCAAGGAAAGTGGTGACT TTCTGTACAGAATGAGGGAT
hu ido2 Δ 4/5       #835               GAGTTCTTAGGCATTCGTCA TAGCAAGGAAAGTGGTGACT TTCTGTACAGAATGAGGGAT
hu ido2 R235        #835               GAGTTCTTAGGCATTCGTCA TAGCAAGGAAAGTGGTGACT TTCTGTACAGAATGAGGGAT
hu ido2       Stop  #835               GAGTTCTTAGGCATTCGTCA TAGCAAGGAAAGTGGTGACT TTCTGTACAGAATGAGGGAT
hu ido2 R235 Stop   #835               GAGTTCTTAGGCATTCGTCA TAGCAAGGAAAGTGGTGACT TTCTGTACAGAATGAGGGAT
                                       ............................................................
                    #792               GAGTTCTTAGGCATTCGTCA TAGCAAGGAAAGTGGTGACT TTCTGTACAGAATGAGGGAT
                                        E  F  L  G  I  R  H   S  K  E  S  G  D  F   L  Y  R  M  R  D
                                       _______Bsm I___Exon 9____>|<__________Bsr G I   Exon 10_
```

Figure 16E

```
wt hu ido2          #895    TACATGCCTCCTTCCCATAA GGCCTTCATAGAAGACATCC ACTCAGCACCTTCCCTGAGG
hu ido2 Δ 3/4/6     #895    TACATGCCTCCTTCCCATAA GGCCTTCATAGAAGACATCC ACTCAGCACCTTCCCTGAGG
hu ido2 Δ 6/8       #895    TACATGCCTCCTTCCCATAA GGCCTTCATAGAAGACATCC ACTCAGCACCTTCCCTGAGG
hu ido2 Δ 8         #895    TACATGCCTCCTTCCCATAA GGCCTTCATAGAAGACATCC ACTCAGCACCTTCCCTGAGG
hu ido2 Δ 4/5       #895    TACATGCCTCCTTCCCATAA GGCCTTCATAGAAGACATCC ACTCAGCACCTTCCCTGAGG
hu ido2 R235        #895    TACATGCCTCCTTCCCATAA GGCCTTCATAGAAGACATCC ACTCAGCACCTTCCCTGAGG
hu ido2       Stop  #895    TACATGCCTCCTTCCCATAA GGCCTTCATAGAAGACATCC ACTCAGCACCTTCCCTGAGG
                            ............................................................
                    #852    TACATGCCTCCTTCCCATAA GGCCTTCATAGAAGACATCC ACTCAGCACCTTCCCTGAGG
                             Y  M  P  P  S  H  K   A  F  I  E  D  I   H  S  A  P  S  L  R
                                                        Exon 10

wt hu ido2          #955    GACTACATCCTGTCATCTGG ACAGGACCACTTGCTGACAG CTTATAACCAGTGTGTGCAG
hu ido2 Δ 3/4/6     #955    GACTACATCCTGTCCTCTGG ACAGGACCACTTGCTGACAG CTTATAACCAGTGTGTGCAG
hu ido2 Δ 6/8       #955    GACTACATCCTGTCCTCTGG ACAGGACCACTTGCTGACAG CTTATAACCAGTGTGTGCAG
hu ido2 Δ 8         #955    GACTACATCCTGTCCTCTGG ACAGGACCACTTGCTGACAG CTTATAACCAGTGTGTGCAG
hu ido2 Δ 4/6       #955    GACTACATCCTGTCCTCTGG ACAGGACCACTTGCTGACAG CTTATAACCAGTGTGTGCAG
hu ido2 R235W       #955    GACTACATCCTGTCCTCTGG ACAGGACCACTTGCTGACAG CTTATAACCAGTGTGTGCAG
hu ido2 stop        #955    GACTACATCCTGTCCTCTGG ACAGGACCACTTGCTGACAG CTTATAACCAGTGTGTGCAG
                            ............................................................
                    #912    GACTACATCCTGTCCTCTGG ACAGGACCACTTGCTGACAG CTTATAACCAGTGTGTGCAG
                             D  Y  I  L  S  S  G   Q  D  H  L  L  T  A   Y  N  Q  C  V  Q
                                                        Exon 10

wt hu ido2          #1015   GCCCTGGCAGAGCTGCGGAG CTATCACATCACCATGGTCA CCAAATACCTCATCACAGCT
hu ido2 Δ 3/4/6     #1015   GCCCTGGCAGAGCTGCGGAG CTATCACATCACCATGGTCA CCAAATACCTCATCACAGCT
hu ido2 Δ 6/8       #1015   GCCCTGGCAGAGCTGCGGAG CTATCACATCACCATGGTCA CCAAATACCTCATCACAGCT
hu ido2 Δ 8         #1015   GCCCTGGCAGAGCTGCGGAG CTATCACATCACCATGGTCA CCAAATACCTCATCACAGCT
hu ido2 Δ 4/5       #1015   GCCCTGGCAGAGCTGCGGAG CTATCACATCACCATGGTCA CCAAATACCTCATCACAGCT
hu ido2 R235W       #1015   GCCCTGGCAGAGCTGCGGAG CTATCACATCACCATGGTCA CCAAATACCTCATCACAGCT
hu ido2 stop        #1015   GCCCTGGCAGAGCTGCGGAG CTAACACATCACCATGGTCA CCAAATACCTCATCACAGCT
                            ............................................................
                    #972    GCCCTGGCAGAGCTGCGGAG CTATCACATCACCATGGTCA CCAAATACCTCATCACAGCT
                             A  L  A  E  L  R  S   YX H  I  T  M  V  T   K  Y  L  I  T  A
                                                 Exon 10           BstEII
```

Figure 16F

```
wt hu ido2              #1075      GCAGCCAAGGCAAAGCATGG GAAGCCAAACCATCTCCCAG GGCCTCCTCAGGCTTTAAAA
hu ido2 Δ 3/4/6         #1075      GCAGCCAAGGCAAAGCATGG GAAGCCAAACCATCTCCCAG GGCCTCCTCAGGCTTTAAAA
hu ido2 Δ 6/8           #1075      GCAGCCAAGGCAAAGCATGG GAAGCCAAACCATCTCCCAG GGCCTCCTCAGGCTTTAAAA
hu ido2 Δ 8             #1075      GCAGCCAAGGCAAAGCATGG GAAGCCAAACCATCTCCCAG GGCCTCCTCAGGCTTTAAAA
hu ido2 Δ 4/5           #1075      GCAGCCAAGGCAAAGCATGG GAAGCCAAACCATCTCCCAG GGCCTCCTCAGGCTTTAAAA
hu ido2 R235W           #1075      GCAGCCAAGGCAAAGCATGG GAAGCCAAACCATCTCCCAG GGCCTCCTCAGGCTTTAAAA
hu ido2 Stop            #1075      GCAGCCAAGGCAAAGCATGG GAAGCCAAACCATCTCCCAG GGCCTCCTCAGGCTTTAAAA
                                   ............................................................
                        #1032      GCAGCCAAGGCAAAGCATGG GAAGCCAAACCATCTCCCAG GGCCTCCTCAGGCTTTAAAA
                                    A  A  K  A  K  H  G   K  P  N  H  L  P  G   P  P  Q  A  L  K
                                   ______________________________Exon 10______BSE R I_________

wt hu ido2              #1135      GACAGGGGCACAGGTGGAAC CGCAGTTATGAGCTTTCTTA AGAGTGTCAGGGATAAGACC
hu ido2 Δ 3/4/6         #1135      GACAGGGGCACAGGTGGAAC CGCAGTTATGAGCTTTCTTA AGAGTGTCAGGGATAAGACC
hu ido2 Δ 6/8           #1135      GACAGGGGCACAGGTGGAAC CGCAGTTATGAGCTTTCTTA AGAGTGTCAGGGATAAGACC
hu ido2 Δ 8             #1135      GACAGGGGCACAGGTGGAAC CGCAGTTATGAGCTTTCTTA AGAGTGTCAGGGATAAGACC
hu ido2 Δ 4/5           #1135      GACAGGGGCACAGGTGGAAC CGCAGTTATGAGCTTTCTTA AGAGTGTCAGGGATAAGACC
hu ido2 R235W           #1135      GACAGGGGCACAGGTGGAAC CGCAGTTATGAGCTTTCTTA AGAGTGTCAGGGATAAGACC
hu ido2 Stop            #1135      GACAGGGGCACAGGTGGAAC CGCAGTTATGAGCTTTCTTA AGAGTGTCAGGGATAAGACC
                                   ............................................................
                        #1092      GACAGGGGCACAGGTGGAAC CGCAGTTATGAGCTTTCTTA AGAGTGTCAGGGATAAGACC
                                    D  R  G  T  G  G  T   A  V  M  S  F  L  K   S  V  R  D  K  T
                                   ______________________________Exon 10_______________________

wt hu ido2              #1195      TTGGAGTCAATCCTTCACCC ACGTGGTTAGGAT
hu ido2 Δ 3/4/6         #1195      TTGGAGTCAATCCTTCACCC ACGTGGTTAG
hu ido2 Δ 6/8 (C155)    #1195      TTGGAGTCAATCCTTCACCC ACGTGGTTAG
hu ido2 Δ 8             #1195      TTGGAGTCAATCCTTCACCC ACGTGGTTAG
hu ido2 Δ 4/5           #1195      TTGGAGTCAATCCTTCACCC ACGTGGTTAG
hu ido2 R235W           #1195      TTGGAGTCAATCCTTCACCC ACGTGGTTAG
hu ido2 Stop            #1195      TTGGAGTCAATCCTTCACCC ACGTGGTTAG
                                   ............................................................
                        #1152      TTGGAGTCAATCCTTCACCC ACGTGGTTAGGAT
                                    L  E  S  I  L  H  P   R  G
                                   __________Exon 10_______
```

Figure 16G

| Position | Target sequences |
|---|---|
| 58 | AATGTGAAGACAGCAGTGCCATT |
| 64 | AAGACAGCAGTGCCATTGTCTTT |
| 194 | AATTGATTGATGCTCACCAGCTT |
| 490 | AACCTGGAGACCATCATCTCATT |
| 687 | AACCTTAGGACAGATGCATGATT |
| 800 | AAGGAGTTTCCCAAGAGCCCCTT |
| 924 | AATGAGGGATTACATGCCTCCTT |
| 1213 | AAGAGTGTCAGGGATAAGACCTT |

| Position | Sequence |
|---|---|
| 58 | 5′UGUGAAGACAGCAGUGCCAUU<br>UUACACUUCUGUCGUCACGGA 5′ |
| 64 | 5′GACAGCAGUGCCAUUGUCUUU<br>UUCUGUCGUCACGGUAACAGA 5′ |
| 194 | 5′UUGAUUGAUGCUCACCAGCUU<br>UUAACUAACUACGAGUGGUCG 5′ |
| 490 | 5′CCUGGAGACCAUCAUCUCAUU<br>UUGGACCUCUGGUAGUACAGU 5′ |
| 687 | 5′CCUUAGGACAGAUGCAUGAUU<br>UUGGAAGCCUGUCUACGUACU 5′ |
| 800 | 5′GGAGUUUCCCAAGAGCCCCUU<br>UUCCUCAAAGGGUUCUCGGGG 5′ |
| 924 | 5′UGAGGGAUUACAUGCCUCCUU<br>UUACUCCCUAAUGUACGGAGG 5′ |
| 1213 | 5′GAGUGUCAGGGAUAAGACCUU<br>UUCUCACAGUCCCUAUUCUGG 5′ |
| 183 | 5′CAAACUUCCUCAAUUGAUUGAUGCT<br>UUGUUUGAAGGAGUUAACUAACUACGA 5′ |
| 73 | 5′GUGCCAUUGUCUUUGGAAAGCUATC<br>GUCACGGUAACAGAAACCUUUCGAUAG 5′ |
| 1215 | 5′GAGUGUCAGGGAUAAGACCUUGGAG<br>UUCUCACAGUCCCUAUUCUGGAACCUC 5′ |
| 897 | 5′CAAGGAAAGUGGUGACUUUCUGUAC<br>UCGUUCCUUUCACCACUGAAAGACAUG 5′ |
| 841 | 5′GCAGCUCAGAGCACAGUGCUUCATG<br>CACGUCGAGUCUCGUGUCACGAAGUAC 5′ |
| 1128 | 5′GCAUGGGAAGCCAAACCAUCUCCCA<br>UUCGUACCCUUCGGUUUGGUAGAGGGU 5′ |
| 561 | 5′AGAGAAAGAAGCAGUGCCUGGGATA<br>CAUCUCUUUCUUCGUCACGGACCCUAU 5′ |
| 698 | 5′CCUUAGGACAGAUGCAUGAUUAUGT<br>UUGGAAUCCUGUCUACGUACUAAUACA 5′ |

Figure 20A

| Position | Sequence |
|---|---|
| 311 | 5′AAGGAACCCAGAAGGACCGUU<br>UUUUCCUUGGGUCUUCCUGGC 5′ |
| 418 | 5′CCUGGAAACCAUCAUCUCAUU<br>UUGGACCUUUGGUAGUAGUGU 5′ |
| 451 | 5′UGAGGGACUACAUGCCGCCUU<br>UUACUCCCUGAUGUACGGCGG 5′ |
| 885 | 5′AAGGUGCUGCCAAGAUCUCUU<br>UUUUCCACGACGGUUCUAGAG 5′ |
| 427 | 5′CCAGAAGGACCGUUGGAAAUCAGTA<br>UGGGUCUUCCUGGCAACCUUUAGUCAU 5′ |
| 783 | 5′GAAGUACUCUGGAGGAAGUGCAGCC<br>GACUUCAUGAGACCUCCUUCACGUCGG 5′ |
| 858 | 5′CAAGGAAAGUGUUGGCUUUCUACAC<br>ACGUUCCUUUCACAACCGAAAGAUGUG 5′ |
| 272 | 5′CCAUGGGAUUCGUCUGGCAGGAGGG<br>GUGGUACCCUAAGCAGACCGUCCUCCC 5′ |
| 1145 | 5′GUACUGCCAUGCUGAGCUUCUUGAA<br>CCCAUGACGGUACGACUCGAAGAACUU 5′ |
| 756 | 5′CUAUGAAGGUGCUGCCACAGAGCCT<br>CAGAUACUUCCACGACGGUGUCUCGGA 5′ |
| 1172 | 5′GUGUCAGGGAGAAGACCAUGGAGGC<br>CUCACAGUCCCUCUUCUGGUACCUCCG 5′ |
| 14 | 5′GUCAGAGCAUGACGCUGGAGGUGCC<br>UUCAGUCUCGUACUGCGACCUCCACGG 5′ |

Figure 20B

First round of EP

Screening Strategy:
5' probe: SpeI digestion for genomic DNA
wildtype allele 17.0 kb
recombinant allele 12.0 kb
3' probe: SpeI digestion for genomic DNA
wildtype allele 17.0 kb
recombinant allele: 4.7 kb
Neo probe: HindIII digestion for genomic DNA
recombinant allele: 7.5 kb

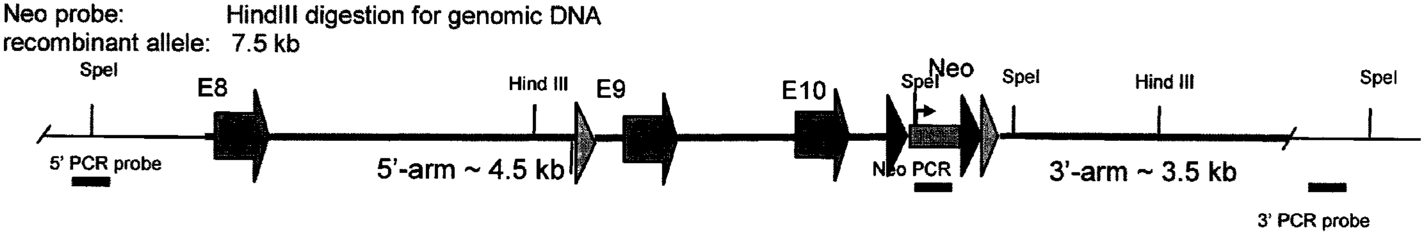

Second round of

FLP EP

Screening Strategy:
PCR with LoxP primers:
wildtype allele 3.8 kb
recombinant allele 1.8 kb

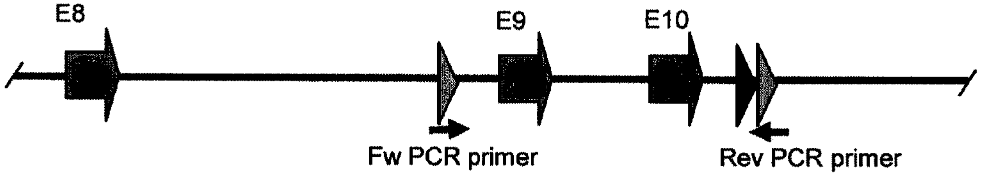

Figure 22

```
   1 AAGCTTTACT CGTAAAGCGA GTTGAAGGAT CATATTTAGT TGCGTTTATG
  51 AGATAAGATT GAAAGCACGT GTAAAATGTT TCCCGCGCGT TGGCACAACT
 101 ATTTACAATG CGGCCAAGTT ATAAAAGATT CTAATCTGAT ATGTTTTAAA
 151 ACACCTTTGC GGCCCGAGTT GTTTGCGTAC GTGACTAGCG AAGAAGATGT
 201 GTGGACCGCA GAACAGATAG TAAAACAAAA CCCTAGTATT GGAGCAATAA
 251 TCGATTTAAC CAACACGTCT AAATATTATG ATGGTGTGCA TTTTTTGCGG
 301 GCGGGCCTGT TATACAAAAA AATTCAAGTA CCTGGCCAGA CTTTGCCGCC
 351 TGAAAGCATA GTTCAAGAAT TTATTGACAC GGTAAAAGAA TTTACAGAAA
 401 AGTGTCCCGG CATGTTGGTG GGCGTGCACT GCACACACGG TATTAATCGC
 451 ACCGGTTACA TGGTGTGCAG ATATTTAATG CACACCCTGG GTATTGCGCC
 501 GCAGGAAGCC ATAGATAGAT TCGAAAAAGC CAGAGGTCAC AAAATTGAAA
 551 GACAAAATTA CGTTCAAGAT TTATTAATTT AATTAATATT ATTTGCATTC
 601 TTTAACAAAT ACTTTATCCT ATTTTCAAAT TGTTGCGCTT CTTCCAGCGA
 651 ACCAAAACTA TGCTTCGCTT GCTCCGTTTA GCTTGTAGCC GATCAGTGGC
 701 GTTGTTCCAA TCGACGGTAG GATTAGGCCG GATATTCTCC ACCACAATGT
 751 TGGCAACGTT GATGTTACGT TTATGCTTTT GGTTTTCCAC GTACGTCTTT
 801 TGGCCGGTAA TAGCCGTAAA CGTAGTGCCG TCGCGCGTCA CGCACAACAC
 851 CGGATGTTTG CGCTTGTCCG CGGGGTATTG AACCGCGCGA TCCGACAAAT
 901 CCACCACTTT GGCAACTAAA TCGGTGACCT GCGCGTCTTT TTCTGCATT
 951 ATTTCGTCTT TCTTTTGCAT GGTTTCCTGG AAGCCGGTGT ACATGCGGTT
1001 TAGATCAGTC ATGACGCGCG TGACCTGCAA ATCTTTGGCC TCGATCTGCT
1051 TGTCCTTGAT GGCAACGATG CGTTCAATAA ACTCTTGTTT TTTAACAAGT
1101 TCCTCGGTTT TTTGCGCCAC CACCGCTTGC AGCGCGTTTG TGTGCTCGGT
1151 GAATGTCGCA ATCAGCTTAG TCACCAACTG TTTGCTCTCC TCCTCCCGTT
1201 GTTTGATCGC GGGATCGTAC TTGCCGGTGC AGAGCACTTG AGGAATTACT
1251 TCTTCTAAAA GCCATTCTTG TAATTCTATG GCGTAAGGCA ATTTGGACTT
1301 CATAATCAGC TGAATCACGC CGGATTTAGT AATGAGCACT GTATGCGGCT
1351 GCAAATACAG CGGGTCGCCC CTTTTCACGA CGCTGTTAGA GGTAGGGCCC
1401 CCATTTTGGA TGGTCTGCTC AAATAACGAT TTGTATTTAT TGTCTACATG
1451 AACACGTATA GCTTTATCAC AAACTGTATA TTTTAAACTG TTAGCGACGT
1501 CCTTGGCCAC GAACCGGACC TGTTGGTCGC GCTCTAGCAC GTACCGCAGG
1551 TTGAACGTAT CTTCTCCAAA TTTAAATTCT CCAATTTTAA CGCGAGCCAT
1601 TTTGATACAC GTGTGTCGAT TTTGCAACAA CTATTGTTTT TTAACGCAAA
1651 CTAAACTTAT TGTGGTAAGC AATAATTAAA TATGGGGGAA CATGCGCCGC
1701 TACAACACTC GTCGTTATGA ACGCAGACGG CGCCGGTCTC GGCGCAAGCG
1751 GCTAAAACGT GTTGCGCGTT CAACGCGGCA AACATCGCAA AAGCCAATAG
1801 TACAGTTTTG ATTTGCATAT TAACGGCGAT TTTTTAAATT ATCTTATTTA
1851 ATAAATAGTT ATGACGCCTA CAACTCCCCG CCCGCGTTGA CTCGCTGCAC
1901 CTCGAGCAGT TCGTTGACGC CTTCCTCCGT GTGGCCGAAC ACGTCGAGCG
```

Figure 23B

```
1951 GGTGGTCGAT GACCAGCGGC GTGCCGCACG CGACGCACAA GTATCTGTAC
2001 ACCGAATGAT CGTCGGGCGA AGGCACGTCG GCCTCCAAGT GGCAATATTG
2051 GCAAATTCGA AAATATATAC AGTTGGGTTG TTTGCGCATA TCTATCGTGG
2101 CGTTGGGCAT GTACGTCCGA ACGTTGATTT GCATGCAAGC CGAAATTAAA
2151 TCATTGCGAT TAGTGCGATT AAAACGTTGT ACATCCTCGC TTTTAATCAT
2201 GCCGTCGATT AAATCGCGCA ATCGAGTCAA GTGATCAAAG TGTGGAATAA
2251 TGTTTTCTTT GTATTCCCGA GTCAAGCGCA GCGCGTATTT TAACAAACTA
2301 GCCATCTTGT AAGTTAGTTT CATTTAATGC AACTTTATCC AATAATATAT
2351 TATGTATCGC ACGTCAAGAA TTAACAATGC GCCCGTTGTC GCATCTCAAC
2401 ACGACTATGA TAGAGATCAA ATAAAGCGCG AATTAAATAG CTTGCGACGC
2451 AACGTGCACG ATCTGTGCAC GCGTTCCGGC ACGAGCTTTG ATTGTAATAA
2501 GTTTTTACGA AGCGATGACA TGACCCCCGT AGTGACAACG ATCACGCCCA
2551 AAAGAACTGC CGACTACAAA ATTACCGAGT ATGTCGGTGA CGTTAAAACT
2601 ATTAAGCCAT CCAATCGACC GTTAGTCGAA TCAGGACCGC TGGTGCGAGA
2651 AGCCGCGAAG TATGGCGAAT GCATCGTATA ACGTGTGGAG TCCGCTCATT
2701 AGAGCGTCAT GTTTAGACAA GAAAGCTACA TATTTAATTG ATCCCGATGA
2751 TTTTATTGAT AAATTGACCC TAACTCCATA CACGGTATTC TACAATGGCG
2801 GGGTTTTGGT CAAAATTTCC GGACTGCGAT TGTACATGCT GTTAACGGCT
2851 CCGCCCACTA TTAATGAAAT TAAAAATTCC AATTTTAAAA AACGCAGCAA
2901 GAGAAACATT TGTATGAAAG AATGCGTAGA AGGAAAGAAA AATGTCGTCG
2951 ACATGCTGAA CAACAAGATT AATATGCCTC CGTGTATAAA AAAAATATTG
3001 AACGATTTGA AAGAAAAACAA TGTACCGCGC GGCGGTATGT ACAGGAAGAG
3051 GTTTATACTA AACTGTTACA TTGCAAACGT GGTTTCGTGT GCCAAGTGTG
3101 AAAACCGATG TTTAATCAAG GCTCTGACGC ATTTCTACAA CCACGACTCC
3151 AAGTGTGTGG GTGAAGTCAT GCATCTTTTA ATCAAATCCC AAGATGTGTA
3201 TAAACCACCA AACTGCCAAA AAATGAAAAC TGTCGACAAG CTCTGTCCGT
3251 TTGCTGGCAA CTGCAAGGGT CTCAATCCTA TTTGTAATTA TTGAATAATA
3301 AAACAATTAT AAATGCTAAA TTTGTTTTTT ATTAACGATA CAAACCAAAC
3351 GCAACAAGAA CATTTGTAGT ATTATCTATA ATTGAAAACG CGTAGTTATA
3401 ATCGCTGAGG TAATATTTAA AATCATTTTC AAATGATTCA CAGTTAATTT
3451 GCGACAATAT AATTTTATTT TCACATAAAC TAGACGCCTT GTCGTCTTCT
3501 TCTTCGTATT CCTTCTCTTT TTCATTTTTC TCCTCATAAA AATTAACATA
3551 GTTATTATCG TATCCATATA TGTATCTATC GTATAGAGTA AATTTTTTGT
3601 TGTCATAAAT ATATATGTCT TTTTTAATGG GGTGTATAGT ACCGCTGCGC
3651 ATAGTTTTTC TGTAATTTAC AACAGTGCTA TTTTCTGGTA GTTCTTCGGA
3701 GTGTGTTGCT TTAATTATTA AATTTATATA ATCAATGAAT TTGGGATCGT
3751 CGGTTTTGTA CAATATGTTG CCGGCATAGT ACGCAGCTTC TTCTAGTTCA
3801 ATTACACCAT TTTTTAGCAG CACCGGATTA ACATAACTTT CCAAAATGTT
3851 GTACGAACCG TTAAACAAAA ACAGTTCACC TCCCTTTTCT ATACTATTGT
```

Figure 23C

```
3901  CTGCGAGCAG TTGTTTGTTG TTAAAAATAA CAGCCATTGT AATGAGACGC
3951  ACAAACTAAT ATCACAAACT GGAAATGTCT ATCAATATAT AGTTGCTGAT
                                                        >>>
4001  ATCATGGAGA TAATTAAAAT GATAACCATC TCGCAAATAA ATAAGTATTT
      >.......................pr........................>
4051  TACTGTTTTC GTAACAGTTT TGTAATAAAA AAACCTATAA ATATTCCGGA
      >..................pr....................>>
4101  TTATTCATAC CGTCCCACCA TCGGGCGCGG ATCAGATCTG CAGCGGCCGC

                      KpnI
                     -------
4151  TCCAGAATTC TAGAAGGTAC CATGGAGCCT CAAAGTCAGA GCATGACGCT
                            >>...........muIDO2............>
4201  GGAGGTGCCG TTGTCCTTGG GGAGATACCA CATTTCTGAG GAATATGGCT
      >.....................muIDO2......................>
4251  TTCTCCTTCC AAATCCTCTG GAAGCACTTC CAGATCATTA CAAGCCTTGG
      >.....................muIDO2......................>
4301  ATGGAAATTG CCCTCAGACT TCCTCACTTA ATCGAGAACC GCCAGCTCCG
      >.....................muIDO2......................>
4351  AGCTCACGTG TACAGGATGC CTCTCCTGGA CTGCAGATTC CTAAAGAGTT
      >.....................muIDO2......................>
4401  ACCGTGAGCA GCGCCTGGCA CACATGGCGC TGGCCGCTAT CACCATGGGA
      >.....................muIDO2......................>
4451  TTCGTCTGGC AGGAGGGGGA AGGCCAACCC CAAAAGGTGC TGCCAAGATC
      >.....................muIDO2......................>
4501  TCTTGCCATT CCTTTTGTTG AGGTATCCAG GAACTTGGGA CTCCCGCCTA
      >.....................muIDO2......................>
4551  TCCTGGTCCA CTCTGACCTG GTGCTGACAA ACTGGACCAA AAGGAACCCA
      >.....................muIDO2......................>
4601  GAAGGACCGT TGGAAATCAG TAACCTGGAA ACCATCATCT CATTTCCGGG
      >.....................muIDO2......................>
4651  GGGAGAGAGC CTGCGGGGCT TCATCCTAGT GACAGTCTTG GTGGAGAAGG
      >.....................muIDO2......................>
4701  CAGCAGTGCC CGGCCTTAAG GCCCTGGTTC AGGGAATGGA GGCCATTCGG
      >.....................muIDO2......................>
4751  CAACACAGTC AGGACACCCT GCTAGAAGCC CTGCAGCAGC TGAGACTCTC
      >.....................muIDO2......................>
4801  CATCCAGGAT ATCACCAGAG CCTTGGCCCA AATGCATGAT TATGTGGACC
```

Figure 23D

```
     >.....................muIDO2......................>
4851 CAGACATATT TTACTCGGTC ATCCGGATCT TCCTCTCTGG GTGGAAGGAC
     >.....................muIDO2......................>
4901 AATCCAGCCA TGCCTGTGGG GCTGGTCTAT GAAGGTGCTG CCACAGAGCC
     >.....................muIDO2......................>
4951 TCTGAAGTAC TCTGGAGGAA GTGCAGCCCA GAGCTCCGTG CTTCATGCCT
     >.....................muIDO2......................>
5001 TCGATGAGTT CCTGGGCATT GAGCATTGCA AGGAAAGTGT TGGCTTTCTA
     >.....................muIDO2......................>
5051 CACAGAATGA GGGACTACAT GCCGCCTTCC CATAAGGCTT TCCTGGAAGA
     >.....................muIDO2......................>
5101 TCTCCACGTA GCTCCTTCTC TGAGAGACTA CATACTGGCC TCTGGTCCTG
     >.....................muIDO2......................>
5151 GGGACTGCCT GATGGCCTAT AACCAGTGTG TGGAGGCCCT GGGAGAGCTG
     >.....................muIDO2......................>
5201 CGCAGTTACC ACATCAATGT CGTGGCCAGA TACATTATCT CCGCTGCCAC
     >.....................muIDO2......................>
5251 CAGGGCCAGG AGCAGGGGGC TAACTAATCC CTCACCCCAT GCCTTGGAAG
     >.....................muIDO2......................>
5301 ACAGGGGCAC TGGGGGTACT GCCATGCTGA GCTTCTTGAA GAGTGTCAGG
     >.....................muIDO2......................>
5351 GAGAAGACCA TGGAGGCCCT CCTGTGTCCT GGTGCTTAGG GTCAAGACAA
     >..............muIDO2................>>
5401 TTCTGCAGAT ATCCAGCACA GTGGCGGCCG CTCGAGTCTA GAGGGCCCGC
5451 GGTTCGAAGG TAAGCCTATC CCTAACCCTC TCCTCGGTCT CGATTCTACG

                                          NheI
                                         ------
5501 CGTACCGGTC ATCATCACCA TCACCATTGA GTTTGCTAGC CACTAGTACC
5551 GACTCTGCTG AAGAGGAGGA AATTCTCCTT GAAGTTTCCC TGGTGTTCAA
5601 AGTAAAGGAG TTTGCACCAG ACGCACCTCT GTTCACTGGT CCGGCGTATT
5651 AAAACACGAT ACATTGTTAT TAGTACATTT ATTAAGCGCT AGATTCTGTG
5701 CGTTGTTGAT TTACAGACAA TTGTTGTACG TATTTTAATA ATTCATTAAA
5751 TTTATAATCT TTAGGGTGGT ATGTTAGAGC GAAAATCAAA TGATTTTCAG
5801 CGTCTTTATA TCTGAATTTA AATATTAAAT CCTCAATAGA TTTGTAAAAT
5851 AGGTTTCGAT TAGTTTCAAA CAAGGGTTGT TTTTCCGAAC CGATGGCTGG
5901 ACTATCTAAT GGATTTTCGC TCAACGCCAC AAAACTTGCC AAATCTTGTA
5951 GCAGCAATCT AGCTTTGTCG ATATTCGTTT GTGTTTTGTT TTGTAATAAA
6001 GGTTCGACGT CGTTCAAAAT ATTATGCGCT TTTGTATTTC TTTCATCACT
```

Figure 23E

6051 GTCGTTAGTG TACAATTGAC TCGACGTAAA CACGTTAAAT AAAGCTTGGA
6101 CATATTTAAC ATCGGGCGTG TTAGCTTTAT TAGGCCGATT ATCGTCGTCG
6151 TCCCAACCCT CGTCGTTAGA AGTTGCTTCC GAAGACGATT TTGCCATAGC
6201 CACACGACGC CTATTAATTG TGTCGGCTAA CACGTCCGCG ATCAAATTTG
6251 TAGTTGAGCT TTTTGGAATT ATTTCTGATT GCGGGCGTTT TTGGGCGGGT
6301 TTCAATCTAA CTGTGCCCGA TTTTAATTCA GACAACACGT TAGAAAGCGA
6351 TGGTGCAGGC GGTGGTAACA TTTCAGACGG CAAATCTACT AATGGCGGCG
6401 GTGGTGGAGC TGATGATAAA TCTACCATCG GTGGAGGCGC AGGCGGGGCT
6451 GGCGGCGGAG GCGGAGGCGG AGGTGGTGGC GGTGATGCAG ACGGCGGTTT
6501 AGGCTCAAAT GTCTCTTTAG GCAACACAGT CGGCACCTCA ACTATTGTAC
6551 TGGTTTCGGG CGCCGTTTTT GGTTTGACCG GTCTGAGACG AGTGCGATTT
6601 TTTTCGTTTC TAATAGCTTC CAACAATTGT TGTCTGTCGT CTAAAGGTGC
6651 AGCGGGTTGA GGTTCCGTCG GCATTGGTGG AGCGGGCGGC AATTCAGACA
6701 TCGATGGTGG TGGTGGTGGT GGAGGCGCTG GAATGTTAGG CACGGGAGAA
6751 GGTGGTGGCG GCGGTGCCGC CGGTATAATT TGTTCTGGTT TAGTTTGTTC
6801 GCGCACGATT GTGGGCACCG GCGCAGGCGC CGCTGGCTGC ACAACGGAAG
6851 GTCGTCTGCT TCGAGGCAGC GCTTGGGGTG GTGGCAATTC AATATTATAA
6901 TTGGAATACA AATCGTAAAA ATCTGCTATA AGCATTGTAA TTTCGCTATC
6951 GTTTACCGTG CCGATATTTA ACAACCGCTC AATGTAAGCA ATTGTATTGT
7001 AAAGAGATTG TCTCAAGCTC GCCGCACGCC GATAACAAGC CTTTTCATTT
7051 TTACTACAGC ATTGTAGTGG CGAGACACTT CGCTGTCGTC GACGTACATG
7101 TATGCTTTGT TGTCAAAAAC GTCGTTGGCA AGCTTTAAAA TATTTAAAAG
7151 AACATCTCTG TTCAGCACCA CTGTGTTGTC GTAAATGTTG TTTTTGATAA
7201 TTTGCGCTTC CGCAGTATCG ACACGTTCAA AAAATTGATG CGCATCAATT
7251 TTGTTGTTCC TATTATTGAA TAAATAAGAT TGTACAGATT CATATCTACG
7301 ATTCGTCATG GCCACCACAA ATGCTACGCT GCAAACGCTG GTACAATTTT
7351 ACGAAAACTG CAAAAACGTC AAAACTCGGT ATAAAATAAT CAACGGGCGC
7401 TTTGGCAAAA TATCTATTTT ATCGCACAAG CCCACTAGCA AATTGTATTT
7451 GCAGAAAACA ATTTCGGCGC ACAATTTTAA CGCTGACGAA ATAAAAGTTC
7501 ACCAGTTAAT GAGCGACCAC CCAAATTTTA TAAAAATCTA TTTTAATCAC
7551 GGTTCCATCA ACAACCAAGT GATCGTGATG GACTACATTG ACTGTCCCGA
7601 TTTATTTGAA ACACTACAAA TTAAAGGCGA GCTTTCGTAC CAACTTGTTA
7651 GCAATATTAT TAGACAGCTG TGTGAAGCGC TCAACGATTT GCACAAGCAC
7701 AATTTCATAC ACAACGACAT AAAACTCGAA AATGTCTTAT ATTTCGAAGC
7751 ACTTGATCGC GTGTATGTTT GCGATTACGG ATTGTGCAAA CACGAAAACT
7801 CACTTAGCGT GCACGACGGC ACGTTGGAGT ATTTTAGTCC GGAAAAAATT
7851 CGACACACAA CTATGCACGT TTCGTTTGAC TGGTACGCGG CGTGTTAACA
7901 TACAAGTTGC TAACGTAATC ATGGTCATAG CTGTTTCCTG TGTGAAATTG
7951 TTATCCGCTC ACAATTCCAC ACAACATACG AGCCGGAAGC ATAAAGTGTA

Figure 23F

```
8001  AAGCCTGGGG TGCCTAATGA GTGAGCTAAC TCACATTAAT TGCGTTGCGC
8051  TCACTGCCCG CTTTCCAGTC GGGAAACCTG TCGTGCCAGC TGCATTAATG
8101  AATCGGCCAA CGCGCGGGGA GAGGCGGTTT GCGTATTGGG CGCTCTTCCG
8151  CTTCCTCGCT CACTGACTCG CTGCGCTCGG TCGTTCGGCT GCGGCGAGCG
8201  GTATCAGCTC ACTCAAAGGC GGTAATACGG TTATCCACAG AATCAGGGGA
8251  TAACGCAGGA AAGAACATGT GAGCAAAAGG CCAGCAAAAG GCCAGGAACC
8301  GTAAAAAGGC CGCGTTGCTG GCGTTTTTCC ATAGGCTCCG CCCCCCTGAC
8351  GAGCATCACA AAAATCGACG CTCAAGTCAG AGGTGGCGAA ACCCGACAGG
8401  ACTATAAAGA TACCAGGCGT TTCCCCCTGG AAGCTCCCTC GTGCGCTCTC
8451  CTGTTCCGAC CCTGCCGCTT ACCGGATACC TGTCCGCCTT TCTCCCTTCG
8501  GGAAGCGTGG CGCTTTCTCA TAGCTCACGC TGTAGGTATC TCAGTTCGGT
8551  GTAGGTCGTT CGCTCCAAGC TGGGCTGTGT GCACGAACCC CCCGTTCAGC
8601  CCGACCGCTG CGCCTTATCC GGTAACTATC GTCTTGAGTC CAACCCGGTA
8651  AGACACGACT TATCGCCACT GGCAGCAGCC ACTGGTAACA GGATTAGCAG
8701  AGCGAGGTAT GTAGGCGGTG CTACAGAGTT CTTGAAGTGG TGGCCTAACT
                 <<................ColE1.................<
8751  ACGGCTACAC TAGAAGGACA GTATTTGGTA TCTGCGCTCT GCTGAAGCCA
      <.....................ColE1......................<
8801  GTTACCTTCG GAAAAAGAGT TGGTAGCTCT TGATCCGGCA AACAAACCAC
      <.....................ColE1......................<
8851  CGCTGGTAGC GGTGGTTTTT TTGTTTGCAA GCAGCAGATT ACGCGCAGAA
      <.....................ColE1......................<
8901  AAAAAGGATC TCAAGAAGAT CCTTTGATCT TTTCTACGGG GTCTGACGCT
      <.....................ColE1......................<
8951  CAGTGGAACG AAAACTCACG TTAAGGGATT TTGGTCATGA GATTATCAAA
      <.....................ColE1......................<
9001  AAGGATCTTC ACCTAGATCC TTTTAAATTA AAAATGAAGT TTTAAATCAA
      <.....................ColE1......................<
9051  TCTAAAGTAT ATATGAGTAA ACTTGGTCTG ACAGTTACCA ATGCTTAATC
      <.....................ColE1......................<
9101  AGTGAGGCAC CTATCTCAGC GATCTGTCTA TTTCGTTCAT CCATAGTTGC
      <.....................ColE1......................<
9151  CTGACTCCCC GTCGTGTAGA TAACTACGAT ACGGGAGGGC TTACCATCTG
      <.....................ColE1......................<
9201  GCCCCAGTGC TGCAATGATA CCGCGAGACC CACGCTCACC GGCTCCAGAT
      <.....................ColE1......................<
9251  TTATCAGCAA TAAACCAGCC AGCCGGAAGG GCCGAGCGCA GAAGTGGTCC
      <.....................ColE1......................<
9301  TGCAACTTTA TCCGCCTCCA TCCAGTCTAT TAATTGTTGC CGGGAAGCTA
```

Figure 23G

```
      <......................ColE1.......................<
9351  GAGTAAGTAG TTCGCCAGTT AATAGTTTGC GCAACGTTGT TGCCATTGCT
      <..............ColE1...............<<
9401  ACAGGCATCG TGGTGTCACG CTCGTCGTTT GGTATGGCTT CATTCAGCTC
9451  CGGTTCCCAA CGATCAAGGC GAGTTACATG ATCCCCCATG TTGTGCAAAA
9501  AAGCGGTTAG CTCCTTCGGT CCTCCGATCG TTGTCAGAAG TAAGTTGGCC
                                         >>.......amp.......>
9551  GCAGTGTTAT CACTCATGGT TATGGCAGCA CTGCATAATT CTCTTACTGT
      >......................amp........................>
9601  CATGCCATCC GTAAGATGCT TTTCTGTGAC TGGTGAGTAC TCAACCAAGT
      >......................amp........................>
9651  CATTCTGAGA ATAGTGTATG CGGCGACCGA GTTGCTCTTG CCCGGCGTCA
      >......................amp........................>
9701  ATACGGGATA ATACCGCGCC ACATAGCAGA ACTTTAAAAG TGCTCATCAT
      >......................amp........................>
9751  TGGAAAACGT TCTTCGGGGC GAAAACTCTC AAGGATCTTA CCGCTGTTGA
      >......................amp........................>
9801  GATCCAGTTC GATGTAACCC ACTCGTGCAC CCAACTGATC TTCAGCATCT
      >......................amp........................>
9851  TTTACTTTCA CCAGCGTTTC TGGGTGAGCA AAAACAGGAA GGCAAAATGC
      >......................amp........................>
9901  CGCAAAAAAG GGAATAAGGG CGACACGGAA ATGTTGAATA CTCATACTCT
      >......................amp........................>
9951  TCCTTTTTCA ATATTATTGA AGCATTTATC AGGGTTATTG TCTCATGAGC
      >......................amp........................>
10001 GGATACATAT TTGAATGTAT TTAGAAAAAT AAACAAATAG GGGTTCCGCG
      >......................amp........................>
10051 CACATTTCCC CGAAAAGTGC CACCTGACGT CTAAGAAACC ATTATTATCA
      >......................amp........................>
10101 TGACATTAAC CTATAAAAAT AGGCGTATCA CGAGGCCCTT TCGTCTCGCG
      >......................amp........................>
10151 CGTTTCGGTG ATGACGGTGA AAACCTCTGA CACATGCAGC TCCCGGAGAC
      >......................amp........................>
10201 GGTCACAGCT TGTCTGTAAG CGGATGCCGG GAGCAGACAA GCCCGTCAGG
      >......................amp........................>
10251 GCGCGTCAGC GGGTGTTGGC GGGTGTCGGG GCTGGCTTAA CTATGCGGCA
      >......................amp........................>
10301 TCAGAGCAGA TTGTACTGAG AGTGCACCAT ATGCGGTGTG AAATACCGCA
```

Figure 23H

```
      >.......amp........>>
10351 CAGATGCGTA AGGAGAAAAT ACCGCATCAG GCGCCATTCG CCATTCAGGC
10401 TGCGCAACTG TTGGGAAGGG CGATCGGTGC GGGCCTCTTC GCTATTACGC
10451 CAGCTGGCGA AAGGGGGATG TGCTGCAAGG CGATTAAGTT GGGTAACGCC
10501 AGGGTTTTCC CAGTCACGAC GTTGTAAAAC GACGGCCAGT GCC
```

Figure 23I

```
   1 AAGCTTTACT CGTAAAGCGA GTTGAAGGAT CATATTTAGT TGCGTTTATG
  51 AGATAAGATT GAAAGCACGT GTAAAATGTT TCCCGCGCGT TGGCACAACT
 101 ATTTACAATG CGGCCAAGTT ATAAAAGATT CTAATCTGAT ATGTTTTAAA
 151 ACACCTTTGC GGCCCGAGTT GTTTGCGTAC GTGACTAGCG AAGAAGATGT
 201 GTGGACCGCA GAACAGATAG TAAAACAAAA CCCTAGTATT GGAGCAATAA
 251 TCGATTTAAC CAACACGTCT AAATATTATG ATGGTGTGCA TTTTTTGCGG
 301 GCGGGCCTGT TATACAAAAA AATTCAAGTA CCTGGCCAGA CTTTGCCGCC
 351 TGAAAGCATA GTTCAAGAAT TTATTGACAC GGTAAAAGAA TTTACAGAAA
 401 AGTGTCCCGG CATGTTGGTG GGCGTGCACT GCACACACGG TATTAATCGC
 451 ACCGGTTACA TGGTGTGCAG ATATTTAATG CACACCCTGG GTATTGCGCC
 501 GCAGGAAGCC ATAGATAGAT TCGAAAAAGC CAGAGGTCAC AAAATTGAAA
 551 GACAAAATTA CGTTCAAGAT TTATTAATTT AATTAATATT ATTTGCATTC
 601 TTTAACAAAT ACTTTATCCT ATTTTCAAAT TGTTGCGCTT CTTCCAGCGA
 651 ACCAAAACTA TGCTTCGCTT GCTCCGTTTA GCTTGTAGCC GATCAGTGGC
 701 GTTGTTCCAA TCGACGGTAG GATTAGGCCG GATATTCTCC ACCACAATGT
 751 TGGCAACGTT GATGTTACGT TTATGCTTTT GGTTTTCCAC GTACGTCTTT
 801 TGGCCGGTAA TAGCCGTAAA CGTAGTGCCG TCGCGCGTCA CGCACAACAC
 851 CGGATGTTTG CGCTTGTCCG CGGGGTATTG AACCGCGCGA TCCGACAAAT
 901 CCACCACTTT GGCAACTAAA TCGGTGACCT GCGCGTCTTT TTTCTGCATT
 951 ATTTCGTCTT TCTTTTGCAT GGTTTCCTGG AAGCCGGTGT ACATGCGGTT
1001 TAGATCAGTC ATGACGCGCG TGACCTGCAA ATCTTTGGCC TCGATCTGCT
1051 TGTCCTTGAT GGCAACGATG CGTTCAATAA ACTCTTGTTT TTTAACAAGT
1101 TCCTCGGTTT TTTGCGCCAC CACCGCTTGC AGCGCGTTTG TGTGCTCGGT
1151 GAATGTCGCA ATCAGCTTAG TCACCAACTG TTTGCTCTCC TCCTCCCGTT
1201 GTTTGATCGC GGGATCGTAC TTGCCGGTGC AGAGCACTTG AGGAATTACT
1251 TCTTCTAAAA GCCATTCTTG TAATTCTATG GCGTAAGGCA ATTTGGACTT
1301 CATAATCAGC TGAATCACGC CGGATTTAGT AATGAGCACT GTATGCGGCT
1351 GCAAATACAG CGGGTCGCCC CTTTTCACGA CGCTGTTAGA GGTAGGGCCC
1401 CCATTTTGGA TGGTCTGCTC AAATAACGAT TTGTATTTAT TGTCTACATG
1451 AACACGTATA GCTTTATCAC AAACTGTATA TTTTAAACTG TTAGCGACGT
1501 CCTTGGCCAC GAACCGGACC TGTTGGTCGC GCTCTAGCAC GTACCGCAGG
1551 TTGAACGTAT CTTCTCCAAA TTTAAATTCT CCAATTTTAA CGCGAGCCAT
1601 TTTGATACAC GTGTGTCGAT TTTGCAACAA CTATTGTTTT TTAACGCAAA
1651 CTAAACTTAT TGTGGTAAGC AATAATTAAA TATGGGGGAA CATGCGCCGC
1701 TACAACACTC GTCGTTATGA ACGCAGACGG CGCCGGTCTC GGCGCAAGCG
1751 GCTAAAACGT GTTGCGCGTT CAACGCGGCA AACATCGCAA AAGCCAATAG
1801 TACAGTTTTG ATTTGCATAT TAACGGCGAT TTTTTAAATT ATCTTATTTA
1851 ATAAATAGTT ATGACGCCTA CAACTCCCCG CCCGCGTTGA CTCGCTGCAC
1901 CTCGAGCAGT TCGTTGACGC CTTCCTCCGT GTGGCCGAAC ACGTCGAGCG
```

Figure 24B

1951 GGTGGTCGAT GACCAGCGGC GTGCCGCACG CGACGCACAA GTATCTGTAC
2001 ACCGAATGAT CGTCGGGCGA AGGCACGTCG GCCTCCAAGT GGCAATATTG
2051 GCAAATTCGA AAATATATAC AGTTGGGTTG TTTGCGCATA TCTATCGTGG
2101 CGTTGGGCAT GTACGTCCGA ACGTTGATTT GCATGCAAGC CGAAATTAAA
2151 TCATTGCGAT TAGTGCGATT AAAACGTTGT ACATCCTCGC TTTTAATCAT
2201 GCCGTCGATT AAATCGCGCA ATCGAGTCAA GTGATCAAAG TGTGGAATAA
2251 TGTTTTCTTT GTATTCCCGA GTCAAGCGCA GCGCGTATTT TAACAAACTA
2301 GCCATCTTGT AAGTTAGTTT CATTTAATGC AACTTTATCC AATAATATAT
2351 TATGTATCGC ACGTCAAGAA TTAACAATGC GCCCGTTGTC GCATCTCAAC
2401 ACGACTATGA TAGAGATCAA ATAAAGCGCG AATTAAATAG CTTGCGACGC
2451 AACGTGCACG ATCTGTGCAC GCGTTCCGGC ACGAGCTTTG ATTGTAATAA
2501 GTTTTTACGA AGCGATGACA TGACCCCCGT AGTGACAACG ATCACGCCCA
2551 AAAGAACTGC CGACTACAAA ATTACCGAGT ATGTCGGTGA CGTTAAAACT
2601 ATTAAGCCAT CCAATCGACC GTTAGTCGAA TCAGGACCGC TGGTGCGAGA
2651 AGCCGCGAAG TATGGCGAAT GCATCGTATA ACGTGTGGAG TCCGCTCATT
2701 AGAGCGTCAT GTTTAGACAA GAAAGCTACA TATTTAATTG ATCCCGATGA
2751 TTTTATTGAT AAATTGACCC TAACTCCATA CACGGTATTC TACAATGGCG
2801 GGGTTTTGGT CAAAATTTCC GGACTGCGAT TGTACATGCT GTTAACGGCT
2851 CCGCCCACTA TTAATGAAAT TAAAAATTCC AATTTTAAAA AACGCAGCAA
2901 GAGAAACATT TGTATGAAAG AATGCGTAGA AGGAAAGAAA AATGTCGTCG
2951 ACATGCTGAA CAACAAGATT AATATGCCTC CGTGTATAAA AAAAATATTG
3001 AACGATTTGA AAGAAAACAA TGTACCGCGC GGCGGTATGT ACAGGAAGAG
3051 GTTTATACTA AACTGTTACA TTGCAAACGT GGTTTCGTGT GCCAAGTGTG
3101 AAAACCGATG TTTAATCAAG GCTCTGACGC ATTTCTACAA CCACGACTCC
3151 AAGTGTGTGG GTGAAGTCAT GCATCTTTTA ATCAAATCCC AAGATGTGTA
3201 TAAACCACCA AACTGCCAAA AAATGAAAAC TGTCGACAAG CTCTGTCCGT
3251 TTGCTGGCAA CTGCAAGGGT CTCAATCCTA TTTGTAATTA TTGAATAATA
3301 AAACAATTAT AAATGCTAAA TTTGTTTTTT ATTAACGATA CAAACCAAAC
3351 GCAACAAGAA CATTTGTAGT ATTATCTATA ATTGAAAACG CGTAGTTATA
3401 ATCGCTGAGG TAATATTTAA AATCATTTTC AAATGATTCA CAGTTAATTT
3451 GCGACAATAT AATTTTATTT TCACATAAAC TAGACGCCTT GTCGTCTTCT
3501 TCTTCGTATT CCTTCTCTTT TTCATTTTTC TCCTCATAAA AATTAACATA
3551 GTTATTATCG TATCCATATA TGTATCTATC GTATAGAGTA AATTTTTTGT
3601 TGTCATAAAT ATATATGTCT TTTTTAATGG GGTGTATAGT ACCGCTGCGC
3651 ATAGTTTTTC TGTAATTTAC AACAGTGCTA TTTTCTGGTA GTTCTTCGGA
3701 GTGTGTTGCT TTAATTATTA AATTTATATA ATCAATGAAT TTGGGATCGT
3751 CGGTTTTGTA CAATATGTTG CCGGCATAGT ACGCAGCTTC TTCTAGTTCA
3801 ATTACACCAT TTTTTAGCAG CACCGGATTA ACATAACTTT CCAAAATGTT
3851 GTACGAACCG TTAAACAAAA ACAGTTCACC TCCCTTTTCT ATACTATTGT

Figure 24C

```
3901  CTGCGAGCAG TTGTTTGTTG TTAAAAATAA CAGCCATTGT AATGAGACGC

3951  ACAAACTAAT ATCACAAACT GGAAATGTCT ATCAATATAT AGTTGCTGAT
                                                       >>>
4001  ATCATGGAGA TAATTAAAAT GATAACCATC TCGCAAATAA ATAAGTATTT
      >.......................pr.........................>
4051  TACTGTTTTC GTAACAGTTT TGTAATAAAA AAACCTATAA ATATTCCGGA
      >...................pr....................>>

                                                    NotI
                                                   --------
4101  TTATTCATAC CGTCCCACCA TCGGGCGCGG ATCAGATCTG CAGCGGCCGC

                        KpnI
                       -------
4151  TCCAGAATTC TAGAAGGTAC CCATGGAGCC CCACAGACCG AATGTGAAGA
                              >>..........huIDO2...........>
4201  CAGCAGTGCC ATTGTCTTTG GAAAGCTATC ACATATCTGA AGAGTATGGC
      >.....................huIDO2.......................>
4251  TTTCTTCTTC CAGATTCTCT GAAAGAACTT CCAGATCATT ATAGGCCTTG
      >.....................huIDO2.......................>
4301  GATGGAAATT GCCAACAAAC TTCCTCAATT GATTGATGCT CACCAGCTTC
      >.....................huIDO2.......................>
4351  AAGCTCATGT GGACAAGATG CCCCTGCTGA GCTGCCAGTT CCTGAAGGGT
      >.....................huIDO2.......................>
4401  CACCGGGAGC AGCGCCTGGC CCACCTGGTC CTGAGCTTCC TCACCATGGG
      >.....................huIDO2.......................>
4451  TTATGTCTGG CAGGAAGGAG AGGCGCAGCC TGCAGAGGTC CTGCCAAGGA
      >.....................huIDO2.......................>
4501  ATCTTGCCCT TCCATTTGTC GAAGTCTCCA GGAACTTGGG GCTCCCTCCT
      >.....................huIDO2.......................>
4551  ATCCTGGTCC ACTCAGACTT GGTGCTGACG AACTGGACCA AAAAAGATCC
      >.....................huIDO2.......................>
4601  AGACGGGTTC CTGGAAATTG GGAACCTGGA GACCATCATC TCATTTCCTG
      >.....................huIDO2.......................>
4651  GGGGAGAGAG CCTGCATGGT TTTATACTGG TGACTGCTTT GGTAGAGAAA
      >.....................huIDO2.......................>
4701  GAAGCAGTGC CTGGGATAAA GGCTCTTGTT CAGGCCACGA ATGCTATCTT
      >.....................huIDO2.......................>
4751  GCAGCCCAAC CAGGAGGCCC TGCTCCAAGC CCTGCAGCGA CTGAGACTGT
```

Figure 24D

```
     >.....................huIDO2......................>
4801 CTATTCAGGA CATCACCAAA ACCTTAGGAC AGATGCATGA TTATGTAGAT
     >.....................huIDO2......................>
4851 CCAGACATAT TTTATGCAGG CATCCGGATC TTTCTCTCTG GGTGGAAAGA
     >.....................huIDO2......................>
4901 CAACCCAGCA ATGCCTGCAG GGCTGATGTA TGAAGGAGTT TCCCAAGAGC
     >.....................huIDO2......................>
4951 CCCTGAAATA CTCCGGCGGG AGTGCAGCTC AGAGCACAGT GCTTCATGCC
     >.....................huIDO2......................>
5001 TTTGATGAGT TCTTAGGCAT TCGTCATAGC AAGGAAAGTG GTGACTTTCT
     >.....................huIDO2......................>
5051 GTACAGAATG AGGGATTACA TGCCTCCTTC CCATAAGGCC TTCATAGAAG
     >.....................huIDO2......................>
5101 ACATCCACTC AGCACCTTCC CTGAGGGACT ACATCCTGTC ATCTGGACAG
     >.....................huIDO2......................>
5151 GACCACTTGC TGACAGCTTA TAACCAGTGT GTGCAGGCCC TGGCAGAGCT
     >.....................huIDO2......................>
5201 GCGGAGCTAT CACATCACCA TGGTCACCAA ATACCTCATC ACAGCTGCAG
     >.....................huIDO2......................>
5251 CCAAGGCAAA GCATGGGAAG CCAAACCATC TCCCAGGGCC TCCTCAGGCT
     >.....................huIDO2......................>
5301 TTAAAAGACA GGGGCACAGG TGGAACCGCA GTTATGAGCT TTCTTAAGAG
     >.....................huIDO2......................>
5351 TGTCAGGGAT AAGACCTTGG AGTCAATCCT TCACCCACGT GGTTAACGCT
     >..................huIDO2....................>>
5401 CGAGTCTAGA GGGCCCGCGG TTCGAAGGTA AGCCTATCCC TAACCCTCTC
5451 CTCGGTCTCG ATTCTACGCG TACCGGTCAT CATCACCATC ACCATTGAGT

        NheI
       ------
5501 TTGCTAGCCA CTAGTACCGA CTCTGCTGAA GAGGAGGAAA TTCTCCTTGA
5551 AGTTTCCCTG GTGTTCAAAG TAAAGGAGTT TGCACCAGAC GCACCTCTGT
5601 TCACTGGTCC GGCGTATTAA AACACGATAC ATTGTTATTA GTACATTTAT
5651 TAAGCGCTAG ATTCTGTGCG TTGTTGATTT ACAGACAATT GTTGTACGTA
5701 TTTTAATAAT TCATTAAATT TATAATCTTT AGGGTGGTAT GTTAGAGCGA
5751 AAATCAAATG ATTTTCAGCG TCTTTATATC TGAATTTAAA TATTAAATCC
5801 TCAATAGATT TGTAAAATAG GTTTCGATTA GTTTCAAACA AGGGTTGTTT
5851 TTCCGAACCG ATGGCTGGAC TATCTAATGG ATTTTCGCTC AACGCCACAA
5901 AACTTGCCAA ATCTTGTAGC AGCAATCTAG CTTTGTCGAT ATTCGTTTGT
```

Figure 24E

5951 GTTTTGTTTT GTAATAAAGG TTCGACGTCG TTCAAAATAT TATGCGCTTT
6001 TGTATTTCTT TCATCACTGT CGTTAGTGTA CAATTGACTC GACGTAAACA
6051 CGTTAAATAA AGCTTGGACA TATTTAACAT CGGGCGTGTT AGCTTTATTA
6101 GGCCGATTAT CGTCGTCGTC CCAACCCTCG TCGTTAGAAG TTGCTTCCGA
6151 AGACGATTTT GCCATAGCCA CACGACGCCT ATTAATTGTG TCGGCTAACA
6201 CGTCCGCGAT CAAATTTGTA GTTGAGCTTT TTGGAATTAT TTCTGATTGC
6251 GGGCGTTTTT GGGCGGGTTT CAATCTAACT GTGCCCGATT TTAATTCAGA
6301 CAACACGTTA GAAAGCGATG GTGCAGGCGG TGGTAACATT TCAGACGGCA
6351 AATCTACTAA TGGCGGCGGT GGTGGAGCTG ATGATAAATC TACCATCGGT
6401 GGAGGCGCAG GCGGGGCTGG CGGCGGAGGC GGAGGCGGAG GTGGTGGCGG
6451 TGATGCAGAC GGCGGTTTAG GCTCAAATGT CTCTTTAGGC AACACAGTCG
6501 GCACCTCAAC TATTGTACTG GTTTCGGGCG CCGTTTTTGG TTTGACCGGT
6551 CTGAGACGAG TGCGATTTTT TTCGTTTCTA ATAGCTTCCA ACAATTGTTG
6601 TCTGTCGTCT AAAGGTGCAG CGGGTTGAGG TTCCGTCGGC ATTGGTGGAG
6651 CGGGCGGCAA TTCAGACATC GATGGTGGTG GTGGTGGTGG AGGCGCTGGA
6701 ATGTTAGGCA CGGGAGAAGG TGGTGGCGGC GGTGCCGCCG GTATAATTTG
6751 TTCTGGTTTA GTTTGTTCGC GCACGATTGT GGGCACCGGC GCAGGCGCCG
6801 CTGGCTGCAC AACGGAAGGT CGTCTGCTTC GAGGCAGCGC TTGGGGTGGT
6851 GGCAATTCAA TATTATAATT GGAATACAAA TCGTAAAAAT CTGCTATAAG
6901 CATTGTAATT TCGCTATCGT TTACCGTGCC GATATTTAAC AACCGCTCAA
6951 TGTAAGCAAT TGTATTGTAA AGAGATTGTC TCAAGCTCGC CGCACGCCGA
7001 TAACAAGCCT TTTCATTTTT ACTACAGCAT TGTAGTGGCG AGACACTTCG
7051 CTGTCGTCGA CGTACATGTA TGCTTTGTTG TCAAAAACGT CGTTGGCAAG
7101 CTTTAAAATA TTTAAAAGAA CATCTCTGTT CAGCACCACT GTGTTGTCGT
7151 AAATGTTGTT TTTGATAATT TGCGCTTCCG CAGTATCGAC ACGTTCAAAA
7201 AATTGATGCG CATCAATTTT GTTGTTCCTA TTATTGAATA AATAAGATTG
7251 TACAGATTCA TATCTACGAT TCGTCATGGC CACCACAAAT GCTACGCTGC
7301 AAACGCTGGT ACAATTTTAC GAAAACTGCA AAAACGTCAA AACTCGGTAT
7351 AAAATAATCA ACGGGCGCTT TGGCAAAATA TCTATTTTAT CGCACAAGCC
7401 CACTAGCAAA TTGTATTTGC AGAAAACAAT TTCGGCGCAC AATTTTAACG
7451 CTGACGAAAT AAAAGTTCAC CAGTTAATGA GCGACCACCC AAATTTTATA
7501 AAAATCTATT TTAATCACGG TTCCATCAAC AACCAAGTGA TCGTGATGGA
7551 CTACATTGAC TGTCCCGATT TATTTGAAAC ACTACAAATT AAAGGCGAGC
7601 TTTCGTACCA ACTTGTTAGC AATATTATTA GACAGCTGTG TGAAGCGCTC
7651 AACGATTTGC ACAAGCACAA TTTCATACAC AACGACATAA AACTCGAAAA
7701 TGTCTTATAT TTCGAAGCAC TTGATCGCGT GTATGTTTGC GATTACGGAT
7751 TGTGCAAACA CGAAAACTCA CTTAGCGTGC ACGACGGCAC GTTGGAGTAT
7801 TTTAGTCCGG AAAAAATTCG ACACACAACT ATGCACGTTT CGTTTGACTG
7851 GTACGCGGCG TGTTAACATA CAAGTTGCTA ACGTAATCAT GGTCATAGCT

Figure 24F

```
7901 GTTTCCTGTG TGAAATTGTT ATCCGCTCAC AATTCCACAC AACATACGAG
7951 CCGGAAGCAT AAAGTGTAAA GCCTGGGGTG CCTAATGAGT GAGCTAACTC
8001 ACATTAATTG CGTTGCGCTC ACTGCCCGCT TTCCAGTCGG GAAACCTGTC
8051 GTGCCAGCTG CATTAATGAA TCGGCCAACG CGCGGGGAGA GGCGGTTTGC
8101 GTATTGGGCG CTCTTCCGCT TCCTCGCTCA CTGACTCGCT GCGCTCGGTC
8151 GTTCGGCTGC GGCGAGCGGT ATCAGCTCAC TCAAAGGCGG TAATACGGTT
8201 ATCCACAGAA TCAGGGGATA ACGCAGGAAA GAACATGTGA GCAAAAGGCC
8251 AGCAAAAGGC CAGGAACCGT AAAAAGGCCG CGTTGCTGGC GTTTTTCCAT
8301 AGGCTCCGCC CCCCTGACGA GCATCACAAA AATCGACGCT CAAGTCAGAG
8351 GTGGCGAAAC CCGACAGGAC TATAAAGATA CCAGGCGTTT CCCCCTGGAA
8401 GCTCCCTCGT GCGCTCTCCT GTTCCGACCC TGCCGCTTAC CGGATACCTG
8451 TCCGCCTTTC TCCCTTCGGG AAGCGTGGCG CTTTCTCATA GCTCACGCTG
8501 TAGGTATCTC AGTTCGGTGT AGGTCGTTCG CTCCAAGCTG GGCTGTGTGC
8551 ACGAACCCCC CGTTCAGCCC GACCGCTGCG CCTTATCCGG TAACTATCGT
8601 CTTGAGTCCA ACCCGGTAAG ACACGACTTA TCGCCACTGG CAGCAGCCAC
8651 TGGTAACAGG ATTAGCAGAG CGAGGTATGT AGGCGGTGCT ACAGAGTTCT
                                         <<........ColE1........<
8701 TGAAGTGGTG GCCTAACTAC GGCTACACTA GAAGGACAGT ATTTGGTATC
     <......................ColE1.......................<
8751 TGCGCTCTGC TGAAGCCAGT TACCTTCGGA AAAAGAGTTG GTAGCTCTTG
     <......................ColE1.......................<
8801 ATCCGGCAAA CAAACCACCG CTGGTAGCGG TGGTTTTTTT GTTTGCAAGC
     <......................ColE1.......................<
8851 AGCAGATTAC GCGCAGAAAA AAAGGATCTC AAGAAGATCC TTTGATCTTT
     <......................ColE1.......................<
8901 TCTACGGGGT CTGACGCTCA GTGGAACGAA AACTCACGTT AAGGGATTTT
     <......................ColE1.......................<
8951 GGTCATGAGA TTATCAAAAA GGATCTTCAC CTAGATCCTT TTAAATTAAA
     <......................ColE1.......................<
9001 AATGAAGTTT TAAATCAATC TAAAGTATAT ATGAGTAAAC TTGGTCTGAC
     <......................ColE1.......................<
9051 AGTTACCAAT GCTTAATCAG TGAGGCACCT ATCTCAGCGA TCTGTCTATT
     <......................ColE1.......................<
9101 TCGTTCATCC ATAGTTGCCT GACTCCCCGT CGTGTAGATA ACTACGATAC
     <......................ColE1.......................<
9151 GGGAGGGCTT ACCATCTGGC CCCAGTGCTG CAATGATACC GCGAGACCCA
     <......................ColE1.......................<
9201 CGCTCACCGG CTCCAGATTT ATCAGCAATA AACCAGCCAG CCGGAAGGGC
```

Figure 24G

```
      <......................ColE1.......................<
 9251 CGAGCGCAGA AGTGGTCCTG CAACTTTATC CGCCTCCATC CAGTCTATTA
      <......................ColE1.......................<
 9301 ATTGTTGCCG GGAAGCTAGA GTAAGTAGTT CGCCAGTTAA TAGTTTGCGC
      <......................ColE1.......................<
 9351 AACGTTGTTG CCATTGCTAC AGGCATCGTG GTGTCACGCT CGTCGTTTGG
      <<
 9401 TATGGCTTCA TTCAGCTCCG GTTCCCAACG ATCAAGGCGA GTTACATGAT
 9451 CCCCCATGTT GTGCAAAAAA GCGGTTAGCT CCTTCGGTCC TCCGATCGTT
                                                         >
 9501 GTCAGAAGTA AGTTGGCCGC AGTGTTATCA CTCATGGTTA TGGCAGCACT
      >.......................amp........................>
 9551 GCATAATTCT CTTACTGTCA TGCCATCCGT AAGATGCTTT TCTGTGACTG
      >.......................amp........................>
 9601 GTGAGTACTC AACCAAGTCA TTCTGAGAAT AGTGTATGCG GCGACCGAGT
      >.......................amp........................>
 9651 TGCTCTTGCC CGGCGTCAAT ACGGGATAAT ACCGCGCCAC ATAGCAGAAC
      >.......................amp........................>
 9701 TTTAAAAGTG CTCATCATTG GAAAACGTTC TTCGGGGCGA AAACTCTCAA
      >.......................amp........................>
 9751 GGATCTTACC GCTGTTGAGA TCCAGTTCGA TGTAACCCAC TCGTGCACCC
      >.......................amp........................>
 9801 AACTGATCTT CAGCATCTTT TACTTTCACC AGCGTTTCTG GGTGAGCAAA
      >.......................amp........................>
 9851 AACAGGAAGG CAAAATGCCG CAAAAAAGGG AATAAGGGCG ACACGGAAAT
      >.......................amp........................>
 9901 GTTGAATACT CATACTCTTC CTTTTTCAAT ATTATTGAAG CATTTATCAG
      >.......................amp........................>
 9951 GGTTATTGTC TCATGAGCGG ATACATATTT GAATGTATTT AGAAAAATAA
      >.......................amp........................>
10001 ACAAATAGGG GTTCCGCGCA CATTTCCCCG AAAAGTGCCA CCTGACGTCT
      >.......................amp........................>
10051 AAGAAACCAT TATTATCATG ACATTAACCT ATAAAAATAG GCGTATCACG
      >.......................amp........................>
10101 AGGCCCTTTC GTCTCGCGCG TTTCGGTGAT GACGGTGAAA ACCTCTGACA
      >.......................amp........................>
10151 CATGCAGCTC CCGGAGACGG TCACAGCTTG TCTGTAAGCG GATGCCGGGA
      >.......................amp........................>
10201 GCAGACAAGC CCGTCAGGGC GCGTCAGCGG GTGTTGGCGG GTGTCGGGGC
```

Figure 24H

```
       >......................amp.......................>
10251  TGGCTTAACT ATGCGGCATC AGAGCAGATT GTACTGAGAG TGCACCATAT
       >................amp.................>>
10301  GCGGTGTGAA ATACCGCACA GATGCGTAAG GAGAAAATAC CGCATCAGGC
10351  GCCATTCGCC ATTCAGGCTG CGCAACTGTT GGGAAGGGCG ATCGGTGCGG
10401  GCCTCTTCGC TATTACGCCA GCTGGCGAAA GGGGGATGTG CTGCAAGGCG
10451  ATTAAGTTGG GTAACGCCAG GGTTTTCCCA GTCACGACGT TGTAAAACGA
10501  CGGCCAGTGC C
```

Figure 24I

NUCLEIC ACID MOLECULES ENCODING INDOLEAMINE 2,3-DIOXYGENASE-2

This application is a continuation-in-part of PCT/US2007/069271, filed on May 18, 2007, which claims priority under 35 U.S.C. §119(e) to U.S. Provisional Patent Application No. 60/801,255, filed on May 18, 2006, U.S. Provisional Patent Application No. 60/886,815, filed on Jan. 26, 2007, and U.S. Provisional Patent Application No. 60/914,472, filed on Apr. 27, 2007. The foregoing applications are incorporated by reference herein.

Pursuant to 35 U.S.C. §202(c), it is acknowledged that the U.S. Government has certain rights in the invention described herein, which was made in part with funds from the National Institutes of Health, Grant No. CA109542.

FIELD OF THE INVENTION

This invention relates generally to the fields of cellular metabolism, oncology, and immunology. Specifically, the invention provides the nucleotide and amino acid sequence of indoleamine 2,3-dioxygenase-2 (IDO2) and methods of use thereof.

BACKGROUND OF THE INVENTION

Tumors, virus-infected cells, and diseased cells characteristically express atypical, potentially immunoreactive antigens. Accumulating evidence suggests that the failure of the immune system to mount an effective response against progressively growing tumors or virally infected cells is not due to a lack of recognizable antigens. Immunosuppression is poorly understood and mechanisms by which cells escape immune surveillance have been poorly explored. Recently, it has been shown that cytotoxic T cells become tolerized by a reduction in local concentrations of tryptophan that are elicited by indoleamine 2,3-dioxygenase-1 (IDO1) activity.

IDO1 is an oxidoreductase that catalyzes the rate-limiting step in tryptophan catabolism. This enzyme is structurally distinct from tryptophan dioxygenase (TDO), which is responsible for dietary tryptophan catabolism in the liver. IDO1 is an IFN-γ target gene that has been suggested to play a role in immunomodulation (Mellor and Munn (1999) Immunol. Today, 20:469-473). Elevation of IDO1 activity depletes the levels of tryptophan in local cellular environments. Induction of IDO1 in antigen-presenting cells, where IDO1 is regulated by IFN-γ, blocks the activation of T cells, which are especially sensitive to tryptophan depletion. T cells must undergo 1-2 rounds of cell division to become activated, but in response to tryptophan depletion they arrest in G1 instead. In this way, IDO1 has been proposed to inhibit the $T_H1$ responses that promote cytotoxic T cell development.

IDO1 has been proposed to modulate gene expression. This modulation is proposed to occur through a pathway involving GCN2, whose activation has been shown to lead to altered gene expression. The proposed pathway involves the following steps. First, IDO1 activity results in the metabolism of tryptophan. Second, the deprivation of tryptophan leads to tRNAs being uncharged. The presence of uncharged tRNAs results in the activation of GCN2 kinase and a general response pathway for amino acid starvation. Third, the active GCN2 kinase phosphorylates serine 52 of the alpha subunit of eukaryotic initiation factor 2 (eIF2α), which is known to be an important translation control mechanism. The regulation of eIF2α activity is governed by the phosphorylation of serine 52. Currently, there are at least three known kinases, i.e., IFN-inducible dsRNA-dependent protein kinase, heme-regulated repressor, and general control (GCN2), which can phosphorylate serine 52 in eIF2α. The phosphorylation of serine 52 in eIF2α prevents the GDP-GTP exchange activity of eIF2α resulting in the suppression of protein synthesis.

GCN2 has been shown to be important for IDO1-dependent responses since a GCN2 knock-out animal phenocopies the IDO1 knock-out animal.

The role of IDO1 in immunosuppression has been demonstrated by the ability of 1-methyl-tryptophan (1MT), a specific and bioactive IDO1 inhibitor (Cady and Sono (1991) Arch. Biochem. Biophys. 291:326-333), to elicit MHC-restricted and T cell-mediated rejection of allogeneic mouse concepti (Mellor et al. (2001) Nat. Immunol. 2:64-68; Munn et al. (1998) Science. 281: 1191-93). This effect is consistent with the high levels of IDO1 expression in placental trophoblast cells (Sedlmayr et al. (2002) Mol. Hum. Reprod. 8:385-391).

Significantly, IDO1 activity has been shown to be elevated frequently in human tumors and/or in cancer patients (Yasui et al. (1986) Proc. Natl. Acad. Sci. USA. 83:6622-26; Taylor and Feng (1991) FASEB J. 5:2516-22). Since IDO1 can modulate immune responses, one logical implication is that IDO1 elevation in cancer may promote tumor immunosuppression (Mellor and Munn (1999) Immunol. Today, 20:469-473; Munn et al. (1999) J. Exp. Med. 189:1363-72; Munn et al. (1998) Science. 281:1191-93). This possibility is supported by the observation that many cancers, including breast cancer, are characterized by a loss of beneficial immune functions that can limit malignant development. For example, $T_H1$ responses (of which IFN-γ production is a hallmark) that promote the production of cytotoxic T cells are suppressed during cancer progression. A resultant hypothesis from this data was that if IDO1 drives cancer progression by blunting T cell activation, then IDO1 inhibition in animals should blunt tumor growth by reversing IDO1-mediated immunosuppression.

Notably, there are two stereoisomers of the IDO1 inhibitor 1MT, e.g., D-1MT and L-1MT. L-1MT inhibits IDO1 and exhibits a characteristic pattern of antitumor activities. In contrast, D-1MT shares the same in vivo properties, but does not inhibit IDO1 itself. One explanation for these results is that D-LMT inhibits an enzyme that is related to, but distinct from IDO1. However, no enzymes related to IDO1 have been identified.

SUMMARY OF THE INVENTION

In accordance with the present invention nucleic acid molecules encoding indoleamine 2,3-dioxygenase-2 (IDO2) and isoforms, splice variants, and mutants thereof are provided. In another embodiment of the instant invention, primers, probes, antisense molecules, and siRNAs for detection and regulation of IDO2 are provided.

Another aspect of the invention includes amino acid sequences of IDO2. Additionally, antibodies immunologically specific for IDO2 are encompassed by this invention.

In yet another embodiment of the instant invention, methods are provided for the screening of compounds for their ability to the modulate activities of IDO2. The screening methods can be performed in vitro or in host cells, or in animals transgenic for IDO2 expression.

BRIEF DESCRIPTION OF THE DRAWINGS

FIGS. 1A and 1B provide amino acid sequences of isoforms of IDO2 (SEQ ID NO: 1 and SEQ ID NO: 2, respectively).

FIGS. 2A and 2B provide amino acid sequences of mouse IDO2 isoforms (SEQ ID NO: 3 and SEQ ID NO: 4, respectively).

FIG. 3A provides a sequence alignment of the amino acid sequences of a human IDO2 (top strand; amino acids 30-416 of SEQ ID NO: 1 shown) and a human IDO1 (bottom strand; amino acids 13-400 of SEQ ID NO: 5). The underlined residues indicate the conserved histidine and aspartic acid residues necessary for heme binding. # indicates identical and + indicates similar amino acids. FIG. 3B provides the amino acid sequence of human IDO1 (GenBank Accession No AAH27882.1; SEQ ID NO: 5). FIG. 3C provides a sequence alignment of the amino acid sequence of a human IDO2 (SEQ ID NO: 2) and the amino acid sequence of a mouse IDO2 (SEQ ID NO: 4). + indicates similar amino acids. FIGS. 3D-3G provide an amino acid and nucleotide alignment of a murine IDO2 (amino acid, SEQ ID NO: 4; nucleotide, SEQ ID NO: 13) and a murine IDO1 (amino acid, SEQ ID NO: 6; nucleotide, SEQ ID NO: 7). The underlined region indicate exon boundaries.

FIG. 4A is a nucleotide sequence of human IDO2 (SEQ ID NO: 8) which encodes SEQ ID NO: 1. The nucleotide sequence in capital letters (SEQ ID NO: 9) is the sequence encoding the human IDO2 protein. FIG. 4B is a nucleotide sequence of mouse IDO2 (SEQ ID NO: 10) which encodes SEQ ID NO: 3. The nucleotide sequence in capital letters (SEQ ID NO: 11) is the sequence encoding the mouse IDO2 protein. FIGS. 4C and 4D are nucleotide sequences (SEQ ID NO: 12 and SEQ ID NO: 13, respectively) encoding human and murine IDO2 proteins, respectively. Underlined nucleotides indicate the first nucleotide of a new exon.

FIGS. 10A-10Q provide a genomic sequence of murine IDO2 (SEQ ID NO: 14) with select restriction enzyme sites and intron/exon boundaries included.

Figure 11U:
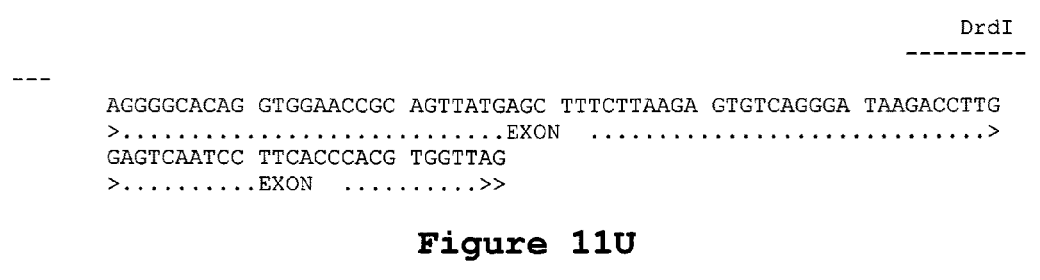

FIGS. 11A-11U provide a genomic sequence of human IDO2 (SEQ ID NO: 15) with select restriction enzyme sites and intron/exon boundaries included.

FIGS. 12A (SEQ ID NOs: 30-43, top to bottom) and 12B (SEQ ID NOs: 44-59, top to bottom) provide a schematic of IDO2 nucleic acid molecules and IDO2 primers for murine and human IDO2, respectively. FIG. 12C provides IDO1 primers and cloning primers (SEQ ID NOs: 60-82, top to bottom).

FIG. 13 provides a schematic of the locations of the introns and exons of IDO2 including exon 1a.

FIG. 14 provides a nucleotide sequence (SEQ ID NO: 20) of IDO2 which comprises 11 exons and encodes SEQ ID NO: 1. Asterisks depict the exon junctions.

FIGS. 15A-15Y is a genomic sequence of human IDO2 (SEQ ID NO: 21) with select restriction enzyme sites and intron/exon boundaries included.

FIGS. 16A-16G provide a nucleotide sequence alignment of a human IDO2 (SEQ ID NO: 12) with IDO2 splice variants and mutants: IDO2 Δ3/4/6 (SEQ ID NO: 22), IDO2 Δ8 (SEQ ID NO: 23), IDO2 Δ6/8 (SEQ ID NO: 24), IDO2 Δ4/5 (SEQ ID NO: 25), IDO2 R235W (SEQ ID NO: 26), IDO2 Y332stop (SEQ ID NO: 27), and a splice variant yielding an alternative exon 8 (SEQ ID NO: 29). SEQ ID NO: 28 is the amino acid sequence. Exon boundaries are indicated and the encoded amino acids are also provided.

FIGS. 20A (SEQ ID NOs: 83-122, top to bottom) and 20B (SEQ ID NOs: 124-147, top to bottom) provide target sequences and siRNA sequences for human and mouse IDO2, respectively.

FIG. 22 is a schematic of a screening strategy for IDO-2 knockin mice upon removal of the selection marker NeoR.

FIGS. 23B-23I provide the sequence of vector pVLmuIDO2 (SEQ ID NO: 162).

FIGS. 24B-24I provide the sequence of vector pVLhuIDO2 (SEQ ID NO: 163).

DETAILED DESCRIPTION OF THE INVENTION

Figure 1C:
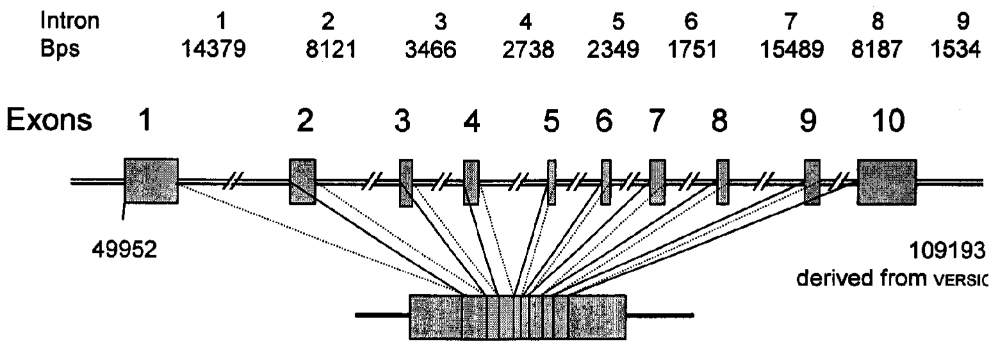
FIG. 1C provides a schematic of the IDO2 genome organization based on GenBank Accession No. NW_923907.1 when the IDO2 isoform comprises 10 coding exons and about 1227 coding bases.

The involvement of IDO1 in immune suppression, particularly the suppression of T cell immunity, has been well documented. As stated hereinabove, there is evidence to suggest that a previously unidentified enzyme related to IDO1 is also involved in immune suppression. Indeed, L-1MT has been shown to be effective at inhibiting IDO1 activity and tumor progression, but the stereoisomer D-1MT does not significantly inhibit IDO1 activity yet retains antitumor properties. Further, at least one IDO1 antisera has been generated which recognizes, in addition to IDO1, a differently regulated protein with a slightly larger apparent molecular weight as determined by Western blot.

In accordance with the instant invention, a novel homolog of IDO has been identified and named indoleamine 2,3-dioxygenase-2 (IDO2, also referred to as indoleamine 2,3-dioxygenase-like-1 (INDOL1) and IDO-NT). Amino acid sequences of human and mouse IDO2 are provided herein (see, e.g., FIGS. 1 and 2, respectively). Nucleotide sequences of human and mouse IDO2 are also provided (see, e.g., FIGS. 4A and 4B, respectively). Notably, IDO2 has approximately 45% sequence identity with human IDO1 (FIG. 3A).

Significantly, IDO2 shares the structural features of IDO1 that are known to be essential for heme binding and tryptophan catabolic activity. Indeed, the histidine and aspartic acid residues required for heme binding are conserved between IDO1 and IDO2 (see FIG. 3A).

Various isoforms, splice variants, and mutant IDO2 nucleic acids and proteins are provided. One isoform of IDO2 is also slightly larger than IDO1 (420 amino acids versus 403 amino acids). This size difference may account for the larger species sometimes seen in Western blots with antisera directed to IDO1. Indeed, portions of the sequence of the IDO1 peptide used to generate the antisera are conserved in IDO2. Based on these facts, it appears that certain IDO1 antisera are capable of cross-reacting with IDO2.

The 5' untranslated region of the IDO2 gene comprising the promoter elements, has a high degree of homology with the consensus sequences for the key immune regulatory transcription factors STAT1 and IRF-7. Significantly, IRF-7 is the master regulator of dendritic cells which present antigen to T cells and control T cell activation versus anergy. This similarity in the 5' regulatory region to the consensus sequence of these immune regulatory transcription factors suggests that IDO2 plays a role in the regulation of the immune response. Indeed, in silico analysis (e.g., an electronic Northern based on serial analysis of gene expression (SAGE)) determined that the highest expression of IDO2 would be in dendritic cells, where IDO1 is also known to be expressed, and pre-dendritic cells (such as JAWS II cells).

IDO2 nucleic acid molecules and proteins may be useful in the diagnosis and prognosis of immune modulation, like IDO1. IDO2 may also be used in the methods described by U.S. Pat. Nos. 6,451,840 and 6,482,416 for IDO1. Furthermore, as described hereinbelow, IDO2 is a candidate therapeutic target for diseases and disorders associated with immune modulation and/or protein misfolding such as cancer, viral infections, and other pathological conditions.

The activation of GCN2 translation control pathway alters the expression of the transcription factor Nuclear Factor IL6 (NFIL6; also known in the literature as C/EBPβ/IL6DBP/TCF5). The CCAAT-enhancer binding protein beta (C/EBPβ) is a basic leucine zipper (bZIP) transcription factor selectively expressed during differentiation of liver, adipose tissue, blood cells, and endocrine pancreas. C/EBPβ encodes four isoforms arising from the differential initiation of translation at four different in-frame AUGs, thereby producing the 40 kDa, 35 kDa, 20 kDa and 8.5 kDa C/EBPβ isoforms. The Lap and LIP isoforms of NF-IL6 have a variety of pleiotropic activities and are involved in regulation cell function, cell growth, and immune response. Lap-1 and Lap-2 have an antiproliferative effect, regulate cell cycle control and cytokine expression, and are pro-inflammatory. LIP is a dominant negative isoform. Therefore, the altered expression of LIP is a relevant biomarker for IDO1 and IDO2 activity in any cell expressing NF-IL6.

IDO1 expression leads to the increase in LIP (also called liver inhibitory protein) which is a dominant negative regulator of Lap1/2 activities, since it lacks certain activation and regulatory domains on LAPs (Liver activation proteins) and can form heterodimers with the LAP proteins, thereby altering their activity. By inference, it may be concluded that the activation of LIP is dependent on the deprivation of tryptophan, the activation of the GCN2 pathway and the increase in LIP production, which in turn results in altered gene expression and cell function. The data described herein support this model since the addition of exogenous tryptophan, even when IDO1 is highly expressed, blocks the production of LIP and activation of the GCN2 pathway.

IDO2 expression also leads to the activation of GCN2 kinase and increased LIP production. However the activation of the GCN2-LIP pathway is not inhibited by the addition of exogenous tryptophan. Therefore, it may be concluded that the mechanism of action for IDO2 is not tryptophan deprivation but rather the direct activation of the GCN2 kinase-LIP pathway. This is may be due to the generation of uncharged tryptophan tRNAs directly, the charging of tRNAs with kynurenine, or some other effect on the GCN2-LIP pathway.

It is also demonstrated herein that IDO2 activity can be inhibited by 1-methyl-D-tryptophan (1M-D-T) which blocks the activation of GCN2 kinase and subsequent altered LIP expression.

The activation of IDO2, like IDO1, has distinct and important properties for the regulation of immune responses. It is known that IDO1 exerts its activity locally by depriving the local cell environment of tryptophan, activating the GCN2 pathway, and suppressing T-cell activation and other immune activities. IDO2 directly activates the GCN2 pathway and exerts its activity globally and systemically in any cell in which it is expressed, including immune T cells and antigen presenting cells. IDO2 may also impact cell activities at distal locations as the altered expression of LIP/LAP is known to affect the expression of soluble growth factors and cytokines that can impact cell responses, like immune activation. One such scenario would be the activation of IDO2 in an antigen presenting cell (APC), such as a dendritic cell, which converts the APC in the presence of antigen to a tolerogenic cell that suppresses the immune response to a particular antigen.

I. Definitions

The term "IDO inhibitor" refers to an agent capable of inhibiting the activity of indoleamine 2,3-dioxygenase (IDO) (such as IDO1 and IDO2) and thereby reversing IDO-mediated immunosuppression. An IDO inhibitor may be a competitive, noncompetitive, or irreversible IDO inhibitor. "A competitive IDO inhibitor" is a compound that reversibly inhibits IDO enzyme activity at the catalytic site (including, without limitation, 1-methyl-tryptophan); "a noncompetitive IDO Inhibitor" is a compound that reversibly inhibits IDO enzyme activity at a non-catalytic site (including, without limitation, norharman); and "an irreversible IDO inhibitor" is a compound that irreversibly destroys IDO enzyme activity by forming a covalent bond with the enzyme (including, without limitation, cyclopropyl/aziridinyl tryptophan derivatives). IDO inhibitors include, without limitation, 1-methyl-DL-tryptophan (1MT; Sigma-Aldrich; St. Louis, Mo.), β-(3-benzofuranyl)-DL-alanine (Sigma-Aldrich), beta-(3-benzo(b)thienyl)-DL-alanine (Sigma-Aldrich), 6-nitro-L-tryptophan (Sigma-Aldrich), indole 3-carbinol (LKT Laboratories; St. Paul, Minn.), 3,3'-diindolylmethane (LKT Laboratories), epigallocatechin gallate (LKT Laboratories), 5-Br-4-Cl-indoxyl 1,3-diacetate (Sigma-Aldrich), 9-vinylcarbazole (Sigma-Aldrich), acemetacin (Sigma-Aldrich), 5-bromo-DL-tryptophan (Sigma-Aldrich), 5-bromoindoxyl diacetate (Sigma-Aldrich), phenyl-TH-DL-trp (3-(N-phenyl-thiohydantoin)-indole) (Sigma-Aldrich), propenyl-TH-DL-trp (3-(N-allyl-thiohydantoin)-indole) (Asinex; Moscow, Russia), methyl-TH-DL-trp (3-(N-methyl-thiohydantoin)-indole) (Sigma-Aldrich), brassinin (LKT Laboratories), 5-methyl-brassinin (Mehta, et al. (1994) Anticancer Res., 14:1209-1213); 3,3'-diindolylmethane (DIM; LKT Laboratories), indole-3-carbinol (I3C; LKT Laboratories), and the IDO inhibitors provided in U.S. patent application Ser. No. 10/550,444 and U.S. Provisional Application 60/730,706. IDO inhibitors may selectively or preferentially inhibit IDO1 (an "IDO1 inhibitor") and/or IDO2 (an "IDO2 inhibitor"). IDO inhibitors include, without limitation, nucleic acid molecules (e.g., siRNA, antisense oligonucleotides), peptides, chemical compounds, and antibodies, or biologically active fragments thereof.

"Pharmaceutically acceptable" indicates approval by a regulatory agency of the Federal government or a state government. "Pharmaceutically acceptable" agents may be listed in the U.S. Pharmacopeia or other generally recognized pharmacopeia for use in animals, and more particularly in humans.

A "carrier" refers to, for example, a diluent, adjuvant, excipient, auxilliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

A "replicon" is any genetic element, for example, a plasmid, cosmid, bacmid, plastid, phage or virus, which is capable of replication largely under its own control. A replicon may be either RNA or DNA and may be single or double stranded. Generally, a "viral replicon" is a replicon which contains the complete genome of the virus. A "sub-genomic replicon" refers to a viral replicon that contains something less than the full viral genome, but is still capable of replicating itself. For example, a sub-genomic replicon may contain most of the genes encoding for the non-structural proteins of the virus, but not most of the genes encoding for the structural proteins.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The terms "percent similarity," "percent identity" and "percent homology," when referring to a particular sequence, are used as set forth in the University of Wisconsin GCG software program.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The term "oligonucleotides" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

Polymerase chain reaction (PCR) has been described in U.S. Pat. Nos. 4,683,195, 4,800,195, and 4,965,188, the entire disclosures of which are incorporated by reference herein.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989, Molecular Cloning: A Laboratory Manual, Cold Spring Harbor Laboratory Press):

$$T_m = 81.5°\ C. + 16.6\ \text{Log}\ [Na+] + 0.41(\%\ G+C) - 0.63(\%\ \text{formamide}) - 600/\#\text{bp in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 μg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 μg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 μg/ml denatured salmon sperm DNA at 42° C., and washed in 0.1×SSC and 0.5% SDS at 65° C. for 15 minutes.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

The term "gene" refers to a nucleic acid comprising an open reading frame encoding a polypeptide, including both exon and (optionally) intron sequences. The nucleic acid may also optionally include non-coding sequences such as promoter or enhancer sequences. The term "intron" refers to a DNA sequence present in a given gene that is not translated into protein, is generally found between exons, and is "spliced out" during processing of the mRNA transcript. As used herein, the term "exon" refers to a nucleic acid sequence found in genomic DNA that is predicted and/or experimentally confirmed to contribute contiguous sequence to a mature (e.g., spliced) mRNA transcript and/or is translated into protein.

As used herein, the phrase "splice variants" refers to RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule, which may encode different amino acid sequences. The term splice variant may also refer to the proteins encoded by the above RNA molecules. As used herein, the phrase "alternative splicing" includes all types of RNA processing that lead to expression of plural protein isoforms from a single gene. As such, the phrase "splice variant" embraces mRNAs transcribed from a given gene that, however processed, collectively encode plural protein isoforms. For example, and by way of illustration only, splice variants can include exon insertions, exon extensions, exon truncations, exon deletions, alternatives in the 5' untranslated region and alternatives in the 3' untranslated region.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expression of jellyfish GFP in vertebrates. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

The term "enhancers" or "enhancer" as used herein can refer to a DNA sequence that is located adjacent to the DNA sequence that encodes a recombinant product. Enhancer elements are typically located upstream of a promoter element or can be located downstream of or within a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

The terms "transfected" and "transfection" as used herein refer to methods of delivering exogenous DNA into a cell. These methods involve a variety of techniques, such as treating cells with high concentrations of salt, an electric field, liposomes, polycationic micelles, or detergent, to render a host cell outer membrane or wall permeable to nucleic acid molecules of interest. These specified methods are not limiting and the invention relates to any transformation technique well known to a person of ordinary skill in the art.

An "antibody" or "antibody molecule" is any immunoglobulin, including antibodies and fragments thereof, that binds to a specific antigen. The term includes polyclonal, monoclonal, chimeric, single domain (Dab) and bispecific antibodies. As used herein, antibody or antibody molecule contemplates recombinantly generated intact immunoglobulin molecules and immunologically active portions of an immunoglobulin molecule such as, without limitation: Fab, Fab', $F(ab')_2$, F(v), scFv, $scFv_2$, scFv-Fc, minibody, diabody, tetrabody, single variable domain (e.g., variable heavy domain, variable light domain), bispecific, Affibody® molecules (Affibody, Bromma, Sweden), and peptabodies (Terskikh et al. (1997) PNAS 94:1663-1668).

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diptheria toxin, *Pseudomonas* exotoxin, and others listed above); alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). In a particular embodiment, the chemotherapeutic agent is selected from the group consisting of: placitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

II. Nucleic Acid Molecules

Nucleic acid molecules encoding the IDO2 proteins of the invention may be prepared by two general methods: (1) synthesis from appropriate nucleotide triphosphates and (2) isolation and/or amplification from biological sources. These methods utilize protocols well known in the art. The availability of nucleotide sequence information, such as the sequences provided herein, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides may be synthesized in stages, due to any size limitations inherent in the oligonucleotide synthetic methods.

Nucleic acid sequences encoding the IDO2 proteins of the invention may be isolated from appropriate biological sources using methods known in the art. In one embodiment, a cDNA clone is isolated from a cDNA expression library, preferably of human origin. In an alternative embodiment, utilizing the sequence information provided by the cDNA sequence, genomic clones encoding altered IDO2 proteins may be isolated. Additionally, cDNA or genomic clones having homology with human and mouse IDO2 may be isolated from other species using oligonucleotide probes corresponding to predetermined sequences within the human and mouse IDO2 encoding nucleic acids.

Figure 13:
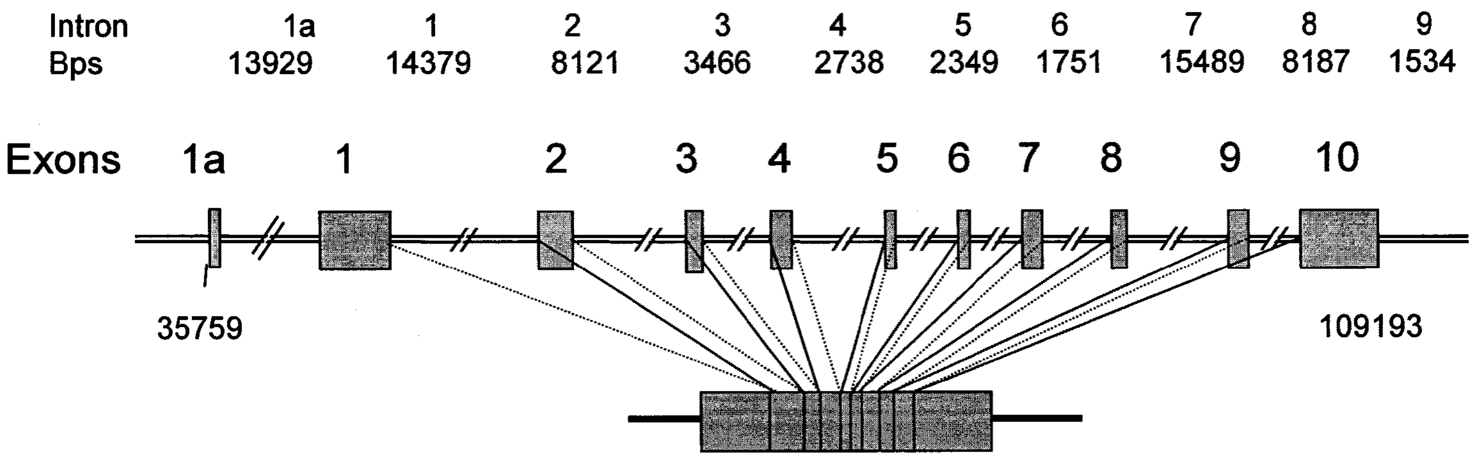

The present invention also encompasses splice variants of IDO2. FIGS. 1C and 13 provide a schematic of the locations of the introns and exons of IDO2. Generally, IDO2 comprises 10 or 11 exons depending on whether exon 1a is included. The genomic region is about 73234 basepairs from the start codon ATG to the stop codon TAG with about 1266 coding bases. FIG. 14 provides a nucleotide sequence of IDO2 comprising all exons.

Exemplary nucleotide sequences encoding human IDO2 are SEQ ID NOs: 8, 9, 12, 15, 20, and 21 and exemplary nucleotide sequences encoding mouse IDO2 are SEQ ID NOs: 10, 11, 13, and 14. The nucleotide sequence of certain splice variants and mutants are also provided in SEQ ID NOs: 22-25. An IDO2 nucleotide sequence may have 75%, 80%, 85%, 90%, 95%, 97%, or 99% homology with any of these nucleic acid molecules.

The instant invention also encompasses IDO2 nucleic acid molecules which lack at least one of the 11 exons depicted in FIGS. 13 and 15A-15Y. For example, the IDO2 nucleic acid molecule may lack any one of the eleven exons (e.g., IDO2 Δ1a, IDO2 Δ1, IDO2 Δ2, IDO2 Δ3, IDO2 Δ4, IDO2 Δ5, IDO2 Δ6, IDO2 Δ7, IDO2 Δ8, IDO2 Δ9, and IDO2 Δ10). The nucleic acid molecule may also lack 2, 3, 4, 5, 6, 7, 8, 9, or 10 exons, wherein the exons are either consecutive or nonconsecutive. In a particular embodiment, the IDO2 splice variants are selected from the group consisting of: IDO2 Δ1a, IDO2 Δ3/4/6, IDO2 Δ8, IDO2 Δ6/8, and IDO2 Δ4/5.

The instant invention also encompasses allelic variants and mutants of IDO2. Natural allelic variants of the instant invention include, without limitation, IDO2 R235W and IDO2 Y332stop.

In accordance with the present invention, nucleic acids having the appropriate level of sequence homology with a nucleic acid molecule encoding IDO2 may be identified by using hybridization and washing conditions of appropriate stringency.

Nucleic acids of the present invention may be maintained as DNA in any convenient vector. IDO2 encoding nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention.

Also encompassed in the scope of the present invention are oligonucleotide probes which specifically hybridize with the IDO2 nucleic acid molecules of the invention. Primers capable of specifically amplifying IDO2 encoding nucleic acids described herein are also contemplated herein. As mentioned previously, such oligonucleotides are useful as probes and primers for detecting, isolating or amplifying altered IDO2 genes.

It will be appreciated by persons skilled in the art that variants (e.g., allelic variants) of IDO2 sequences exist, for example, in the human population, and must be taken into account when designing and/or utilizing oligonucleotides of the invention. Accordingly, it is within the scope of the present invention to encompass such variants, with respect to the IDO2 sequences disclosed herein or the oligonucleotides targeted to specific locations on the respective genes or RNA transcripts. Accordingly, the term "natural allelic variants" is used herein to refer to various specific nucleotide sequences of the invention and variants thereof that would occur in a human population. The usage of different wobble codons and genetic polymorphisms which give rise to conservative or neutral amino acid substitutions in the encoded protein are examples of such variants. Such variants would not demonstrate altered IDO2 activity or protein levels. Additionally, the term "substantially complementary" refers to oligonucleotide sequences that may not be perfectly matched to a target sequence, but such mismatches do not materially affect the ability of the oligonucleotide to hybridize with its target sequence under the conditions described.

The present invention also encompasses antisense nucleic acid molecules which may be targeted to translation initiation sites and/or splice sites to inhibit the expression of IDO2. Such antisense molecules are typically between about 15 and about 30 nucleotides in length and often span the translational start site of mRNA molecules. Antisense constructs may also be generated which contain the entire IDO2 sequence in reverse orientation. Antisense oligonucleotides targeted to any known nucleotide sequence can be prepared by oligonucleotide synthesis according to standard methods.

Small interfering RNA (siRNA) molecules designed to inhibit expression of IDO2 are also encompassed in the instant invention. Typically, siRNA molecules are double-stranded RNA molecules between about 12 and 30 nucleotides in length, more typically about 21 nucleotides in length (see Ausubel et al.). Exemplary siRNAs for human and mouse IDO2 are provided in FIGS. 20A and 20B, respectively.

Several methods of modifying oligodeoxyribo-nucleotides are known in the art. For example, methylphosphonate oligonucleotide analogs may be synthesized wherein the negative charge on the inter-nucleotide phosphate bridge is eliminated by replacing the negatively charged phosphate oxygen with a methyl group. See Uhlmann et al., Chemical Review, 90: 544-584 (1990). Another common modification, which is utilized in a preferred embodiment of the present invention, is the synthesis of oligodeoxyribonucleotide phosphorothioates. In these analogs, one of the phosphate oxygen atoms not involved in the phosphate bridge is replaced by a sulphur atom, resulting in the negative charge being distributed asymmetrically and located mainly on the sulphur atoms. When compared to unmodified oligonucleotides, oligonucleotide phosphorothioates are improved with respect to stability to nucleases, retention of solubility in water and stability to base-catalyzed hydrolysis. See Uhlmann et al., supra at 548-50; Cohen, J. S. (ed.) *Oligodeoxynucleotides: Antisense Inhibitors of Gene Expression*, CRC Press, Inc., Boca Raton, Fla. (1989).

Other modifications of oligodeoxyribonucleotides to produce stable, membrane permeable oligonucleotide analogs are commonly known in the art. For a review of such methods, see generally, Uhlmann et al., supra, and Cohen, supra which also describe methods for synthesis of such molecules. In addition, modified oligoribonucleotides may be utilized in the present invention. However, oligodeoxyribonucleotides are preferred due to their enhanced stability, ease of manufacture and the variety of methods available for analog synthesis.

Still other modifications of the oligonucleotides may include coupling sequences that code for RNase H to the antisense oligonucleotide. This enzyme (RNase H) will then hydrolyze the hybrid formed by the oligonucleotide and the specific targeted mRNA. Alkylating derivatives of oligonucleotides and derivatives containing lipophilic groups can also be used. Alkylating derivatives form covalent bonds with the mRNA, thereby inhibiting their ability to translate proteins. Lipophilic derivatives of oligonucleotides will increase their membrane permeability, thus enhancing penetration into tissue. Besides targeting the mRNAs, other antisense molecules can target the DNA, forming triple DNA helixes (DNA triplexes). Another strategy is to administer sense DNA strands which will bind to specific regulator cis or trans active protein elements on the DNA molecule.

Deoxynucleotide dithioates (phosphorodithioate DNA) may also be utilized in this invention. These compounds which have nucleoside-$OPS_2O$ nucleoside linkages, are phosphorus achiral, anionic and are similar to natural DNA. They form duplexes with unmodified complementary DNA. They also activate RNase H and are resistant to nucleases, making them potentially useful as therapeutic agents. One such compound has been shown to inhibit HIV-1 reverse transcriptase (Caruthers et al., INSERM/NIH Conference on Antisense Oligonucleotides and Ribonuclease H, Arcachon, France 1992).

In accordance with the present invention, antisense oligonucleotides and siRNA may be produced by expression of DNA sequences cloned into plasmid or retroviral vectors. Using standard methodology known to those skilled in the art, it is possible to maintain the antisense RNA-encoding DNA in any convenient cloning vector (see Ausubel et al., eds. *Current Protocols in Molecular Biology*, John Wiley and Sons, Inc., (2005)).

Various genetic regulatory control elements may be incorporated into antisense RNA-encoding expression vectors to facilitate propagation in both eukaryotic and prokaryotic cells. Different promoters may be utilized to drive expression of the antisense sequences, the cytomegalovirus immediate early promoter being preferred as it promotes a high level of expression of downstream sequences. Polyadenylation signal sequences are also utilized to promote mRNA stability. Sequences preferred for use in the invention include, but are not limited to, bovine growth hormone polyadenylation signal sequences or thymidine kinase polyadenylation signal sequences. Antibiotic resistance markers are also included in these vectors to enable selection of transformed cells. These may include, for example, genes that confer hygromycin, neomycin or ampicillin resistance.

Cells and transgenic animals comprising a nucleic acid encoding IDO2 are also encompassed by the instant invention. The term "transgenic animal" is intended to include any non-human animal, preferably vertebrate, in which one or more of the cells of the animal contain heterologous/exogenous nucleic acid encoding IDO2, optionally from a different species. IDO1 encoding nucleic acids may also be inserted. Non-human animals include without limitation, rodents, mice, rats, non-human primates, sheep, dog, cow, amphibians, zebrafish, reptiles, and the like. In a preferred embodiment, the animal is a mouse. In another embodiment, the transgenic animal comprising a heterologous nucleic acid encoding IDO2 has modulated (e.g., increased) susceptibility to cancer and/or infection by microbes (e.g., viruses, bacteria, pathogens) compared to a wild-type mouse. In another embodiment, these transgenic animals exhibit at least one of increased LIP production, decrease in LAPs, decreased activation of GCN2, decreased elf2-α phosphorylation, and modulation of production of pro-inflammatory cytokines.

IDO2 knockout animals are also encompassed by the instant invention. Modifications and/or deletions may render the naturally occurring gene nonfunctional, thereby producing a "knock out" transgenic animal (e.g., $IDO2^{-/-}$). In other words, the transgenic mice comprise homozygous null mutations in the endogenous IDO2 gene. The transgenic animal of the instant invention may comprise a genome comprising a disruption of an endogenous IDO2 gene, wherein the IDO2 gene disruption leads to the failure to express IDO2 and/or a functional IDO2 (e.g., an IDO2 which lacks tryptophan catabolism activity and/or heme binding). The disruption of the endogenous IDO2 can be obtained through the disruption (e.g., insertion of a nucleic acid sequence (e.g., selectable marker) or deletion (e.g., all or part)) of at least one exon. In a particular embodiment, exon 1 is disrupted. In another embodiment, exon 9 and/or 10 is disrupted. Knock-in animals are also encompassed in the present invention as transgenic IDO2 animals. In one preferred embodiment, the IDO2 gene or exons of IDO2 gene are flanked by site specific recombinase recognition sequences such as Cre/LoxP. These mice are conditional knock-out of IDO2 since the portion of the IDO2 gene flanked by the loxP sequences can be excised in vivo upon exposure to the site-specific recombinase Cre, provided into the genome of the offspring by crossing the knock-in IDO2 mouse with a transgenic mouse carrying the Cre recombinase under the control of a tissue-specific or inducible promoter.

The transgenic mouse may also comprise a knockout of the endogenous IDO1 gene. In a particular embodiment, the transgenic animal is devoid of IDO2 activity. In another embodiment, the transgenic animal has undetectable levels of IDO2. In yet another embodiment, the transgenic animal is fertile and transmits the homozygous null mutations to its offspring. In still another embodiment, the IDO2 knockout animal has modulated (e.g., decreased) susceptibility to cancer and/or infection by microbes (e.g., virus, bacteria, fungus, parasite, pathogen) compared to a wild-type animal. In another embodiment, the IDO2 knockout animals exhibit at least one of decreased LIP production, increase in LAPs, increased activation of GCN2, increased elf2-α (phosphorylation, and modulation of production of pro-inflammatory cytokines.

Transgenic animals of the instant invention may be useful for the establishment of a nonhuman model for diseases involving improper expression and/or regulation of IDO2. The transgenic animals may also be useful as in vivo models for drug screening studies for certain human diseases, and for eventual treatment of disorders or diseases associated with IDO2, such as, without limitation, diseases that have an autoimmune component, diseases associated with improper IDO1 and/or IDO2 expression and/or regulation, and the like. In a particular embodiment, the course of microbial infection in mice devoid of IDO2 activity (i.e., knockout) or comprising a heterologous/exogenous nucleic acid encoding IDO2 may be assessed by a) inoculating the transgenic mouse with a microbe; b) inoculating a wild type mouse with the same microbe; and c) determining whether the course of infection in the transgenic mice is altered to that observed in the wild-type mice, thereby determining whether mice devoid of IDO2 or expressing heterologous/exogenous IDO2 are more/less/equally susceptible to infection by the microbe. In yet another embodiment, the susceptibility to cancer instead of a microbe can be determined by the above method.

III. Proteins

IDO2 proteins of the present invention may be prepared in a variety of ways, according to known methods. The proteins may be purified from appropriate sources, e.g., transformed bacterial or animal cultured cells or tissues, by immunoaffinity purification. The availability of nucleic acid molecules encoding IDO2 protein enables production of the protein using in vitro expression methods and cell-free expression systems known in the art. In vitro transcription and translation systems are commercially available, e.g., from Promega Biotech (Madison, Wis.) or Gibco-BRL (Gaithersburg, Md.).

Alternatively, larger quantities of IDO2 protein may be produced by expression in a suitable prokaryotic or eukaryotic system. For example, part or all of a DNA molecule encoding for IDO2 may be inserted into a plasmid vector adapted for expression in a bacterial cell, such as *E. coli*. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

IDO2 protein produced by gene expression in a recombinant prokaryotic or eukaryotic system may be purified according to methods known in the art. A commercially available expression/secretion system can be used, whereby the recombinant protein is expressed and thereafter secreted from the host cell, and readily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

IDO2 protein of the invention, prepared by the aforementioned methods, may be analyzed according to standard procedures. For example, such protein may be subjected to amino acid sequence analysis, according to known methods.

The instant invention encompasses the amino acid sequences encoded by the nucleic acid molecules described herein. Exemplary amino acid sequences of human IDO2 are SEQ ID NO: 1, 2, and 29 and exemplary amino acid sequences of murine IDO2 are SEQ ID NO: 3 and 4. An IDO2 amino acid sequence may have 75%, 80%, 85%, 90%, 95%, 97%, or 99% homology with these sequences.

IV. Antibodies

The present invention also encompasses antibodies capable of immunospecifically binding to proteins of the invention. Specifically, the antibodies may specifically bind to IDO2 to the exclusion of IDO1. Alternatively, antibodies can be generated which recognize both IDO2 and IDO1. The antibodies may also be generated to bind IDO2 splice variants and mutants of the instant invention either in addition to IDO2 and/or IDO1 or to the exclusion of other IDO2 proteins. Polyclonal antibodies directed toward IDO2 protein and variants thereof may be prepared according to standard methods. In a particular embodiment, monoclonal antibodies are prepared, which react immunospecifically with the various epitopes of the IDO2 protein. Monoclonal antibodies may be prepared according to general methods known in the art. For example, polyclonal and monoclonal antibodies may be prepared as described in Current Protocols in Molecular Biology, Ausubel et al. eds. Antibodies may be prepared by chemical cross-linking, hybrid hybridoma techniques and/or by expression of recombinant antibody fragments expressed in host cells, such as bacteria or yeast cells. The antibody molecules may then be isolated and purified from the expression system. The antibodies optionally comprise a purification tag by which the antibody can be purified.

The purity of the antibody molecules of the invention may be assessed using standard methods known to those of skill in the art, including, but not limited to, ELISA, immunohistochemistry, ion-exchange chromatography, affinity chromatography, immobilized metal affinity chromatography (IMAC), size exclusion chromatography, polyacrylamide gel electrophoresis (PAGE), western blotting, surface plasmon resonance and mass spectroscopy.

Polyclonal or monoclonal antibodies that immunospecifically interact with IDO2 proteins can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

Additionally, target-specific antibodies, optionally selected by a functional assay, may be isolated. The crystal structure may then be obtained for the antibody. This structure yields a pharmacore upon which subsequent drug design can be based. Alternatively, the protein crystallography may be bypassed altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

V. Therapeutic Uses

The present invention also encompasses methods for tumor suppression. Specifically, a therapeutically effective amount of at least one IDO2 inhibitor (optionally one which does not inhibit IDO1) can be administered to a patient, in need thereof, for the treatment of cancer. Cancers that may be treated using the present protocol include, but are not limited to: prostate cancers, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma.

The at least one IDO2 inhibitor (optionally one which does not inhibit IDO1) may also be administered in combination with at least one signal transduction inhibitor (STI), as described, in the context of IDO inhibitors, in PCT/US04/05155 and PCT/US04/05154 and U.S. patent application Ser. Nos. 10/550,444 and 10/551,151, with at least one chemotherapeutic agent, and/or at least one immunomodulator, as described in U.S. patent application Ser. Nos. 10/550,444 and 10/551,151.

The present invention also encompasses pharmaceutical compositions comprising at least one of the IDO2 inhibitor(s) (optionally one which does not inhibit IDO1) in a pharmaceutically acceptable carrier. Such a pharmaceutical composition may be administered, in a therapeutically effective amount, to a patient in need thereof for the treatment of cancer. The pharmaceutical compositions may further comprise at least one STI, at least one chemotherapeutic agent, and/or at least one immunomodulator.

The present invention also encompasses methods for the treatment of chronic viral infections (see U.S. patent application Ser. Nos. 10/550,444 and 10/551,151). Specifically, a therapeutically effective amount of at least one IDO2 inhibitor (optionally one which does not inhibit IDO1) can be administered to a patient having a chronic viral infection. Additionally, at least one chemotherapeutic agent and/or at least one antiviral agent may be co-administered with the at least one IDO2 inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, and human immunodeficiency virus (HIV). Notably, parasitic infections (e.g. malaria) may also be treated by the above methods wherein compounds known to treat the parasitic conditions may also be co-administered.

Suitable antiviral agents include, without limitation: acyclovir; gangcyclovir; foscarnet; ribavirin; and antiretrovirals such as, for example, nucleoside analogue reverse transcriptase inhibitors (e.g., azidothymidine (AZT), ddl, ddC, 3TC, d4T), non-nucleoside reverse transcriptase inhibitors (e.g., efavirenz, nevirapine), nucleotide analogue reverse transcriptase inhibitors, and protease inhibitors.

The present invention also encompasses pharmaceutical compositions comprising at least one of the IDO2 inhibitor (optionally one which does not inhibit IDO1) in a pharmaceutically acceptable carrier for the treatment of chronic viral infections. Such a pharmaceutical composition may be administered, in a therapeutically effective amount, to a patient in need thereof for the treatment of a chronic viral infection. The pharmaceutical compositions may further comprise at least one chemotherapeutic agent and/or at least one antiviral agent.

The pharmaceutical compositions of the present invention can be administered by any suitable route, for example, by injection, by oral, pulmonary, nasal or other modes of administration. In general, pharmaceutical compositions of the present invention, comprise, among other things, pharmaceutically acceptable diluents, preservatives, solubilizers, emulsifiers, adjuvants and/or carriers. Such compositions can include diluents of various buffer content (e.g., Tris-HCl, acetate, phosphate), pH and ionic strength; and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, Pa. 18042) pages 1435-1712 which are herein incorporated by reference. The pharmaceutical composition of the present invention can be prepared, for example, in liquid form, or can be in dried powder form (e.g., lyophilized).

In yet another embodiment, the pharmaceutical compositions of the present invention can be delivered in a controlled release system, such as using an intravenous infusion, an implantable osmotic pump, a transdermal patch, liposomes, or other modes of administration. In a particular embodiment, a pump may be used (see Langer, supra; Sefton, CRC Crit. Ref. Biomed. Eng. (1987) 14:201; Buchwald et al., Surgery (1980) 88:507; Saudek et al., N. Engl. J. Med. (1989) 321: 574). In another embodiment, polymeric materials may be employed (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann. Neurol. (1989) 25:351; Howard et al., J. Neurosurg. (1989) 71:105). In yet another embodiment, a controlled release system can be placed in proximity of the target tissues of the animal, thus requiring only a fraction of the systemic dose (see, e.g., Goodson, in Medical Applications of Controlled Release, supra, (1984) vol. 2, pp. 115-138). In particular, a controlled release device can be introduced into an animal in proximity to the site of inappropriate immune activation or a tumor. Other controlled release systems are discussed in the review by Langer (Science (1990) 249:1527-1533).

IDO2 may also be used to tolerize the immune system for a desired antigen. The IDO2 may be delivered as a nucleic acid molecule and/or a protein, optionally in a pharmaceutically acceptable carrier. The IDO2 may be administered to antigen presenting cells with the desired antigen in vivo or in vitro. For example, the antigen presenting cells, optionally obtained from the patient to be treated, can be treated ex vivo and then administered to the patient. These methods may be used to treat, for example, diabetes, lupus, Myastenia Gravis, Crohn's disease, and other autoimmune disorders.

IDO2 inhibitors as described hereinabove may also be used to alter the immune system to become active against a particular antigen. The antigen may be "foreign", e.g., viral, bacterial, and tumor specific antigens. Alternatively, the antigen may be a "self" antigen, e.g., amyloid, scrappie prions, and other misfolded proteins. The administration of the IDO2 inhibitors to patients would helpful in treating disorders/diseases associated with the particular antigen. The IDO2 inhibitors may be administered to APCs in vivo, in vitro, or ex vivo. The APCs may be loaded with the antigen of interest.

IDO2 and IDO2 inhibitors may also be administered to patients in need thereof to modulate the production of pro-inflammatory cytokines (e.g., IL6, TNFα, CD14, IL-1β, IL-8, IL-12, MCP1, m-CSF, G-CSF, and iNOS). IDO2 inhibitors would decrease LIP production, thereby leading to an apparent increase in LAPs, which regulate pro-inflammatory cytokines. IDO2, administered as a nucleic acid molecule and/or protein, or agents which augment IDO2 expression levels or activity would increase LIP activity, thereby causing a decrease in LAP activities.

IDO2 may also be involved in the production of proteins possessing a modified tryptophan amino acid. Specifically, IDO2 may generate kynurenine tRNAs in place of tryptophan tRNAs. As such, kynurenine may be incorporated into a peptide. The ability to incorporate a modified amino acid into a protein implicates IDO2 as an epigenetic post transcriptional modifier of gene function. The modifications by IDO2 may relate not only to normal biological function but also encompass modifications which affect disease states. For example, modified or misfolded proteins due to the incorporation of IDO2 altered amino acids may be causative factors in several diseases or disorders including, without limitation, cancer, immune disease, Alzheimer's, prion disorders, metabolic disorders, cardiovascular disease, Parkinson's, Huntington's, age-related disorders, and neurological disorders. Indeed, it has been previously demonstrated that the nitrosylation of tryptophan in beta amyloid results in the misfolding of the protein and abnormal amyloid production. Similarly, the incorporation of kynurenine into a protein may provide a "normal" biological role in altering protein function. However, under chronic conditions brought about by over-expression or over-activity of IDO2 (such as a chronic inflammation), the incorporation kynurenine may lead to "abnormal" gene products and/or expression which could alter critical factors controlling cell growth, differentiation, and function. Accordingly, the administration of IDO2 inhibitors to patients having disorders or diseases associated with proteins altered by IDO2 may be therapeutic. In order to determine if IDO2 inhibition would be therapeutic for a particular disease, the proteins associated with the disease may be screened for the presence of kynurenine and/or screened to determine if the protein is misfolded.

In addition to the IDO2 inhibitors described hereinabove, the splice variants and mutants of the instant invention may be employed to inhibit IDO2 and/or IDO1 activity in a subject. As described hereinbelow in Example 2, IDO2 splice variants and mutants (e.g., natural allelic variants R235W and Y332stop) can inhibit the activity of IDO2. Accordingly, IDO2 splice variants and mutants and/or nucleic acid molecules encoding the IDO2 splice variants and mutants may be administered to a subject in accordance with the methods described hereinabove as an IDO2 inhibitor.

VI. Screening Methods

The biochemistry of IDO has been well established, the enzyme having first been isolated in 1963 (Higuchi, K., et al. (1963) Federation Proc. 22:243 (abstr.); Shimizu, T., et al. (1978) J. Biol. Chem. 253:4700-6). IDO is a monomeric, heme-containing oxidoreductase with a molecular weight of approximately 41 kDa. To maintain the active ferrous form during in vitro catalysis, the enzyme requires methylene blue in combination with either superoxide or a reductant such as ascorbic acid. In vivo, it is suggested that a flavin or tetrahydrobiopterin may fulfill the role of the methylene blue dye and that there is likely to be a specific site for noncompetitive IDO inhibitors. Active enzyme can be produced by expressing the cloned, His-tagged version of the mammalian gene in bacteria (Littlejohn, T. K., et al. (2000) Prot. Exp. Purif. 19:22-29). This provides a convenient source of enzyme for biochemical analysis. A conventional biochemical assay for IDO activity based on spectaphotometric measurement of the production of kynurenine (the hydrolysis product of N-formyl-kynurenine) from tryptophan (Daubener, W., et al. (1994) J. Immunol. Methods 168:39-47) may be used as the read-out for both the enzymatic and cell-based assays. An enzymatic assay provides a facile, high-throughput screen for identifying compounds with IDO inhibitory activity. This assay may also be used to determine Ki values for specific compounds, which is important for the development of SAR (structure activity relationship) around the different compound series. A cell-based assay can confirm the IDO inhibitory activity of identified compounds and address the initial issue of bioavailability—the ability of compounds to inhibit intracellular IDO. Specificity for IDO inhibition may be examined in the cell-based assay by comparing against the other known tryptophan catabolizing enzyme tryptophan dioxygenase (TDO, also referred to in the literature as TDO2).

Because of the homology between IDO1 and IDO2, methods employed for screening for inhibitors of IDO1 activity may be employed for screening compounds which modulate IDO2 activity of the IDO2 proteins described herein. Indeed, as demonstrated hereinbelow, IDO2 can produce kynurenine from tryptophan, thereby allowing the above enzyme assays to be employed with IDO2. Inhibitors may be specific for IDO2 or may effectively inhibit both IDO1 and IDO2. For example, D-1MT does not inhibit IDO1, but is an inhibitor of IDO2 activity. IDO inhibitors, as described hereinabove, may also be screened for their ability to inhibit IDO2. While the above describes the screening of compounds to identify inhibitors of IDO2, the screening assays can be employed to screen for modulators of IDO2 activity, e.g., for compounds that increase IDO2 expression levels or activity and/or compounds which decrease IDO2 activity.

In accordance with the present invention, the nucleotide sequences of both human and mouse IDO2 have been determined. For biochemical studies, IDO2 protein, optionally tagged with a purification tag which allows the isolation of the protein, may be expressed and isolated from an expression system. For example, C-terminal His-tagged IDO2 protein may be produced in *E. coli* using the IPTG-inducible pET5a vector system and isolated over a nickel column. The yield of the partially purified protein can be verified by gel electrophoresis and the concentration estimated by comparison to protein standards. To assay IDO2 enzymatic activity, a 96-well plate spectraphotometric assay for kynurenine production may be run following published procedures (Littlejohn, T. K., et al. (2000) Prot. Exp. Purif. 19:22-29; Takikawa, O., et al. (1988) J. Biol. Chem. 263:2041-8; see also U.S. patent application Ser. Nos. 10/550,444 and 10/551,151).

With regard to cell-based assays, cells, e.g., COS-1 cells and 293 cells, may be transfected (e.g., transiently transfected) with a plasmid expressing IDO2 (see Munn et al. (1999) J. Exp. Med. 189:1363-1372 for an exemplary method). Optionally, a companion set of cells is transfected with a TDO or IDO expressing plasmid. After transfection, the cells are contacted with the test compound. Subsequently, the supernatant can be spectraphotometrically assayed for kynurenine as described for the enzyme assay.

The following examples are provided to illustrate various embodiments of the present invention. The examples are illustrative and are not intended to limit the invention in any way.

Example 1

Reagents

Blasticidin (Invitrogen; Carlsbad, Calif.) was prepared as a 1000× solution at 5 mg/mL in sterile water and stored in 500 μL aliquots frozen at −20° C. Zeocin (Zeo; Invitrogen) was prepared as 100 mg/mL aliquots and stored frozen at −20° C.

Doxycycline (Dox; Sigma, St. Louis, Mo.) was prepared as a 20 mg/mL master stock in ethanol and stored frozen at −20° C. The working 100× stock (2 μg/mL) was prepared by diluting the master stock 1:10,000 in growth media. The working stock was stored in 500 μL aliquots and stored frozen and in the dark at −20° C.

1-Methyl-D-Tryptophan (1M-D-T; Sigma-Aldrich Cat # 45283) was solubilized in DMSO/0.1 NHCL as a 100 mM stock solution and stored in 100 μL aliquots at −20° C. 1-Methyl-L-Tryptophan (1M-L-T; Sigma-Aldrich Cat # 447439) was solubilized in DMSO/0.1 N HCL as a 100 mM stock solution and stored in 100 μL aliquots at −20° C. 1-Methyl-DL-Tryptophan (1M-DL-T; Sigma-Aldrich Cat # 860646) was solubilized in DMSO/0.1 N HCL as a 100 mM stock solution and stored in 100 μL aliquots at −20° C. 5-(indol-3-methyl)-3-methyl-2-thio-Hydantoin (MTH; Sigma-Aldrich Cat # M6006) was solubilized in DMSO as a 100 mM stock solution and stored in 100 μL aliquots at −20° C. L-Tryptophan (Tryp; Sigma-Aldrich Cat # T0254) was solubilized in DMSO as a 100 mM stock solution and stored in 100 μL aliquots frozen at −20° C.

Dulbecco's Modified Eagle Medium (DMEM) was obtained from Mediatech, Inc. (Herndon, Va.; Cat# 10-013-CV). Alpha minimum essential medium (α-MEM) was obtained from Invitrogen and contains ribonucleosides and deoxynucleosides/4 mM glutamax/1 mM sodium pyruvate and was stored at 4° C. Trypsin EDTA (1×) was obtained from Mediatech (Cat # 25-053-CI) 10 mL aliquots were stored frozen at −20° C. until use. Fetal bovine serum (FBS) was obtained from Hyclone (Logan, Utah; Cat # SV30014.03) and 50 mL aliquots were stored frozen at −20° C. until use. Penicillin/streptomycin 100× (Pen/Strep) was obtained from Mediatech (Cat# 30-002-C) which contained 10,000 I.U. Penicillin/mL and 10,000 μg/mL Streptomycin. L-Glutamine (L-glut) was obtained from Mediatech (Cat # 25-005-CV) as a 200 mM solution (29.23 mg/mL with 8.5 g/L NaCl). Opti-mem was obtained from Invitrogen (Cat # 31985-062) and stored in 10 mL aliquots at 4° C.

Antibodies to the phosphorylated eIF2α (anti-eIF2α-P (ser52)) were affinity purified. Rabbit polyclonal antibodies raised against the short amino acid sequence containing the phosphorylated Ser-52 (Santa Cruz Biotechnology, Santa Cruz, Calif., sc-12412). For Western blotting, anti-eIF2α-P was diluted at 1:200 in blocking buffer (PBS/0.1% tween-20, 3% w/v non-fat dry milk, phosphatase inhibitor cocktail (Calbiochem, La Jolla, Calif., Cat #524625)).

Antibodies to the c-terminal region of C/EBPβ were affinity purified rabbit polyclonal antibodies raised against a peptide corresponding to the C-terminus of C/EBPβ of rat origin (Santa Cruz Biotechnology, sc-150). For Western blotting anti-C/EBPβ was diluted at 1:200 in blocking buffer (PBS/0.1% tween-20, 3% w/v non-fat dry milk).

Anti-V5-Horse radish peroxidase (HRP) conjugated antibody was purchased from Invitrogen and stored at 4° C. For Western blotting anti-V5-HRP was diluted at 1:5000 in blocking buffer (PBS/0.1% tween-20, 3% w/v non-fat dry milk). Affinity purified goat anti-rabbit IgG antibody and affinity purified horse anti-mouse IgG antibody conjugated to HRP (Cell Signaling technologies, Danvers, Mass., cat #7074 and #7076, respectively) were typically diluted 1:1000 in blocking buffer (PBS/0.1% tween-20, 3% w/v non-fat dry milk).

GM-CSF was stored frozen at −20° C. as a 1000× solution (5 mg/mL). Interferon-γ (IFN-γ), IL-10, and lipopolysaccharide (LPS) were stored frozen at −20° C. as a 1000× solution.

Methods

Western Analysis: Cell lysates were prepared as follows:

Cells were removed from the dish by scrapping or pipetting in PBS and collected by centrifugation (2000 rpm/5 minutes). The supernatant was discarded and the cell pellet was lysed in RIPA buffer [50 mM Tris-HCl pH 7.4/150 mM NaCl/1% Triton x-100/1% Sodium deoxycholate/0.1% SDS] plus a protease inhibitor cocktail (Calbiochem Cat # 539134). Typically $5\times10^5$ cells were resuspended in 200 μL of RIPA buffer. Cells lysates were vortexed and incubated on ice or frozen at −20° C. until use. Prior to use lysates were clarified by centrifugation (10,000 rpm/15 minutes) and heat denatured at 95° C. in SDS/sample buffer (100 mM Tris/25% glycerol/2% SDS/0.01% bromophenol blue/25 mM DTT). Proteins were separated by PAGE using NuPAGE® Gels (Invitrogen) and transferred at 100 Volts on to Immobilon-NC Nitrocellulose membranes (Millipore, Billerica, Mass., Cat # HAHY00010) in transfer buffer (25 mM Tris pH 8.3/192 mM glycine/20% methanol). The protein containing membranes were typically blocked at room temperature for 1 hour in blocking buffer (PBS/0.1% tween-20, 3% w/v non-fat dry milk). Primary antibody was added to the blot in blocking buffer at the suggested dilution, incubated by shaking at room temperature for 1 hour or at 4° C. for 12-18 hours and washed 5-6 times in PBS/0.1% Tween. For secondary antibody applications, the secondary antibody containing HRP was added in blocking buffer at the appropriate dilution, incubated by shaking at room temperature for 1 hour, and washed 5-6 times in PBS/0.1% Tween. The western membranes were developed by Chemiluminescence using SuperSignal® West Pico substrate (Pierce, Rockford, Ill., Cat # 34078), exposed to autography film for an appropriate period of time (3 seconds to 18 hours), and developed.

Kynurenine detection assay: This assay measures the product of the indoleamine 2,3-dioxygenase conversion of L-tryptophan to N-formyl-kynurenine by acid hydrolysis to kynurenine, which is measured indirectly though the absorbance (480 nm) of imine produced by the reaction of the aromatic amino group of klynurenine with p-dimethylaminobenzaldehyde (Ehrlich's reagent) as described by Takikawa et al. (J. Biol. Chem. (1988) 263:2041-2048). Typically, 200 μL of media from the test sample is combined with 12.5 μL of 30% TCA and incubated at 50° C. for 30 minutes. Evaporation was avoided by sealing the rim of the plate or tubes with parafilm. Samples are clarified by centrifugation for 10 minutes at 3-10K rpm. 100 μL of the supernatant was removed to a fresh well in an assay plate and mixed with 100 μL of fresh Ehrlich's reagent (2% p-dimethylaminobenzaldehyde w/v with glacial acetic acid). The plates were incubated for 10-30 minutes at room temperature and the absorbance was read at 490 nm. Typically, assays were performed in triplicate and the data analyzed using Excel software program (Microsoft). Background/control samples were typically derived from media from uninduced cells or cells that lack IDO1/2 expression vectors. Typically, control values were averaged and subtracted from the sample values.

Surforhodamine B calorimeter assay: This assay is used to assess cell density and is based on the measurement of cellular protein content and performed as described Vichai and Kirtikara (Nature Protocols (2006) 1:1112). For a 96 well dish, sample wells were maintained in 200 μL of media and fixed by adding 100 μL of cold 10% (wt/v)TCA to each well and the plates were incubated at 4° C. for at least 1 hour. The supernatant may be removed and saved for Kynurenine detection assay. The plates are then washed four times by dipping the plate slowly into a 2 liter beaker of tap water. The wash is removed by gently flicking or blotting the plate. The water in the 2 liter beaker is changed after each wash. Any excess water was blotted and the plates were air dried. Plates can be stored indefinitely at room temperature at this stage. For analysis, 100 μL of 0.057% (wt/v) Surforhodamine B (SRB)/1% acetic acid (v/v) solution was added and the plates incubated at room temperature for 30 minutes. Plates were then rinsed four times in 1% acetic acid by dipping in a 2 L beaker of wash solution, as performed with the first wash. The plates were then allowed to air dry in an exhaust hood. Sample wells were then developed by adding 200 μL of 10 mM Tris base (pH 10.5), incubating at room temperature for 30 minutes with gentle shaking, and measuring the optical density (O.D.) at 510 nm. Typically samples were performed in triplicate and the data analyzed using Excel software program (Microsoft).

Cell Culture: 293-T-REx™ cells (Invitrogen) constitutively express a tet operator repressor protein and were maintained in DMEM/10% FBS/1XPen/Strep/2 mM L-glut/blasticidin (5 ng/mL) at 37° C. with a 5% $CO_2$ in air atmosphere and typically split prior to confluency. Cells were passaged by splitting the culture 1/10—by removing media by aspiration, washing 1× with PBS, incubating with 0.25% trypsin/EDTA until the cells detach, disbursing the cells in fresh growth media, and plating at 1/10 dilutions in fresh growth media. For long term cryopreservation, cells are detached from the plate as described above, collected by centrifugation, resuspended in freeze medium (growth medium/10% DMSO), stored in 1.8 mL cyropreservation vials (~2–5×$10^6$ cells per vial) in liquid nitrogen vapor storage tanks.

JawsII (ATCC CRL-11904) is an immortalized mouse dendritic cell line derived from the bone marrow of p53 knockout Blk/6 mouse (U.S. Pat. No. 5,648,219). Cells were maintained in DMEM/10% FBS supplemented with GM-CSF at 5 ng/mL and grown at 37° C. with a 5% $CO_2$ in air atmosphere. For maintenance floating cells are removed by pipetting. Detached cells were removed by rinsing in 0.25% trypsin/EDTA and pooled with the floating cells. Cells were collected by centrifugation (1000 rpm 1 minute) and resuspended in fresh media, and subcultured at a 1:2 ratio. For long term cryopreservation, floating and adherent cells were detached and pooled from the plate as described above, collected by centrifugation, resuspended in freeze medium (growth medium/5% DMSO), stored in 1.8 mL cyropreservation vials (~2–5×$10^6$ cells per vial) in liquid nitrogen vapor storage tanks.

Transfection: Typically, T-REx™ cells were transfected by lipofection whereby complexes are formed by mixing 1.6 μg of circular plasmid and 4 μL Lipofectamine 2000 (Invitrogen) in a final volume of 400 μL Optimem, as per protocol. These complexes were then added directly to expanding cultures of cells for a total of 6 to 20 hours. After 24-48 hours, cells were either split and placed in media and selection antibiotic (typically 100 ug/mL Zeo) or induced with Dox for transient expression.

RNA preparation: Total RNA was prepared from tissue and cultured cells using PureLink™ Micro-to-Midi Total RNA Purification System (Invitrogen, Cat # 12183-018). For RNA preparation from tissue, the tissue (~10 mg) was cut into small pieces and mixed with 500 μL of kit lysis buffer and passaged through a 21 G needle in lysis buffer several times until the lysate was well homogenized. Then the lystae was passaged over the spin homogenizer column (Invitrogen). The supernatants were then processed as standard lysates. Briefly 1 volume of 70% Ethanol was added to the lysates, mixed well by vortexing, and loaded on to the RNA spin column, as described. Following the first wash, the samples were treated with RNase-free Dnase-I on the column as described in the protocol. The RNA was eluted in nuclease-free water and immediately stored at −80° C. The concentration of RNA was determined spectrophotometrically (O.D. at 260 nm).

Reverse Transcription: c-DNA was prepared from total RNA that was reverse transcribed using ThermoScript™ RT-PCR system (Invitrogen) according to the manufacturer's protocol. Briefly, 1-2 μL of RNA ranging from 0.01 to 1 μg of total RNA was mixed with either a specific reverse strand primer (10 pm) or a random hexamer (50 ng), 1 mM dNTP, 1× cDNA synthesis buffer, 20 mM DTT/40 U RNaseOUT™, and 15 units of ThermoScript™ RT in a 20 μL volume. Reaction conditions varied, but typically the reaction was heated to 55° C. for 2 minutes and incubated at 52° C. for the specific primer for 60 minutes and terminated by heating at 85° C. for 5 minutes. For random priming the reactions were incubated at 25° C. for 20 minutes and then 50 minutes at 50° C.

PCR: Double stranded molecules were generated by PCR amplification under the appropriate cycling conditions (typically, 2 minute denaturation at 95° C.; followed by 30 cycles of 30 seconds at 95° C. (denaturation); 30 seconds at 55° C. (annealing); and 30 seconds at 72° C. (extension); and a final 2 minute extension at 72° C.). Typically, 50 μL reaction mixes contained template DNA (0.2-100 ng), 10 pmoles of each primer flanking the target sequence, 0.2 mM of each dNTPs, appropriate $MgCl_2$ concentrations (1-2.5 mM), and 3-4 units of Taq Polymerase. For cloning, PCR products were typically purified using a commercially available PCR product clean-up procedure (Promega or Qiagen) and eluted in sterile $dH_2O$.

Results

The complete open reading frames (ORF) of the murine and human IDO2 mRNA have been delineated and confirmed by sequence analysis by RT-PCR. The exons corresponding to the ORF have been mapped by comparison to the genomic sequence in the GenBank and Celera Databases.

Both IDO1 and IDO2 are present on chromosome 8. The distance between the coding regions varies between the sequences available for human and mouse. In the mouse, the distance between the last exon of IDO1 and the first exon of IDO2 is about 4500 bases. The distance between the two genes, as determined from the available human genomic region, is about 20,000 bases.

Amino acid sequences of human and murine IDO2 are provided in FIGS. 1 and 2, respectively. Coding regions of human and murine IDO2 are provided in FIGS. 4A and 4B, respectively. FIGS. 3A, 3C, and 3D provide sequence alignments of human IDO1 and IDO2 amino acid sequences, human and murine IDO2 amino acid sequences, and murine IDO1 and IDO2 nucleotide and amino acid sequences, respectively.

The complete coding regions of murine IDO1 and IDO2 were cloned in-frame with the V5/His TAG coding region in pcDNA4/TO (Invitrogen) which contains a regulatory region that is repressed by the tetracyclin regulated repressor (TetR). The complete coding regions of IDO1 and IDO2 were generated using gene specific primers [IDO2 5'KpnATG (TCCG-GTACCATGGAGCCTCAAAGTCAG, SEQ ID NO: 16) and IDO1 5'KpnATG (ATCCGGTACCATGGCACTCAG-TAAAATA, SEQ ID NO: 17)] and 3' primers that were gene specific and removed the termination codon [IDO2minstop (TGTCCTGGTGCTAAGGGTCAAGACAATTCT, SEQ ID NO: 18) and IDO1minus stop (TGAGTTGGCCTAAGGGT-CAAGACAATTCT, SEQ ID NO: 19)]. The IDO1and 2 coding regions where then cloned in-frame with the V5/His carboxyl terminal Tag in the pcDNA4 TO vector (Invitrogen).

Figure 5:
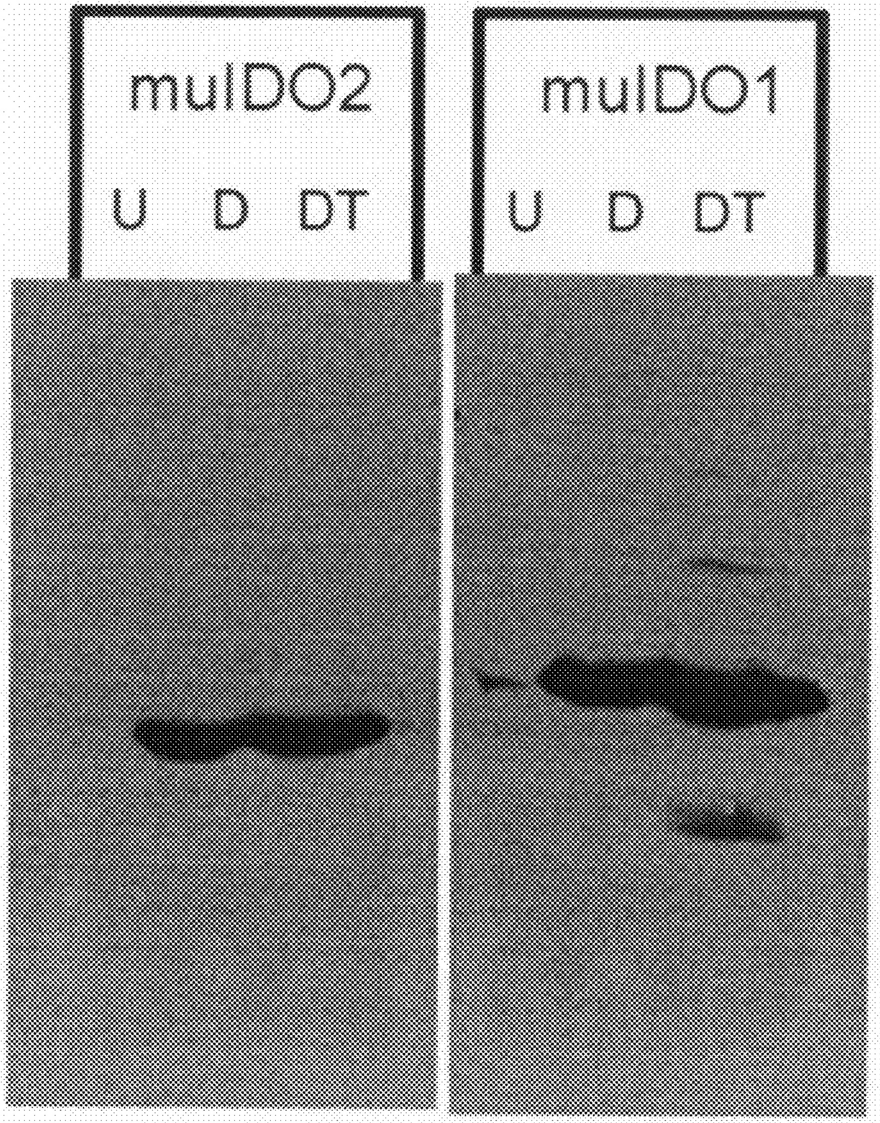
FIG. 5 provides a Western blot of murine IDO1 and IDO2 expression in T-REx™-293 cells. U is untreated cells, D is doxycycline treated cells, and DT refers to doxycycline and tryptophan treated cells.

Murine IDO1 and IDO2 were expressed as fusions with a C-terminal V5 epitope. Both were detected by Western blot analysis in T-REx™-293 cells following the addition of doxycycline (2 μg/mL) or doxycycline combined with tryptophan (100 μM) (FIG. 5). Little or no IDO1 or IDO2 was detected in the absence of doxycycline. IDO2 migrates slightly faster (apparent lower molecule weight) than IDO1. Both proteins were detected using an HRP-conjugated antibody to the V5 C-terminal tag (Invitrogen). Bound antibody was detected by chemiluminescence (SuperSignal® West Pico, Pierce).

Figure 6:
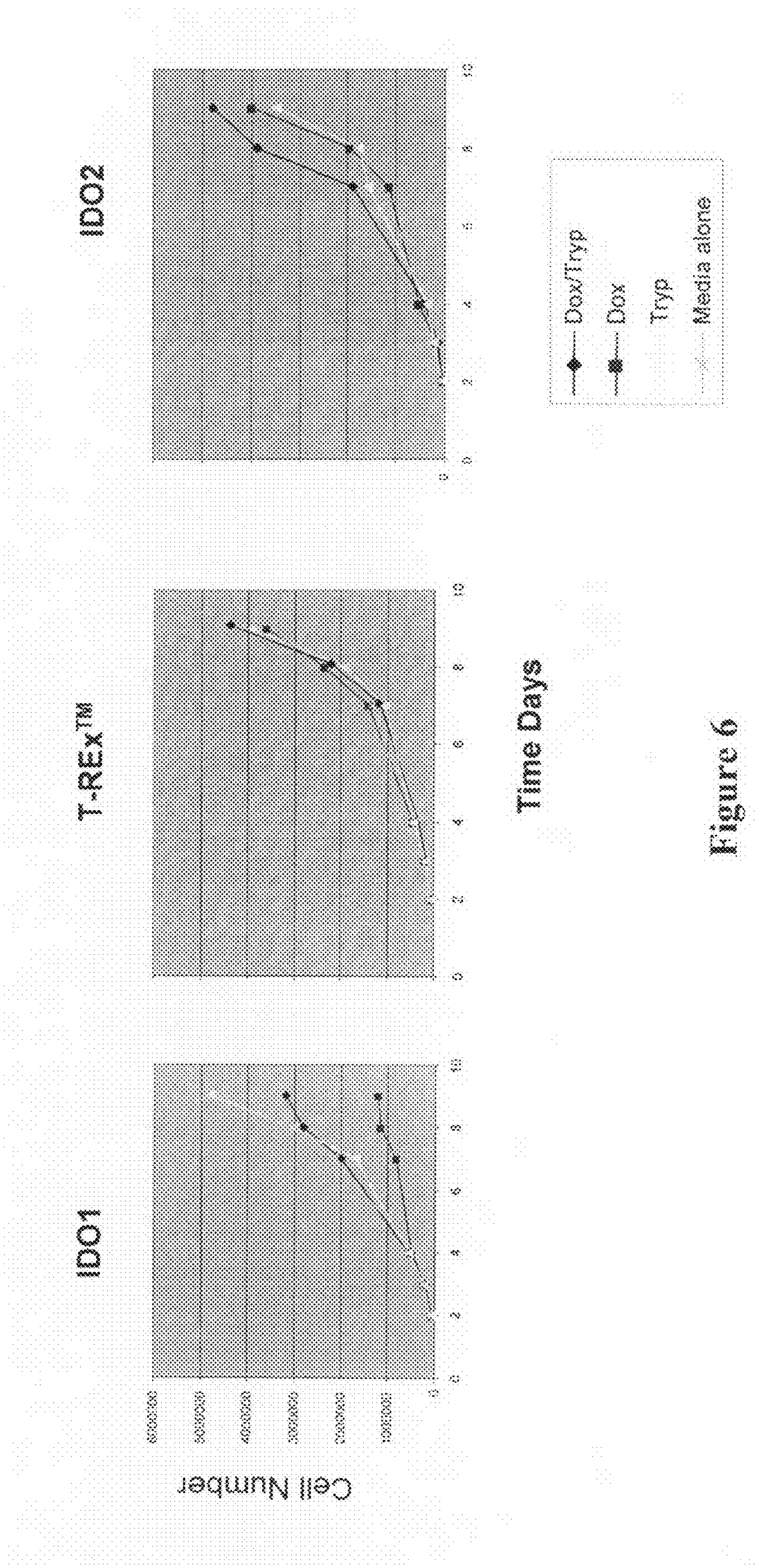
FIG. 6 provides graphs of the growth of T-Rex™ cells with no vector (center panel), pcDNA4TO-muIDO1 (left panel) or pcDNA4TO-muIDO2 (right panel). Cells were grown in media alone or in the presence of doxycycline, tryptophan, or both doxycycline and tryptophan.

The growth characteristics of T-REx™ expressing IDO1 and IDO2 were also examined. FIG. 6 shows that growth curves of the T-REx™ cells with no vector (center panel), pcDNA4TO-muIDO1 (left panel) or pcDNA4TO-muIDO2 (right panel). Cells were grown unsupplemented (media alone), or in the presence of doxycycline (Dox-20 ng/mL), tryptophan (Tryp-100 μM) or both doxycycline and tryptophan (Dox/Tryp). All cells grew normally in the absence of doxycycline (media alone) or in the presence of additional Tryptophan (100 μM). In the presence of doxycycline (20 ng/mL) the IDO1 expressing cells grow less well due to deprivation of tryptophan from the media. IDO1 expressing cells in the presence of doxycycline and tryptophan grew well until day 8-10. IDO2 expressing cells consistently grew better in the presence of doxycycline and tryptophan. For IDO2 containing cells, no significant changes in cell growth was observed following doxycycline or tryptophan additions alone. Similarly the growth characteristic of T-REx™ cells with no vector was unaffected by the doxycycline, tryptophan or dox/tryp treatments.

Figure 7:
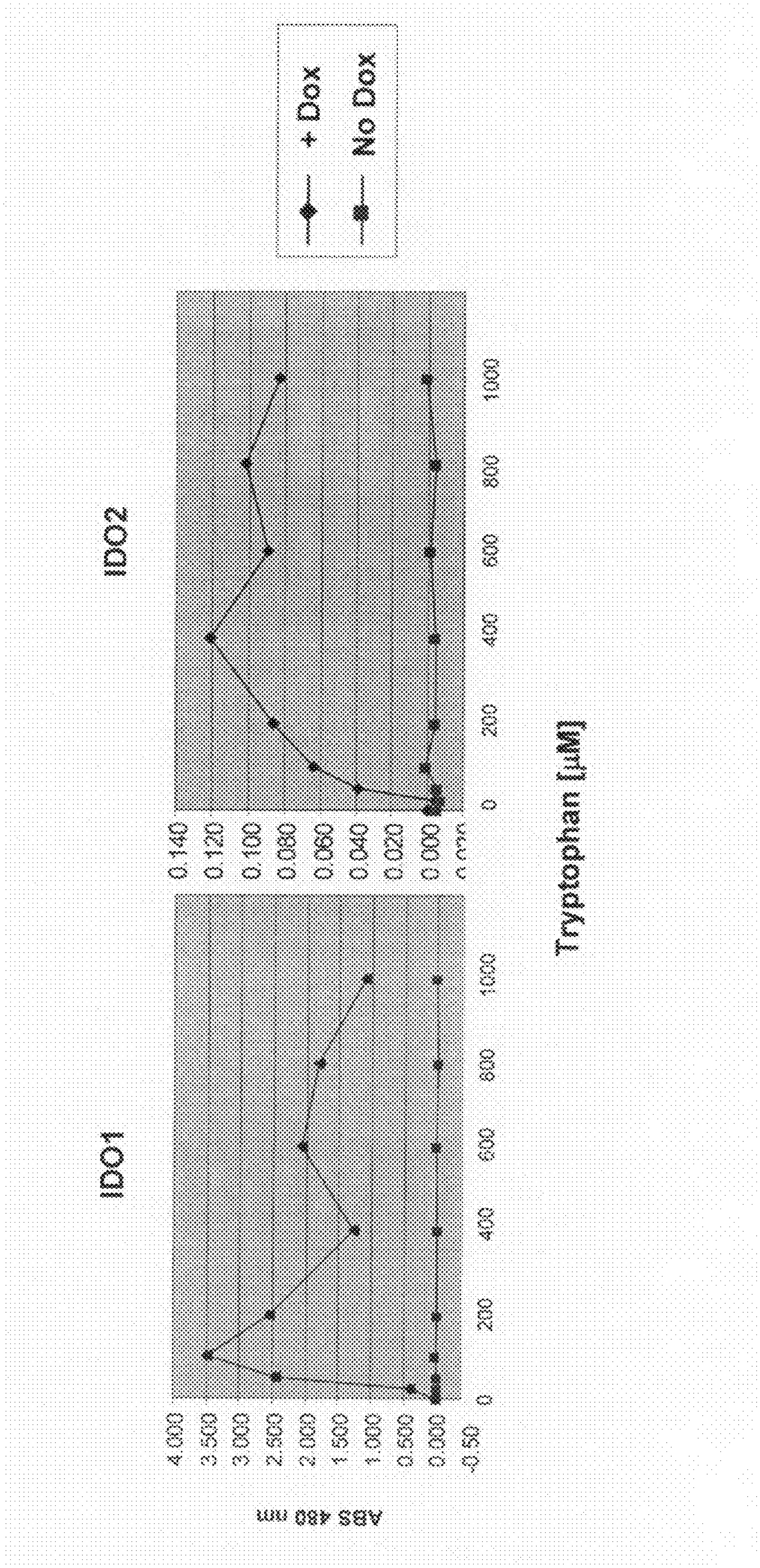
FIG. 7 provides graphs demonstrating the ability of IDO1 and IDO2 expressing 293 cells to metabolize tryptophan. A kynurenine assay was conducted to determine the ability of IDO1 and IDO2 expressing cells to metabolize tryptophan. The expression of IDO1 or IDO2 was induced by the presence of doxycycline. The cells were also exposed to increasing amounts of tryptophan.

The ability of IDO1 and IDO2 expressing 293 cells to metabolize tryptophan was also studied (FIG. 7). The kynurenine assay indicates that tryptophan is metabolized in IDO1 and IDO2 expressing cells. The assay was performed in triplicate on media harvested 72 hours in the absence of induction (no doxycycline) or following induction with doxycycline (20 ng/mL). Cells were also exposed to increasing amounts of supplemental tryptophan to the media (0 to 1000 μM). Significantly higher levels of kynurenine were detected in both IDO1 and IDO2 expressing cells when the tryptophan levels were higher than media alone. No significant kynurenine was detected in IDO2 expressing cells in the absence of supplemental tryptophan. These data suggest that IDO1 and IDO2 possess indoleamine dioxygenase activity. However the activity of IDO2 is far lower than that of IDO1 (note the abs scale is different between IDO1 and IDO2 experiments). Taken together these data suggest the IDO2, although possessing weak indoleamine dioxygenase activity, may have a different and preferred substrate than IDO1. Potential substrates of IDO2 include, without limitation, hydroxyl tryptophan, serotonin, melatonin, indoleacrylate, methyl-tryptamine, and indole-3-propanoate. Alternatively, IDO2 may require a co-factor for its full activation that is different that that present for IDO1.

Figure 8A:
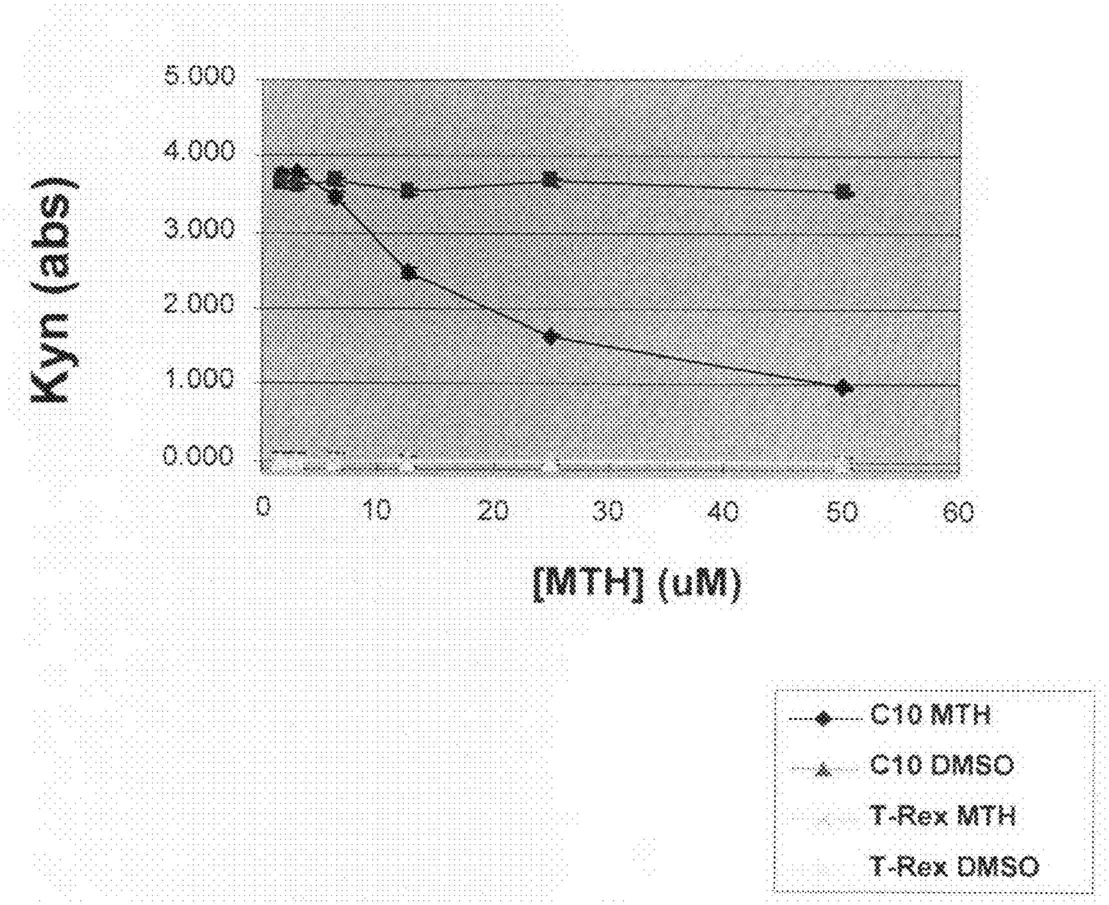
FIG. 8A provides a graph demonstrating the inhibition of IDO1 by methyl thiohydantione (MTH). T-Rex cells or IDO1 expressing T-Rex cells (C10) were treated with doxycycline in the presence of increasing concentrations of DMSO (carrier) or a known IDO1 inhibitor (MTH). The cells were maintained in growth media plus supplements for 5 days, after which the media was harvested and subjected to analysis for the presence of kynurenine.

IDO1 expressing 293 cells metabolize tryptophan and can be inhibited by methyl thiohydantione (MTH). T-REx™ cells or IDO1 expressing T-REx™ cells were treated with doxycycline in the presence of increasing concentrations of DMSO (carrier) or known IDO1 inhibitor (MTH). The cells were maintained in growth media plus supplements for 5 days, after which the media was harvested and subjected to analysis for the presence of kynurenine. The decrease in kynurenine production in the IDO1 expressing cells was observed in a dose dependent manner while no changes in kynurenne were observed in DMSO only treated cells (FIG. 8A). The control T-REx™ cells (no vector) do not produce any detectable kynurenine. The presence of inhibitor was not toxic to the cells. These data demonstrate the ability to use this cell based assay to assess indoleamine dioxygenase activity of IDO1 by using a known IDO1 inhibitor.

Figure 8B:
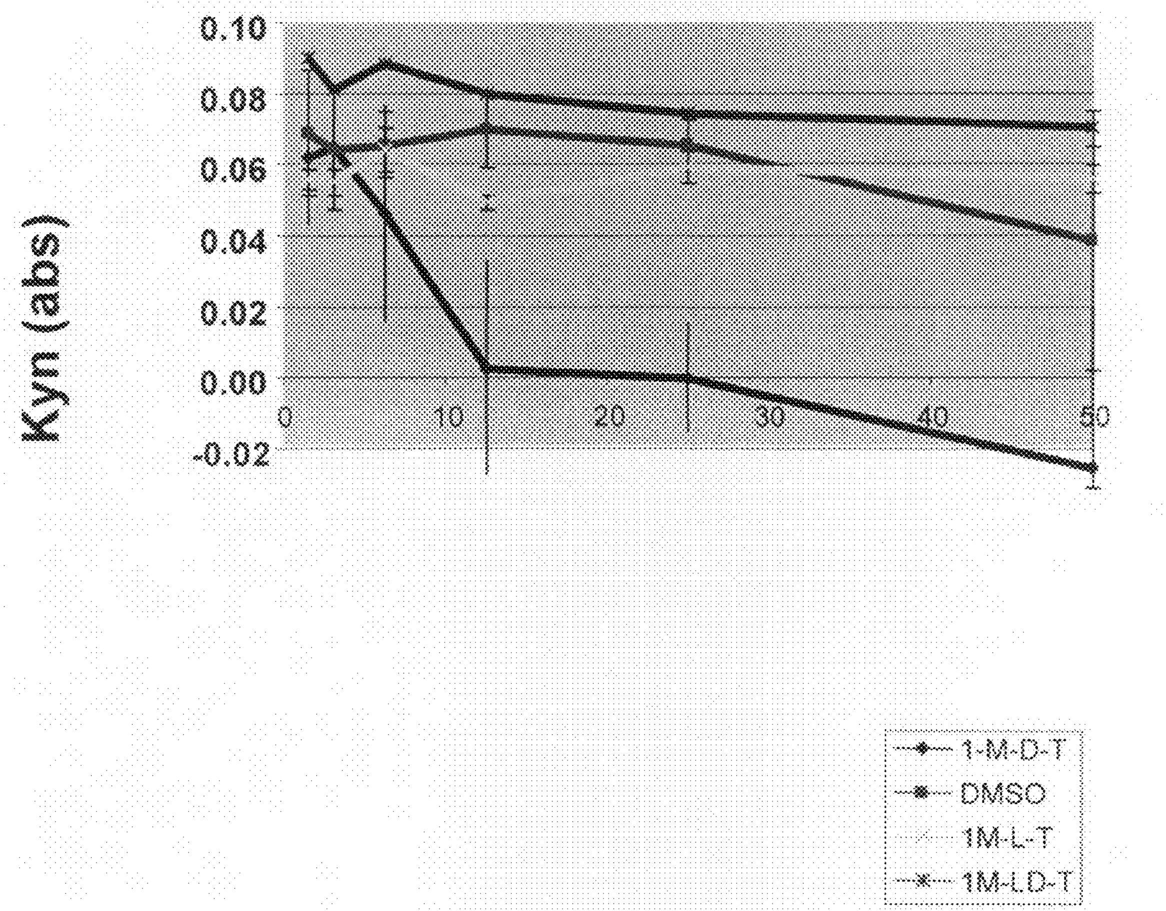
FIG. 8B provides a graph demonstrating that IDO2 metabolizes tryptophan and can be inhibited by 1-methyl-D-tryptophan (1M-D-T). IDO2 expressing T-Rex cells were treated with doxycycline in the presence of increasing concentrations of DMSO (carrier) or the D, L and mixed DL racemic isomers of 1-methyl-tryptophan, (1M-D-T, 1M-L-T and 1M-LD-T, respectively). The cells were maintained in growth media plus supplements for 5 days after which the media was harvested and subjected to analysis for the presence of kynurenine.

IDO2 expressing 293 cells metabolize tryptophan and can be inhibited by 1-methyl-D-tryptophan (1M-D-T). IDO2 expressing T-REx™ cells were treated with doxycycline in the presence of increasing concentrations of DMSO (carrier) or a variety of potential inhibitors, including the D, L and mixed DL racemic isomers of 1 methyl-tryptophan, (1M-D-T, 1M-L-T and 1M-LD-T, respectively) (FIG. 8B). The cells were maintained in growth media plus supplements for 5 days, after which the media was harvested and subjected to analysis for the presence of kynurenine. The decrease in kynurenine production in the IDO2 expressing cells was observed only with 1M-D-T in a dose dependent manner while no changes in kynurenine levels was observed in DMSO only treated cells or the other inhibitors. The control T-REx™ cells (no vector) do not produce any detectable kynurenine and were used as background absorbance values which were subtracted from the experimentally obtained values. The presence of inhibitor was not toxic to the cells.

Figure 9A:
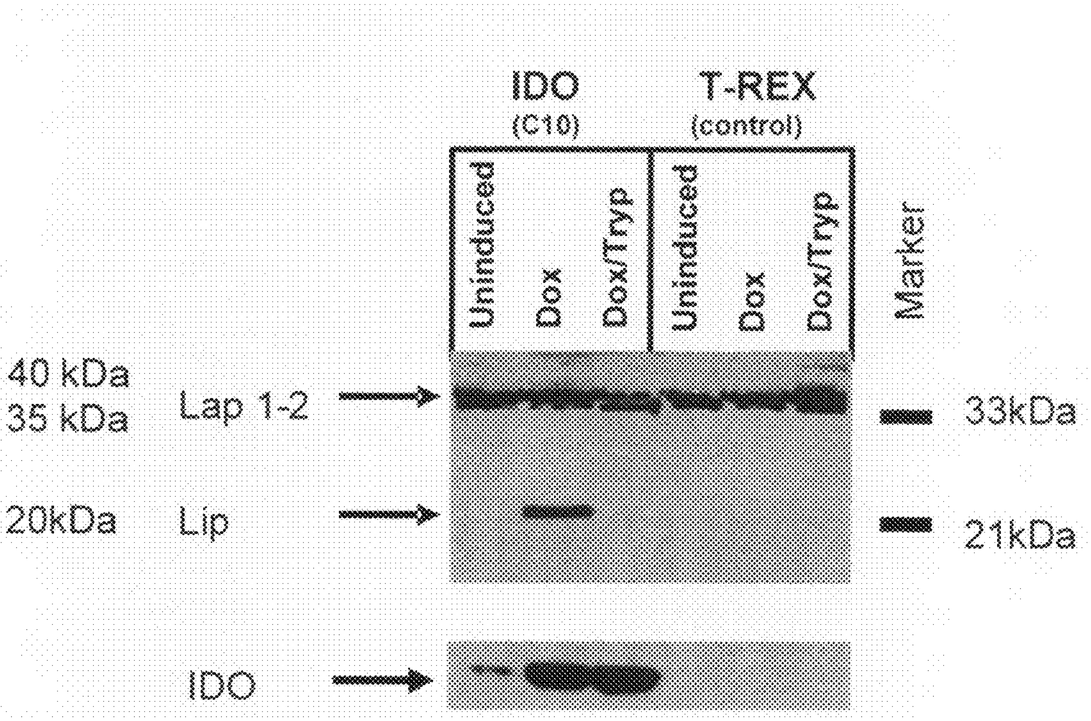
FIG. 9A is a Western blot demonstrating that IDO1 and tryptophan deprivation stimulates the expression of the LIP isoforms of NFIL-6. T-REx™ cells (control) and T-REx™ cells expressing IDO1 were either uninduced or induced with doxycycline in the presence or absence of added tryptophan (100 μM).

FIG. 9A demonstrates that IDO1 induces LIP expression. IDO1 is expressed in these cells when stimulated by doxycycline. When doxycycline is added to these cells, LIP is expressed (72 hours after stimulation). However, in the presence of exogenously added tryptophan (100 μM) the expression of LIP is eliminated; even when IDO1 is expressed. These data demonstrate that the LIP activation occurs via tryptophan deprivation, GCN2 activation, and differential LIP synthesis.

Figure 9B:
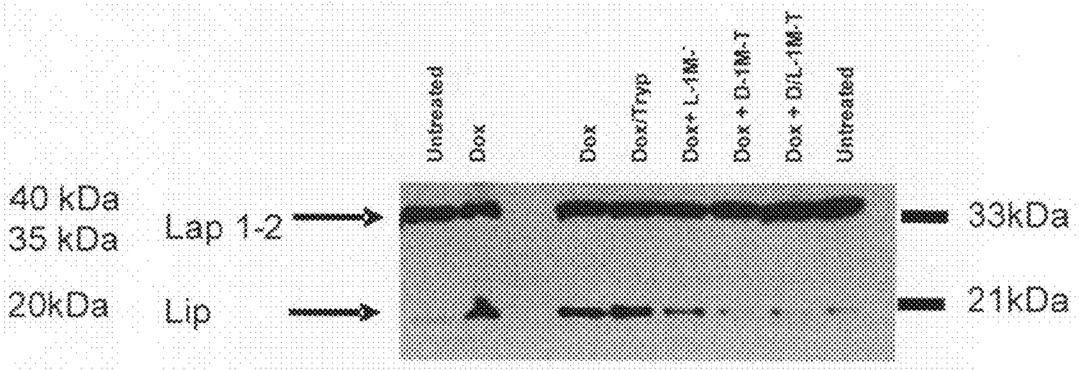
FIG. 9B is a Western blot demonstrating that IDO2, regardless of tryptophan levels, stimulates the expression of the LIP isoforms of NFIL-6. T-REx™ cells (control) and T-REx™ cells expressing IDO2 were either uninduced or induced with doxycycline in the presence or absence of added tryptophan. Cells were also optionally treated with the D, L and mixed DL racemic isomers of 1-methyl-tryptophan, (1M-D-T, 1M-L-T and 1M-LD-T, respectively).

FIG. 9B demonstrates that the same activation of LIP occurs following IDO2 activation, but it is not inhibited by excess tryptophan. These data show that IDO2 activates the same pathway leading to LIP activation but that this pathway is not dependent on tryptophan deprivation. Also this data shows that the IDO2 activation of LIP is inhibited by the D isoform and, to a lesser extent, the L isoform of 1 methyl tryptophan. The selectivity for the D isoform to inhibit IDO2's activation of LIP demonstrates that IDO2 and IDO1 activities can be distinguished pharmacologically.

Figure 9C:
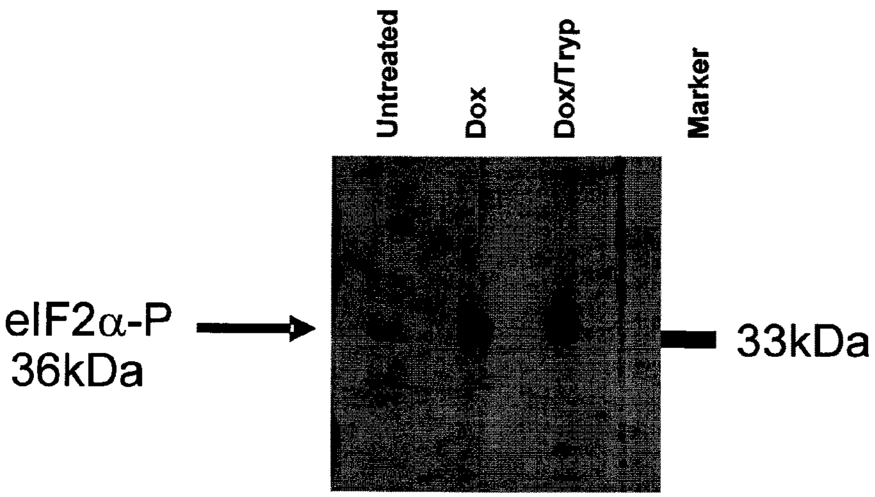
FIG. 9C is a Western blot demonstrating that IDO2 expression results in the phosphorylation of eIF2α. T-REx™ cells expressing IDO2 were either uninduced or induced with doxycycline in the presence or absence of added tryptophan.

FIG. 9C provides a Western blot demonstrating that, like IDO2's activation of LIP expression, IDO2 also activates the GCN2 kinase leading to elf2-α phosphorylation (the protein target of GCN2). This activity is dependent of IDO2 expression which is not inhibited by excess tryptophan. These data suggest that IDO2 functions within this pathway but the activation of GCN2 kinase, phosphorylation of elf2-alpha, and LIP expression is not dependent on tryptophan deprivation. Unlike IDO1, which activates GCN2 kinase pathway through the deprivation of tryptophan and can be relieved by exogenous tryptophan, the IDO2 mechanism of action is different and can not be relieved by exogenous tryptophan. Therefore, IDO2 functions more directly in activating the GCN2 pathway, perhaps by acting on the tryptophanyl-tRNA directly.

FIGS. 12A-12C provide schematics of murine and human IDO2 as well as primers which can be employed to amplify regions of IDO2.

Example 2

Figure 17:
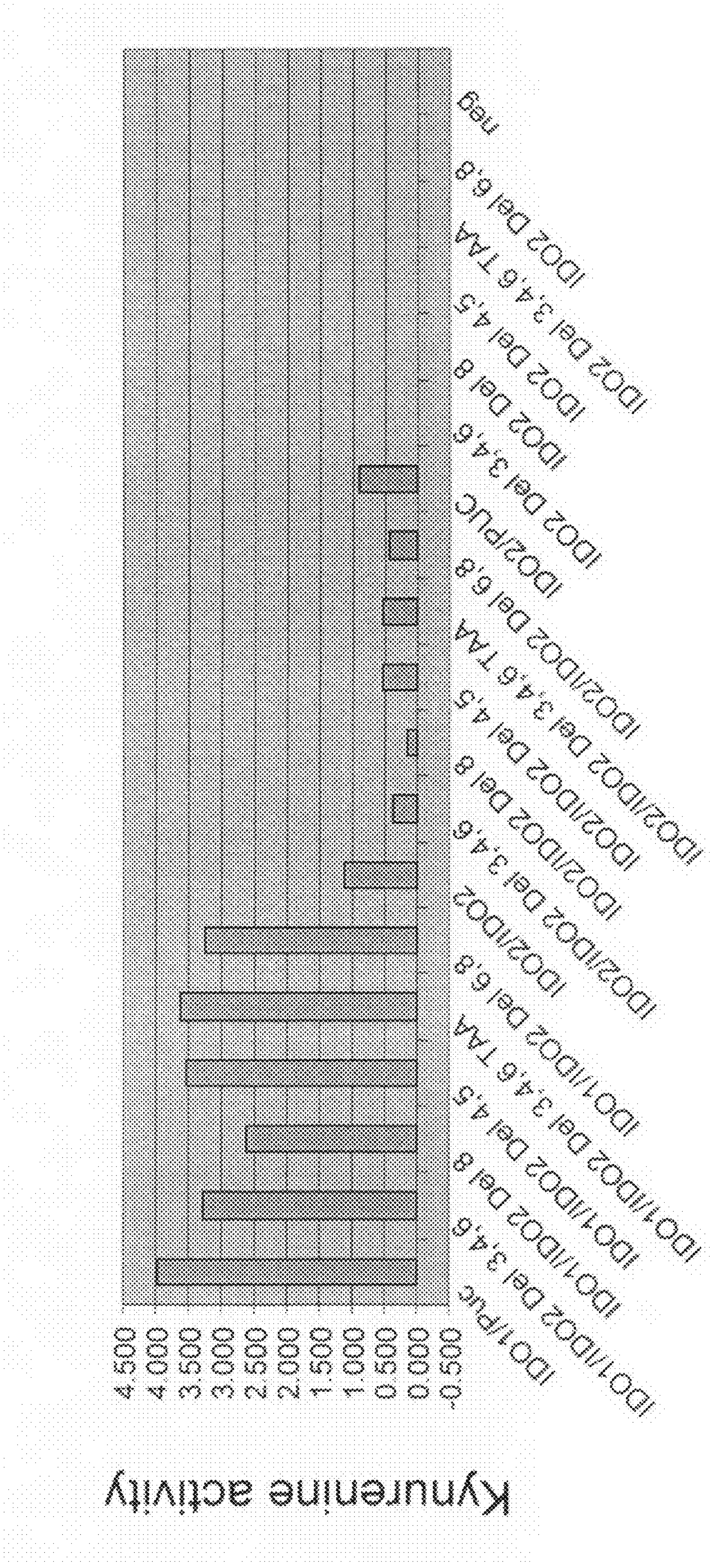
FIG. 17 is a graph of the kynurenine activity of various IDO2 splice variants or mutants alone or co-expressed with IDO2, IDO1, or empty vector (Puc).

Human IDO2 cDNAs were cloned from RNA isolated from normal human liver. Splice variants were identified which lead to alternative reading frames and/or early termination of the primary sequence of IDO2. These splice variants are IDO2 Δ3/4/6, IDO2 Δ8, IDO2 Δ6/8, and IDO2 Δ4/5. FIG. 16 provides the nucleotide sequences of these splice variants. Vectors comprising the splice variants were transiently transfected into 293 (T-Rex™) cells and a kynurenine detection assay was performed as described hereinabove to determine the presence of indole dioxygenase activity with the expressed IDO2 splice variants. As seen in FIG. 17, the tested splice variants did not possess detectable indole dioxygenase activity.

Two prominent single nucleotide polymorphisms (SNP) were also cloned. These two SNPs are not linked (i.e., they are not on the same allele) and are differentially represented in various populations as indicated by the SNP database. The R235W SNP encoded in exon 8 alters the arginine (R) present at amino acid position 235 to a tryptophan (W). The SNP at amino acid position 332 intoduces a stop codon at Tyrosine 332 (Y332stop). Both SNPs render the IDO2 molecule inactive when assayed for the production of kynurenine following a transient transfection assay as described hereinabove. As such these SNPs may be important indicators/markers for the propensity or resistance to certain disease states.

Additionally, as seen in FIGS. 15A-15Y and 16, an alternative splice site exists in exon 8 of IDO2, leading to an alternate sequence for exon 8.

When the alternatively spliced variants are co-expressed with either wild-type IDO1 or IDO2 lower, the indole dioxygenase activity, as assessed by the kynurenine detection assay, is reduced compared to wild-type IDO1 or IDO2 alone, even though IDO1 or IDO2 protein levels are the same in each reaction (see FIG. 17). These data indicate that an RNA or peptide product of the truncated IDO2 and/or alternatively spliced IDO2 may function to inhibit IDO1 and IDO2 activity. Such interactions may be dependent on direct or indirect protein-protein interactions between the truncated product and the full length IDO1 and IDO2 peptides. Alternatively the spliced variants may inhibit co-factor activity and the normal activation of IDO1/2 enzyme via changes in the oxidative state of the Fe component of coordinated Heme group. Nevertheless the negative interaction of these splice variants suggests the utility of a compound or peptide whose interaction with the splice variants or full length IDO1 or IDO2 will block the negative and inhibitory interactions resulting in increased IDO1 or IDO2 activity. Applications for such a compound or peptide include diseases that have an autoimmune component.

Example 3

Figure 18:
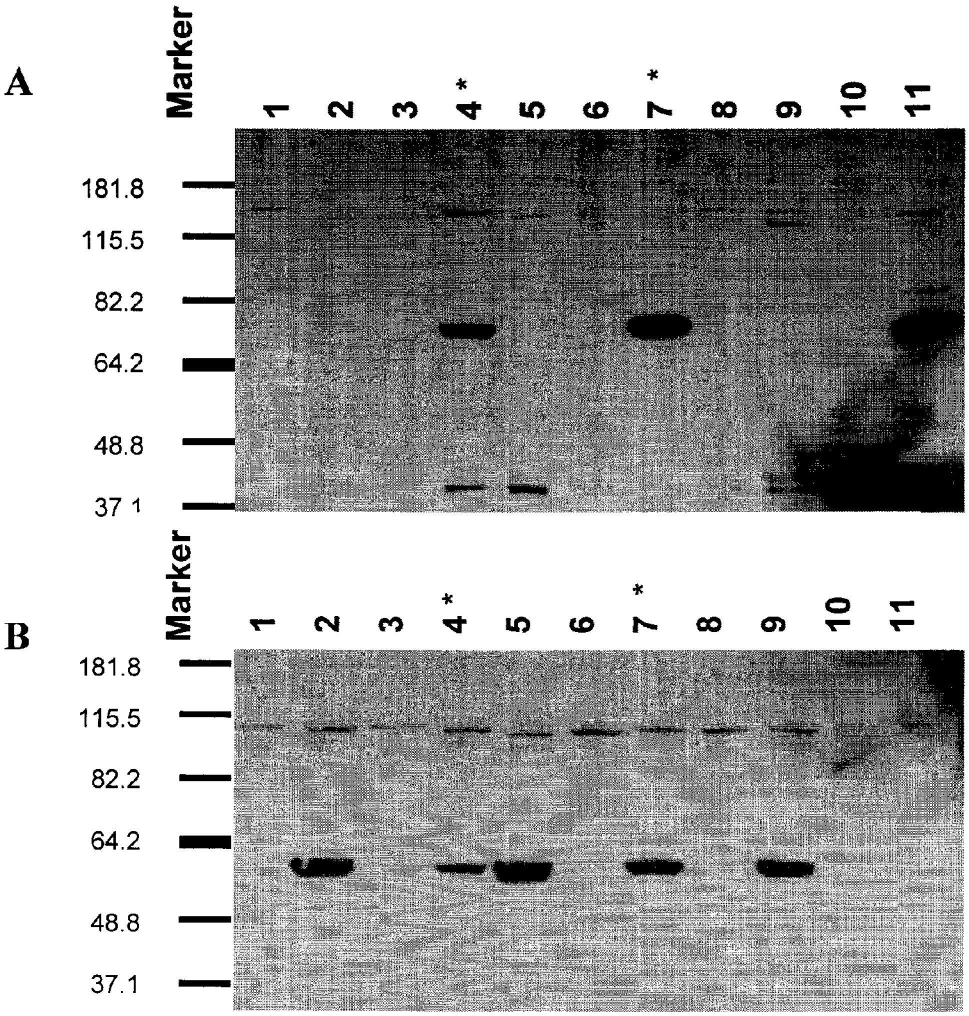
FIGS. 18A and 18B are images of Western blots of cellular lysates of 293 cells expressing the following: 1: no IDOs, 2: mouse IDO2 (WT), 3: human IDO2 (WT), 4: mouse IDO1/IDO2, 5: mouse IDO2, 6: mouse IDO2/1 chimera, 7: human IDO1/mouse IDO2, 8: human IDO2 (R-W), 9: mouse IDO2 (R-W), 10: hu8man IDO2 (Y-*), 11: human IDO1. The Western blot in FIG. 18A was probed with an anti-IDO1 polyclonal sera (1:200) and the Western blot in FIG. 18B was probed with an anti-muIDO2 monoclonal antibody (MAb 7.4.6; 1:100).

Monoclonal antibodies specific to mouse IDO2 were generated using standard techniques. FIG. 18 provides images of Western blots which demonstrate the species and IDO-isoform specificity of the generated monoclonal antibodies. Mouse or human IDO1 and/or IDO2 were expressed in 293 (T-REX) cells. Additionally, the R235W (R-W) and Y332stop (Y-*) isoforms of human and mouse IDO2 were also expressed in 293 (T-REX) cells. As seen in FIG. 18B, monoclonal antibodies derived from hybridoma clones (7.4.6, 7.4.9 and 8.8.6) are specific to mouse IDO2 protein and do not recognize the human or mouse IDO1 proteins (shown reacting with rabbit polyclonal sera directed to both human and mouse IDO1). FIG. 18A demonstrates the reactivity of an IDO1 polyclonal sera which recognizes both human and mouse IDO1.

Example 4

Figure 19:
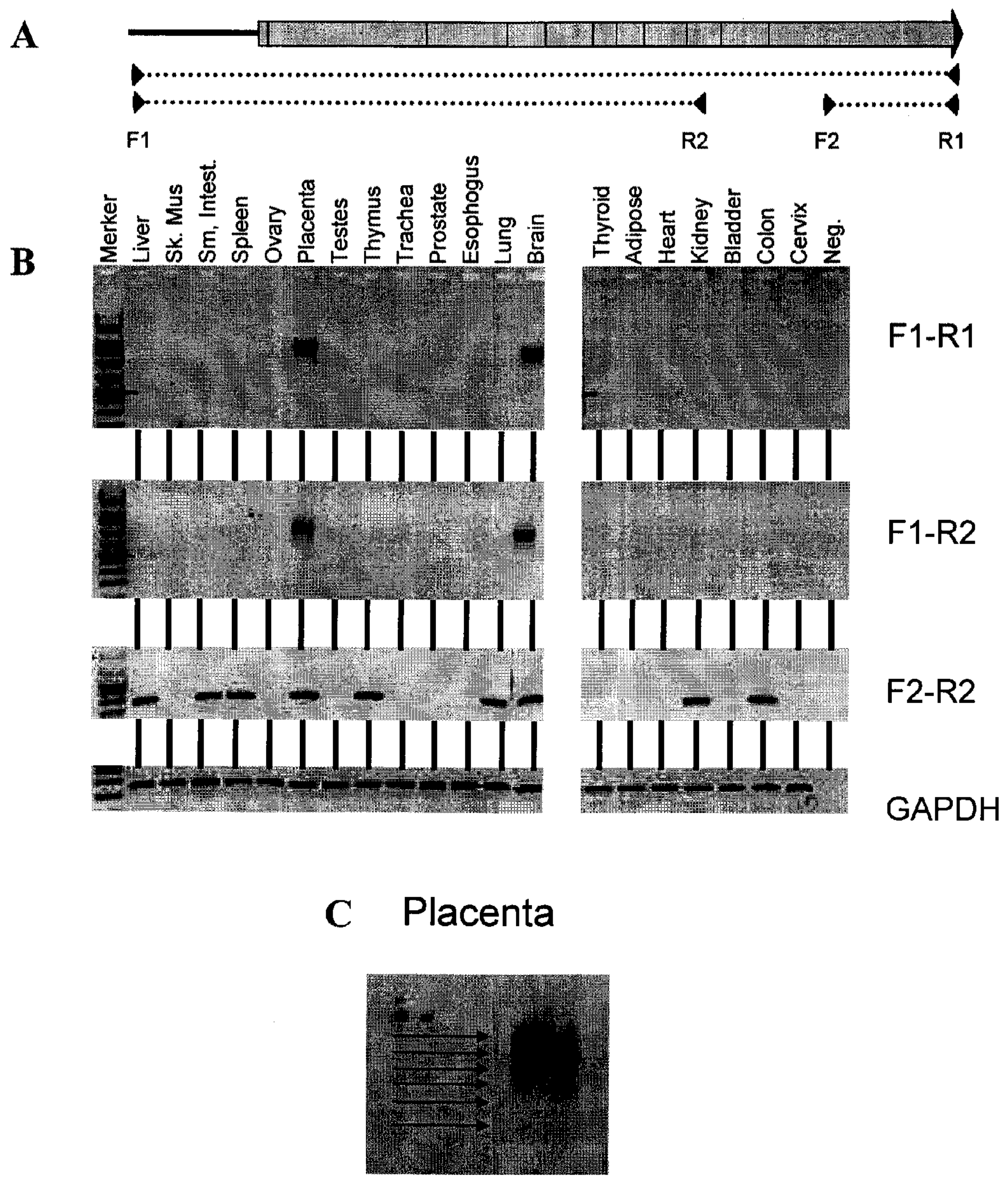
FIG. 19A is a schematic of human IDO2 mRNA and the location of the primers used for RT-PCR.
FIG. 19B provides images of the RT-PCR assays performed on total RNA from the indicated tissues. The primers used in the RT-PCR are indicated at the right of the panels and GAPDH is provided as a control.
FIG. 19C is an image of an agarose gel demonstrating the presence of various IDO2 isoforms in human placenta.

The tissue specific expression of human IDO2 was determined using T-PCR. A human tissue panel of total RNA (Ambion, Austin, Tex.) was analyzed by RT-PCR. The RT reaction utilized oligo-dt priming followed by the specific amplification using primers specific to different regions of the IDO2 mRNA (FIG. 19A). Primer F1 recognized a region in the 5' untranslated region of the mRNA. Transcripts containing this region of the gene (exon 1a) are detected only in the placenta and brain (FIG. 19B). In contrast, primers specific to the 3' end of the gene (primers spanning exons 9-10) demonstrated a broader pattern of expression. The presence of splice variants can be detected in both the placenta (FIG. 19C) and brain tissue. Without being bound by theory, this data suggests that there may be alternative promoters initiating at exon 1a and at exon 1, as exon 1 is more widely expressed than exon 1a. Primers F2-R2 were used because exons 9 and 10 are present in all splice variants detected so far.

Example 5

The present example describes the generation of an indoleamine 2,3-dioxygenase-2 (IDO-2) gene conditional knockout allele in mice using homologous recombination in mouse embryonic stem cells and subsequent blastocyst injection of the appropriate targeted ES cells.

The mouse IDO-2 gene is located on chromosome 8, only 6 kb downstream from the IDO gene. The fact that the two genes are so close together makes it less desirable to attempt to knock out IDO-2 function by eliminating the first exons. As described herein, IDO-2 is organized into ten exons. Exons 9 and 10 play a crucial role for the enzyme function. As such, a conditional allele that upon recombination will eliminate only these two exons was created.

RP23-339B16 BAC clone (which contains both IDO and IDO2 genes) was used for generating the homologous arms and the conditional KO region for the gene targeting vector, as well as the southern probes for screening targeted events. The recombination targeting vector (FIG. 21) will result in the Cre-dependent deletion of exons 9 and 10. Exons 9 and 10 were chosen because the analogous structural domain of IDO1 constitutes the major catalytic domain of the enzyme. Similarly in vitro mutagenesis studies on IDO2 demonstrate that this region is required for enzymatic activity.

Figure 21:
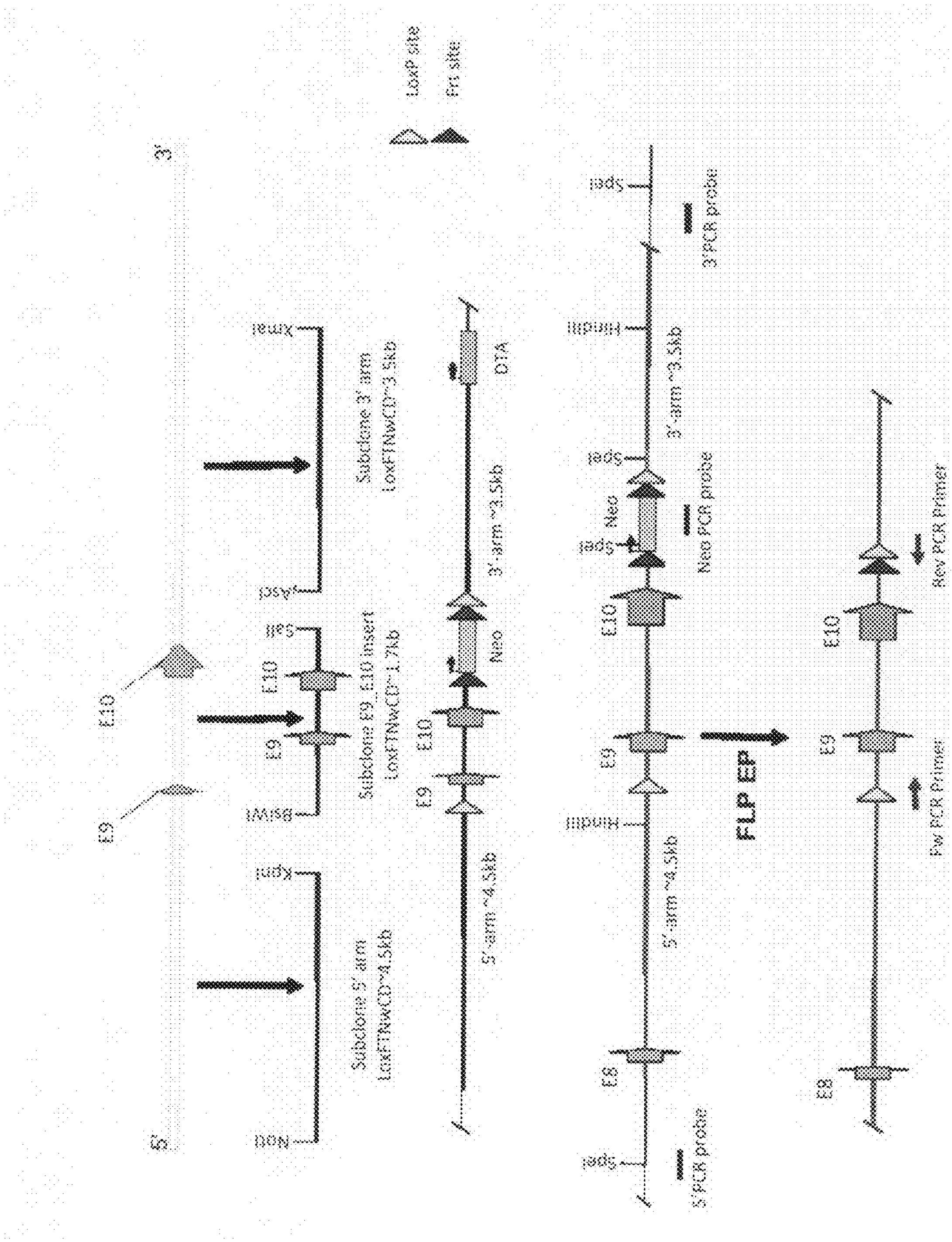
FIG. 21 is a schematic of a target vector strategy for the construction of a conditional IDO2 knockout mice strain. Removal of exons 9 and 10 in the IDO2 gene happens upon crossing with a transgenic Cre mouse expressing Cre recombinase under the control of tissue specific promoters.

As demonstrated in FIG. 21, the unconditional knock-out was generated using a positive (Neo) and negative (dipteria toxin A; DTA) selection approach, whereby the DNA construct possesses a DTA expression cassette distal from the homologous arms to negatively select for non-homologous recombination and a neomycin positive selection cassette flanked by the sites for the FLP recombinase. In addition, the targeting vector has two Lox-P sites for the Cre recombinase each flanking exons 9 and 10, which allows for the Cre-dependent excision of exons 9 and 10. Embryonic stem (ES) cells (C57/B16) were electroporated with the targeting construct and the surviving $Neo^R$ transfected clones were screened by Southern analysis to identify ES cells carrying targeted IDO2 alleles. Six of the ES cell clones containing the recombinant targeted conditional allele were electroporated with Flp recombinase-expressing plasmid to eliminate the neo cassette. Two positive FLP treated $Neo^{(-)}$ clones expanded for further analysis using long-range PCR and Southern analysis. Selected clones with normal karyotypes were either injected into blastocysts (to generate a conditional IDO2-knockout chimeric embryo) or electroporated with CRE recombinase to remove exons 9 and 10. Four CRE treated ES cell clones were identified to possess the proper exon 9/10 deletion using PCR analysis, expanded, and injected into blastocysts (to generate an IDO2 knockout chimeric mouse embryo).

The 5' homologous arm (4.5 kb), 3' homologous arm (3.5 kb) and conditional KO region (1.7 kb) were generated by PCR. The fragments were cloned in the LoxFtNwCD or (for sequencing purposes) PCR 4.0 vectors and confirmed by restriction digestion and end-sequencing.

The final vector was obtained by standard molecular cloning. Aside from the homologous arms, the final vector also contains loxP sequences flanking the conditional KO region (0.25 kb), Frt sequences flanking the Neo expression cassette (for positive selection of the ES cells), and a DTA expression cassette (for negative expression of the ES cells). The final vector was confirmed by both restriction digestion and end sequencing analysis. NotI was used for linearizing the final vector prior to electroporation.

The 5' and 3' external probes were generated by PCR and were tested by genomic Southern analysis for screening of the ES cells. The probes were cloned in the pCR4.0 backbone and confirmed by sequencing. A screening strategy for mIDO-2 knockouts is provided in FIG. 22.

The offspring of the chimera pups for the conditional and unconditional IDO2 knockout animals were born, analyzed for germline transmission of the modified IDO2 alleles, and subsequently bred to homozygosity.

As indicated hereinabove, the homologous arms were generated by PCR. The 5'-arm was cloned into LoxFtNwCD in NotI/KpnI sites, upstream from loxP site. The template was BAC clone RP23-339B16 and the primers used were:

LDI_IDO2_5'F: Tm 57.8 (SEQ ID NO: 148)
actggcggccgcATGCCGAATCTATTACCATTACTGCC

LDI_IDO2_5'R: Tm 60.4 (SEQ ID NO: 149)
actgggtaccACACCTTCATAGACCAGCCCCACA

The E9/E10 CKO region was cloned in BsiWI/SalI sites, upstream from FRT site. The template was BAC clone RP23-339B16 and the primers used were:

LDI_IDO2_INSF: Tm 60.4 (SEQ ID NO: 150)
actgcgtacgcatatgTGTGGGGCTGGTCTATGAAGGTGT LDI_IDO2_INSR: Tm 52.8 (SEQ ID NO: 151)
actggtcgacGGGATATAGCACAAGAACAGCTAAG The 3' arm was cloned in LoxFtNwCD in AscI/XmaI sites. BAC clone RP23-339B16 was used as the template and the primers used were:

LDI_IDO2_3'F: Tm 52.8 (SEQ ID NO: 152)
actgggcgcgccCTTAGCTGTTCTTGTGCTATATCCC

LDI_IDO2_3'R: Tm 56.8 (SE ID NO: 153)
actgcccgggGGTGTCTGTGAGATTTTGAGAATAGTCC

The 5' and 3' arms and the CKO region were end sequenced. The sequence of the 5' end of the 5' arm was determined to be:

(SEQ ID NO: 154)
ATGCCGAATCTATTACCATTACTGCCAAGTCCCATTGGGAGAAAAACTAA
AGTGTGCATTCGTGCATGTGTGCGTGTACGTGTGTGTCTAGAACTGAAAA
TTTTATTTCCTTGCAAGTATCAGACTAGAGTTTTCCTGGCCTGCTAGGTC
CTCTGTTGCCTCTCCCCACCATGTCCCCAATTTGACTCCTGACACAGCAC
TGGCACTTGGCATTTTTCTAGAATTACACATTTTCCTGACTTTTCTCTTG
ACTACCGCCAGAGGAAATTTCTCTTAAAGGGGCTCCTGTGGCTGTGCTCA
ATCTAGTCGGATGAGTCAGGGAAATTCCCACATTAAAGCTAAACTGATCA
GTGGCCTTAATCCCATCTGAAAAGTCCTCCTGCCCTGTCCTGTAATAAAT
ATATCATGGTGACCGGAACAGCTCATAGTATTAAGAGTCCTAGGAATTCG
GTTGGGAACCTTGGGGAGCTATTTTTAGAATCCTACCCTCCAGTGTCTTT
CAAAGGAATCATTTCTACTTCCTCTTGGCAGAGACTTGATAAGAACCAGA
AGGGGACTTTGTTTGCATCGACATAAGTTCCGGGCAATGACACTTTTTAT
CTGGTATTTGGCATAAAGGCCATCCCTCCACTTCAAATGCTGAGACTGTT
TACTGTGCCGCTAAGTGGCTGTACAAGATCCTAAATGTAGCTGTAGTTTC
AACAAACATCTGGATTGTTGGGAGTTTCCAGTAGACTTCTCTTTAAAATC
TCAGCCTCGCTATTCTGCATCTATCCCGAGTTTCTCATTTGCTTCTTTAA
AACACAGTTTTATTTAAGAGTGGATGTCCTGTGGAAATGAGATGTATTCC
CTCCAGTTCCCAGCC.

The sequence of the 3' end of 5' arm was determined to be:

(SEQ ID NO: 155)
TGAGTGTATGCTCGTGTATGTATGTGAGCACTGCAGGTGTCTGCATGGTG
TGCCATGGTGCTCCACTGGGCTTCATGCTGTGCTCCCCTAGGCTTCAGTC
AAGTCAAGACTAGGTCAAGTCATGGAGGGTAAACAGAAGAGAGAGAGAGC
AGAAAATGAGGGACACAGGAAGGGTAGAGGGGGAAAGAGAGGGTTGTGAA
GCTCACGCGTCATCAGGAGCCCCAGGCTTTCTTCTTCCAGCCGCCCATAG
GCTCTGGTGCCCACAACATTGGTTACAACCCCGCTCTCCATCATCATGCT
TGTCATCACTGCTGTGACAAACCGCTTAATAATGGTTCTCACGGAACATT
AAAAGCCAAGCCAAGTTTAACACCTCGAACATTTCCAAGTGTTATGGGGA
ATAACAGTTAAGTGTCTGGGTGTGCTTGTGTGTAATTGGGAATCTGTAGT
GGTGGGGTTACCAGTGTCAGGCCACAGTGTTTGTGATGAGCAGAGGGGTC
GGGGTCTTTCTCAGATCCCTTATCTTGTCCTGTCAATGGTGGTGATGTAA
TAGGTGCACGCCTGTGACAGAGCTGTTTAAAGCATTGTAAGACCAATGAG
TAAAGTTCCTACCCTTGCTTCTCCTTTAAGTGAGGCAGAAAAAGGCTCCA
CCATGACGTGGTGTAAAGATGAAGTCAATCTAATACTTCCTTGGATACTC
TAGCAAGCTTCATTCACACTTTTTATTTCTTCCTCTTCCTCTTCCTCTTC
CTCTTCCTCTTCCTCTTCCTCTTCCCCTCCTCCTCTTCCTCCTCCTCTTC
CTCCTCCTCTTCCTCCTCCTCCTCTTCCTCCTTCTCCTCTTCCTCCTCCC
CCTCCCCTTCCCCTGTGCTCCTCATTATTATTATTATTGCTCCTGTCTAG
GTGGAAGGACAATCCAGCCATGCCTGTGGGGCTGGTCTATGAAGGTGT.

The sequence of the 5' end of CKO region (E9) was determined to be:

(SEQ ID NO: 156)
GGTACCAAAGGCCGCAATGGCCAAACCTGCAGGAAGTACCAGAGCTCCCT
AGGTTCTAGAACCGGTGACGTCAAGCTCGAATAACTTCGTATAATGTATG
CTATACGAAGTTATCCTGCAGGTCGATCGAGACCGTACGCTATGTGTGGG
GCTGGTCTATGAAGGTGTTGCCACAGAGCCTCTGAAGTACTCTGGAGGAA
GTGCAGCCCAGAGCTCCGTGCTTCATGCCTTCGATGAGTTCCTGGGCATT
GAGCATTGCAAGGAAAGTGGTGAGCAGCAGTCTGATCTCACCTATGCTTT
GATGGGACAGCGAGGTAGACTAGGGAGACATCTCTAGCAACTGATAAAGA
CGGGTGTAAATGAAAATGTCCTGAAGTTTATCCTTGCCTAAGCCAGCAGG
CAGCTGTGTGCATGTGCCCTCTCTTACACTGAGTTAGTCAGTATTGGGGC
ATCGGATCTTATTAGGGTCTTCCAACAGTCCTGTGACCTGGGTTGTTCAC
TGTCCTGTTGGCTGGGGTCTTTTATCCGCAGATTCCCCTTTCTACAATGA
GGTGATAATGTCACATTGAAAGGCCAGTCTGGAGCAGCAAGTGATAGTGC
TGAACTTCTCTGCTAAAGCCTTTCCCATGAAATGCCCCAGCCTCCCACTG
AATCTATGTGGACCAGGCGAGGGAGCCCATCGCTTTGAAGCCTTTAAAA
T.

The sequence of the CKO region (E10) was determined to be:

(SEQ ID NO: 157)
CAGAAATGAACATTTGAGCATTTGGCAGCTATAACAAAAGCCCGACAAGG
CTGAGGGAGAGCCCTATCAAGCATTTCTGGTACCTGAGTGTTTGGAACAG
TGGGCAAACCCTCCCAAATGTCTGCCTCGAGCTAACGTATTTCTCCCGGC
TGTTTCTTTCAGTTGGCTTTCTACACAGAATGAGGGACTACATGCCGCCT
TCCCATAAGGCTTTCCTGGAAGATCTCCACGTAGCTCCTTCTCTGAGAGA
CTACATACTGGCCTCTGGTCCTGGGGACTGCCTGATGGCCTATAACCAGT
GTGTGGAGGCCCTGGGAGAGCTGCGCAGTTACCACATCAATGTCGTGGCC
AGATACATTATCTCCGCTGCCACCAGGGCCAGGAGCAGGGGGCTAACTAA
TCCCTCACCCCATGCCTTGGAAGACAGGGGCACTGGGGGTACTGCCATGC
TGAGCTTCTTGAAGAGTGTCAGGGAGAAGACCATGGAGGCCCTCCTGTGT
CCTGGTGCTTAGCAGTCATGTCCTGCACCCTAACACTTAGATGTTCTCAT
CCTGCATCCCAGCGTTAGAGGTTCACATCCTGCATCCTAGTGCTTAGCTG
TTCTTGTGCTATATCCCGTCGACCAAGTTCCTATACTTTCTAGAGAATAG
GAACTTCGGATCCACGATTCGAGGGCCCCTGCAGGTCAATTCTACCGGGT
AGGGGAGGCGCTTTTCCCAAGGCAGTCTGGAGCATGCGCTTTANCAGCCC
CGCTGGGCACTTGGCGCTACACAAGTGGCCTCTGGCCTCGCACACATTCC
ACA.

The sequence of the 5' end of 3' arm was determined to be:

(SEQ ID NO: 158)
ATCCCAGCGCTTAGCAGTCATCTCCTGCATCCTAGTCCTTAGCATTTTAT
ATCCAGCATCTTAGTGCTTAGAGATTCACATCCTGCATCCTAGAGCTTAG

-continued

CATTTTATATCCAGCATCCTTGTGCGTATCAGCTATGTTTTGTATCCTGC
TTAGCAGTTAACATCCTGCATCCTAGTACTTATCTGTTCTCATCCTGCAT
CCTAGAGCTTAGCAGTCAGGTCCCGTGGGAGCAAGAACCAGGGTCTGAGC
TCTGTCTGAGCCCAAGCATGGCTTTACTGCTTTGTTAATTGTGGCTCCCA
CCTCCACCCCACCCCAGCCAGTTTGCTTGCTAGAAGCCTTTCTGCACTGC
CTAATCCCCCTGCCTCACAGCAGAGAGCTGCAGCCATGACCTCCTCATTC
AGTATTAGGTGGACAAGTCGGAGATACCCAAACTCAATTTTAAAAGAATC
AAGTTGCTTTTGGGGCATGTTACTTCATCTTTTCTTACCCTGGGCCTCTA
TGACCTCCTCATTCAGTATTAGGTGGACAAGTCGGAGATACCCAAACTCA
ATTTTAAAAGAATCAAGTTGCTTTT.

The sequence of the 3' end of 3' arm was determined to be:

(SEQ ID NO: 159)
AGCTCTAAGAGAAGGAATACAGCTTGGGACAGAGTTTGTTTTGAAGTGGG
GTTCAGGTGCATTTCCTGGGTGTGTCCCTCATTTGGGGGTGTTAGGAGGC
AGACAATGCTAAGGGCATGGTTTGATATGGTAGACTGACCATCCTGGGGT
CCCTTCAGCTTGTGACACTCGCTGTACTGCTGGACTCTGCTGAGCCCTTT
GAAGCCAGGACTCCTCCTCTGCTGCAGGAGTGCAGTGTCCTTCTTGCTGT
ATGAAGCTGGGACAATGCTCTTTGGCCTTCATACTGGACATCCCATTGAG
AAGCTTGTCACTCTGTAGAGAATAGACATCGCCCCCTTGTGGTTGTGAGG
CTGCCCAGGACTTACTGCGGGGGGGGGGGGGGCATGTTGTCCAGCATAAG
GAGAGAAGACCCCACTGCATGCTGCTGGGAAAAGGAAAGTAACGTTCAGA
GTAGTTTCTACTGGCTGCCTGCGCTCTCACGCCTGTAAGAACAAACGTCC
TAATGTCTGCATGTGGAGGAAGGAGCCAGGGGTGCTTAGGGTGCTGTTGG
TCCCACCAATGTACTACTCATCTGGAAGACCTTGTCTTGGTTTTCTTGCC
ACTGGGACAAAGTGGGATTGGGTATCAGTCTCCCCATGTCGGGCAAATGT
ACTTGAACAAGCAGCATGGTGGACCAGACATGGGACTATTCTCAAAATCT
CACAGACACCCCCGGGGGGCATGTTACTTCATCTTTTCTTACCCTGGGCC
TCT.

The sequence of the 5' probe (SEQ ID NO: 160) is:

CTAGGGAGTCAGGAAGTCACACTGGTGAAGAGTGGGGGTGTGGGATGACC
ACACTGAGGAGTCACACTTGAGGAAGGGGGGTGGCCACACTGAGGAGTGT
CTGAAAGCATTGAGACTGTACATCTCAGGTTATCAGGGCTTCAGAGAAAA
CAGACAGGGAGAAGAGACAAGAACTGGATTCTGTGCGCAAAGGGGGAAAA
GCAAGCAGATGTGAAGGGTGTGCTGTTAGAGTTTATCTAAAGATGTTTCT
TTCAGAAATAAAGAGATATAAGCTTTAATTTGGATGAAATAAATGTGGTC
TAATTTCCCAGAATGTAGAGGAACTCACTAATGTAGCAAGATTGGCCTTT
CAAAGCAGACCAAAGACATTGAGAATTAAGATAGCTATGATGGCGTGCTT
CCTTAGGTGGAAGTCCTATATGGAATCCCATACTCCCCAAATGTGACTGG
TCG.

The sequence of the 3' probe (SEQ ID NO: 161) is:

AGGCAGGAGGGTCAGGAGTTCAAGGCCAGCCTAGTATACATGCAACAGTG

TCTCAAAAATCAAAACAGAGAGGAGGGCAGGAAAGGAGAAGGGAGCCAGG

GAGAGAAGGGAAGAGGAAGGGAGGGAGGGGGAAATGGAGGGAGGGGGAGA

TGGAGGGAGGGGGAGATGGAGGGAGGGGGAGATGGAGGGAGGGGGAGATG

GAGGGAGGGGGAGATGGAGGGAGGGGGATGGGAAAGAGGGTTTACAGCCC

TGGTTTATCTTGAACAGAATCCTTACTTTGTCCCTCAGAGTGACAGGACT

GAAAAGATTGTCCCAGGATTTTGGCTGCAAAGCAAGGTCCACTCAGAGAC

CACAGAGCTCG.

Example 6

Production of Recombinant IDO2 using Baculovirus Expression Vectors

Figure 23A:
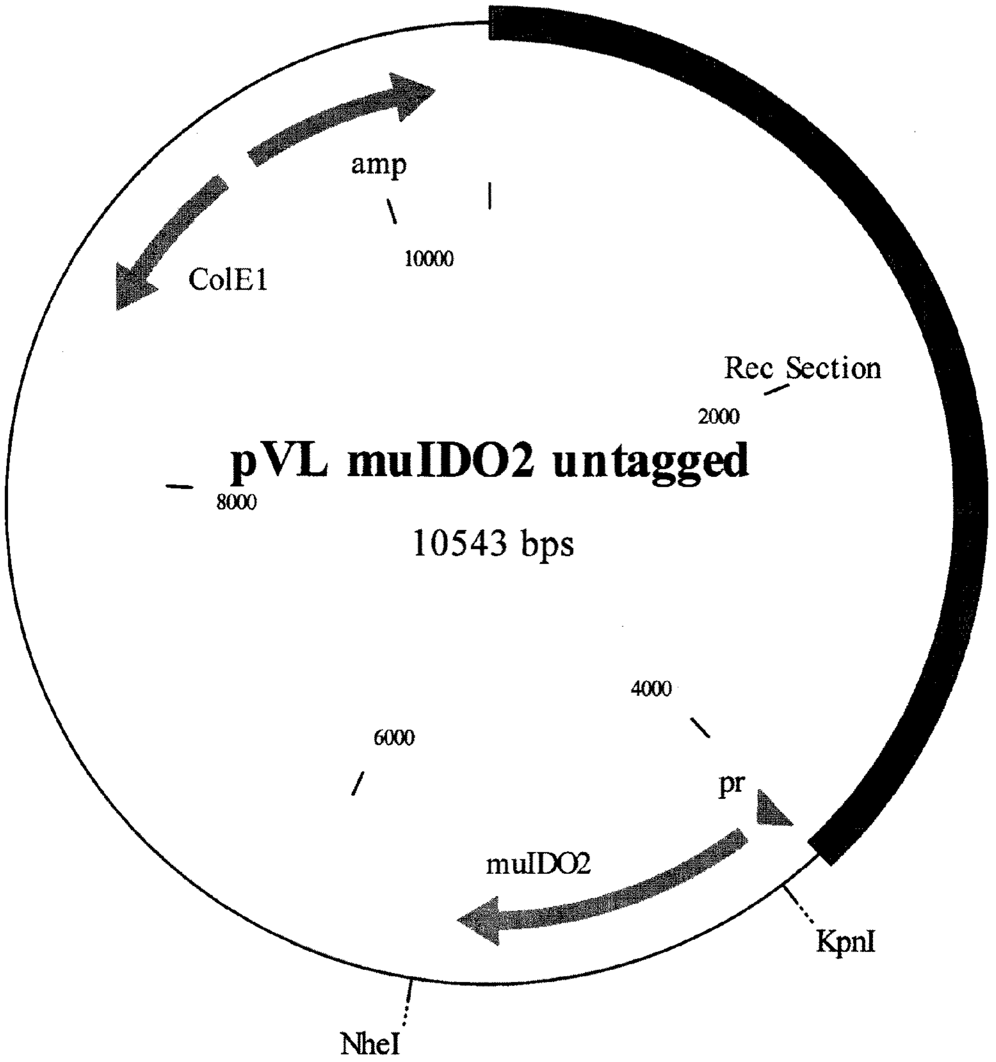
FIG. 23A is a schematic of vector pVLmuIDO2.
Figure 24A:
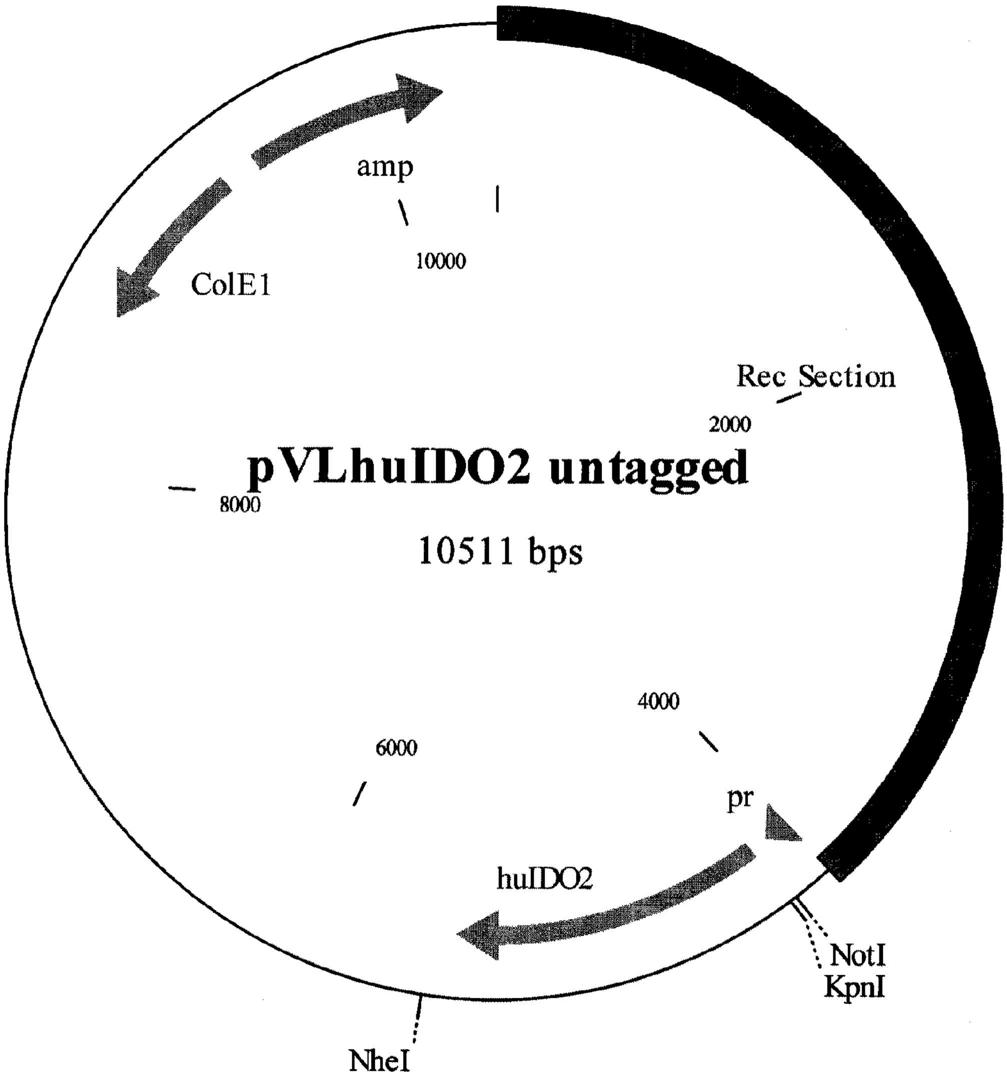
FIG. 24A is a schematic of vector pVLhuIDO2.

The recombinant transfer vectors (pVLmuIDO2, pVL-huIDO2; FIGS. 23 and 24, respectively) containing the complete coding regions of murine and human IDO2, respectively, were derived from eukaryotic expression vectors, pcDNAmuIDO2 and pcDNAhuIDO2. The KpnI/NheI insert fragments containing the complete ORF of pcDNAmuIDO2 and huIDO2 were cloned into KpnI/NheI digested pVL1392 recombination vector that was modified to contain KpnI, XbaI, NheI, SpeI multiple cloning sites at the original KpnI site (See FIGS. 23 and 24). The resulting vectors were analyzed by gel electrophoresis to verify the size and integrity of the inserted genes and inserted coding regions were also analyzed by standard diodeoxynucleotide automated sequencing (Macrogen, Inc., Rockville, Md.).

Approximately 2 μg of each purified recombination transfer vector, pVLmuIDO2 and pVLhuIDO2, was mixed with 0.5 μg of Baculogold linearized baculovirus DNA (Pharmingen, BD Biosciences, Franklin Lakes, N.J.) and added to 6 μL of Cell fectin (Invitrogen, Carlsbad, Calif.) in a total volume of 200 μL sf900II serum free medium (sf900II-SFM). The solution was incubated at room temperature for 30 minutes, supplemented with 800 μL of sf900II SFM (Gibco-BRL, Carlsbad, Calif.), mixed and added to $1\times10^6$ cells of the *Spodoptera frugiperda* cell line, Sf9, in a 6 well plate. Cells were incubated at 28° C. for 4 hours after which the media was replaced with 2 mL sf900II-SFM 5% FCS. Supernatants containing the recombinant baculovirus (recBV) were harvested after six days and stored at 4° C. indefinitely.

"High Five" cells (Invitrogen) were plated at $1\times10^5$ per well (24 well dish) in 0.5 mL "Express Five" medium (Invitrogen) and incubated at 28° C. for 24 hours. Media was replaced with 0.5 mL of media containing varying dilutions of recBVs containing the muIDO2 and huIDO2 ORFs. Typically 3, 10, 30 and 100 μL of a 1/100 dilution of the recBV viral stock were used. After 24 hours the cells were microscopically examined for signs of infection such as cell rounding, detachment and failure to divide. Optimal titers are established when 100% of the cells show signs of infection.

After 48 hours the media was removed and the cells collected and lysed in 400 μL of RIPA buffer, clarified by centrifugations and supplemented with Laemmli SDS PAGE running buffer. Briefly the lysates were heated to 80° C. for 10 minutes and 4 μL of material was subjected to SDS polyacrylamide gel electrophoresis (10% SDS-PAGE, Invitrogen) and either Coomassie blue stained or transferred to nitrocellulose membrane for Western analysis. For Western analysis, SDS-PAGE gel blots were typically blocked 1 hour at room temperature in PBS/0.1% Tween 20 and 3% nonfat dry milk, incubated with primary and secondary antibodies. Typically membranes are incubated for 1 hour at room temperature in blocking buffer, and then incubated with affinity purified rabbit anti-IDO2 antibody diluted at 1:5000 in blocking buffer. Membranes were washed at room temperature 3-5 times for 10 minutes each in washing buffer (PBS, 0.1% tween), after which the membrane was incubated with HRP-conjugated goat-anti-rabbit antibody (Santa Cruz) in blocking buffer for 1 hour at room temperature, followed by five 10 minutes washes in washing buffer. The membrane was prepared for exposure to X-ray film using a chemiluminescence method with SuperSignal® West Pico chemiluminescent substrate (Pierce cat. no. 34078, Rockford, Ill.). The highest dilution that gave the maximum amount of protein productions was used.

High five cells grown in Express Five-SFM media were plated at $2\times10^7$ cells per T175 flask in 30 mL of media. After four hours the media was removed and recBV was added at 5-10 infectious units per cell in 6 mL of media. The flask was rocked every 10-15 minutes to ensure infection of every cell over the period of 1 hour, after which an additional 15 mL of media was added. After 24 hours the media in each flask was supplemented with tryptophan (final 100 μM) and hemin (5 μM final). After 64 hours, the infected cells were dislodged by the addition of glass beads. The cell suspension was separated from the glass beads by pipetting and pelleted by centrifugation (3,000 rpm 5 minutes). The cell pellet was either frozen or processed immediately.

The cell pellet, containing approximately $1.8\times10^8$ cells, was resuspended in 40 mL 50 mM tris pH 8.8 and sonicated, 4×10 second pulses, on ice. The suspension was adjusted to 50 mM NaCl, 1% octylglucoside, vortexed, and clarified by centrifugation, 20 minutes at 13,000 rpm, at 4° C. The supernatant was passed over a DEAE-Sephacel column equilibrated in Tris pH 8.8, 50 mM NaCl, 1 mM EDTA (EQ buffer). The column was washed with 10 column volumes of equilibration buffer. The IDO2 proteins were eluted with 50 mM Tris pH 8.8, 0.5 M NaCl, 1 mM EDTA.

The eluted fractions were subjected to SDS-PAGE analysis followed by staining with Coomassie brilliant blue R-250. Peak IDO2 containing fractions were combined and dialyzed against EQ buffer. The dialysate was applied to a Mono Q column using the AKTAPurifier 100 fast protein liquid chromatography (FPLC) system. The column was equilibrated in EQ buffer and eluted using a linear gradient of EQ buffer with increasing NaCl 50 mM to 1 M. Elution profile was established by dual spectroscopic measurements at 280 nm and 403 nm and SDS-PAGE followed by staining with Coomassie brilliant blue R-250 and/or Western analysis. The 404/280 absorbance ratio was approximately 1.8-2.0. Peak IDO2 eluates were contained in the 400-500 mM NaCl fractions. An additional peak containing IDO2 was also observed eluting at 250 nM NaCl which may contain mostly dimeric forms of the muIDO2 protein. Indeed, the early eluting peak contained IDO2 dimers as determined by a non-heat denatured sample analyzed by SDS-PAGE, whereby an 120 kDa band can be seen in samples not reduced or heated, while upon heating the larger bands resolves into a single major protein band at ~55 kDa. Both mIDO2 containing peaks were pooled and concentrated approximated 5 fold by centrifugal filtration (Amicon Ultra-4, Billerica, Mass.).

The concentrated material was applied to a gel filtration column, Superdex™200 (GE Healthcare, Piscataway, N.J.), equilibrated in EQ buffer. Fractions were collected and analyzed by SDS-PAGE/Coomassie staining and confirmed by Western analysis. IDO2 containing fractions were pooled and concentrated to approximately 2 μg/μL by centrifugal filtration (Amicon Ultra-4). The purified protein material exhibited 404-280 nM ratios of 1.5 to 1.8.

Figure 25A:
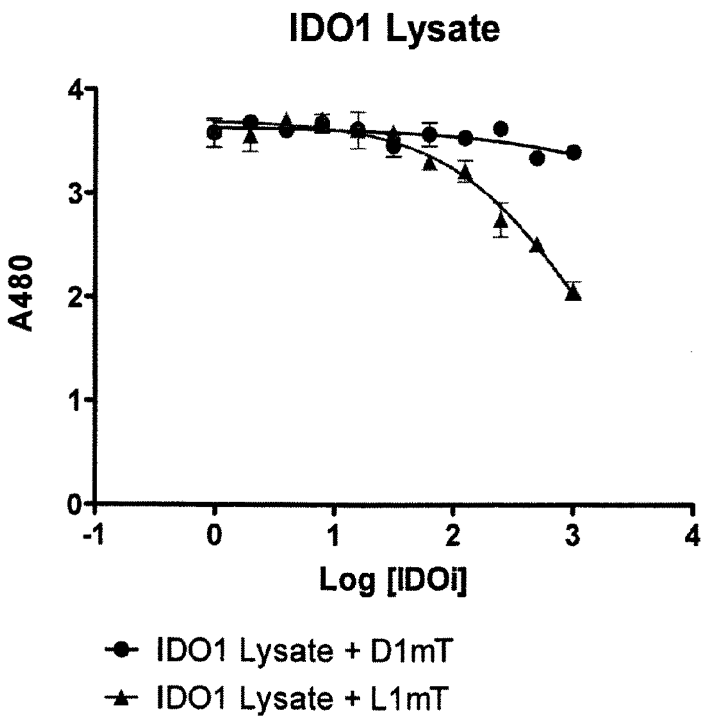
FIGS. 25A and 25B are graphs of the inhibition studies of varying amounts of D-1-methyl-tryptophan and L-1-methyl-tryptophan on IDO1 and IDO2 whole cell lysates, respectively.
Figure 25B:
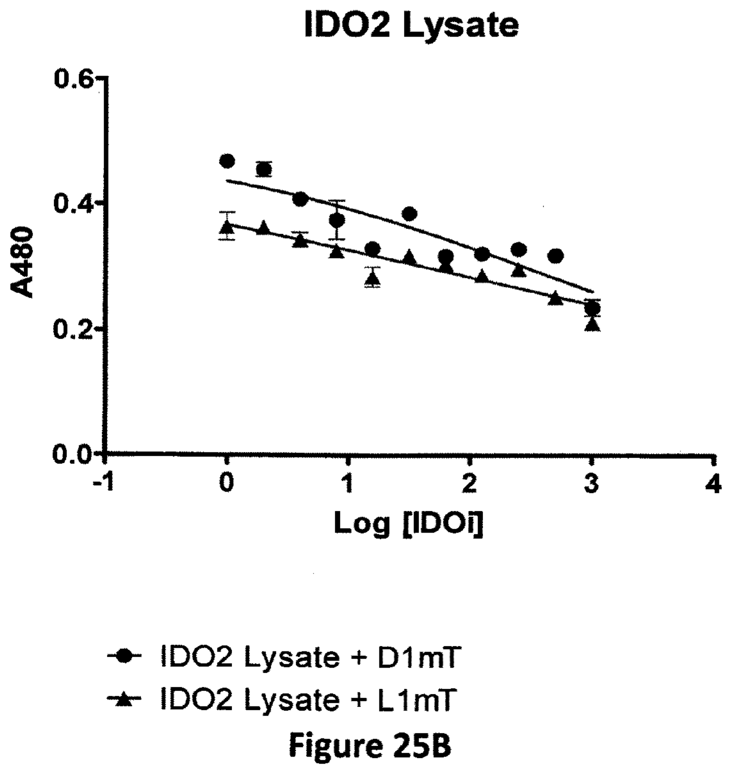

IDO2 activity was measured as the amount of kynurenine formed from L-tryptophan. The standard assay conditions consisted of a mixture containing 50 mM Pipes pH 6.5, between 50 and 600 nM of rmuIDO2 or rhuIDO2 (where 100 nM of rIDO2 is approximately 5.5 μg protein per mL reaction), 200 U catalase (0.2 mg/mL, sp act. ~1000 U/mg), 200 μM L-tryptophan, 10 μM methylene blue and 20 mM ascorbic acid. The mixture was incubated at various times ranging from 15 minutes to 4 hours at 37° C. before the reaction was stopped by adding trichloroacetic acid (TCA) to 3% final. The samples were then heated to 50-60° C. for 30 minutes to convert N-formyl-kynureneine to kynurenine, clarified by centrifugation, and supernatants (100 μL) were removed to a new dish, mixed with 100 μL Ehrlich's reagent (2% p-dimethylaminobenzaldehyde w/v in glacial acetic acid), and incubated 10-30 minutes at room temperature. Absorbance at 490 nm was determined on a plate reader and the data collected and analyzed using Excel software (Microsoft). Typically, samples were analyzed in triplicate and control values were typically averaged and subtracted from sample values. Enzyme activity was estimated based on the conversion of tryptophan to kynurenine using linear regression analysis based on an absorbance standard curve derived from assay measurements on known amounts of kynurenine. Inhibitions studies were performed whereby varying amounts (0-100 μM) of D or L stereoisomers of 1-methyl tryptophan (D-1MT or L-1MT) or MTH-trp and demonstrate that the purified recIDO2 proteins are inhibited by D-1MT (FIG. 25).

Example 7

Polyclonal rabbit anti-murine and anti-human IDO2 was prepared. Antisera were raised against a mixture of murine and human GST-IDO2 fusion protein. Antisera were screened for reactivity against the immunizing antigen by ELISA and western, and samples with high titer were purified by affinity chromatography. Specifically, antiserum was pre-absorbed to protein column containing GST. Since IDO2 and IDO1 possess conserved amino acid domains, the GST-unbound serum was passed over an IDO1-His-tagged peptide column. The unbound material was then affinity purified on an antigen specific peptide column containing human and mouse His-tagged IDO2. The resulting antibody was analyzed and determined to be IDO2 specific with no cross-reactivity with IDO1.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

Several publications and patent documents are cited in the foregoing specification in order to more fully describe the state of the art to which this invention pertains. The disclosure of each of these citations is incorporated by reference herein.

What is claimed is:

1. An isolated nucleic acid molecule encoding an indoleamine 2,3-dioxygenase-2 (IDO2) protein comprising an amino acid sequence having at least 90% identity with SEQ ID NO: 1.

2. The nucleic acid molecule of claim 1, wherein said amino acid sequence has at least 95% identity with SEQ ID NO: 1.

3. The nucleic acid molecule of claim 1, wherein said amino acid sequence has at least 97% identity with SEQ ID NO: 1.

4. The nucleic acid molecule of claim 1, wherein said amino acid sequence has at least 99% identity with SEQ ID NO: 1.

5. The nucleic acid molecule of claim 1, wherein said amino acid sequence is SEQ ID NO: 1.

* * * * *

UNITED STATES PATENT AND TRADEMARK OFFICE

CERTIFICATE OF CORRECTION

PATENT NO. : 8,058,416 B2
APPLICATION NO. : 12/273296
DATED : November 15, 2011
INVENTOR(S) : George C. Prendergast et al.

It is certified that error appears in the above-identified patent and that said Letters Patent is hereby corrected as shown below:

In the Specification

At column 1, lines 12-15, please delete the paragraph:

"Pursuant to 35 U.S.C. §202(c), it is acknowledged that the U.S. Government has certain rights in the invention described herein, which was made in part with funds from the National Institutes of Health, Grant No. CA109542."

and insert therefor:

--This invention was made with government support under Grant No. CA109542 awarded by the National Institutes of Health. The government has certain rights in the invention.--

Signed and Sealed this
First Day of September, 2015

Michelle K. Lee

Michelle K. Lee
*Director of the United States Patent and Trademark Office*

SEQUENCE LISTING

```
<160> NUMBER OF SEQ ID NOS: 163

<210> SEQ ID NO 1
<211> LENGTH: 420
<212> TYPE: PRT
<213> ORGANISM: Homo Sapiens

<400> SEQUENCE: 1

Met Leu His Phe His Tyr Tyr Asp Thr Ser Asn Lys Ile Met Glu Pro
1               5                   10                  15

His Arg Pro Asn Val Lys Thr Ala Val Pro Leu Ser Leu Glu Ser Tyr
            20                  25                  30

His Ile Ser Glu Glu Tyr Gly Phe Leu Leu Pro Asp Ser Leu Lys Glu
        35                  40                  45

Leu Pro Asp His Tyr Arg Pro Trp Met Glu Ile Ala Asn Lys Leu Pro
    50                  55                  60

Gln Leu Ile Asp Ala His Gln Leu Gln Ala His Val Asp Lys Met Pro
65                  70                  75                  80

Leu Leu Ser Cys Gln Phe Leu Lys Gly His Arg Glu Gln Arg Leu Ala
                85                  90                  95

His Leu Val Leu Ser Phe Leu Thr Met Gly Tyr Val Trp Gln Glu Gly
            100                 105                 110

Glu Ala Gln Pro Ala Glu Val Leu Pro Arg Asn Leu Ala Leu Pro Phe
        115                 120                 125

Val Glu Val Ser Arg Asn Leu Gly Leu Pro Pro Ile Leu Val His Ser
    130                 135                 140

Asp Leu Val Leu Thr Asn Trp Thr Lys Lys Asp Pro Asp Gly Asn Leu
145                 150                 155                 160
```

```
Glu Ile Gly Asn Leu Glu Thr Ile Ile Ser Phe Pro Gly Gly Glu Ser
                165                 170                 175

Leu His Gly Phe Ile Leu Val Thr Ala Leu Val Glu Lys Glu Ala Val
            180                 185                 190

Pro Gly Ile Lys Ala Leu Val Gln Ala Thr Asn Ala Ile Leu Gln Pro
        195                 200                 205

Asn Gln Glu Ala Leu Leu Gln Ala Leu Gln Arg Leu Arg Leu Ser Ile
    210                 215                 220

Gln Asp Ile Thr Lys Thr Leu Gly Gln Met His Asp Tyr Val Asp Pro
225                 230                 235                 240

Asp Ile Phe Tyr Ala Gly Ile Arg Ile Phe Leu Ser Gly Trp Lys Asp
                245                 250                 255

Asn Pro Ala Met Pro Ala Gly Leu Met Tyr Glu Gly Val Ser Gln Glu
            260                 265                 270

Pro Leu Lys Tyr Ser Gly Gly Ser Ala Ala Gln Ser Thr Val Leu His
        275                 280                 285

Ala Phe Asp Glu Phe Leu Gly Ile Arg His Ser Lys Glu Ser Gly Asp
    290                 295                 300

Phe Leu Tyr Arg Met Arg Asp Tyr Met Pro Pro Ser His Lys Ala Phe
305                 310                 315                 320

Ile Glu Asp Ile His Ser Ala Pro Ser Leu Arg Asp Tyr Ile Leu Ser
                325                 330                 335

Ser Gly Gln Asp His Leu Leu Thr Ala Tyr Asn Gln Cys Val Gln Ala
            340                 345                 350

Leu Ala Glu Leu Arg Ser Tyr His Ile Thr Met Val Thr Lys Tyr Leu
        355                 360                 365

Ile Thr Ala Ala Ala Lys Ala Lys His Gly Lys Pro Asn His Leu Pro
    370                 375                 380

Gly Pro Pro Gln Ala Leu Lys Asp Arg Gly Thr Gly Gly Thr Ala Val
385                 390                 395                 400

Met Ser Phe Leu Lys Ser Val Arg Asp Lys Thr Leu Glu Ser Ile Leu
                405                 410                 415

His Pro Arg Gly
            420


<210> SEQ ID NO 2
<211> LENGTH: 405
<212> TYPE: PRT
<213> ORGANISM: Homo Sapiens

<400> SEQUENCE: 2

Met Glu Pro His Arg Pro Asn Val Lys Thr Ala Val Pro Leu Ser Leu
 1               5                  10                  15

Glu Ser Tyr His Ile Ser Glu Glu Tyr Gly Phe Leu Leu Pro Asp Ser
            20                  25                  30

Leu Lys Glu Leu Pro Asp His Tyr Arg Pro Trp Met Glu Ile Ala Asn
        35                  40                  45

Lys Leu Pro Gln Leu Ile Asp Ala His Gln Leu Gln Ala His Val Asp
    50                  55                  60

Lys Met Pro Leu Leu Ser Cys Gln Phe Leu Lys Gly His Arg Glu Gln
65                  70                  75                  80

Arg Leu Ala His Leu Val Leu Ser Phe Leu Thr Met Gly Tyr Val Trp
                85                  90                  95

Gln Glu Gly Glu Ala Gln Pro Ala Glu Val Leu Pro Arg Asn Leu Ala
            100                 105                 110
```

```
Leu Pro Phe Val Glu Val Ser Arg Asn Leu Gly Leu Pro Pro Ile Leu
        115                 120                 125

Val His Ser Asp Leu Val Leu Thr Asn Trp Thr Lys Lys Asp Pro Asp
    130                 135                 140

Gly Phe Leu Glu Ile Gly Asn Leu Glu Thr Ile Ile Ser Phe Pro Gly
145                 150                 155                 160

Gly Glu Ser Leu His Gly Phe Ile Leu Val Thr Ala Leu Val Glu Lys
                165                 170                 175

Glu Ala Val Pro Gly Ile Lys Ala Leu Val Gln Ala Thr Asn Ala Ile
            180                 185                 190

Leu Gln Pro Asn Gln Glu Ala Leu Leu Gln Ala Leu Gln Arg Leu Arg
        195                 200                 205

Leu Ser Ile Gln Asp Ile Thr Lys Thr Leu Gly Gln Met His Asp Tyr
    210                 215                 220

Val Asp Pro Asp Ile Phe Tyr Ala Gly Ile Arg Ile Phe Leu Ser Gly
225                 230                 235                 240

Trp Lys Asp Asn Pro Ala Met Pro Ala Gly Leu Met Tyr Glu Gly Val
                245                 250                 255

Ser Gln Glu Pro Leu Lys Tyr Ser Gly Gly Ser Ala Ala Gln Ser Thr
            260                 265                 270

Val Leu His Ala Phe Asp Glu Phe Leu Gly Ile Arg His Ser Lys Glu
        275                 280                 285

Ser Gly Asp Phe Leu Tyr Arg Met Arg Asp Tyr Met Pro Pro Ser His
    290                 295                 300

Lys Ala Phe Ile Glu Asp Ile His Ser Ala Pro Ser Leu Arg Asp Tyr
305                 310                 315                 320

Ile Leu Ser Ser Gly Gln Asp His Leu Leu Thr Ala Tyr Asn Gln Cys
                325                 330                 335

Val Gln Ala Leu Ala Glu Leu Arg Ser Tyr His Ile Thr Met Val Thr
            340                 345                 350

Lys Tyr Leu Ile Thr Ala Ala Ala Lys Ala Lys His Gly Lys Pro Asn
        355                 360                 365

His Leu Pro Gly Pro Pro Gln Ala Leu Lys Asp Arg Gly Thr Gly Gly
    370                 375                 380

Thr Ala Val Met Ser Phe Leu Lys Ser Val Arg Asp Lys Thr Leu Glu
385                 390                 395                 400

Ser Ile Leu His Pro
                405


<210> SEQ ID NO 3
<211> LENGTH: 398
<212> TYPE: PRT
<213> ORGANISM: Mus musculus

<400> SEQUENCE: 3

Met Thr Leu Glu Val Pro Leu Ser Leu Gly Arg Tyr His Ile Ser Glu
 1               5                  10                  15

Glu Tyr Gly Phe Leu Leu Pro Asn Pro Leu Glu Ala Leu Pro Asp His
            20                  25                  30

Tyr Lys Pro Trp Met Glu Ile Ala Leu Arg Leu Pro His Leu Ile Glu
        35                  40                  45

Asn Arg Gln Leu Arg Ala His Val Tyr Arg Met Pro Leu Leu Asp Cys
    50                  55                  60

Arg Phe Leu Lys Ser Tyr Arg Glu Gln Arg Leu Ala His Met Ala Leu
65                  70                  75                  80
```

```
Ala Ala Ile Thr Met Gly Phe Val Trp Gln Glu Gly Glu Gly Gln Pro
                85                  90                  95

Gln Lys Val Leu Pro Arg Ser Leu Ala Ile Pro Phe Val Glu Val Ser
            100                 105                 110

Arg Asn Leu Gly Leu Pro Pro Ile Leu Val His Ser Asp Leu Val Leu
        115                 120                 125

Thr Asn Trp Thr Lys Arg Asn Pro Glu Gly Pro Leu Glu Ile Ser Asn
    130                 135                 140

Leu Glu Thr Ile Ile Ser Phe Pro Gly Gly Glu Ser Leu Arg Gly Phe
145                 150                 155                 160

Ile Leu Val Thr Val Leu Val Glu Lys Ala Ala Val Pro Gly Leu Lys
                165                 170                 175

Ala Leu Val Gln Gly Met Glu Ala Ile Arg Gln His Ser Gln Asp Thr
            180                 185                 190

Leu Leu Glu Ala Leu Gln Gln Leu Arg Leu Ser Ile Gln Asp Ile Thr
        195                 200                 205

Arg Ala Leu Ala Gln Met His Asp Tyr Val Asp Pro Asp Ile Phe Tyr
    210                 215                 220

Ser Val Ile Arg Ile Phe Leu Ser Gly Trp Lys Asp Asn Pro Ala Met
225                 230                 235                 240

Pro Val Gly Leu Val Tyr Glu Gly Ala Ala Thr Glu Pro Leu Lys Tyr
                245                 250                 255

Ser Gly Gly Ser Ala Ala Gln Ser Ser Val Leu His Ala Phe Asp Glu
            260                 265                 270

Phe Leu Gly Ile Glu His Cys Lys Glu Ser Val Gly Phe Leu His Arg
        275                 280                 285

Met Arg Asp Tyr Met Pro Pro Ser His Lys Ala Phe Leu Glu Asp Leu
    290                 295                 300

His Val Ala Pro Ser Leu Arg Asp Tyr Ile Leu Ala Ser Gly Pro Gly
305                 310                 315                 320

Asp Cys Leu Met Ala Tyr Asn Gln Cys Val Glu Ala Leu Gly Glu Leu
                325                 330                 335

Arg Ser Tyr His Ile Asn Val Val Ala Arg Tyr Ile Ile Ser Ala Ala
            340                 345                 350

Thr Arg Ala Arg Ser Arg Gly Leu Thr Asn Pro Ser Pro His Ala Leu
        355                 360                 365

Glu Asp Arg Gly Thr Gly Gly Thr Ala Met Leu Ser Phe Leu Lys Ser
    370                 375                 380

Val Arg Glu Lys Thr Met Glu Ala Leu Leu Cys Pro Gly Ala
385                 390                 395


<210> SEQ ID NO 4
<211> LENGTH: 403
<212> TYPE: PRT
<213> ORGANISM: Mus musculus

<400> SEQUENCE: 4

Met Glu Pro Gln Ser Gln Ser Met Thr Leu Glu Val Pro Leu Ser Leu
 1               5                  10                  15

Gly Arg Tyr His Ile Ser Glu Glu Tyr Gly Phe Leu Leu Pro Asn Pro
            20                  25                  30

Leu Glu Ala Leu Pro Asp His Tyr Lys Pro Trp Met Glu Ile Ala Leu
        35                  40                  45

Arg Leu Pro His Leu Ile Glu Asn Arg Gln Leu Arg Ala His Val Tyr
    50                  55                  60
```

-continued

Arg Met Pro Leu Leu Asp Cys Arg Phe Leu Lys Ser Tyr Arg Glu Gln
65 70 75 80

Arg Leu Ala His Met Ala Leu Ala Ala Ile Thr Met Gly Phe Val Trp
85 90 95

Gln Glu Gly Glu Gly Gln Pro Gln Lys Val Leu Pro Arg Ser Leu Ala
100 105 110

Ile Pro Phe Val Glu Val Ser Arg Asn Leu Gly Leu Pro Pro Ile Leu
115 120 125

Val His Ser Asp Leu Val Leu Thr Asn Trp Thr Lys Arg Asn Pro Glu
130 135 140

Gly Pro Leu Glu Ile Ser Asn Leu Glu Thr Ile Ile Ser Phe Pro Gly
145 150 155 160

Gly Glu Ser Leu Arg Gly Phe Ile Leu Val Thr Val Leu Val Glu Lys
165 170 175

Ala Ala Val Pro Gly Leu Lys Ala Leu Val Gln Gly Met Glu Ala Ile
180 185 190

Arg Gln His Ser Gln Asp Thr Leu Leu Glu Ala Leu Gln Gln Leu Arg
195 200 205

Leu Ser Ile Gln Asp Ile Thr Arg Ala Leu Ala Gln Met His Asp Tyr
210 215 220

Val Asp Pro Asp Ile Phe Tyr Ser Val Ile Arg Ile Phe Leu Ser Gly
225 230 235 240

Trp Lys Asp Asn Pro Ala Met Pro Val Gly Leu Val Tyr Glu Gly Ala
245 250 255

Ala Thr Glu Pro Leu Lys Tyr Ser Gly Gly Ser Ala Ala Gln Ser Ser
260 265 270

Val Leu His Ala Phe Asp Glu Phe Leu Gly Ile Glu His Cys Lys Glu
275 280 285

Ser Val Gly Phe Leu His Arg Met Arg Asp Tyr Met Pro Pro Ser His
290 295 300

Lys Ala Phe Leu Glu Asp Leu His Val Ala Pro Ser Leu Arg Asp Tyr
305 310 315 320

Ile Leu Ala Ser Gly Pro Gly Asp Cys Leu Met Ala Tyr Asn Gln Cys
325 330 335

Val Glu Ala Leu Gly Glu Leu Arg Ser Tyr His Ile Asn Val Val Ala
340 345 350

Arg Tyr Ile Ile Ser Ala Ala Thr Arg Ala Arg Ser Arg Gly Leu Thr
355 360 365

Asn Pro Ser Pro His Ala Leu Glu Asp Arg Gly Thr Gly Gly Thr Ala
370 375 380

Met Leu Ser Phe Leu Lys Ser Val Arg Glu Lys Thr Met Glu Ala Leu
385 390 395 400

Leu Cys Pro

<210> SEQ ID NO 5
<211> LENGTH: 403
<212> TYPE: PRT
<213> ORGANISM: Homo Sapiens

<400> SEQUENCE: 5

Met Ala His Ala Met Glu Asn Ser Trp Thr Ile Ser Lys Glu Tyr His
1 5 10 15

Ile Asp Glu Glu Val Gly Phe Ala Leu Pro Asn Pro Gln Glu Asn Leu
20 25 30

Pro Asp Phe Tyr Asn Asp Trp Met Phe Ile Ala Lys His Leu Pro Asp

-continued

```
        35                  40                  45

Leu Ile Glu Ser Gly Gln Leu Arg Glu Arg Val Glu Lys Leu Asn Met
    50                  55                  60

Leu Ser Ile Asp His Leu Thr Asp His Lys Ser Gln Arg Leu Ala Arg
65                  70                  75                  80

Leu Val Leu Gly Cys Ile Thr Met Ala Tyr Val Trp Gly Lys Gly His
                85                  90                  95

Gly Asp Val Arg Lys Val Leu Pro Arg Asn Ile Ala Val Pro Tyr Cys
            100                 105                 110

Gln Leu Ser Lys Lys Leu Glu Leu Pro Pro Ile Leu Val Tyr Ala Asp
        115                 120                 125

Cys Val Leu Ala Asn Trp Lys Lys Lys Asp Pro Asn Lys Pro Leu Thr
    130                 135                 140

Tyr Glu Asn Met Asp Val Leu Phe Ser Phe Arg Asp Gly Asp Cys Ser
145                 150                 155                 160

Lys Gly Phe Phe Leu Val Ser Leu Leu Val Glu Ile Ala Ala Ala Ser
                165                 170                 175

Ala Ile Lys Val Ile Pro Thr Val Phe Lys Ala Met Gln Met Gln Glu
            180                 185                 190

Arg Asp Thr Leu Leu Lys Ala Leu Leu Glu Ile Ala Ser Cys Leu Glu
        195                 200                 205

Lys Ala Leu Gln Val Phe His Gln Ile His Asp His Val Asn Pro Lys
    210                 215                 220

Ala Phe Phe Ser Val Leu Arg Ile Tyr Leu Ser Gly Trp Lys Gly Asn
225                 230                 235                 240

Pro Gln Leu Ser Asp Gly Leu Val Tyr Glu Gly Phe Trp Glu Asp Pro
                245                 250                 255

Lys Glu Phe Ala Gly Gly Ser Ala Gly Gln Ser Ser Val Phe Gln Cys
            260                 265                 270

Phe Asp Val Leu Leu Gly Ile Gln Gln Thr Ala Gly Gly Gly His Ala
        275                 280                 285

Ala Gln Phe Leu Gln Asp Met Arg Arg Tyr Met Pro Pro Ala His Arg
    290                 295                 300

Asn Phe Leu Cys Ser Leu Glu Ser Asn Pro Ser Val Arg Glu Phe Val
305                 310                 315                 320

Leu Ser Lys Gly Asp Ala Gly Leu Arg Glu Ala Tyr Asp Ala Cys Val
                325                 330                 335

Lys Ala Leu Val Ser Leu Arg Ser Tyr His Leu Gln Ile Val Thr Lys
            340                 345                 350

Tyr Ile Leu Ile Pro Ala Ser Gln Gln Pro Lys Glu Asn Lys Thr Ser
        355                 360                 365

Glu Asp Pro Ser Lys Leu Glu Ala Lys Gly Thr Gly Gly Thr Asp Leu
    370                 375                 380

Met Asn Phe Leu Lys Thr Val Arg Ser Thr Thr Glu Lys Ser Leu Leu
385                 390                 395                 400

Lys Glu Gly


<210> SEQ ID NO 6
<211> LENGTH: 407
<212> TYPE: PRT
<213> ORGANISM: Mus musculus

<400> SEQUENCE: 6

Met Ala Leu Ser Lys Ile Ser Pro Thr Glu Gly Ser Arg Arg Ile Leu
 1               5                  10                  15
```

```
Glu Asp His His Ile Asp Glu Asp Val Gly Phe Ala Leu Pro His Pro
            20                  25                  30

Leu Val Glu Leu Pro Asp Ala Tyr Ser Pro Trp Val Leu Val Ala Arg
        35                  40                  45

Asn Leu Pro Val Leu Ile Glu Asn Gly Gln Leu Arg Glu Glu Val Glu
    50                  55                  60

Lys Leu Pro Thr Leu Ser Thr Asp Gly Leu Arg Gly His Arg Leu Gln
65                  70                  75                  80

Arg Leu Ala His Leu Ala Leu Gly Tyr Ile Thr Met Ala Tyr Val Trp
                85                  90                  95

Asn Arg Gly Asp Asp Asp Val Arg Lys Val Leu Pro Arg Asn Ile Ala
            100                 105                 110

Val Pro Tyr Cys Glu Leu Ser Glu Lys Leu Gly Leu Pro Pro Ile Leu
        115                 120                 125

Ser Tyr Ala Asp Cys Val Leu Ala Asn Trp Lys Lys Lys Asp Pro Asn
    130                 135                 140

Gly Pro Met Thr Tyr Glu Asn Met Asp Ile Leu Phe Ser Phe Pro Gly
145                 150                 155                 160

Gly Asp Cys Asp Lys Gly Phe Phe Leu Val Ser Leu Leu Val Glu Ile
                165                 170                 175

Ala Ala Ser Pro Ala Ile Lys Ala Ile Pro Thr Val Ser Ser Ala Val
            180                 185                 190

Glu Arg Gln Asp Leu Lys Ala Leu Glu Lys Ala Leu His Asp Ile Ala
        195                 200                 205

Thr Ser Leu Glu Lys Ala Lys Glu Ile Phe Lys Arg Met Arg Asp Phe
    210                 215                 220

Val Asp Pro Asp Thr Phe Phe His Val Leu Arg Ile Tyr Leu Ser Gly
225                 230                 235                 240

Trp Lys Cys Ser Ser Lys Leu Pro Glu Gly Leu Leu Tyr Glu Gly Val
                245                 250                 255

Trp Asp Thr Pro Lys Met Phe Ser Gly Gly Ser Ala Gly Gln Ser Ser
            260                 265                 270

Ile Phe Gln Ser Leu Asp Val Leu Leu Gly Ile Lys His Glu Ala Gly
        275                 280                 285

Lys Glu Ser Pro Ala Glu Phe Leu Gln Glu Met Arg Glu Tyr Met Pro
    290                 295                 300

Pro Ala His Arg Asn Phe Leu Phe Phe Leu Glu Ser Ala Pro Pro Val
305                 310                 315                 320

Arg Glu Phe Val Ile Ser Arg His Asn Glu Asp Leu Thr Lys Ala Tyr
                325                 330                 335

Asn Glu Cys Val Asn Gly Leu Val Ser Val Arg Lys Phe His Leu Ala
            340                 345                 350

Ile Val Asp Thr Tyr Ile Met Lys Pro Ser Lys Lys Lys Pro Thr Asp
        355                 360                 365

Gly Asp Lys Ser Glu Glu Pro Ser Asn Val Glu Ser Arg Gly Thr Gly
    370                 375                 380

Gly Thr Asn Pro Met Thr Phe Leu Arg Ser Val Lys Asp Thr Thr Glu
385                 390                 395                 400

Lys Ala Leu Leu Ser Trp Pro
                405
```

<210> SEQ ID NO 7
<211> LENGTH: 1224
<212> TYPE: DNA

<213> ORGANISM: Mus musculus

<400> SEQUENCE: 7

```
atggcactca gtaaaatatc tcctacagaa ggttctagaa ggatccttga agaccaccac     60
atagatgaag atgtgggctt tgctctacca catccactgg tggagctgcc cgacgcatac    120
agcccctggg tccttgtggc tagaaatctg cctgtgctga ttgagaacgg gcagcttcga    180
gaagaagttg aaaagctgcc cacactgagc acggacggac tgagaggaca caggttacag    240
cgcctggcac acctggccct ggggtacatc accatggcgt atgtgtggaa ccgaggggat    300
gacgatgttc gaaaggtgct gccccgcaat attgctgttc cctactgcga gctctcagag    360
aagttgggcc tgcctcctat tctgtcttat gcagactgtg tcctggcaaa ctggaagaaa    420
aaggacccca atgggcccat gacatacgag aacatggaca ttctgttctc atttcctggt    480
ggggactgcg acaagggctt cttcctcgtc tctctattgg tggaaatcgc agcttctcct    540
gcaatcaaag caatccccac tgtatccagt gcagtagagc gtcaagacct gaaagcattg    600
gaaaaggcac tgcacgacat agctaccagt ctggagaaag ccaaggaaat ttttaagagg    660
atgcgtgact ttgtggaccc agacacgttt ttccacgttc tccgcatata tctgtctggc    720
tggaaatgca gctccaagct gccagaaggt ctgctgtatg agggggtctg ggacacccca    780
aaaatgtttt caggggggcag tgcaggccag agcagcatct tccagagtct tgatgtcctt    840
ctgggaataa aacacgaggc tggcaaagaa tctcctgcag aattcctcca ggaaatgaga    900
gagtacatgc ctccagccca ccggaacttc cttttcttct tagagtcagc tcccccagtc    960
cgtgagtttg tcatttcaag acacaatgaa gacttgacga aagcttataa cgagtgtgtg   1020
aatggtctgg tctctgtgag aaagttccac ctcgcaatag tagatactta cattatgaaa   1080
ccttcgaaga agaagcccac tgatggcgac aagtcggaag agccctcaaa tgtggaaagc   1140
agagggactg gggggtacgaa tcccatgact ttcctaagga gtgtgaaaga tacaaccgag   1200
aaagctcttc tgagttggcc ttag                                          1224
```

<210> SEQ ID NO 8
<211> LENGTH: 2279
<212> TYPE: DNA
<213> ORGANISM: Homo Sapiens

<400> SEQUENCE: 8

```
agtccagatg atagttaaga aagcagtaag aatacagaga gtccacaatg agatgaaaat     60
gcactgccag ttgaaacatc ctcctacact ggagctttat aaatatttta aagacaagga    120
ttggattaga tttgacatta gaaatgtacc ataatacaga aggcaatgga cacctaaaga    180
acagaatgaa aaccttctta ggaaatgaag cttgacactt cacccaccag gccaccacaa    240
gaatgttgca ttttcattat tatgatactt caaacaaaat aatggagccc cacagaccga    300
atgtgaagac agcagtgcca ttgtctttgg aaagctatca catatctgaa gagtatggct    360
ttcttcttcc agattctctg aaagaacttc cagatcatta taggccttgg atggaaattg    420
ccaacaaact tcctcaattg attgatgctc accagcttca agctcatgtg gacaagatgc    480
ccctgctgag ctgccagttc ctgaagggtc accgggagca gcgcctggcc cacctggtcc    540
tgagcttcct caccatgggt tatgtctggc aggaaggaga ggcgcagcct gcagaggtcc    600
tgccaaggaa tcttgccctt ccatttgtcg aagtctccag gaacttgggg ctccctccta    660
tcctggtcca ctcagacttg gtgctgacga actggaccaa aaaagatcca gacgggaacc    720
tggagaccat catctcattt cctgggggag agagcctgca tggttttata ctggtgactg    780
```

-continued

```
ctttggtaga gaaagaagca gtgcctggga taaaggctct tgttcaggcc acgaatgcta    840

tcttgcagcc caaccaggag gccctgctcc aagccctgca gcgactgaga ctgtctattc    900

aggacatcac caaaacctta ggacagatgc atgattatgt agatccagac atattttatg    960

caggcatccg gatctttctc tctggatgga aagacaaccc agcaatgcct gcagggctga   1020

tgtatgaagg agtttcccaa gagcccctga aatactccgg cgggagtgca gctcagagca   1080

cagtgcttca tgcctttgat gagttcttag gcattcgtca tagcaaggaa agtggtgact   1140

ttctgtacag aatgagggat tacatgcctc cttcccataa ggccttcata gaagacatcc   1200

actcagcacc ttccctgagg gactacatcc tgtcatctgg acaggaccac ttgctgacag   1260

cttataacca gtgtgtgcag gccctggcag agctgcggag ctatcacatc accatggtca   1320

ccaaatacct catcacagct gcagccaagg caaagcatgg gaagccaaac catctcccag   1380

ggcctcctca ggctttaaaa gacaggggca caggtggaac cgcagttatg agctttctta   1440

agagtgtcag ggataagacc ttggagtcaa tccttcaccc acgtggttga gaggctgccc   1500

tctccccagc aatgcagagc cccatggag ggcaggtggg cctggagaat gagggtcagg   1560

gttctgcctg ggatcatcca ggaaggatct cagccctatt catgtttctg ctctacagag   1620

cactatattc tccttgttga gagctgttgg cttcacaaag gagagttgat gtggccaagc   1680

ctttccctcc ctacctgatc actgcttaac ggcatgtata atggatactt cctcatgcag   1740

aacccccaga ggagtgactg tatgccattc tctttgccaa gtaatagaaa accaatctaa   1800

atgtcaaaaa tcagataaaa ttgcctgggg atacattact tgttgatttt cttaaaaaac   1860

aaattcactt aacaattcat taagttcata ctgagcactg cctccaagat taaaaccagg   1920

atttctgtgg tcccagacca gccctcttct ccctgaatgt gttgagttgg tggcaggagg   1980

ttggaaatgc tccagtggag atgggaagat agaggatgct gacaataagg acttggaagt   2040

cactagtgtg aaaatgagca gttaatgata tgggaacgga tgagactttc cacgtggtac   2100

ctagatttgc aaattctatt gtaatgcctt tatttttaga agaattattc tctcttctta   2160

ctctgaaaat ctgtatttgt aaaatgaatg aatggatcct atataagtaa ataagaaaac   2220

tgggaataag tagtaaatca atgtgtttag tgtgcaaata aatgtaaatg cttttattg    2279
```

<210> SEQ ID NO 9
<211> LENGTH: 1245
<212> TYPE: DNA
<213> ORGANISM: Homo Sapiens

<400> SEQUENCE: 9

```
atgttgcatt ttcattatta tgatacttca aacaaaataa tggagcccca cagaccgaat     60

gtgaagacag cagtgccatt gtctttggaa agctatcaca tatctgaaga gtatggcttt    120

cttcttccag attctctgaa agaacttcca gatcattata ggccttggat ggaaattgcc    180

aacaaacttc ctcaattgat tgatgctcac cagcttcaag ctcatgtgga caagatgccc    240

ctgctgagct gccagttcct gaagggtcac cgggagcagc gcctggccca cctggtcctg    300

agcttcctca ccatgggtta tgtctggcag gaaggagagg cgcagcctgc agaggtcctg    360

ccaaggaatc ttgcccttcc atttgtcgaa gtctccagga acttggggct ccctcctatc    420

ctggtccact cagacttggt gctgacgaac tggaccaaaa aagatccaga cgggaacctg    480

gagaccatca tctcatttcc tgggggagag agcctgcatg gttttatact ggtgactgct    540

ttggtagaga aagaagcagt gcctgggata aaggctcttg ttcaggccac gaatgctatc    600

ttgcagccca accaggaggc cctgctccaa gccctgcagc gactgagact gtctattcag    660
```

-continued

```
gacatcacca aaaccttagg acagatgcat gattatgtag atccagacat attttatgca    720

ggcatccgga tctttctctc tggatggaaa gacaacccag caatgcctgc agggctgatg    780

tatgaaggag tttcccaaga gcccctgaaa tactccggcg ggagtgcagc tcagagcaca    840

gtgcttcatg cctttgatga gttcttaggc attcgtcata gcaaggaaag tggtgacttt    900

ctgtacagaa tgagggatta catgcctcct tcccataagg ccttcataga agacatccac    960

tcagcacctt ccctgaggga ctacatcctg tcatctggac aggaccactt gctgacagct   1020

tataaccagt gtgtgcaggc cctggcagag ctgcggagct atcacatcac catggtcacc   1080

aaatacctca tcacagctgc agccaaggca aagcatggga agccaaacca tctcccaggg   1140

cctcctcagg ctttaaaaga caggggcaca ggtggaaccg cagttatgag ctttcttaag   1200

agtgtcaggg ataagacctt ggagtcaatc cttcacccac gtggt                   1245
```

```
<210> SEQ ID NO 10
<211> LENGTH: 2464
<212> TYPE: DNA
<213> ORGANISM: Mus musculus

<400> SEQUENCE: 10
```

```
cgcacaagta caaccacaca gaagacacag ctggaaagct ccctggcctg ggcattcctc     60

tggggcagag acctcacgcg aaaatatgga gcctcaaagt cagagcatga cgctggaggt    120

gccgttgtcc ttggggagat accacatttc tgaggaatat ggctttctcc ttccaaatcc    180

tctggaagca cttccagatc attacaagcc ttggatggaa attgccctca gacttcctca    240

cttaatcgag aaccgccagc tccgagctca cgtgtacagg atgcctctcc tggactgcag    300

attcctaaag agttaccgtg agcagcgcct ggcacacatg gcgctggccg ctatcaccat    360

gggattcgtc tggcaggagg gggaaggcca accccaaaag gtgctgccaa gatctcttgc    420

cattcctttt gttgaggtat ccaggaactt gggactcccg cctatcctgg tccactctga    480

cctggtgctg acaaactgga ccaaaaggaa cccagaagga ccgttggaaa tcagtaacct    540

ggaaaccatc atctcatttc cgggggagga gagcctgcgg ggcttcatcc tagtgacagt    600

cttggtggag aaggcagcag tgcccggcct taaggccctg gttcagggaa tggaggccat    660

tcggcaacac agtcaggaca ccctgctaga agccctgcag cagctgagac tctccatcca    720

ggatatcacc agagccttgg cccaaatgca tgattatgtg gacccagaca tattttactc    780

ggtcatccgg atcttcctct ctgggtggaa ggacaatcca gccatgcctg tggggctggt    840

ctatgaaggt gctgccacag agcctctgaa gtactctgga ggaagtgcag cccagagctc    900

cgtgcttcat gccttcgatg agttcctggg cattgagcat tgcaaggaaa gtgttggctt    960

tctacacaga atgagggact acatgccgcc ttcccataag gctttcctgg aagatctcca   1020

cgtagctcct tctctgagag actacatact ggcctctggt cctggggact gcctgatggc   1080

ctataaccag tgtgtggagg ccctgggaga gctgcgcagt taccacatca atgtcgtggc   1140

cagatacatt atctccgctg ccaccagggc caggagcagg gggctaacta atccctcacc   1200

ccatgccttg gaagacaggg gcactggggg tactgccatg ctgagcttct tgaagagtgt   1260

cagggagaag accatggagg ccctcctgtg tcctggtgct tagcagtcat gtcctgcacc   1320

ctaacactta gatgttctca tcctgcatcc cagcgttaga ggttcacatc ctgcatccta   1380

gtgcttagct gttcttgtgc tatatcccag cgcttagcag tcatgtcctg catcctagtg   1440

cttagcattt tatatccagc attttagtgc ttagagattc acatcctgca tcctagagct   1500

tagcatttta tatccagcat ccttgtgcgt atcagctatg ttttgtatcc tgcttagcag   1560
```

-continued

```
ttaacatcct gcatcctagt acttatctgt tctcatcctg catcctagag cttagcagtc   1620

aggtcccgtg ggagcaagaa ccagggtctg agctctgtct gagcccaagc atggctttac   1680

tgctttgtta attgtggctc ccacctccac cccaccccag ccagtttgct tgctagaagc   1740

ctttctgcac tgcctaatcc ccctgcctca cagcagagag ctgcagccat gacctcctca   1800

ttcagtatta ggtggacaag tcggagatac ccaaactcaa ttttaaaaga atcaagttgc   1860

ttttggggca tgttacttca tcttttctta ccctgggcct cttcccttct tccctacctc   1920

cctcgtccct tagtctttca cccctctctc tttctccttt tgtcaccctc cccctcccct   1980

gcttactctc ttttcccttc ccccctctcc tcatccctcc ttcctttctt ccttcccttt   2040

ttgtctgtga agcaccaggt ctgatgggcc tcaaactgtg atcttcctgt ctcacccttc   2100

aaaggttatg tgtatgtgac gtgtgtgtgt gtgtgtgtgt gtgtgtgtgt gtgtgtgttc   2160

gtttcttttg tttttcccta gtggagatga cacccaaaga tttgcacata ccaggcaatt   2220

gctccaccac ctgactacag tcccagctct ctgtattcct gaaggaaagt cttgatgagt   2280

tgcctaggct ggtattgagc tctttagccc aggcaggcct tagtctgagt agctgggatg   2340

tacagggatg agccactgag ccatgctgct gctgctaacg atgatgacga tgatgatgat   2400

gaagattatg ataactacag tcactgcaat aatgacggca aagataatga aaaaaaaaaa   2460

aaaa                                                                2464
```

<210> SEQ ID NO 11
<211> LENGTH: 1194
<212> TYPE: DNA
<213> ORGANISM: Mus musculus

<400> SEQUENCE: 11

```
atgacgctgg aggtgccgtt gtccttgggg agataccaca tttctgagga atatggcttt     60

ctccttccaa atcctctgga agcacttcca gatcattaca agccttggat ggaaattgcc    120

ctcagacttc ctcacttaat cgagaaccgc cagctccgag ctcacgtgta caggatgcct    180

ctcctggact gcagattcct aaagagttac cgtgagcagc gcctggcaca catggcgctg    240

gccgctatca ccatgggatt cgtctggcag gagggggaag gccaacccca aaaggtgctg    300

ccaagatctc ttgccattcc ttttgttgag gtatccagga acttgggact cccgcctatc    360

ctggtccact ctgacctggt gctgacaaac tggaccaaaa ggaacccaga aggaccgttg    420

gaaatcagta acctggaaac catcatctca tttccggggg gagagagcct gcggggcttc    480

atcctagtga cagtcttggt ggagaaggca gcagtgcccg gccttaaggc cctggttcag    540

ggaatggagg ccattcggca acacagtcag gacaccctgc tagaagccct gcagcagctg    600

agactctcca tccaggatat caccagagcc ttggcccaaa tgcatgatta tgtggaccca    660

gacatatttt actcggtcat ccggatcttc ctctctgggt ggaaggacaa tccagccatg    720

cctgtggggc tggtctatga aggtgctgcc acagagcctc tgaagtactc tggaggaagt    780

gcagcccaga gctccgtgct tcatgccttc gatgagttcc tgggcattga gcattgcaag    840

gaaagtgttg gctttctaca cagaatgagg gactacatgc cgccttccca taaggctttc    900

ctggaagatc tccacgtagc tccttctctg agagactaca tactggcctc tggtcctggg    960

gactgcctga tggcctataa ccagtgtgtg gaggccctgg gagagctgcg cagttaccac   1020

atcaatgtcg tggccagata cattatctcc gctgccacca gggccaggag cagggggcta   1080

actaatccct caccccatgc cttggaagac aggggcactg gggtactgc catgctgagc   1140

ttcttgaaga gtgtcaggga gaagaccatg gaggccctcc tgtgtcctgg tgct         1194
```

<210> SEQ ID NO 12
<211> LENGTH: 1227
<212> TYPE: DNA
<213> ORGANISM: Homo sapiens

<400> SEQUENCE: 12
atggagcccc acagaccgaa tgtgaagaca gcagtgccat tgtctttgga aagctatcac 60
atatctgaag agtatggctt tcttcttcca gattctctga aagaacttcc agatcattat 120
aggccttgga tggaaattgc caacaaactt cctcaattga ttgatgctca ccagcttcaa 180
gctcatgtgg acaagatgcc cctgctgagc tgccagttcc tgaagggtca ccgggagcag 240
cgcctggccc acctggtcct gagcttcctc accatgggtt atgtctggca ggaaggagag 300
gcgcagcctg cagaggtcct gccaaggaat cttgcccttc catttgtcga agtctccagg 360
aacttggggc tccctcctat cctggtccac tcagacttgg tgctgacgaa ctggaccaaa 420
aaagatccag acgggttcct ggaaattggg aacctggaga ccatcatctc atttcctggg 480
ggagagagcc tgcatggttt tatactggtg actgctttgg tagagaaaga agcagtgcct 540
gggataaagg ctcttgttca ggccacgaat gctatcttgc agcccaacca ggaggccctg 600
ctccaagccc tgcagcgact gagactgtct attcaggaca tcaccaaaac cttaggacag 660
atgcatgatt atgtagatcc agacatattt tatgcaggca tccggatctt tctctctggg 720
tggaaagaca acccagcaat gcctgcaggg ctgatgtatg aaggagtttc ccaagagccc 780
ctgaaatact ccggcgggag tgcagctcag agcacagtgc ttcatgcctt tgatgagttc 840
ttaggcattc gtcatagcaa ggaaagtggt gactttctgt acagaatgag ggattacatg 900
cctccttccc ataaggcctt catagaagac atccactcag caccttccct gagggactac 960
atcctgtcat ctggacagga ccacttgctg acagcttata accagtgtgt gcaggccctg 1020
gcagagctgc ggagctatca catcaccatg gtcaccaaat acctcatcac agctgcagcc 1080
aaggcaaagc atgggaagcc aaaccatctc ccagggcctc ctcaggcttt aaaagacagg 1140
ggcacaggtg gaaccgcagt tatgagcttt cttaagagtg tcagggataa gaccttggag 1200
tcaatccttc acccacgtgg ttaggat 1227

<210> SEQ ID NO 13
<211> LENGTH: 1218
<212> TYPE: DNA
<213> ORGANISM: Mus musculus

<400> SEQUENCE: 13
atggagcctc aaagtcagag catgacgctg gaggtgccgt tgtccttggg gagataccac 60
atttctgagg aatatggctt tctccttcca aatcctctgg aagcacttcc agatcattac 120
aagccttgga tggaaattgc cctcagactt cctcacttaa tcgagaaccg ccagctccga 180
gctcacgtgt acaggatgcc tctcctggac tgcagattcc taaagagtta ccgtgagcag 240
cgcctggcac acatggcgct ggccgctatc accatgggat tcgtctggca ggagggggaa 300
ggccaacccc aaaaggtgct gccaagatct cttgccattc cttttgttga ggtatccagg 360
aacttgggac tcccgcctat cctggtccac tctgacctgg tgctgacaaa ctggaccaaa 420
aggaacccag aaggaccgtt ggaaatcagt aacctggaaa ccatcatctc atttccgggg 480
ggagagagcc tgcggggctt catcctagtg acagtcttgg tggagaaggc agcagtgccc 540
ggccttaagg ccctggttca gggaatggag gccattcggc aacacagtca ggacaccctg 600
ctagaagccc tgcagcagct gagactctcc atccaggata tcaccagagc cttggcccaa 660

```
atgcatgatt atgtggaccc agacatattt tactcggtca tccggatctt cctctctggg    720

tggaaggaca atccagccat gcctgtgggg ctggtctatg aaggtgttgc cacagagcct    780

ctgaagtact ctggaggaag tgcagcccag agctccgtgc ttcatgcctt cgatgagttc    840

ctgggcattg agcattgcaa ggaaagtgtt ggctttctac acagaatgag ggactacatg    900

ccgccttccc ataaggcttt cctggaagat ctccacgtag ctccttctct gagagactac    960

atactggcct ctggtcctgg ggactgcctg atggcctata accagtgtgt ggaggccctg   1020

ggagagctgc gcagttacca catcaatgtc gtggccagat acattatctc cgctgccacc   1080

agggccagga gcagggggct aactaatccc tcaccccatg ccttggaaga caggggcact   1140

gggggtactg ccatgctgag cttcttgaag agtgtcaggg agaagaccat ggaggccctc   1200

ctgtgtcctg gtgcttag                                                 1218
```

<210> SEQ ID NO 14
<211> LENGTH: 52386
<212> TYPE: DNA
<213> ORGANISM: Mus musculus

<400> SEQUENCE: 14

```
tagttagaag gcagctcgtt tccagacaga tcatgccggg ccagcacagt tccacgagga     60

gcgatttttt tggatggggg aagaaagtga agaagaggag aaagaggaaa agggggtgaa    120

gggtcgcggt ctcagtcttt tatttgtgcc atgacataga tgccaggtaa tgaatgatga    180

atgatgcgca caggtgaagc ataggcctgc ctggagtgta tggtggttgc catggcaaca    240

gacccaagag ggtccttgtc gcttagggat gatgtcatag ctggattccg aggctggttg    300

taaagcagtt tctgatgcta acaatacata tatatgtaat gataacaaag aaaaagaggc    360

catgaatttg aaaggaagga aagaagttag gaaggaagga aggaaggaag gaaggaagga    420

aggaaggaag gaaggaagga aggaaggaag gaaggaaaga agatgggaat ttggagagat    480

gaaagggaag aatgatataa atacatttta atttcagcaa ataaatacat tttcaaagat    540

aaaaagccaa taaagagaaa ccctgtctcg aaaaaacaac aacaaaccaa aaacaaacaa    600

acaaacaagc caataaaact gactcctagt ttagtcattt tgatacactg tcagaatccc    660

tcaggaacca aactcatgtt gagtatggat ctgcacagcc atagctgaga gttaagttcg    720

tgtctcccac tttgtccctg gatttaacag cccctttctc atactttatg aatgagaagg    780

gaaagggggt gggggcttct cttggagtca gcattttaat tcctaatctt cattgttgac    840

ttactacttg gctttctttc agaataaatt tgcggccatc ctggagttca acctcagggc    900

aaggttctcc cctaccgctg aagcaccgca caagtacaac cacacagaag acacagctgg    960

aaagctccct ggcctgggca ttcctctggg gcagagacct cacgcgaaaa tatggagcct   1020

caaagtcaga gcatgacgct ggaggtgccg ttgtccttgg ggagatacca catttctgag   1080

gaatatggct ttctccttcc aaatcctctg gtaaggattg gcttgtcctg gtcagcacat   1140

gtgtctggat tgttagtctt taccttatgt ggttattgga aggttcggta taagtcacca   1200

gctggaggaa gagtgggaat acagtcctgt gagtcccgga agagcagagg caactgctac   1260

tggggacagc acaaagccag tggtcccctc cccccagccc ccaaagtttc cttaaatcta   1320

tggtagttag cactgactaa tcagaagcaa aggtgctatc agagaggaga gactggatgg   1380

agacatgccc taaggacaat tagaacccta taactacagc aaagagtgga catgcacaca   1440

accacatggt gtgacacaga ataatggagt ggccccactg tatatccact ctgctttgga   1500

gacaggttcg ccatgcatcc cagacctaag cagccaaagg gcttagcctt ctgtgttgat   1560
```

-continued

```
gcaaaccagt ttatcttact tgctggtgac agcagagata atgggagacc tgcaatgttt   1620
ttagagccag taagaagatt agatgttatc gggaatttcc gatactcgtg aggaatgttg   1680
gaaaacaagc aggcctgact ttcagtccaa ctgcacagca gtctctagta tacctgctct   1740
tgttaagtgt agtctgggct tgggagacat atgccggcaa agtgctagtg gcaaagccca   1800
tgcttttggc atcttttaaa aactgaccgt acctaaggga gggtgaaggc cactgagtta   1860
aaagtccagg gacccgatgt tgcagtcgcg gtaactgctg atcagcacca actcacctag   1920
ttcctctctt acttgtgatt aaaaatatca gggtctcaaa cacctatcac agtgagactc   1980
ttgttgtttt gaaacagaga atattgattt atgtagccca ggctggccac ttgcctccac   2040
ttccttactg ctgggaccat agctgaactc ccacagcaga tccttttgtg ttgaacggta   2100
ctggagggat ctaattgaag agaactaagt tctccacaga aagatgtcag ctacgacatc   2160
ggtcatagac atctgcaagc tgtccaggtt aggggttagt cattagaacc agggccagat   2220
ctcacagctt gaatcaagcc aggccttcct gctgctctct cacggacagt taggaagcag   2280
actgtactct gacatgatag cttgcagccg acggctcccg gctcctctgt gctccttgtc   2340
acgcaggccc tgctataaac taaagtgtct gacatgactt cctggtgcct cgtaaagtta   2400
ttaaaagtca gatttctcct ttgttctcgg aattggttcg agagccctca ggggatttgc   2460
tgagggtgtg tgtgtgtgtg tgtgtgtgtg tgtgtgtgtg tgtattctaa gagtgcttcc   2520
ctaaaagggt cctctgtact gtcaacggat ctttcatagt ctctctctcc ctgtctccct   2580
gtctctctgt ctttctgtct ctctgtctct ctctgtttct gtctttctgt ctctgtctgt   2640
ctgtctgtct gtctatctct gtgtgtgtgt gtgtattttg aaggtaggag gatctgagcc   2700
tgaactacac acagctagat cctgtgactc tgtctcaaaa cagagacaca atcaaactct   2760
caactaatcg aaacaccaca aggcacactc cattctgggt gtgtggtctc agtccagcgt   2820
attcccatcc ttccaagttt acaggagagg aagggctgat ggcagataca cccttgtcat   2880
tactgggcat gtgtcctgag tttggaaaga gaacactgcc aagcagggga acgaatatca   2940
gggcaggcca tagctctggg gctttctggg ctgctttcct ctttgtaaat actgggacca   3000
ggcagacata cagataagac acaatagcaa catcaagttt ccccccctatt tgttagaaag   3060
gttctatggt atggtgtgat ggatgggtac cccttaaaag aggtccctag tgctgttcac   3120
acagaaagga aatattccct gtcccaccca gctactcatt tatagcccag taatttcaat   3180
atgattcttt ctgtttcaat tttctttcat tcaagtgatg gttttcaatg tctttttttgt   3240
taaaggaaga ggaagaaacc ttgactagga tcaggtcctg gctgctccaa aggtcaagac   3300
agactcagtt cgacttcact ggacaaacag tcctgcaact ttacactggt tgggaaagaa   3360
cagtgggttt ggcccagtcc agtgccctag ggcatagcca agacctgttc ttcttgggcc   3420
aagggcaagt ggtaggtggc agaccttccc catctctttc agaaagtctc acttaagaaa   3480
acctagctgg ctagcaagtt caagggtata aattacccta tccagctgtt tctatcaatt   3540
caaagacttc caatttttag tgtctctatg gaactttgct cctcgaatct gtaaaaatac   3600
cacaagaatt ctttgctaag acatctgtcc tctgtgtata tttgggagga caagacatct   3660
ttttcagatg aagaatgtga ggaaatcagt ttgcaggaga ggaggcagtt aagaggaggc   3720
agcaagaggc tggcctgcag cagagctatg accccaagtg ccaggcccac tctgaaaatt   3780
gatttaacac ccttcctaaa cacaatgtga ctgctacttg agtcatttcc tctcacagca   3840
ctaagggcag ggcaggttag agcagtgggt cctgggctgt ggggtgagac ctttagggga   3900
gtttcaacaa acaatccaga tgccagagcc ccaccctgtt tattcagact ctagacccaa   3960
```

-continued

```
gagctgtacg ctgggaaggc cagataggga gaacaagcca gagaatgcca gacagggagc   4020
acaagccagc aaagtcagcc gtgaaggtgc cacggccaat agagactcct aagtgcgaaa   4080
ataaataaac tgatgacatg cccactccat gcttaagggg aaagtagatc agagagggag   4140
agagagagag agagagagag gcacccagag gcagaggcct ctggacgatt ccgtagtaga   4200
tagagaaagc agactgaaga tggccaccag actggacatg gccaaggcta cctgggagga   4260
aaggaagaac aacagaagtc agagaataga gaaaacctag tgagagaagc aggaaggggt   4320
tgggggggtg gatggagaga agttagcaat gacagcaggg ttctaagaag aaagagttgg   4380
ggaggggaga tcctgtgagc tggagggagt ggagtgagtg gaggggaaga gctgagaagg   4440
gacagatgct agcaggggct ttgagatgta cagcaggtac ttgtgatagg tgactggagg   4500
ccactggtga ccacatgtcc cttctgcaag aggtaaggga aaacattcct ttaggtagag   4560
ggaaaccagt gtcacaagtc cctgaggaaa gctggctttt tatctaaccc ccagaaatcc   4620
tcctgtagtc caggtgaagc tcatttctgg acatacagac tgccttttgg agtttgggga   4680
actggagttt cctttggacc tgacagtcag gagacgttgc acatgtaacg taggggtaga   4740
cacaagactg acaggaatgg caatgagaga ggacaacctc cagggaaaaa ccaacatgtc   4800
ccttctcatt cagaaattct aagcacttgg ttgaagcatt gggccacagc tggagagaag   4860
accggatagg aaattaattg ccacggacat ctgtattttt cagataagac aaaaaggaag   4920
aggtctaaca ttgtcctgaa atatgaggtt gccactgatg atctctggac acatcagact   4980
agtcagatag gggacttgaa acacaatgaa tccagagtct gtagtagaga caaagaggcc   5040
agattgcaaa atggttaatc ttgatcaagg ctggaaaatg tgtatggaaa taagagagac   5100
tgtaatatct taagaatggg gtttgtcctt gtgccagtat taaagaacaa caacaaaaaa   5160
aaaaaaaaaa gaaaaagaaa aagaaagaaa gaaagaaaga gagaaagaaa gaaagagaaa   5220
aagaaaaatg gaggaaagtc atggggaaac aggtaatcag gcttgaatta aaaaaataaa   5280
aaaataaaat aaaaagttaa aggacttgac tagtcccagg tttctgcaca gatgaattaa   5340
aaaatgaaaa gaaaagaaaa gaaaagaaaa gaaaagaaag ggaaaaaaag aaaaaaagaa   5400
aggaaaaaaa aaggaaagag aaaaacaaaa gacaggaaaa gaagggagga aggaagaaga   5460
gaaagaaaga aagacagaca gaaagagaga gagaaaggaa ggaagaaagg aagagagaaa   5520
gaaagaaaga aagaaagaaa gaaagaaaga aagaaaggaa ggaaggagga aggaaggaag   5580
gaaagaaaga aaagaaaaga aaagaaaaga aaagaaaaga aaagaaatga aaagaaaaga   5640
aaagaaaaga aaagaaaaga aaagaaaaga aaagaaaaga aaagagagga aggaagacag   5700
aggaaagggc ctggctgctt gtaggtactg tagcccggga gatcatagcc agaggcaagg   5760
acagctaggg aaatccagag tggtcatgac cgtgaaccac ttgaggagag ggaagagaaa   5820
agggcagccc agcccccagg ctagagaagt ttagggttgg ggcagggttt gtcagccagt   5880
gggtctttgt aactcccgag aacttgtagg cggctttgat atgctaagta ggcacctcag   5940
cctttcctct tgggtttgaa acccagaagg cctcagcaag tgggacaagc caagcccaac   6000
ttggaaagca gagttttaaa gggtgaaaca accaaccaaa aaggttcact ctcttctagc   6060
aagacgctta tgctgcaaag agacttaaga caatccggga gcaaggacag gacacacgct   6120
gaggatggga tgctaaatca gccctggaaa atacgtgtct aatacaggag gctctcgccc   6180
aagatctatt ggtttcctag cacagccgta aaatggctag ctattttaga acagtaacca   6240
gttctctgaa ctccatgcca gcctgtcccc aagtttccag ccctctgctt caaacacttc   6300
ttccaaccct tccaccctca atttcccaac agtcttctta aacaattcct tctccccatt   6360
```

-continued

```
ctcccaagac tagccactcc aaacggtaac aaccatatct tccataccaa ctgccttctc   6420
ttctccctct gctagcccaa tccccctcc ttccctgact cagctggctc ttttatactc   6480
tatccagttc ctagtcatcc aagaagcaac caatgcttag ggtcataggg tcaagccttt   6540
gtaacagcta aaagttctta aagaggccag ttgactcgca actggagacc ctttattact   6600
tatttatttt tatgtctatg agtacactgt agctgtcttc agacacacac cagaaaaggg   6660
catcagatcc cattacaggg ttgtgagcca ccatgtggtt gctgggaatt gaactcagga   6720
cctatggaag agcaatcagg gctcttaacc ccgccgagct catctggaga ccctttaaag   6780
ggccaggagc ccaagataaa tcacattaca gttacatatg acccaaactc aggtgagcta   6840
gaccagtgaa gacttagact gatttctgga attaaggcac tgggcctgca gcacttccct   6900
ccaaagcctg cagtgcagaa tctgcccagg cctttcccag gctccggtag cttcaacagc   6960
ttcctggcta ctagctcctg gcatctttcc accccttcct tatatggcct tctgctgctc   7020
agtgtcttct cccctgatgc cttttcttct tcttttctta caaggatgct gctcattggt   7080
ttttaagacc caagctaatc ccagataatc tcatcagtaa agagccctct ccaaatagta   7140
tcacatactt agttcctaag gggacaactt atttgtgttc taagacttgg ggcaaagtat   7200
gagcagatgg tgcaatctta ggaatgctga ctgaaagaac tgtcttgtcc ctagattccc   7260
aaacctgatc tgtcaggaat gaatggggga aaaaagccca ggacaatgac aggcaagagt   7320
gtaaaatatc agtggtcgcc aaggggcttc gggacataaa ttcagtgagt gagtgcattc   7380
ttaccacgta tgaagaccat gccaaacaca gacataaata acgaaaatta aagattaaaa   7440
gtaaataaat tggccagatg tcatggcaaa tgcctgcatt cctagcaact agcagaagca   7500
ggaaggtatc aagttctagg cctgcctgta acactgaaca catatgagac cagcctgaga   7560
tatgtagaca aacaaaaacaa aacaaaacga aagaccattg atcaatcaat aacataaacg   7620
ttcaggaaac acaggccaca caatcaggga ggctttgcct ttgtttaggg gctgggtttt   7680
tttttatatt ttcctttcct tgttcttctt cttgtttgtt tgctttttgt ttgtttgttt   7740
gcttgcttgc ttgcttttgt tttttcaaga cagggtttct ccgtgtaggc atctctggct   7800
atcctggaac tcattctgta gataaggctg tctttgaact cagagatctg cttgcctctg   7860
ccttcttaag gccgggacta aaggtgtgca cagtcactgc cacctacctg ctgtttcttt   7920
atcccctgca ttagtcaccc tcccacaccc gccagagctc tgggatagag actctgtgtt   7980
agggaatgga gcctacagct tccatcaggt gctatgtttt aattcacatt ttctattcct   8040
cttttctcat ttgtctgggg tgattctttt ggacaaaaaa aaatgttatc ttttataatt   8100
actaattagg atacaaacgt taaaatatat ctataatgta ctcttgtata tcattcataa   8160
tacctatttc gtattatact tccttatagt atatagcata ttttgataac aaggtcacga   8220
ggtcccaggc ctggaaccaa ctttttccta tgtaattggt tgaagttact gacaccgtag   8280
tagacttagc cctctggaaa cagcctttgg caatgaattt gactctgttt cagacaacca   8340
tcactttcct ggaaacggcc tctggcccat tcattacata tttcttgccc atctgtgaca   8400
cgctctgggt acaatcagca tgactcacta agagggtgtt cccgtttgct tctggtttct   8460
gtgagaaaac aaacaaaagc aactctggga ggcaagggtt tattcagatt ataagtccct   8520
gtcacagtca atcgctgagg gatgccaggt caagagctca agcagggccc tggatgcagg   8580
aagcagaaat cagagaaatg atgctctgtg gcttcctctc aattcacacc tcccgggacc   8640
acctgcctag ggatggcccc acccatagtg ggctggacct ccctccatca atcactaatc   8700
aagaaaacac cccacagatt tgtctacagg ccgatctggt agagacaatt tctcagtgaa   8760
```

-continued

```
ggctccttct gacttaatgt caagttggca aaaactaaca ggcacagatg ggaaccagtc   8820
ataacagtgc tctgtacagt tctcccattg ctctttagaa tggtctcaca tggcctctca   8880
caatgctcac acagcttctc ctgggaattt aatgcccctt gcttcaactt ctctttgctg   8940
tgccatgatg ctagcctttc ctatgtccaa tcccccaccc acatccactg aggttcttgt   9000
agactagaac cttccacatg agacagacta ccttaaccct tgtcttaggg gtaggctggc   9060
agggttacta tttctataaa acatactttc aattccattt taacgtttca tatgtattat   9120
atatatttat attatcaatg tagtgatgct aaatagacaa acagatgact taagtcttaa   9180
tgatgatcct ataagaattc ctaaaatata tctgtggtta ttaagctctt ttatagtggg   9240
acagccatta agtccttttc taattgtcaa aactgcaatg agaactctgc cagtctccca   9300
agtgtctcta gttaattgct attagatcgt aaccagactt tctcctactc agagcacatt   9360
ccaagcggtt gtaagacaat cagtcaaagt ttataaaaag ggacaattta tatatatcct   9420
gctaggacag aagataaaat attggctggt tttgtcgata ctaagcttca ctaataactt   9480
agttatggtt tgaacccttc agtgaacagg gtgatggatg ttgagcagga tttttactcc   9540
tcatggatat gcatgtaaac tttctctgtt gtaaacttat atatcaattt atgatttgat   9600
ttttgtgtgt gaacttgtga tgaactttgt aacatgtgat cattctgaaa gatgtataag   9660
tactaaggac aaagagatga gaggcagata gagttgaatc cccccccccc ccccccaaga   9720
atcaatcatt tcccttccta gaatttttgc tcctgtagag aatttttcac tttccccact   9780
taggatcttt ctgcctttcc ccttagttag ctttcgtagg aaacttttta caacttagta   9840
ataaatgcta taatcatttt tcgaagtgtc cccttttctt cctgtgactt ccgactagca   9900
ggccgaaagt tagagtggaa cagcttctgc tgagatagtg cgaaggctat ctactttatc   9960
ctttgctgtt tgaggaagat gtgctaagtg ccagagactg cagtttctgg cctccgagga  10020
acacagaagg caggtcagct acagtagcat cgagaagaac ccaacaagaa agaagagctc  10080
catgccaggg ctggcagcat tcctatgttt tatgtaatat ttactgctga gcaggggata  10140
atatctgaca tcatatgtta cttatacatt tttgttgatt aaaaactata ataatcatcc  10200
cttctcagca cccacagaaa accaaggcat gtggatctct gtgagcttgg ggccagcctg  10260
gttcacatgg tgagttccag gtcagctggt gttacataac atgaccttgt ctcaaaaata  10320
taataataat aacaataata atacaatatt atatatttta taataaataa taacaatcac  10380
tagtattaaa ataaaaataa aagaaaatat aaaatcatgc ttgttaaata ttgctttata  10440
ggacattatt tgactgtctt ttaacctggc aaatacccat cagcattctt tctcaaaact  10500
cagtaccact cgaggcctcc ttgacccact gtctcggtta ttcagcacta atgatctaag  10560
tgtatttttg gcacacagtt catattgtag acagcacttt gtaatttttt tcttttatgt  10620
ttactttttt tttttaactt ggataaataa gtataggcca ggacatttat ctgtaaaaag  10680
aaaggatgtg tattggaaag tttctatgag ctttgtgtca gaaggggttt ggcctggcca  10740
ctgaccacat gtgctaggga gggagagtta acctcccctc tccccatggg gagccttagc  10800
tgtttattct gttgctgtgg taagatgtcc tggtaagcaa cagaggcagg gagggagggg  10860
tttgtttggg ttcacagttc agcagaagcc acaggtggcc tgaccttaag gcatctggcc  10920
ttgtcgcacc cacacccaga gccacgggga tcttagctgc cgttctcatc gttccatagt  10980
ctagggtcta ggcccatgta atgatgccac ccacagccat cctaactaga caaacaacca  11040
ctcagagctg tgcccagagg ctcacctctc agtcattcca gaccccgtta aacagacggc  11100
cagtactaac tgttacactt tctgtatttc agtgtgggaa gaacaaaaga gaagcctcat  11160
```

-continued

```
ggcacaaaca cccaccgatt aagacaagca tcagcatgaa gactagaaac aatattaaac  11220
aatattaaaa gtgactttgg gaagagggga aatttttaag tatgatttaa gaccagaaaa  11280
cgagtgagat gtggtttgtt tcattattcc attaggaaca gctatttaaa atacacataa  11340
aggacaccat acctgggata tatactgggt tttagtctgg actaaaggat gacacttggt  11400
ttttaaacaa aggaaaaatt gagtgactaa agcttatgaa aattgaactt gcagaaatct  11460
aaaaatttaa atctagaata gtaacaaatt gatatcatca attcgggagt tacatagatc  11520
acctaacaaa ccacattggg acctcctaag tgttatcatt ttagacaaga gggtaagaat  11580
cggggtactc tttcgtctac tttagagagt tcatgctttt ttgaatgccc tgttagcaat  11640
gttgatccag aagactacat catcttcttc tttatgaatt gggaagccag caacaaagca  11700
actgagtagc aaaggcttat tcttggctaa gaataggaga catgagaaac aaactcacaa  11760
gttcactccg cgatctgttg tggttatagg cataggatca aggagttgag tgggaaggag  11820
aggctagtaa tcaggggaca tattgttact gggagacatg ttcaagtatt tcctaagact  11880
aggtggagat ttcccaggaa atccatcaat atatcttttt caactatttt aaaaacttca  11940
ctcatttatt ttagtatgtg tgtgaaaaag agacagagat atatagagag agaaaggggg  12000
agggagggag aaggagacgg ggaaagaaag acagggagat agagagacag agaaaaaaga  12060
cagagggagg aatgggtaga gggaaaggga gagagagaag agggtcagag agaggggggg  12120
agagagagaa agaaaagggg gggaggggaa aagggagaga gaaatagaga cagagaggga  12180
gggagggaaa gaagaaggaa agggggaggg ggagggggag agagagaaag acacacacac  12240
acacacacac acacacacac acacacacac acacacgggg gtggggggag agagaatgct  12300
gatgtcatag tgtgccactg gagatcagtg gacaactgtc tcaggaacta gttctctcct  12360
gccaccttgt gggatgcagg atgaccttag atcctacctg ctggctagcc tacctttccc  12420
atcttttatg gatctttctt gtcagaaacg aatgactgtg atgttactga ggttggttgg  12480
catggagcat gcaatgtagg tgttatattg tgaaggtaga ggtgtttagc agtcactccg  12540
gcacttatct gagacccaaa taattctggc caacctacct gaagagcaac ctctggccta  12600
tactatcttg ttataaaagg aaatcagatt aaagccagga agacattctc taggctaact  12660
aggaagactt ctctctcctg ccctctacac tgaaacattc ctctttaaaa aaattatgtg  12720
tctttggaat tattattatt agtattagta gtagtatttt ggttgctatt gttgcacatg  12780
ttaagcaatg agctaacatt tcccatcatg cctaccatca tataaatgtt aggtttgagt  12840
tcggggctaa gcagaccaca tttccatgtc atcttacagg tacttgcagg cccaccatag  12900
aacagttgta gaactctgac aaacttccag agctccgctg aacttcagaa aatactgaat  12960
cccagaggtc ccacaagtct ctatcctcct ctctgcagaa ccctcagagc tgattctggg  13020
cttcctggtg ctacacggaa atataaaaca acccgtctga atgtatcaga caaattccct  13080
agataaccag acggtagaga gcaatggcta agtcacatcc cccagggatg ggggaacctc  13140
actaattaat taaatggtaa atgtggtagg tacatgtacg aactgacatc aaagaagatg  13200
catgctgtct aaccagaaac ttgcctggtg ctactgtctc tagtatgata aatttaaatc  13260
tgacagttag gagtaaccaa tataattctg tactttcttc agtctctaga gcagagactc  13320
tcaacctgtg gtttgagacc cccttttggag cttgcatatc agagattttg catagccaat  13380
atttacacta ttatttgtaa cttgtaacaa ctttacagtt atgaagtagc aacaaaataa  13440
ctttatggtt gcgggggggg gggggtcacc acaacatgag gaactgtatt aaagagttgc  13500
acacggtatt aggaagggtg agaccccgtg ctatagagga aaggctggaa agtcaaatgg  13560
```

```
tttttacatg agttgtagtg ctgcctaaga ggagtgttta gcaatcttct gggtaagact  13620
caaagagacc cagaagccta gcaatacccg tggtagaggt gtcacctcct actcaaatgg  13680
gttgtaaaac acctttcaaa ctgctctcct ctcttctgga ttactggcaa gccttggtcc  13740
ctgtctgtgg ttgtcagact caggctgtgt caatcactta gcggatggat aactggctac  13800
agagctccac cagaaggtca gcttccgtat gtctggggtg aggaccagga gcctgtgggt  13860
tgaatcgttc ccaagggata aaagtactgt ggacgctgag tgcactcgga tgctttgtgg  13920
ttgcgtttgt ctgttgagct tacagcagtc catgcatgag acattggaaa caaagagctg  13980
cagccttcct ctgggatcta aggggaaaga atagactgca gcctagagtc ttggttctca  14040
gaaatgaact gtttaaggtt tctcacgtaa gctaggaagg cagagcccag ctaggtttca  14100
tttaattatg atgggattcc ttatttaggt accaaagaag gaaaaggctc ctctggtgat  14160
ggttagtgac agcttctttt ctgggtccca gccaatcaag gggcatctg agttctacag  14220
actttaagtg cgtgattttt ctatttcaaa gtaaacacga gatattctag cccagcattt  14280
gagtcactat gttcaaatat attctaaaat gcccagatca caccagcgag attaagtaag  14340
ttggcagttc acagatacat caacatgaat ctatctttct ttctttcttt ctttctttct  14400
ttctttcttt ctttctttct ttctttcttt cattcattat ctatttatct gcctacctat  14460
catctatcta cctacctagc tatctagcta tgtctatctt ccagtccgta aatctatctc  14520
tgtgcatcta tctatctatc tatctatcta tctatctatc tatctatcta tctatctatc  14580
tatctatctt tcattatcta tttatctgtc tacctatcat ctatctacct acctagctat  14640
ctagctatgt ctatcttcca gtctgtaaat ctatctctgt gcatctatct atctatctat  14700
ctatctatct ctatcattta tcaaccatct ttctatccat catccatctc tctctctctc  14760
atatctctct catatatata catatgcata tgtatacgag atcctttctc ctgaggaagg  14820
agtcaagatt cacagtccta ggcaagtgct gtactcctgg gcaatagggc agcctttgct  14880
tttattctta gtctttctct tgatgccaac caaatgcgta tcagcttcaa ttctgctctc  14940
ttcagctgtg tacctgcagc tgtttcctgg agaaaatgac accatcaacc atttctctcc  15000
aggacaaagg ctgggtgggc tgggaggggt gcgggtggag tgagtgcagg acaggagacc  15060
aaaggctgaa ccagatgacg gtcttgccca gaacgcctcc acccgtccag aactacagcc  15120
gctgctcccc atgcagtttg actctgaaag tataacaacg taaaaacaga attctaggcc  15180
tttaggccca ggcttgagaa tgtggccttt gtaaaggtat gctaatcata aaagagatag  15240
cgacattcct ctacccaccc gcttcctggg ttcaaagagt gctcattcaa agaaagtcac  15300
cctgaggatt accagaacct gcaatgcaaa tgtgctattg ttagaggctc ttagaagctg  15360
tcttgagagt taacacttac caggtattcc ttgtgactct tgtaacttta cacttccttg  15420
tgactcttaa ctggtatctt tggtatcttc caacaatgcc ctccccactt ccttgagttt  15480
cggtttcttc ctttaaatac ccccttaccc agctactcgg ggtgccacgg tcctctaccc  15540
ctgcgtggtg tatgaccatg ggcccgagag cgcttttgaa taaaaatcct cttgcaattt  15600
gcagcaagac ccgtttcttg tgggtgattt tggggtgtcg cctctcctga gtcagaacgt  15660
gggggagccc tcacattgtg ggtctttcaa ctcgaggctt ccagttcgtc ctgagttact  15720
ttagagtcaa agaaagaaaa gggaagatta aatgaagttc aaaacctcca cagcgtatgg  15780
caagatgttg gaaatactag ggatgcaagt caaccaggag ttttagccca gaatcacagg  15840
agatctagat gttcatgacc ccgaccccca cccccctaaac ccaacttcca cccccacccc  15900
cgccacccca acagcaacaa gaagtgacac gtgggtctcc tgttgatctc tgcctctcca  15960
```

```
gagctggact ttcaagtgtc ctggcttatt actgtccctc tgtgttgtca catttgctca  16020
gggtcagctc tcctctcctc ttcccggttc ttagcataac gcttattcct ctctgtagtc  16080
tcacagcctg atctttaccc ccagtgagct gagaaactgg atccatggga agctaagccc  16140
ctcacttctg catctgccag gatgcatctc cttctccgct cctcttcttc ctcatgcctt  16200
gctgcctctg tgtcccccgc ccccctcttc ttcccagtgt tcctcttcca gcagcagacc  16260
atgaactcca tactgctctt atccctagaa gacctctgta aaagcaggtt ccctttcatt  16320
gatgtctctc ctaaaaagtc catcacatcg ccccacactt ccccagcaca ggaccatttg  16380
gacttagctt ccaagatcct gttctcagtt tcaatagcaa aggtgtagag aaactggcat  16440
gaacctcttt gtgttgcttt gtctctaagg gatggccttc ttttaactct tgccttggac  16500
tgggctcagt gggccctcct caatccgtgc gaatcagagg acagatgggc gccgtagagt  16560
cggcgagtga caaacagaaa cggcggcgag tgtgtagaat ctgagtgtat ttttacaaag  16620
tgaacaccag tcttatatag tacagaaaat aaagggatag gatgtcacag caggcaaagt  16680
acattgaagt tacctgacac aaaacaaagt aatgacttca aaaggacttt caggaaccag  16740
gtaatagtta cagtaaagat aaaacagctc tgcttagggt cagctaagga caggtaagga  16800
tttcacaccc tactcacaat ttgtgctact cctttgaacc ttgtgaaagc tagcaccagg  16860
gagttctgct ctagcagacc ttctcatgaa taatgcaata ccacaaaccc cctatttcct  16920
aggacttgat aaattctttc atgagtataa cttggctgtt cttttaagta tctgtgggga  16980
agctccattt gtcagaagaa ttcaccaact tgcttctaat atgcaatgta gcctgctata  17040
cctggctgta caagattcct gtctcagtgg gattctctaa ctctttcatg gtaaacccac  17100
ctattagcta ggccatggtg tattcccttg tttgggttag acttggctac tgtcctaagt  17160
cctaagtaat caccctgcag accagccctg agctattcta gctctgttct ttgtaatgcc  17220
taattagttt caccatttct actagaagta aatttgaatg ttactgaata ggtaacattc  17280
tcactgaatt tctactgaat tccaagctcg tcggcttcaa gaattttcta ggacgttgga  17340
acactggtgg aggcttacct atgttaaaat tcaaccttta aaggcactta taataaaaca  17400
atactaaaag agagcatgtg catccatata ccagactaac acggggatag ggtatgagta  17460
tacaggttat gagaatgcca aggttctagg aggttgagtt tccttgaaac tctttgcctc  17520
catgagtgct tccaggcctc tcggcctgtc aagcagactt cactggagtg ggtatagcaa  17580
actctgtatc gatgcccttg atcttctgat tattgccttt cataaaatta tcttacattt  17640
tgactgccat atggtctttc tctatggctc attgaacccc gagagtgttc tttttatctg  17700
tgccagtgga gtcagttcct gtgcctacct tgtaaatatc cccagtgtgc taatctaggc  17760
tttccttggt gtttcggttt gcataacctt aagaagcact ggccacactc tgtgctttct  17820
cttttagtga cttctgagtc acacttcttg gcacatcatt tgaatttcta cagaagtgga  17880
agctgaattg attgagaact agctttttgc ctactctgat ctctacttgc atttcctgta  17940
tgtgctctga cccattgcat ggctgctctg ttcataaaca cggtcatggt tttcacccca  18000
tttcttcata actcagaggc cctatgggct ccatccatgt tttgtgtaca atttttttatt  18060
tttttatttt attttatttt ggtttttcga gacagggttt ctctgtgtag tcctggctgt  18120
cctggaactc actctgtaga ccaggctggc ctccaactca gaaatctgcc tgcctctgcc  18180
tcccaagtgc tgggattaaa ggcgcgcttg accaccgccc tgcttcctgt acattttctg  18240
aaaggccaaa tcaccttctt ttgcaacgca tacagctttc cgctgagatc gcccaggtct  18300
gttgcttgtt ttcagaagct gacacagaca atgggagtgg aggagtttca gtacaagtcg  18360
```

```
attcatagag atagatgcag cctaactggg cagcccaagc cttcaattgc agctatgctg  18420
gaggctgaag caggggggacc tcaaggtcaa cggcagcctg agaaactcac agagactgtc  18480
tcaaaataaa aaatatatat ataaaataaa actatacact tgactcttat ctacaatgta  18540
gtacgtggga ggaggctgag gtcgaagact gtgagtttga tcagcctggg ctacatagca  18600
aacatctgcc tcaaaagact ggaaatacaa aactaaaagt gaagaaaaga gaagccacgt  18660
tcagacttca aaaccaggct ccattgtcat gtttctggga ctattcccta tccattccca  18720
gagtagactg acagaattag cccccacccc ttctcgagcg tctcaagccc acacctgagc  18780
atagagcatg tgatttacat ggggatccat ttttcctcca cttctcccct cccgtgttat  18840
atgatcggag cctaaggtct gtaaccttgt cagctgcgtg tccgtgtggc tagtctagcc  18900
taaggccagg cttgccggaa gttctcttgg cacacctggg ttgacttgac ttctcctgaa  18960
gagcattcca aagctgctct ctgtaaaatt ctcagctgtt tctatttgaa atgcaggaag  19020
cacttccaga tcattacaag ccttggatgg aaattgccct cagacttcct cacttaatcg  19080
agaaccgcca gctccgagct cacgtgtaca gggtacgtcg atttgttctt tgcttcatgc  19140
tcctcctctc cccacccgtt ccgtctccat atccctttcc ttctcagctc tctgggagtg  19200
aaacggttga cctggcagtg ggaaccgact gtcaccactg aggctttcag caaacctgtc  19260
ttccttagtg cgcacaaaca gcacctgaga tgtgtcaagt cctcatcgtg tttgtgcaaa  19320
agacgatgat agatgagact tgaaaataaa ttctggggaa acgaggaaga cacacattgg  19380
agattggtgg gagccgcttg gcctgcttct gtaaaagcct gcctgtcagg cagagtcaag  19440
ccaggggctg aatgttctgt taatctcgga ggaaggaaca cggaggaata gaggcctctg  19500
gatgagtaca gatatcagat atacatcagc cgctgtctct gctggcttgt gactttgctt  19560
cccgtgatac tacagagtat ataaagcctt agagaattaa actcaaggct gctgcagcac  19620
tgactggata gccttcccgg tttttaagct ttgtttctga gtcttctttt ccatctctcc  19680
tacaatcctc actcacccct cagaagacct gttcaacttt gtactggcag gaccggcagg  19740
ggagatgctc agtggacttg tcccaagtca cgtggtcact gctctgcttc ctctgggcag  19800
gtaccttgac cttagtgtgt tacatactag tcagatcaaa tgtctttctg atttttaaac  19860
tcagagtcag tcttggctat gtagaagaag tgaaatccat agacaccaca ttagaatctg  19920
catgcaccta agtatatgac gcacgtctgt gacagagcga gcaatttccc tccaaaagga  19980
ataagaaaaa tatgaccccc acagaagaca ttcttccatt caggaatttt atagtaagtg  20040
tgaaacggag agttggcctc agaatcttgc ttccttcttt gagaaatgga tgaagttctc  20100
atttaatggt tgtgagcatc aatggctttt gtaaggaccc tccccctcct catcttcatc  20160
tgtcacaagc acaccacaag atgtcagatg ttcaagcaag gcgctccacc ctccaggacc  20220
ttctttgctg atgcttaatg tccaattatg agttgatttt taaaaatatt cattgaatga  20280
tccttatagc atattcagaa atcaggacag gcagctggcc ttggtaatac tctagataac  20340
ccccccctctg aaccccccac tgaggctgaa gaccatgtaa gaaagtgcaa ctaaaggagt  20400
taattgttgc acaaaactca cacaaagcct cacaaaggta gtttgtacac gctgttgaca  20460
cattacacta acaaaaacat cgaggggaaa aaagatggga aacagtagaa gataataatt  20520
aatggtgacc tatggcctac acacacacac acacacacac acacacacac acacacacac  20580
acacacacat gcacacatca ccacacacgt gtgtatgcat atgctcacac atgtacaaac  20640
atatatcacc acatatgtga cacacacata cacactcata tcaccacaca catgtgtaca  20700
cacatgcaca cacacacatc accacacaca tatgcataca taggaacata tagtacacac  20760
```

atatcaccac atagatggca cacacacact cacataccat cacatatatg catgcatata 20820
gacatgcaca cacatgcccc cccacacaaa cacacatata tgtacaaaac ctatagtgaa 20880
cacactaccc tgagtcaagc tatgagtttt aagaacatac atactgtccc ccaaaactcg 20940
tcacaaggtg ttttgtcctc aaagggaaag ctcctctcta tctaactgat gtctagaacc 21000
cacaaatatg ttagttgtgt accagagggg acggcgggtg gttagttagt agagggtctc 21060
ccacaaaccc atgtgtctgt cttcatccac catcttttac actgatgaat gagttactag 21120
ccagtaactc atgcagtgag gcaaagcagt tatgatggtt ctgggtgaca agcaagtgaa 21180
gagtattggt gaggatacta agcacgcgca tgcactttgc tacaactagt ctgtcatgtg 21240
aactgccatc tcacagaaac attcatacaa aaaaaagtgc agatgaatat gcaaagctgt 21300
ttgctgtagc cactttcata gcaacggtaa atacaatgta acagaaatac aatgtaacag 21360
aagacaggag agcagaagga gaagcccatg aatctccatt cacaaatata tctgttacat 21420
aaatgaaaag ggacagatat taagtggtca cgtaggcacc tgcctgtatc cttccgccac 21480
gctacacatc tttgctctgt agtttactga gcattaggaa gttcgcgaca gtatctatat 21540
gcagaattat tgaacctcta cttcaacaac atgtgcatgt gagcttaata tttatagatg 21600
atagaggtag aaatagacat atttactatc tgacagagtc ctaacatgta gcccaggatg 21660
gctttgaatt agacatcttc ctatctccgc ctccagagtg ctggtatcag tcttcataaa 21720
gacttctata tgaaaacaaa tgtcctgttt tctatgtatt cgccttcgtg tcaaactata 21780
cttttcaaga agttcaagaa gtgatgtcca caagaacctg atgtgtgtca gaaacactca 21840
gctccccagt gaagttggca ggagggctcg cctggttcag agaagccttg cgtgctccct 21900
gagttctgag aggagagtat cgaggttaat tctcccaggt taaatacgca atcaaataat 21960
gtcagggaga tgacgggtgt gtgtcgtcct cccagaccat ctgtgactgt ttgagtaagc 22020
aaaaggattg actaaaaagc tatcatttcc ttttcagtcc ctacagtcac ttttgaatca 22080
caggtatgtt taggaggtga ggccaacaat cctgaaatgt gcagggactc tccagaaagc 22140
agtcatcatc ccctggacct cgttccttta caccgaggcg tcctggcttg taggtggcct 22200
tcttcaacaa ctgaggggtg acaaggacaa agcctgagaa gacacagcct agattgtgaa 22260
gactttgaaa gatttttata ctgactgcat gctaaaatat cttttatacg ttgactcaac 22320
aaagtacatt atcagaacta attttacttc ttgtttgcct taaaaaaaaa aaagtggctg 22380
ctgaaagtat acgagatcct ttctcctgag gaaggagtca agattcacag tcctaggcaa 22440
gtgctgtact cctgggcaat agggcagcct ttgcttttat tcttagtctt tctcttgatg 22500
ccaaccaaat gcgtatcagc ttcaattctg ctctcttcag ctgtgtacct gcagctgttt 22560
cctggagaaa atgacaccat caaccatttc tctccaggac aaaggctggg tgggctggga 22620
ggggtgcggg tggagtgagt gcaggacagg agaccaaagg ctgaaccaga tgacggtctt 22680
gcccagaacg cctccacccg tccagaacta cagccgctgc tccccatgca gtttgactct 22740
gaaagtataa caacgtaaaa acagaattct aggcctttag gcccaggctt gagaatgtgg 22800
cctttgtaaa ggtatgctaa tcataaaaga gatagcgaca ttcctctacc cacccgcttc 22860
ctgggttcaa agagtgctca ttcaaagaaa gtcaccctga ggattaccag aacctgcaat 22920
gcaaatgtgc tattgttaga ggctcttaga agctgtcttg agagttaaca cttaccaggt 22980
attccttgtg actcttgtaa ctttacactt ccttgtgact cttaactggt atctttggta 23040
tcttccaaca atgccctccc cacttccttg agtttcggtt tcttccttta aatacccccct 23100 tacccagcta ctcggggtgc cacggtcctc taccccctgcg tggtgtatga ccatgggccc 23160

-continued

```
gagagcgctt ttgaataaaa atcctcttgc aatttgcagc aagacccgtt tcttgtgggt  23220
gattttgggg tgtcgcctct cctgagtcag aacgtggggg agccctcaca ttgtgggtct  23280
ttcaactcga ggcttccagt tcgtcctgag ttactttaga gtcaaagaaa gaaaagggaa  23340
gattaaatga agttcaaaac ctccacagcg tatggcaaga tgttggaaat actagggatg  23400
caagtcaacc aggagtttta gcccagaatc acaggagatc tagatgttca tgaccccgac  23460
ccccaccccc taaacccaac ttccaccccc acccccgcca ccccaacagc aacaagaagt  23520
gacacgtggg tctcctgttg atctctgcct ctccagagct ggactttcaa gtgtcctggc  23580
ttattactgt ccctctgtgt tgtcacattt gctcagggtc agctctcctc tcctcttccc  23640
ggttcttagc ataacgctta ttcctctctg tagtctcaca gcctgatctt tacccccagt  23700
gagctgagaa actggatcca tgggaagcta agcccctcac ttctgcatct gccaggatgc  23760
atctccttct ccgctcctct tcttcctcat gccttgctgc ctctgtgtcc cccgcccccc  23820
tcttcttccc agtgttcctc ttccagcagc agaccatgaa ctccatactg ctcttatccc  23880
tagaagacct ctgtaaaagc aggttccctt tcattgatgt ctctcctaaa aagtccatca  23940
catcgcccca cacttcccca gcacaggacc atttggactt agcttccaag atcctgttct  24000
cagtttcaat agcaaaggtg tagagaaact ggcatgaacc tctttgtgtt gctttgtctc  24060
taagggatgg ccttctttta actcttgcct tggactgggc tcagtgggcc ctcctcaatc  24120
cgtgcgaatc agaggacaga tgggcgccgt agagtcggcg agtgacaaac agaaacggcg  24180
gcgagtgtgt agaatctgag tgtattttta caaagtgaac accagtctta tatagtacag  24240
aaaataaagg gataggatgt cacagcaggc aaagtacatt gaagttacct gacacaaaac  24300
aaagtaatga cttcaaaagg actttcagga accaggtaat agttacagta aagataaaac  24360
agctctgctt agggtcagct aaggacaggt aaggatttca caccctactc acaatttgtg  24420
ctactccttt gaaccttgtg aaagctagca ccagggagtt ctgctctagc agaccttctc  24480
atgaataatg caataccaca aaccccctat ttcctaggac ttgataaatt ctttcatgag  24540
tataacttgg ctgttctttt aagtatctgt ggggaagctc catttgtcag aagaattcac  24600
caacttgctt ctaatatgca atgtagcctg ctatacctgg ctgtacaaga ttcctgtctc  24660
agtgggattc tctaactctt tcatggtaaa cccacctatt agctaggcca tggtgtattc  24720
ccttgtttgg gttagacttg gctactgtcc taagtcctaa gtaatcaccc tgcagaccag  24780
ccctgagcta ttctagctct gttctttgta atgcctaatt agtttcacca tttctactag  24840
aagtaaattt gaatgttact gaataggtaa cattctcact gaatttctac tgaattccaa  24900
gctcgtcggc ttcaagaatt ttctaggacg ttggaacact ggtggaggct tacctatgtt  24960
aaaattcaac ctttaaaggc acttataata aaacaatact aaaagagagc atgtgcatcc  25020
atataccaga ctaacacggg gatagggtat gagtatacag gttatgagaa tgccaaggtt  25080
ctaggaggtt gagtttcctt gaaactcttt gcctccatga gtgcttccag gcctctcggc  25140
ctgtcaagca gacttcactg gagtgggtat agcaaactct gtatcgatgc ccttgatctt  25200
ctgattattg cctttcataa aattatctta catttgact gccatatggt ctttctctat  25260
ggctcattga accccgagag tgttcttttt atctgtgcca gtggagtcag ttcctgtgcc  25320
taccttgtaa atatccccag tgtgctaatc taggctttcc ttggtgtttc ggtttgcata  25380
accttaagaa gcactggcca cactctgtgc tttctctttt agtgacttct gagtcacact  25440
tcttggcaca tcatttgaat ttctacagaa gtggaagctg aattgattga gaactagctt  25500
tttgcctact ctgatctcta cttgcatttc ctgtatgtgc tctgacccat tgcatggctg  25560
```

-continued

```
ctctgttcat aaacacggtc atggttttca ccccatttct tcataactca gaggccctat  25620
gggctccatc catgttttgt gtacaatttt ttattttttt attttatttt attttggttt  25680
ttcgagacag ggtttctctg tgtagtcctg gctgtcctgg aactcactct gtagaccagg  25740
ctggcctcca actcagaaat ctgcctgcct ctgcctccca agtgctggga ttaaaggcgc  25800
gcttgaccac cgccctgctt cctgtacatt ttctgaaagg ccaaatcacc ttcttttgca  25860
acgcatacag ctttccgctg agatcgccca ggtctgttgc ttgttttcag aagctgacac  25920
agacaatggg agtggaggag tttcagtaca agtcgattca tagagataga tgcagcctaa  25980
ctgggcagcc caagccttca attgcagcta tgctggaggc tgaagcaggg ggacctcaag  26040
gtcaacggca gcctgagaaa ctcacagaga ctgtctcaaa ataaaaaata tatatataaa  26100
ataaaactat acacttgact cttatctaca atgtagtacg tgggaggagg ctgaggtcga  26160
agactgtgag tttgatcagc ctgggctaca tagcaaacat ctgcctcaaa agactggaaa  26220
tacaaaacta aaagtgaaga aaagagaagc cacgttcaga cttcaaaacc aggctccatt  26280
gtcatgtttc tgggactatt ccctatccat tcccagagta gactgacaga attagccccc  26340
acccccttctc gagcgtctca agcccacacc tgagcataga gcatgtgatt tacatgggga  26400
tccatttttc ctccacttct cccctcccgt gttatatgat cggagcctaa ggtctgtaac  26460
cttgtcagct gcgtgtccgt gtggctagtc tagcctaagg ccaggcttgc cggaagttct  26520
cttggcacac ctgggttgac ttgacttctc ctgaagagca ttccaaagct gctctctgta  26580
aaattctcag ctgtttctat ttgaaatgca ggaagcactt ccagatcatt acaagccttg  26640
gatggaaatt gccctcagac ttcctcactt aatcgagaac cgccagctcc gagctcacgt  26700
gtacagggta cgtcgatttg ttctttgctt catgctcctc ctctccccac ccgttccgtc  26760
tccatatccc tttccttctc agctctctgg gagtgaaacg gttgacctgg cagtgggaac  26820
cgactgtcac cactgaggct ttcagcaaac ctgtcttcct tagtgcgcac aaacagcacc  26880
tgagatgtgt caagtcctca tcgtgtttgt gcaaaagacg atgatagatg agacttgaaa  26940
ataaattctg ggaaacgag gaagacacac attggagatt ggtgggagcc gcttggcctg  27000
cttctgtaaa agcctgcctg tcaggcagag tcaagccagg ggctgaatgt tctgttaatc  27060
tcggaggaag gaacacggag gaatagaggc ctctggatga gtacagatat cagatataca  27120
tcagccgctg tctctgctgg cttgtgactt tgcttcccgt gatactacag agtatataaa  27180
gccttagaga attaaactca aggctgctgc agcactgact ggatagcctt cccggttttt  27240
aagctttgtt tctgagtctt cttttccatc tctcctacaa tcctcactca cccctcagaa  27300
gacctgttca actttgtact ggcaggaccg gcaggggaga tgctcagtgg acttgtccca  27360
agtcacgtgg tcactgctct gcttcctctg ggcaggtacc ttgaccttag tgtgttacat  27420
actagtcaga tcaaatgtct ttctgatttt taaactcaga gtcagtcttg gctatgtaga  27480
agaagtgaaa tccatagaca ccacattaga atctgcatgc acctaagtat atgacgcacg  27540
tctgtgacag agcgagcaat ttccctccaa aaggaataag aaaaatatga cccccacaga  27600
agacattctt ccattcagga attttatagt aagtgtgaaa cggagagttg gcctcagaat  27660
cttgcttcct tctttgagaa atggatgaag ttctcattta atggttgtga gcatcaatgg  27720
cttttgtaag gaccctcccc ctcctcatct tcatctgtca caagcacacc acaagatgtc  27780
agatgttcaa gcaaggcgct ccaccctcca ggaccttctt tgctgatgct taatgtccaa  27840
ttatgagttg atttttaaaa atattcattg aatgatcctt atagcatatt cagaaatcag  27900
gacaggcagc tggccttggt aatactctag ataacccccc ctctgaaccc cccactgagg  27960
```

```
ctgaagacca tgtaagaaag tgcaactaaa ggagttaatt gttgcacaaa actcacacaa  28020
agcctcacaa aggtagtttg tacacgctgt tgacacatta cactaacaaa aacatcgagg  28080
ggaaaaaaga tgggaaacag tagaagataa taattaatgg tgacctatgg cctacacaca  28140
cacacacaca cacacacaca cacacacaca cacacacaca cacatgcaca catcaccaca  28200
cacgtgtgta tgcatatgct cacacatgta caaacatata tcaccacata tgtgacacac  28260
acatacacac tcatatcacc acacacatgt gtacacacat gcacacacac acatcaccac  28320
acacatatgc atacatagga acatatagta cacacatatc accacataga tggcacacac  28380
acactcacat accatcacat atatgcatgc atatagacat gcacacacat gcccccccac  28440
acaaacacac atatatgtac aaaacctata gtgaacacac taccctgagt caagctatga  28500
gttttaagaa catacatact gtcccccaaa actcgtcaca aggtgttttg tcctcaaagg  28560
gaaagctcct ctctatctaa ctgatgtcta gaacccacaa atatgttagt tgtgtaccag  28620
aggggacggc gggtggttag ttagtagagg gtctcccaca aacccatgtg tctgtcttca  28680
tccaccatct tttacactga tgaatgagtt actagccagt aactcatgca gtgaggcaaa  28740
gcagttatga tggttctggg tgacaagcaa gtgaagagta ttggtgagga tactaagcac  28800
gcgcatgcac tttgctacaa ctagtctgtc atgtgaactg ccatctcaca gaaacattca  28860
tacaaaaaaa agtgcagatg aatatgcaaa gctgtttgct gtagccactt tcatagcaac  28920
ggtaaataca atgtaacaga aatacaatgt aacagaagac aggagagcag aaggagaagc  28980
ccatgaatct ccattcacaa atatatctgt tacataaatg aaaagggaca gatattaagt  29040
ggtcacgtag gcacctgcct gtatccttcc gccacgctac acatctttgc tctgtagttt  29100
actgagcatt aggaagttcg cgacagtatc tatatgcaga attattgaac ctctacttca  29160
acaacatgtg catgtgagct taatatttat agatgataga ggtagaaata gacatattta  29220
ctatctgaca gagtcctaac atgtagccca ggatggcttt gaattagaca tcttcctatc  29280
tccgcctcca gagtgctggt atcagtcttc ataaagactt ctatatgaaa acaaatgtcc  29340
tgttttctat gtattcgcct tcgtgtcaaa ctatactttt caagaagttc aagaagtgat  29400
gtccacaaga acctgatgtg tgtcagaaac actcagctcc ccagtgaagt tggcaggagg  29460
gctcgcctgg ttcagagaag ccttgcgtgc tccctgagtt ctgagaggag agtatcgagg  29520
ttaattctcc caggttaaat acgcaatcaa ataatgtcag ggagatgacg ggtgtgtgtc  29580
gtcctcccag accatctgtg actgtttgag taagcaaaag gattgactaa aaagctatca  29640
tttccttttc agtccctaca gtcacttttg aatcacaggt atgtttagga ggtgaggcca  29700
acaatcctga aatgtgcagg gactctccag aaagcagtca tcatcccctg gacctcgttc  29760
ctttacaccg aggcgtcctg gcttgtaggt ggccttcttc aacaactgag gggtgacaag  29820
gacaaagcct gagaagacac agcctagatt gtgaagactt tgaaagattt ttatactgac  29880
tgcatgctaa aatatctttt atacgttgac tcaacaaagt acattatcag aactaatttt  29940
acttcttgtt tgccttaaaa aaaaaaaagt ggctgctgaa aattttcaaa gaaaacccgt  30000
gactcattgc atgattctcg tgatcggggc tgtggtcaat ccgcacgcag aactgcttca  30060
atccttcttg attctgtgac ctccgagacg aaaattcctc tttggttccc gcaggggtgt  30120
ttagcctcaa atttcaagtc atcctcttcc ccctagcggc cggaggagga agggctctgc  30180
ataccccagc ccgcccctag gaagccaatg tccccagcgt tttacaagtg gcgcatgccc  30240
tctgaggcaa gcctgcggag caaagggagt gaagtggtgg cgagagctga agagatgagc  30300
aatgagccgg tggcagccag gcaggacagg gaagctggcg tggtcggatt gtgtactgat  30360
```

-continued gctgtttttc agggtggccc tttccgtgtc accaggagct gtggtttcca atggggatga 30420
agtggggaca gagctgggtg gaaagccccg ccacctcatc tggctgggct gtggttgttt 30480
gagcatcaga gcaagcttta tatccagccg atccatggtt tttgtggggg actttacatc 30540
cctaacctca ctgggtctcg ctgcgttcaa aattttaata cagttacagg gttcgagaag 30600
ctgagggctt ccaggtatta catatctatt aatgctgctg tgcgggcttg gagggaagaa 30660
cttatctcgc cctcaatgct tactctgtga tcctcaaagc aatagatgga gaccagtgta 30720
tggcacaaac tgggcacatc ctaggccatg gaccccagga cctggcacct cctctactgc 30780
attcctctaa gagctggttt aagtgggtgt gcatgaagct aatagctgca atagctgtgg 30840
gaccctcaag tcacgggtcc tggtcctggt cctccaccgt tgttttttgt tttttggttt 30900
ttgtttttgt tttttgtttt ttgttttttt tttttggctt tgttttgttt tgttttgttt 30960
tgttttgttt tgttttgttt tttcagctgc taatcctttt aatctcttga ctagatgcct 31020
ctcctggact gcagattcct aaagagttac cgtgagcagc gcctggcaca catggcgctg 31080
gccgctatca ccatgggatt cgtctggcag gagggggaag gccaacccca aaaggtgagg 31140
agcaaggaga aatcaggctc tgctgaggtc cctgcacctg gaattacgac accagctcca 31200
ggttccgttg cctagtttcc aaaaatcagc ggaaggcaag aaaagagggt tagatttttt 31260
ttttccattt ttcttttctt ttctttttct tttttttttt cttttgctac ggagctgatt 31320
ttcttttaga ctaatgtcca ctttcaaaga ctccagccat tccaataata tgtgaggagc 31380
ttccttaggc cccaaggact cagaaaacac cctgcagaat tttatacttc taaatacatt 31440
ggttattatg actttcataa ttaccccatt gtacagacat ctggggatct gtcccaagct 31500
caaggccttt gtcccagagc agcctgggga cagttgggaa agccagtttc tgagtccact 31560
gaagtagcca tccttctcca gtacaacttg gacacttcct tatttcctta ttctgcccag 31620
ctgattgctg ctttagttta ttaacccttt gtctaactcc ctccaataac tttctagttt 31680
cagtctgtcc ctcagagcac aaaccctttc ttctctaccc ctggaggaaa ctaatatttc 31740
ttttgagtca tggtcttaca aagcagcccc aaaccagtct agaacctgct ctcttgtcca 31800
agttgttctc caacctgtga tcttcttgcc ccggccttcc aaatgctggc attgcagtca 31860
ctccaggcac gtgacaccct gtgcagttat gctcccagtc agtgttggga tggaatccag 31920
gacctgtgtg tgccgagtga atactttatc actcaacagg acctccgttt tctcttcctt 31980
tcccctaagt ttctctttcc cagaaatcaa ggtgttgaca tcattccaga atgcgtgaga 32040
agcccgaggt gtgcttcaag ggctcatctt acccacagag aaacacttga gaccaagaag 32100
caaggacagc acagagctcc tgttccttca gactctaaca cgataccata ttgtatctca 32160
tctaaaggac tcgagtgtct agggtctgct gttggaaagt ttaaaaccca ggccagtgtg 32220
acagaacctc ctgatgagtt ctgctgcata ggccccctaa accaatctcc tgaattatga 32280
gttagagagg aggaagcaat gtccagcccc caaggccatc ccaggctcat cacccctcat 32340
tttggaagtc ttccctgacc ttcccagtgg aagtgtctga ctcacatctt cccattctcc 32400
ccagccctga cttctgtgga tgcttggcag agctctacgc cctgtaagct gtaactgttc 32460
tctacctaaa gcacacctct tccctaactc ggaggaagaa agaatggcag acacagatct 32520
ttagactctt cagtcctggg ctggggagac gactcagtgg gtaaattggg agcaagcagg 32580
ccgagacact gaagctaaga ttcccacaac cagtgagaaa actggcacag gcagcaggga 32640
gcaagagaga ccctgtctca aacatggtgg aaggtgtcaa ctggagtcca cacattcccc 32700
ttggcatgaa tgtgcctaca tttacgtctg tctgtctgtc tgtctgtctg tctctctgtg 32760

-continued

```
tctctctcac acacacacac aaacagacag agagagacag agacagggag aaatttctat  32820
tttagaagga aaatgattgg ggggagggga acataaaaat gttcttttgt tgttgttgtt  32880
tgtttgtttg tttgtttgtt tttacacctc taccagtttg gcctttccat ggccgggacc  32940
tcatggacct gagcatctgc tctggactgt ggacagatag agatctgtac tcaagggaca  33000
ccccaaacgt tagtgggtga aagggtaggg ctatggacag gggctttgca acctgaaggg  33060
tccttggggc gtgagcgaga agcttgtgtt tcagtggagt cctgaacggg tgttaggagg  33120
ttgatgtcat accccaggtc ggaaccctag caaatcatgt taagagtcag aagagacaaa  33180
ggacggtcaa gggggggggg gtctgtcatt gagtgactac ctgacgttat ggggcttgac  33240
tcatgaggtg acacaaacat cagttctgca agctgaaatt ctctgtcctc tttatccttt  33300
ctggggtgcg ctctctatct ctctgtctct gtctctgtct gtctgtctgt ctgtctgtct  33360
gtctgtcttt ctcctatccc cccctctctc acacacacat atacacacct ctgttttttt  33420
ttatctatgt acatctttac ttctattttg catcatgtgc atctagcctt gtatctatat  33480
atagatcata tatattattt ataatctatc atccatctag aaagcacttt accttgatag  33540
ttcttagtct ttgatttaca ttaaacattt tggtgaaata attctctttc tccttttctc  33600
ctccttctcc tcctccttct ttctcctcct cttccttctc ctcctttttc tcctgtctcc  33660
tcttcttcct cctcttcctc ctcctcctct ttctcctgtc tcctcttctt cctcctcttc  33720
ctggtacagt ttccagaggt tctgtttatc atgtgcacag tgtattccat ctctgggttt  33780
tgcatctctt gaaatgtgtt ctcataacca gcattctcac cgggtctctc ccatgaagca  33840
tgtgtagggt ataggtgtgg aacattcaga gaattcgtgc ttggtctcca ggtcgcttat  33900
cacaggcaac cgtgatgatt ttctctgcca gtagaatata ctaattgtct ggattcctgt  33960
cctaaaggtg ctgccaagat ctcttgccat tccttttgtt gaggtatcca ggaacttggg  34020
actcccgcct atcctggtcc actctgacct ggtgctgaca aactggacca aaaggaaccc  34080
agaagggtaa ggagggaaag gattccttca gttagcagca gattgagaaa agactcagga  34140
cttgaactgt cttcgcagaa aagactcagg gtcttagggc tgttttatag tgagctgtgt  34200
gctcccattc atttaattta gggttccaat aaaagggaat gcacacattt aaacctgaga  34260
catttcttct tcctgggctc tcaggcacac tggcttgctg cttccagtgc ccatctggat  34320
ctcttaatca gactgtcagc ctccagctgt aataatgaca ctgggctgtt ttttctcagc  34380
atgttctgtg ttccattcaa gtcaggttag gatggggtgt ctggaggtga tctctatggt  34440
tctgaataaa tgatttcacg tgggtggaat tctgattcac accatctatt ctgtctagtt  34500
tacaccattc cacacttgtc ccgggcacaa aagcatctgt ttattgactt ttcaacaaac  34560
aaccaatcca tggaaacttc attttcacag ttgaatctgt ctcaggcggt cgacgcaagg  34620
cagcatttac ttttgttata aattaaaaca gcaaacaaga agtccaggct ggacataaag  34680
ggacctttct tggcatgctg gttgtaggta gccatgcagt gctgaaagag atggttgaga  34740
tctgctgtgg accctttcaa gagacccttc cttttaagaa ctggggaggg ctcctcttat  34800
ctacagtctg ctgagcctta gaacttcatg ctttctggga tgatgatgtc atatgacgat  34860
gatgtcatat gataatgtta catgatgtca tacgatgttg atgttgtatg gtgatgctat  34920
atgatgaatg gtatcatgat ggcatcatat gttgatgata agcttgtttg tgactgggga  34980
ctgaatgaac cttcacctgt gaggcaggag ctccacccct gttttctatc cccagccctc  35040
tcttcagcgt ttatttagat acagtttctc tcacaatgcc aaagctgacc tgaaattcac  35100
actgtagcat aagcagtccc tgacttggtg atccttagac ctcctcagcc ccttgactat  35160
```

-continued

```
ctgccactaa cagcatgcac aaccaggcct gacttggtct ttgaccaatt atacagcaac  35220
gaaaaactga tctgcattga aagctactaa atctaactta gaattggagt aggtgagatg  35280
ataaatatgt gcgcctggac tattgtgaag ctgggtttgt gattcaaggg aaattgggag  35340
atgaagtctt aagggaggtg acagggttga aaacaacccc aggaaatgaa tgtcccatca  35400
agtgaggtac agcacccaga gatgcaaatg caagcctgga gctcccccac cgtatttctt  35460
ctgagccatc atcttcctga gtcttttaag atgtctaccc agggcttatt aagtgctttg  35520
aagaaatgaa agaaatagaa gcaacacccc cccccacctc cacccccacc acccaaacag  35580
ttcagtattg agacaaagta gctcttaaca caagtcaaag aacaacataa acagtatctt  35640
cagaactcca gggggaacag cagggaaagc atggtgcctg accagacgct gatgtaaggc  35700
cactcctaac aggtgggtag gattagagta actgaagtgg ggtctgcacc gagaggcagc  35760
tagagagagg caagcaagaa tgtgtacata cacagacaca cgacacgggc tgtcaagtga  35820
gatctggttt ctgctgtcac ccagtggctc actgtccatc ctaggtgggt cctgatccgt  35880
acatgtgcca gggcattgca gatgagtgtg ggagcctggg tacccgggac ctcaagaatt  35940
atatctggtt actaactaag ttgttttctt tttttttttc tttttctctt tgttatcacc  36000
aataactatt atgcgaccag accgttggaa atcaggtaag atgtgccttt agaaccaccc  36060
actgttacct ttaaaggctt gtgataaagc aagagggtgg catggtcagc tgtatggatg  36120
gaatagcatc agctgtctat gaactcctga aaattcgaag tgcattaaaa agtcaatagt  36180
ccaagcagta gctctgatgg aggttagctt ctaggggtgc agggattaat ttttcttaac  36240
cacattttcc tgtatgtcca tgatttaaaa aaaaagtgta gtgtaagaaa agaaaccgtg  36300
gctctgtgaa aactggcaga gatttcttat ttctgaagaa catcagcaaa aggccagaaa  36360
caggcaggtc acagtgacag aagggtccct ttgtaatccc ttcttacctg atgggctgga  36420
gcccttgtga gtaggtgtgg tctatagtca taggctccac cttccccggg gagcagagct  36480
agcagaggag ccagagtcac atcctgcgct ctctctctct ctctctctca cacacacaca  36540
cacacacaca cacacacaca cacacacaca caccctcctc agctctgtgg agcatacagg  36600
tggatggcaa atattcccca ggctaacacc tctgctggac cgaggagatg tgtgactcac  36660
ctccgctttg ctgttttgag gtttgaggct gggctttgct tatgtttgag atgctgggga  36720
caacgcagat gtgtgcagat actcatctgg gttctgtatc aggtcagatt tggctctgat  36780
gggaagacag gacagcagca ggttgattag aaatgacctc cctcctcctc ctcctcctct  36840
tcttcttctt cttcttcttc ttcttcttct tcttcttctt cttcttcttc ttcttcttct  36900
tcttcttctt cttcttcttc ttcttcttct tcttcttctt cttcttcttc ttccacacat  36960
tatattctat ccacagtttc tcctccccta ctcctcccag tcctcctctc acttctcctt  37020
tccctagatc tactcctact tttccaaaaa aaaaaaaaaa aaaaagcaag cctcctggag  37080
ctatcctcca aacctgccct gacatagtta caaacagcag cccctcattt caaggcttga  37140
tgaggcaacc cactaggagg acaaggatcc aaagagcagg caagagtcag agacactctt  37200
ccactcccac tattcggagt tccacaggaa cacgaaacta cacacaacca caacatatga  37260
gcagacggcg taggtcacgc cgatgcaggt tctgtgattg tcacttcagt ctctgtgagc  37320
ccccatgagg tcggcttgtt tttgattccg tgggctgtgt tctcctggcg ttctcaaccc  37380
ctctgactac tgtagtctgt cctgcccctc ttctgtagcg ttcctggagc tccacctact  37440
gtttggatgt ggtaatgaca ggcttccggc cgcggttctg tggcagcaat tcatccttgg  37500
gttagaactc tagtcaggca cgcaggcaca cacccataat ggtcatagtt ctcaggtcat  37560
```

-continued aggaatttgg ctctaactga tctgattttc ttcttttctt ggtctcttcc tccagtaacc 37620
tggaaaccat catctcattt ccggggggag agagcctgcg gggcttcatc ctagtgacag 37680
tcttggtgga gaaggcagca gtgcccggcc ttaaggtatc ttcttactca cccggccctc 37740
tccctatggt ggttttcccc acgtggacag acagaggcct cctcctccta gggttgacga 37800
tgaagagaca tatctgagtt ctagcctgtg gtgtcagtgc ccttttagcc tggagtgaac 37860
cgacttctcc gtctacaccc aggtaccaca cgctgagtgc aacagacacc cactgcgcta 37920
gctgttccac ttcatggacc tgcagaagct agagactcag aggtcaaaaa gaaaaagact 37980
gttttatgga aaggcagata aaggcatatc catgcatatc tgtagggatg ccagagtaga 38040
aacgactgtg atatgggaaa cccagaagga atgagaaagc acttgtgttg aggctcttga 38100
tgtcacaatt tacgctccag agatattcca gtagtgtggg ctactccgtg gcgatctgca 38160
tcccgcgggg gttttaataa aaaaagttac ttcgtagcac ctcaactgag aacgtggatc 38220
ttattcctag gccctggttc agggaatgga ggccattcgg caacacagtc aggacaccct 38280
gctagaagcc ctgcagcagc tgagactctc catccaggat atcaccagag ccttggccca 38340
aatgcatggt aagatactgg agcagcgtct ccagtggcct ggacttgggc aggtcctacg 38400
tggatgatgg tggtccatct ctccacaaga tggcgctagt gttctatatt tagcgtaaag 38460
cgtcccagtc agagaattgt tttttttttt ttttttccag tcggcagaaa tatttttttt 38520
agaatcgttc tttatagttt cgtgtggttg gggtagcttc ccttctccag ggtccagata 38580
cgactttggc atgctgatct cttaacgaag cctgggagat tggatgggcc acaaggggga 38640
atgttggtta tacaggttag gcttgctggc gggcagggct gtcccgtggg ggcgtctgta 38700
aggccctcaa gagtcatttg cttttcctct ctgaccatgt tacaaatcca gaaagaccct 38760
catgatccgc tgaaggaggt ccaaggaccc ggagagctcc ccaattagac tccttccaag 38820
ccatctgatc ctgagacaaa tttctctatg tgatgacttt ttttcaaggt tttagaacta 38880
gctgtattca cacacgtggc gaaggagaag gacacgtgtc cacacttttc aaagatggca 38940
acagtatcct ccacaccatc ccatgaagcc cttagtgtgg gcacgccctc ctcgcgtctc 39000
cggatggagg atatgtccta gcctctgaaa tacttgcagt caaaataggg cactagtgag 39060
gacagtttag tccagtgttc agtgagtttt catccccagt gctgagacgc catgggaagg 39120
gcagtgttcc tggcacacaa gcaggctgac aacagcctat cagacaagga cacacagcta 39180
aggggctaag ggctgtccga tgatccttac tcagtgtggc actgaggagc ggaaacaggt 39240
cgccaccacc ttgcctctat gcaggcacct tgccagcagt acagagtcag caaggggagg 39300
cgcttgccat actataacag ttaccataaa agagagatca tgtttaaaaa caaaatcaaa 39360
cgctggaagg cataggcagg gggtcgtgcg tgtccttggc acggagtctg gtctgcatgg 39420
gctgcttttg tgtgtgattc ggagagcgtg gctgggtgga ttccctccac tcccaaaccc 39480
ccaactagat tttaccaata accaatcact gtgtttagag cccagcttca gcaagcatcc 39540
tgggtttccc tcaggacatc cttccttcct tcccaggcat gtagggtcca taaaaatgcc 39600
ttttgtggac atcggaggcc cactgcgctg caagccaagt ccccaggcct ttgcccagcc 39660
taacatagtt gtacaaataa ggtttgttta atgccatttg caagcaaaaa ttctccactg 39720
aaatatggtc ccaggactgt tcgttagctc ttacgtaaga aatgattcag gaagaacagg 39780
ttggaaatat aatcccccat actttcttct gaagttttca tcttttatac ttaagttctt 39840
aactcatcta ttatcatctg catgtgctat gagatagcaa atgaattcaa tctccctcct 39900
gcaggtaacg tccacatggt ctctccttag atttggttaa aggagcaggt tttctgcagt 39960

-continued

```
ggcctctgct ctttcccttt gggtgtgtct ctctgctctg ggtgccctta gtctcttctt  40020
ccttttctct ggaaagttcc ctccctggtt ttcttcttca ggggcctggc tgtctctcgg  40080
gagccttagc aggaaccaca aaaagaaaca cagaaaccaa accctcaaat ggggacttag  40140
ttcaagctgc attaagtatg gattctgata ttatacgtgc aatttctatc acggaaggaa  40200
aacaggccaa gggactagaa gcagcataaa atattagtct gcatttcctg atgacttctt  40260
ctaactcatt tgtcacggtt gctgggtggt ctttatctgt cacatgctgt cttgacacaa  40320
ggacccctct ctggtataca ccttcattgg ctacccagtt tccctgtgtg agaattcagc  40380
atctgcattt tcatgcgcag ggttccttga gtttcttcca aaggaaggca gatgcctaaa  40440
ttctgtttta tcaacagtta tttgcattct tgtgtgtggc aaacatatct ttttatttag  40500
ttacttctgc gctgtttgtt tctaccttat agaatgaagc aggtatttaa acgttaactt  40560
ggaatccagc cctttggtaa actacattct tattgattac agcagtaatt tacagggtta  40620
gctgggtttc tatgcagaga tcttgttgct gagacgtatg cttaggttca tcattaatta  40680
tctttttctt aaaaataatt ttccctcaca taatatatcc ttcccctttt ctcccctcag  40740
tttctgccca ccttccctcc cacccagatc caccaccttc tgtgttacac tggaaaacca  40800
acaggcttct aaggggtaat aataaaataa agtaagagaa aacaaaaact atcatgttaa  40860
gttggacaag acaaacaaac agatggaaag gagcctggga aaaggcacat gcacacacac  40920
acacacacac acacacacac acacacacac caagagacaa aaagtcagct gtaagtgcac  40980
atgcatccac acactcagga taccacaaaa cactaaacca gaaatcatag catatataca  41040
aaggacctgt agggtaaaaa aaaaaaaaaa aaaaaaaaaa aaaagtgtgt gtgtgtgtgt  41100
gtgtgtgtgt gtgtgtgtgt gatagagaga gagagagaga gatgggggga gggagaggga  41160
gagggagagg gggagggagg agaaggagag ggagaggaag agagggagga gagggagaga  41220
gagggagaga gggagagggg gagggaggag aggaagagag ggagagaggg agagggagga  41280
gagagaggga gagagggaga gggggaggga ggagaaggag agagagaggg aggagaggag  41340
ggagggggag gggaggggga ggggaggggg aggggagggg gagggggagg ggaggagaaa  41400
cagacagaga gagacagaca cagagatatg agacagagag acagatcctg tctagagcgc  41460
tggcgagttt tatgtgaact cagcacatat agatcatcta agaggagagc tcctcagtgc  41520
agaagaggcc ctcatagggc agggctgtgc tcaagcctgt ggggcatttt ctcaattagt  41580
gattgatggg gaggacccag cccatcgtga gtggagccac ccctgggctg gtggtccagg  41640
tttctataag agagcaggct gagcaaccta tgaggatcaa gccagtaagc agcgtccctc  41700
cacggtctct gcatcagctc ctgcctccag gtgccatccc tgttggcgtt cctgtcctga  41760
gttcccttga ttaggaagca cggtgtggaa gcatacgatg gataaatgct ttgttcctca  41820
agttgcttgg gtcaggttgg tttttcacag tgatagcaac cgtaaccaag acaacatgtg  41880
aagtaaaata aaagataaaa ataagataca ctcttgaaaa tggagggggt aggagtccct  41940
gttgtgacat tatgagagac tgaacctcca aagacgccat tttgtttgac ttctgctgca  42000
gtctagtact ggacatgcag cctgccctaa gaggtgggga ccaggagggg aagcagtgat  42060
cgggatgtaa aatgaatgaa tgaatgagtg aatgaatgaa tgaatgaatg aggaaaagag  42120
tattttgttt tcccagtgag acttccttag agaaaactaa atttttgttt tcaagtagct  42180
gtcacttgga ggcagcatct gggtgagggg tgagtgctgt gtccacttct cctctcagct  42240
gtgaccctgt gtggtgcaga ccagtgaagg ccctgtgcat gctgtgactt cgttgacctt  42300
ggtgattgaa aaggccttgt tttcttggtg tccttcaccc cccccctcc gcccaactct  42360
```

-continued

```
taatttctgt tttctctacc atatggttct ctgagcactg aggggtgggg gttgatggaa  42420
acatcaaaga ccatttataa ctgagtgttc cgaggtctct cactctctgc acactgtctg  42480
gctgtgggtc tctgcgtttg tttcctatct gctgcaggag gaagcctgtc cgatggtgac  42540
ggagcaaggc gctgatctct gagaacagca gaacatcatc aagagtcatt gtgttgcgtt  42600
ttgttttttg ttttgtttt tgtttttgtt ttaaagtcaa tattatttag tttccccccct  42660
aggtccctgg gctatctagt ttcagcatgt tggtcaccca atcaatttcg ggcatgaatt  42720
ccattgtgtg gagtgggact taagtcaaat cagacgtagc ttagatgctt ctataaactt  42780
tgtacaactg cactagcata tcttgcaaac aggataccat tgtagaacaa agggtctgta  42840
actggctata cacacacaca cacacacaca cacacacaca cacacacaca catatatatt  42900
atattatata ttatatatta attatatatt tatgaatcac ttttgaaata tctaccgaat  42960
atattttata ttttcatgta aattctattg tatctatcaa catgatcact tggctttacc  43020
tttaattcat taagttgtgt aaaatagtaa tgcatacaca tcccacttcc tatgcaaagg  43080
gctggatact gtacttaaca atctggagaa gaagcaaaca tcaaagtcta ggggaggtcc  43140
cagaaaacag gctagctcag gggacacagt cgcactggtg aagaccaccc tggggagtca  43200
caccctagaa gggagagtgt aaccatacta aggaatcaca cttgaggaga ggtgagacta  43260
ccctggggag tcacacctga gaagagaggg tgtgaccacc ctagggagtc aggaagtcac  43320
actggtgaag agtgggggtg tgggatgacc acactgagga gtcacacttg aggaaggggg  43380
gtggccacac tgaggagtgt ctgaaagcat tgagactgta catctcaggt tatcagggct  43440
tcagagaaaa cagacaggga gaagagacaa gaactggatt ctgtgcgcaa agggggaaaa  43500
gcaagcagat gtgaagggtg tgctgttaga gtttatctaa agatgtttct ttcagaaata  43560
aagagatata agctttaatt tggatgaaat aaatgtggtc taatttccca gaatgtagag  43620
gaactcacta atgtagcaag attggccttt caaagcagac caaagacatt gagaattaag  43680
atagctatga tggcgtgctt ccttaggtgg aagtcctata tggaatccca tactccccaa  43740
atgtgactgg tcggtgcagc ttggggctaa cagctctgtt gacctgtggt gacccctgga  43800
aagccctgtg ggatagagga actcctggat gtcagtcatt tgctctgcct ctcttgtgaa  43860
agcagtggtc tctgtttttc ttccttctct cggcttttca tattctcttg catatcctgt  43920
ttatttgaaa tgtttcttaa aggatgctca tagtctctca ctggtggtgg tgaagtacaa  43980
aaccctgctg cacagcaaac agagggggcc agcatacgga acggattaac agccctatga  44040
gagcccacac gctcttcaag agaacattcc atctgtattt gctgctgcca ttctgggatc  44100
tgcatacatc agataggagt gggaagccct gggaaaacag cagggtccaa ggcacatgtg  44160
gccaattgct ttttgcccat ggtaaagttc acatttgatt gctttccaga ttatgtggac  44220
ccagacatat tttactcggt catccggatc ttcctctctg ggtaagtaca gcttaattgg  44280
tttcctgctt gagacctgta gagttcccca gatttgtgcg aggatagaca gacagaagct  44340
tcctaaagta agaagtatag caagtgactc aagctggcaa agtcaccacc tgggtccact  44400
ctaggaggct ggaccccaaa atgatcagaa ggaaaaaggt tccaacaaag ctgggaactt  44460
aaatccaaaa ggggcaaaag gggctgtctt cagccaccag agggagacca tggaccctct  44520
gagaaccccca acgtgatgac aggggcaaaa attaaagatg ggagagagag tgggcaggga  44580
gaatgtgggg aggagatgga agggagggta gaggagagaa aggctggaaa atgatagcta  44640
cttctttgtc ccttgacctt tgaggacata gcattcaggg gacccatcag gagacaagag  44700
tccaggctgt cacctgacag aaccatcaat gccttgatct tagactccct ctccttcgga  44760
```

```
gttgtgagaa atacagtatg attgatcata ttcagcttga agtattttgc tatggtggta  44820
gcaggtaccc ttgatttgtc tcacggctat acacttctct gtctgtctgc ctacctcgca  44880
tgccccctgc tccatcaagc acatgtcttc acccagttat ttctaccttg acaagcttta  44940
accaggttgc catccaattc accaaccaac agagccgatt cacttttgaa cgtttgtgtc  45000
ttgttgactt ggaggtgccg gtgatgttat cagaagcatc caagctgtgc ctggagacag  45060
caagagacag accagatgcc gaatctatta ccattactgc caagtcccat tgggagaaaa  45120
actaaagtgt gcattcgtgc atgtgtgcgt gtacgtgtgt gtctagaact gaaaatttta  45180
tttccttgca agtatcagac tagagttttc ctggcctgct aggtcctctg ttgcctctcc  45240
ccaccatgtc cccaatttga ctcctgacac agcactggca cttggcattt ttctagaatt  45300
acacattttc ctgacttttc tcttgactac cgccagagga aatttctctt aaaggggctc  45360
ctgtggctgt gctcaatcta gtcggatgag tcagggaaat tcccacatta aagctaaact  45420
gatcagtggc cttaatccca tctgaaaagt cctcctgccc tgtcctgtaa taaatatatc  45480
atggtgaccg gaacagctca tagtattaag agtcctagga attcggttgg gaaccttggg  45540
gagctatttt tagaatccta ccctccagtg tctttcaaag gaatcatttc tacttcctct  45600
tggcagagac ttgataagaa ccagaagggg actttgtttg catcgacata agttccgggc  45660
aatgacactt tttatctggt atttggcata aaggccatcc ctccacttca aatgctgaga  45720
ctgtttactg tgccgctaag tggctgtaca agatcctaaa tgtagctgta gtttcaacaa  45780
acatctggat tgttgggagt ttccagtaga cttctcttta aaatgtcagc ctcgctattc  45840
tgcatctatc ccgagtttct catttgcttc tttaaaacac agttttattt aagagtggat  45900
gtcctgtgga aatgagatgt attccctcca gttcccagcc tgccacaggt ctcagagagg  45960
ccaggaacgg ggggcccagg ttgctctgca gggaaacatc gcctcatttt gttgtctgcc  46020
ttaacttcct ctttccttgg gattgctaga aatacaccag gagcaggtct aaaaataacc  46080
ttaccgtaga ggccagaatt taaaatggcc ccatcccttt acaaatggca gctcagccct  46140
acgtggagaa agaggcagtt gtgtctccca gtgctgctgg ggatggggtg taaaaacaga  46200
cccaagttca tcatctgacc tcagagctgg tgttttctgc atcaccttca gcatggctgg  46260
ctttggcgaa ggcactccag cgagtgctga aaggacattg cctgatgacg tccttggcat  46320
ttgtcatatc tgatagatcc cttaagcact ggttgtgccg tactgactga aaagctcttt  46380
tctccttcct tccttccttc cttccttcct tccttccttc cttccttcct tccaataaat  46440
ccatagtgag ggcctaccac atcctagaca ccactgtatg tgctggaaac agcagtaaag  46500
aaaagcagtc acgtggtcct tgtggagcct gtgacttcag gatggggaga aggtattgac  46560
aaagcaaacc gaatcaaagc aaacatccaa cagtatgtgt tacaactaga ggctgcatga  46620
agcaatgccg ggtaggatgc gggctgctag ggagggacca ctgggtgtgg tggctcaggt  46680
atcttgttta ctgatatcta gaaataccac atccccagtg atatgggaac agatgtcaca  46740
ggcaatggag tgctctcaga agaagattcc tgttgtaaga ggagggaaca gttcctgtga  46800
caggaggagg gagcagacat gaagaataga cttagatgta tgtgagaagg aggatgcctg  46860
ccattgtgga ggactctcag tgtgggcagt gctgccttcc tttctgagtg gcacagtcct  46920
gtttggggct gcaggttgtc agtacccctc ctgagtgggg tagggtggca gagaacaaga  46980
ttacaaagaa agcatcagag gtggacccaa ggggaagatg ccgagatgga gatgaatgtc  47040
aaccatcttg aagatgaggg gagaggtgga gagtatacag cctgtgggtc ctgacgcctg  47100
tcacagagaa acagaaacat gtgcgtgccc ttggccgctc tggacacaga ttgcagccca  47160
```

-continued tgtgctggtg tggaccaggt ccattatcca caccgtcgtc atgtctgcaa catcacttgc 47220
tcataaaata ccattctaca gtttctctag ccccgaactc ttatatttgt ttttgggttg 47280
ttcacaggcc tctttggatt ccattcaaat cctcgaacag gtgcaagaag cagattcccc 47340
tacagactag gggaactgag ggtcagaaag gctgtgcact gtagctgaga gatgagagtg 47400
gcagcaggca ttcttagcct ccagggttgc tagaacaata aatagctggt gcttaccgaa 47460
tgtctaatgt gctccagaca cctggcaaat agtatttgag tcggatctta caatgaccca 47520
taagctaagt atgaatgtca atgccaaaca tagctcttat ctcaaaggaa taagagttag 47580
tttattcttt ggccaaatat taatgcccag aaacacagat tccagttgtc ccaaattaac 47640
atgttccact ggggaaatga aggagttttc atagctcaag ggcaaagcaa gttaccaatc 47700
aaggggtttt ttgagaacac tggtgggggc cccaggcagg caagttacag caaacaagaa 47760
ctctgtacat agtcacatgc agacgggtag tggaagcctg ttgtctacta ggtcaataca 47820
ttccaaacca tcaaagatac tgggtcaggc aggacggagt taaagatagc ccattgtcgt 47880
ttgactctgg atcttcaaac tttccaactc tccacgatca atcagttttg tagaatcttt 47940
aacataggca tggcttcccc ctccctcctc ccacacaccc cagcgccacc tggaacttca 48000
gtttatacta acactactca gacaagggag ccaaggctct gagaggtccc atgtgctaac 48060
ccagggctag caaccaatgc acagtagagc ttagattctg tatctgccca gaatagagac 48120
cttgtcccac agtttgtgtg acgctccctt ctacctgtgt atcctttctt cttctttctt 48180
atgctgtatc tcttttctga acatgacttc ctcagttggt taccattgaa attcactaat 48240
cggttgactt taaacagcca ccaaatctgg caacctggcc acttgctgtg ttggcagcct 48300
cagagcagag tctggggaaa ggtctaggat gcaggtgggg ggagctagcc tgaacacaag 48360
gcttggattg acagggagca gaaacagcca tgtaaacctg ctacttgccc tgtcaaccag 48420
gggctggttt gcttgctggc aaaagaggtc aatgtgcttc ttggcgaagg tagacatcta 48480
tgggataaag aaaagtagac tgcaacttag agatgcatgt gtgtgtgtgt gtgtgtgtgt 48540
gtgtgtgtgt gtgtgttcct ggaatgctgg gggtctggga acttagctca agtctttgat 48600
tctttaggaa agaaggtaaa aattgcctgg tcctatctac tgtcaagtgg tcggggtgag 48660
agagtgagtg tatgctcgtg tatgtatgtg agcactgcag gtgtctgcat ggtgtgccat 48720
ggtgctccac tgggcttcat gctgtgctcc cctaggcttc agtcaagtca agactaggtc 48780
aagtcatgga gggtaaacag aagagagaga gagcagaaaa tgagggacac aggaagggta 48840
gagggggaaa gagagggttg tgaagctcac gcgtgatcag gagccccagg ctttcttctt 48900
ccagccgccc ataggctctg gtgcccacaa cattggttac aaccccgctc tccatcatca 48960
tgcttgtcat cactgctgtg acaaaccgct taataatggt tctcacggaa cattaaaagc 49020
caagccaagt ttaacacctc gaacatttcc aagtgttatg gggaataaca gttaagtgtc 49080
tgggtgtgct tgtgtgtaat tgggaatctg tagtggtggg gttaccagtg tcaggccaca 49140
gtgtttgtga tgagcagagg ggtcggggtc tttctcagat ccccttatctt gtcctgtcaa 49200 tggtggtgat gtaataggtg cacgcctgtg acagagctgt ttaaagcatt gtaagaccaa 49260
tgagtaaagt tcctaccctt gcttctcctt taagtgaggc agaaaaaggc tccaccatga 49320
cgtggtgtaa agatgaagtc aatctaatac ttccttggat actctagcaa gcttcattca 49380
cactttttat ttcttcctct tcctcttcct cttcctcttc ctcttcctct tcctcttccc 49440
ctcctcctct tcctcctcct cttcctcctc ctcttcctcc tcctcctctt cctccttctc 49500
ctcttcctcc tccccctccc cttcccctgt gctcctcatt attattatta ttgctcctgt 49560

-continued ctaggtggaa ggacaatcca gccatgcctg tggggctggt ctatgaaggt gttgccacag 49620
agcctctgaa gtactctgga ggaagtgcag cccagagctc cgtgcttcat gccttcgatg 49680
agttcctggg cattgagcat tgcaaggaaa gtggtgagca gcagtctgat ctcacctatg 49740
ctttgatggg acagcgaggt agactaggga gacatctcta gcaactgata aagacgggtg 49800
taaatgaaaa tgtcctgaag tttatccttg cctaagccag caggcagctg tgtgcatgtg 49860
ccctctctta cactgagtta gtcagtattg gggcatcgga tcttattagg gtcttccaac 49920
agtcctgtga cctgggttgt tcactgtcct gttggctggg gtcttttatc cgcagattcc 49980
cctttctaca atgaggtgat aatgtcacat tgaaaggcca gtctggagca gcaagtgata 50040
gtgctgaact tctctgctaa agcctttccc atgaaatggc ccagcctccc actgaatcta 50100
tgtggaccag gcgagggagc ccatcgcttt gaagccttta aaatagttgt tattgatttt 50160
tctggcagca tagagctatc ctttaatgac taccaaaaaa aaaaatattg ctaccaaact 50220
ttaatttgga tcagaaccaa aaagaattaa aactctctgg cacgaacctg ttctctggaa 50280
cagtcagggt tgtttctggg tttcagcatt tgattttagt cactgactct caacaaccaa 50340
ccaaccaaac aaacaaacaa acaaccaaac aaccaaacaa caacaacaaa acctaaccca 50400
aacaacaaca gttaaaggtg taatggtttt caagaaaaca ctgagttttc agtgtttcgg 50460
cttctctggg tttttactaa aatacctgct taccaatgtc gtctctacgt gcacagtaac 50520
ttccatttcc tgccccccctg cccgcccccc atttataagt atctagcaaa cagaattcac 50580
cagagtgttc tgtgtttgtg tgtgtgcgtg tagactcgtc tcttagtcct cagcagggaa 50640
taccacatca gtcatacaca cggagcagta gatttctgtc caactttatt atctgagaga 50700
tgtttgcttc tttttctccc ctgtgtctcc tgtcaacaac cagaaatgaa catttgagca 50760
tttggcagct ataacaaaag cccgacaagg ctgagggaga gccctatcaa gcatttctgg 50820
tacctgagtg tttggaacag tgggcaaacc ctcccaaatg tctgcctcga gctaacgtat 50880
ttctcccggc tgtttctttc agttggcttt ctacacagaa tgagggacta catgccgcct 50940
tcccataagg ctttcctgga agatctccac gtagctcctt ctctgagaga ctacatactg 51000
gcctctggtc ctggggactg cctgatggcc tataaccagt gtgtggaggc cctgggagag 51060
ctgcgcagtt accacatcaa tgtcgtggcc agatacatta tctccgctgc caccagggcc 51120
aggagcaggg ggctaactaa tccctcaccc catgccttgg aagacagggg cactgggggt 51180
actgccatgc tgagcttctt gaagagtgtc agggagaaga ccatggaggc cctcctgtgt 51240
cctggtgctt agcagtcatg tcctgcaccc taacacttag atgttctcat cctgcatccc 51300
agcgttagag gttcacatcc tgcatcctag tgcttagctg ttcttgtgct atatcccagc 51360
gcttagcagt catgtcctgc atcctagtgc ttagcatttt atatccagca tcttagtgct 51420
tagagattca catcctgcat cctagagctt agcattttat atccagcatc cttgtgcgta 51480
tcagctatgt tttgtatcct gcttagcagt taacatcctg catcctagta cttatctgtt 51540
ctcatcctgc atcctagagc ttagcagtca ggtcccgtgg gagcaagaac cagggtctga 51600
gctctgtctg agcccaagca tggctttact gctttgttaa ttgtggctcc cacctccacc 51660
ccaccccagc cagtttgctt gctagaagcc tttctgcact gcctaatccc cctgcctcac 51720
agcagagagc tgcagccatg acctcctcat tcagtattag gtggacaagt cggagatacc 51780
caaactcaat tttaaaagaa tcaagttgct tttggggcat gttacttcat cttttcttac 51840
cctgggcctc ttcccttctt ccctacctcc ctcgtccctt agtctttcac ccctctctct 51900
ttctcctttt gtcaccctcc ccctcccctg cttactctct tttcccttcc cccctctcct 51960

-continued catccctcct tcctttcttc cttccctttt tgtctgtgaa gcaccaggtc tgatgggcct 52020
caaactgtga tcttcctgtc tcacccttca aaggttatgt gtatgtgacg tgtgtgtgtg 52080
tgtgtgtgtg tgtgtgtgtg tgtgtgtgtt cgtttctttt gtttttccct agtggagatg 52140
acacccaaag atttgcacat accaggcaat tgctccacca cctgactaca gtcccagctc 52200
tctgtattcc tgaaggaaag tcttgatgag ttgcctaggc tggtattgag ctctttagcc 52260
caggcaggcc ttagtctgag tagctgggat gtacagggat gagccactga gccatgctgc 52320
tgctgctaac gatgatgacg atgatgatga tgaagattat gataactaca gtcactgcaa 52380
taatga 52386

<210> SEQ ID NO 15
<211> LENGTH: 61540
<212> TYPE: DNA
<213> ORGANISM: Homo sapiens

<400> SEQUENCE: 15
ccaaaagttg tttggtagga gagggttgag gctgggagag gtggctcatg cctgtaatcc 60
cagcactttg ggaggccaag gtgggtggat ctcctgaggt caggagttcc agaccagcct 120
ggtcaacatg gtgaaacccc atctctacta aaaatacaaa aaattggcgt ggtggtgggt 180
gcctacaatc ccaattactt gggagactga ggcaggataa tcgctcgaac ctgggaggca 240
gaggttgcag tgagcagaga tcgcgccact gcactcaagc ctaaccaaca ggggcaaaac 300
tctaggacta gagctaaggt atcaaaaaaa aaaaaaaaaa aaaaaagaag tagagtgttt 360
aattaaataa tttgttcttg ctgtaaaatg taaagtagat attcctcttc aaagactttc 420
ctccccgtct aattaggaat aaatagtaac ttctcttaga agcaaaattt attcaaagac 480
ctgtgctaac attcttaaat atctgctagc cacaataagg aaatcaatgt actttatgtt 540
cttagctccc acaatttagc ctaaatattt tccctggcat gtttatactg gtctaagcaa 600
gcattaggtc atagcctgtt cctcttcctt atttaaaagt gtttttacct ttctcagcgt 660
tccacaagtt acttcctcct tcctttgttc tcctctacct gtgcctcttt taaaaagttc 720
taagttgcta gccaattggg acaaatacag aatgtaaggt cccattccag ccaacggaaa 780
ctggacacag cagtagggtg gatgtgtcag gttataaatg accctgtctc ctttgtttgg 840
tgtactctag tggcaaaact gctggcaagt gtacctttc tgcaggaagt aaaaatggcc 900
ttactaaata aattaaattt atgttcaagt gctatttctt tttttttttt tttcgagatg 960
gaatttcact tttgttgccc agcctggagt gcaatggcgc gatctcggct cactgcaacc 1020
tccacctccc aggttcaagc aattctcctg cctcagcctc ccgagtagct gggattacag 1080
gcatgcgcca ccacgctcgg ctaattttgt atttttagta gagatggggt ttctccatga 1140
tgaggctggt ctcaaactcc tgacctcagg tgatccgcct gccttggcct tccaaagtgc 1200
cttggccttc caaagtggcg tgagccactg cgcccagcct cgagtgctat ttctttacgg 1260
cacggaagaa caaacatttc aaacaatgct attaccaagt ttgttagtat ttattatctc 1320
atttgctaaa cctaaaaaat atatatcctt ctttaacgtg atcgaatatt tcaaaaagtt 1380
attgtgttgt ttcttaaaat aaatcaatca taatcctaga ctatgttact caaactacat 1440
acaacacctt ctgagcttct ggcaggccct tcctcccctc cctgctcacc acagatcact 1500
ggaataattg tctgcatgta acttctaatt ttgaagtggt tgtggtttat caaacctgga 1560
acatggcact tccaagtaca tgagctaagg tcacagtaag actcaagccc cttcaacaga 1620
atacctggaa tttctctgtt aaagattttc tcctttacct gactacatgt ttgtaatgca 1680

-continued gatccctcca ggagcgctta cttataaact gtcctggatc actaacgcga cattttgatg 1740
taaattagtt tatcttgacg tgctaatggt agaaaaaaag agaacatgag gaaacttggg 1800
tgctttcagg gctggtagga aggattaaat ctttgcggca atttctgaga aggggaagga 1860
aaccttgcta acaattttga tagtttactc catttggctg gagtaactct gatccatttg 1920
tcaaattcac gatggagcag gtacctgtta gggtacaggt ttgataaacc acaaccacag 1980
gtctatttca tttctccttt tccaaagtgg aacaaatttg tctctggggt taaaactgct 2040
tttctcatat tggtgtgtaa gagaaaatga gggaatttct ttgagtttgt ttggtttgtc 2100
tgtttgttta agcagcattt tttaaataat ttactcagcc ctgtctcaga gaaagtccat 2160
gatgatctgg aattcaacct cagggaaaag ttctctcctg tgcctgagac actgcgcaac 2220
taactggaac cgaaggatgg aacctgggtg tttaatttat taggaacaat tgattcttca 2280
gtgacacttt ccatgcagat acttcaaaca aaataatgga gccccacaga ccgaatgtga 2340
agacagcagt gccattgtct ttggaaagct atcacatatc tgaagagtat ggctttcttc 2400
ttccagattc tctggtaagg atagagcctt ggtaaggata ggtcagaata tgtttcttga 2460
gatgttggtt ggtttgtttt ttaaaaatgt atgtgattat taagagacca atataaatat 2520
caagttgttt acctgagaaa gatgctacaa agagcataga ttatcattac tatcaaaaga 2580
gaagtgacag ataccacaga gaacaggtca aatggaacat tttttgtttc agtttctttt 2640
gactagattg tcaggccaga gaaattataa gcaaacctgt agttatcaag aaaaagcatg 2700
aacttaaata taaataaaga acaaatacag agcctcagca cctggaacat ggcacttcca 2760
agtacatgag ctaaggtcac agtaagactc aagccccttc aacagagtac ctggaatttc 2820
tctgttaaag attttctcct ttgcatgact acatgtttgt aatgcagatc cccccaggag 2880
cgcttactta taaactgtcc tggatcacta tcgcgacatt ttgatgtaaa ttagtttatc 2940
ttgacttgct aatggtagaa aaaaagagaa catgaggaaa cttgggtgct ttcagggctg 3000
gtaggaagga ttaaatcttt gtggcaattt ctgagaaggg gaaggaaacc ttgctaacaa 3060
acaatacctc tttcttaatt ctacttaggg ctcaaattgt aatgcaaatc tttttcatca 3120
tttagccctt ataaacactg tttttctcat ctggtgtggt ccaaggccta gaacattaaa 3180
actatcaaag cttttacaga ccatcaggtg tcatcccccct ctttctacat ctgagctagc 3240
tgaaatccag aggaaatgac ttgctgaaag tcatgagtgg caaaagcaga actagttctg 3300
cttataactc ttgactttta gttattatta ttattaatta ttattattac atcctaaatg 3360
agggccaagg ccactcagtt aaaaatcgtg ggtccaggc caggtgcagt ggctcacgcc 3420
tataatccca gcacttttgg gaggccaagg caggtggatc acttgaggtt caggagttca 3480
agaccaggtt gatcaacatg gtgaaacccc gtctctacta aaaatacaaa aattggccag 3540
gcgtggtggc acatgcctgt agttccagct attggggagg ctgaggcagg agaatccttg 3600
aacccaggag ggggaggttg caatgagtgg agatcatgct gttgggaatg aagtttttgg 3660
tgtcacagaa aaagaatgaa catgggaaca aatgatctct cagcaaaagg acctttactt 3720
tctgcagaaa gggtgctact caatagctgt ccagccacga gagcacacca aacaaaggag 3780
acagagttat ttataacctg acgcatctac cctactgctg tgtccagctt ccattggctg 3840
gaataggacc tcacatttta cactttaccc aatcggctat tagtttaaaa ctttttttaat 3900
tggataaggg aacagaacaa agaaagaaaa gcaagttgcc cagggatagt taaggaaaca 3960
tctccatata aggaatggca tgcactatgg gctggggctt ttctagttct gtacagacat 4020
gccggagcaa gctacgacag ctgatttgga cagccactaa tagtggctag caatcttata 4080
gtaagaaatt gtgacttttt ataatctttg aagaactttc ccatttctga cagtgccact 4140
gcactccagc ctgggcaaca agagcgaaac tcgtctcaaa acaaaacaaa acaaaacaaa 4200
acaaaacaaa acagctctct actcttggaa gcagcagagt ttttatcttc atttatatca 4260
ctccggtaac actcagaagt agacaagcct cagggtaggt attcagtaaa agcccactga 4320
attccacact attctttaat catagttaaa tggcaaatta ggctggaggg tgggggtgga 4380
acctctccaa aattactgca atgactgcaa catcggaccc caagattttt tttttttttt 4440
ctgagataga atctctttct atcgcccagg ctggagtgca gtggcactgt gagaaatggg 4500
aatggaccgg actgtttcct ctgacactgc cactaggttg accaagtgtc cctatttgtt 4560
aggtactgga tggacgcctg acatgcaaga ctctcagtgc taaatcagga aagtgctggg 4620
acaattcgga tgagtcggtc acgctaagtt gcacttaata gctcttgtga ctttgactga 4680
attacaaaca tcccctgacc ctcaattttc acatttactg gatggagatc tggtgccacc 4740
tccactagat tgctatggag aatgaatgtg aaagcatttt cataaatcca gtgtaaggac 4800
cagaagccag tcttctgacc ttgagccagt gcttgttaaa aactccactc tatacatcta 4860
acccaattca ggaatatcct gcctagttcc aaaggaagaa aagaccaaat tgctcttatt 4920
gggattaaat gcgtacactg agctgaggaa aaacagtatt acaaatgagc taaacatgac 4980
gtagatccac agttgtagaa ttcccctctt tgttctttcc tctttcataa ctacggaaac 5040
agatgagaaa catttacggc atcaggttct tgtgatgctc cctgcctgat atgctatggt 5100
tttgttaatg gaatgtccat tcctgagctt atgcagaaaa aagtcccttg ggaaagtggt 5160
tttactgtgt tatgttcatt ttccccatag ttctcaaaat gtacttcctt gtttcagttt 5220
taattttctt tcattggtgt gaccattttc aactgctccc tttctgggaa gaggtagcag 5280
acggacattt tcatcaaaat ctgccccagg ttgcttcaca gataaggagg gacccagcca 5340
ctaaaatcac caggcagagt gttgcaagag tagatagaga atcacaattg gctgccctgc 5400
tcaaggggac accagatctt actttcgttt agttgaaagg caagcgtcag agtcgggagg 5460
ctgtaccttc atgtccagtg gcctcacaga agttccttca gtatctcttt tagatgaaac 5520
tcttttagaa gttccttcag tatctctttt ggtttctcac tatagatagt tacttgaaca 5580
tgtctgaaga aaacgtggtc aagacagtga ataaaaaaaa ttctggtttt gggaagcagt 5640
ctgacttagt ttcaaatatt ctatcccact gtttctgtca atgttcaaac ctttccaagc 5700
tccaacattt attgtggaaa atgtgtgcct caccaactca tgcaaataaa tgtttcatgt 5760
gccctacgtg tgtagagggg gcatggatgt gtgtttttgg agggagggct aatttttctt 5820
tagacatgga gaatacgagg aaattagctt ggcatcaaga aggttacagc aggagacaag 5880
agtgaagaga actgagagag cccggaaatg aggctctgga gttcagattt tttttttttt 5940
gagatggcgt cttgtacccc aggttggagt gcaatggcaa aatctcagct cactgcaacc 6000
tccgcctccc gggttcaagc gattctcctg cctcagcctc ctgagtagct gggattacag 6060
gcatgagcca ccatgcctgg ctaattctgt agttttagta cagatggggt ttctccatgt 6120
tggtcaggct ggtctcaaac tcccaacctc aggtgatcca ccctccttgg cctcccaaag 6180
ttcaaggatt acagccatga accactgcgc ctggcctaat ttttgtattt ttagtagaga 6240
cagggtttca ccatgttggt caggctggtc ttgaactcct gacctcgtga tctgcccacc 6300
tcagcctcat gaagtgctgg gattacaggc atgagccaca gggccaggcc tggagttcag 6360
atttaacaca tcctgtaaat gacatgatgc atctgatatt tgaagagttt tcctcaaaga 6420
atgttacatg caaggtggtt tagagttgtt gtttccggct atatagcaaa agtacttggg 6480

-continued

```
gagttttaaa aaatactgat gccgaagctc cacctagaat agttcattca gaatctctag   6540
cataattgac ctcagtactt gaaatatgat tattataaat gttagtcaac tgctttttta   6600
ggctctatga ctgatagaaa tctttcactt ttatatcatc tccagttaat gagtcccata   6660
aattgaaatc tagtgtttaa atttttactt catatttatt tttactgatt gttttattat   6720
tattattttt gagacagagt ccgctttgtc gcccaggcta gagtgcagtg acgccatctc   6780
ggctccctgc aacctccgcc tcctgggttc aaacgattct cctgcctcag cctcctgagt   6840
agctgggatt acaggagccc accaccaacc acacccagct aatttttgta tttttagtag   6900
acggggtttc gccatgttgg ccaggctggt ctcgaacccc tgacctcaag tgatccaccc   6960
gcctcggccc tctgtctcaa aacaaaaaca aaaacaataa caaaactttt ctcttctacc   7020
cgagatgttt aagtttaaat cacaccattt gtacaaaaat tccctgtctt gtccttaaaa   7080
ataatttgta atcactagct agttttgaga tcgattgcca tctaaccgaa tgccatttgt   7140
tctctctctc tagtttcaac ttaataaccc tttctgcatt ttctattctt tcaaaatttt   7200
tccggccatt ttattgtttc tatttagtga aaatttattc actggtttct atgcctaagg   7260
gcatttagga agttgcttag gatacagacg tgataaaaag accagtgtaa aaactctcca   7320
ctcctagaca ttatattcta gtcctcatct cctgtcattt aagtcctcag tgattctatg   7380
cacttttgct tttggtttgg gcagatgctc tgagtttaat gtttctctga gatgaggacc   7440
ccctattcaa ctcacaaatc ccataaggag gcctctgtgc ctttgctggt gccccagaca   7500
gggtgctgat gcttacttat cttcaagatt gtgaagtcag atttaatagt atagtcgttt   7560
gccagagctg ctgtaacagt agccacaaac agttgggctt aaaataccac aaacaggagg   7620
gcttaaatca cagaagttga ttttctcaca gttcttgagg caggaagtcc aagatcaagg   7680
tgtcgtggag ttggtttctt ctgatgtctt gctccttggc ttgtagatgg cctccttatt   7740
attgtgtcct cacatggtct tttctccact atgcacaaat tccctatgtc tctctctctt   7800
tttttttttt tttttttttt ttgagacaga gttgcactct gtcacccagg ctggagtgca   7860
gtggtgcaat ctcggctcac tgcaaccttt gcctcccggg ttcaagcaat tctcctgcct   7920
cagtctcctg aatagctggt attacaggtg cgcaccacaa agcccagcta atttttgta    7980
tttttagtag agatagggtt tcgctatttt ggtcaggttg gttttgaact cctggcctca   8040
agtgatccgc gcacctcggc ctctcaaagt gctaggatta caggcataag ctactgtgcc   8100
cagtctcccc ctgtctcttt gtgtccaaat ttcctcttct ttagggacac caatcagatt   8160
aaattggacc caccctaaag gcctcatttc aatgtacctc cttcaagggc ctatctccaa   8220
atacagttat atttttaggt actagggcta gggcttcagc ataggaattt gggggagaca   8280
caatttagca catagcagaa aatataaggc caggaaaaaa tattctggca tgctagatgg   8340
actcattaac aaatattaac caatataaac caattaacaa atatttcttt aatatttgcc   8400
tttttttttt tttttttttg aaacagagtt tcactcttgt tgcctaggct ggagtgcagt   8460
ggcacgttct tggctcactg aaacctctgc ctcctgggtt caagtgattc tcctgcctca   8520
tcctcccaag tagctgggat tacaggtgcg ggccatcaca cccggcttat tttttgtatt   8580
tttagtagag atggggtttc actatgttgg ccaggctggt ctcgaacttc tgacctcagg   8640
tgatccacct gccttggcat ctgaaaatgc tggggttaca ggttgcctgg tgatttttaa   8700
gaggaatgac tgagctctca tgccaggtgg ggggaggggga cagagaaagt tgaatactct   8760
gacgatagcc atgatccata gctctgaagc ttagactcga atctacccat cccgcaagga   8820
agaaaacaaa gaaataaaaa agaagaaaag aaatctccca atgtcaggtc ccaccctctt   8880
```

-continued

```
tagaagtaat ttcagcaaaa ctttgttgct attttggcat gtcctctact gtagtagctt   8940
gtcaaaatac tgtccccaaa cgttttctat atttctagat tttactgttt aatgtataat   9000
aataatgttc taacattaaa acgtaaccat agcaatgctc cgactcactt gatctttaaa   9060
tatattgttg aactcaattt tgtgacatct tcagaattgt ctttttgtat tcataaatag   9120
caacagtgga tagttgcctt ggttagtgtt attatttcaa ggattaatct ttaggttacg   9180
ttttcttcat aagatgcatt agatgacttt tttttttttt tttttgagac agagtcttgc   9240
tctgttgctc agactggagt gcagtggtgc agtctcagct cactgcaatc tccacctcct   9300
ggctcaagag agtctctcga ctcagcctcc tgagtagctg ggattacagg cacgcaccac   9360
catgcctggc taatttttgt atccttttta gtaaagacgg gatttcccca tgttggccag   9420
gctgatctcc aactcctgac ctcaagtgat ccatctggct tggcctccca aagtgctggg   9480
attacaggca tgagccacca cacgcagcca attagatgcc ttctcatgct tttctgtgtt   9540
gtgaaacaga tcatctatcc gttgatatag catagctctt cagactacag acattttagg   9600
ctataagttt tgaattacat tttctattcc ctttatgctt cttgttctag ttaggttttt   9660
tatttctaaa taaaaatatg aatttttgca atttcccaaa tgcgaactca actgaaattt   9720
tcaagtgtat tagcaaaatt tattcatagc agcctcttac atttcattaa gaattgattt   9780
tttcttattc cctgttgaag tttgtttata aaatatagta atagtaataa ctatatagaa   9840
agtgttcact ttgtagtagg ccctatgtta actttaacta cactttttaa atctaagcct   9900
catagtagtc ttggatggat gcggtggctc acgcctgtaa ccccagcact ttgggaggct   9960
gaggcgggtg gatcacgatg tcaggagttc aagaccagcc tggccaacat ggtgacactg  10020
tctctactaa aaagacaaaa atcagccgga cgtggtggta tacacctgta gtcccagcta  10080
tttgggatgc tgagtcagga gaattgcttg aacccaggtg gtggaggttg cagtgaaccg  10140
agatcacaca agtgcactct agcctggatg acagagtgag actccatctc aaaaaaaaaa  10200
aaaaaaaaaa aaagagatca ataaataaaa taaataaata atcctcacaa tagtcttcac  10260
catttgcaaa tgatccattt gacaataaat gaattcagca ctatcatgga aatatatttc  10320
caagctgacc agttttctcc atttccaccc cacttcaatc caccttcatg tagccctagg  10380
actattgtct cctccccttg tttccttatt tccattcctg ttcagctgta acacattctg  10440
ttcatagcag tcaagtgatg cttacaaatg gaaatcaggc tagaggtggt agttcacacc  10500
tataattcca gcattttggg aggctgaggc aggaggatca catgaggcca ggagtttgag  10560
accagcctgg gcaacatagc gagaccccat ctctacaaaa ataaaaaaga attagctgtg  10620
catgatccta tgtgcctgtg ttccagctac ttgggaggct gaggtgggaa gattgcttga  10680
cccagggagt ttgaggctgc aataagctat atttgtacca ctacactcca gtgtgggtga  10740
cagagtgaga tcctgtctct aaaaaaacgta aaatgaaaat aaaaccttga tagtttgctc  10800
tttaaaactc ttcctacagg gcccctgtga tgctcacctg tctctagaag ggcatgtaat  10860
agctctttct ccttcacttt actttgatgc aatgtcagaa cagcttcttt ccatcaaaac  10920
ttaaaccttt gatttcattt aaaatcatct gcttcaaatt ctaatctttc tgatagttta  10980
ggttctaatt tttctgatgt taatattgtc acccaagttt cctgttcata tttacctggt  11040
ttattttatt tttattttta tttatgtatt tgagatggag tctagctctg tcacccaggc  11100
tggagtgcag tggtgcgatc tcagctcact gcaaccttcg cctcctgggt tcacgccatt  11160
ctcctgcctc agcctcccga gtagctggga ttacagggac ccgccaccat gcccggctca  11220
ttttttgtat ttctactaga gacgtggttt caccgtgtta gccaggatgg tcttgatctc  11280
```

-continued

```
ctgacctcgt gatctgcccg catcggcctc ctagagtgct gggattacag gcgtgagcca  11340
ccgcgcccag actttatttt attttttgag acgaagtctt gctctcttcc ccaggctgga  11400
gtgcagtggc ttgatctcag ctcactgcaa cctctgcctc ccaggttcag gcgattctcc  11460
cgcctctgcc tcccaggttc aggcgattct cccgcctcag cctcccgaac agctggggtt  11520
acagatgcct gctaccacac ccagctaatt tttttctttt tttggagaca gtctcactct  11580
gtcgcccagg ctggagtgca ctggcgtgat ctcagctcac tgcaacctcc gcctcctggg  11640
ttcaagcgat tctcctgcat caacctccta agtagctggg attacagacg tctgccacca  11700
catcaaacta atttttgtat ttttagtagc tgagattata ggctcgtgtc accacgcctg  11760
gctaattttt gtatttttag tagagacggg gtttcaccat gatggccagg ctcgtcttga  11820
acctctgacc tcaagtgatc tgcccatctc agcctcccaa agtgctggga ttacaggtgt  11880
gagccactgg gcctggcacc tggtttattt ttgtgcatgc ttttattttt aattttccta  11940
tgctactttc ttagccaaaa tttatactta atctaatcaa gcattaatct aacaaagagt  12000
ttagtgttca tataaaatac agttttacaa atctgttttt ctttaaatta taaatttgtt  12060
aagaaaatta tccaaagaat gatccagaaa caaaagaatg gctgtgtgtc ttttcaatat  12120
catcctggag cattgtctca accatctcac tttacggtga ctaaaacatc tagaggtttt  12180
ccctttgttt tctgtacttc ttagtattga ttaatactgt tgtgctactt cagtctgaag  12240
ttccatgtta atctgtagat tttttttttt ttttttgaga cagtgtctcg ctctgtcgcc  12300
caggctggag tgcagtggtg cgattggctc actgcaagct ctgcctccca ggttcaggcc  12360
attctcctgc cttagcctcc cgagtagctg ggactacagg tgcccgccac cacgctgggc  12420
taattttttc tatttttttt tttaggagag acggggtttc accgtgttag ccaggatggt  12480
cttgatctcc tgacttcgtg atctgcctac cttggcctcc caaagtgctg ggattacagg  12540
cgtgagccac tgtgcccggc tgttaatttg tagattttta tacagaaaag cagcaaaata  12600
tttctgttga gtagaaaata taactccaat gcttatgact gtattcctta taggacacta  12660
actcattatg tgtctaacct agcaatttta tgtcaacact attttctcaa acctctataa  12720
actttggctg ggcacagtgg gtcacacctg taatcttagc actttgagag gctgaggcag  12780
gtggatcacc ttaggtcagg agttcaagac aaggctggcc aacatggcaa aaccccatct  12840
ctactaaaga tacaaaaaat tagccaggca tggtgacatg cccctgtaat cccagctact  12900
caggaggctg aggcaggaga atctcttgaa ctcaggaggt ggagccaaga tcatgccact  12960
gcattccagc ctgagcaata gggtgaaact gtgcctcaaa atgaataaat aaaataaata  13020
aataagtcag agattgtgaa taggatgttg gatataccca agttatgaat taattaggag  13080
cttgaaccca ggaggcagag gttgcagtga gctgagatcg caccactgca ctttagcctg  13140
agcgatagag tgaaactgtg tctcaatcaa tcaatcaatc agagattgtg agtaggatgt  13200
tggatgtacc caagttatga attaattagg agcttgaacc caggtttgtc tcagatcctc  13260
agggactgaa gacttccaag tgaattatgg gtaatgtata ggtctatact actccaaatt  13320
tacagttttc agacttccct gggttctcat ggaccttcca tgtcatttct atgtttaggt  13380
tgaggtccct ggtcttttct cctctgtaat taatttcaca cccaccccta tctcaactca  13440
cacaacttga tcttcactcc catctgctaa gaaattgagt ccataaaaag tgaactcctt  13500
taaactctag atcttctact gctgcaagga cagacattcc attctggctc tctctctcct  13560
cctttgcttc ttccagtcct ttgctccttc tgcattctgt tactctcctc tctcctttgt  13620
cttcaatctc tccctcttgc aatagccaac tataaactgc tcaagcttct cattcttaaa  13680
```

-continued

```
agatctctct gaaatgcaaa ttccctactg ccttatggct ctccttcaaa agtaatctac  13740
attttctcta ttttctaatt cctcaacaca ctaacgtttg aaccctgctt ctatgaccct  13800
gacctaaatt tctattaaat gtacatagat aaactaatat atatttgtga cttcctaata  13860
ttgttttgtt ttttaaagag gtcaatctta ctttaactct gtaatgatgc ggttgacctt  13920
ctgatgattc tctacttctg tgaaatcctc tactgtcttg actttttaat taatttattt  13980
ttttttgaga cggagtctcg ctctgttgcc caggatggag tgcagtggca caatctcggc  14040
tcactgcaag ctccacctcc cgggttcatg ccattctcct gcctcagcct cccgagtagc  14100
tgggactaca ggtgcccgcc aacacgccca gctaattttt ttgtattttt agtagagacg  14160
gggtttcacc gtgttagcca ggatggtctt gatctcctga cctcgtgatc tgcctgcatt  14220
ggcctcccaa agagttggga ttataggcgt gagccaccgc acctggccct actgtcttga  14280
cttttatagg gtcattctat tcaagctcat tgagcgtctg tcactatgtt tttgatctgt  14340
attgctggaa tcagttcctc tatctgcctt gtgaatattc tccattgtgc taatctaggc  14400
ttctcctttc atttttcata ttccctcaca tggctttata cactcttgtg gttttaacca  14460
caatataggg tttttactgt agttatgctt tcaaattgta tacttctttt tttttttttt  14520
ttttgaaatg gagtgttact ctgttactcc agtctggagt gcagtggtac gatcttggct  14580
cactgcaact ttcgcctccc aggttcaagc gattctccta catcagcctc ccgagtagct  14640
gggattacag gcatgtgcca acacgcctgc ctaatttttt atttttagta gagacaggat  14700
ttcaccatgt tggtcaagcc cgtcacaaac tcctgacctt aggtgatccg ccctcctcgg  14760
cctccccaag tgctgaaatt acaggtatga gccatcgtgc ccagccccaa ttgtatgttt  14820
ctaatatgac ttttctcctg aactttaaac tgtgtatcca acttctcagc acagtcatat  14880
cttttgattc cacaggtaat ttaatgtcaa tatatttaaa aatgaattta ccacctttat  14940
ccccactctt tgactttcac ctgcatttct gtttcaattc ttgtttccat ccattcattt  15000
gctcacctaa ttcataaaca tggaaatcat cctcaattcc tcttcttctt agcccaaaaa  15060
ttcaattgtg caggttatgc actgagaaaa agagcctcag gttaggggga taaatcagag  15120
attggtgaac tttttctgaa gggccaaata ctaactgctt taagcttgct taccatatgg  15180
tttatgttgc aactaccaac tctcctgctg taatgtaaaa gcaaccatag atagcatgta  15240
aacaaatgag acaggctggg tgccaatgaa aattcacgaa aattaatgta gtttactgtc  15300
ccttgggtga gagttggggg tcactgaaat tcggactatg tcttacttgg ctaaaccaca  15360
ggcctagagt gggccataaa tggagctatt gggctagtga ttttcttgcc ttaagccccc  15420
agccccaaat ttaataatca catcatttta atttcatttt ccaagtgtat ctttaatata  15480
tggcttctcc tttccaaatt cactgtcatt acctaagttt agtccttgaa caatatttta  15540
aaggcttcct tatctgactt tatatcttaa agtcctacaa atttatcttc ctaaaattca  15600
aatcaaacca tgtcaccaac ttacagaaag ggaaaattca tatattctac acacagcaca  15660
tttcatgtaa ctttctaggc tcatctttca tcatcctttt gatgcaggat tttctgctcc  15720
tcagctcagc gaaatccagg atcttgtctc atgaccagga agaattaggc aggtggacat  15780
agtgaagggt gaggatgacg gaatttatta agcaaaaggg gagttctctg caaagagagg  15840
ggtttcacca gcagtctccc acctcacaat ggagcaccag gactttcaca cacaaactga  15900
aaaggctagg ctcctcccca gcataaggca tgaattcctg gtggttccac cagttttcct  15960
actatgcatg tgggtgtgcc caagcaaacc ataggtagta tcagaaaagg caacatttga  16020
ttggttaaaa ggcattattc acccaagcaa accataggta gtatcagaaa aggcaacatt  16080
```

-continued

```
tgattggtta aaaggcatta ttcagaaaga atcaatcggg aaagggtgag ccaatagggg  16140
aagttctccc tctgggtcac gggtttcatc tgggaccagg agtctggcct ttcagccttt  16200
agactgtttt aggcttgaag gtgggtttca cagggaccct tccctatctg cctaggcatc  16260
tgtctgcctc ctgcctctat cactttctct tgagttttat attttagcaa cactgagtca  16320
tctttgtccc aggaagcacc tacatctgtt tatctgctgt cccctctacc tttactacct  16380
tcccttcttc acatttatac ccagaaaagt cacttcccct ccaaaaattg ggatcaactg  16440
tcatattttt atgaatattt cactttaatt cctcacaaca gctgacagaa ttaactactt  16500
cctcttcttt gcaagttatt tggctcacac agatatcagt aattaaacat attttactgc  16560
attggcatat atctgactaa tgtgtttttc tcccgtacta ggcaatatgc tccttagtca  16620
tctgtgtatc tgaggtgagc acagggccta actagcatat ggtgcattct caatgttcgt  16680
tcaactgcat tgacttgaat tcccctgaag actgaaatgt gaaaatagct actctcggaa  16740
gccccttcc agagaggtct aaaatattta catgtttcta ttttaaatgc agaaagaact  16800
tccagatcat tataggcctt ggatggaaat tgccaacaaa cttcctcaat tgattgatgc  16860
tcaccagctt caagctcatg tggacaaggt attcttctct tcaccccctc atcacattct  16920
gttttcatca tcataccact tttctttctt agccttgtgg aagtgtgtca attgtcctgg  16980
gaaactgttc attaccattg aacttatcag caaagctata tcttccttcc tgaaaaacag  17040
aatgacccct tcgtaatctg atacatgtgt tttcctaagg ttttcagagc cagcacaaaa  17100
caatgcctga cacatgccaa taactcacca aatgtttgtt taaagaagaa tctgggtggg  17160
aatgataaac taactaatgg acaaggtatc gcctaagaag gtcagcttgg aaattctcag  17220
gttcctcatt ccatgtacgt actcaaggct ctgttgttac tgagggggtc taacttgatt  17280
ttgtcctagg tgttatagaa tagttaaatg gagggaattt ctgaattata aaattggcca  17340
tgggttctac aaaacatcca ataagcctgt aaattccaca aaagtgttga ttaggctgat  17400
acaaaggtaa ttgcagtttt tgccattact tttaatgaca aaaaccacaa acacttttgt  17460
accaacctaa tagctatgta accctgaaaa agttactcaa ctctgtaatc ccatttcctt  17520
atttataaaa tgagagaaac tctggtctca cagtattgtt atgggaagta aatcactttc  17580
aaagtggccc ttttgtagtt cttgtcctat aatagcattc agtatacatt cattacttct  17640
ctgtagtctc ttctccatct gtcctaatct atcagtttgg agtaccacat aattgcggaa  17700
gtccatgaaa agttttccgc tctccaaaat ttccctttgc tgatggataa tatttaatgt  17760
ctagaattac aaattctttt taaaatactc attgaatgtt tgctttgtgc aaagcactag  17820
aaccttgtaa aagatgagta agggactggc ttcaatgtct gtgaagatag caaactaaac  17880
agagtaattt ctttgcctga tagataaaat gttgtgttga catgaccaaa gaaatccaaa  17940
aataagaaaa aaactatctg taaacacaga aaaatagaga aaagttccaa tgatggaata  18000
aaaatttaaa ggattttttt gaacgtatta agcaaatcat gtataaaatc cagaaataag  18060
tttacaggac ccatgtcaag gatttaacca aagcagaggg agatccccat gagtcccctt  18120
ttcccatctc agaatagcag agaagagaag caagggaagc ctggaacagt tggcaagagg  18180
gcaggttaga attcagtttg tgaattatga ggtcgtctgc cgtaggcatt taccaggctt  18240
tatttgattt aactgccata aaggaagaga aggacttgtt aaattggggc tcctcttagc  18300
acagcattga aaccagtccc tattccttct tggccttttg gctaaaattg agtgtgaaat  18360
ctatcaccta acatttgtac tgggtttagg ctgggtgtgg tggctcacgc ctgtaatcct  18420
agcactttgg gaggccaagg ctggcggatt gcctgagctc aggagttcga gaccagcctg  18480
```

-continued agaaacatgg tgaaaccatg tctctactaa aaatagaaaa aattagcagg gtatggtggc 18540
acatgcctgt agtcccagct atttgggagg ctggggcaga agaatcactt gaacccagga 18600
gacagaggtt gcagttagct gagatcacac cactgaactc tagcctgggc cacagagtga 18660
gactctgtct caaaaaacaa aacaaaacaa acaaacaaat atatatatat taaaatacaa 18720
atttttactg ggtttaatag tgtcttccta gaagtcatgt tcatgcataa tctgtgaaag 18780
tggtcttatt tggaaatagg gtgtgtacag ttgtattcga gttaagctga ggtgatactg 18840
gattaaattg tatatgatga gtgtccttat aagaagagga aaaattaaac acaggaacat 18900
agactcaagg gaaaacatca cgtgaagatg gaggtagaat tggaatgatg cattgacaag 18960
ccaagatgtg ccaaggattg ctggcagtca ccaggagtta ggagacaggc atggaacaga 19020
atggaacaaa ttctccctca gaggctccag aagaaatcaa ccctattgat accttaattt 19080
gggacttcta tcttccataa ctgtggcaga gtacatttct gctattttaa gtcatgatgt 19140
ttgtggtcat tagttatggc agcgcataaa actaacacaa cactcttggt ctctatcgct 19200
tctttttttt tttttttttt ttgagacaga gtctcactct gtctcccagg ctggaatgca 19260
gtggtgcaat cttggctcac tgcaacctcc agctcccagg ttcaagcaat tctcctgcct 19320
cagcctcctg agtagctggg actacaggca cccgccacca tgcccatgta atttttgtat 19380
ttgtagtaga gacggggttt caccatattg gccaggctgg tctcgaactc ctaaccttgt 19440
gatccaccag cctcagcctc ccaaagccct gggattacag gcctgagcca ccatgcacgg 19500
cctctatccc tactcttaat tgcctggaaa atacctaaca aatgaaggcc agtttttaga 19560
ctttaccacc aaaggctgaa attgaaacag gaattgtttg tgagaagcaa acacaatagt 19620
ttcgagagac tgaatcagtt agcaatttcc tgtgagaggc aaatgtaata gtttctagaa 19680
ccacagatgg agctataaca aaaacatgtg ttctctggat cctttacttg ctacagacaa 19740
cacaataagt gaatttacag ctttgatctt acagtgcacc taagccaacc accttgtctt 19800
agaatgtctc aacataccta tctgtatctt gaaacaaaat atattaattg ccttagaccc 19860
attcactcac atttcctagg aagacatgat cagagggagc tatgcaagaa gaaatccagc 19920
agaactctgg aaatacaata agaaaatcca tattagacac taatcttaat aaaactaacc 19980
ttcgttcatg aatttgaata gacaaaatta ccaaataata tggaaaaaat gggcaactca 20040
aaaagaagag ggtagcccac ttggcattca ggaccaatgg cctccaataa ataagatgat 20100
attagtgctt taaatatttt atttagtgta tccagtatat tgccttccta aattaagtga 20160
aagctgatat ataaaaagaa ctattagaaa taaaaaacca cacacatccc agaactcctc 20220
aatataaacc taacaaattc agtaaaacat tgattgcaaa aaatatatat agtgacttag 20280
ggacttcctt gataaatttc ataaagcata aagaaaaatc aaagagtgca aaccatcaga 20340
aaaatacaaa tatataaaaa agagaaatac aggtgatcca aattcctttt aatggaatcc 20400
cataagcaga tgggtggagg aaaagtaaaa cttccaacat ataagcacaa aatttttaga 20460
ccttaagaaa tatttgagtt ttttatatca gaaagacagt gttggggtga gggttggggg 20520
gcacatgtaa atactcagat aaaattgtga attttctagg gtaaagaaat ctgcatattc 20580
atagaaaaca aaaatgaaaa atagtttatt tacagagtaa atacatacga ctgtttacct 20640
gtaatgctaa atattaaaag acagtttctt ttcttttttt tgagacagag tttcactctt 20700
gtcgcccagg ctggagtgca gtggtgctat atcgactcac tgcaacctct gcctctgggt 20760
tcaagcaatt gtcctgcctc agcttcccga gtagctggga ttacaggcac ccgccaccac 20820
acccagctca tttttgtatt tttattagag acggggtttc accatgttgg ccaggctggt 20880

-continued

```
ctcaaactcc tgacctcagg tgatccaccc gccttggcct cccaaagtgc tgggattaca  20940
ggcgtgagcc accgtgctgg cctaaaagac aatttcatac ctatttgtat ggctaatttt  21000
ttaaaaatct ggccatatca aaatactgaa gaggacgtat agcaatagag actttcattc  21060
attgctggtt gaaatgcaaa atggtacagc cagtttgaaa actagcttgg cagattctta  21120
taaaatgaaa catagattta ccatgcaact cagcaatggc attcctaagc atttatccaa  21180
gtaaatggaa aatgtatgtt cccagaaaaa aaatccatat atgaatgttt ataacagctt  21240
tattcataat caccaaaaaa aaaaaaaaat ctggaagaaa acaggatatc cttcaaccgg  21300
ggaatgaata aaccaaatta taataattgt aaattgtggg atggatagtg gaatagtatt  21360
cagcgataca aatgattgag caattaattt gtgcaatgac agggatgaac cttaaataca  21420
tttacctaaa tgaaagatgt caggcctata ttgtatgatt cttttcaaat gactttttag  21480
aaagggcaaa actagaagga ttaaatatag ctttatggtt actagagaca ggtaaggagt  21540
gggtagttga ctgcaaaggt aatatatagg ggaatgttta gcatgatgaa actgttttat  21600
atggcactca ggtgatggat atatggctct aggcactgaa aaacccatgg aattgtatgt  21660
cacaaagaat ggactttcat gtatgcaaat tttaaaaaat aaaccagaaa attgggagaa  21720
tactaggatg gaatgcagac tgtgataaat aaaactaact ggactctcag caaactaaca  21780
caggaacaga acaccaaaca ccgcatgttc ttacttataa gtgggagttg aacaatgaga  21840
acacaaggac acagagaggg gaacatcaca caccggggcc tgttgtgggg tgggggggcta  21900
ggggagggag agcattagga caaataccta aagcatgagg ggcttaaaac ctagatgatg  21960
ggttgacagg cgcagcaaac caccatggca catgtataca tatgtaacaa accagcacat  22020
tctgcacatg tatcccagaa cttaaagcaa atttttaaaa aagtaaaaaa aaaaaaaaca  22080
aacaacaaca cctaactgga ctacaaatgc actatataac ttcgatgaag agagtgggga  22140
gtagggaaag gaacggactt aaattactcc agaaaatagt gttgtgttgt gactagaatc  22200
tataaggctt acggtaaatg aaactttaca ggatcactat actctaattg gtaaatcagt  22260
ttttcatggg gtgcgggtga acagttgtga aactgcttta catgtagtca tacctttgca  22320
ttttgcagat atttcaattt ttacaaattg aagattcgta gcaaccttgc atcaagcaag  22380
tctgtcaacc ccatttttcc aatagtgtgt acgcatttgg tgtctgtgtg tcatattttg  22440
ataattataa caatagttaa aactttttct ttactattac atctgttaca gtgatctgtg  22500
atcagtgatc tttaatgtta ctatcataat cgttttgaag gtgccataaa ctgtgcccct  22560
ataagtcctg aaacttaatt gataaatgta tgtgttctga ctgctccact gaccagccat  22620
tgccccatct ctctccccct cctcaggcct cctgatttcc tgagacataa taatattgaa  22680
attaggccaa ttaataatcc tacaatggcc tctaagtgtt caagtgaaag gagttgcatg  22740
tctctcactt taaaaatcta aaactagagg ctggtcatgg tggctcaggc ctctaatccc  22800
agcactttgg gaagccaagg cggggagatc acctgagttc aggacttcga gaccagcctg  22860
gccaacatgg cgaaactctg tcttgactaa aaatgcaaaa attagccagg catggtggtg  22920
cacacctgta atcctagcta ctcaggagac tgaggcagaa caatcgtttg aaccctggaa  22980
atggaggttg cagtgagcct agattgtgcg attgcactcc agccagggca acaagagtaa  23040
aactccttct caaaaaaaaa aaaaaaaata tctaaagcta gaaatgatta agcttggtga  23100
gaaagtcatg tcaaaaccag ataggcttaa agctgggcct cttttgccaa acagccaagc  23160
tgggagtgca aaggaaaagc ttttgaagaa aattaaaagt gctactccag tgaacatacg  23220
aatgataaga aagcaaaaga gccttattgc tggtatagag gaagtttgag tattttggat  23280
```

-continued

```
agaagatcaa accagccaca acttccctta aaccaaagcc taattcaaag aaaggcccta  23340
attctcttca attctacaaa gtctgagagg gctgaagaag ctgtagtaaa aaagttttaa  23400
accagcagaa tctggttcat gaagtatgag gctagaagcc atctccacaa cataaaagtg  23460
caaggtgaag cagcaagtgc tgatggagaa gctgcagcta attatccaga agatccagct  23520
aaaatcatca atgaaggtgg ctacatttat tttttatttt tgttatttat taatttattt  23580
attttgagac aaagtcttgc tctgtccccc aggctggagt gtggtggcat gatgttggct  23640
cactgcaacc tccacctcct aggttcaagc aattctcctg cctcagcctt cccagtacct  23700
gggattacag gcatctgcca caacgcctga ctaatttttg tatctttggt agagacgggg  23760
tttcaccaca ttggccaggc tggtcttgaa ctcctgacct caggtgatcc acccgccttg  23820
gcctcccaaa gagctggatt acaggcatga gccaccacgc ctggccagtg gctacattta  23880
aaaataggtg ttcaatgcag acaaaaccat cttttattgg aagaagattc caaccaggac  23940
ttttttttt ttttttttt tgagacagag tctcactctg tcgccaggct ggagtgcagt  24000
gatgcgatct cagctcactg caatctctgc ctcccgggtt caagtgtttc ccctgcctca  24060
gcctcctgag tagctgggac tacaggcacg tgccaccatg cccagctaat tttgcagtt  24120
ttagtagaga cggggtttca ccatgttggc caagatggtc tctatctctg acctcgtgat  24180
ccaccccct tggcctccca aagtgctggg attacaggtg tgagccactg cgcccggccc  24240
aggactttca tagttagaaa aaagtcaatg cctagcttga aaggacaggc tgactctctt  24300
gttaggggct agtgcagctg gtgactttaa gttgaagcca gtgctcattt accattcctg  24360
aaatcttagg gcccttacca gctatgctaa atctactctg cctgtgctct gtaaacggac  24420
aataaggcct ggatgatggc atatctattt acagcatgct ttactgaata ctttaagctc  24480
actgttgcga cctactgctc agaaaaaaat attcctttca aaatattact gcttattaac  24540
aatgcctctg gtcacccaag agctctactg gagatataca ggaaataaat gttgttttca  24600
tgtctgctaa cacatttgtt ctgcaaccta tggatcaagg ggtcattttg gctttcaagt  24660
cttattattt aagaactata ctttgtaagg ctattcctga cacagataat gatccctctg  24720
aagaatctgg gcaaagtcaa atggaaacct ggaaaggatt cactattcta gatactatta  24780
aaagcattca tgattcatgg aggacgtcaa aataaaaaca ttaataggag tttgcaagaa  24840
gtcaaccctc atggatgact ttgaggggtt caagacttga gcagaggaag tcactggaga  24900
tgtcgcagaa atagtatgag aactaaaatt agaagtggaa tctgatttta taactgagtt  24960
gctgcaatct tacgattgaa cttttctttt cttttttttt tgagatgccc ctgctgagct  25020
gccagttcct gaagggtcac cgggagcagc gcctggccca cctggtcctg agcttcctca  25080
ccatgggtta tgtctggcag gaaggagagg cgcagcctgc agaggtgagg gccagagagc  25140
agcttctcct gttacccggc aggttacctg cgcctggagt aacgtgctcc ctgcttggtg  25200
ctaccctgtt ttcctggaaa atgggtactt tcttcttctc gatgggcatc agtttaagca  25260
acgatgaagg gctcatttat tatttattat tattattttt ttattttatt ttgagccagt  25320
ctcactctgt cactcaggct ggagggcagt ggggtgatct tggctcactg caacctcccc  25380
ttccaggttc aagcaattct cctgcctcag cctttcttgt agctgagact acaggcaccc  25440
accaccacac ctggctaatt tttgtatttt tagtagagat gggtttcacc atgttgccca  25500
ggctggtctc gaactcttga cctcaggtaa tctgcctgcc tgggcttccc acagtgctgg  25560
gattataggc gtgagccact gcgttcagcc tgaagggcca tttaaatgaa ggattttttt  25620
attttaattt ttctgactaa gagctaattt gtttttttaaa ctggtagcta tttcttcctt  25680
```

-continued

```
ttataagctt ttgaatgttt gtttgtttgt ttttggcact ctcttccaag aatgtttgaa  25740
gacctgcatt tgaaggcaga ttgccttttt gctttaaaac agggttgcac catgttgccc  25800
aggctggagt gcagtggtgc aatcatagct cactgcagcc tcaactcctc ccaggctcaa  25860
gcaaccctcc cacctcagcc tcctgagaag ctggggctac cagcatgtac cgccacaccc  25920
agctaatgtt aaaaattttt tgtagagatg agggtcttgc tgttttgccc aggctgatct  25980
taaactcctg gcctcaagtg atcctcctgc ctttgcctcc tgtgctggga ttacaggcgt  26040
gagccaccat gccgggcctg aagacagact ctgagaattc ataaaaacct cacagcattt  26100
tgtactctta tgtatataaa ttatctaggt tgctcttcat aatcctgtaa agtaacaaga  26160
gccataccgg cccattttac aactgaaaag cacagacact tatttcctta atcaaggtca  26220
gacagcaaat tagtggaaaa gccaaggcca gaacccaggt cttctgattt tactagtgca  26280
gccttctttc cccaggggac acattgacat ttacaacact catctttatt tttttttaa  26340
tactgctttc tatccagcca attattagtc tgtcttttaa taattcatcc aaatctcttc  26400
tgaatcattg cataactttg tacagtttcc acccacagtg tcttttactt ttatttttgg  26460
aagtaactgt ttttaaaagt tactgttatt tttaaaagtg tgccttcccc agaaatcagg  26520
gagttaccca tgtcctagaa ctccacggtg aagagaacag cctgtgccca tcgtgtttgc  26580
ctgattgatc ctacctcttg tctctcgggg aaacacagga gactcaggga agaggaaaag  26640
tgtagagtca ttgcagcctt gttatttgtc aatgcatctc ttttcttttt ctttttcttt  26700
ttttgataca gagtttcact cttgtcgccc aggctagagt gcagtggcgt gatctcggct  26760
cactgcaacc tcggcttcct gggtccaagg gattctcctg actcagtctc ctgagtagct  26820
gggattacag gcacctgccg ccacggccag ctaatttttt ttgtattttt agtagagacg  26880
ggtttcacca cgttggccag gctgatctcg aactcctgac ctcaggtgat ccacccacct  26940
gagcctccca aagtgctgtg attacaggca tgggccccag cacccggcca gtgcattgca  27000
ttttttttt tttttcgag acggagtctc actctgtcac ccaggctgga gtgcagtggc  27060
acgatcttgg ctcactgcaa gctccgcctc ccaggttcac gccagtctcc tatctcagcc  27120
tcccaagtaa ctgggactac aggcgcccac cacaacgcct ggctaatttt tatattttta  27180
gtaaagacgg cgtttcacca tgttagccag gatggtctcg atctcttgac ctcgtgatct  27240
gcccgccttc gcctcccaaa gtgctgggat tacaggcgtg agccaccgtg cccggcgtgc  27300
atttttaaaa gtgtgtctga tgctgaaaag tttgaagtct aggcacgtcc cagtgggtcc  27360
tctttatacc atcccctctg caaaccatta tcctaaattg gggtttgggg gagagaagag  27420
tgacagtgga aagaagtctc cacctcccag ctgtgccctg gtagttccag gggacccgga  27480
ggctccccac acccaccacc ccgcctcaga tcacctttca ctttctttgt ttctcctccc  27540
ttgacttttc agctcagaaa gtacctggct ctccaatgcc ttctgaggaa agtttacccg  27600
aggttcacat tgcaagactc attaaagctc tttagtgttt tccacccgag aaaaaattca  27660
agggaaaaat gaagacaaaa gcagggcatt cttaatggat attttatctt aaggagaaat  27720
gaaaatggag atggaagagg gggcacaagg atggggtttg aatctagact cgttcagcct  27780
ttacctccga tagagaacct catacagctt ttctggactt ctggctgata aagagccgtg  27840
gagggttcct tggataaaaa aggttgaagg gggtctgtcc tgtggtggct tacttgaagg  27900
tattactggg tttgacttat ggagtaagag acggagtcag tttccccaca ggctgaggca  27960
gtctgtcctc atgcttttct agggcactgt ggtctcccag gctcatacct aggtgcacac  28020
acaggtttct gcatctagct ttgtatctct atgagtcggt caatcaataa atctatctat  28080
```

-continued

```
catctgtcta ctgatctatc atctatctat ctagctagct atcatctctc tatcatctat  28140
ctatgtatct atcatctctc tctatatatg tgtgtatata tatatatata tgtatatata  28200
tatttctatc cttccatcta cttacctatc tatcaaaatt tttttccgtt gataatattc  28260
tcgggcccca gtttatgttt aattgttttg gtaatgcctt tctttgcaca gtcagtttac  28320
agaggttatt ttatattcta tatgtatgtg tggtccagcg ttgtaatttt cacatatatt  28380
gcaccgtgta ctcataagca gtatttccac tgggtcatta acagaaagat atgtgtgcgg  28440
catatgaatg tgcatcactc aggtaattca agcttggttc ccagatcatt tctgtaccac  28500
aggattgccg aaataaaaga caaccatggt tatttcctct gctgcaagct ttctagaata  28560
tgctatttgt ctggatttat atctgaaagg tcctgccaag gaatcttgcc cttccatttg  28620
tcgaagtctc caggaacttg gggctccctc ctatcctggt ccactcagac ttggtgctga  28680
cgaactggac caaaaaagat ccagacgggt aaggaaggaa gagaatgctt tgaatttcca  28740
taactttccc ccaggaaaca cccaggcttt tttttataat tagggaagtt catatttatg  28800
gtctgccgta tggttccaaa gaaggggtga gcttgaccaa aaattcaaat atcacaggcc  28860
ccagaagttt cctcttaatc cattctgaac acattggctc agaccatttt gtcttgtttg  28920
tttccacatg acgtgtgaat ttctcaacct gaccttcaag ctcctgcaaa atcagctttt  28980
atttgttctt tctcttcaaa ctgtttattc cctaagatgc cctccattca tatcaggtta  29040
aaaccagttg gctttgataa gtaatcatta tataatgatc agaagagaat gattatggat  29100
gaattcagag cagatgctcc aggtgggttg gattgagaat ttgattaata attccatcta  29160
ttccaccaaa gtcacatcat tcctttgaca gttgggctgg gaataggggc atttgtctac  29220
agaaggaata gcatgagatt ttaacaaaca agaaattcaa caaacagaat tagacagatg  29280
atctgagatg ttaaattttc ctttcacctt aatttttgca gccaaattta tttcagctct  29340
agatgaaaga gacagcactt tcttttgtgg ctgactacaa cagctgaaga ttcactgagg  29400
tttgatatga ggaagaactt cctcagccat gggattgcca gaggcgatga tgggaatcta  29460
cttaaaaggg ttacatattt agtagacagc ctagatttta agactaattt atgtgccccg  29520
gccgggcccg gtggctcacc cctgtaatcc cggcactttg ggaggctgag gcaggtggat  29580
catctgaggt caggagttga agaccagcct ggccaacatg gtgaaacccc gtctctacta  29640
aaaatacaaa aaaattagcc gggcatggtg gcacatacct gtaatgccag ctgctcggga  29700
ggctgaggca ggagaattgc ttgaacgaag gaagtagagg ttgcagtgag cgaaatcatg  29760
ccattgcact ccagcctagg tgacaaactc tgtctcaaaa gaaaaaaaaa ttatgtgccc  29820
cattggaaga agtgagattc ggccatctca tctctctcgg gagctctgag ccctggagtt  29880
ttatgttttc tgcaattatg aattgtgatc cttgattaat tatgctttaa taataaaatg  29940
ggtgactact gaaagctgct gaatctgggt aagaatttgg atgaaaaaaa taatatatgt  30000
gcgtaattta ttctgttcaa ggtactgaat attgaataag ctggatttat tactcaaaga  30060
gaaagacaga ataagagaag gttgaaggga aaaatgactg tactagaatg gtagtcaaaa  30120
atgcaacaac aggcaggtgc agcggctcat gcctataatc ccagcacatt gggaggccca  30180
ggtgggcagg tcacctgaga tcaggagttt gagaccagcg tggccaacat ggccaaaccc  30240
cctctctact aaaaatacaa aaattagcca ggtgtggcag tgggtgcctg caatcccagc  30300
tactcaggag gctgaggcag gagaatcact tgaacctggg aggcagaggt tgcagtaagc  30360
tgagactgca ccactgcact ccagcctggg tgacagagtg agatcctatc tcaaaaacaa  30420
acaaaacaaa acaaaacaat aacaaaaaag ctattaatag cttcctaggg agtaagagtg  30480
```

-continued

```
aagggctagt ttaattccag agatgcggac acagtcctgg gtctcaccaa ttattctgct  30540
tggtaattac cttttgaagc cttttaatat gcctaacaca gagctaagtg ctatgaagaa  30600
atgaaagaaa tagaagcaaa gtactcccca tgtggttaaa taacaagaca ctacatgaca  30660
aatgtcaaag agtgactcaa acaatatgtc ctttagaatt tcagagaaat gacatcaatg  30720
caggctttac aagtcagtaa aaatcttggt gatgaggcag aacttgatgt aaggcaaatc  30780
ctaaaagttg agtaggaatc aactagctag aataaaatgt ggggttgtgg taaatacaaa  30840
aatgtaagat gagtgaaata acttatttat ttatttattt attttcagag acggagtctc  30900
cctctgtctc ccaggctgga gtgcagtggc atgatctcgg ctcactgcaa cctctgcctc  30960
ctgggtttga gcaattctcc tgcctcagcc tcctgagtag ctgggattgc aggcacctac  31020
caccacaccc gactaatttt tgtattttta gagagatggg gttttaccac gttggccagt  31080
ctggtatcga atcctcgacc tcataatcca cctgcctcag ccttccaaag tgctaggatt  31140
acaggcatga gccactgtgc ccagcctaat aatatattaa gatggccaca ggccaaatat  31200
tctggggctg gaatgtgagt ggaaatgtcg ctcacccttt atcacatagc accccatagt  31260
ccagccacaa cttgcagaat tcaaagtaag tgtggatgtg tgtgtgcctg cagtgccttg  31320
cacacaagtg tgcatgcctg tggacatgtg accctagaag ttattaatat atctggttta  31380
caaactgaat tgttctttta tttttttct ctcttggtgg tcatcaataa ctgaaattgg  31440
gctagattcc tggaaattgg gtaagttctc agaaatcatt tacgcacttt agaatccagg  31500
ccaaatttaa aatcttacaa taaaacaaag aacaaagcat gctaaattat atgtataata  31560
taatatcaac catataaaat gcataaaaaa tatactagaa ggaaatgtgc ctaaaattca  31620
cagtctaaaa tttaacagtg attgcctctt ccttgtatag ataagggatt ttttttact  31680
gtattttcca gtctgtacat aataaaacaa gtaatgtgca atgcaaacaa aacaaaatga  31740
aactttatca aatttcagta actccttgaa gtttaatttt ttttttgaga ctgagtctta  31800
gtctgttgcc caggttggag tgcagtggtg tgatctcggc tcactgcaac ctctgcctct  31860
gggttcaagg gattctcctg cctcagcctc ccgagtacct gagattacag gcacccacca  31920
ccacacctgg ctaattttg tatttttagt tgagacagcg tttcactata ttggccaggc  31980
aggtcttgaa ctcctgacct caggtgatcc acccgccttg gcctcccaaa gtgctgggat  32040
tgcaggcgtg agccactgca cccagttgaa gtttaatagt gtgaaaaaaa tatttctcat  32100
ctcactatat cttctatggg aggccagatt gcagattgtc tacagaaaaa tcccttcaaa  32160
agaccttgtt attacataga ctggagctca tggggcaggt ctggtccaca catccttagg  32220
ctccgcttct cctggaaaac aaaaatagcc tctgatccag tgttgcctct cccatcacca  32280
aacctcagct tctatcgcca aactcatcaa ataagagtgt ccagtagaaa aactgggcag  32340
atgggggcac agaaggtgaa gacatcattt cccaagctaa tgttgctgct ggaacaatgt  32400
aagtcttgac tttgtcttgg tttggtttgg tttgacattg gtttgttttt catctttgtc  32460
tcatgcttaa aatgtgaagg gcaaatatga tccttagagt taaggtttta ggttttgtag  32520
atgttttact ccatttaaat gacagcagat catttagaaa tgattcctct gtaacagcct  32580
tccagatccc attcgattgt acagcattga gatagataga tagatagata gatagataga  32640
tagatagata gatagacgga atttggccct gtgttcccac ccatatctca tgtcaaattg  32700
taaccccac atgtcaggag agggatccag tgggaggtga caggatcatg gggttggatt  32760
tccccaatgc tattctcatg atagtgagtt ctcacaatat ctcattatta ttattattat  32820
tattattatt gcaacagagt ctcactctat ctcccaggct ggagtgcagt ggtgtcatct  32880
```

-continued

```
cggctctctg caacctcttg cctcagtctc ttgcgtagct gggattacag gcatgccccg  32940
ccatgcccag ctaatttttg tatttttagt agagacggag tttcaccatg ttggccaggc  33000
tgatctcgaa ctcctgacct caggtaatct gcctacctcg ctctcccaaa gtgctggaat  33060
tacaggcgtg agccactgtg cctggccagt tctcacaaga tctgatggtt taaaagtgtg  33120
gcacttcccc cacctcctgc cgccatgtaa gatgcttgct tacccttcca ccatgattga  33180
aaagtttcat gaggcctcct agccatgctt cctggtaagc ctaaggatct ctgagtcaat  33240
tacacctcgt ttctttataa attacccagt ctcaggtatt tctttatagc agtgtaagaa  33300
tgaactaata cacacataaa cagattagag gcagcactgg cctgagttgt gaaactcttc  33360
ccagcctggt cctgcgatta gctggctata tgaccttgga caagctgctt tgcttctctg  33420
ggccatggtt tcatacctgc aaaaaaaaga gcatggactt ggctgttgcc tgggtctctc  33480
tagccctgtg gagaatcagc tacatctctt actaggaact tctcattcag ccagttattc  33540
cactgcggag atggtccagg accattaggg ccatgctaga cattgggagg ctgcctgtca  33600
ggtgaacatg aaattgaact tatctgttct ctttcctccc tgaatgttgc tgaaggtaga  33660
tgcccatcct cagggctgtc ttacggagag gagaaagttg tgcagtgatt ccaccctgca  33720
gttatctaac tcggcaggga actctgggca gtgagtactc acggtacagt ctccacacct  33780
ctaatcatgt gctcctctcc ttcccaagga acctggagac catcatctca tttcctgggg  33840
gagagagcct gcatggtttt atactggtga ctgctttggt agagaaagaa gcagtgcctg  33900
ggataaaggt atcttctcac ttgatagcac cttttctttt taaatgagct tgagctttac  33960
ttcccactca gtgcctttcc tgcagtggat ttctcaacac aaatgaacat agaccttgtc  34020
ctgcttagtt caagtctgag agaagagatc taagctctag gccaccatat ttgctccctt  34080
ttctcaattc ctataaaact cggaatggac cttttgtcca ttcaacaaac aggcattggt  34140
ttgggcaatg ggaaattgga tcgaacaaga cagacatttt cccagccctg acagaagctt  34200
atgatggata cagtggatga agatggatta acgtggatta caggtgtgag ccactgcacc  34260
gggcctcaaa ctggaaattc ttcaggagtc agacaggtat caggaaggct ggatagaaga  34320
caaaagacag tgatgcagct tgtgatcaac tacagcgtta atgccttgcc taaaaatatt  34380
tcagttagat ttctgccttc gctctgtcgc tcaggccaga gtgcaatggc gtggttttag  34440
ctcactgcaa tctccacctc ccaggttcaa gcaattctcc tccctcagcc tcctaagtag  34500
tgcacgccac cacgcctggc taatttttgt atttttagta gagacagggt ttcaccatgt  34560
tggtcaggct ggcctcgaac tcctgacctc gtgatctgct tgcctcagcc tcccaaagtg  34620
ctgggattac aggtgtgagc caccctgccc agccaacact acctcccttg ataagcatat  34680
gttgagcacc tactggtcct caatagggtg acccatttct gctatattat agcgctttct  34740
ttctctctca gtagttaaac tccatggtta ctttagttct catccatgtg tttagtccat  34800
tagaagatac agagtcaaat atcggccttc caagtgtagt tcagatgaag tagagactca  34860
aggaagacaa ggaagtcttc ccagcagagg ggattctaga gctgggggct ctgtagaatc  34920
tgtctgtgta ttagtccatt ttcacactgt tataaacata ctacctgaga ctgggtaatt  34980
tataaaggaa agaagtttaa ttgactcata gttctgcatg gatggggagg cctcaggaaa  35040
cttacagcca tggaggaaag tgaaggggaa gcaagaacct cttcacgagg cagcaggaga  35100
gagagcaaag gggggagctg ccaaacactt ttatacaatc agattttgtg aaaactctcc  35160
ctcgtatcat gagaacagta tgggagagcc cacccccata attcaatcac ctcccaccag  35220
gtccctccat cagcctgtgg ggattaccat ccaagatgag atttgggtgg ggacacagat  35280
```

-continued ttcaacacag atttaaatct gactttatat gagagcttcg gagcaaggat gccccagttg 35340
gagatgcagt agaactgatc ataacgtgac aaatccgaga gaagaagagt aaaataatag 35400
tactcaggcc cttgggaggt gcaagaagta acagccagat gaaattccag aaacacttac 35460
ctaggggtct gtctgggagg tccccaggga gcttctggct gtcaggccaa ccccacagtg 35520
gatctagctt aggacgttcc caggaagctc tgacaaactg tccggtcctc ccctgggttc 35580
caacagtatg aggcttactc tgcctgcatg gactttaagg gagtgctaat aagttgtgta 35640
catgcatctc atccctaggc tcttgttcag gccacgaatg ctatcttgca gcccaaccag 35700
gaggccctgc tccaagccct gcagcgactg agactgtcta ttcaggacat caccaaaacc 35760
ttaggacaga tgcatggtaa gatgcttccg aagctcctga aggatccccc aggggtcctg 35820
ggctctgctt aggggaagag ggcctgggga ccaggcatgt cctgaagggg gtgataatac 35880
attcatccac cagatgacgc tggtggacta tctttgtttt aggttaaaca catattatct 35940
tggagagcta ttgtcacagc tttgtattct ccctctcctt tatattctcc cgtgattaag 36000
atggtttccc ttctgcagtg gccagatatt tcttaggcat gttgaggtct tgcctgaagc 36060
ttgagaggag gggatgggat gcacagtaat gttggtcgcg cgtgccccat cctgcagtgt 36120
taggtactgc agagcaggtt gtctacactc tgtaatgccc cttttattct aaccccctgt 36180
gttggttcct gagatgtctg accttggttt taagccttgt ctaatggatg gcctgtattc 36240
cctttctgta gctagggcag gctgatttgt caaaggtagg aaagttgtca gaatcaaaat 36300
ggagtcactt gtgttgaata aaaattttta aaccttgaca aatagagctg gggaaggcta 36360
caaagagaga gctcccgtgt ataaatgcct gataacaaaa tcttttccaa aggactgaaa 36420
aaatcaccac cttgcacaaa ggccatcaca accttacata cacaaaaaaa tacttacaca 36480
acgacatctg cccagcaact gcctttccaa cattggcctt gtgccaccct ttttattgat 36540
gctcatagcc aaggttaatg atctcaaaac agttacataa ttgtcctcat ttttccttta 36600
aaaacctttg tcttccttta tctttctgaa tacccacatg gtttattatg gcacatgtat 36660
tcccattgca atgccctatt ccagaataaa tatcagtttc cattagggag cctctccctg 36720
ttaatctgct taacacaggc atggtcagtt acggggccca accttcctgg accggttaca 36780
tcttattctg gttactgcat tcagtttcca acatctggga ggctcttcaa attcttctct 36840
cagaggaatc tgaagaatgt atgtgtttag gaggatgtga gagaggggtg tggtttctta 36900
acaagagaat atcagagtct aagtatcatt ttccctgaat cttgcttccc tgcaggaaag 36960
aaagattctg ggaaaagaga gtgtttacaa gaagcaggac tggagggagg gagaaagacg 37020
ctaggtactg ccaagcttta ttatcttgta ttaaaaaagt aaatataatt tgtcatccca 37080
gcctctcagc actagtagaa atctatctga agtcacagga ttaggtatta tccacttcct 37140
ggttttatag tttatatttg tattttctct atttccttga attttaattt taaagccctc 37200
atgatcacat cagtaggtct tctgccaaac agctccctta agttgtatgg tggctttgcc 37260
aagctgaaat gagatgagat gtgttttagc tttgccaaga aagcctgagt ccatcactta 37320
ggatagcaag gctattaggg agatagtgca ggtgtcttca gatcacatgg atgagcaaaa 37380
ggaagcaatt ttggaagatt atgagaaacc ttccaacagg tcccagtgta catagcagta 37440
agatggtgca tgcagtgtct aactgtcaca ggctttccta gggctcactt tcagactcac 37500
ttcttttttt tttttttttt ttttgtgaga tggagtctca ctctgtcact caggctggag 37560
tgcagtggca cgatcttggc tcactgcaag ctctgcctcc cgggttcaag cgattctctt 37620
gcctcagtct ccctagtagc tggattata ggcatgcacc accatgccca gctaattttt 37680

-continued

```
gtatttttag tagagatggg gtttcgccat gttggccagg ctggtctcga actcctgacc  37740
tcaggtgatc tgcctacctt ggcctcccaa agtgctggga ttacagccgt gagccactgc  37800
gcccagctca gactcacttt ttaggcccag gccaacctgc tgtgttctcc tgctcagctt  37860
ctgcaggagg tctcatcgtc taaggaggtc ccagggctac cgcccttgtt ttctcaaaag  37920
gcacatttc ccacacagac ataatttcgt ttcagtgttt tactcctagt cacattcatc  37980
tatatggaca aatagctgaa tggattggac tgtgttttct aaagatggcc ccatgccatc  38040
ctgcgcgctc ctccacagcg tggcctgggc attcctttcg accaggggtg gactctgtgc  38100
ccctacttgt gatgtacgtg ttgccaatag aatgtagtat aggggatagc acagacttct  38160
gaggcaagac tagaagaggt gatgcaggtt taaccttgtg tcctgagcca ctaggtaaaa  38220
agtccaccta ccctgagatc actctgctgt gcaaacgaca caggcaaacc acatcaaaga  38280
gccatgtggg ttctccagtt ggcttctgcc caggagtgaa ggtgccctca gatggttcta  38340
ggctcccatc ccaacttatg tcctgtcttg aagtcttccc aactgaggca ccagccactg  38400
tggagcagag tcaagccatt gccatcttgt tctgcccaga ttccccatca acagaatata  38460
gtggtttttt cacacctcta tgtttggagt ggtttctatg cagcaatagt aaccacaaga  38520
aataaagtta taaaaatagt aacaaacact agaaactgca agatttaagg aatcacctga  38580
atgctccagt cattgtctct ggtttgtaat gataaacttt cttctgcgtg ataaatagag  38640
cttggctgga ctttttccct ctgcttccat tccccaaaat ggagcgtacc aaacaattgc  38700
ttctttcaga gcccagcttt agcaagagtc atgagctcta atcccttcat ccataaatac  38760
ttcctttcca ggcacgtaga gcccttcaca ctcagggctg agtagaaaat gcctgttgca  38820
gactgcagtg gcgttttgga gagccaccct cctggtacct gagtcactag tcctttgccc  38880
agcttttctc agttttgtaa agcgctcact tctgagtgga agacagaacc agcccggtct  38940
attttcataa tctgccccca taaggcagaa gtccacacgg tactggaaac ataaccatat  39000
ctatgtcagt ctgccactgc ctgccgcctg tcaaccgtgc gtgtctgcat ccagtccttc  39060
tttggagctg ctttccagcg actcagccag atctgagctt tctgactcat tggaaggtta  39120
aactattttc agactttcaa gtgttgagat tattaagaca tgtgtttttt tttttcttct  39180
ttttttggca tgcttactga tcgcccctgt tctctaggaa gtaatgttct tcttggaaaa  39240
ggtgaaggat atttttctcc ccaaaaagcc atggaaatgt ttgcctttat ttacttccaa  39300
attaacagaa tttccagctt ttgcttgacc catcggcgca ttggcagcgt taagaatttt  39360
ttcttttagc agtaatgagg agtcgaaggg tttcttccta accatttagt gtatgcattt  39420
aaatcaggtt tctttttgag taaattgggg ctaagctgta gtgtgaactt ctgctactgt  39480
tcctttctca ttagttcact tgatttcatg gaaggaattt tccatctcag cctgtgaact  39540
tattttgtct aaactcaatt ggaaagtaat taacactgag attcttcttt aataaattct  39600
atatgataat aaaatcatac aaacatctct ttatttttct ttttgaccta gaaaagatgt  39660
tcacaggcca gacctggtgg ctgaagcctg taatcccagc acactgagag gaagaggcgg  39720
gtggatcaca tgaggtcagt ccgagggcag ggtagccaac gtggtgaaac cccatctcta  39780
gtaaaaacac aaaaattagc tgggcatggt ggcacatgcc tgcaatccca gctactcagg  39840
aggctgaggc aggagaatca cttgaacctg ggagatggaa gttgcagtga gcctagatcc  39900
tgccactgca ctccagcctg ggcgacagag tgagactctg tccccaaaaa aataaataaa  39960
taaaagatgt tcacaatata ttgttaagtg aaaaaagcag gctacataac ttgcataata  40020
tgagtgcatt ttaataaaaa tatacatatt tagcaaaata aaaggacaaa tggtatttat  40080
```

-continued

```
taaaatattt acgttgatta tttcaacaca gaggatgata gttgattttg cttaatttct  40140
tccctccttc ttttcaattt gaattttcta taatgaagat tgtttctttt tctttctttc  40200
tttttttttt ttgagatgga gtttcgctct tgttgcccag gctggggtgc gatggcgcca  40260
tctcggttca ccacaacctc tgcgtcccag gtttaagtga ttcttctgcc tcagcctccc  40320
tagtagctgg gattataggc gtgtgccacc acacccggct gattttgtat ttttagtaga  40380
gacgggcttt ctccatgttg gtcaggctgg tctcgaactc ctgaccttag gtgatctgcc  40440
cacctcagcc tcccaaagtg ctgggattac aggcatgagc caccgcgcct ggactgatta  40500
tttttaaat agggttagaa agtgaggaag ttactaaact ccgattagcc caaatatgcc  40560
ccagtgggtc cttctggcag agtaaatgtc tcggttcagc ctgaatctgg gaaattgttc  40620
ctacggttca gcctgaatct gggaaattgt tcctacctta taaactggag tatccttcag  40680
aaatgacatt tactcaaact tccttttagg cagactgcat aatagcaatt tttaatatta  40740
accatttaaa aaaaaccttc agattaatta acaccaaaag aataattggg aaaatacaac  40800
tcctcacttt aaaaaagaaa caaccaaagt aaatactaaa aaactatatg atgttatatt  40860
atctaagctt agtttactgc aaagatcaag agcacactac tagttgacgg cctctattca  40920
cactgttcat agccctcgct cgcttctcca gccattcact cactcatgca aaaggtctgt  40980
acacacaatg atgcctgatg gtataatagg aaccttaaca tttcaattaa aaggcaaaat  41040
gaggacactt accatcagcc tataaaatta ttcttattat tcttcttctt cttctcctcc  41100
tcctcctcct cttcttcctt cttcttcttc ttcttcttct ccttctcctt ctccttctcc  41160
ttctccttct ccttctcctt ctccttctcc ttcttcttct tcctcttctt cttcttcttc  41220
ttcttctttt ttttttgaga tggagtcttg ctctgttgcc caggctggag tgcagtggtg  41280
tgatctcggc tcactgcaac ctctgcctcc caggttcaag ctattctcct gcctcagcct  41340
cccaagtaac tgggattaca ggtgcatgcc accacgcccg gataattttt tgtattttta  41400
ctagggatgg ggtttcacca tgttggccag gctagtctct aactcctgac ctcaagtgat  41460
ccacctgcct cggcctccca aagtgctggg tgtgggcggc aagccaccca ggtgccaagg  41520
caagagacag agggcacgag ctgttccagt ataatgagga aaatatatag aataagaata  41580
gttatactag aaatagatta tagatatgat tacatatgaa tatcattctt cattagtttg  41640
tagcactact ctttattcca gtattataat aatctttgtt ctacaattat aacctaggaa  41700
aaaccaggcc atacagagat aggagctaaa gggacagggt gagaagtgac cagaagagtg  41760
tgagccttct gttatgcccg gacagggcca ctagagggct ccttggtcta gcggtaacgc  41820
ccgcgtctgg gaagatgcct gtcacctaac ggaccgtggt ctagcggtag cgtcagtgcc  41880
tagaaaaggc actcttttta aatatacttt ttatttttgt ttaatcttcc ctgatttcct  41940
atagatctga gatatgtcat gcttattttc attgctatct aaaaatctca ataaacttta  42000
tacctaagag taaaaaaaaa aaaaaagaaa agaaaaggcg ctcgttactt agccgaccgg  42060
gaaagggagt ctccctttcc ccgggggagt tagagaagac tctgctccac cacctcttgt  42120
ggagggcctg acatgagtca ggcctgcctg cagtcatctg gaggcctaac cgtctccctg  42180
tgatgctgtg cttcagcggt cacgctccta gtcctgaaca cctggctccg ccttttagat  42240
agcagtagca gaattagtga aagtactaaa agtctttgaa atgcagaagt aatggcgtaa  42300
gctgtcacgt ctctctctcc gcctcagctg ccaaacagag aagggtcccc tgtccagtgg  42360
acacgtgact tgggtgacct tacctgtcat tggagacgac tcatactcct taccctgccc  42420
cttgccttgt atctaataaa taacagctca atctggcatt tggggccact actggtctcc  42480
```

-continued

```
gcatcttggt ggtagtggtc ccccgggccc agccgtcttt tattctatct ctttgtcttg  42540
tgtctttatt tctaccatct cttgtctccg cacacgagga gaaaaaccca cagaccctgt  42600
agggctggcc cctacagctg ggaattacag gcatgagcca ccgcatccag ccagcctaaa  42660
attcttctga aggataataa tatagtactt gaagacacgg tttgaaaaaa atcatactaa  42720
atgaaagggc accattttac aagcactaga actacattaa acttaaatga attccaacac  42780
tcttaataat gtaactcaaa aacaagtcta gtgttaacaa aagctccaat aactaaaact  42840
acattaacag gcacaatgaa cattgtaaac gccgctaatt ggcaccaagt ttaatagggc  42900
agacaatatt ttcttctgca ttcacactta ctcagttaca ctgttgaaaa atgctgctgc  42960
tcaagctatg aatgctttac aaaagaaatc attttaataa atacagtaaa tgctaaaact  43020
ctagctaaac tattatgcaa gatatacaac caagacaaat acaaattcat aatacaagca  43080
acttgcattc aaaatgaact ctaccactat attttattaa aagggcagac tttatgaatt  43140
aacccagctg cttcctgaat tacaaaagtg gcatgactca atatgaaaat aagaaactgt  43200
ctacaaattt ctgacagtaa taaattgtaa tatacaatac atgcaggagt cttacggaag  43260
aataaactct cctaggaaac aaaaatattt tatactttta aaatccaaag taaaaaaaaa  43320
agaaatcatt gccagatgcg gtggctcatg cctgtaatcc aagcactttg ggaggccaag  43380
gcaggatcgc ttgagcccag gagtttgaga ccagcctggg caacatagca aaaccccatc  43440
tctacaaaaa aatacaaaaa ttagatggta atggtggtga gcgcctgtgg ttccagctac  43500
ccaggaggct gaggtgggag gatgcacctc aaggctgcaa tgagccaagg tcacaccatt  43560
gtactgaagc ctggggacag agtgagaccc tgtctcaata agtaaataaa taaatatctt  43620
ttatgaaaaa gattctctag tcagaattaa cacctcaact agccaaacat caggaagtta  43680
cattacagct acttaataca caaagggaca cattttcacc agtcgttgtc ttctgatatt  43740
tctattccag aaacacacac tctcacttcc ctacactccc catcccatca tttcttcaga  43800
gcatggaaac agaatttgtt gaacaccaga aatctcttgc tatggtggta cataagtcat  43860
aacatttgtt gctgcccagc agcaggtatg aagccggctg gtgactggct agcaaatgcc  43920
tattctgtaa gctcctcact tagcccatct gtagctctga cttctccacc aattcccttc  43980
tctcctttca cagcctttct gagtttctga gggataattt cagaggttcc atataactgt  44040
caaagcctat ggtagacatg gcaaagtgaa aatcctctcc actggccatt tctgtttctc  44100
ttgggggcat ctttcacttg cctcaggtgt tataaagctg atgaacacac gtacacgttg  44160
tttaacactt tcttgggcat ttcccatttg agatatggca tgtttcatta tcctagtgac  44220
atgtgcaatc agaaaatgta tattttgttc tctgcaactt tcttttgaaa aatgtatatt  44280
tgaacaaaat atacattttt tgtatcttca tgaccattca tgctgtcctc actgtcatca  44340
tgaggctcta tataacataa tgactcctcc agggcagtct tcggaaattc ccagtgcaga  44400
agcacgtgtc atacagcagt ccccattcat ctccagtgca gctctggctg gctcccatgt  44460
ctgatcagct gtttggttgg acagaaaatg actgcaaggg aatcagttcc agtgtgagct  44520
ctgtttgcag aactcagact cccctccctc ccatgttaat gcttttttc ttcttctttt  44580
ttttttttt tttttttga cagagtctca ttctgtcacc caggctggag tgcaatgcta  44640
tgatctcggc tcactacaac ctgtgcctcc ccggttcaag caattctcgt gcctcaactt  44700
cccgagtagc tgagattaca ggtgcacacc accacacccc actaattttt ttgtattttt  44760
agtagagacg gggttttgcc atgttgccaa ggctggtgtc aaactcctga gctcaggaaa  44820
tccaccttcc tcagcctccc aaagtgctag gattacaggc gtgagccacc atgcccagcc  44880
```

-continued

```
ccatgttaat gcttctaaag tttgccctca cttctttaga aattccttca gtacatcctt  44940
taagacttcc tctagtgagt gtctgctggt ggtaaactct cccctctaaa agttgcttta  45000
tttctcctca attcctgaag gatatttttg ctagcagcta tattctttta gatgttgaac  45060
atatcggtac aaaagcttct ggtttccatg gttgctattg agatgttagc tgtcggttta  45120
tctttctccc ctgactatgt gtacctgttt ctctgtatct gtctactttt tgggttgctc  45180
aatttattgg ccttgggctt cattctgctg ctgctttttt tttttttttt tttttgagat  45240
ggagtcttcc tctgttgccc aggctggagt gcagtggtgc aatcttggct caatgcaacc  45300
tctgcctctc ggttcaagcg attctcctgc ctcagcctac cgagtagctg ggattacagg  45360
cacctgccaa cacgccaggc taatttttgt atttttagta gaaataggat ttcactatgt  45420
tggccaggct ggtctcaaac tcttgacttc aggtgatcca cccacctcag tctcccaaag  45480
tgctaagatt acaggcctga gccaccacgc ctggccacaa tttttaaact ttttattttt  45540
acaggcacct gccaacatgc acaactaatt tttgtatttt tagtagaaac aggatttcac  45600
tgtgttggcc aggctggtct caaactcttg acctcaggtc atccaccacc ttggtctccc  45660
aaagtgctag gattacaggc gggagccacc atgcctggcc aaaattgtta aactttttat  45720
tttcttcctc aagaggatga gaagaaaggt caattgtaag ctttagaagt cttgcccaat  45780
agccaatctg agaatattct ccgtaaacat tcaccagagg cagccagtga ccatgggata  45840
cttttggtga gaggaattga ttgctggggt caggaatggg aggaaagcat acttctcatt  45900
agataccttg ttgaacttcg taaattgtgt gccaaatgca tgtcttacct agacttcata  45960
aattaatttc tttaaaaata atcaaagaca attttttaaa gacttattta atttaaggtg  46020
attataaaac atccagtata ctttcactat taaaaaagta agtattcctg tctgggcttg  46080
gtggatcaca cctgtaatcc cagcactctg ggaggctgag gtggtcggat catgaggtca  46140
agagattgag accatcctgg ccaatatgat gaaaccatgt ctctcctaaa aatacaaaaa  46200
ctagctgggc gtagtggcgt gcctgtagtc ctagttactc aggaagctga ggcaggagaa  46260
tcgcttgaac ccaggaggcg gaggttgcag tgaactgaga tcgtgccact gcactccagt  46320
gtggcaacag agtgagactc catcttcaaa aaaaaaaaaa agtattccta aacagcatat  46380
tatcatgata tattattttg ttttgtaggg ttttgaacct tgtctaaaaa gaattaaaat  46440
gtataaattt cttcctgcaa tttccctatt tcactaaggg tcattcacat tggtcatata  46500
gacatagcac attttcacca ctatatagca gcattttgta caaatagact acaatttact  46560
tattctgcac ttatttctgt ttgtttgttt tgctatgaaa agcaatgtca ttacatatat  46620
tcatgcccat agctacaagt ttacatattt caggttttct gtagggtgga caccagggag  46680
ttgaattgtt caacaggact ttacattcat ctttagtttt attggccaac accaaattgt  46740
tcttcacaat gtttgaacta agttgaaatt ccacctcccc atcacattta gttttgtcaa  46800
cttcatttct tcattcatta attcattcat tcagtctttt gtttatttgt ttattgccag  46860
tctgataggc gtatagtggt gcttcatcat ggttttactt tgcatttctc tgattttctt  46920
tttaaatttt taaaaaatta tttttatgta gaaacaaggt ctcgctacat ggcccaggct  46980
ggtcttgaac tcctggcttc aaatgatcct cccacattgg cctttcaaag taccgagatt  47040
gattataggc gtgtgccact gtggccagct gatttccctg atttctgatg agttaacaat  47100
ctcttctttc tctctctctc tctctgtgta tacaggtact caccattcgt gcctattttc  47160
tgtaaaatat gtggctttcc tcattttttt tttttttttt tttttttgag gcagagtctc  47220
gctctgttgc aggctagagt gcagtggtgc gatcttggct caccacaacc tccacttcct  47280
```

-continued

```
gggttcgagc aattctcctg cctcagcctt cagagtagct gggactacag gcgtgcacca  47340
ccatgcccag ctaattttg tatttttagt agagattggg tttcactatg ttggccagac  47400
tggtctcaaa ctcctgactt tgtgatctgc ccacctcagc ctcccaaagt gctgggatta  47460
caggagtgag ccactgcgcc cagccatctt tcctcatttt tatactaatt aggcttttat  47520
cttacttgtt ttttttaatg ttttttgtac actctgaagg ctgatttttg ttaattgtat  47580
gtgttgcatt ttttatggtt tgtcttatgc cttttgaaag taaaagttct taatttaaat  47640
atagccaacc tgtaaatcat ttgtgaaagt ctgtggttta agaggtcttg aataagaaat  47700
tatcccatca tcataagtca taaatacttt tttgttgttg ttgagacaga atctcatttt  47760
gttgtccagg ctggagtgca gtgggttgat ctcagctcac tgcaacctct gcctcctggg  47820
ttcagcaatt ctcctgcctc agcctcccaa gtagctgtga taataagcat gtgccaccac  47880
accagtctaa tttttgtatt tttagtggag acaggatttc atcatgttgg ccaggctggt  47940
ctcaaactcc tgacttcaag tgatccacct gtctcagcct cccaaagtgc tgggattata  48000
ggtgtgaacc accatgcctg gcccataaat acatttttat gtattttctt ctaaagttgt  48060
tttgtctttc actttttagt ttttaattca catataatta ctacttgcta cttataatta  48120
tctgtaagta gtatgagatg agaaataaat tctatttccc tcctatggat aagcacaaac  48180
ctgcagtatt agcacagtct tatgtcagat tttctaaaat gaatgggtgt gttttctagg  48240
ctctctgttc tgtttcatta tctgtctttt cctgcaacga tatcatctgc cttaaaaact  48300
ctagccttgt ggtattcctc attttcaagc agagcaaacc ccgtcacctt gcttttctcc  48360
tccagcatcg cttgtgctat cctggactaa gaccttcata tagactgtta gaatcatcta  48420
gccaagttcc attttaaaaa tctatgttgg agctgggcgc ggtggctcac gcctgtaatc  48480
ccagcacttt gggaggctga ggagggcaga tcacttgagg tcaggagttg gagaccagcc  48540
tgatgaaacc ccgtctctac taaaaataca aaaattagct ggacgttggg cacttgaatt  48600
ctagctactc aggaggctga ggcaggagaa tcgcttgaac ctggcaggcg gggggtgcag  48660
tgagccgcga tcatgccact gtactccagc ctgggtgaca gagtgaggct ccatctccaa  48720
aaataaataa ataaataaaa taaaatatct atgttggaaa ttttgtacaa attttattaa  48780
atgtctacat taatttggag aaaaatgact tgattttgat tatctattca atatttctgt  48840
attatgaata aggcaaaaag agaggcagag aatagcataa aataataact aaaattcctg  48900
ggtaaaccac ctcaaatcat ttcttcatat ggctcaatat tcttttgtga catggcctga  48960
aatatatcca gacagagaac tcttctcttc aatacatttc ttcttttagg tattcatatt  49020
gagttttcct gtccatgaac atggtataag agagtatatc ccttcgggag gccaaggtgg  49080
gtggatcacc tgaggtcagg agtttgagac gagcctggcc aacatggtaa agtcccatct  49140
ctactaaaaa cccaagaatt atccaggtgt ggtgacacat gcctgtagtc ccagctactc  49200
aggatgctga agcaggagaa ttgcttgaac caaggaggcg gaggttgcaa tgagccaagg  49260
tcatgccatt gcactccagc ctgggtgaag agcgagactc catctcaaaa aaaaaaaaaa  49320
aaaaaaaaag aaaacgagaa tatatccttt catttactag tttttcttca atttctttca  49380
agataaaggg cttacctatc ttctgcttta ttcatagtta cttgatattt ttgtttctaa  49440
taaatatggt gtctgtctat ttacctgcct cttacctgtt catttccagt ttcaaaaatg  49500
atgttgatat ttgaatatta accttaaatc tagcaccttg gtaaacacta ttattcattc  49560
taataattat cagtagatta tatgtgtttt ttatttataa atcatattgt ttgagtagca  49620
tgctttgctt cttcatttat aaaatttaca acttttattt ctttttaata atttttttct  49680
```

-continued

```
tattctcctg gctaggactt ctaacacagt attgagtgga agtgctgatc cttgtttagt  49740
ttcacatttg aaaaaagatt gcttttacta tttcactgtt aagtataata tgcaccatag  49800
gctttctgtg gattcctttt atccatttaa gaacatctct tattcctaat tagctgaagt  49860
tttctgcatg tttgttttca tcatgagtgg attttttac atctattgaa atcattttac  49920
atagaagata tttcacacct attgaaatgg tcatttcact tttccttctt taatatgtta  49980
agttgggcaa aatattaaag tatcacctgt cattctgctt cagcaaaaag tagtagtgtc  50040
ttagcagtat tggtgaaaag acagcatcaa ataaaaaaga tgtagaagta ggacccagta  50100
aaaatctagc gcatggggca ttgtcacatg taagcagaca gaatgtgaca ccaccaagga  50160
gcatctgaag ggctggaggc tgaaggaaga catgagtcac ccaggctcat ggacacttca  50220
gagaaattag ggagcaggaa gaagaaatag gatcaaagac tacgtatgtt ggttggaaaa  50280
ggaagctgat ggtatggaga tgttattatt taggtctcac ataaaagatg tagataaata  50340
ggtagatagg tagatagatg atagatagag agatagatag ataaatacat agatagatag  50400
atgataaata gatgttgtta tttaggcctc acataaagat gtagacagat tagacagaca  50460
gatgatagat agatagatag atagatagat agatagatag atagacgata gatagataga  50520
tagataatct cagaaacaga gacacagtga tctcagtaag ataggcatat gccaggtgac  50580
agaattcaga ggggtcccac tacgtgaaaa caatagaaca accttcgaaa agaaatttag  50640
tacaaataag agggcaggct tccttacata caagttagta aactggaaga atcagttatc  50700
ctcaaacatt ggaatagatc aaaaatagtt gtttatatta atgaaggtag ctaaacatga  50760
agctaagtga acctgtctct gacctagtgt ggcaatccct gggcaaggga cacttgctcc  50820
gctcttgtat ccttcactga atattcagac tttcagttaa gcatcggtga atttagtttt  50880
catctcttgt gaaaaccttg agagaggtaa ttctctctgc ttttcttctt ttcccttcct  50940
tcattttctc aaacattgcc tgtttaaaat acgaaatttt aaaagatggc cttgttctct  51000
tttttgttgt tattattaag tacagagaaa ggaagaacca caaatagcaa agggcaacat  51060
atggaatagt ttagaagttc cgggagcacc catgagggca actgcagaag agaacattct  51120
atcccccgtt gctgcagctt tcattccagg tctccatgca tatcagatag ggaaggaact  51180
ccgggacagc agcagggccc atgcacatgt aaccaattgc tttctttgcc tgtagtaaag  51240
ttcacatttt gattgcttct ccagattatg tagatccaga catattttat gcaggcatcc  51300
ggatctttct ctctgggtaa gtatagttca gttgttttcc tgtgtgaagt ctctgtagca  51360
ttgactgaat gtataagggg acgaagagac agaagcttcc tagcgtaaga aacataccaa  51420
gtgactcttg ctagggatcc actctcaggt aaaagaagtg ggataccatc tgcacaacaa  51480
ataacactga gggctaagta tttcagttaa gagtgtttgt tcctaggcag ttcagatcca  51540
tttatattca cttttcttag aatcctagct caatgacaga agaagaaaaa cacagtatgt  51600
cactcacaca gttctatcac ttacatctac tttttcttct tgttattaag gcatgtagaa  51660
ggctggggag tgtagtatag agttggatag catcgaagct ttcttctaaa gttcctggaa  51720
gagctacact gtggtttgaa cgaatgtgtc cctccaaaat tcatatgtta aaacctaatt  51780
gtgatggtga ggtattcgaa ggtgggttct ctgggaggtg attatgtctc ctctgagagg  51840
agaagacaat cccctgagtg gaactaatgc ccttataaag gggctggagg gagttcactt  51900
ggcccttttt gctccttttt tcttccattc cttgtccctt ccactatgtg aggacacggg  51960
agttgaggca ttaccttgga cgtggagacc aggccctcac cagacactga acttgccagc  52020
accttgatct tggacttccc agcctccaga actgtgagaa atacatttct gttatgggta  52080
```

gtccccaact caatacagtt tgacttacca ttttttgact ttatgttggt gcaaaagcat 52140
acatattcag tagaaactac tttgagtacc catacaacca ttctgttttt cacatttggt 52200
acagtattta ataaattcca taacatattc aacatgttga cataaataag ctttgcgtta 52260
ggtgattttg cccaactgtg ggctaatgta agtgttctga gcacatttaa gggcagctag 52320
gctaagctaa ggtgtttggt aggtcagatg tattaaatgc attttttgtc ttatgatatt 52380
ttcaacttac attgggttta tcaggatgta acccactgtg aattaaggaa tatctgtatt 52440
tacaaattac ccagtctaat gtattttgtt gtagcaacag gaacaaacta aaacactacc 52500
ccaaaccatt tttttcatat tttctgagta ctcttctttt gtcacatggc ttgaaatttc 52560
ttcacataga gaactctact attattttat tttattttat tttattttat tttttgagac 52620
agagtcttgc tcttttcacc caggctggag tgcagtggtg ccatcttggc tcacggcaac 52680
ctctgcctcc tggattcaaa ctactctcct gcctcagcct cccgagtagc tgcgattaca 52740
ggtggctgcc accaagcctg gctaattctt gtatttttag tagagacgga gtattgccat 52800
gttagtcagg ctggtctcga actcctgacc tcaggtgatc tgcccacctt ggcctcccaa 52860
aatgttggga ttacaggctt gagccaccac gtctggctga taactctact tttagatact 52920
ctctttgctt aaacaaatta gccattcctt ccttgacatg ttttaatcag attgccttcc 52980
tattaacttc ggaaattaag agtttctgct atgtttttgt ttaattttta aacagtgaaa 53040
aatgaaaggt ggaggcaatg gctggatgag gtgaatatgt caaatagata tcatctagtg 53100
ggccatctta ttaactagga gacacctgaa gtgctatcaa tagaaataat ctgaagctgt 53160
gtctggatac agcaagagac atgcaaatgc taaaaatcta ctatattaca ttggtgcaag 53220
gacagagtag caacacatac taagtatttt ctccagattg ggtgtgtttg acgtgtgaag 53280
cacttcaaac agagtccagc ctgggaggga gtggggatgg aatcctcctt gtagagggta 53340
cagagtggaa gcaagaaggt ttccaagatt gagagtaatg ggtgtatggt ttatggggga 53400
aagggaaaac aaaaagaagg gtgcagaaat ggagctggga gtgtgtttta gtatttaggc 53460
tttctctgta tacctttgat aggattagaa aaagaaaaat ggaccatttt taaaaatttc 53520
atgctaccac atagcaggct tatactatag atgcagaaac agactgggat ttaggaagca 53580
ccccaattct ggaaaatccc tttttgcttc acattgctct ctaaatctgt atgttttccc 53640
ttgttacgta acaatttacc acaaatttag cagcttaaaa caatatgcat tcattgtttc 53700
acaattctgt aagtcggaat cataggcaag ctcaactgac ttttccattt agggtcgcaa 53760
aaggccgaag tcaatttatc tattgggctg ggctcttaac tgaagatctg ggaagaatt 53820
cccttcaaaa ctcatttagg ttgttgtcag aattcagtgt tttgtggttc tagaactgag 53880
atctgtttcc ttgttggctg tcagacagga gctgctctca gcttcttgag gcatccagta 53940
ttccttatca tgtgtttttt tttttccatc tcagcactgg cacttttttt tttttttttt 54000
ttgagacaga gtcttgcttt gtcacccagg ctggggtgca gtggcacgat ctcggctcac 54060
cacaacctcc atctcccggg ttcaagtgat tctcctgcct cagcctcccg agtagctggg 54120
attacaggca cccgccacca gcccggctga tttttgtatt tttcatagag atgtggtctc 54180
accatgttgg ccaggctggt cttgaactcc tgacctcaag tgatcctccc acttcagcct 54240
cccaaagtgc tgagattaca ggcatgagcc atcatgccca gccagcactg acaattctaa 54300
tccttctagc actttgattc cttctcacct ctccttctgc ctctagccag agaaaactct 54360
ctgattttaa aggtcttatg tgattagatt cagcttacct aggtaattca ggataactcc 54420
ctatgtcaag gtcaactgat taataacctt aattacacct gcaaagtccc ctttgccata 54480

-continued

```
atatatcata ctgacagaca tgctatagca taatactaat agttctaaga attatgataa  54540
gaatcttgga aaaccatttt tagaattata cctaccacag tatccttcaa gggataaatt  54600
gattctactt cttctctatg tcagaagcat ctgatgagga tgaactatat attctgaaat  54660
ccccatgatt agatgtgtac tagaaggtga ttttactttc attaaaataa attcggagtc  54720
attgacacat tttatctttg atttacataa atgcctccgc tctgtttctt accctcaaaa  54780
tatttcccat gtagctaagt ggccagtacc gaatcctaca tgcattaata agtgtagatg  54840
gacaaaaata tctggattac tgagaattcc cattagcatt gtctagaaaa atgtaaattt  54900
gctttttgt tcttgattta tcctattttt gatttattat ttatatttat ttatttattt  54960
atttatttt agatggaggt ctcgctttgt cgcccaggct ggagcgcaat ggcgcaatct  55020
tggctcactg caacctctgc ctcccaggtt caagctttcc tcctgcctca gcctcccaag  55080
tagctgggac tacaggcacc tgccacagtg cccggctaat ttttgtattt tcagtagaga  55140
cagggtttg ccctgtgggc caggctgttc ttgaactcct gacctcaggt gatctgccca  55200
ccttggtccc ccaaagtgct gggattacag gcatgagcca ccacacctgg cctttttgct  55260
tactttttaa aaacattttt atttaggaga atggagatat ttcatatgta gatgacacat  55320
attcattccc tttagttccc acacacattc aatttcttga ggaagttagc ctttgcaaaa  55380
aaaaaaaaat gatctcattt ttttttcccc actaaaactt ctcattttct tggggttgct  55440
agaaagttgc tacaagaaag gctaaaaata attgtgccta cagatatttg aaaggaaaat  55500
agttcctctt ttttcacagt agcagcttgg acctgagaat gtatgggagc aataattggg  55560
ctgctcaaag aaacacaatt tcccttcctc agactagaat taccaaccta gagaacatga  55620
gtttttaaag tagatgtgct tcttttatct ttttggactt gtatgctggt gttttctctg  55680
tcaccttcac tgtggaaatc ctcttgaggg tgaggcactg aaagcagatt gattaatgtc  55740
tcttggccat ttgagacatt ggatggctct tttaagttgg ccacgttctt tcaagaacta  55800
tgcttgggct acatattctg gatatataat acatacttgt aggatgttat ttttaaatca  55860
ttcatttatc acatatttag tgagtgccta ccccatgtca gttctaggtg ctggaaatag  55920
agcagtaaaa ccaaccctca acttggcccc tctggagctt acatttcaat gcggtgggtg  55980
gggggatgga caattaatac acaagtaaat ctaataaaag cgtcatacaa tatacattac  56040
aatggtaagc acaatgaaga aatggaaagc tggatagaga gtattagaga ctgtcgaatg  56100
tagtggccaa attttcctgt ttattgtggt ccaagagtgc cacagccctc tatgacattt  56160
gagcagacac ctggaggaag tgagggagtg agccgccaag aaggaatggc aagtgcaata  56220
accctgaggt gggagcgtgt tggtcgtggt ggaagagctg caggaagcca gcagggccgc  56280
aacactcagg ggagaataag aaagagtgag gtgacagtag agaccggatc atgtagagct  56340
ttgtcagctt cttttctgag tgagatggac aacacggaca cgttttgaaa agaataacaa  56400
tgtgatctgc cttcagttgc aaatcatctc tgtattgact gagtaggaaa taaactccaa  56460
gaataaagac ggaaacaggg aaaatattta agaagcgatc attacaatcc agggtggtgg  56520
cttgtactag ggtacaaggg ctaaaggtgt tgagaaatgg tcagattctg gatatatact  56580
gaaatcaaag ttgatggaaa gatatgagtc aaagataatt tgcaggtttt ggggtcctgg  56640
ttcactgaaa gaacagagac atcatttact ccaatgagga agactatagg aggaacaggt  56700
ttagcaaaga agaaaggaaa tcaggagatc agtttgggga cacggtcata tcaagtaggc  56760
agttggatgt atgggtctgg aatataggggg agtggtctag ctatcagtgt aaatagcttt  56820
ttacatttgt aaatagtcag gatataggct tttctttttc tttttgtgag acacagtctt  56880
```

-continued

```
gctctttcgc ccaaactgga gtgcaatggc acaatctcag ctcactgcaa cctctgcctc  56940
tgggttcaag cgatactcct gcctcagcct cccgagtagc tgggactaca ggtgtgcacc  57000
accataccag gctaattttt gtgtttttaa tggaaatggg gtttcaccat gttgaccagg  57060
ctggtgtcaa actcctgacc tcaatcgatc tccccgcctg ggcctcccaa agtgctggga  57120
ttacaggcat gagccacccc atccagctgg gatatagttg ttttctaaat ctatgaggct  57180
agagaagacc atttgggaat tgagagcagt gagcagtcca cggactgacc ctttgagagt  57240
gcaacattta gcagtactca agatgggaag gagctagtga aaaagcccca aatgactaca  57300
taagaccatc aaccagatta caaagaaaga cccgaacatg tgtgcccata tatcacccaa  57360
cagcagttat gtctttcatg tttcttcccc ataaaatgtt gttcatcaac tttattagac  57420
tagggtctta acattggaca aatcacaaaa cctctctgga gcctatttta tttttcaaca  57480
gctgtaggaa gcaaatacaa attggaaatc taaggctcag aaagatttgt acaaagttac  57540
acagtaatga aaggggagcc gggattccca ctcactctaa agaatatgat aaaatggcta  57600
gtattcactg aatgcttaac atgttccagg ccctgggcag gtattatttt aattagttct  57660
cacaataatc caataaggga gatactaatt tactcagatg agaaagctga ggctcagaga  57720
ggttaatgaa ctaagccaag gctcactgtt aataaatagc aaaggtaaaa ttaaattcca  57780
tatctgcttg agatagaggc cttgctccta atagctgcag cctgtcaggg cctggcagca  57840
gtaacctctc ctttcctctt cccaccattc ccctgcactg ctttctgtac cgcatctctt  57900
ttcagagtga tgttgcccca attgcggagg ccactgtgct gtttatccag tgaaagctgt  57960
agcacagcca acccaaagcg tccccagtga aaacaacctg gctccttaca gcacttccag  58020
cctcagagca gtatttgaaa aatatcatga acagcaaaca cagcagtctg tctgtggctt  58080
ttatatgtgt atatggtgtg tgtgtatgtc ccttctcttg agcaaaataa cttttagaat  58140
tatagaaaaa aaatgtgcaa catcaatgtg gatctgctgt ttaaactcat aacagagaaa  58200
gtagcttgtt tctggctata ggaggaaaag acgatattcc ttagtaaaaa tggaaatcca  58260
catatggggt tcttgtaaaa atgaagatag aaaattgcaa gtttggggat caagttctgg  58320
ttctatcatc ctttaacagt atgaccctgg aaccttaatt gctttgagtc tttgttactt  58380
tatctatgaa atgaagtatt taaaaaaact ccaaaaatct gtcctgatgt acacacaaga  58440
ggtcaaatga gaaaatgaat gtgaagatgc tttataaact atacagcatg gtaggtgcaa  58500
atgtgacatg aacttgtttt ggacacatta taaagtcacc cccacaaact gtgattgttc  58560
aagactatgc aaagtcagac acaggaaaat aagtaaaaca gatggaggca taaagagggg  58620
gaactcagag aaaacagtga agaacaggaa tcaggaagac aaaggagagg aaaggtgggg  58680
aggagaggag aaggaaaggg ggaagggaat ggaggagagg agaacagctg cttcacagag  58740
catggccggc agcccagtcc cagcctttct gcatgtccct gacttcagcc tctggcgagg  58800
cacaggctta ctctgtgctt cctgctgtta ctcttcttat ccatccttat tatcaatacc  58860
tgtggtcaac aaagtatttg ataaaggcat cctcaaagtc aggtaacatc tgtacgttat  58920
agattacaaa gttgagtaat atccagaatt ggtagtttaa cgtgatgact tcttaacaat  58980
tatcactgtt tcagggaagg gcaaaggtgt gtgtgtgtgt gtgttcatct gtgtgtatct  59040
gtgtatgtaa ttgtgggtgt ttgtgtatat ttgtgaggct ctttacttgg cggagttaaa  59100
aagtatctgc tcatcaaggt tgagattagc aaaggaagtg aagatttttc cagagcccct  59160
aaaatgtgcc ttttgaccaa cactgaggac atctttataa ctgagtatgt gcaataaata  59220
tgtcttggga cctgtgccac aaattcctct ctaaatagcc tttacctctc tggaataacc  59280
```

```
ctttagatga ggaagaaaag ggctgtgatt ttatagcttg ttatgaagct ggagtgaaga  59340
tgatgcttca gtacttaccc tacaaagata cccccaatcc ctcaccctaa aattaccatt  59400
gaaatcatgt tccctttctc attcactctc agtttccatg tcagaaaata taccattacc  59460
tccctgcacc cctttcatct ctctcacttt tctcttgctt agatggaaag acaacccagc  59520
aatgcctgca gggctgatgt atgaaggagt ttcccaagag cccctgaaat actccggcgg  59580
gagtgcagct cagagcacag tgcttcatgc ctttgatgag ttcttaggca ttcgtcatag  59640
caaggaaagt ggtaagtcag acattttgtt ttcccttgag agtagaggga ggaagaggag  59700
aggtgttttt tttttttcca attgataaaa ccaaatataa attaaaatgt catgaagttt  59760
atacttctct aagtcagcca agaaactgca tgactgccaa tgtttttgtg tcaagccaat  59820
taatattgga atatcagatg tcagcttgat cttgggtttt acttccaaat cttaaaatgt  59880
tgctctgttt ccaactgttc actatcactt tggtttggat ctttagacac tagcttcctt  59940
tttctgaaat gggggagaga tgtggagttt gaaggctatg agtctgggcc agctggaaac  60000
aggtctggga tcttccaaga aagtccttcc ccacaaaatg gtgcaacttc tagccaaatc  60060
tatttatacc agcagaggga tctatcaccc tggaagcttg aaattgttca ttttcttacc  60120
tgccaggatc aagttaagtt tttaacagtt gcaaaaagac acttcatact atggagtttt  60180
caagttggat tagaagaaaa agaatcacca gaacttagtg tcgtagattc aagtcacttc  60240
tctaaaactg tcataatttt tcacggattt tggcatttgg tgacattaat ggttgattta  60300
cttaccatgc ataatattaa acccataacg aatttcctat aaatatctat tgatttgatt  60360
tttaaatcac ttggcttcaa gaggctatta ctaaaacagt gactcattct ttatcttttt  60420
tgccttcacg ggctttatat aactttctcc ttttcttgtg ctccctccaa aacaaagcac  60480
tgagaaaaca aaattcacca gagtattcag ctagtcagtt caagggtttg tgttctacat  60540
ttgaagatat tccttatagc agctaccaac gggatacttt gtttacattt gttgtgtagt  60600
aaatatttat atattggcaa acaaatctag ttccaactct gtcatctgag atgttcttac  60660
tttgtttcct cttctccatc tcctgtcaac tgttagaaat atacatttga gtacgtgaag  60720
tctgcaaaca aaagggccaa ggtagatttg agttagaaca ccagcaacag tttctggtgc  60780
attcttgtct gaaaaagcag agaagattgg gcaccgtggg tcatgcctgt aatcccaaaa  60840
ttttggaagt ctgaggcagg tggatcgctt gagcccagga gttcaagaca agcctgggca  60900
acatagcaag aacccgtctc tactaaaagg aatacaaaaa aatattagct gggtgtggtg  60960
gcgcacacct gtagtttcag ctactcagaa gactgaggtg ggaggatcac ttgaactcag  61020
gggcagaggt ggcagtaagc tgagatcaca ccactgcact ccagcctggg caacagagca  61080
agatctcatc tagagaaaaa aaaaataaaa aagaagaaga agcagacgag ctctgctata  61140
tttccatgtg gagctatgac gttatgctgt attgtttctt tcaggtgact ttctgtacag  61200
aatgagggat tacatgcctc cttcccataa ggccttcata gaagacatcc actcagcacc  61260
ttccctgagg gactacatcc tgtcatctgg acaggaccac ttgctgacag cttataacca  61320
gtgtgtgcag gccctggcag agctgcggag ctatcacatc accatggtca ccaaatacct  61380
catcacagct gcagccaagg caaagcatgg gaagccaaac catctcccag ggcctcctca  61440
ggctttaaaa gacaggggca caggtggaac cgcagttatg agctttctta agagtgtcag  61500
ggataagacc ttggagtcaa tccttcaccc acgtggttag                        61540
```

<210> SEQ ID NO 16
<211> LENGTH: 27
<212> TYPE: DNA

<213> ORGANISM: Artificial Sequence
<220> FEATURE:
<223> OTHER INFORMATION: Primer

<400> SEQUENCE: 16
tccggtacca tggagcctca aagtcag 27

<210> SEQ ID NO 17
<211> LENGTH: 28
<212> TYPE: DNA
<213> ORGANISM: Artificial Sequence
<220> FEATURE:
<223> OTHER INFORMATION: Primer

<400> SEQUENCE: 17
atccggtacc atggcactca gtaaaata 28

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
tgtcctggtg ctaagggtca agacaattct 30

<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
tgagttggcc taagggtcaa gacaattct 29

<210> SEQ ID NO 20
<211> LENGTH: 1266
<212> TYPE: DNA
<213> ORGANISM: Homo sapiens

<400> SEQUENCE: 20
atgttgcatt ttcattatta tgatacttca aacaaaataa tggagcccca cagaccgaat 60
gtgaagacag cagtgccatt gtctttggaa agctatcaca tatctgaaga gtatggcttt 120
cttcttccag attctctgaa agaacttcca gatcattata ggccttggat ggaaattgcc 180
aacaaacttc ctcaattgat tgatgctcac cagcttcaag ctcatgtgga caagatgccc 240
ctgctgagct gccagttcct gaagggtcac cgggagcagc gcctggccca cctggtcctg 300
agcttcctca ccatgggtta tgtctggcag gaaggagagg cgcagcctgc agaggtcctg 360
ccaaggaatc ttgcccttcc atttgtcgaa gtctccagga acttggggct ccctcctatc 420
ctggtccact cagacttggt gctgacgaac tggaccaaaa aagatccaga cgggttcctg 480
gaaattggga acctggagac catcatctca tttcctgggg gagagagcct gcatggtttt 540
atactggtga ctgctttggt agagaaagaa gcagtgcctg ggataaaggc tcttgttcag 600
gccacgaatg ctatcttgca gcccaaccag gaggccctgc tccaagccct gcagcgactg 660
agactgtcta ttcaggacat caccaaaacc ttaggacaga tgcatgatta tgtagatcca 720
gacatatttt atgcaggcat ccggatcttt ctctctgggt ggaaagacaa cccagcaatg 780
cctgcagggc tgatgtatga aggagtttcc caagagcccc tgaaatactc cggcgggagt 840
gcagctcaga gcacagtgct tcatgccttt gatgagttct taggcattcg tcatagcaag 900
gaaagtggtg actttctgta cagaatgagg gattacatgc ctccttccca taaggccttc 960
atagaagaca tccactcagc accttccctg agggactaca tcctgtcatc tggacaggac 1020
cacttgctga cagcttataa ccagtgtgtg caggccctgg cagagctgcg gagctatcac 1080
atcaccatgg tcaccaaata cctcatcaca gctgcagcca aggcaaagca tgggaagcca 1140
aaccatctcc cagggcctcc tcaggcttta aaagacaggg gcacaggtgg aaccgcagtt 1200
atgagctttc ttaagagtgt cagggataag accttggagt caatccttca cccacgtggt 1260
taggat 1266

<210> SEQ ID NO 21
<211> LENGTH: 73660
<212> TYPE: DNA
<213> ORGANISM: Homo sapiens

<400> SEQUENCE: 21
ccctggcctt ggaagatgcc ctagagacgc tgaggtggtt gtacttttgc cataggagtg 60
gcagccagag aactgagccc aatgaatgca aaggctggtg cctggaaata ttgtgacttt 120
gccacagaaa gaagatggag aattttaaag ttggaaatct gcctggtaag ggatcatttg 180
ctggtgtctg caaagttgag tccatacaca ctggtttgga aatttcagtc cagatgatag 240
ttaagaaagc agtaagaata cagagagtcc acaatgagat gaaaatgcac tgccagttga 300
aacatcctcc tacactggag ctttataaat attttaaaga caaggattgg attagatttg 360
acattagaaa tgtaccataa tacagaaggc aatggacacc taaagaacag aatgaaaacc 420
ttcttaggaa atgaagcttg acacttcacc caccaggcca ccacaagaat gttgcatttt 480
cattattatg gtaagtacac tggtaacttc ttttctaacc tcgtatgcat aatgtaaaca 540
tcaagactga caatttgggg ctagcaactc aattggaaaa tcactgttct ctattgtaaa 600
attcctaatt atgtttccct agaaattgca aagtgcacat gtacttgcat ttaatgtttg 660
gtccatgggc tgaatgcttt gtgcattact tttctggttg ttgttgttgt tgttgttgtt 720
gttgttgttg ttgttgtttt gagacagagt ctcactctgt tgccaggctg gagtgcagtg 780
gcatgatctc ggctcactgc aacctctgcc tcccaggttc aagcaattct tctgccacag 840
ccttccaagt aactgggatt acaggcgctc accaccacac cctgctaatt tttgtacttt 900
tagtagagac ggggtttcac catgttggcc aggctggcct caaactcctg acctcaagtg 960
atccacctgc tttgacctcc caaaatgctg ggattacagg catgagccac cttgcccagc 1020
ctgtgcatta cttttgagga cacatttgac aatggcacag tcaagaacac cacataaagt 1080
agtattggca gattatgaaa tagcaattgt tttggaagac agcaaaacct gaagtatttt 1140
cagacatgta cattatgaag tattatacct tctttaacta tgtgcaagtt aaaatcagtc 1200
ataactgaaa atcaaaaggg caataatgaa catacttcat ccagaagagg tatccacaaa 1260
acttctgaaa gaggtcttag tatatccagg gatggagata ttattacaat gtattatcca 1320
aatgatggaa gttttctctt gctgatagaa tgcatccacc tactaacatc agtaagtaca 1380
ggtttaacaa tttaccagaa atgtactgga ggaaatatga atatgcttcc agatttattc 1440
tacctaaagg atctggctct attttacaag gtcatctatt ttacaaggta ctgtagatgc 1500
attttgatga aaaaaattac cctgctattg attttgaggt ctggtattat gatagagcaa 1560
aaactatcca aaagagattt aattcaagtc attgcaaaat cttggaaaat gtgtgagaaa 1620
tcttacacat ggaaaggagg aagtaaagat ggtagcttaa acatgtgttc cactgtgaac 1680

-continued

```
aattctctgc aaacccaccc ccaaaagtca aggaggctga caggctgaag aaagaggctg   1740
tcaaatctag tttctcagaa aaagaaaaat taatagggac ttaagaacag aagccatata   1800
tctgccctga gatgagctgg tggatcctca cactgttacc cccagaccca gggcttatat   1860
accacaggga aagacaattg cagtaatttg cttaacggca ggatttacgg caagtacatg   1920
ctcttaagag tagattaagt agtaacctta gaggcattcc tagaactgga gttaatcaga   1980
agtcaacaca gtggattagc atccaagatg gagttgcttt agcctccaca aagagaaaat   2040
gaagataaat ttggtccatg ctaattaggg ggtgttccat ttgtttgaaa ctgaaatcta   2100
taatttccaa agaagaaaat aaacgtggaa gtcgtccttc ctttttggta tgcatagaca   2160
atctggcagt gttaggcccc taaggcctta tcacctcctc cttctgtggg tcaaacttta   2220
cagtgagagg aaagacatct tttaaaagaa gaataatcat gactagttta atcatgacta   2280
gttcatcttc cctgcaatag atacccatat ttaacatacc tattgtacaa agaatatgat   2340
tgcacagcta caactttggg acaaactcct tttctgccgc tttcaatgat cgtcttccaa   2400
aatcagaaca gcttttgaat tttattttgt gaaaaatgtc gtttgagtga cacagtaaac   2460
tctgtggagc tctgtggata cagttgaatg atggctccca gtttatcatg caggtgggat   2520
tatattccaa cagttatgtt tcacagaaag gcaaaataac caggtacgga aaaaatgaaa   2580
aatttgcagc ttacatcaaa cagaaattgc agtgtctttc atctctttaa agttttctaa   2640
tcaaaattct agtttcatc aattaaaact ttatttaggt agatacattt aataagtaac   2700
tttttgttgg cttaaaggga atgaacttta tgtaatgtaa ctgtctattt caggaagctt   2760
ttctatgaga atttaaaact acaccaaaat atcttctttt tttttttttt gagacaaggt   2820
gtcacattgt ctctcaggct ggagtgcagt ggtgtgatcc tagctcactg tagccttgaa   2880
ttcctgggct caactgatcc tgctacctca accccccacg tagctaggac tacaggcctg   2940
caccaccaca tctggctaat tttttatatt tttgtagaga aatggtctgg ctacgttgcc   3000
caggctggtc ccaaactcct ggcctcaggt gatcctcctg cgtcaacctc ccaaagtgtt   3060
gggattacag gtgtgagcaa acctgccatc tcaaaacatg tgtattttaa tgagacaaca   3120
aagatcaagg gaactttagt ccttacaatg taatgatcaa aaaagtgaaa tagataatca   3180
acataacatt gcttgtagac catgcaaaca atcttattgc atttgtatat ttgtaatgaa   3240
ctgttttata ataacaaaat gtaaaatgtg tattttattt gtccttttat tgttttccta   3300
cttcttagac atgttaagaa ctatggaaaa agatatggga gtttgtgaaa atttaaataa   3360
ttcatattta tattacaaga aacagatatt agaatatgtt tgttttatat ttcttttgta   3420
gcagaatttt ctagccaggc attgtggctt acacctgtaa ttccagcact ttgggaggct   3480
gaggtgggac aatcacttaa gcccaagagt ttgaaatcag tgagggcaac atagtgagac   3540
tctatctcta caaaaaattc tctatctata tctatataaa ggaattttgt gaggaaaact   3600
atatattttg tatataaatg aattttatca ggaaatatat ctgtaaatga attttataaa   3660
atatagcatc actttatcct tgatttattt catttaataa ttattttaaa gtaatatact   3720
aataaactca ttttaaaaac tgctatgacc ataaaactat tagagataac ataagagaaa   3780
atctaggtga ccttgggttt ggagataact ttttatatat aacaccaaag gcgcaatcaa   3840
tgaaaaaaaa tgacaagctc tatatcacat atcaatatta aaatgtgatc tgtgaaaggc   3900
atcgtcaaga gaacaaaaag acaagccaca gactgggaga aaatatttgc aaaagacata   3960
tgtgataaaa gacaattatc aaaatataca aataattctt aaaactcaaa aataagaaaa   4020
tgaacaactc agttaaataa tgggcaaaag atctcaacag aaaccccatc aaagaagaaa   4080
```

-continued

```
cacagtggca agcatatgaa aatatgatct acatcatatg ccattaggaa attgcaaatt   4140
aaaacaatga gataccacta catttctaca ttggtgaaaa ttccaagtac tgacagcact   4200
ctcagtgctg gtgaggatat ggtgcagtag aaatccacac tcatgccggg cacagtggct   4260
catgcctgta atcccagcac tttgggaggc tgaggcgggt ggatcaccag gtcaggagtt   4320
tgagatcagc ctgaccaaca tggtgaaacc ccggctctac taaaaataca aaaattagcc   4380
cggtgtggtg gcgggcgcct gctactcggg agtctgaggc aggagaatcg cttgaaccca   4440
ggaggtggag gttgcagtga gccgagatgg cgccactgca ctctagcctg ggcgacagag   4500
caagactcca tctcaaaaaa aaaaaaaaaa aaaagaggcc aggagtggtg gctcacacct   4560
gtaatcccag cactttggga gactgaggta ggcggatcac ttgaggtcag gagttggaga   4620
ccagccttgc caacatgaca aaaccctgtc tctactaaaa ccacaaaaat tagccaggag   4680
tattggcaca tgcctgtagt cccagttact cgggaggctg agacaggaga atttcttgaa   4740
cccgggaggc ggaggctgca gtgagccgat atcgcaccac tgtactccag cctgaacgac   4800
agggcgagac tctgtctcaa aaaaaaaaaa aaaaaaaaaa aaaaggaaag aaagaaagaa   4860
agaaaaaaga aaattccgtg attgcagtct ttacgtattt atttgttatt aagtacagta   4920
aaataaagaa ggatagatgt catggaaaat gtcacgaaaa taaaagagtt aaaaaaaaaa   4980
aaaagtaggc tgcaatgcca gatgcctgaa aagttaatca acgaaaggac ttaaatgtcc   5040
ccattgaatt taggaacaaa gaagtaatta atgaactggg caaaaacact caatgtacca   5100
gcgttatcga tttagaaact gaaactaagt atatctgatg ttgcttttag gaaacaagta   5160
aatgaggtcc taaaaagtta aactgtgacc atattttctt tcctttttct aatttctcct   5220
tgggccattt ccaaaaagcc ctaatacccc gactgataga aatggatacc ttgctgtgca   5280
ctggtactac tgtgattcat ggaaagctga tcatgcaacc caagacgcca aaattcccag   5340
ccttactgtt acgaaagaaa gtttctaagc acaattgtct ctagccaact tcctcttagt   5400
aagaaagagg ccaggcaggg cttcatgcag ggtacagccc tgagtttctt actgcgtggt   5460
aagtttctgg ggctgggagt aaagcagcgt gaccgaaagc agtacaaagt tctaccggac   5520
acgcagatcc cggtcctaca aatatgaggt ccataatgag actgagatat cattcatcca   5580
acaaatattt attgaatacc aaacattggg cttacggcta aaggaaaata caaagttgtg   5640
ttggatatgg gttctgtttt caaggagctt ataatctaat aggaaagatg aggttactac   5700
attagtagca atcagaccag atagaactgg aagtgtgatg taaatgaggt acagattgat   5760
tgtagaattt tgcagaaaga aaacaattct gaagaaatgt tcatggaagt attagcagtt   5820
gagatgtatc ttaaaagata agtggggttc ctgttggaaa cattcaaaac tctctcttct   5880
agctatttta aaatacgcaa tatattatta actatggtca ccttactgtg ctatagaaca   5940
ctagaactta ttcctactat ctaactataa ttttgtaccc actaaccaac ctctccctgt   6000
ccctcctccc cctattcatc ccaccctctg gtaaccactg ttctactctc tgcttcccaa   6060
aacaaagaaa tgatcactgt ttcggtgatg gagatgtcaa ttaccctgat ttgatcatta   6120
cacattgcat acatgtatag aaatatcaca tgcaactctt aagtatatac cattcttatg   6180
taccaaatac aaataaaatt gaaaaaaaaa aaaaactttg gctgggcgcg gtaggtcatg   6240
ccagcacttt gggaggctga ggcaggcgga tcacctgagg tcaggagttc cagaccagcc   6300
tggccaacat ggtgaaaccc aatctcttct aaaaaataca aaaattagct tggtgtggtg   6360
gcaggggccc gtaatcccag ctactcagga ggctgaggca ggagaaatgc ttgaacctgg   6420
aaggcagagg ctacagtgag ccgagatcat gccactgcac ttcagcctgg gtgacaaagc   6480
```

-continued

```
aagactccat ctcaaaaaaa aaaaaaaaaa agcctcctga gtaactggga ctacaggcat   6540
gcgacaatac tcccggctct ctttttaaaa atgagaagta gaagtagtgg tgactgtcaa   6600
gaaagtattt tggaaaaata ctatgaataa ccagaccaaa gaaaccaaat accagttgtt   6660
tcaggagcag taaatcattt ttgagggctt gagcaaaggt cttgctagaa aggtgcttag   6720
gggtcagatt ttggacataa tgccaggcca agaaaatttg cactttattt cattaacaat   6780
gaggagctct tgaaagtttt attggcagga cctaagatag ttacagaccc acaagtaaca   6840
tgggtctaga ccttgggaac aagaaaagtc aagatcgagt atgcagactt gggaaccgag   6900
tataactaat ggttaagatt aaataaaaat acataagaac actgagatag agaaatggct   6960
cattaatgct gcaaatgtct gcatgtttag ggatgaaata gaaaaagaag tcagaaaaat   7020
acagttcaaa caataggaaa gaaaaccaga aatgcatgat tctaagaaat gaatgggtgg   7080
acatggtggc tcacatctgt aatcccagca ctttgggagg ccgaggcaga aggatagcta   7140
cagcccagga gttcaagacc acccagagca acacagcaaa accccatctc tacaaaaaac   7200
aaaaataaaa attagccaag catggtggta cacacctgta gtcccagcta ctcactcaac   7260
aggctgaggc agaaggatca cttgagccca ggaggtgaag gatacagtaa gctatgattg   7320
caccattgca ctccagcctg gctgagagaa tgagagcttg tttccaaaaa taaaaaataa   7380
gaaagaattt ttagaatgag aggaaaacaa catgaaacat gagaaaaata acattccctg   7440
ttatatggta ggtgcttcgc ttatagtttc tcattaattc atcatgtaat gtctctggga   7500
taaacattat ggatttcctg cagaaacaga agctcagaat tttatgccag gtgttgaaag   7560
gccatgtagc taatagatga tagaacacag actcacactc tggtagtcct gagttaacag   7620
tagaaaagtc ctgggctggg cgtggtggtt cacgcctgta atcccagcat tttgggaggt   7680
tgaggcaggc agatcaccag aggtcaggag tttgagacca gcctggccaa catgactaaa   7740
gcctgtctct accaaaacca caattaccca gcgtggtggc gggcacttat agtaccaact   7800
actcaggagg ctgaggcaga agaattgctt gaacctggga ggtagaggtt tcagtgaggc   7860
aagatcaagc cacggcactc cagcctgggt gacagaatga gactctgtat aacaaacaaa   7920
caaacaaaat cagtaagaaa gtcccagact aagaggcatc aaatcaggat tctactccaa   7980
ctctgatgcc agcttccagg aatacacttg ataagttgtt tcattcccat aaatcttggg   8040
tgattcgtgt ttaatgagag cattgaactg aatcatttat tctatgactc agttctaata   8100
tttcacaatt ctatggttgt ataatattac aggaaattct tgagaaggtg cagagggaat   8160
ggatgaaaaa aaccacatga ctaacataaa aaataatggg gccatctttt catttgagat   8220
tgaaggaaag aacgagagga caattaaaca tgcagagtct gagaacttgc atttaggagg   8280
cataagatgc tgaactgcaa aattggttag atattgggct gaagagaatt gagaattttt   8340
taataataaa aactcttggc agggcgcagt ggctcacgcc tgtaatccca gcagtttggg   8400
aggctgaggt gggtggatca cttgaggtca ggagtttgag accagcgtga ctaacgtggg   8460
gaaaccccgt ctttaagaaa aatgcaaaaa atattagctg ggtgtggtgg tacaagcctg   8520
taatcccagc tacttgagag gcttaggcag gaggatcacg tgagcccagg aggtggaggt   8580
tgcagtaagc cgagattgtg ccactgtact ccagtctgga tgacagaggg acactatctc   8640
aaaaaacaaa caaacactct taagaaatta ggtgtagaaa gaatgttcct caataccata   8700
aaggccatat gtaagaaacc tatagctggc cgggcgcggt ggctcaagcc tgtaatccca   8760
gcactctagg aggccgaggc gggcagatcg cgaggtcagg agatcgagac catcctggct   8820
aacacagtga aaccccgtct ctactaaaaa tacaaaaaat tagccgggcg aggtggctgg   8880
```

-continued

```
tgcctgtagt cccagctact cgggaggctg aggcaggaga atggcgtgaa ccccgggggg   8940
cggagcctgc agtgagctga gatcgcgcca ctgcactcca gcctgggcga cagcgagact   9000
ccatctcaaa aaaaaaaaaa aaaaaaaaaa ggaaacctat agctaacatc atactgaatg   9060
gtgaacagtt gaatgctttc gtctaagaac tggaacaaga caagcacgcc aactctcacc   9120
actcttactc aacatagtac tttaagtcct agccagagca atcaaacagg ggaagtggat   9180
aattgagaat ggctcgagag gtgctgtggc tcagtcctgt tgtcctggca cagaaggagc   9240
tgaggccagg cgttcaagaa tggctcctag atgtctcata aggaaccata aatcaaacaa   9300
ctttcaaaac tgaaacctgc gtgagaacgg ttgcattagt taatctggga gcttcctgct   9360
ttttttagc tttcatattt atcttagaga aagggaggaa ggagagatgt gtatggatac   9420
ataagcattc aaatacattt gtgtataatc ttatgaccag aattcaggtc caatgaacaa   9480
aaaggtaggg tcttcggaat ttccccagtg agatctatga cctgaatatt attacgcaag   9540
gatccacttt gggattacag gcgtgaacca ctacacccag cccaggactt tcctgctgtt   9600
aactcaggac taccacaatg tgagtctctg ttctgtaatg cccaaccttg tttttactaa   9660
ccccgctttt agactccccg ttttccttta atcacctagc cttgtttcca cctgaattga   9720
ctctccctta gctaagagag ccagacagac tccatcttgg ctctttcact ggcagcccct   9780
tcctcaagga cttagcttgt gcaagctgac tcccagcaca tccaggaatg caattaactg   9840
gtaagatact gtggcaagct atatccgcaa ttcacaggaa ttcgtctgat tgataacgcc   9900
caaagccccg agtctatcac cttgtaatag tcttaaagcc cctgcacctg gaactgttta   9960
ctttcctgta accatttatc cttttaactt tttgcctaat ttatttctgt aaaattgttt  10020
taactggacc cccctcccct ttctaaacca aagtataaaa gaaaatctag tcccttcttt  10080
ggggctgaga gaattttgag cgatagccgt ctctcggtcg ctggctaata aaggattctt  10140
aatttgtctg aaagtgtggc gtttttccaa ctcgttcagg tacaacagtt ctagcatcta  10200
ttagctatgt ggcctttcaa cacctggcat aaaattctga acaatggctt ggaaattaag  10260
ataccttagc tctagtcctt gctctgctaa taattaatag agtgaaactg gacagggtta  10320
ttcacatgtg tgtgcctcag tttactgtta actgaagaat gacaaagttc ataaatttga  10380
aaaggagagg tttcttatat ggggttgcaa cctgcagggt ggccatgcta cagtctggga  10440
agcattgcct ctggctggaa gccagaaaca ggcactttca gggtcagaag aataagacag  10500
agatttatgc tgaatggggt gaccaaatat acatattcaa taggctatag gaggagttat  10560
gaatatttat gaaaggagaa atgtgtacat gtgcaatttg gcttcatgcc ccttcatggg  10620
acctacattc aaaaaatggc agccttagca tgatctgagg gaggatcttt cagccctctg  10680
aggtcaaaag tgaaggagag gacaggaaac cctcactgtg tgttctccgt aggggccaga  10740
accactgcat gtttggtgaa cctggctggt tgttatgttg aaactgcaaa agggagggat  10800
aacagtcagg tgcttgtttg ataccagggg tagaggagac tttcaaaagg gctggtttct  10860
gtttagccct tagggaagaa tgtctaaaga gaattaccta caagggtata acgaggagtg  10920
tctgacattc catctagtaa tgaactagaa ctcagttttc aagttaactc tgggaccctc  10980
ttagccaaga agaggtccat tcagttggtt gaagagctta ggatttcatt tatatctctc  11040
atcactaatc tgcaaaagct ggtagtgaaa ccgcctttgc aaaattatga ctgagacagc  11100
gaaagagatc taacttaatc gattccgtct tgcttctaac ctccaagctg tccttattca  11160
ttcccgggca taggctgaac taactccggg agaagcttag tttatagttt ttagtttaaa  11220
acaaagatag taacagccct ttcccaaagc agacctcctt cttgccttgg aactagactg  11280
```

cctttagtgg gactaacatt agccacaaga ttagaaactg tggcttagga gtcatacagc 11340
tggaggctac aagattctga ctctccctaa actgctccta agatcagtcc ttgagatatt 11400
ttgcagaccc tgtacttgat ggatcaggtg gcaccaccca gattgataaa gtggctcatc 11460
tgatcttgtg gcccccaccc aggaactgac tcagcacaag aagagagctt tgactctcta 11520
tgatttcatc tctgacccgt cagcactcct ggctcgctgg cctccctcag gccaccaagt 11580
tgtccttaaa aactctgctc ccactgggcg gtggctcatg cctgtaatcc cagcactttg 11640
ggaggccaag gcaggcggat cacaaggtca ggagattgag accatctggc taacatggta 11700
aaccctgtct ctactaaaag tacaaaaaat tagctgggca tggtggcacg cacctgtagt 11760
cccagctact cgggaggctg aggcaggaga atcacttgaa cctgggaggc agaggttaca 11820
gtgagccgag atcatgccac tgcactccag cctgggcaac agagtgagag acttcatctc 11880
aaaaaaataa atagataaat aacctccgct ccctgaatga atgctcccgg agactgattt 11940
gaatcataat aaaactccag tctcccgcac agcctgctct tcatgaatta ctctttctct 12000
attgcaaatc ccctgtcttg ataaattggc tctgtctaga cagtgggcaa ggtgacctca 12060
ctgggcagtt acagtagtac ccacttcata agtgaaatca cttatcttag tggtagggtc 12120
ccaaaagttg tttggtagga gagggttgag gctgggagag gtggctcatg cctgtaatcc 12180
cagcactttg ggaggccaag gtgggtggat ctcctgaggt caggagttcc agaccagcct 12240
ggtcaacatg gtgaaacccc atctctacta aaaatacaaa aaattggcgt ggtggtgggt 12300
gcctacaatc ccaattactt gggagactga ggcaggataa tcgctcgaac ctgggaggca 12360
gaggttgcag tgagcagaga tcgcgccact gcactcaagc ctaaccaaca ggggcaaaac 12420
tctaggacta gagctaaggt atcaaaaaaa aaaaaaaaaa aaaaaagaag tagagtgttt 12480
aattaaataa tttgttcttg ctgtaaaatg taaagtagat attcctcttc aaagactttc 12540
ctccccgtct aattaggaat aaatagtaac ttctcttaga agcaaaattt attcaaagac 12600
ctgtgctaac attcttaaat atctgctagc cacaataagg aaatcaatgt actttatgtt 12660
cttagctccc acaatttagc ctaaatattt tccctggcat gtttatactg gtctaagcaa 12720
gcattaggtc atagcctgtt cctcttcctt atttaaaagt gtttttacct ttctcagcgt 12780
tccacaagtt acttcctcct tcctttgttc tcctctacct gtgcctcttt taaaaagttc 12840
taagttgcta gccaattggg acaaatacag aatgtaaggt cccattccag ccaacggaaa 12900
ctggacacag cagtagggtg gatgtgtcag gttataaatg accctgtctc ctttgtttgg 12960
tgtactctag tggcaaaact gctggcaagt gtacctttc tgcaggaagt aaaaatggcc 13020
ttactaaata aattaaattt atgttcaagt gctatttctt tttttttttt tttcgagatg 13080
gaatttcact tttgttgccc agcctggagt gcaatggcgc gatctcggct cactgcaacc 13140
tccacctccc aggttcaagc aattctcctg cctcagcctc ccgagtagct gggattacag 13200
gcatgcgcca ccacgctcgg ctaattttgt atttttagta gagatggggt ttctccatga 13260
tgaggctggt ctcaaactcc tgacctcagg tgatccgcct gccttggcct tccaaagtgc 13320
cttggccttc caaagtggcg tgagccactg cgcccagcct cgagtgctat ttctttacgg 13380
cacggaagaa caaacatttc aaacaatgct attaccaagt ttgttagtat ttattatctc 13440
atttgctaaa cctaaaaaat atatatcctt ctttaacgtg atcgaatatt tcaaaaagtt 13500
attgtgttgt ttcttaaaat aaatcaatca taatcctaga ctatgttact caaactacat 13560
acaacacctt ctgagcttct ggcaggccct tcctcccctc cctgctcacc acagatcact 13620
ggaataattg tctgcatgta acttctaatt ttgaagtggt tgtggtttat caaacctgga 13680

-continued

```
acatggcact tccaagtaca tgagctaagg tcacagtaag actcaagccc cttcaacaga  13740
atacctggaa tttctctgtt aaagattttc tcctttacct gactacatgt ttgtaatgca  13800
gatccctcca ggagcgctta cttataaact gtcctggatc actaacgcga cattttgatg  13860
taaattagtt tatcttgacg tgctaatggt agaaaaaaag agaacatgag gaaacttggg  13920
tgctttcagg gctggtagga aggattaaat ctttgcggca atttctgaga aggggaagga  13980
aaccttgcta acaattttga tagtttactc catttggctg gagtaactct gatccatttg  14040
tcaaattcac gatggagcag gtacctgtta gggtacaggt ttgataaacc acaaccacag  14100
gtctatttca tttctccttt tccaaagtgg aacaaatttg tctctggggt taaaactgct  14160
tttctcatat tggtgtgtaa gagaaaatga gggaatttct ttgagtttgt ttggtttgtc  14220
tgtttgttta agcagcattt tttaaataat ttactcagcc ctgtctcaga gaaagtccat  14280
gatgatctgg aattcaacct cagggaaaag ttctctcctg tgcctgagac actgcgcaac  14340
taactggaac cgaaggatgg aacctgggtg tttaatttat taggaacaat tgattcttca  14400
gtgacacttt ccatgcagat acttcaaaca aaataatgga gccccacaga ccgaatgtga  14460
agacagcagt gccattgtct ttggaaagct atcacatatc tgaagagtat ggctttcttc  14520
ttccagattc tctggtaagg atagagcctt ggtaaggata ggtcagaata tgtttcttga  14580
gatgttggtt ggtttgtttt ttaaaaatgt atgtgattat taagagacca atataaatat  14640
caagttgttt acctgagaaa gatgctacaa agagcataga ttatcattac tatcaaaaga  14700
gaagtgacag ataccacaga gaacaggtca aatggaacat tttttgtttc agtttctttt  14760
gactagattg tcaggccaga gaaattataa gcaaacctgt agttatcaag aaaaagcatg  14820
aacttaaata taaataaaga acaaatacag agcctcagca cctggaacat ggcacttcca  14880
agtacatgag ctaaggtcac agtaagactc aagccccttc aacagagtac ctggaatttc  14940
tctgttaaag attttctcct ttgcatgact acatgtttgt aatgcagatc cccccaggag  15000
cgcttactta taaactgtcc tggatcacta tcgcgacatt ttgatgtaaa ttagtttatc  15060
ttgacttgct aatggtagaa aaaaagagaa catgaggaaa cttgggtgct ttcagggctg  15120
gtaggaagga ttaaatcttt gtggcaattt ctgagaaggg gaaggaaacc ttgctaacaa  15180
acaatacctc tttcttaatt ctacttaggg ctcaaattgt aatgcaaatc tttttcatca  15240
tttagccctt ataaacactg tttttctcat ctggtgtggt ccaaggccta gaacattaaa  15300
actatcaaag cttttacaga ccatcaggtg tcatccccct ctttctacat ctgagctagc  15360
tgaaatccag aggaaatgac ttgctgaaag tcatgagtgg caaaagcaga actagttctg  15420
cttataactc ttgactttta gttattatta ttattaatta ttattattac atcctaaatg  15480
agggccaagg ccactcagtt aaaaatcgtg gggtccaggc caggtgcagt ggctcacgcc  15540
tataatccca gcacttttgg gaggccaagg caggtggatc acttgaggtt caggagttca  15600
agaccaggtt gatcaacatg gtgaaacccc gtctctacta aaaatacaaa aattggccag  15660
gcgtggtggc acatgcctgt agttccagct attggggagg ctgaggcagg agaatccttg  15720
aacccaggag gggaggttg caatgagtgg agatcatgct gttgggaatg aagtttttgg  15780
tgtcacagaa aaagaatgaa catgggaaca aatgatctct cagcaaaagg acctttactt  15840
tctgcagaaa gggtgctact caatagctgt ccagccacga gagcacacca aacaaaggag  15900
acagagttat ttataacctg acgcatctac cctactgctg tgtccagctt ccattggctg  15960
gaataggacc tcacatttta cactttaccc aatcggctat tagtttaaaa ctttttttaat  16020
tggataaggg aacagaacaa agaaagaaaa gcaagttgcc cagggatagt taaggaaaca  16080
```

-continued

```
tctccatata aggaatggca tgcactatgg gctggggctt ttctagttct gtacagacat  16140
gccggagcaa gctacgacag ctgatttgga cagccactaa tagtggctag caatcttata  16200
gtaagaaatt gtgacttttt ataatctttg aagaactttc ccatttctga cagtgccact  16260
gcactccagc ctgggcaaca agagcgaaac tcgtctcaaa acaaaacaaa acaaaacaaa  16320
acaaaacaaa acagctctct actcttggaa gcagcagagt ttttatcttc atttatatca  16380
ctccggtaac actcagaagt agacaagcct cagggtaggt attcagtaaa agcccactga  16440
attccacact attctttaat catagttaaa tggcaaatta ggctggaggg tgggggtgga  16500
acctctccaa aattactgca atgactgcaa catcggaccc caagattttt tttttttttt  16560
ctgagataga atctctttct atcgcccagg ctggagtgca gtggcactgt gagaaatggg  16620
aatggaccgg actgtttcct ctgacactgc cactaggttg accaagtgtc cctatttgtt  16680
aggtactgga tggacgcctg acatgcaaga ctctcagtgc taaatcagga aagtgctggg  16740
acaattcgga tgagtcggtc acgctaagtt gcacttaata gctcttgtga ctttgactga  16800
attacaaaca tcccctgacc ctcaattttc acatttactg gatggagatc tggtgccacc  16860
tccactagat tgctatggag aatgaatgtg aaagcatttt cataaatcca gtgtaaggac  16920
cagaagccag tcttctgacc ttgagccagt gcttgttaaa aactccactc tatacatcta  16980
acccaattca ggaatatcct gcctagttcc aaaggaagaa aagaccaaat tgctcttatt  17040
gggattaaat gcgtacactg agctgaggaa aaacagtatt acaaatgagc taaacatgac  17100
gtagatccac agttgtagaa ttcccctctt tgttctttcc tctttcataa ctacggaaac  17160
agatgagaaa catttacggc atcaggttct tgtgatgctc cctgcctgat atgctatggt  17220
tttgttaatg gaatgtccat tcctgagctt atgcagaaaa aagtcccttg ggaaagtggt  17280
tttactgtgt tatgttcatt ttccccatag ttctcaaaat gtacttcctt gtttcagttt  17340
taattttctt tcattggtgt gaccattttc aactgctccc tttctgggaa gaggtagcag  17400
acggacattt tcatcaaaat ctgccccagg ttgcttcaca gataaggagg gacccagcca  17460
ctaaaatcac caggcagagt gttgcaagag tagatagaga atcacaattg gctgccctgc  17520
tcaaggggac accagatctt actttcgttt agttgaaagg caagcgtcag agtcgggagg  17580
ctgtaccttc atgtccagtg gcctcacaga agttccttca gtatctcttt tagatgaaac  17640
tcttttagaa gttccttcag tatctctttt ggtttctcac tatagatagt tacttgaaca  17700
tgtctgaaga aaacgtggtc aagacagtga ataaaaaaaa ttctggtttt gggaagcagt  17760
ctgacttagt ttcaaatatt ctatcccact gtttctgtca atgttcaaac ctttccaagc  17820
tccaacattt attgtggaaa atgtgtgcct caccaactca tgcaaataaa tgtttcatgt  17880
gccctacgtg tgtagagggg gcatggatgt gtgtttttgg agggagggct aatttttctt  17940
tagacatgga gaatacgagg aaattagctt ggcatcaaga aggttacagc aggagacaag  18000
agtgaagaga actgagagag cccggaaatg aggctctgga gttcagattt tttttttttt  18060
gagatggcgt cttgtacccc aggttggagt gcaatggcaa aatctcagct cactgcaacc  18120
tccgcctccc gggttcaagc gattctcctg cctcagcctc ctgagtagct gggattacag  18180
gcatgagcca ccatgcctgg ctaattctgt agttttagta cagatggggt ttctccatgt  18240
tggtcaggct ggtctcaaac tcccaacctc aggtgatcca ccctccttgg cctcccaaag  18300
ttcaaggatt acagccatga accactgcgc ctggcctaat ttttgtattt ttagtagaga  18360
cagggtttca ccatgttggt caggctggtc ttgaactcct gacctcgtga tctgccccacc  18420
tcagcctcat gaagtgctgg gattacaggc atgagccaca gggccaggcc tggagttcag  18480
```

-continued

```
atttaacaca tcctgtaaat gacatgatgc atctgatatt tgaagagttt tcctcaaaga  18540
atgttacatg caaggtggtt tagagttgtt gtttccggct atatagcaaa agtacttggg  18600
gagttttaaa aaatactgat gccgaagctc cacctagaat agttcattca gaatctctag  18660
cataattgac ctcagtactt gaaatatgat tattataaat gttagtcaac tgctttttta  18720
ggctctatga ctgatagaaa tctttcactt ttatatcatc tccagttaat gagtcccata  18780
aattgaaatc tagtgtttaa atttttactt catatttatt tttactgatt gttttattat  18840
tattattttt gagacagagt ccgctttgtc gcccaggcta gagtgcagtg acgccatctc  18900
ggctccctgc aacctccgcc tcctgggttc aaacgattct cctgcctcag cctcctgagt  18960
agctgggatt acaggagccc accaccaacc acacccagct aatttttgta tttttagtag  19020
acggggtttc gccatgttgg ccaggctggt ctcgaacccc tgacctcaag tgatccaccc  19080
gcctcggccc tctgtctcaa aacaaaaaca aaaacaataa caaaactttt ctcttctacc  19140
cgagatgttt aagtttaaat cacaccattt gtacaaaaat tccctgtctt gtccttaaaa  19200
ataatttgta atcactagct agttttgaga tcgattgcca tctaaccgaa tgccatttgt  19260
tctctctctc tagtttcaac ttaataaccc tttctgcatt ttctattctt tcaaaatttt  19320
tccggccatt ttattgtttc tatttagtga aaatttattc actggtttct atgcctaagg  19380
gcatttagga agttgcttag gatacagacg tgataaaaag accagtgtaa aaactctcca  19440
ctcctagaca ttatattcta gtcctcatct cctgtcattt aagtcctcag tgattctatg  19500
cacttttgct tttggtttgg gcagatgctc tgagtttaat gtttctctga gatgaggacc  19560
ccctattcaa ctcacaaatc ccataaggag gcctctgtgc ctttgctggt gccccagaca  19620
gggtgctgat gcttacttat cttcaagatt gtgaagtcag atttaatagt atagtcgttt  19680
gccagagctg ctgtaacagt agccacaaac agttgggctt aaaataccac aaacaggagg  19740
gcttaaatca cagaagttga ttttctcaca gttcttgagg caggaagtcc aagatcaagg  19800
tgtcgtggag ttggtttctt ctgatgtctt gctccttggc ttgtagatgg cctccttatt  19860
attgtgtcct cacatggtct tttctccact atgcacaaat tccctatgtc tctctctctt  19920
tttttttttt tttttttttt ttgagacaga gttgcactct gtcacccagg ctggagtgca  19980
gtggtgcaat ctcggctcac tgcaaccttt gcctcccggg ttcaagcaat tctcctgcct  20040
cagtctcctg aatagctggt attacaggtg cgcaccacaa agcccagcta atttttttgta  20100
tttttagtag agatagggtt tcgctatttt ggtcaggttg gttttgaact cctggcctca  20160
agtgatccgc gcacctcggc ctctcaaagt gctaggatta caggcataag ctactgtgcc  20220
cagtctcccc ctgtctcttt gtgtccaaat ttcctcttct ttagggacac caatcagatt  20280
aaattggacc caccctaaag gcctcatttc aatgtacctc cttcaagggc ctatctccaa  20340
atacagttat atttttaggt actagggcta gggcttcagc ataggaattt gggggagaca  20400
caatttagca catagcagaa aatataaggc caggaaaaaa tattctggca tgctagatgg  20460
actcattaac aaatattaac caatataaac caattaacaa atatttcttt aatatttgcc  20520
tttttttttt tttttttttg aaacagagtt tcactcttgt tgcctaggct ggagtgcagt  20580
ggcacgttct tggctcactg aaacctctgc ctcctgggtt caagtgattc tcctgcctca  20640
tcctcccaag tagctgggat tacaggtgcg ggccatcaca cccggcttat tttttgtatt  20700
tttagtagag atggggtttc actatgttgg ccaggctggt ctcgaacttc tgacctcagg  20760
tgatccacct gccttggcat ctgaaaatgc tggggttaca ggttgcctgg tgatttttaa  20820
gaggaatgac tgagctctca tgccaggtgg ggggagggga cagagaaagt tgaatactct  20880
```

-continued

```
gacgatagcc atgatccata gctctgaagc ttagactcga atctacccat cccgcaagga  20940
agaaaacaaa gaaataaaaa agaagaaaag aaatctccca atgtcaggtc ccaccctctt  21000
tagaagtaat ttcagcaaaa ctttgttgct attttggcat gtcctctact gtagtagctt  21060
gtcaaaatac tgtccccaaa cgttttctat atttctagat tttactgttt aatgtataat  21120
aataatgttc taacattaaa acgtaaccat agcaatgctc cgactcactt gatctttaaa  21180
tatattgttg aactcaattt tgtgacatct tcagaattgt ctttttgtat tcataaatag  21240
caacagtgga tagttgcctt ggttagtgtt attatttcaa ggattaatct ttaggttacg  21300
ttttcttcat aagatgcatt agatgacttt tttttttttt tttttgagac agagtcttgc  21360
tctgttgctc agactggagt gcagtggtgc agtctcagct cactgcaatc tccacctcct  21420
ggctcaagag agtctctcga ctcagcctcc tgagtagctg ggattacagg cacgcaccac  21480
catgcctggc taatttttgt atccttttta gtaaagacgg gatttcccca tgttggccag  21540
gctgatctcc aactcctgac ctcaagtgat ccatctggct tggcctccca aagtgctggg  21600
attacaggca tgagccacca cacgcagcca attagatgcc ttctcatgct tttctgtgtt  21660
gtgaaacaga tcatctatcc gttgatatag catagctctt cagactacag acattttagg  21720
ctataagttt tgaattacat tttctattcc ctttatgctt cttgttctag ttaggttttt  21780
tatttctaaa taaaaatatg aatttttgca atttcccaaa tgcgaactca actgaaattt  21840
tcaagtgtat tagcaaaatt tattcatagc agcctcttac atttcattaa gaattgattt  21900
tttcttattc cctgttgaag tttgtttata aaatatagta atagtaataa ctatatagaa  21960
agtgttcact ttgtagtagg ccctatgtta actttaacta cactttttaa atctaagcct  22020
catagtagtc ttggatggat gcggtggctc acgcctgtaa ccccagcact ttgggaggct  22080
gaggcgggtg gatcacgatg tcaggagttc aagaccagcc tggccaacat ggtgacactg  22140
tctctactaa aaagacaaaa atcagccgga cgtggtggta tacacctgta gtcccagcta  22200
tttgggatgc tgagtcagga gaattgcttg aacccaggtg gtggaggttg cagtgaaccg  22260
agatcacaca agtgcactct agcctggatg acagagtgag actccatctc aaaaaaaaaa  22320
aaaaaaaaaa aaagagatca ataaataaaa taaataaata atcctcacaa tagtcttcac  22380
catttgcaaa tgatccattt gacaataaat gaattcagca ctatcatgga aatatatttc  22440
caagctgacc agttttctcc atttccaccc cacttcaatc caccttcatg tagccctagg  22500
actattgtct cctccccttg tttccttatt tccattcctg ttcagctgta acacattctg  22560
ttcatagcag tcaagtgatg cttacaaatg gaaatcaggc tagaggtggt agttcacacc  22620
tataattcca gcattttggg aggctgaggc aggaggatca catgaggcca ggagtttgag  22680
accagcctgg gcaacatagc gagaccccat ctctacaaaa ataaaaaaga attagctgtg  22740
catgatccta tgtgcctgtg ttccagctac ttgggaggct gaggtgggaa gattgcttga  22800
cccagggagt ttgaggctgc aataagctat atttgtacca ctacactcca gtgtgggtga  22860
cagagtgaga tcctgtctct aaaaaacgta aaatgaaaat aaaaccttga tagtttgctc  22920
tttaaaactc ttcctacagg gcccctgtga tgctcacctg tctctagaag ggcatgtaat  22980
agctctttct ccttcacttt actttgatgc aatgtcagaa cagcttcttt ccatcaaaac  23040
ttaaaccttt gatttcattt aaaatcatct gcttcaaatt ctaatctttc tgatagttta  23100
ggttctaatt tttctgatgt taatattgtc acccaagttt cctgttcata tttacctggt  23160
ttattttatt tttattttta tttatgtatt tgagatggag tctagctctg tcacccaggc  23220
tggagtgcag tggtgcgatc tcagctcact gcaaccttcg cctcctgggt tcacgccatt  23280
```

-continued

```
ctcctgcctc agcctcccga gtagctggga ttacagggac ccgccaccat gcccggctca  23340
tttttgtat ttctactaga gacgtggttt caccgtgtta gccaggatgg tcttgatctc  23400
ctgacctcgt gatctgcccg catcggcctc ctagagtgct gggattacag gcgtgagcca  23460
ccgcgcccag actttatttt attttttgag acgaagtctt gctctcttcc ccaggctgga  23520
gtgcagtggc ttgatctcag ctcactgcaa cctctgcctc ccaggttcag gcgattctcc  23580
cgcctctgcc tcccaggttc aggcgattct cccgcctcag cctcccgaac agctggggtt  23640
acagatgcct gctaccacac ccagctaatt tttttctttt tttggagaca gtctcactct  23700
gtcgcccagg ctggagtgca ctggcgtgat ctcagctcac tgcaacctcc gcctcctggg  23760
ttcaagcgat tctcctgcat caacctccta agtagctggg attacagacg tctgccacca  23820
catcaaacta atttttgtat ttttagtagc tgagattata ggctcgtgtc accacgcctg  23880
gctaattttt gtatttttag tagagacggg gtttcaccat gatggccagg ctcgtcttga  23940
acctctgacc tcaagtgatc tgcccatctc agcctcccaa agtgctggga ttacaggtgt  24000
gagccactgg gcctggcacc tggtttattt ttgtgcatgc ttttattttt aatttcccta  24060
tgctactttc ttagccaaaa tttatactta atctaatcaa gcattaatct aacaaagagt  24120
ttagtgttca tataaaatac agttttacaa atctgttttt ctttaaatta taaatttgtt  24180
aagaaaatta tccaaagaat gatccagaaa caaaagaatg gctgtgtgtc ttttcaatat  24240
catcctggag cattgtctca accatctcac tttacggtga ctaaaacatc tagaggtttt  24300
ccctttgttt tctgtacttc ttagtattga ttaatactgt tgtgctactt cagtctgaag  24360
ttccatgtta atctgtagat tttttttttt ttttttgaga cagtgtctcg ctctgtcgcc  24420
caggctggag tgcagtggtg cgattggctc actgcaagct ctgcctccca ggttcaggcc  24480
attctcctgc cttagcctcc cgagtagctg ggactacagg tgcccgccac cacgctgggc  24540
taattttttc tatttttttt tttaggagag acggggtttc accgtgttag ccaggatggt  24600
cttgatctcc tgacttcgtg atctgcctac cttggcctcc caaagtgctg ggattacagg  24660
cgtgagccac tgtgcccggc tgttaatttg tagattttta tacagaaaag cagcaaaata  24720
tttctgttga gtagaaaata taactccaat gcttatgact gtattcctta taggacacta  24780
actcattatg tgtctaacct agcaatttta tgtcaacact attttctcaa acctctataa  24840
actttggctg ggcacagtgg gtcacacctg taatcttagc actttgagag gctgaggcag  24900
gtggatcacc ttaggtcagg agttcaagac aaggctggcc aacatggcaa aaccccatct  24960
ctactaaaga tacaaaaaat tagccaggca tggtgacatg cccctgtaat cccagctact  25020
caggaggctg aggcaggaga atctcttgaa ctcaggaggt ggagccaaga tcatgccact  25080
gcattccagc ctgagcaata gggtgaaact gtgcctcaaa atgaataaat aaaataaata  25140
aataagtcag agattgtgaa taggatgttg gatataccca agttatgaat taattaggag  25200
cttgaaccca ggaggcagag gttgcagtga gctgagatcg caccactgca ctttagcctg  25260
agcgatagag tgaaactgtg tctcaatcaa tcaatcaatc agagattgtg agtaggatgt  25320
tggatgtacc caagttatga attaattagg agcttgaacc caggtttgtc tcagatcctc  25380
agggactgaa gacttccaag tgaattatgg gtaatgtata ggtctatact actccaaatt  25440
tacagttttc agacttccct gggttctcat ggaccttcca tgtcatttct atgtttaggt  25500
tgaggtccct ggtcttttct cctctgtaat taatttcaca cccaccccta tctcaactca  25560
cacaacttga tcttcactcc catctgctaa gaaattgagt ccataaaaag tgaactcctt  25620
taaactctag atcttctact gctgcaagga cagacattcc attctggctc tctctctcct  25680
```

-continued

```
cctttgcttc ttccagtcct ttgctccttc tgcattctgt tactctcctc tctcctttgt  25740
cttcaatctc tccctcttgc aatagccaac tataaactgc tcaagcttct cattcttaaa  25800
agatctctct gaaatgcaaa ttccctactg ccttatggct ctccttcaaa agtaatctac  25860
attttctcta ttttctaatt cctcaacaca ctaacgtttg aaccctgctt ctatgaccct  25920
gacctaaatt tctattaaat gtacatagat aaactaatat atatttgtga cttcctaata  25980
ttgttttgtt ttttaaagag gtcaatctta ctttaactct gtaatgatgc ggttgacctt  26040
ctgatgattc tctacttctg tgaaatcctc tactgtcttg actttttaat taatttattt  26100
ttttttgaga cggagtctcg ctctgttgcc caggatggag tgcagtggca caatctcggc  26160
tcactgcaag ctccacctcc cgggttcatg ccattctcct gcctcagcct cccgagtagc  26220
tgggactaca ggtgcccgcc aacacgccca gctaattttt ttgtattttt agtagagacg  26280
gggtttcacc gtgttagcca ggatggtctt gatctcctga cctcgtgatc tgcctgcatt  26340
ggcctcccaa agagttggga ttataggcgt gagccaccgc acctggccct actgtcttga  26400
cttttatagg gtcattctat tcaagctcat tgagcgtctg tcactatgtt tttgatctgt  26460
attgctggaa tcagttcctc tatctgcctt gtgaatattc tccattgtgc taatctaggc  26520
ttctcctttc atttttcata ttccctcaca tggctttata cactcttgtg gttttaacca  26580
caatataggg tttttactgt agttatgctt tcaaattgta tacttctttt tttttttttt  26640
ttttgaaatg gagtgttact ctgttactcc agtctggagt gcagtggtac gatcttggct  26700
cactgcaact ttcgcctccc aggttcaagc gattctccta catcagcctc ccgagtagct  26760
gggattacag gcatgtgcca acacgcctgc ctaatttttt atttttagta gagacaggat  26820
ttcaccatgt tggtcaagcc cgtcacaaac tcctgacctt aggtgatccg ccctcctcgg  26880
cctccccaag tgctgaaatt acaggtatga gccatcgtgc ccagccccaa ttgtatgttt  26940
ctaatatgac ttttctcctg aactttaaac tgtgtatcca acttctcagc acagtcatat  27000
cttttgattc cacaggtaat ttaatgtcaa tatatttaaa aatgaattta ccacctttat  27060
ccccactctt tgactttcac ctgcatttct gtttcaattc ttgtttccat ccattcattt  27120
gctcacctaa ttcataaaca tggaaatcat cctcaattcc tcttcttctt agcccaaaaa  27180
ttcaattgtg caggttatgc actgagaaaa agagcctcag gttaggggga taaatcagag  27240
attggtgaac tttttctgaa gggccaaata ctaactgctt taagcttgct taccatatgg  27300
tttatgttgc aactaccaac tctcctgctg taatgtaaaa gcaaccatag atagcatgta  27360
aacaaatgag acaggctggg tgccaatgaa aattcacgaa aattaatgta gtttactgtc  27420
ccttgggtga gagttggggg tcactgaaat tcggactatg tcttacttgg ctaaaccaca  27480
ggcctagagt gggccataaa tggagctatt gggctagtga ttttcttgcc ttaagccccc  27540
agccccaaat ttaataatca catcatttta atttcatttt ccaagtgtat ctttaatata  27600
tggcttctcc tttccaaatt cactgtcatt acctaagttt agtccttgaa caatatttta  27660
aaggcttcct tatctgactt tatatcttaa agtcctacaa atttatcttc ctaaaattca  27720
aatcaaacca tgtcaccaac ttacagaaag ggaaaattca tatattctac acacagcaca  27780
tttcatgtaa ctttctaggc tcatctttca tcatcctttt gatgcaggat tttctgctcc  27840
tcagctcagc gaaatccagg atcttgtctc atgaccagga agaattaggc aggtggacat  27900
agtgaagggt gaggatgacg gaatttatta agcaaaaggg gagttctctg caaagagagg  27960
ggtttcacca gcagtctccc acctcacaat ggagcaccag gactttcaca cacaaactga  28020
aaaggctagg ctcctcccca gcataaggca tgaattcctg gtggttccac cagttttcct  28080
```

-continued

```
actatgcatg tgggtgtgcc caagcaaacc ataggtagta tcagaaaagg caacatttga  28140
ttggttaaaa ggcattattc acccaagcaa accataggta gtatcagaaa aggcaacatt  28200
tgattggtta aaaggcatta ttcagaaaga atcaatcggg aaagggtgag ccaatagggg  28260
aagttctccc tctgggtcac gggtttcatc tgggaccagg agtctggcct ttcagccttt  28320
agactgtttt aggcttgaag gtgggtttca cagggaccct tccctatctg cctaggcatc  28380
tgtctgcctc ctgcctctat cactttctct tgagttttat attttagcaa cactgagtca  28440
tctttgtccc aggaagcacc tacatctgtt tatctgctgt cccctctacc tttactacct  28500
tcccttcttc acatttatac ccagaaaagt cacttcccct ccaaaaattg ggatcaactg  28560
tcatattttt atgaatattt cactttaatt cctcacaaca gctgacagaa ttaactactt  28620
cctcttcttt gcaagttatt tggctcacac agatatcagt aattaaacat attttactgc  28680
attggcatat atctgactaa tgtgtttttc tcccgtacta ggcaatatgc tccttagtca  28740
tctgtgtatc tgaggtgagc acagggccta actagcatat ggtgcattct caatgttcgt  28800
tcaactgcat tgacttgaat tcccctgaag actgaaatgt gaaaatagct actctcggaa  28860
gccccttcc agagaggtct aaaatattta catgtttcta ttttaaatgc agaaagaact  28920
tccagatcat tataggcctt ggatggaaat tgccaacaaa cttcctcaat tgattgatgc  28980
tcaccagctt caagctcatg tggacaaggt attcttctct tcaccccctc atcacattct  29040
gttttcatca tcataccact tttctttctt agccttgtgg aagtgtgtca attgtcctgg  29100
gaaactgttc attaccattg aacttatcag caaagctata tcttccttcc tgaaaaacag  29160
aatgacccct tcgtaatctg atacatgtgt tttcctaagg ttttcagagc cagcacaaaa  29220
caatgcctga cacatgccaa taactcacca aatgtttgtt taaagaagaa tctgggtggg  29280
aatgataaac taactaatgg acaaggtatc gcctaagaag gtcagcttgg aaattctcag  29340
gttcctcatt ccatgtacgt actcaaggct ctgttgttac tgagggggtc taacttgatt  29400
ttgtcctagg tgttatagaa tagttaaatg gagggaattt ctgaattata aaattggcca  29460
tgggttctac aaaacatcca ataagcctgt aaattccaca aaagtgttga ttaggctgat  29520
acaaaggtaa ttgcagtttt tgccattact tttaatgaca aaaaccacaa acacttttgt  29580
accaacctaa tagctatgta accctgaaaa agttactcaa ctctgtaatc ccatttcctt  29640
atttataaaa tgagagaaac tctggtctca cagtattgtt atgggaagta aatcactttc  29700
aaagtggccc ttttgtagtt cttgtcctat aatagcattc agtatacatt cattacttct  29760
ctgtagtctc ttctccatct gtcctaatct atcagtttgg agtaccacat aattgcggaa  29820
gtccatgaaa agttttccgc tctccaaaat ttccctttgc tgatggataa tatttaatgt  29880
ctagaattac aaattctttt taaaatactc attgaatgtt tgctttgtgc aaagcactag  29940
aaccttgtaa aagatgagta agggactggc ttcaatgtct gtgaagatag caaactaaac  30000
agagtaattt ctttgcctga tagataaaat gttgtgttga catgaccaaa gaaatccaaa  30060
aataagaaaa aaactatctg taaacacaga aaaatagaga aaagttccaa tgatggaata  30120
aaaatttaaa ggattttttt gaacgtatta agcaaatcat gtataaaatc cagaaataag  30180
tttacaggac ccatgtcaag gatttaacca aagcagaggg agatccccat gagtcccctt  30240
ttcccatctc agaatagcag agaagagaag caagggaagc ctggaacagt tggcaagagg  30300
gcaggttaga attcagtttg tgaattatga ggtcgtctgc cgtaggcatt taccaggctt  30360
tatttgattt aactgccata aaggaagaga aggacttgtt aaattggggc tcctcttagc  30420
acagcattga aaccagtccc tattccttct tggccttttg gctaaaattg agtgtgaaat  30480
```

ctatcaccta acatttgtac tgggtttagg ctgggtgtgg tggctcacgc ctgtaatcct 30540
agcactttgg gaggccaagg ctggcggatt gcctgagctc aggagttcga gaccagcctg 30600
agaaacatgg tgaaaccatg tctctactaa aaatagaaaa aattagcagg gtatggtggc 30660
acatgcctgt agtcccagct atttgggagg ctggggcaga agaatcactt gaacccagga 30720
gacagaggtt gcagttagct gagatcacac cactgaactc tagcctgggc cacagagtga 30780
gactctgtct caaaaaacaa aacaaaacaa acaaacaaat atatatatat taaaatacaa 30840
atttttactg ggtttaatag tgtcttccta gaagtcatgt tcatgcataa tctgtgaaag 30900
tggtcttatt tggaaatagg gtgtgtacag ttgtattcga gttaagctga ggtgatactg 30960
gattaaattg tatatgatga gtgtccttat aagaagagga aaaattaaac acaggaacat 31020
agactcaagg gaaaacatca cgtgaagatg gaggtagaat tggaatgatg cattgacaag 31080
ccaagatgtg ccaaggattg ctggcagtca ccaggagtta ggagacaggc atggaacaga 31140
atggaacaaa ttctccctca gaggctccag aagaaatcaa ccctattgat accttaattt 31200
gggacttcta tcttccataa ctgtggcaga gtacatttct gctattttaa gtcatgatgt 31260
ttgtggtcat tagttatggc agcgcataaa actaacacaa cactcttggt ctctatcgct 31320
tctttttttt tttttttttt ttgagacaga gtctcactct gtctcccagg ctggaatgca 31380
gtggtgcaat cttggctcac tgcaacctcc agctcccagg ttcaagcaat tctcctgcct 31440
cagcctcctg agtagctggg actacaggca cccgccacca tgcccatgta atttttgtat 31500
ttgtagtaga gacggggttt caccatattg gccaggctgg tctcgaactc ctaaccttgt 31560
gatccaccag cctcagcctc ccaaagccct gggattacag gcctgagcca ccatgcacgg 31620
cctctatccc tactcttaat tgcctggaaa atacctaaca aatgaaggcc agtttttaga 31680
ctttaccacc aaaggctgaa attgaaacag gaattgtttg tgagaagcaa acacaatagt 31740
ttcgagagac tgaatcagtt agcaatttcc tgtgagaggc aaatgtaata gtttctagaa 31800
ccacagatgg agctataaca aaaacatgtg ttctctggat cctttacttg ctacagacaa 31860
cacaataagt gaatttacag ctttgatctt acagtgcacc taagccaacc accttgtctt 31920
agaatgtctc aacataccta tctgtatctt gaaacaaaat atattaattg ccttagaccc 31980
attcactcac atttcctagg aagacatgat cagagggagc tatgcaagaa gaaatccagc 32040
agaactctgg aaatacaata agaaaatcca tattagacac taatcttaat aaaactaacc 32100
ttcgttcatg aatttgaata gacaaaatta ccaaataata tggaaaaaat gggcaactca 32160
aaaagaagag ggtagcccac ttggcattca ggaccaatgg cctccaataa ataagatgat 32220
attagtgctt taaatatttt atttagtgta tccagtatat tgccttccta aattaagtga 32280
aagctgatat ataaaaagaa ctattagaaa taaaaaacca cacacatccc agaactcctc 32340
aatataaacc taacaaattc agtaaaacat tgattgcaaa aaatatatat agtgacttag 32400
ggacttcctt gataaatttc ataaagcata aagaaaaatc aaagagtgca aaccatcaga 32460
aaaatacaaa tatataaaaa agagaaatac aggtgatcca aattcctttt aatggaatcc 32520
cataagcaga tgggtggagg aaaagtaaaa cttccaacat ataagcacaa aatttttaga 32580
ccttaagaaa tatttgagtt ttttatatca gaaagacagt gttggggtga gggttggggg 32640
gcacatgtaa atactcagat aaaattgtga attttctagg gtaaagaaat ctgcatattc 32700
atagaaaaca aaaatgaaaa atagtttatt tacagagtaa atacatacga ctgtttacct 32760
gtaatgctaa atattaaaag acagtttctt ttcttttttt tgagacagag tttcactctt 32820
gtcgcccagg ctggagtgca gtggtgctat atcgactcac tgcaacctct gcctctgggt 32880

-continued

```
tcaagcaatt gtcctgcctc agcttcccga gtagctggga ttacaggcac ccgccaccac  32940
acccagctca tttttgtatt tttattagag acggggtttc accatgttgg ccaggctggt  33000
ctcaaactcc tgacctcagg tgatccaccc gccttggcct cccaaagtgc tgggattaca  33060
ggcgtgagcc accgtgctgg cctaaaagac aatttcatac ctatttgtat ggctaatttt  33120
ttaaaaatct ggccatatca aaatactgaa gaggacgtat agcaatagag actttcattc  33180
attgctggtt gaaatgcaaa atggtacagc cagtttgaaa actagcttgg cagattctta  33240
taaaatgaaa catagattta ccatgcaact cagcaatggc attcctaagc atttatccaa  33300
gtaaatggaa aatgtatgtt cccagaaaaa aaatccatat atgaatgttt ataacagctt  33360
tattcataat caccaaaaaa aaaaaaaaat ctggaagaaa acaggatatc cttcaaccgg  33420
ggaatgaata aaccaaatta taataattgt aaattgtggg atggatagtg gaatagtatt  33480
cagcgataca aatgattgag caattaattt gtgcaatgac agggatgaac cttaaataca  33540
tttacctaaa tgaaagatgt caggcctata ttgtatgatt cttttcaaat gactttttag  33600
aaagggcaaa actagaagga ttaaatatag ctttatggtt actagagaca ggtaaggagt  33660
gggtagttga ctgcaaaggt aatatatagg ggaatgttta gcatgatgaa actgttttat  33720
atggcactca ggtgatggat atatggctct aggcactgaa aaacccatgg aattgtatgt  33780
cacaaagaat ggactttcat gtatgcaaat tttaaaaaat aaaccagaaa attgggagaa  33840
tactaggatg gaatgcagac tgtgataaat aaaactaact ggactctcag caaactaaca  33900
caggaacaga acaccaaaca ccgcatgttc ttacttataa gtgggagttg aacaatgaga  33960
acacaaggac acagagaggg gaacatcaca caccggggcc tgttgtgggg tggggggcta  34020
ggggagggag agcattagga caaataccta aagcatgagg ggcttaaaac ctagatgatg  34080
ggttgacagg cgcagcaaac caccatggca catgtataca tatgtaacaa accagcacat  34140
tctgcacatg tatcccagaa cttaaagcaa atttttaaaa aagtaaaaaa aaaaaaaaca  34200
aacaacaaca cctaactgga ctacaaatgc actatataac ttcgatgaag agagtgggga  34260
gtagggaaag gaacggactt aaattactcc agaaaatagt gttgtgttgt gactagaatc  34320
tataaggctt acggtaaatg aaactttaca ggatcactat actctaattg gtaaatcagt  34380
ttttcatggg gtgcgggtga acagttgtga aactgcttta catgtagtca tacctttgca  34440
ttttgcagat atttcaattt ttacaaattg aagattcgta gcaaccttgc atcaagcaag  34500
tctgtcaacc ccatttttcc aatagtgtgt acgcatttgg tgtctgtgtg tcatattttg  34560
ataattataa caatagttaa aactttttct ttactattac atctgttaca gtgatctgtg  34620
atcagtgatc tttaatgtta ctatcataat cgttttgaag gtgccataaa ctgtgcccct  34680
ataagtcctg aaacttaatt gataaatgta tgtgttctga ctgctccact gaccagccat  34740
tgccccatct ctctccccct cctcaggcct cctgatttcc tgagacataa taatattgaa  34800
attaggccaa ttaataatcc tacaatggcc tctaagtgtt caagtgaaag gagttgcatg  34860
tctctcactt taaaaatcta aaactagagg ctggtcatgg tggctcaggc ctctaatccc  34920
agcactttgg gaagccaagg cggggagatc acctgagttc aggacttcga gaccagcctg  34980
gccaacatgg cgaaactctg tcttgactaa aaatgcaaaa attagccagg catggtggtg  35040
cacacctgta atcctagcta ctcaggagac tgaggcagaa caatcgtttg aaccctggaa  35100
atggaggttg cagtgagcct agattgtgcg attgcactcc agccagggca acaagagtaa  35160
aactccttct caaaaaaaaa aaaaaaaata tctaaagcta gaaatgatta agcttggtga  35220
gaaagtcatg tcaaaaccag ataggcttaa agctgggcct cttttgccaa acagccaagc  35280
```

tgggagtgca aaggaaaagc ttttgaagaa aattaaaagt gctactccag tgaacatacg 35340
aatgataaga aagcaaaaga gccttattgc tggtatagag gaagtttgag tattttggat 35400
agaagatcaa accagccaca acttccctta aaccaaagcc taattcaaag aaaggcccta 35460
attctcttca attctacaaa gtctgagagg gctgaagaag ctgtagtaaa aaagttttaa 35520
accagcagaa tctggttcat gaagtatgag gctagaagcc atctccacaa cataaaagtg 35580
caaggtgaag cagcaagtgc tgatggagaa gctgcagcta attatccaga agatccagct 35640
aaaatcatca atgaaggtgg ctacatttat tttttatttt tgttatttat taatttattt 35700
attttgagac aaagtcttgc tctgtccccc aggctggagt gtggtggcat gatgttggct 35760
cactgcaacc tccacctcct aggttcaagc aattctcctg cctcagcctt cccagtacct 35820
gggattacag gcatctgcca caacgcctga ctaatttttg tatctttggt agagacgggg 35880
tttcaccaca ttggccaggc tggtcttgaa ctcctgacct caggtgatcc acccgccttg 35940
gcctcccaaa gagctggatt acaggcatga gccaccacgc ctggccagtg gctacattta 36000
aaaataggtg ttcaatgcag acaaaaccat cttttattgg aagaagattc caaccaggac 36060
tttttttttt tttttttttt tgagacagag tctcactctg tcgccaggct ggagtgcagt 36120
gatgcgatct cagctcactg caatctctgc ctcccgggtt caagtgtttc ccctgcctca 36180
gcctcctgag tagctgggac tacaggcacg tgccaccatg cccagctaat tttgcagtt 36240
ttagtagaga cggggtttca ccatgttggc caagatggtc tctatctctg acctcgtgat 36300
ccaccccccct tggcctccca aagtgctggg attacaggtg tgagccactg cgcccggccc 36360
aggactttca tagttagaaa aaagtcaatg cctagcttga aaggacaggc tgactctctt 36420
gttaggggct agtgcagctg gtgactttaa gttgaagcca gtgctcattt accattcctg 36480
aaatcttagg gcccttacca gctatgctaa atctactctg cctgtgctct gtaaacggac 36540
aataaggcct ggatgatggc atatctattt acagcatgct ttactgaata ctttaagctc 36600
actgttgcga cctactgctc agaaaaaaat attcctttca aaatattact gcttattaac 36660
aatgcctctg gtcacccaag agctctactg gagatataca ggaaataaat gttgttttca 36720
tgtctgctaa cacatttgtt ctgcaaccta tggatcaagg ggtcattttg gctttcaagt 36780
cttattattt aagaactata ctttgtaagg ctattcctga cacagataat gatccctctg 36840
aagaatctgg gcaaagtcaa atggaaacct ggaaaggatt cactattcta gatactatta 36900
aaagcattca tgattcatgg aggacgtcaa aataaaaaca ttaataggag tttgcaagaa 36960
gtcaaccctc atggatgact ttgaggggtt caagacttga gcagaggaag tcactggaga 37020
tgtcgcagaa atagtatgag aactaaaatt agaagtggaa tctgatttta taactgagtt 37080
gctgcaatct tacgattgaa cttttctttt cttttttttt tgagatgccc ctgctgagct 37140
gccagttcct gaagggtcac cgggagcagc gcctggccca cctggtcctg agcttcctca 37200
ccatgggtta tgtctggcag gaaggagagg cgcagcctgc agaggtgagg gccagagagc 37260
agcttctcct gttacccggc aggttacctg cgcctggagt aacgtgctcc ctgcttggtg 37320
ctaccctgtt ttcctggaaa atgggtactt tcttcttctc gatgggcatc agtttaagca 37380
acgatgaagg gctcatttat tatttattat tattattttt ttattttatt ttgagccagt 37440
ctcactctgt cactcaggct ggagggcagt ggggtgatct tggctcactg caacctcccc 37500
ttccaggttc aagcaattct cctgcctcag cctttcttgt agctgagact acaggcaccc 37560
accaccacac ctggctaatt tttgtatttt tagtagagat gggtttcacc atgttgccca 37620
ggctggtctc gaactcttga cctcaggtaa tctgcctgcc tgggcttccc acagtgctgg 37680

-continued

```
gattataggc gtgagccact gcgttcagcc tgaagggcca tttaaatgaa ggattttttt  37740
attttaattt ttctgactaa gagctaattt gtttttttaaa ctggtagcta tttcttcctt  37800
ttataagctt ttgaatgttt gtttgtttgt ttttggcact ctcttccaag aatgtttgaa  37860
gacctgcatt tgaaggcaga ttgccttttt gctttaaaac agggttgcac catgttgccc  37920
aggctggagt gcagtggtgc aatcatagct cactgcagcc tcaactcctc ccaggctcaa  37980
gcaaccctcc cacctcagcc tcctgagaag ctggggctac cagcatgtac cgccacaccc  38040
agctaatgtt aaaaattttt tgtagagatg agggtcttgc tgttttgccc aggctgatct  38100
taaactcctg gcctcaagtg atcctcctgc ctttgcctcc tgtgctggga ttacaggcgt  38160
gagccaccat gccgggcctg aagacagact ctgagaattc ataaaaacct cacagcattt  38220
tgtactctta tgtatataaa ttatctaggt tgctcttcat aatcctgtaa agtaacaaga  38280
gccataccgg cccattttac aactgaaaag cacagacact tatttcctta atcaaggtca  38340
gacagcaaat tagtggaaaa gccaaggcca gaacccaggt cttctgattt tactagtgca  38400
gccttctttc cccaggggac acattgacat ttacaacact catctttatt ttttttttaa  38460
tactgctttc tatccagcca attattagtc tgtcttttaa taattcatcc aaatctcttc  38520
tgaatcattg cataactttg tacagtttcc acccacagtg tcttttactt ttatttttgg  38580
aagtaactgt ttttaaaagt tactgttatt tttaaaagtg tgccttcccc agaaatcagg  38640
gagttaccca tgtcctagaa ctccacggtg aagagaacag cctgtgccca tcgtgtttgc  38700
ctgattgatc ctacctcttg tctctcgggg aaacacagga gactcaggga agaggaaaag  38760
tgtagagtca ttgcagcctt gttatttgtc aatgcatctc ttttcttttt ctttttcttt  38820
ttttgataca gagtttcact cttgtcgccc aggctagagt gcagtggcgt gatctcggct  38880
cactgcaacc tcggcttcct gggtccaagg gattctcctg actcagtctc ctgagtagct  38940
gggattacag gcacctgccg ccacggccag ctaatttttt ttgtattttt agtagagacg  39000
ggtttcacca cgttggccag gctgatctcg aactcctgac ctcaggtgat ccacccacct  39060
gagcctccca aagtgctgtg attacaggca tgggccccag cacccggcca gtgcattgca  39120
tttttttttt tttttcgag acggagtctc actctgtcac ccaggctgga gtgcagtggc  39180
acgatcttgg ctcactgcaa gctccgcctc ccaggttcac gccagtctcc tatctcagcc  39240
tcccaagtaa ctgggactac aggcgcccac cacaacgcct ggctaatttt tatattttta  39300
gtaaagacgg cgtttcacca tgttagccag gatggtctcg atctcttgac ctcgtgatct  39360
gcccgccttc gcctcccaaa gtgctgggat tacaggcgtg agccaccgtg cccggcgtgc  39420
atttttaaaa gtgtgtctga tgctgaaaag tttgaagtct aggcacgtcc cagtgggtcc  39480
tctttatacc atcccctctg caaaccatta tcctaaattg gggtttgggg gagagaagag  39540
tgacagtgga aagaagtctc cacctcccag ctgtgccctg gtagttccag gggacccgga  39600
ggctccccac acccaccacc ccgcctcaga tcacctttca ctttctttgt ttctcctccc  39660
ttgacttttc agctcagaaa gtacctggct ctccaatgcc ttctgaggaa agtttacccg  39720
aggttcacat tgcaagactc attaaagctc tttagtgttt tccacccgag aaaaaattca  39780
agggaaaaat gaagacaaaa gcagggcatt cttaatggat attttatctt aaggagaaat  39840
gaaaatggag atggaagagg gggcacaagg atggggtttg aatctagact cgttcagcct  39900
ttacctccga tagagaacct catacagctt ttctggactt ctggctgata aagagccgtg  39960
gagggttcct tggataaaaa aggttgaagg gggtctgtcc tgtggtggct tacttgaagg  40020
tattactggg tttgacttat ggagtaagag acggagtcag tttccccaca ggctgaggca  40080
```

-continued

```
gtctgtcctc atgcttttct agggcactgt ggtctcccag gctcatacct aggtgcacac  40140
acaggtttct gcatctagct ttgtatctct atgagtcggt caatcaataa atctatctat  40200
catctgtcta ctgatctatc atctatctat ctagctagct atcatctctc tatcatctat  40260
ctatgtatct atcatctctc tctatatatg tgtgtatata tatatatata tgtatatata  40320
tatttctatc cttccatcta cttacctatc tatcaaaatt tttttccgtt gataatattc  40380
tcgggcccca gtttatgttt aattgttttg gtaatgcctt tctttgcaca gtcagtttac  40440
agaggttatt ttatattcta tatgtatgtg tggtccagcg ttgtaatttt cacatatatt  40500
gcaccgtgta ctcataagca gtatttccac tgggtcatta acagaaagat atgtgtgcgg  40560
catatgaatg tgcatcactc aggtaattca agcttggttc ccagatcatt tctgtaccac  40620
aggattgccg aaataaaaga caaccatggt tatttcctct gctgcaagct ttctagaata  40680
tgctatttgt ctggatttat atctgaaagg tcctgccaag gaatcttgcc cttccatttg  40740
tcgaagtctc caggaacttg gggctccctc ctatcctggt ccactcagac ttggtgctga  40800
cgaactggac caaaaaagat ccagacgggt aaggaaggaa gagaatgctt tgaatttcca  40860
taactttccc ccaggaaaca cccaggcttt tttttataat tagggaagtt catatttatg  40920
gtctgccgta tggttccaaa gaaggggtga gcttgaccaa aaattcaaat atcacaggcc  40980
ccagaagttt cctcttaatc cattctgaac acattggctc agaccatttt gtcttgtttg  41040
tttccacatg acgtgtgaat ttctcaacct gaccttcaag ctcctgcaaa atcagctttt  41100
atttgttctt tctcttcaaa ctgtttattc cctaagatgc cctccattca tatcaggtta  41160
aaaccagttg gctttgataa gtaatcatta tataatgatc agaagagaat gattatggat  41220
gaattcagag cagatgctcc aggtgggttg gattgagaat ttgattaata attccatcta  41280
ttccaccaaa gtcacatcat tcctttgaca gttgggctgg gaataggggc atttgtctac  41340
agaaggaata gcatgagatt ttaacaaaca agaaattcaa caaacagaat tagacagatg  41400
atctgagatg ttaaatttc ctttcacctt aatttttgca gccaaattta tttcagctct  41460
agatgaaaga gacagcactt tcttttgtgg ctgactacaa cagctgaaga ttcactgagg  41520
tttgatatga ggaagaactt cctcagccat gggattgcca gaggcgatga tgggaatcta  41580
cttaaaaggg ttacatattt agtagacagc ctagatttta agactaattt atgtgccccg  41640
gccgggcccg gtggctcacc cctgtaatcc cggcactttg ggaggctgag gcaggtggat  41700
catctgaggt caggagttga agaccagcct ggccaacatg gtgaaacccc gtctctacta  41760
aaaatacaaa aaaattagcc gggcatggtg gcacatacct gtaatgccag ctgctcggga  41820
ggctgaggca ggagaattgc ttgaacgaag gaagtagagg ttgcagtgag cgaaatcatg  41880
ccattgcact ccagcctagg tgacaaactc tgtctcaaaa gaaaaaaaaa ttatgtgccc  41940
cattggaaga agtgagattc ggccatctca tctctctcgg gagctctgag ccctggagtt  42000
ttatgttttc tgcaattatg aattgtgatc cttgattaat tatgctttaa taataaaatg  42060
ggtgactact gaaagctgct gaatctgggt aagaatttgg atgaaaaaaa taatatatgt  42120
gcgtaattta ttctgttcaa ggtactgaat attgaataag ctggatttat tactcaaaga  42180
gaaagacaga ataagagaag gttgaaggga aaaatgactg tactagaatg gtagtcaaaa  42240
atgcaacaac aggcaggtgc agcggctcat gcctataatc ccagcacatt gggaggccca  42300
ggtgggcagg tcacctgaga tcaggagttt gagaccagcg tggccaacat ggccaaaccc  42360
cctctctact aaaaatacaa aaattagcca ggtgtggcag tgggtgcctg caatcccagc  42420
tactcaggag gctgaggcag gagaatcact tgaacctggg aggcagaggt tgcagtaagc  42480
```

-continued tgagactgca ccactgcact ccagcctggg tgacagagtg agatcctatc tcaaaaacaa 42540
acaaaacaaa acaaaacaat aacaaaaaag ctattaatag cttcctaggg agtaagagtg 42600
aagggctagt ttaattccag agatgcggac acagtcctgg gtctcaccaa ttattctgct 42660
tggtaattac cttttgaagc cttttaatat gcctaacaca gagctaagtg ctatgaagaa 42720
atgaaagaaa tagaagcaaa gtactcccca tgtggttaaa taacaagaca ctacatgaca 42780
aatgtcaaag agtgactcaa acaatatgtc ctttagaatt tcagagaaat gacatcaatg 42840
caggctttac aagtcagtaa aaatcttggt gatgaggcag aacttgatgt aaggcaaatc 42900
ctaaaagttg agtaggaatc aactagctag aataaaatgt ggggttgtgg taaatacaaa 42960
aatgtaagat gagtgaaata acttatttat ttatttattt attttcagag acggagtctc 43020
cctctgtctc ccaggctgga gtgcagtggc atgatctcgg ctcactgcaa cctctgcctc 43080
ctgggtttga gcaattctcc tgcctcagcc tcctgagtag ctgggattgc aggcacctac 43140
caccacaccc gactaatttt tgtattttta gagagatggg gttttaccac gttggccagt 43200
ctggtatcga atcctcgacc tcataatcca cctgcctcag ccttccaaag tgctaggatt 43260
acaggcatga gccactgtgc ccagcctaat aatatattaa gatggccaca ggccaaatat 43320
tctggggctg gaatgtgagt ggaaatgtcg ctcacccttt atcacatagc accccatagt 43380
ccagccacaa cttgcagaat tcaaagtaag tgtggatgtg tgtgtgcctg cagtgccttg 43440
cacacaagtg tgcatgcctg tggacatgtg accctagaag ttattaatat atctggttta 43500
caaactgaat tgttctttta ttttttttct ctcttggtgg tcatcaataa ctgaaattgg 43560
gctagattcc tggaaattgg gtaagttctc agaaatcatt tacgcacttt agaatccagg 43620
ccaaatttaa aatcttacaa taaaacaaag aacaaagcat gctaaattat atgtataata 43680
taatatcaac catataaaat gcataaaaaa tatactagaa ggaaatgtgc ctaaaattca 43740
cagtctaaaa tttaacagtg attgcctctt ccttgtatag ataagggatt tttttttact 43800
gtattttcca gtctgtacat aataaaacaa gtaatgtgca atgcaaacaa aacaaaatga 43860
aactttatca aatttcagta actccttgaa gtttaatttt ttttttgaga ctgagtctta 43920
gtctgttgcc caggttggag tgcagtggtg tgatctcggc tcactgcaac ctctgcctct 43980
gggttcaagg gattctcctg cctcagcctc ccgagtacct gagattacag gcacccacca 44040
ccacacctgg ctaatttttg tatttttagt tgagacagcg tttcactata ttggccaggc 44100
aggtcttgaa ctcctgacct caggtgatcc acccgccttg gcctcccaaa gtgctgggat 44160
tgcaggcgtg agccactgca cccagttgaa gtttaatagt gtgaaaaaaa tatttctcat 44220
ctcactatat cttctatggg aggccagatt gcagattgtc tacagaaaaa tcccttcaaa 44280
agaccttgtt attacataga ctggagctca tggggcaggt ctggtccaca catccttagg 44340
ctccgcttct cctggaaaac aaaaatagcc tctgatccag tgttgcctct cccatcacca 44400
aacctcagct tctatcgcca aactcatcaa ataagagtgt ccagtagaaa aactgggcag 44460
atgggggcac agaaggtgaa gacatcattt cccaagctaa tgttgctgct ggaacaatgt 44520
aagtcttgac tttgtcttgg tttggtttgg tttgacattg gtttgttttt catctttgtc 44580
tcatgcttaa aatgtgaagg gcaaatatga tccttagagt taaggtttta ggttttgtag 44640
atgttttact ccatttaaat gacagcagat catttagaaa tgattcctct gtaacagcct 44700
tccagatccc attcgattgt acagcattga gatagataga tagatagata gatagataga 44760
tagatagata gatagacgga atttggccct gtgttcccac ccatatctca tgtcaaattg 44820 taaccccac atgtcaggag agggatccag tgggaggtga caggatcatg gggttggatt 44880

-continued

```
tccccaatgc tattctcatg atagtgagtt ctcacaatat ctcattatta ttattattat  44940
tattattatt gcaacagagt ctcactctat ctcccaggct ggagtgcagt ggtgtcatct  45000
cggctctctg caacctcttg cctcagtctc ttgcgtagct gggattacag gcatgccccg  45060
ccatgcccag ctaatttttg tatttttagt agagacggag tttcaccatg ttggccaggc  45120
tgatctcgaa ctcctgacct caggtaatct gcctacctcg ctctcccaaa gtgctggaat  45180
tacaggcgtg agccactgtg cctggccagt tctcacaaga tctgatggtt taaaagtgtg  45240
gcacttcccc cacctcctgc cgccatgtaa gatgcttgct taccccttcca ccatgattga  45300
aaagtttcat gaggcctcct agccatgctt cctggtaagc ctaaggatct ctgagtcaat  45360
tacacctcgt ttctttataa attacccagt ctcaggtatt tctttatagc agtgtaagaa  45420
tgaactaata cacacataaa cagattagag gcagcactgg cctgagttgt gaaactcttc  45480
ccagcctggt cctgcgatta gctggctata tgaccttgga caagctgctt tgcttctctg  45540
ggccatggtt tcatacctgc aaaaaaaaga gcatggactt ggctgttgcc tgggtctctc  45600
tagccctgtg gagaatcagc tacatctctt actaggaact tctcattcag ccagttattc  45660
cactgcggag atggtccagg accattaggg ccatgctaga cattgggagg ctgcctgtca  45720
ggtgaacatg aaattgaact tatctgttct ctttcctccc tgaatgttgc tgaaggtaga  45780
tgcccatcct cagggctgtc ttacggagag gagaaagttg tgcagtgatt ccaccctgca  45840
gttatctaac tcggcaggga actctgggca gtgagtactc acggtacagt ctccacacct  45900
ctaatcatgt gctcctctcc ttcccaagga acctggagac catcatctca tttcctgggg  45960
gagagagcct gcatggtttt atactggtga ctgctttggt agagaaagaa gcagtgcctg  46020
ggataaaggt atcttctcac ttgatagcac cttttctttt taaatgagct tgagctttac  46080
ttcccactca gtgcctttcc tgcagtggat ttctcaacac aaatgaacat agaccttgtc  46140
ctgcttagtt caagtctgag agaagagatc taagctctag gccaccatat ttgctccctt  46200
ttctcaattc ctataaaact cggaatggac cttttgtcca ttcaacaaac aggcattggt  46260
ttgggcaatg ggaaattgga tcgaacaaga cagacatttt cccagccctg acagaagctt  46320
atgatggata cagtggatga agatggatta acgtggatta caggtgtgag ccactgcacc  46380
gggcctcaaa ctggaaattc ttcaggagtc agacaggtat caggaaggct ggatagaaga  46440
caaaagacag tgatgcagct tgtgatcaac tacagcgtta atgccttgcc taaaaatatt  46500
tcagttagat ttctgccttc gctctgtcgc tcaggccaga gtgcaatggc gtggttttag  46560
ctcactgcaa tctccacctc ccaggttcaa gcaattctcc tccctcagcc tcctaagtag  46620
tgcacgccac cacgcctggc taatttttgt atttttagta gagacagggt ttcaccatgt  46680
tggtcaggct ggcctcgaac tcctgacctc gtgatctgct tgcctcagcc tcccaaagtg  46740
ctgggattac aggtgtgagc caccctgccc agccaacact acctcccttg ataagcatat  46800
gttgagcacc tactggtcct caatagggtg acccatttct gctatattat agcgctttct  46860
ttctctctca gtagttaaac tccatggtta ctttagttct catccatgtg tttagtccat  46920
tagaagatac agagtcaaat atcggccttc caagtgtagt tcagatgaag tagagactca  46980
aggaagacaa ggaagtcttc ccagcagagg ggattctaga gctgggggct ctgtagaatc  47040
tgtctgtgta ttagtccatt ttcacactgt tataaacata ctacctgaga ctgggtaatt  47100
tataaaggaa agaagtttaa ttgactcata gttctgcatg gatggggagg cctcaggaaa  47160
cttacagcca tggaggaaag tgaaggggaa gcaagaacct cttcacgagg cagcaggaga  47220
gagagcaaag gggggagctg ccaaacactt ttatacaatc agattttgtg aaaactctcc  47280
```

-continued

```
ctcgtatcat gagaacagta tgggagagcc cacccccata attcaatcac ctcccaccag  47340
gtccctccat cagcctgtgg ggattaccat ccaagatgag atttgggtgg ggacacagat  47400
ttcaacacag atttaaatct gactttatat gagagcttcg gagcaaggat gccccagttg  47460
gagatgcagt agaactgatc ataacgtgac aaatccgaga gaagaagagt aaaataatag  47520
tactcaggcc cttgggaggt gcaagaagta acagccagat gaaattccag aaacacttac  47580
ctaggggtct gtctgggagg tccccaggga gcttctggct gtcaggccaa ccccacagtg  47640
gatctagctt aggacgttcc caggaagctc tgacaaactg tccggtcctc ccctgggttc  47700
caacagtatg aggcttactc tgcctgcatg gactttaagg gagtgctaat aagttgtgta  47760
catgcatctc atccctaggc tcttgttcag gccacgaatg ctatcttgca gcccaaccag  47820
gaggccctgc tccaagccct gcagcgactg agactgtcta ttcaggacat caccaaaacc  47880
ttaggacaga tgcatggtaa gatgcttccg aagctcctga aggatccccc aggggtcctg  47940
ggctctgctt aggggaagag ggcctgggga ccaggcatgt cctgaagggg gtgataatac  48000
attcatccac cagatgacgc tggtggacta tctttgtttt aggttaaaca catattatct  48060
tggagagcta ttgtcacagc tttgtattct ccctctcctt tatattctcc cgtgattaag  48120
atggtttccc ttctgcagtg gccagatatt tcttaggcat gttgaggtct tgcctgaagc  48180
ttgagaggag gggatgggat gcacagtaat gttggtcgcg cgtgccccat cctgcagtgt  48240
taggtactgc agagcaggtt gtctacactc tgtaatgccc cttttattct aaccccctgt  48300
gttggttcct gagatgtctg accttggttt taagccttgt ctaatggatg gcctgtattc  48360
cctttctgta gctagggcag gctgatttgt caaaggtagg aaagttgtca gaatcaaaat  48420
ggagtcactt gtgttgaata aaaattttta aaccttgaca aatagagctg gggaaggcta  48480
caaagagaga gctcccgtgt ataaatgcct gataacaaaa tcttttccaa aggactgaaa  48540
aaatcaccac cttgcacaaa ggccatcaca accttacata cacaaaaaaa tacttacaca  48600
acgacatctg cccagcaact gcctttccaa cattggcctt gtgccaccct ttttattgat  48660
gctcatagcc aaggttaatg atctcaaaac agttacataa ttgtcctcat ttttccttta  48720
aaaacctttg tcttccttta tctttctgaa tacccacatg gtttattatg gcacatgtat  48780
tcccattgca atgccctatt ccagaataaa tatcagtttc cattagggag cctctccctg  48840
ttaatctgct taacacaggc atggtcagtt acggggccca accttcctgg accggttaca  48900
tcttattctg gttactgcat tcagtttcca acatctggga ggctcttcaa attcttctct  48960
cagaggaatc tgaagaatgt atgtgtttag gaggatgtga gagaggggtg tggtttctta  49020
acaagagaat atcagagtct aagtatcatt ttccctgaat cttgcttccc tgcaggaaag  49080
aaagattctg ggaaaagaga gtgtttacaa gaagcaggac tggagggagg gagaaagacg  49140
ctaggtactg ccaagcttta ttatcttgta ttaaaaaagt aaatataatt tgtcatccca  49200
gcctctcagc actagtagaa atctatctga agtcacagga ttaggtatta tccacttcct  49260
ggttttatag tttatatttg tattttctct atttccttga attttaattt taaagccctc  49320
atgatcacat cagtaggtct tctgccaaac agctccctta agttgtatgg tggctttgcc  49380
aagctgaaat gagatgagat gtgttttagc tttgccaaga aagcctgagt ccatcactta  49440
ggatagcaag gctattaggg agatagtgca ggtgtcttca gatcacatgg atgagcaaaa  49500
ggaagcaatt ttggaagatt atgagaaacc ttccaacagg tcccagtgta catagcagta  49560
agatggtgca tgcagtgtct aactgtcaca ggctttccta gggctcactt tcagactcac  49620
ttcttttttt tttttttttt ttttgtgaga tggagtctca ctctgtcact caggctggag  49680
```

-continued

```
tgcagtggca cgatcttggc tcactgcaag ctctgcctcc cgggttcaag cgattctctt  49740
gcctcagtct ccctagtagc tgggattata ggcatgcacc accatgccca gctaattttt  49800
gtatttttag tagagatggg gtttcgccat gttggccagg ctggtctcga actcctgacc  49860
tcaggtgatc tgcctacctt ggcctcccaa agtgctggga ttacagccgt gagccactgc  49920
gcccagctca gactcacttt ttaggcccag gccaacctgc tgtgttctcc tgctcagctt  49980
ctgcaggagg tctcatcgtc taaggaggtc ccagggctac cgcccttgtt ttctcaaaag  50040
gcacattttc ccacacagac ataatttcgt ttcagtgttt tactcctagt cacattcatc  50100
tatatggaca aatagctgaa tggattggac tgtgttttct aaagatggcc ccatgccatc  50160
ctgcgcgctc ctccacagcg tggcctgggc attcctttcg accaggggtg gactctgtgc  50220
ccctacttgt gatgtacgtg ttgccaatag aatgtagtat aggggatagc acagacttct  50280
gaggcaagac tagaagaggt gatgcaggtt taaccttgtg tcctgagcca ctaggtaaaa  50340
agtccaccta ccctgagatc actctgctgt gcaaacgaca caggcaaacc acatcaaaga  50400
gccatgtggg ttctccagtt ggcttctgcc caggagtgaa ggtgccctca gatggttcta  50460
ggctcccatc ccaacttatg tcctgtcttg aagtcttccc aactgaggca ccagccactg  50520
tggagcagag tcaagccatt gccatcttgt tctgcccaga ttccccatca acagaatata  50580
gtggtttttt cacacctcta tgtttggagt ggtttctatg cagcaatagt aaccacaaga  50640
aataaagtta taaaaatagt aacaaacact agaaactgca agatttaagg aatcacctga  50700
atgctccagt cattgtctct ggtttgtaat gataaacttt cttctgcgtg ataaatagag  50760
cttggctgga ctttttccct ctgcttccat tccccaaaat ggagcgtacc aaacaattgc  50820
ttctttcaga gcccagcttt agcaagagtc atgagctcta atcccttcat ccataaatac  50880
ttcctttcca ggcacgtaga gcccttcaca ctcagggctg agtagaaaat gcctgttgca  50940
gactgcagtg gcgttttgga gagccaccct cctggtacct gagtcactag tcctttgccc  51000
agcttttctc agttttgtaa agcgctcact tctgagtgga agacagaacc agcccggtct  51060
attttcataa tctgccccca taaggcagaa gtccacacgg tactggaaac ataaccatat  51120
ctatgtcagt ctgccactgc ctgccgcctg tcaaccgtgc gtgtctgcat ccagtccttc  51180
tttggagctg ctttccagcg actcagccag atctgagctt tctgactcat tggaaggtta  51240
aactattttc agactttcaa gtgttgagat tattaagaca tgtgtttttt tttttcttct  51300
ttttttggca tgcttactga tcgcccctgt tctctaggaa gtaatgttct tcttggaaaa  51360
ggtgaaggat atttttctcc ccaaaaagcc atggaaatgt ttgcctttat ttacttccaa  51420
attaacagaa tttccagctt ttgcttgacc catcggcgca ttggcagcgt taagaatttt  51480
ttcttttagc agtaatgagg agtcgaaggg tttcttccta accatttagt gtatgcattt  51540
aaatcaggtt tctttttgag taaattgggg ctaagctgta gtgtgaactt ctgctactgt  51600
tcctttctca ttagttcact tgatttcatg gaaggaattt tccatctcag cctgtgaact  51660
tattttgtct aaactcaatt ggaaagtaat taacactgag attcttcttt aataaattct  51720
atatgataat aaaatcatac aaacatctct ttatttttct ttttgaccta gaaaagatgt  51780
tcacaggcca gacctggtgg ctgaagcctg taatcccagc acactgagag gaagaggcgg  51840
gtggatcaca tgaggtcagt ccgagggcag ggtagccaac gtggtgaaac cccatctcta  51900
gtaaaaacac aaaaattagc tgggcatggt ggcacatgcc tgcaatccca gctactcagg  51960
aggctgaggc aggagaatca cttgaacctg ggagatggaa gttgcagtga gcctagatcc  52020
tgccactgca ctccagcctg ggcgacagag tgagactctg tccccaaaaa aataaataaa  52080
```

taaaagatgt tcacaatata ttgttaagtg aaaaaagcag gctacataac ttgcataata 52140
tgagtgcatt ttaataaaaa tatacatatt tagcaaaata aaaggacaaa tggtatttat 52200
taaaatattt acgttgatta tttcaacaca gaggatgata gttgattttg cttaatttct 52260
tccctccttc ttttcaattt gaattttcta taatgaagat tgtttctttt tctttctttc 52320
ttttttttt ttgagatgga gtttcgctct tgttgcccag gctggggtgc gatggcgcca 52380
tctcggttca ccacaacctc tgcgtcccag gtttaagtga ttcttctgcc tcagcctccc 52440
tagtagctgg gattataggc gtgtgccacc acacccggct gattttgtat ttttagtaga 52500
gacgggcttt ctccatgttg gtcaggctgg tctcgaactc ctgaccttag gtgatctgcc 52560
cacctcagcc tcccaaagtg ctgggattac aggcatgagc caccgcgcct ggactgatta 52620
ttttttaaat agggttagaa agtgaggaag ttactaaact ccgattagcc caaatatgcc 52680
ccagtgggtc cttctggcag agtaaatgtc tcggttcagc ctgaatctgg gaaattgttc 52740
ctacggttca gcctgaatct gggaaattgt tcctacctta taaactggag tatccttcag 52800
aaatgacatt tactcaaact tccttttagg cagactgcat aatagcaatt tttaatatta 52860
accatttaaa aaaaaccttc agattaatta acaccaaaag aataattggg aaaatacaac 52920
tcctcacttt aaaaaagaaa caaccaaagt aaatactaaa aaactatatg atgttatatt 52980
atctaagctt agtttactgc aaagatcaag agcacactac tagttgacgg cctctattca 53040
cactgttcat agccctcgct cgcttctcca gccattcact cactcatgca aaaggtctgt 53100
acacacaatg atgcctgatg gtataatagg aaccttaaca tttcaattaa aaggcaaaat 53160
gaggacactt accatcagcc tataaaatta ttcttattat tcttcttctt cttctcctcc 53220
tcctcctcct cttcttcctt cttcttcttc ttcttcttct ccttctcctt ctccttctcc 53280
ttctccttct ccttctcctt ctccttctcc ttcttcttct tcctcttctt cttcttcttc 53340
ttcttctttt ttttttgaga tggagtcttg ctctgttgcc caggctggag tgcagtggtg 53400
tgatctcggc tcactgcaac ctctgcctcc caggttcaag ctattctcct gcctcagcct 53460
cccaagtaac tgggattaca ggtgcatgcc accacgcccg gataattttt tgtattttta 53520
ctagggatgg ggtttcacca tgttggccag gctagtctct aactcctgac ctcaagtgat 53580
ccacctgcct cggcctccca aagtgctggg tgtgggcggc aagccaccca ggtgccaagg 53640
caagagacag agggcacgag ctgttccagt ataatgagga aaatatatag aataagaata 53700
gttatactag aaatagatta tagatatgat tacatatgaa tatcattctt cattagtttg 53760
tagcactact ctttattcca gtattataat aatctttgtt ctacaattat aacctaggaa 53820
aaaccaggcc atacagagat aggagctaaa gggacagggt gagaagtgac cagaagagtg 53880
tgagccttct gttatgcccg gacagggcca ctagagggct ccttggtcta gcggtaacgc 53940
ccgcgtctgg gaagatgcct gtcacctaac ggaccgtggt ctagcggtag cgtcagtgcc 54000
tagaaaaggc actcttttta aatatacttt ttatttttgt ttaatcttcc ctgatttcct 54060
atagatctga gatatgtcat gcttattttc attgctatct aaaaatctca ataaacttta 54120
tacctaagag taaaaaaaaa aaaaaagaaa agaaaaggcg ctcgttactt agccgaccgg 54180
gaaagggagt ctccctttcc ccgggggagt tagagaagac tctgctccac cacctcttgt 54240
ggagggcctg acatgagtca ggcctgcctg cagtcatctg gaggcctaac cgtctccctg 54300
tgatgctgtg cttcagcggt cacgctccta gtcctgaaca cctggctccg ccttttagat 54360
agcagtagca gaattagtga aagtactaaa agtctttgaa atgcagaagt aatggcgtaa 54420
gctgtcacgt ctctctctcc gcctcagctg ccaaacagag aagggtcccc tgtccagtgg 54480

```
acacgtgact tgggtgacct tacctgtcat tggagacgac tcatactcct taccctgccc  54540
cttgccttgt atctaataaa taacagctca atctggcatt tggggccact actggtctcc  54600
gcatcttggt ggtagtggtc ccccgggccc agccgtcttt tattctatct ctttgtcttg  54660
tgtctttatt tctaccatct cttgtctccg cacacgagga gaaaaaccca cagaccctgt  54720
agggctggcc cctacagctg ggaattacag gcatgagcca ccgcatccag ccagcctaaa  54780
attcttctga aggataataa tatagtactt gaagacacgg tttgaaaaaa atcatactaa  54840
atgaaagggc accattttac aagcactaga actacattaa acttaaatga attccaacac  54900
tcttaataat gtaactcaaa aacaagtcta gtgttaacaa aagctccaat aactaaaact  54960
acattaacag gcacaatgaa cattgtaaac gccgctaatt ggcaccaagt ttaatagggc  55020
agacaatatt ttcttctgca ttcacactta ctcagttaca ctgttgaaaa atgctgctgc  55080
tcaagctatg aatgctttac aaaagaaatc attttaataa atacagtaaa tgctaaaact  55140
ctagctaaac tattatgcaa gatatacaac caagacaaat acaaattcat aatacaagca  55200
acttgcattc aaaatgaact ctaccactat attttattaa aagggcagac tttatgaatt  55260
aacccagctg cttcctgaat tacaaaagtg gcatgactca atatgaaaat aagaaactgt  55320
ctacaaattt ctgacagtaa taaattgtaa tatacaatac atgcaggagt cttacggaag  55380
aataaactct cctaggaaac aaaaatattt tatactttta aaatccaaag taaaaaaaaa  55440
agaaatcatt gccagatgcg gtggctcatg cctgtaatcc aagcactttg ggaggccaag  55500
gcaggatcgc ttgagcccag gagtttgaga ccagcctggg caacatagca aaaccccatc  55560
tctacaaaaa aatacaaaaa ttagatggta atggtggtga gcgcctgtgg ttccagctac  55620
ccaggaggct gaggtgggag gatgcacctc aaggctgcaa tgagccaagg tcacaccatt  55680
gtactgaagc ctggggacag agtgagaccc tgtctcaata agtaaataaa taaatatctt  55740
ttatgaaaaa gattctctag tcagaattaa cacctcaact agccaaacat caggaagtta  55800
cattacagct acttaataca caaagggaca cattttcacc agtcgttgtc ttctgatatt  55860
tctattccag aaacacacac tctcacttcc ctacactccc catcccatca tttcttcaga  55920
gcatggaaac agaatttgtt gaacaccaga aatctcttgc tatggtggta cataagtcat  55980
aacatttgtt gctgcccagc agcaggtatg aagccggctg gtgactggct agcaaatgcc  56040
tattctgtaa gctcctcact tagcccatct gtagctctga cttctccacc aattcccttc  56100
tctcctttca cagcctttct gagtttctga gggataattt cagaggttcc atataactgt  56160
caaagcctat ggtagacatg gcaaagtgaa aatcctctcc actggccatt tctgtttctc  56220
ttgggggcat ctttcacttg cctcaggtgt tataaagctg atgaacacac gtacacgttg  56280
tttaacactt tcttgggcat ttcccatttg agatatggca tgtttcatta tcctagtgac  56340
atgtgcaatc agaaaatgta tattttgttc tctgcaactt tcttttgaaa aatgtatatt  56400
tgaacaaaat atacattttt tgtatcttca tgaccattca tgctgtcctc actgtcatca  56460
tgaggctcta tataacataa tgactcctcc agggcagtct tcggaaattc ccagtgcaga  56520
agcacgtgtc atacagcagt ccccattcat ctccagtgca gctctggctg gctcccatgt  56580
ctgatcagct gtttggttgg acagaaaatg actgcaaggg aatcagttcc agtgtgagct  56640
ctgtttgcag aactcagact cccctccctc ccatgttaat gctttttttc ttcttctttt  56700
tttttttttt ttttttttga cagagtctca ttctgtcacc caggctggag tgcaatgcta  56760
tgatctcggc tcactacaac ctgtgcctcc ccggttcaag caattctcgt gcctcaactt  56820
cccgagtagc tgagattaca ggtgcacacc accacacccc actaattttt ttgtattttt  56880
```

-continued

```
agtagagacg gggttttgcc atgttgccaa ggctggtgtc aaactcctga gctcaggaaa  56940
tccaccttcc tcagcctccc aaagtgctag gattacaggc gtgagccacc atgcccagcc  57000
ccatgttaat gcttctaaag tttgccctca cttctttaga aattccttca gtacatcctt  57060
taagacttcc tctagtgagt gtctgctggt ggtaaactct cccctctaaa agttgcttta  57120
tttctcctca attcctgaag gatatttttg ctagcagcta tattctttta gatgttgaac  57180
atatcggtac aaaagcttct ggtttccatg gttgctattg agatgttagc tgtcggttta  57240
tctttctccc ctgactatgt gtacctgttt ctctgtatct gtctactttt tgggttgctc  57300
aatttattgg ccttgggctt cattctgctg ctgctttttt tttttttttt tttttgagat  57360
ggagtcttcc tctgttgccc aggctggagt gcagtggtgc aatcttggct caatgcaacc  57420
tctgcctctc ggttcaagcg attctcctgc ctcagcctac cgagtagctg ggattacagg  57480
cacctgccaa cacgccaggc taatttttgt atttttagta gaaataggat ttcactatgt  57540
tggccaggct ggtctcaaac tcttgacttc aggtgatcca cccacctcag tctcccaaag  57600
tgctaagatt acaggcctga gccaccacgc ctggccacaa tttttaaact ttttattttt  57660
acaggcacct gccaacatgc acaactaatt tttgtatttt tagtagaaac aggatttcac  57720
tgtgttggcc aggctggtct caaactcttg acctcaggtc atccaccacc ttggtctccc  57780
aaagtgctag gattacaggc gggagccacc atgcctggcc aaaattgtta aactttttat  57840
tttcttcctc aagaggatga gaagaaaggt caattgtaag ctttagaagt cttgcccaat  57900
agccaatctg agaatattct ccgtaaacat tcaccagagg cagccagtga ccatgggata  57960
cttttggtga gaggaattga ttgctggggt caggaatggg aggaaagcat acttctcatt  58020
agataccttg ttgaacttcg taaattgtgt gccaaatgca tgtcttacct agacttcata  58080
aattaatttc tttaaaaata atcaaagaca atttttaaa gacttattta atttaaggtg  58140
attataaaac atccagtata ctttcactat taaaaaagta agtattcctg tctgggcttg  58200
gtggatcaca cctgtaatcc cagcactctg ggaggctgag gtggtcggat catgaggtca  58260
agagattgag accatcctgg ccaatatgat gaaaccatgt ctctcctaaa aatacaaaaa  58320
ctagctgggc gtagtggcgt gcctgtagtc ctagttactc aggaagctga ggcaggagaa  58380
tcgcttgaac ccaggaggcg gaggttgcag tgaactgaga tcgtgccact gcactccagt  58440
gtggcaacag agtgagactc catcttcaaa aaaaaaaaaa agtattccta aacagcatat  58500
tatcatgata tattattttg ttttgtaggg ttttgaacct tgtctaaaaa gaattaaaat  58560
gtataaattt cttcctgcaa tttccctatt tcactaaggg tcattcacat tggtcatata  58620
gacatagcac attttcacca ctatatagca gcattttgta caaatagact acaatttact  58680
tattctgcac ttatttctgt ttgtttgttt tgctatgaaa agcaatgtca ttacatatat  58740
tcatgcccat agctacaagt ttacatattt caggttttct gtagggtgga caccagggag  58800
ttgaattgtt caacaggact ttacattcat ctttagtttt attggccaac accaaattgt  58860
tcttcacaat gtttgaacta agttgaaatt ccacctcccc atcacattta gttttgtcaa  58920
cttcatttct tcattcatta attcattcat tcagtctttt gtttatttgt ttattgccag  58980
tctgataggc gtatagtggt gcttcatcat ggttttactt tgcatttctc tgattttctt  59040
tttaaatttt taaaaaatta tttttatgta gaaacaaggt ctcgctacat ggcccaggct  59100
ggtcttgaac tcctggcttc aaatgatcct cccacattgg cctttcaaag taccgagatt  59160
gattataggc gtgtgccact gtggccagct gatttccctg atttctgatg agttaacaat  59220
ctcttctttc tctctctctc tctctgtgta tacaggtact caccattcgt gcctattttc  59280
```

```
tgtaaaatat gtggctttcc tcattttttt tttttttttt ttttttgag gcagagtctc  59340
gctctgttgc aggctagagt gcagtggtgc gatcttggct caccacaacc tccacttcct  59400
gggttcgagc aattctcctg cctcagcctt cagagtagct gggactacag gcgtgcacca  59460
ccatgcccag ctaatttttg tatttttagt agagattggg tttcactatg ttggccagac  59520
tggtctcaaa ctcctgactt tgtgatctgc ccacctcagc ctcccaaagt gctgggatta  59580
caggagtgag ccactgcgcc cagccatctt tcctcatttt tatactaatt aggcttttat  59640
cttacttgtt ttttttaatg ttttttgtac actctgaagg ctgattttttg ttaattgtat  59700
gtgttgcatt ttttatggtt tgtcttatgc cttttgaaag taaaagttct taatttaaat  59760
atagccaacc tgtaaatcat ttgtgaaagt ctgtggttta agaggtcttg aataagaaat  59820
tatcccatca tcataagtca taaatacttt tttgttgttg ttgagacaga atctcatttt  59880
gttgtccagg ctggagtgca gtgggttgat ctcagctcac tgcaacctct gcctcctggg  59940
ttcagcaatt ctcctgcctc agcctcccaa gtagctgtga taataagcat gtgccaccac  60000
accagtctaa tttttgtatt tttagtggag acaggatttc atcatgttgg ccaggctggt  60060
ctcaaactcc tgacttcaag tgatccacct gtctcagcct cccaaagtgc tgggattata  60120
ggtgtgaacc accatgcctg gcccataaat acatttttat gtattttctt ctaaagttgt  60180
tttgtctttc actttttagt ttttaattca catataatta ctacttgcta cttataatta  60240
tctgtaagta gtatgagatg agaaataaat tctatttccc tcctatggat aagcacaaac  60300
ctgcagtatt agcacagtct tatgtcagat tttctaaaat gaatgggtgt gttttctagg  60360
ctctctgttc tgtttcatta tctgtctttt cctgcaacga tatcatctgc cttaaaaact  60420
ctagccttgt ggtattcctc attttcaagc agagcaaacc ccgtcacctt gcttttctcc  60480
tccagcatcg cttgtgctat cctggactaa gaccttcata tagactgtta gaatcatcta  60540
gccaagttcc attttaaaaa tctatgttgg agctgggcgc ggtggctcac gcctgtaatc  60600
ccagcacttt gggaggctga ggagggcaga tcacttgagg tcaggagttg gagaccagcc  60660
tgatgaaacc ccgtctctac taaaaataca aaaattagct ggacgttggg cacttgaatt  60720
ctagctactc aggaggctga ggcaggagaa tcgcttgaac ctggcaggcg gggggtgcag  60780
tgagccgcga tcatgccact gtactccagc ctgggtgaca gagtgaggct ccatctccaa  60840
aaataaataa ataaataaaa taaaatatct atgttggaaa ttttgtacaa attttattaa  60900
atgtctacat taatttggag aaaaatgact tgattttgat tatctattca atatttctgt  60960
attatgaata aggcaaaaag agaggcagag aatagcataa aataataact aaaattcctg  61020
ggtaaaccac ctcaaatcat ttcttcatat ggctcaatat tcttttgtga catggcctga  61080
aatatatcca gacagagaac tcttctcttc aatacatttc ttcttttagg tattcatatt  61140
gagttttcct gtccatgaac atggtataag agagtatatc ccttcgggag gccaaggtgg  61200
gtggatcacc tgaggtcagg agtttgagac gagcctggcc aacatggtaa agtcccatct  61260
ctactaaaaa cccaagaatt atccaggtgt ggtgacacat gcctgtagtc ccagctactc  61320
aggatgctga agcaggagaa ttgcttgaac caaggaggcg gaggttgcaa tgagccaagg  61380
tcatgccatt gcactccagc ctgggtgaag agcgagactc catctcaaaa aaaaaaaaaa  61440
aaaaaaaaag aaaacgagaa tatatccttt catttactag tttttcttca atttctttca  61500
agataaaggg cttacctatc ttctgcttta ttcatagtta cttgatattt ttgtttctaa  61560
taaatatggt gtctgtctat ttacctgcct cttacctgtt catttccagt ttcaaaaatg  61620
atgttgatat ttgaatatta accttaaatc tagcaccttg gtaaacacta ttattcattc  61680
```

-continued

```
taataattat cagtagatta tatgtgtttt ttatttataa atcatattgt ttgagtagca  61740
tgctttgctt cttcatttat aaaatttaca acttttattt ctttttaata attttttttct  61800
tattctcctg gctaggactt ctaacacagt attgagtgga agtgctgatc cttgtttagt  61860
ttcacatttg aaaaaagatt gcttttacta tttcactgtt aagtataata tgcaccatag  61920
gctttctgtg gattcctttt atccatttaa gaacatctct tattcctaat tagctgaagt  61980
tttctgcatg tttgttttca tcatgagtgg attttttttac atctattgaa atcattttac  62040
atagaagata tttcacacct attgaaatgg tcatttcact tttccttctt taatatgtta  62100
agttgggcaa aatattaaag tatcacctgt cattctgctt cagcaaaaag tagtagtgtc  62160
ttagcagtat tggtgaaaag acagcatcaa ataaaaaaga tgtagaagta ggacccagta  62220
aaaatctagc gcatggggca ttgtcacatg taagcagaca gaatgtgaca ccaccaagga  62280
gcatctgaag ggctggaggc tgaaggaaga catgagtcac ccaggctcat ggacacttca  62340
gagaaattag ggagcaggaa gaagaaatag gatcaaagac tacgtatgtt ggttggaaaa  62400
ggaagctgat ggtatggaga tgttattatt taggtctcac ataaaagatg tagataaata  62460
ggtagatagg tagatagatg atagatagag agatagatag ataaatacat agatagatag  62520
atgataaata gatgttgtta tttaggcctc acataaagat gtagacagat tagacagaca  62580
gatgatagat agatagatag atagatagat agatagatag atagacgata gatagataga  62640
tagataatct cagaaacaga gacacagtga tctcagtaag ataggcatat gccaggtgac  62700
agaattcaga ggggtcccac tacgtgaaaa caatagaaca accttcgaaa agaaatttag  62760
tacaaataag agggcaggct tccttacata caagttagta aactggaaga atcagttatc  62820
ctcaaacatt ggaatagatc aaaaatagtt gtttatatta atgaaggtag ctaaacatga  62880
agctaagtga acctgtctct gacctagtgt ggcaatccct gggcaaggga cacttgctcc  62940
gctcttgtat ccttcactga atattcagac tttcagttaa gcatcggtga atttagtttt  63000
catctcttgt gaaaaccttg agagaggtaa ttctctctgc ttttcttctt ttcccttcct  63060
tcattttctc aaacattgcc tgtttaaaat acgaaatttt aaaagatggc cttgttctct  63120
tttttgttgt tattattaag tacagagaaa ggaagaacca caaatagcaa agggcaacat  63180
atggaatagt ttagaagttc cgggagcacc catgagggca actgcagaag agaacattct  63240
atcccccgtt gctgcagctt tcattccagg tctccatgca tatcagatag ggaaggaact  63300
ccgggacagc agcagggccc atgcacatgt aaccaattgc tttctttgcc tgtagtaaag  63360
ttcacatttt gattgcttct ccagattatg tagatccaga catattttat gcaggcatcc  63420
ggatctttct ctctgggtaa gtatagttca gttgttttcc tgtgtgaagt ctctgtagca  63480
ttgactgaat gtataagggg acgaagagac agaagcttcc tagcgtaaga aacataccaa  63540
gtgactcttg ctagggatcc actctcaggt aaaagaagtg ggataccatc tgcacaacaa  63600
ataacactga gggctaagta tttcagttaa gagtgtttgt tcctaggcag ttcagatcca  63660
tttatattca cttttcttag aatcctagct caatgacaga agaagaaaaa cacagtatgt  63720
cactcacaca gttctatcac ttacatctac tttttcttct tgttattaag gcatgtagaa  63780
ggctggggag tgtagtatag agttggatag catcgaagct ttcttctaaa gttcctggaa  63840
gagctacact gtggtttgaa cgaatgtgtc cctccaaaat tcatatgtta aaacctaatt  63900
gtgatggtga ggtattcgaa ggtgggttct ctgggaggtg attatgtctc ctctgagagg  63960
agaagacaat cccctgagtg gaactaatgc ccttataaag gggctggagg gagttcactt  64020
ggcccttttt gctccttttt tcttccattc cttgtccctt ccactatgtg aggacacggg  64080
```

agttgaggca ttaccttgga cgtggagacc aggccctcac cagacactga acttgccagc 64140
accttgatct tggacttccc agcctccaga actgtgagaa atacatttct gttatgggta 64200
gtccccaact caatacagtt tgacttacca ttttttgact ttatgttggt gcaaaagcat 64260
acatattcag tagaaactac tttgagtacc catacaacca ttctgttttt cacatttggt 64320
acagtattta ataaattcca taacatattc aacatgttga cataaataag ctttgcgtta 64380
ggtgattttg cccaactgtg ggctaatgta agtgttctga gcacatttaa gggcagctag 64440
gctaagctaa ggtgtttggt aggtcagatg tattaaatgc attttttgtc ttatgatatt 64500
ttcaacttac attgggttta tcaggatgta acccactgtg aattaaggaa tatctgtatt 64560
tacaaattac ccagtctaat gtattttgtt gtagcaacag gaacaaacta aaacactacc 64620
ccaaaccatt tttttcatat tttctgagta ctcttctttt gtcacatggc ttgaaatttc 64680
ttcacataga gaactctact attattttat tttattttat tttattttat tttttgagac 64740
agagtcttgc tcttttcacc caggctggag tgcagtggtg ccatcttggc tcacggcaac 64800
ctctgcctcc tggattcaaa ctactctcct gcctcagcct cccgagtagc tgcgattaca 64860
ggtggctgcc accaagcctg gctaattctt gtatttttag tagagacgga gtattgccat 64920
gttagtcagg ctggtctcga actcctgacc tcaggtgatc tgcccacctt ggcctcccaa 64980
aatgttggga ttacaggctt gagccaccac gtctggctga taactctact tttagatact 65040
ctctttgctt aaacaaatta gccattcctt ccttgacatg ttttaatcag attgccttcc 65100
tattaacttc ggaaattaag agtttctgct atgtttttgt ttaattttta aacagtgaaa 65160
aatgaaaggt ggaggcaatg gctggatgag gtgaatatgt caaatagata tcatctagtg 65220
ggccatctta ttaactagga gacacctgaa gtgctatcaa tagaaataat ctgaagctgt 65280
gtctggatac agcaagagac atgcaaatgc taaaaatcta ctatattaca ttggtgcaag 65340
gacagagtag caacacatac taagtatttt ctccagattg ggtgtgtttg acgtgtgaag 65400
cacttcaaac agagtccagc ctgggaggga gtggggatgg aatcctcctt gtagagggta 65460
cagagtggaa gcaagaaggt ttccaagatt gagagtaatg ggtgtatggt ttatggggga 65520
aagggaaaac aaaaagaagg gtgcagaaat ggagctggga gtgtgtttta gtatttaggc 65580
tttctctgta tacctttgat aggattagaa aaagaaaaat ggaccatttt taaaaatttc 65640
atgctaccac atagcaggct tatactatag atgcagaaac agactgggat ttaggaagca 65700
ccccaattct ggaaaatccc tttttgcttc acattgctct ctaaatctgt atgttttccc 65760
ttgttacgta acaatttacc acaaatttag cagcttaaaa caatatgcat tcattgtttc 65820
acaattctgt aagtcggaat cataggcaag ctcaactgac ttttccattt agggtcgcaa 65880
aaggccgaag tcaatttatc tattgggctg ggctcttaac tgaagatctg ggaagaatt 65940 cccttcaaaa ctcatttagg ttgttgtcag aattcagtgt tttgtggttc tagaactgag 66000
atctgtttcc ttgttggctg tcagacagga gctgctctca gcttcttgag gcatccagta 66060
ttccttatca tgtgtttttt tttttccatc tcagcactgg cacttttttt ttttttttt 66120 ttgagacaga gtcttgcttt gtcacccagg ctggggtgca gtggcacgat ctcggctcac 66180
cacaacctcc atctcccggg ttcaagtgat tctcctgcct cagcctcccg agtagctggg 66240
attacaggca cccgccacca gcccggctga tttttgtatt tttcatagag atgtggtctc 66300
accatgttgg ccaggctggt cttgaactcc tgacctcaag tgatcctccc acttcagcct 66360
cccaaagtgc tgagattaca ggcatgagcc atcatgccca gccagcactg acaattctaa 66420
tccttctagc actttgattc cttctcacct ctccttctgc ctctagccag agaaaactct 66480

```
ctgattttaa aggtcttatg tgattagatt cagcttacct aggtaattca ggataactcc  66540
ctatgtcaag gtcaactgat taataacctt aattacacct gcaaagtccc ctttgccata  66600
atatatcata ctgacagaca tgctatagca taatactaat agttctaaga attatgataa  66660
gaatcttgga aaaccatttt tagaattata cctaccacag tatccttcaa gggataaatt  66720
gattctactt cttctctatg tcagaagcat ctgatgagga tgaactatat attctgaaat  66780
ccccatgatt agatgtgtac tagaaggtga ttttactttc attaaaataa attcggagtc  66840
attgacacat tttatctttg atttacataa atgcctccgc tctgtttctt accctcaaaa  66900
tatttcccat gtagctaagt ggccagtacc gaatcctaca tgcattaata agtgtagatg  66960
gacaaaaata tctggattac tgagaattcc cattagcatt gtctagaaaa atgtaaattt  67020
gctttttgt tcttgattta tcctattttt gatttattat ttatatttat ttatttattt  67080
atttattttt agatggaggt ctcgctttgt cgcccaggct ggagcgcaat ggcgcaatct  67140
tggctcactg caacctctgc ctcccaggtt caagctttcc tcctgcctca gcctcccaag  67200
tagctgggac tacaggcacc tgccacagtg cccggctaat tttgtattt tcagtagaga  67260
cagggttttg ccctgtgggc caggctgttc ttgaactcct gacctcaggt gatctgccca  67320
ccttggtccc ccaaagtgct gggattacag gcatgagcca ccacacctgg cctttttgct  67380
tactttttaa aaacattttt atttaggaga atggagatat ttcatatgta gatgacacat  67440
attcattccc tttagttccc acacacattc aatttcttga ggaagttagc ctttgcaaaa  67500
aaaaaaaaat gatctcattt ttttttcccc actaaaactt ctcattttct tggggttgct  67560
agaaagttgc tacaagaaag gctaaaaata attgtgccta cagatatttg aaaggaaaat  67620
agttcctctt ttttcacagt agcagcttgg acctgagaat gtatgggagc aataattggg  67680
ctgctcaaag aaacacaatt tcccttcctc agactagaat taccaaccta gagaacatga  67740
gtttttaaag tagatgtgct tcttttatct ttttggactt gtatgctggt gttttctctg  67800
tcaccttcac tgtggaaatc ctcttgaggg tgaggcactg aaagcagatt gattaatgtc  67860
tcttggccat ttgagacatt ggatggctct tttaagttgg ccacgttctt tcaagaacta  67920
tgcttgggct acatattctg gatatataat acatacttgt aggatgttat ttttaaatca  67980
ttcatttatc acatatttag tgagtgccta ccccatgtca gttctaggtg ctggaaatag  68040
agcagtaaaa ccaaccctca acttggcccc tctggagctt acatttcaat gcggtgggtg  68100
gggggatgga caattaatac acaagtaaat ctaataaaag cgtcatacaa tatacattac  68160
aatggtaagc acaatgaaga aatggaaagc tggatagaga gtattagaga ctgtcgaatg  68220
tagtggccaa attttcctgt ttattgtggt ccaagagtgc cacagccctc tatgacattt  68280
gagcagacac ctggaggaag tgagggagtg agccgccaag aaggaatggc aagtgcaata  68340
accctgaggt gggagcgtgt tggtcgtggt ggaagagctg caggaagcca gcagggccgc  68400
aacactcagg ggagaataag aaagagtgag gtgacagtag agaccggatc atgtagagct  68460
ttgtcagctt cttttctgag tgagatggac aacacggaca cgttttgaaa agaataacaa  68520
tgtgatctgc cttcagttgc aaatcatctc tgtattgact gagtaggaaa taaactccaa  68580
gaataaagac ggaaacaggg aaaatattta agaagcgatc attacaatcc agggtggtgg  68640
cttgtactag ggtacaaggg ctaaaggtgt tgagaaatgg tcagattctg gatatatact  68700
gaaatcaaag ttgatggaaa gatatgagtc aaagataatt tgcaggtttt ggggtcctgg  68760
ttcactgaaa gaacagagac atcatttact ccaatgagga agactatagg aggaacaggt  68820
ttagcaaaga agaaaggaaa tcaggagatc agtttgggga cacggtcata tcaagtaggc  68880
```

-continued

```
agttggatgt atgggtctgg aatataggggg agtggtctag ctatcagtgt aaatagcttt  68940
ttacatttgt aaatagtcag gatataggct tttctttttc tttttgtgag acacagtctt  69000
gctctttcgc ccaaactgga gtgcaatggc acaatctcag ctcactgcaa cctctgcctc  69060
tgggttcaag cgatactcct gcctcagcct cccgagtagc tgggactaca ggtgtgcacc  69120
accataccag gctaattttt gtgtttttaa tggaaatggg gtttcaccat gttgaccagg  69180
ctggtgtcaa actcctgacc tcaatcgatc tccccgcctg ggcctcccaa agtgctggga  69240
ttacaggcat gagccacccc atccagctgg gatatagttg ttttctaaat ctatgaggct  69300
agagaagacc atttgggaat tgagagcagt gagcagtcca cggactgacc ctttgagagt  69360
gcaacattta gcagtactca agatgggaag gagctagtga aaaagcccca aatgactaca  69420
taagaccatc aaccagatta caaagaaaga cccgaacatg tgtgcccata tatcacccaa  69480
cagcagttat gtctttcatg tttcttcccc ataaaatgtt gttcatcaac tttattagac  69540
tagggtctta acattggaca aatcacaaaa cctctctgga gcctatttta tttttcaaca  69600
gctgtaggaa gcaaatacaa attggaaatc taaggctcag aaagatttgt acaaagttac  69660
acagtaatga aaggggagcc gggattccca ctcactctaa agaatatgat aaaatggcta  69720
gtattcactg aatgcttaac atgttccagg ccctgggcag gtattatttt aattagttct  69780
cacaataatc caataaggga gatactaatt tactcagatg agaaagctga ggctcagaga  69840
ggttaatgaa ctaagccaag gctcactgtt aataaatagc aaaggtaaaa ttaaattcca  69900
tatctgcttg agatagaggc cttgctccta atagctgcag cctgtcaggg cctggcagca  69960
gtaacctctc ctttcctctt cccaccattc ccctgcactg ctttctgtac cgcatctctt  70020
ttcagagtga tgttgcccca attgcggagg ccactgtgct gtttatccag tgaaagctgt  70080
agcacagcca acccaaagcg tccccagtga aaacaacctg gctccttaca gcacttccag  70140
cctcagagca gtatttgaaa aatatcatga acagcaaaca cagcagtctg tctgtggctt  70200
ttatatgtgt atatggtgtg tgtgtatgtc ccttctcttg agcaaaataa cttttagaat  70260
tatagaaaaa aaatgtgcaa catcaatgtg gatctgctgt ttaaactcat aacagagaaa  70320
gtagcttgtt tctggctata ggaggaaaag acgatattcc ttagtaaaaa tggaaatcca  70380
catatggggt tcttgtaaaa atgaagatag aaaattgcaa gtttggggat caagttctgg  70440
ttctatcatc ctttaacagt atgaccctgg aaccttaatt gctttgagtc tttgttactt  70500
tatctatgaa atgaagtatt taaaaaaact ccaaaaatct gtcctgatgt acacacaaga  70560
ggtcaaatga gaaaatgaat gtgaagatgc tttataaact atacagcatg gtaggtgcaa  70620
atgtgacatg aacttgtttt ggacacatta taaagtcacc cccacaaact gtgattgttc  70680
aagactatgc aaagtcagac acaggaaaat aagtaaaaca gatggaggca taaagagggg  70740
gaactcagag aaaacagtga agaacaggaa tcaggaagac aaaggagagg aaaggtgggg  70800
aggagaggag aaggaaaggg ggaagggaat ggaggagagg agaacagctg cttcacagag  70860
catggccggc agcccagtcc cagcctttct gcatgtccct gacttcagcc tctggcgagg  70920
cacaggctta ctctgtgctt cctgctgtta ctcttcttat ccatccttat tatcaatacc  70980
tgtggtcaac aaagtatttg ataaaggcat cctcaaagtc aggtaacatc tgtacgttat  71040
agattacaaa gttgagtaat atccagaatt ggtagtttaa cgtgatgact tcttaacaat  71100
tatcactgtt tcagggaagg gcaaaggtgt gtgtgtgtgt gtgttcatct gtgtgtatct  71160
gtgtatgtaa ttgtgggtgt ttgtgtatat ttgtgaggct ctttacttgg cggagttaaa  71220
aagtatctgc tcatcaaggt tgagattagc aaaggaagtg aagatttttc cagagcccct  71280
```

-continued

```
aaaatgtgcc ttttgaccaa cactgaggac atctttataa ctgagtatgt gcaataaata  71340
tgtcttggga cctgtgccac aaattcctct ctaaatagcc tttacctctc tggaataacc  71400
ctttagatga ggaagaaaag ggctgtgatt ttatagcttg ttatgaagct ggagtgaaga  71460
tgatgcttca gtacttaccc tacaaagata cccccaatcc ctcaccctaa aattaccatt  71520
gaaatcatgt tccctttctc attcactctc agtttccatg tcagaaaata taccattacc  71580
tccctgcacc cctttcatct ctctcacttt tctcttgctt agatggaaag acaacccagc  71640
aatgcctgca gggctgatgt atgaaggagt ttcccaagag cccctgaaat actccggcgg  71700
gagtgcagct cagagcacag tgcttcatgc ctttgatgag ttcttaggca ttcgtcatag  71760
caaggaaagt ggtaagtcag acattttgtt ttcccttgag agtagaggga ggaagaggag  71820
aggtgttttt tttttttcca attgataaaa ccaaatataa attaaaatgt catgaagttt  71880
atacttctct aagtcagcca agaaactgca tgactgccaa tgtttttgtg tcaagccaat  71940
taatattgga atatcagatg tcagcttgat cttgggtttt acttccaaat cttaaaatgt  72000
tgctctgttt ccaactgttc actatcactt tggtttggat ctttagacac tagcttcctt  72060
tttctgaaat gggggagaga tgtggagttt gaaggctatg agtctgggcc agctggaaac  72120
aggtctggga tcttccaaga aagtccttcc ccacaaaatg gtgcaacttc tagccaaatc  72180
tatttatacc agcagaggga tctatcaccc tggaagcttg aaattgttca ttttcttacc  72240
tgccaggatc aagttaagtt tttaacagtt gcaaaaagac acttcatact atggagtttt  72300
caagttggat tagaagaaaa agaatcacca gaacttagtg tcgtagattc aagtcacttc  72360
tctaaaactg tcataatttt tcacggattt tggcatttgg tgacattaat ggttgattta  72420
cttaccatgc ataatattaa acccataacg aatttcctat aaatatctat tgatttgatt  72480
tttaaatcac ttggcttcaa gaggctatta ctaaaacagt gactcattct ttatcttttt  72540
tgccttcacg ggctttatat aactttctcc ttttcttgtg ctccctccaa aacaaagcac  72600
tgagaaaaca aaattcacca gagtattcag ctagtcagtt caagggtttg tgttctacat  72660
ttgaagatat tccttatagc agctaccaac gggatacttt gtttacattt gttgtgtagt  72720
aaatatttat atattggcaa acaaatctag ttccaactct gtcatctgag atgttcttac  72780
tttgtttcct cttctccatc tcctgtcaac tgttagaaat atacatttga gtacgtgaag  72840
tctgcaaaca aaagggccaa ggtagatttg agttagaaca ccagcaacag tttctggtgc  72900
attcttgtct gaaaaagcag agaagattgg gcaccgtggg tcatgcctgt aatcccaaaa  72960
ttttggaagt ctgaggcagg tggatcgctt gagcccagga gttcaagaca agcctgggca  73020
acatagcaag aacccgtctc tactaaaagg aatacaaaaa aatattagct gggtgtggtg  73080
gcgcacacct gtagtttcag ctactcagaa gactgaggtg ggaggatcac ttgaactcag  73140
gggcagaggt ggcagtaagc tgagatcaca ccactgcact ccagcctggg caacagagca  73200
agatctcatc tagagaaaaa aaaaataaaa aagaagaaga agcagacgag ctctgctata  73260
tttccatgtg gagctatgac gttatgctgt attgtttctt tcaggtgact ttctgtacag  73320
aatgagggat tacatgcctc cttcccataa ggccttcata gaagacatcc actcagcacc  73380
ttccctgagg gactacatcc tgtcatctgg acaggaccac ttgctgacag cttataacca  73440
gtgtgtgcag gccctggcag agctgcggag ctatcacatc accatggtca ccaaatacct  73500
catcacagct gcagccaagg caaagcatgg gaagccaaac catctcccag ggcctcctca  73560
ggctttaaaa gacaggggca caggtggaac cgcagttatg agctttctta agagtgtcag  73620
ggataagacc ttggagtcaa tccttcaccc acgtggttag                        73660
```

<210> SEQ ID NO 22
<211> LENGTH: 890
<212> TYPE: DNA
<213> ORGANISM: Homo sapiens

<400> SEQUENCE: 22
ggcttatgga gccccacaga ccgaatgtga agacagcagt gccattgtct ttggaaagct 60
atcacatatc tgaagagtat ggctttcttc ttccagattc tctgaaagaa cttccagatc 120
attataggcc ttggatggaa attgccaaca aacttcctca attgattgat gctcaccagc 180
ttcaagctca tgtggacaag attcctggaa attgggctct tgttcaggcc acgaatgcta 240
tcttgcagcc caaccaggag gccctgctcc aagccctgca gcgactgaga ctgtctattc 300
aggacatcac caaaacctta ggacagatgc atgattatgt agatccagac atattttatg 360
caggcatccg gatctttctc tctggatgga aagacaaccc agcaatgcct gcagggctga 420
tgtatgaagg agtttcccaa gagcccctga aatactccgg cgggagtgca gctcagagca 480
cagtgcttca tgcctttgat gagttcttag gcattcgtca tagcaaggaa agtggtgact 540
ttctgtacag aatgagggat tacatgcctc cttcccataa ggccttcata gaagacatcc 600
actcagcacc ttccctgagg gactacatcc tgtcctctgg acaggaccac ttgctgacag 660
cttataacca gtgtgtgcag gccctggcag agctgcggag ctatcacatc accatggtca 720
ccaaatacct catcacagct gcagccaagg caaagcatgg gaagccaaac catctcccag 780
ggcctcctca ggctttaaaa gacaggggca caggtggaac cgcagttatg agctttctta 840
agagtgtcag ggataagacc ttggagtcaa tccttcaccc acgtggttag 890

<210> SEQ ID NO 23
<211> LENGTH: 1177
<212> TYPE: DNA
<213> ORGANISM: Homo sapiens

<400> SEQUENCE: 23
ggcttatgga gccccacaga ccgaatgtga agacagcagt gccattgtct ttggaaagct 60
atcacatatc tgaagagtat ggctttcttc ttccagattc tctgaaagaa cttccagatc 120
attataggcc ttggatggaa attgccaaca aacttcctca attgattgat gctcaccagc 180
ttcaagctca tgtggacaag atgcccctgc tgagctgcca gttcctgaag ggtcaccggg 240
agcagcgcct ggcccacctg gtcctgagct tcctcaccat gggttatgtc tggcaggaag 300
gagaggcgca gcctgcagag gtcctgccaa ggaatcttgc ccttccattt gtcgaagtct 360
ccaggaactt ggggctccct cctatcctgg tccactcaga cttggtgctg acgaactgga 420
ccaaaaaaga tccagacgga ttcctggaaa ttgggaacct ggagaccatc atctcatttc 480
ctgggggaga gagcctgcat ggttttatac tggtgactgc tttggtagag aaagaagcag 540
tgcctgggat aaaggctctt gttcaggcca cgaatgctat cttgcagccc aaccaggagg 600
ccctgctcca agccctgcag cgactgagac tgtctattca ggacatcacc aaaaccttag 660
gacagatgca tgatggaaag acaacccagc aatgcctgca gggctgatgt atgaaggagt 720
ttcccaagag cccctgaaat actccggcgg gagtgcagct cagagcacag tgcttcatgc 780
ctttgatgag ttcttaggca ttcgtcatag caaggaaagt ggtgactttc tgtacagaat 840
gagggattac atgcctcctt cccataaggc cttcatagaa gacatccact cagcaccttc 900
cctgagggac tacatcctgt cctctggaca ggaccacttg ctgacagctt ataaccagtg 960
tgtgcaggcc ctggcagagc tgcggagcta tcacatcacc atggtcacca aatacctcat 1020
cacagctgca gccaaggcaa agcatgggaa gccaaaccat ctcccagggc ctcctcaggc 1080
tttaaaagac aggggcacag gtggaaccgc agttatgagc tttcttaaga gtgtcaggga 1140
taagaccttg gagtcaatcc ttcacccacg tggttag 1177

<210> SEQ ID NO 24
<211> LENGTH: 1077
<212> TYPE: DNA
<213> ORGANISM: Homo sapiens

<400> SEQUENCE: 24
ggcttatgga gccccacaga ccgaatgtga agacagcagt gccattgtct ttggaaagct 60
atcacatatc tgaagagtat ggctttcttc ttccagattc tctgaaagaa cttccagatc 120
attataggcc ttggatggaa attgccaaca aacttcctca attgattgat gctcaccagc 180
ttcaagctca tgtggacaag atgcccctgc tgagctgcca gttcctgaag ggtcaccggg 240
agcagcgcct ggcccacctg gtcctgagct tcctcaccat gggttatgtc tggcaggaag 300
gagaggcgca gcctgcagag gtcctgccaa ggaatcttgc ccttccattt gtcgaagtct 360
ccaggaactt ggggctccct cctatcctgg tccactcaga cttggtgctg acgaactgga 420
ccaaaaaaga tccagacgga ttcctggaaa ttgggctctt gttcaggcca cgaatgctat 480
cttgcagccc aaccaggagg ccctgctcca agccctgcag cgactgagac tgtctattca 540
ggacatcacc aaaaccttag gacagatgca tgatggaaag acaacccagc aatgcctgca 600
gggctgatgt atgaaggagt ttcccaagag cccctgaaat actccggcgg gagtgcagct 660
cagagcacag tgcttcatgc ctttgatgag ttcttaggca ttcgtcatag caaggaaagt 720
ggtgactttc tgtacagaat gagggattac atgcctcctt cccataaggc cttcatagaa 780
gacatccact cagcaccttc cctgagggac tacatcctgt cctctggaca ggaccacttg 840
ctgacagctt ataaccagtg tgtgcaggcc ctggcagagc tgcggagcta tcacatcacc 900
atggtcacca aatacctcat cacagctgca gccaaggcaa agcatgggaa gccaaaccat 960
ctcccagggc ctcctcaggc tttaaaagac aggggcacag gtggaaccgc agttatgagc 1020
tttcttaaga gtgtcaggga taagaccttg gagtcaatcc ttcacccacg tggttag 1077

<210> SEQ ID NO 25
<211> LENGTH: 1096
<212> TYPE: DNA
<213> ORGANISM: Homo sapiens

<400> SEQUENCE: 25
ggcttatgga gccccacaga ccgaatgtga agacagcagt gccattgtct ttggaaagct 60
atcacatatc tgaagagtat ggctttcttc ttccagattc tctgaaagaa cttccagatc 120
attataggcc ttggatggaa attgccaaca aacttcctca attgattgat gctcaccagc 180
ttcaagctca tgtggacaag atgcccctgc tgagctgcca gttcctgaag ggtcaccggg 240
agcagcgcct ggcccacctg gtcctgagct tcctcaccat gggttatgtc tggcaggaag 300
gagaggcgca gcctgcagag ggaacctgga gaccatcatc tcatttcctg ggggagagag 360
cctgcatggt tttatactgg tgactgcttt ggtagagaaa gaagcagtgc ctgggataaa 420
ggctcttgtt caggccacga atgctatctt gcagcccaac caggaggccc tgctccaagc 480
cctgcagcga ctgagactgt ctattcagga catcaccaaa accttaggac agatgcatga 540
ttatgtagat ccagacatat tttatgcagg catccggatc tttctctctg gatggaaaga 600
caacccagca atgcctgcag ggctgatgta tgaaggagtt tcccaagagc ccctgaaata 660

```
ctccggcggg agtgcagctc agagcacagt gcttcatgcc tttgatgagt tcttaggcat    720

tcgtcatagc aaggaaagtg gtgactttct gtacagaatg agggattaca tgcctccttc    780

ccataaggcc ttcatagaag acatccactc agcaccttcc ctgagggact acatcctgtc    840

ctctggacag gaccacttgc tgacagctta taaccagtgt gtgcaggccc tggcagagct    900

gcggagctat cacatcacca tggtcaccaa atacctcatc acagctgcag ccaaggcaaa    960

gcatgggaag ccaaaccatc tcccagggcc tcctcaggct ttaaaagaca ggggcacagg   1020

tggaaccgca gttatgagct ttcttaagag tgtcagggat aagaccttgg agtcaatcct   1080

tcacccacgt ggttag                                                   1096
```

```
<210> SEQ ID NO 26
<211> LENGTH: 1229
<212> TYPE: DNA
<213> ORGANISM: Homo sapiens

<400> SEQUENCE: 26

ggcttatgga gccccacaga ccgaatgtga agacagcagt gccattgtct ttggaaagct     60

atcacatatc tgaagagtat ggctttcttc ttccagattc tctgaaagaa cttccagatc    120

attataggcc ttggatggaa attgccaaca aacttcctca attgattgat gctcaccagc    180

ttcaagctca tgtggacaag atgcccctgc tgagctgcca gttcctgaag ggtcaccggg    240

agcagcgcct ggcccacctg gtcctgagct tcctcaccat gggttatgtc tggcaggaag    300

gagaggcgca gcctgcagag gtcctgccaa ggaatcttgc ccttccattt gtcgaagtct    360

ccaggaactt ggggctccct cctatcctgg tccactcaga cttggtgctg acgaactgga    420

ccaaaaaaga tccagacgga ttcctggaaa ttgggaacct ggagaccatc atctcatttc    480

ctgggggaga gagcctgcat ggttttatac tggtgactgc tttggtagag aaagaagcag    540

tgcctgggat aaaggctctt gttcaggcca cgaatgctat cttgcagccc aaccaggagg    600

ccctgctcca agccctgcag cgactgagac tgtctattca ggacatcacc aaaaccttag    660

gacagatgca tgattatgta gatccagaca tattttatgc aggcatctgg atctttctct    720

ctggatggaa agacaaccca gcaatgcctg cagggctgat gtatgaagga gtttcccaag    780

agcccctgaa atactccggc gggagtgcag ctcagagcac agtgcttcat gcctttgatg    840

agttcttagg cattcgtcat agcaaggaaa gtggtgactt tctgtacaga atgagggatt    900

acatgcctcc ttcccataag gccttcatag aagacatcca ctcagcacct tccctgaggg    960

actacatcct gtcctctgga caggaccact tgctgacagc ttataaccag tgtgtgcagg   1020

ccctggcaga gctgcggagc tatcacatca ccatggtcac caaatacctc atcacagctg   1080

cagccaaggc aaagcatggg aagccaaacc atctcccagg gcctcctcag gctttaaaag   1140

acaggggcac aggtggaacc gcagttatga gctttcttaa gagtgtcagg gataagacct   1200

tggagtcaat ccttcaccca cgtggttag                                     1229
```

```
<210> SEQ ID NO 27
<211> LENGTH: 1225
<212> TYPE: DNA
<213> ORGANISM: Homo sapiens

<400> SEQUENCE: 27

tatggagccc cacagaccga atgtgaagac agcagtgcca ttgtctttgg aaagctatca     60

catatctgaa gagtatggct ttcttcttcc agattctctg aaagaacttc cagatcatta    120

taggccttgg atggaaattg ccaacaaact tcctcaattg attgatgctc accagcttca    180
```

```
agctcatgtg gacaagatgc ccctgctgag ctgccagttc ctgaagggtc accgggagca    240

gcgcctggcc cacctggtcc tgagcttcct caccatgggt tatgtctggc aggaaggaga    300

ggcgcagcct gcagaggtcc tgccaaggaa tcttgccctt ccatttgtcg aagtctccag    360

gaacttgggg ctccctcctg tcctggtcca ctcagacttg gtgctgacga actggaccaa    420

aaaagatcca gacggattcc tggaaattgg gaacctggag accatcatct catttcctgg    480

gggagagagc ctgcatggtt ttatactggt gactgctttg gtagagaaag aagcagtgcc    540

tgggataaag gctcttgttc aggccacgaa tgctatcttg cagcccaacc aggaggccct    600

gctccaagcc ctgcagcgac tgagactgtc tattcaggac atcaccaaaa ccttaggaca    660

gatgcatgat tatgtagatc cagacatatt ttatgcaggc atccggatct ttctctctgg    720

atggaaagac aacccagcaa tgcctgcagg gctgatgtat gaaggagttt cccaagagcc    780

cctgaaatac tccggcggga gtgcagctca gagcacagtg cttcatgcct ttgatgagtt    840

cttaggcatt cgtcatagca aggaaagtgg tgactttctg tacagaatga gggattacat    900

gcctccttcc cataaggcct tcatagaaga catccactca gcaccttccc tgagggacta    960

catcctgtcc tctggacagg accacttgct gacagcttat aaccagtgtg tgcaggccct   1020

ggcagagctg cggagctaac acatcaccat ggtcaccaaa tacctcatca cagctgcagc   1080

caaggcaaag catgggaagc caaaccatct cccagggcct cctcaggctt taaaagacag   1140

gggcacaggt ggaaccgcag ttatgagctt tcttaagagt gtcagggata agaccttgga   1200

gtcaatcctt cacccacgtg gttag                                          1225
```

<210> SEQ ID NO 28
<211> LENGTH: 407
<212> TYPE: PRT
<213> ORGANISM: Homo sapiens

<400> SEQUENCE: 28

```
Met Glu Pro His Arg Pro Asn Val Lys Thr Ala Val Pro Leu Ser Leu
 1               5                  10                  15

Glu Ser Tyr His Ile Ser Glu Glu Tyr Gly Phe Leu Leu Pro Asp Ser
            20                  25                  30

Leu Lys Glu Leu Pro Asp His Tyr Arg Pro Trp Met Glu Ile Ala Asn
        35                  40                  45

Lys Leu Pro Gln Leu Ile Asp Ala His Gln Leu Gln Ala His Val Asp
    50                  55                  60

Lys Met Pro Leu Leu Ser Cys Gln Phe Leu Lys Gly His Arg Glu Gln
65                  70                  75                  80

Arg Leu Ala His Leu Val Leu Ser Phe Leu Thr Met Gly Tyr Val Trp
                85                  90                  95

Gln Glu Gly Glu Ala Gln Pro Ala Glu Val Leu Pro Arg Asn Leu Ala
            100                 105                 110

Leu Pro Phe Val Glu Val Ser Arg Asn Leu Gly Leu Pro Pro Ile Leu
        115                 120                 125

Val His Ser Asp Leu Val Leu Thr Asn Trp Thr Lys Lys Asp Pro Asp
    130                 135                 140

Gly Phe Leu Glu Ile Gly Asn Leu Glu Thr Ile Ile Ser Phe Pro Gly
145                 150                 155                 160

Gly Glu Ser Leu His Gly Phe Ile Leu Val Thr Ala Leu Val Glu Lys
                165                 170                 175

Glu Ala Val Pro Gly Ile Lys Ala Leu Val Gln Ala Thr Asn Ala Ile
            180                 185                 190
```

```
Leu Gln Pro Asn Gln Glu Ala Leu Leu Gln Ala Leu Gln Arg Leu Arg
        195                 200                 205

Leu Ser Ile Gln Asp Ile Thr Lys Thr Leu Gly Gln Met His Asp Tyr
    210                 215                 220

Val Asp Pro Asp Ile Phe Tyr Ala Gly Ile Arg Ile Phe Leu Ser Gly
225                 230                 235                 240

Trp Lys Asp Asn Pro Ala Met Pro Ala Gly Leu Met Tyr Glu Gly Val
                245                 250                 255

Ser Gln Glu Pro Leu Lys Tyr Ser Gly Gly Ser Ala Ala Gln Ser Thr
            260                 265                 270

Val Leu His Ala Phe Asp Glu Phe Leu Gly Ile Arg His Ser Lys Glu
        275                 280                 285

Ser Gly Asp Phe Leu Tyr Arg Met Arg Asp Tyr Met Pro Pro Ser His
    290                 295                 300

Lys Ala Phe Ile Glu Asp Ile His Ser Ala Pro Ser Leu Arg Asp Tyr
305                 310                 315                 320

Ile Leu Ser Ser Gly Gln Asp His Leu Leu Thr Ala Tyr Asn Gln Cys
                325                 330                 335

Val Gln Ala Leu Ala Glu Leu Arg Ser Tyr His Ile Thr Met Val Thr
            340                 345                 350

Lys Tyr Leu Ile Thr Ala Ala Ala Lys Ala Lys His Gly Lys Pro Asn
        355                 360                 365

His Leu Pro Gly Pro Pro Gln Ala Leu Lys Asp Arg Gly Thr Gly Gly
    370                 375                 380

Thr Ala Val Met Ser Phe Leu Lys Ser Val Arg Asp Lys Thr Leu Glu
385                 390                 395                 400

Ser Ile Leu His Pro Arg Gly
                405
```

<210> SEQ ID NO 29
<211> LENGTH: 101
<212> TYPE: DNA
<213> ORGANISM: Homo sapiens

<400> SEQUENCE: 29
gacacgggag ttgaggcatt accttggacg tggagaccag gccctcacca gacactgaac 60
ttgccagcac cttgatcttg gacttcccag cctccagaac t 101

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
actctgacct ggtgctgaca aact 24

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
tgcaggatgt gaacctctaa cgct 24

<210> SEQ ID NO 32

<211> LENGTH: 24
<212> TYPE: DNA
<213> ORGANISM: Artificial Sequence
<220> FEATURE:
<223> OTHER INFORMATION: Primer

<400> SEQUENCE: 32
tggagcctca aagtcagagc atga 24

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
agtttgtcag caccaggtca gagt 24

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
tgcctgatgg cctataacca gtgt 24

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35
tgcaggatgt gaacctctaa cgct 24

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
aaccacacag aagacacagc tgga 24

<210> SEQ ID NO 37
<211> LENGTH: 24
<212> TYPE: DNA
<213> ORGANISM: Artificial Sequence
<220> FEATURE:
<223> OTHER INFORMATION: Primer

<400> SEQUENCE: 37
tgagggcaat ttccatccaa ggct 24

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
accgcacaag tacaaccaca caga 24

<210> SEQ ID NO 39
<211> LENGTH: 22
<212> TYPE: DNA
<213> ORGANISM: Artificial Sequence
<220> FEATURE:
<223> OTHER INFORMATION: Primer

<400> SEQUENCE: 39
agccttatgg gaaggcggca tg 22

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
actgatttcc aacggtcctt c 21

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
tcggagctgg cggttctcga t 21

<210> SEQ ID NO 42
<211> LENGTH: 19
<212> TYPE: DNA
<213> ORGANISM: Artificial Sequence
<220> FEATURE:
<223> OTHER INFORMATION: Primer

<400> SEQUENCE: 42
aaggtgctgc caagatctc 19

<210> SEQ ID NO 43
<211> LENGTH: 18
<212> TYPE: DNA
<213> ORGANISM: Artificial Sequence
<220> FEATURE:
<223> OTHER INFORMATION: Primer

<400> SEQUENCE: 43
cttcatgcct tcgatgag 18

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
agagaaagaa gcagtgcctg ggat 24

<210> SEQ ID NO 45
<211> LENGTH: 24
<212> TYPE: DNA
<213> ORGANISM: Artificial Sequence
<220> FEATURE:

<223> OTHER INFORMATION: Primer

<400> SEQUENCE: 45
taagctgtca gcaagtggtc ctgt 24

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46
tgagacactg cgcaactaac tgga 24

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
atcccaggca ctgcttcttt ctct 24

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
acaggaccac ttgctgacag ctta 24

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
acgtgggtga aggattgact ccaa 24

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
tgttggcaat ttccatccaa ggc 23

<210> SEQ ID NO 51
<211> LENGTH: 24
<212> TYPE: DNA
<213> ORGANISM: Artificial Sequence
<220> FEATURE:
<223> OTHER INFORMATION: Primer

<400> SEQUENCE: 51
aaccacgtgg gtgaaggatt gact 24

<210> SEQ ID NO 52

<211> LENGTH: 22
<212> TYPE: DNA
<213> ORGANISM: Artificial Sequence
<220> FEATURE:
<223> OTHER INFORMATION: Primer

<400> SEQUENCE: 52
ttcagtgaca ctttccatgc ag 22

<210> SEQ ID NO 53
<211> LENGTH: 22
<212> TYPE: DNA
<213> ORGANISM: Artificial Sequence
<220> FEATURE:
<223> OTHER INFORMATION: Primer

<400> SEQUENCE: 53
atggagcccc acagaccgaa tg 22

<210> SEQ ID NO 54
<211> LENGTH: 22
<212> TYPE: DNA
<213> ORGANISM: Artificial Sequence
<220> FEATURE:
<223> OTHER INFORMATION: Primer

<400> SEQUENCE: 54
gaagggcaag attccttggc ag 22

<210> SEQ ID NO 55
<211> LENGTH: 22
<212> TYPE: DNA
<213> ORGANISM: Artificial Sequence
<220> FEATURE:
<223> OTHER INFORMATION: Primer

<400> SEQUENCE: 55
attgatgctc accagcttca ag 22

<210> SEQ ID NO 56
<211> LENGTH: 22
<212> TYPE: DNA
<213> ORGANISM: Artificial Sequence
<220> FEATURE:
<223> OTHER INFORMATION: Primer

<400> SEQUENCE: 56
cttcatacat cagccctgca gg 22

<210> SEQ ID NO 57
<211> LENGTH: 22
<212> TYPE: DNA
<213> ORGANISM: Artificial Sequence
<220> FEATURE:
<223> OTHER INFORMATION: Primer

<400> SEQUENCE: 57
gtagagaaag aagcagtgcc tg 22

<210> SEQ ID NO 58
<211> LENGTH: 22
<212> TYPE: DNA
<213> ORGANISM: Artificial Sequence
<220> FEATURE:
<223> OTHER INFORMATION: Primer

<400> SEQUENCE: 58
ggcatccgga tctttctctc tg 22

<210> SEQ ID NO 59
<211> LENGTH: 23
<212> TYPE: DNA
<213> ORGANISM: Artificial Sequence
<220> FEATURE:
<223> OTHER INFORMATION: Primer

<400> SEQUENCE: 59
ctaaccacgt gggtgaagga ttg 23

<210> SEQ ID NO 60
<211> LENGTH: 18
<212> TYPE: DNA
<213> ORGANISM: Artificial Sequence
<220> FEATURE:
<223> OTHER INFORMATION: Primer

<400> SEQUENCE: 60
ggtactgcca tgctgagc 18

<210> SEQ ID NO 61
<211> LENGTH: 21
<212> TYPE: DNA
<213> ORGANISM: Artificial Sequence
<220> FEATURE:
<223> OTHER INFORMATION: Primer

<400> SEQUENCE: 61
aagctgcccg ttctcaatca g 21

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
ctcgtatgtc atgggcccat tg 22

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
gaagttccgg tgggctggag gc 22

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
ggtgctgccc cgcaataatg c 21

<210> SEQ ID NO 65
<211> LENGTH: 20
<212> TYPE: DNA
<213> ORGANISM: Artificial Sequence
<220> FEATURE:

<223> OTHER INFORMATION: Primer

<400> SEQUENCE: 65
ccagagtctt gatgtccttc 20

<210> SEQ ID NO 66
<211> LENGTH: 21
<212> TYPE: DNA
<213> ORGANISM: Artificial Sequence
<220> FEATURE:
<223> OTHER INFORMATION: Primer

<400> SEQUENCE: 66
cctcaaatgt ggaaagcaga g 21

<210> SEQ ID NO 67
<211> LENGTH: 28
<212> TYPE: DNA
<213> ORGANISM: Artificial Sequence
<220> FEATURE:
<223> OTHER INFORMATION: Primer

<400> SEQUENCE: 67
atccggtacc atggagcctc aaagtcag 28

<210> SEQ ID NO 68
<211> LENGTH: 24
<212> TYPE: DNA
<213> ORGANISM: Artificial Sequence
<220> FEATURE:
<223> OTHER INFORMATION: Primer

<400> SEQUENCE: 68
gttgagctct ccaggaactt ggga 24

<210> SEQ ID NO 69
<211> LENGTH: 27
<212> TYPE: DNA
<213> ORGANISM: Artificial Sequence
<220> FEATURE:
<223> OTHER INFORMATION: Primer

<400> SEQUENCE: 69
agtgttgaat tcctacagga aatgagg 27

<210> SEQ ID NO 70
<211> LENGTH: 27
<212> TYPE: DNA
<213> ORGANISM: Artificial Sequence
<220> FEATURE:
<223> OTHER INFORMATION: Primer

<400> SEQUENCE: 70
ctgaaagctt ataaccagtg tgtggag 27

<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
catcctgtac acgtgagctc g 21

<210> SEQ ID NO 72

<211> LENGTH: 24
<212> TYPE: DNA
<213> ORGANISM: Artificial Sequence
<220> FEATURE:
<223> OTHER INFORMATION: Primer

<400> SEQUENCE: 72
tggagagctc aacaaaagga atgg 24

<210> SEQ ID NO 73
<211> LENGTH: 30
<212> TYPE: DNA
<213> ORGANISM: Artificial Sequence
<220> FEATURE:
<223> OTHER INFORMATION: Primer

<400> SEQUENCE: 73
ctgtaggaat tcaacacttt ccttgcaatg 30

<210> SEQ ID NO 74
<211> LENGTH: 24
<212> TYPE: DNA
<213> ORGANISM: Artificial Sequence
<220> FEATURE:
<223> OTHER INFORMATION: Primer

<400> SEQUENCE: 74
tataagcttt caggcagtcc ccag 24

<210> SEQ ID NO 75
<211> LENGTH: 21
<212> TYPE: DNA
<213> ORGANISM: Artificial Sequence
<220> FEATURE:
<223> OTHER INFORMATION: Primer

<400> SEQUENCE: 75
gaagacacag ctggaaagct c 21

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
ccatgctgac ctccaggctc 20

<210> SEQ ID NO 77
<211> LENGTH: 28
<212> TYPE: DNA
<213> ORGANISM: Artificial Sequence
<220> FEATURE:
<223> OTHER INFORMATION: Primer

<400> SEQUENCE: 77
atccggtacc atggcactca gtaaaata 28

<210> SEQ ID NO 78
<211> LENGTH: 24
<212> TYPE: DNA
<213> ORGANISM: Artificial Sequence
<220> FEATURE:
<223> OTHER INFORMATION: Primer

<400> SEQUENCE: 78
gaagtgtaca agctgcccac actg 24

<210> SEQ ID NO 79
<211> LENGTH: 22
<212> TYPE: DNA
<213> ORGANISM: Artificial Sequence
<220> FEATURE:
<223> OTHER INFORMATION: Primer

<400> SEQUENCE: 79
gaggatgcat gactttgtgg ac 22

<210> SEQ ID NO 80
<211> LENGTH: 23
<212> TYPE: DNA
<213> ORGANISM: Artificial Sequence
<220> FEATURE:
<223> OTHER INFORMATION: Primer

<400> SEQUENCE: 80
agcttgtaca cttcttctcg aag 23

<210> SEQ ID NO 81
<211> LENGTH: 24
<212> TYPE: DNA
<213> ORGANISM: Artificial Sequence
<220> FEATURE:
<223> OTHER INFORMATION: Primer

<400> SEQUENCE: 81
gtcatgcatc ctcttaaaaa taac 24

<210> SEQ ID NO 82
<211> LENGTH: 33
<212> TYPE: DNA
<213> ORGANISM: Artificial Sequence
<220> FEATURE:
<223> OTHER INFORMATION: Primer

<400> SEQUENCE: 82
gtcgcgctag caaactcaat ggtgatggtg atg 33

<210> SEQ ID NO 83
<211> LENGTH: 23
<212> TYPE: DNA
<213> ORGANISM: Artificial Sequence
<220> FEATURE:
<223> OTHER INFORMATION: Target sequence

<400> SEQUENCE: 83
aatgtgaaga cagcagtgcc att 23

<210> SEQ ID NO 84
<211> LENGTH: 23
<212> TYPE: DNA
<213> ORGANISM: Artificial Sequence
<220> FEATURE:
<223> OTHER INFORMATION: Target sequence

<400> SEQUENCE: 84
aagacagcag tgccattgtc ttt 23

<210> SEQ ID NO 85
<211> LENGTH: 23
<212> TYPE: DNA
<213> ORGANISM: Artificial Sequence
<220> FEATURE:

<223> OTHER INFORMATION: Target sequence

<400> SEQUENCE: 85
aattgattga tgctcaccag ctt 23

<210> SEQ ID NO 86
<211> LENGTH: 23
<212> TYPE: DNA
<213> ORGANISM: Artificial Sequence
<220> FEATURE:
<223> OTHER INFORMATION: Target sequence

<400> SEQUENCE: 86
aacctggaga ccatcatctc att 23

<210> SEQ ID NO 87
<211> LENGTH: 23
<212> TYPE: DNA
<213> ORGANISM: Artificial Sequence
<220> FEATURE:
<223> OTHER INFORMATION: Target sequence

<400> SEQUENCE: 87
aaccttagga cagatgcatg att 23

<210> SEQ ID NO 88
<211> LENGTH: 23
<212> TYPE: DNA
<213> ORGANISM: Artificial Sequence
<220> FEATURE:
<223> OTHER INFORMATION: Target sequence

<400> SEQUENCE: 88
aaggagtttc ccaagagccc ctt 23

<210> SEQ ID NO 89
<211> LENGTH: 23
<212> TYPE: DNA
<213> ORGANISM: Artificial Sequence
<220> FEATURE:
<223> OTHER INFORMATION: Target sequence

<400> SEQUENCE: 89
aatgagggat tacatgcctc ctt 23

<210> SEQ ID NO 90
<211> LENGTH: 23
<212> TYPE: DNA
<213> ORGANISM: Artificial Sequence
<220> FEATURE:
<223> OTHER INFORMATION: Target sequence

<400> SEQUENCE: 90
aagagtgtca gggataagac ctt 23

<210> SEQ ID NO 91
<211> LENGTH: 21
<212> TYPE: RNA
<213> ORGANISM: Artificial Sequence
<220> FEATURE:
<223> OTHER INFORMATION: siRNA

<400> SEQUENCE: 91
ugugaagaca gcagugccau u 21

<210> SEQ ID NO 92

<211> LENGTH: 21
<212> TYPE: RNA
<213> ORGANISM: Artificial Sequence
<220> FEATURE:
<223> OTHER INFORMATION: siRNA

<400> SEQUENCE: 92
gacagcagug ccauugucuu u 21

<210> SEQ ID NO 93
<211> LENGTH: 21
<212> TYPE: RNA
<213> ORGANISM: Artificial Sequence
<220> FEATURE:
<223> OTHER INFORMATION: siRNA

<400> SEQUENCE: 93
uugauugaug cucaccagcu u 21

<210> SEQ ID NO 94
<211> LENGTH: 21
<212> TYPE: RNA
<213> ORGANISM: Artificial Sequence
<220> FEATURE:
<223> OTHER INFORMATION: siRNA

<400> SEQUENCE: 94
ccuggagacc aucaucucau u 21

<210> SEQ ID NO 95
<211> LENGTH: 21
<212> TYPE: RNA
<213> ORGANISM: Artificial Sequence
<220> FEATURE:
<223> OTHER INFORMATION: siRNA

<400> SEQUENCE: 95
ccuuaggaca gaugcaugau u 21

<210> SEQ ID NO 96
<211> LENGTH: 21
<212> TYPE: RNA
<213> ORGANISM: Artificial Sequence
<220> FEATURE:
<223> OTHER INFORMATION: siRNA

<400> SEQUENCE: 96
ggaguuuccc aagagccccu u 21

<210> SEQ ID NO 97
<211> LENGTH: 21
<212> TYPE: RNA
<213> ORGANISM: Artificial Sequence
<220> FEATURE:
<223> OTHER INFORMATION: siRNA

<400> SEQUENCE: 97
ugagggauua caugccuccu u 21

<210> SEQ ID NO 98
<211> LENGTH: 21
<212> TYPE: RNA
<213> ORGANISM: Artificial Sequence
<220> FEATURE:
<223> OTHER INFORMATION: siRNA

<400> SEQUENCE: 98
gagugucagg gauaagaccu u 21

<210> SEQ ID NO 99
<211> LENGTH: 25
<212> TYPE: DNA
<213> ORGANISM: Artificial Sequence
<220> FEATURE:
<223> OTHER INFORMATION: siRNA

<400> SEQUENCE: 99
caaacuuccu caauugauug augct 25

<210> SEQ ID NO 100
<211> LENGTH: 25
<212> TYPE: DNA
<213> ORGANISM: Artificial Sequence
<220> FEATURE:
<223> OTHER INFORMATION: siRNA

<400> SEQUENCE: 100
gugccauugu cuuuggaaag cuatc 25

<210> SEQ ID NO 101
<211> LENGTH: 25
<212> TYPE: DNA
<213> ORGANISM: Artificial Sequence
<220> FEATURE:
<223> OTHER INFORMATION: siRNA

<400> SEQUENCE: 101
gugccauugu cuuuggaaag cuatc 25

<210> SEQ ID NO 102
<211> LENGTH: 25
<212> TYPE: RNA
<213> ORGANISM: Artificial Sequence
<220> FEATURE:
<223> OTHER INFORMATION: siRNA

<400> SEQUENCE: 102
caaggaaagu ggugacuuuc uguac 25

<210> SEQ ID NO 103
<211> LENGTH: 25
<212> TYPE: DNA
<213> ORGANISM: Artificial Sequence
<220> FEATURE:
<223> OTHER INFORMATION: siRNA

<400> SEQUENCE: 103
gcagcucaga gcacagugcu ucatg 25

<210> SEQ ID NO 104
<211> LENGTH: 25
<212> TYPE: RNA
<213> ORGANISM: Artificial Sequence
<220> FEATURE:
<223> OTHER INFORMATION: siRNA

<400> SEQUENCE: 104
gcaugggaag ccaaaccauc uccca 25

<210> SEQ ID NO 105
<211> LENGTH: 25
<212> TYPE: DNA
<213> ORGANISM: Artificial Sequence
<220> FEATURE:

<223> OTHER INFORMATION: siRNA

<400> SEQUENCE: 105
agagaaagaa gcagugccug ggata 25

<210> SEQ ID NO 106
<211> LENGTH: 25
<212> TYPE: DNA
<213> ORGANISM: Artificial Sequence
<220> FEATURE:
<223> OTHER INFORMATION: siRNA

<400> SEQUENCE: 106
ccuuaggaca gaugcaugau uaugt 25

<210> SEQ ID NO 107
<211> LENGTH: 21
<212> TYPE: RNA
<213> ORGANISM: Artificial Sequence
<220> FEATURE:
<223> OTHER INFORMATION: siRNA

<400> SEQUENCE: 107
aggcacugcu gucuucacau u 21

<210> SEQ ID NO 108
<211> LENGTH: 21
<212> TYPE: RNA
<213> ORGANISM: Artificial Sequence
<220> FEATURE:
<223> OTHER INFORMATION: siRNA

<400> SEQUENCE: 108
agacaauggc acugcugucu u 21

<210> SEQ ID NO 109
<211> LENGTH: 21
<212> TYPE: RNA
<213> ORGANISM: Artificial Sequence
<220> FEATURE:
<223> OTHER INFORMATION: siRNA

<400> SEQUENCE: 109
gcuggugagc aucaaucaau u 21

<210> SEQ ID NO 110
<211> LENGTH: 21
<212> TYPE: RNA
<213> ORGANISM: Artificial Sequence
<220> FEATURE:
<223> OTHER INFORMATION: siRNA

<400> SEQUENCE: 110
ugacaugaug gucuccaggu u 21

<210> SEQ ID NO 111
<211> LENGTH: 21
<212> TYPE: RNA
<213> ORGANISM: Artificial Sequence
<220> FEATURE:
<223> OTHER INFORMATION: siRNA

<400> SEQUENCE: 111
ucaugcaucu guccgaaggu u 21

<210> SEQ ID NO 112

<211> LENGTH: 21
<212> TYPE: RNA
<213> ORGANISM: Artificial Sequence
<220> FEATURE:
<223> OTHER INFORMATION: siRNA

<400> SEQUENCE: 112
ggggcucuug ggaaacuccu u 21

<210> SEQ ID NO 113
<211> LENGTH: 21
<212> TYPE: RNA
<213> ORGANISM: Artificial Sequence
<220> FEATURE:
<223> OTHER INFORMATION: siRNA

<400> SEQUENCE: 113
ggaggcaugu aaucccucau u 21

<210> SEQ ID NO 114
<211> LENGTH: 21
<212> TYPE: RNA
<213> ORGANISM: Artificial Sequence
<220> FEATURE:
<223> OTHER INFORMATION: siRNA

<400> SEQUENCE: 114
ggucuuaucc cugacacucu u 21

<210> SEQ ID NO 115
<211> LENGTH: 27
<212> TYPE: RNA
<213> ORGANISM: Artificial Sequence
<220> FEATURE:
<223> OTHER INFORMATION: siRNA

<400> SEQUENCE: 115
agcaucaauc aauugaggaa guuuguu 27

<210> SEQ ID NO 116
<211> LENGTH: 27
<212> TYPE: RNA
<213> ORGANISM: Artificial Sequence
<220> FEATURE:
<223> OTHER INFORMATION: siRNA

<400> SEQUENCE: 116
gauagcuuuc caaagacaau ggcacug 27

<210> SEQ ID NO 117
<211> LENGTH: 27
<212> TYPE: RNA
<213> ORGANISM: Artificial Sequence
<220> FEATURE:
<223> OTHER INFORMATION: siRNA

<400> SEQUENCE: 117
cuccaagguc uuaucccuga cacucuu 27

<210> SEQ ID NO 118
<211> LENGTH: 27
<212> TYPE: RNA
<213> ORGANISM: Artificial Sequence
<220> FEATURE:
<223> OTHER INFORMATION: siRNA

<400> SEQUENCE: 118
guacagaaag ucaccacuuu ccuugcu 27

<210> SEQ ID NO 119
<211> LENGTH: 27
<212> TYPE: RNA
<213> ORGANISM: Artificial Sequence
<220> FEATURE:
<223> OTHER INFORMATION: siRNA

<400> SEQUENCE: 119
caugaagcac ugugcucuga gcugcac 27

<210> SEQ ID NO 120
<211> LENGTH: 27
<212> TYPE: RNA
<213> ORGANISM: Artificial Sequence
<220> FEATURE:
<223> OTHER INFORMATION: siRNA

<400> SEQUENCE: 120
ugggagaugg uuuggcuucc caugcuu 27

<210> SEQ ID NO 121
<211> LENGTH: 27
<212> TYPE: RNA
<213> ORGANISM: Artificial Sequence
<220> FEATURE:
<223> OTHER INFORMATION: siRNA

<400> SEQUENCE: 121
uaucccaggc acugcuucuu ucucuac 27

<210> SEQ ID NO 122
<211> LENGTH: 27
<212> TYPE: RNA
<213> ORGANISM: Artificial Sequence
<220> FEATURE:
<223> OTHER INFORMATION: siRNA

<400> SEQUENCE: 122
uaucccaggc acugcuucuu ucucuac 27

<210> SEQ ID NO 123
<211> LENGTH: 27
<212> TYPE: RNA
<213> ORGANISM: Artificial Sequence
<220> FEATURE:
<223> OTHER INFORMATION: siRNA

<400> SEQUENCE: 123
acauaaucau gcaucugucc uaagguu 27

<210> SEQ ID NO 124
<211> LENGTH: 21
<212> TYPE: RNA
<213> ORGANISM: Artificial Sequence
<220> FEATURE:
<223> OTHER INFORMATION: siRNA

<400> SEQUENCE: 124
aaggaaccca gaaggaccgu u 21

<210> SEQ ID NO 125
<211> LENGTH: 21
<212> TYPE: RNA
<213> ORGANISM: Artificial Sequence
<220> FEATURE:

<223> OTHER INFORMATION: siRNA

<400> SEQUENCE: 125
ccuggaaacc aucaucucau u 21

<210> SEQ ID NO 126
<211> LENGTH: 21
<212> TYPE: RNA
<213> ORGANISM: Artificial Sequence
<220> FEATURE:
<223> OTHER INFORMATION: siRNA

<400> SEQUENCE: 126
ugagggacua caugccgccu u 21

<210> SEQ ID NO 127
<211> LENGTH: 21
<212> TYPE: RNA
<213> ORGANISM: Artificial Sequence
<220> FEATURE:
<223> OTHER INFORMATION: siRNA

<400> SEQUENCE: 127
aaggugcugc caagaucucu u 21

<210> SEQ ID NO 128
<211> LENGTH: 25
<212> TYPE: DNA
<213> ORGANISM: Artificial Sequence
<220> FEATURE:
<223> OTHER INFORMATION: siRNA

<400> SEQUENCE: 128
ccagaaggac cguuggaaau cagta 25

<210> SEQ ID NO 129
<211> LENGTH: 25
<212> TYPE: RNA
<213> ORGANISM: Artificial Sequence
<220> FEATURE:
<223> OTHER INFORMATION: siRNA

<400> SEQUENCE: 129
gaaguacucu ggaggaagug cagcc 25

<210> SEQ ID NO 130
<211> LENGTH: 25
<212> TYPE: RNA
<213> ORGANISM: Artificial Sequence
<220> FEATURE:
<223> OTHER INFORMATION: siRNA

<400> SEQUENCE: 130
caaggaaagu guuggcuuuc uacac 25

<210> SEQ ID NO 131
<211> LENGTH: 25
<212> TYPE: RNA
<213> ORGANISM: Artificial Sequence
<220> FEATURE:
<223> OTHER INFORMATION: siRNA

<400> SEQUENCE: 131
ccaugggauu cgucuggcag gaggg 25

<210> SEQ ID NO 132

<211> LENGTH: 25
<212> TYPE: RNA
<213> ORGANISM: Artificial Sequence
<220> FEATURE:
<223> OTHER INFORMATION: siRNA

<400> SEQUENCE: 132
guacugccau gcugagcuuc uugaa 25

<210> SEQ ID NO 133
<211> LENGTH: 25
<212> TYPE: DNA
<213> ORGANISM: Artificial Sequence
<220> FEATURE:
<223> OTHER INFORMATION: siRNA

<400> SEQUENCE: 133
cuaugaaggu gcugccacag agcct 25

<210> SEQ ID NO 134
<211> LENGTH: 25
<212> TYPE: RNA
<213> ORGANISM: Artificial Sequence
<220> FEATURE:
<223> OTHER INFORMATION: siRNA

<400> SEQUENCE: 134
gugucaggga gaagaccaug gaggc 25

<210> SEQ ID NO 135
<211> LENGTH: 25
<212> TYPE: RNA
<213> ORGANISM: Artificial Sequence
<220> FEATURE:
<223> OTHER INFORMATION: siRNA

<400> SEQUENCE: 135
gucagagcau gacgcuggag gugcc 25

<210> SEQ ID NO 136
<211> LENGTH: 21
<212> TYPE: RNA
<213> ORGANISM: Artificial Sequence
<220> FEATURE:
<223> OTHER INFORMATION: siRNA

<400> SEQUENCE: 136
cgguccuucu ggguuccuuu u 21

<210> SEQ ID NO 137
<211> LENGTH: 21
<212> TYPE: RNA
<213> ORGANISM: Artificial Sequence
<220> FEATURE:
<223> OTHER INFORMATION: siRNA

<400> SEQUENCE: 137
ugugaugaug guuuccaggu u 21

<210> SEQ ID NO 138
<211> LENGTH: 21
<212> TYPE: RNA
<213> ORGANISM: Artificial Sequence
<220> FEATURE:
<223> OTHER INFORMATION: siRNA

<400> SEQUENCE: 138
ggcggcaugu agucccucau u 21

<210> SEQ ID NO 139
<211> LENGTH: 21
<212> TYPE: RNA
<213> ORGANISM: Artificial Sequence
<220> FEATURE:
<223> OTHER INFORMATION: siRNA

<400> SEQUENCE: 139
gagaucuugg cagcaccuuu u 21

<210> SEQ ID NO 140
<211> LENGTH: 27
<212> TYPE: RNA
<213> ORGANISM: Artificial Sequence
<220> FEATURE:
<223> OTHER INFORMATION: siRNA

<400> SEQUENCE: 140
uacugauuuc caacgguccu ucugggu 27

<210> SEQ ID NO 141
<211> LENGTH: 27
<212> TYPE: RNA
<213> ORGANISM: Artificial Sequence
<220> FEATURE:
<223> OTHER INFORMATION: siRNA

<400> SEQUENCE: 141
ggcugcacuu ccuccagagu acuucag 27

<210> SEQ ID NO 142
<211> LENGTH: 27
<212> TYPE: RNA
<213> ORGANISM: Artificial Sequence
<220> FEATURE:
<223> OTHER INFORMATION: siRNA

<400> SEQUENCE: 142
guguagaaag ccaacacuuu ccuugca 27

<210> SEQ ID NO 143
<211> LENGTH: 27
<212> TYPE: RNA
<213> ORGANISM: Artificial Sequence
<220> FEATURE:
<223> OTHER INFORMATION: siRNA

<400> SEQUENCE: 143
cccuccugcc agacgaaucc cauggug 27

<210> SEQ ID NO 144
<211> LENGTH: 27
<212> TYPE: RNA
<213> ORGANISM: Artificial Sequence
<220> FEATURE:
<223> OTHER INFORMATION: siRNA

<400> SEQUENCE: 144
uucaagaagc ucagcauggc aguaccc 27

<210> SEQ ID NO 145
<211> LENGTH: 27
<212> TYPE: RNA
<213> ORGANISM: Artificial Sequence
<220> FEATURE:

<223> OTHER INFORMATION: siRNA

<400> SEQUENCE: 145
aggcucugug gcagcaccuu cauagac 27

<210> SEQ ID NO 146
<211> LENGTH: 27
<212> TYPE: RNA
<213> ORGANISM: Artificial Sequence
<220> FEATURE:
<223> OTHER INFORMATION: siRNA

<400> SEQUENCE: 146
gccuccaugg ucuucucccu gacacuc 27

<210> SEQ ID NO 147
<211> LENGTH: 27
<212> TYPE: RNA
<213> ORGANISM: Artificial Sequence
<220> FEATURE:
<223> OTHER INFORMATION: siRNA

<400> SEQUENCE: 147
ggcaccucca gcgucaugcu cugacuu 27

<210> SEQ ID NO 148
<211> LENGTH: 38
<212> TYPE: DNA
<213> ORGANISM: Artificial Sequence
<220> FEATURE:
<223> OTHER INFORMATION: Primer

<400> SEQUENCE: 148
actggcggcc gcatgccgaa tctattacca ttactgcc 38

<210> SEQ ID NO 149
<211> LENGTH: 34
<212> TYPE: DNA
<213> ORGANISM: Artificial Sequence
<220> FEATURE:
<223> OTHER INFORMATION: Primer

<400> SEQUENCE: 149
actgggtacc acaccttcat agaccagccc caca 34

<210> SEQ ID NO 150
<211> LENGTH: 40
<212> TYPE: DNA
<213> ORGANISM: Artificial Sequence
<220> FEATURE:
<223> OTHER INFORMATION: Primer

<400> SEQUENCE: 150
actgcgtacg catatgtgtg gggctggtct atgaaggtgt 40

<210> SEQ ID NO 151
<211> LENGTH: 35
<212> TYPE: DNA
<213> ORGANISM: Artificial Sequence
<220> FEATURE:
<223> OTHER INFORMATION: Primer

<400> SEQUENCE: 151
actggtcgac gggatatagc acaagaacag ctaag 35

<210> SEQ ID NO 152

<211> LENGTH: 37
<212> TYPE: DNA
<213> ORGANISM: Artificial Sequence
<220> FEATURE:
<223> OTHER INFORMATION: Primer

<400> SEQUENCE: 152
actgggcgcg cccttagctg ttcttgtgct atatccc 37

<210> SEQ ID NO 153
<211> LENGTH: 38
<212> TYPE: DNA
<213> ORGANISM: Artificial Sequence
<220> FEATURE:
<223> OTHER INFORMATION: Primer

<400> SEQUENCE: 153
actgcccggg ggtgtctgtg agattttgag aatagtcc 38

<210> SEQ ID NO 154
<211> LENGTH: 865
<212> TYPE: DNA
<213> ORGANISM: Artificial Sequence
<220> FEATURE:
<223> OTHER INFORMATION: Synthetic Sequence

<400> SEQUENCE: 154
atgccgaatc tattaccatt actgccaagt cccattggga gaaaaactaa agtgtgcatt 60
cgtgcatgtg tgcgtgtacg tgtgtgtcta gaactgaaaa ttttatttcc ttgcaagtat 120
cagactagag ttttcctggc ctgctaggtc ctctgttgcc tctccccacc atgtccccaa 180
tttgactcct gacacagcac tggcacttgg catttttcta gaattacaca ttttcctgac 240
ttttctcttg actaccgcca gaggaaattt ctcttaaagg ggctcctgtg gctgtgctca 300
atctagtcgg atgagtcagg gaaattccca cattaaagct aaactgatca gtggccttaa 360
tcccatctga aaagtcctcc tgccctgtcc tgtaataaat atatcatggt gaccggaaca 420
gctcatagta ttaagagtcc taggaattcg gttgggaacc ttggggagct atttttagaa 480
tcctaccctc cagtgtcttt caaaggaatc atttctactt cctcttggca gagacttgat 540
aagaaccaga aggggacttt gtttgcatcg acataagttc cgggcaatga cactttttat 600
ctggtatttg gcataaaggc catccctcca cttcaaatgc tgagactgtt tactgtgccg 660
ctaagtggct gtacaagatc ctaaatgtag ctgtagtttc aacaaacatc tggattgttg 720
ggagtttcca gtagacttct ctttaaaatg tcagcctcgc tattctgcat ctatcccgag 780
tttctcattt gcttctttaa aacacagttt tatttaagag tggatgtcct gtggaaatga 840
gatgtattcc ctccagttcc cagcc 865

<210> SEQ ID NO 155
<211> LENGTH: 948
<212> TYPE: DNA
<213> ORGANISM: Artificial Sequence
<220> FEATURE:
<223> OTHER INFORMATION: Synthetic Sequence

<400> SEQUENCE: 155
tgagtgtatg ctcgtgtatg tatgtgagca ctgcaggtgt ctgcatggtg tgccatggtg 60
ctccactggg cttcatgctg tgctccccta ggcttcagtc aagtcaagac taggtcaagt 120
catggagggt aaacagaaga gagagagagc agaaaatgag ggacacagga agggtagagg 180
gggaaagaga gggttgtgaa gctcacgcgt gatcaggagc cccaggcttt cttcttccag 240
ccgcccatag gctctggtgc ccacaacatt ggttacaacc ccgctctcca tcatcatgct 300
tgtcatcact gctgtgacaa accgcttaat aatggttctc acggaacatt aaaagccaag 360
ccaagtttaa cacctcgaac atttccaagt gttatgggga ataacagtta agtgtctggg 420
tgtgcttgtg tgtaattggg aatctgtagt ggtggggtta ccagtgtcag gccacagtgt 480
ttgtgatgag cagaggggtc ggggtctttc tcagatccct tatcttgtcc tgtcaatggt 540
ggtgatgtaa taggtgcacg cctgtgacag agctgtttaa agcattgtaa gaccaatgag 600
taaagttcct acccttgctt ctcctttaag tgaggcagaa aaaggctcca ccatgacgtg 660
gtgtaaagat gaagtcaatc taatacttcc ttggatactc tagcaagctt cattcacact 720
ttttatttct tcctcttcct cttcctcttc ctcttcctct tcctcttcct cttcccctcc 780
tcctcttcct cctcctcttc ctcctcctct tcctcctcct cctcttcctc cttctcctct 840
tcctcctccc cctcccettc ccctgtgctc ctcattatta ttattattgc tcctgtctag 900
gtggaaggac aatccagcca tgcctgtggg gctggtctat gaaggtgt 948

<210> SEQ ID NO 156
<211> LENGTH: 700
<212> TYPE: DNA
<213> ORGANISM: Artificial Sequence
<220> FEATURE:
<223> OTHER INFORMATION: Synthetic Sequence

<400> SEQUENCE: 156
ggtaccaaag gccgcaatgg ccaaacctgc aggaagtacc agagctccct aggttctaga 60
accggtgacg tcaagctcga ataacttcgt ataatgtatg ctatacgaag ttatcctgca 120
ggtcgatcga gaccgtacgc tatgtgtggg gctggtctat gaaggtgttg ccacagagcc 180
tctgaagtac tctggaggaa gtgcagccca gagctccgtg cttcatgcct tcgatgagtt 240
cctgggcatt gagcattgca aggaaagtgg tgagcagcag tctgatctca cctatgcttt 300
gatgggacag cgaggtagac tagggagaca tctctagcaa ctgataaaga cgggtgtaaa 360
tgaaaatgtc ctgaagttta tccttgccta agccagcagg cagctgtgtg catgtgccct 420
ctcttacact gagttagtca gtattggggc atcggatctt attagggtct tccaacagtc 480
ctgtgacctg ggttgttcac tgtcctgttg gctggggtct tttatccgca gattcccctt 540
tctacaatga ggtgataatg tcacattgaa aggccagtct ggagcagcaa gtgatagtgc 600
tgaacttctc tgctaaagcc tttcccatga aatggcccag cctcccactg aatctatgtg 660
gaccaggcga gggagcccat cgctttgaag cctttaaaat 700

<210> SEQ ID NO 157
<211> LENGTH: 803
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (744)...(744)
<223> OTHER INFORMATION: n = a, c, t, g

<400> SEQUENCE: 157
cagaaatgaa catttgagca tttggcagct ataacaaaag cccgacaagg ctgagggaga 60
gccctatcaa gcatttctgg tacctgagtg tttggaacag tgggcaaacc ctcccaaatg 120
tctgcctcga gctaacgtat ttctcccggc tgtttctttc agttggcttt ctacacagaa 180
tgagggacta catgccgcct tcccataagg ctttcctgga agatctccac gtagctcctt 240

-continued

```
ctctgagaga ctacatactg gcctctggtc ctggggactg cctgatggcc tataaccagt    300

gtgtggaggc cctgggagag ctgcgcagtt accacatcaa tgtcgtggcc agatacatta    360

tctccgctgc caccagggcc aggagcaggg ggctaactaa tccctcaccc catgccttgg    420

aagacagggg cactgggggt actgccatgc tgagcttctt gaagagtgtc agggagaaga    480

ccatggaggc cctcctgtgt cctggtgctt agcagtcatg tcctgcaccc taacacttag    540

atgttctcat cctgcatccc agcgttagag gttcacatcc tgcatcctag tgcttagctg    600

ttcttgtgct atatcccgtc gacgaagttc ctatactttc tagagaatag gaacttcgga    660

tccacgattc gagggcccct gcaggtcaat tctaccgggt aggggaggcg cttttcccaa    720

ggcagtctgg agcatgcgct ttancagccc cgctgggcac ttggcgctac acaagtggcc    780

tctggcctcg cacacattcc aca                                           803
```

<210> SEQ ID NO 158
<211> LENGTH: 575
<212> TYPE: DNA
<213> ORGANISM: Artificial Sequence
<220> FEATURE:
<223> OTHER INFORMATION: Synthetic Sequence

<400> SEQUENCE: 158

```
atcccagcgc ttagcagtca tgtcctgcat cctagtgctt agcattttat atccagcatc     60

ttagtgctta gagattcaca tcctgcatcc tagagcttag cattttatat ccagcatcct    120

tgtgcgtatc agctatgttt tgtatcctgc ttagcagtta acatcctgca tcctagtact    180

tatctgttct catcctgcat cctagagctt agcagtcagg tcccgtggga gcaagaacca    240

gggtctgagc tctgtctgag cccaagcatg gctttactgc tttgttaatt gtggctccca    300

cctccacccc accccagcca gtttgcttgc tagaagcctt tctgcactgc ctaatccccc    360

tgcctcacag cagagagctg cagccatgac ctcctcattc agtattaggt ggacaagtcg    420

gagataccca aactcaattt taaaagaatc aagttgcttt tggggcatgt tacttcatct    480

tttcttaccc tgggcctcta tgacctcctc attcagtatt aggtggacaa gtcggagata    540

cccaaactca attttaaaag aatcaagttg ctttt                              575
```

<210> SEQ ID NO 159
<211> LENGTH: 753
<212> TYPE: DNA
<213> ORGANISM: Artificial Sequence
<220> FEATURE:
<223> OTHER INFORMATION: Synthetic Sequence

<400> SEQUENCE: 159

```
agctctaaga gaaggaatac agcttgggac agagtttgtt ttgaagtggg gttcaggtgc     60

atttcctggg tgtgtccctc atttgggggt gttaggaggc agacaatgct aagggcatgg    120

tttgatatgg tagactgacc atcctggggt cccttcagct tgtgacactc gctgtactgc    180

tggactctgc tgagcccttt gaagccagga ctcctcctct gctgcaggag tgcagtgtcc    240

ttcttgctgt atgaagctgg gacaatgctc tttggccttc atactggaca tcccattgag    300

aagcttgtca ctctgtagag aatagacatc gccccccttgt ggttgtgagg ctgcccagga    360

cttactgcgg gggggggggg ggcatgttgt ccagcataag gagagaagac cccactgcat    420

gctgctggga aaaggaaagt aacgttcaga gtagtttcta ctggctgcct gcgctctcac    480

gcctgtaaga acaaacgtcc taatgtctgc atgtggagga aggagccagg ggtgcttagg    540

gtgctgttgg tcccaccaat gtactactca tctggaagac cttgtcttgg ttttcttgcc    600
```

```
actgggacaa agtgggattg ggtatcagtc tccccatgtc gggcaaatgt acttgaacaa    660

gcagcatggt ggaccagaca tgggactatt ctcaaaatct cacagacacc cccgggggc    720

atgttacttc atcttttctt accctgggcc tct                                753
```

<210> SEQ ID NO 160
<211> LENGTH: 453
<212> TYPE: DNA
<213> ORGANISM: Artificial Sequence
<220> FEATURE:
<223> OTHER INFORMATION: Synthetic Sequence

<400> SEQUENCE: 160

```
ctagggagtc aggaagtcac actggtgaag agtgggggtg tgggatgacc acactgagga     60

gtcacacttg aggaaggggg gtggccacac tgaggagtgt ctgaaagcat tgagactgta    120

catctcaggt tatcagggct tcagagaaaa cagacaggga gaagagacaa gaactggatt    180

ctgtgcgcaa agggggaaaa gcaagcagat gtgaagggtg tgctgttaga gtttatctaa    240

agatgtttct ttcagaaata aagagatata agctttaatt tggatgaaat aaatgtggtc    300

taatttccca gaatgtagag gaactcacta atgtagcaag attggccttt caaagcagac    360

caaagacatt gagaattaag atagctatga tggcgtgctt ccttaggtgg aagtcctata    420

tggaatccca tactccccaa atgtgactgg tcg                                453
```

<210> SEQ ID NO 161
<211> LENGTH: 361
<212> TYPE: DNA
<213> ORGANISM: Artificial Sequence
<220> FEATURE:
<223> OTHER INFORMATION: Synthetic Sequence

<400> SEQUENCE: 161

```
aggcaggagg gtcaggagtt caaggccagc ctagtataca tgcaacagtg tctcaaaaat     60

caaaacagag aggagggcag gaaaggagaa gggagccagg gagagaaggg aagaggaagg    120

gagggagggg gaaatggagg gagggggaga tggagggagg gggagatgga gggaggggga    180

gatggaggga gggggagatg gagggagggg gagatggagg gagggggatg ggaaagaggg    240

tttacagccc tggtttatct tgaacagaat ccttactttg tccctcagag tgacaggact    300

gaaaagattg tcccaggatt ttggctgcaa agcaaggtcc actcagagac cacagagctc    360

g                                                                   361
```

<210> SEQ ID NO 162
<211> LENGTH: 10543
<212> TYPE: DNA
<213> ORGANISM: Artificial Sequence
<220> FEATURE:
<223> OTHER INFORMATION: Synthetic Sequence

<400> SEQUENCE: 162

```
aagctttact cgtaaagcga gttgaaggat catatttagt tgcgtttatg agataagatt     60

gaaagcacgt gtaaaatgtt tcccgcgcgt tggcacaact atttacaatg cggccaagtt    120

ataaaagatt ctaatctgat atgttttaaa acacctttgc ggcccgagtt gtttgcgtac    180

gtgactagcg aagaagatgt gtggaccgca gaacagatag taaaacaaaa ccctagtatt    240

ggagcaataa tcgatttaac caacacgtct aaatattatg atggtgtgca ttttttgcgg    300

gcgggcctgt tatacaaaaa aattcaagta cctggccaga ctttgccgcc tgaaagcata    360

gttcaagaat ttattgacac ggtaaaagaa tttacagaaa agtgtcccgg catgttggtg    420
```

-continued

```
ggcgtgcact gcacacacgg tattaatcgc accggttaca tggtgtgcag atatttaatg    480
cacaccctgg gtattgcgcc gcaggaagcc atagatagat tcgaaaaagc cagaggtcac    540
aaaattgaaa gacaaaatta cgttcaagat ttattaattt aattaatatt atttgcattc    600
tttaacaaat actttatcct attttcaaat tgttgcgctt cttccagcga accaaaacta    660
tgcttcgctt gctccgttta gcttgtagcc gatcagtggc gttgttccaa tcgacggtag    720
gattaggccg gatattctcc accacaatgt tggcaacgtt gatgttacgt ttatgctttt    780
ggttttccac gtacgtcttt tggccggtaa tagccgtaaa cgtagtgccg tcgcgcgtca    840
cgcacaacac cggatgtttg cgcttgtccg cggggtattg aaccgcgcga tccgacaaat    900
ccaccacttt ggcaactaaa tcggtgacct gcgcgtcttt tttctgcatt atttcgtctt    960
tcttttgcat ggtttcctgg aagccggtgt acatgcggtt tagatcagtc atgacgcgcg   1020
tgacctgcaa atctttggcc tcgatctgct tgtccttgat ggcaacgatg cgttcaataa   1080
actcttgttt tttaacaagt tcctcggttt tttgcgccac caccgcttgc agcgcgtttg   1140
tgtgctcggt gaatgtcgca atcagcttag tcaccaactg tttgctctcc tcctcccgtt   1200
gtttgatcgc gggatcgtac ttgccggtgc agagcacttg aggaattact tcttctaaaa   1260
gccattcttg taattctatg gcgtaaggca atttggactt cataatcagc tgaatcacgc   1320
cggatttagt aatgagcact gtatgcggct gcaaatacag cgggtcgccc cttttcacga   1380
cgctgttaga ggtagggccc ccatttgga tggtctgctc aaataacgat ttgtatttat   1440
tgtctacatg aacacgtata gctttatcac aaactgtata ttttaaactg ttagcgacgt   1500
ccttggccac gaaccggacc tgttggtcgc gctctagcac gtaccgcagg ttgaacgtat   1560
cttctccaaa tttaaattct ccaattttaa cgcgagccat tttgatacac gtgtgtcgat   1620
tttgcaacaa ctattgtttt ttaacgcaaa ctaaacttat tgtggtaagc aataattaaa   1680
tatgggggaa catgcgccgc tacaacactc gtcgttatga acgcagacgg cgccggtctc   1740
ggcgcaagcg gctaaaacgt gttgcgcgtt caacgcggca aacatcgcaa aagccaatag   1800
tacagttttg atttgcatat taacggcgat tttttaaatt atcttattta ataaatagtt   1860
atgacgccta caactccccg cccgcgttga ctcgctgcac ctcgagcagt tcgttgacgc   1920
cttcctccgt gtggccgaac acgtcgagcg ggtggtcgat gaccagcggc gtgccgcacg   1980
cgacgcacaa gtatctgtac accgaatgat cgtcgggcga aggcacgtcg gcctccaagt   2040
ggcaatattg gcaaattcga aaatatatac agttgggttg tttgcgcata tctatcgtgg   2100
cgttgggcat gtacgtccga acgttgattt gcatgcaagc cgaaattaaa tcattgcgat   2160
tagtgcgatt aaaacgttgt acatcctcgc ttttaatcat gccgtcgatt aaatcgcgca   2220
atcgagtcaa gtgatcaaag tgtggaataa tgttttcttt gtattcccga gtcaagcgca   2280
gcgcgtattt taacaaacta gccatcttgt aagttagttt catttaatgc aactttatcc   2340
aataatatat tatgtatcgc acgtcaagaa ttaacaatgc gcccgttgtc gcatctcaac   2400
acgactatga tagagatcaa ataaagcgcg aattaaatag cttgcgacgc aacgtgcacg   2460
atctgtgcac gcgttccggc acgagctttg attgtaataa gtttttacga agcgatgaca   2520
tgacccccgt agtgacaacg atcacgccca aaagaactgc cgactacaaa attaccgagt   2580
atgtcggtga cgttaaaact attaagccat ccaatcgacc gttagtcgaa tcaggaccgc   2640
tggtgcgaga agccgcgaag tatggcgaat gcatcgtata acgtgtggag tccgctcatt   2700
agagcgtcat gtttagacaa gaaagctaca tatttaattg atcccgatga ttttattgat   2760
aaattgaccc taactccata cacggtattc tacaatggcg gggttttggt caaaatttcc   2820
```

-continued

```
ggactgcgat tgtacatgct gttaacggct ccgcccacta ttaatgaaat taaaaattcc   2880

aattttaaaa aacgcagcaa gagaaacatt tgtatgaaag aatgcgtaga aggaaagaaa   2940

aatgtcgtcg acatgctgaa caacaagatt aatatgcctc cgtgtataaa aaaaatattg   3000

aacgatttga aagaaaacaa tgtaccgcgc ggcggtatgt acaggaagag gtttatacta   3060

aactgttaca ttgcaaacgt ggtttcgtgt gccaagtgtg aaaaccgatg tttaatcaag   3120

gctctgacgc atttctacaa ccacgactcc aagtgtgtgg gtgaagtcat gcatctttta   3180

atcaaatccc aagatgtgta taaaccacca aactgccaaa aatgaaaac tgtcgacaag   3240

ctctgtccgt ttgctggcaa ctgcaagggt ctcaatccta tttgtaatta ttgaataata   3300

aaacaattat aaatgctaaa tttgtttttt attaacgata caaaccaaac gcaacaagaa   3360

catttgtagt attatctata attgaaaacg cgtagttata atcgctgagg taatatttaa   3420

aatcattttc aaatgattca cagttaattt gcgacaatat aattttattt tcacataaac   3480

tagacgcctt gtcgtcttct tcttcgtatt ccttctcttt ttcatttttc tcctcataaa   3540

aattaacata gttattatcg tatccatata tgtatctatc gtatagagta aattttttgt   3600

tgtcataaat atatatgtct tttttaatgg ggtgtatagt accgctgcgc atagtttttc   3660

tgtaatttac aacagtgcta ttttctggta gttcttcgga gtgtgttgct ttaattatta   3720

aatttatata atcaatgaat ttgggatcgt cggttttgta caatatgttg ccggcatagt   3780

acgcagcttc ttctagttca attacaccat tttttagcag caccggatta acataacttt   3840

ccaaaatgtt gtacgaaccg ttaaacaaaa acagttcacc tcccttttct atactattgt   3900

ctgcgagcag ttgtttgttg ttaaaaataa cagccattgt aatgagacgc acaaactaat   3960

atcacaaact ggaaatgtct atcaatatat agttgctgat atcatggaga taattaaaat   4020

gataaccatc tcgcaaataa ataagtattt tactgttttc gtaacagttt tgtaataaaa   4080

aaacctataa atattccgga ttattcatac cgtcccacca tcgggcgcgg atcagatctg   4140

cagcggccgc tccagaattc tagaaggtac catggagcct caaagtcaga gcatgacgct   4200

ggaggtgccg ttgtccttgg ggagatacca catttctgag gaatatggct ttctccttcc   4260

aaatcctctg gaagcacttc cagatcatta caagccttgg atggaaattg ccctcagact   4320

tcctcactta atcgagaacc gccagctccg agctcacgtg tacaggatgc ctctcctgga   4380

ctgcagattc ctaaagagtt accgtgagca gcgcctggca cacatggcgc tggccgctat   4440

caccatggga ttcgtctggc aggaggggga aggccaaccc caaaaggtgc tgccaagatc   4500

tcttgccatt ccttttgttg aggtatccag gaacttggga ctcccgccta tcctggtcca   4560

ctctgacctg gtgctgacaa actggaccaa aaggaaccca gaaggaccgt tggaaatcag   4620

taacctggaa accatcatct catttccggg gggagagagc ctgcggggct tcatcctagt   4680

gacagtcttg gtggagaagg cagcagtgcc cggccttaag gccctggttc agggaatgga   4740

ggccattcgg caacacagtc aggacaccct gctagaagcc ctgcagcagc tgagactctc   4800

catccaggat atcaccagag ccttggccca aatgcatgat tatgtggacc cagacatatt   4860

ttactcggtc atccggatct tcctctctgg gtggaaggac aatccagcca tgcctgtggg   4920

gctggtctat gaaggtgctg ccacagagcc tctgaagtac tctggaggaa gtgcagccca   4980

gagctccgtg cttcatgcct tcgatgagtt cctgggcatt gagcattgca aggaaagtgt   5040

tggctttcta cacagaatga gggactacat gccgccttcc cataaggctt tcctggaaga   5100

tctccacgta gctccttctc tgagagacta catactggcc tctggtcctg gggactgcct   5160

gatggcctat aaccagtgtg tggaggccct gggagagctg cgcagttacc acatcaatgt   5220
```

-continued

```
cgtggccaga tacattatct ccgctgccac cagggccagg agcagggggc taactaatcc   5280
ctcaccccat gccttggaag acaggggcac tgggggtact gccatgctga gcttcttgaa   5340
gagtgtcagg gagaagacca tggaggccct cctgtgtcct ggtgcttagg gtcaagacaa   5400
ttctgcagat atccagcaca gtggcggccg ctcgagtcta gagggcccgc ggttcgaagg   5460
taagcctatc cctaaccctc tcctcggtct cgattctacg cgtaccggtc atcatcacca   5520
tcaccattga gtttgctagc cactagtacc gactctgctg aagaggagga aattctcctt   5580
gaagtttccc tggtgttcaa agtaaaggag tttgcaccag acgcacctct gttcactggt   5640
ccggcgtatt aaaacacgat acattgttat tagtacattt attaagcgct agattctgtg   5700
cgttgttgat ttacagacaa ttgttgtacg tattttaata attcattaaa tttataatct   5760
ttagggtggt atgttagagc gaaaatcaaa tgattttcag cgtctttata tctgaattta   5820
aatattaaat cctcaataga tttgtaaaat aggtttcgat tagtttcaaa caagggttgt   5880
ttttccgaac cgatggctgg actatctaat ggattttcgc tcaacgccac aaaacttgcc   5940
aaatcttgta gcagcaatct agctttgtcg atattcgttt gtgttttgtt ttgtaataaa   6000
ggttcgacgt cgttcaaaat attatgcgct tttgtatttc tttcatcact gtcgttagtg   6060
tacaattgac tcgacgtaaa cacgttaaat aaagcttgga catatttaac atcgggcgtg   6120
ttagctttat taggccgatt atcgtcgtcg tcccaaccct cgtcgttaga agttgcttcc   6180
gaagacgatt ttgccatagc cacacgacgc ctattaattg tgtcggctaa cacgtccgcg   6240
atcaaatttg tagttgagct ttttggaatt atttctgatt gcgggcgttt ttgggcgggt   6300
ttcaatctaa ctgtgcccga ttttaattca gacaacacgt tagaaagcga tggtgcaggc   6360
ggtggtaaca tttcagacgg caaatctact aatggcggcg gtggtggagc tgatgataaa   6420
tctaccatcg gtggaggcgc aggcggggct ggcggcggag gcggaggcgg aggtggtggc   6480
ggtgatgcag acggcggttt aggctcaaat gtctctttag gcaacacagt cggcacctca   6540
actattgtac tggtttcggg cgccgttttt ggtttgaccg gtctgagacg agtgcgattt   6600
ttttcgtttc taatagcttc caacaattgt tgtctgtcgt ctaaaggtgc agcgggttga   6660
ggttccgtcg gcattggtgg agcgggcggc aattcagaca tcgatggtgg tggtggtggt   6720
ggaggcgctg gaatgttagg cacgggagaa ggtggtggcg gcggtgccgc cggtataatt   6780
tgttctggtt tagtttgttc gcgcacgatt gtgggcaccg gcgcaggcgc cgctggctgc   6840
acaacggaag gtcgtctgct tcgaggcagc gcttggggtg gtggcaattc aatattataa   6900
ttggaataca aatcgtaaaa atctgctata agcattgtaa tttcgctatc gtttaccgtg   6960
ccgatattta acaaccgctc aatgtaagca attgtattgt aaagagattg tctcaagctc   7020
gccgcacgcc gataacaagc cttttcattt ttactacagc attgtagtgg cgagacactt   7080
cgctgtcgtc gacgtacatg tatgctttgt tgtcaaaaac gtcgttggca agctttaaaa   7140
tatttaaaag aacatctctg ttcagcacca ctgtgttgtc gtaaatgttg tttttgataa   7200
tttgcgcttc cgcagtatcg acacgttcaa aaaattgatg cgcatcaatt ttgttgttcc   7260
tattattgaa taaataagat tgtacagatt catatctacg attcgtcatg gccaccacaa   7320
atgctacgct gcaaacgctg gtacaatttt acgaaaactg caaaaacgtc aaaactcggt   7380
ataaaataat caacgggcgc tttggcaaaa tatctatttt atcgcacaag cccactagca   7440
aattgtattt gcagaaaaca atttcggcgc acaattttaa cgctgacgaa ataaaagttc   7500
accagttaat gagcgaccac ccaaatttta taaaaatcta ttttaatcac ggttccatca   7560
acaaccaagt gatcgtgatg gactacattg actgtcccga tttatttgaa acactacaaa   7620
```

ttaaaggcga gctttcgtac caacttgtta gcaatattat tagacagctg tgtgaagcgc 7680
tcaacgattt gcacaagcac aatttcatac acaacgacat aaaactcgaa aatgtcttat 7740
atttcgaagc acttgatcgc gtgtatgttt gcgattacgg attgtgcaaa cacgaaaact 7800
cacttagcgt gcacgacggc acgttggagt attttagtcc ggaaaaaatt cgacacacaa 7860
ctatgcacgt ttcgtttgac tggtacgcgg cgtgttaaca tacaagttgc taacgtaatc 7920
atggtcatag ctgtttcctg tgtgaaattg ttatccgctc acaattccac acaacatacg 7980
agccggaagc ataaagtgta aagcctgggg tgcctaatga gtgagctaac tcacattaat 8040
tgcgttgcgc tcactgcccg ctttccagtc gggaaacctg tcgtgccagc tgcattaatg 8100
aatcggccaa cgcgcgggga gaggcggttt gcgtattggg cgctcttccg cttcctcgct 8160
cactgactcg ctgcgctcgg tcgttcggct gcggcgagcg gtatcagctc actcaaaggc 8220
ggtaatacgg ttatccacag aatcagggga taacgcagga aagaacatgt gagcaaaagg 8280
ccagcaaaag gccaggaacc gtaaaaaggc cgcgttgctg gcgtttttcc ataggctccg 8340
cccccctgac gagcatcaca aaaatcgacg ctcaagtcag aggtggcgaa acccgacagg 8400
actataaaga taccaggcgt ttccccctgg aagctccctc gtgcgctctc ctgttccgac 8460
cctgccgctt accggatacc tgtccgcctt tctcccttcg ggaagcgtgg cgctttctca 8520
tagctcacgc tgtaggtatc tcagttcggt gtaggtcgtt cgctccaagc tgggctgtgt 8580
gcacgaaccc cccgttcagc ccgaccgctg cgccttatcc ggtaactatc gtcttgagtc 8640
caacccggta agacacgact tatcgccact ggcagcagcc actggtaaca ggattagcag 8700
agcgaggtat gtaggcggtg ctacagagtt cttgaagtgg tggcctaact acggctacac 8760
tagaaggaca gtatttggta tctgcgctct gctgaagcca gttaccttcg gaaaaagagt 8820
tggtagctct tgatccggca aacaaaccac cgctggtagc ggtggttttt ttgtttgcaa 8880
gcagcagatt acgcgcagaa aaaaaggatc tcaagaagat cctttgatct tttctacggg 8940
gtctgacgct cagtggaacg aaaactcacg ttaagggatt ttggtcatga gattatcaaa 9000
aaggatcttc acctagatcc ttttaaatta aaaatgaagt tttaaatcaa tctaaagtat 9060
atatgagtaa acttggtctg acagttacca atgcttaatc agtgaggcac ctatctcagc 9120
gatctgtcta tttcgttcat ccatagttgc ctgactcccc gtcgtgtaga taactacgat 9180
acgggagggc ttaccatctg gccccagtgc tgcaatgata ccgcgagacc cacgctcacc 9240
ggctccagat ttatcagcaa taaaccagcc agccggaagg gccgagcgca gaagtggtcc 9300
tgcaacttta tccgcctcca tccagtctat taattgttgc cgggaagcta gagtaagtag 9360
ttcgccagtt aatagtttgc gcaacgttgt tgccattgct acaggcatcg tggtgtcacg 9420
ctcgtcgttt ggtatggctt cattcagctc cggttcccaa cgatcaaggc gagttacatg 9480
atcccccatg ttgtgcaaaa aagcggttag ctccttcggt cctccgatcg ttgtcagaag 9540
taagttggcc gcagtgttat cactcatggt tatggcagca ctgcataatt ctcttactgt 9600
catgccatcc gtaagatgct tttctgtgac tggtgagtac tcaaccaagt cattctgaga 9660
atagtgtatg cggcgaccga gttgctcttg cccggcgtca atacgggata ataccgcgcc 9720
acatagcaga actttaaaag tgctcatcat tggaaaacgt tcttcggggc gaaaactctc 9780
aaggatctta ccgctgttga gatccagttc gatgtaaccc actcgtgcac ccaactgatc 9840
ttcagcatct tttactttca ccagcgtttc tgggtgagca aaaacaggaa ggcaaaatgc 9900
cgcaaaaaag ggaataaggg cgacacggaa atgttgaata ctcatactct tcctttttca 9960
atattattga agcatttatc agggttattg tctcatgagc ggatacatat ttgaatgtat 10020

-continued

```
ttagaaaaat aaacaaatag gggttccgcg cacatttccc cgaaaagtgc cacctgacgt  10080

ctaagaaacc attattatca tgacattaac ctataaaaat aggcgtatca cgaggccctt  10140

tcgtctcgcg cgtttcggtg atgacggtga aaacctctga cacatgcagc tcccggagac  10200

ggtcacagct tgtctgtaag cggatgccgg gagcagacaa gcccgtcagg gcgcgtcagc  10260

gggtgttggc gggtgtcggg gctggcttaa ctatgcggca tcagagcaga ttgtactgag  10320

agtgcaccat atgcggtgtg aaataccgca cagatgcgta aggagaaaat accgcatcag  10380

gcgccattcg ccattcaggc tgcgcaactg ttgggaaggg cgatcggtgc gggcctcttc  10440

gctattacgc cagctggcga aagggggatg tgctgcaagg cgattaagtt gggtaacgcc  10500

agggttttcc cagtcacgac gttgtaaaac gacggccagt gcc                    10543
```

<210> SEQ ID NO 163
<211> LENGTH: 10511
<212> TYPE: DNA
<213> ORGANISM: Artificial Sequence
<220> FEATURE:
<223> OTHER INFORMATION: Synthetic Sequence

<400> SEQUENCE: 163

```
aagctttact cgtaaagcga gttgaaggat catatttagt tgcgtttatg agataagatt     60

gaaagcacgt gtaaaatgtt tcccgcgcgt tggcacaact atttacaatg cggccaagtt    120

ataaaagatt ctaatctgat atgttttaaa acacctttgc ggcccgagtt gtttgcgtac    180

gtgactagcg aagaagatgt gtggaccgca gaacagatag taaaacaaaa ccctagtatt    240

ggagcaataa tcgatttaac caacacgtct aaatattatg atggtgtgca ttttttgcgg    300

gcgggcctgt tatacaaaaa aattcaagta cctggccaga ctttgccgcc tgaaagcata    360

gttcaagaat ttattgacac ggtaaaagaa tttacagaaa agtgtcccgg catgttggtg    420

ggcgtgcact gcacacacgg tattaatcgc accggttaca tggtgtgcag atatttaatg    480

cacaccctgg gtattgcgcc gcaggaagcc atagatagat tcgaaaaagc cagaggtcac    540

aaaattgaaa gacaaaatta cgttcaagat ttattaattt aattaatatt atttgcattc    600

tttaacaaat actttatcct attttcaaat tgttgcgctt cttccagcga accaaaacta    660

tgcttcgctt gctccgttta gcttgtagcc gatcagtggc gttgttccaa tcgacggtag    720

gattaggccg gatattctcc accacaatgt tggcaacgtt gatgttacgt ttatgctttt    780

ggttttccac gtacgtcttt tggccggtaa tagccgtaaa cgtagtgccg tcgcgcgtca    840

cgcacaacac cggatgtttg cgcttgtccg cggggtattg aaccgcgcga tccgacaaat    900

ccaccacttt ggcaactaaa tcggtgacct gcgcgtcttt tttctgcatt atttcgtctt    960

tcttttgcat ggtttcctgg aagccggtgt acatgcggtt tagatcagtc atgacgcgcg   1020

tgacctgcaa atctttggcc tcgatctgct tgtccttgat ggcaacgatg cgttcaataa   1080

actcttgttt tttaacaagt tcctcggttt tttgcgccac caccgcttgc agcgcgtttg   1140

tgtgctcggt gaatgtcgca atcagcttag tcaccaactg tttgctctcc tcctcccgtt   1200

gtttgatcgc gggatcgtac ttgccggtgc agagcacttg aggaattact tcttctaaaa   1260

gccattcttg taattctatg gcgtaaggca atttggactt cataatcagc tgaatcacgc   1320

cggatttagt aatgagcact gtatgcggct gcaaatacag cgggtcgccc cttttcacga   1380

cgctgttaga ggtagggccc ccattttgga tggtctgctc aaataacgat ttgtatttat   1440

tgtctacatg aacacgtata gctttatcac aaactgtata ttttaaactg ttagcgacgt   1500

ccttggccac gaaccggacc tgttggtcgc gctctagcac gtaccgcagg ttgaacgtat   1560
```

-continued

```
cttctccaaa tttaaattct ccaattttaa cgcgagccat tttgatacac gtgtgtcgat   1620
tttgcaacaa ctattgtttt ttaacgcaaa ctaaacttat tgtggtaagc aataattaaa   1680
tatgggggaa catgcgccgc tacaacactc gtcgttatga acgcagacgg cgccggtctc   1740
ggcgcaagcg gctaaaacgt gttgcgcgtt caacgcggca aacatcgcaa aagccaatag   1800
tacagttttg atttgcatat taacggcgat tttttaaatt atcttattta ataaatagtt   1860
atgacgccta caactccccg cccgcgttga ctcgctgcac ctcgagcagt tcgttgacgc   1920
cttcctccgt gtggccgaac acgtcgagcg ggtggtcgat gaccagcggc gtgccgcacg   1980
cgacgcacaa gtatctgtac accgaatgat cgtcgggcga aggcacgtcg gcctccaagt   2040
ggcaatattg gcaaattcga aaatatatac agttgggttg tttgcgcata tctatcgtgg   2100
cgttgggcat gtacgtccga acgttgattt gcatgcaagc cgaaattaaa tcattgcgat   2160
tagtgcgatt aaaacgttgt acatcctcgc ttttaatcat gccgtcgatt aaatcgcgca   2220
atcgagtcaa gtgatcaaag tgtggaataa tgtttttcttt gtattcccga gtcaagcgca   2280
gcgcgtattt taacaaacta gccatcttgt aagttagttt catttaatgc aactttatcc   2340
aataatatat tatgtatcgc acgtcaagaa ttaacaatgc gcccgttgtc gcatctcaac   2400
acgactatga tagagatcaa ataaagcgcg aattaaatag cttgcgacgc aacgtgcacg   2460
atctgtgcac gcgttccggc acgagctttg attgtaataa gtttttacga agcgatgaca   2520
tgacccccgt agtgacaacg atcacgccca aaagaactgc cgactacaaa attaccgagt   2580
atgtcggtga cgttaaaact attaagccat ccaatcgacc gttagtcgaa tcaggaccgc   2640
tggtgcgaga agccgcgaag tatggcgaat gcatcgtata acgtgtggag tccgctcatt   2700
agagcgtcat gtttagacaa gaaagctaca tatttaattg atcccgatga ttttattgat   2760
aaattgaccc taactccata cacggtattc tacaatggcg gggttttggt caaaatttcc   2820
ggactgcgat tgtacatgct gttaacggct ccgcccacta ttaatgaaat taaaaattcc   2880
aattttaaaa aacgcagcaa gagaaacatt tgtatgaaag aatgcgtaga aggaaagaaa   2940
aatgtcgtcg acatgctgaa caacaagatt aatatgcctc cgtgtataaa aaaaatattg   3000
aacgatttga aagaaaacaa tgtaccgcgc ggcggtatgt acaggaagag gtttatacta   3060
aactgttaca ttgcaaacgt ggtttcgtgt gccaagtgtg aaaaccgatg tttaatcaag   3120
gctctgacgc atttctacaa ccacgactcc aagtgtgtgg gtgaagtcat gcatctttta   3180
atcaaatccc aagatgtgta taaaccacca aactgccaaa aaatgaaaac tgtcgacaag   3240
ctctgtccgt ttgctggcaa ctgcaagggt ctcaatccta tttgtaatta ttgaataata   3300
aaacaattat aaatgctaaa tttgtttttt attaacgata caaaccaaac gcaacaagaa   3360
catttgtagt attatctata attgaaaacg cgtagttata atcgctgagg taatatttaa   3420
aatcattttc aaatgattca cagttaattt gcgacaatat aattttattt tcacataaac   3480
tagacgcctt gtcgtcttct tcttcgtatt ccttctcttt ttcatttttc tcctcataaa   3540
aattaacata gttattatcg tatccatata tgtatctatc gtatagagta aatttttgt    3600
tgtcataaat atatatgtct tttttaatgg ggtgtatagt accgctgcgc atagtttttc   3660
tgtaatttac aacagtgcta ttttctggta gttcttcgga gtgtgttgct ttaattatta   3720
aatttatata atcaatgaat ttgggatcgt cggttttgta caatatgttg ccggcatagt   3780
acgcagcttc ttctagttca attacaccat tttttagcag caccggatta acataacttt   3840
ccaaaatgtt gtacgaaccg ttaaacaaaa acagttcacc tccctttttct atactattgt  3900
ctgcgagcag ttgtttgttg ttaaaaataa cagccattgt aatgagacgc acaaactaat   3960
```

-continued atcacaaact ggaaatgtct atcaatatat agttgctgat atcatggaga taattaaaat 4020
gataaccatc tcgcaaataa ataagtattt tactgttttc gtaacagttt tgtaataaaa 4080
aaacctataa atattccgga ttattcatac cgtcccacca tcgggcgcgg atcagatctg 4140
cagcggccgc tccagaattc tagaaggtac ccatggagcc ccacagaccg aatgtgaaga 4200
cagcagtgcc attgtctttg gaaagctatc acatatctga agagtatggc tttcttcttc 4260
cagattctct gaaagaactt ccagatcatt ataggccttg gatggaaatt gccaacaaac 4320
ttcctcaatt gattgatgct caccagcttc aagctcatgt ggacaagatg cccctgctga 4380
gctgccagtt cctgaagggt caccgggagc agcgcctggc ccacctggtc ctgagcttcc 4440
tcaccatggg ttatgtctgg caggaaggag aggcgcagcc tgcagaggtc ctgccaagga 4500
atcttgccct tccatttgtc gaagtctcca ggaacttggg gctccctcct atcctggtcc 4560
actcagactt ggtgctgacg aactggacca aaaaagatcc agacgggttc ctggaaattg 4620
ggaacctgga gaccatcatc tcatttcctg gggagagag cctgcatggt tttatactgg 4680
tgactgcttt ggtagagaaa gaagcagtgc ctgggataaa ggctcttgtt caggccacga 4740
atgctatctt gcagcccaac caggaggccc tgctccaagc cctgcagcga ctgagactgt 4800
ctattcagga catcaccaaa accttaggac agatgcatga ttatgtagat ccagacatat 4860
tttatgcagg catccggatc tttctctctg ggtggaaaga caacccagca atgcctgcag 4920
ggctgatgta tgaaggagtt tcccaagagc ccctgaaata ctccggcggg agtgcagctc 4980
agagcacagt gcttcatgcc tttgatgagt tcttaggcat tcgtcatagc aaggaaagtg 5040
gtgactttct gtacagaatg agggattaca tgcctccttc ccataaggcc ttcatagaag 5100
acatccactc agcaccttcc ctgagggact acatcctgtc atctggacag gaccacttgc 5160
tgacagctta taaccagtgt gtgcaggccc tggcagagct gcggagctat cacatcacca 5220
tggtcaccaa atacctcatc acagctgcag ccaaggcaaa gcatgggaag ccaaaccatc 5280
tcccagggcc tcctcaggct ttaaaagaca ggggcacagg tggaaccgca gttatgagct 5340
ttcttaagag tgtcagggat aagaccttgg agtcaatcct tcacccacgt ggttaacgct 5400
cgagtctaga gggcccgcgg ttcgaaggta agcctatccc taaccctctc ctcggtctcg 5460
attctacgcg taccggtcat catcaccatc accattgagt ttgctagcca ctagtaccga 5520
ctctgctgaa gaggaggaaa ttctccttga agtttccctg gtgttcaaag taaaggagtt 5580
tgcaccagac gcacctctgt tcactggtcc ggcgtattaa aacacgatac attgttatta 5640
gtacatttat taagcgctag attctgtgcg ttgttgattt acagacaatt gttgtacgta 5700
ttttaataat tcattaaatt tataatcttt agggtggtat gttagagcga aaatcaaatg 5760
attttcagcg tctttatatc tgaatttaaa tattaaatcc tcaatagatt tgtaaaatag 5820
gtttcgatta gtttcaaaca agggttgttt ttccgaaccg atggctggac tatctaatgg 5880
attttcgctc aacgccacaa aacttgccaa atcttgtagc agcaatctag ctttgtcgat 5940
attcgtttgt gttttgtttt gtaataaagg ttcgacgtcg ttcaaaatat tatgcgcttt 6000
tgtatttctt tcatcactgt cgttagtgta caattgactc gacgtaaaca cgttaaataa 6060
agcttggaca tatttaacat cgggcgtgtt agctttatta ggccgattat cgtcgtcgtc 6120
ccaaccctcg tcgttagaag ttgcttccga agacgatttt gccatagcca cacgacgcct 6180
attaattgtg tcggctaaca cgtccgcgat caaatttgta gttgagcttt ttggaattat 6240
ttctgattgc gggcgttttt gggcgggttt caatctaact gtgcccgatt ttaattcaga 6300
caacacgtta gaaagcgatg gtgcaggcgg tggtaacatt tcagacggca aatctactaa 6360

-continued

```
tggcggcggt ggtggagctg atgataaatc taccatcggt ggaggcgcag gcggggctgg   6420
cggcggaggc ggaggcggag gtggtggcgg tgatgcagac ggcggtttag gctcaaatgt   6480
ctctttaggc aacacagtcg gcacctcaac tattgtactg gtttcgggcg ccgtttttgg   6540
tttgaccggt ctgagacgag tgcgattttt ttcgtttcta atagcttcca acaattgttg   6600
tctgtcgtct aaaggtgcag cgggttgagg ttccgtcggc attggtggag cgggcggcaa   6660
ttcagacatc gatggtggtg gtggtggtgg aggcgctgga atgttaggca cgggagaagg   6720
tggtggcggc ggtgccgccg gtataatttg ttctggttta gtttgttcgc gcacgattgt   6780
gggcaccggc gcaggcgccg ctggctgcac aacggaaggt cgtctgcttc gaggcagcgc   6840
ttggggtggt ggcaattcaa tattataatt ggaatacaaa tcgtaaaaat ctgctataag   6900
cattgtaatt tcgctatcgt ttaccgtgcc gatatttaac aaccgctcaa tgtaagcaat   6960
tgtattgtaa agagattgtc tcaagctcgc cgcacgccga taacaagcct tttcattttt   7020
actacagcat tgtagtggcg agacacttcg ctgtcgtcga cgtacatgta tgctttgttg   7080
tcaaaaacgt cgttggcaag ctttaaaata tttaaaagaa catctctgtt cagcaccact   7140
gtgttgtcgt aaatgttgtt tttgataatt tgcgcttccg cagtatcgac acgttcaaaa   7200
aattgatgcg catcaatttt gttgttccta ttattgaata aataagattg tacagattca   7260
tatctacgat tcgtcatggc caccacaaat gctacgctgc aaacgctggt acaattttac   7320
gaaaactgca aaaacgtcaa aactcggtat aaaataatca acgggcgctt tggcaaaata   7380
tctattttat cgcacaagcc cactagcaaa ttgtatttgc agaaaacaat ttcggcgcac   7440
aattttaacg ctgacgaaat aaaagttcac cagttaatga gcgaccaccc aaattttata   7500
aaaatctatt ttaatcacgg ttccatcaac aaccaagtga tcgtgatgga ctacattgac   7560
tgtcccgatt tatttgaaac actacaaatt aaaggcgagc tttcgtacca acttgttagc   7620
aatattatta gacagctgtg tgaagcgctc aacgatttgc acaagcacaa tttcatacac   7680
aacgacataa aactcgaaaa tgtcttatat ttcgaagcac ttgatcgcgt gtatgtttgc   7740
gattacggat tgtgcaaaca cgaaaactca cttagcgtgc acgacggcac gttggagtat   7800
tttagtccgg aaaaaattcg acacacaact atgcacgttt cgtttgactg gtacgcggcg   7860
tgttaacata caagttgcta acgtaatcat ggtcatagct gtttcctgtg tgaaattgtt   7920
atccgctcac aattccacac aacatacgag ccggaagcat aaagtgtaaa gcctggggtg   7980
cctaatgagt gagctaactc acattaattg cgttgcgctc actgcccgct ttccagtcgg   8040
gaaacctgtc gtgccagctg cattaatgaa tcggccaacg cgcggggaga ggcggtttgc   8100
gtattgggcg ctcttccgct tcctcgctca ctgactcgct gcgctcggtc gttcggctgc   8160
ggcgagcggt atcagctcac tcaaaggcgg taatacggtt atccacagaa tcaggggata   8220
acgcaggaaa gaacatgtga gcaaaaggcc agcaaaaggc caggaaccgt aaaaaggccg   8280
cgttgctggc gtttttccat aggctccgcc cccctgacga gcatcacaaa aatcgacgct   8340
caagtcagag gtggcgaaac ccgacaggac tataaagata ccaggcgttt ccccctggaa   8400
gctccctcgt gcgctctcct gttccgaccc tgccgcttac cggatacctg tccgcctttc   8460
tcccttcggg aagcgtggcg ctttctcata gctcacgctg taggtatctc agttcggtgt   8520
aggtcgttcg ctccaagctg ggctgtgtgc acgaaccccc cgttcagccc gaccgctgcg   8580
ccttatccgg taactatcgt cttgagtcca acccggtaag acacgactta tcgccactgg   8640
cagcagccac tggtaacagg attagcagag cgaggtatgt aggcggtgct acagagttct   8700
tgaagtggtg gcctaactac ggctacacta gaaggacagt atttggtatc tgcgctctgc   8760
```

-continued

```
tgaagccagt taccttcgga aaaagagttg gtagctcttg atccggcaaa caaaccaccg   8820

ctggtagcgg tggttttttt gtttgcaagc agcagattac gcgcagaaaa aaaggatctc   8880

aagaagatcc tttgatcttt tctacggggt ctgacgctca gtggaacgaa aactcacgtt   8940

aagggatttt ggtcatgaga ttatcaaaaa ggatcttcac ctagatcctt ttaaattaaa   9000

aatgaagttt taaatcaatc taaagtatat atgagtaaac ttggtctgac agttaccaat   9060

gcttaatcag tgaggcacct atctcagcga tctgtctatt tcgttcatcc atagttgcct   9120

gactccccgt cgtgtagata actacgatac gggagggctt accatctggc cccagtgctg   9180

caatgatacc gcgagaccca cgctcaccgg ctccagattt atcagcaata aaccagccag   9240

ccggaagggc cgagcgcaga agtggtcctg caactttatc cgcctccatc cagtctatta   9300

attgttgccg ggaagctaga gtaagtagtt cgccagttaa tagtttgcgc aacgttgttg   9360

ccattgctac aggcatcgtg gtgtcacgct cgtcgtttgg tatggcttca ttcagctccg   9420

gttcccaacg atcaaggcga gttacatgat cccccatgtt gtgcaaaaaa gcggttagct   9480

ccttcggtcc tccgatcgtt gtcagaagta agttggccgc agtgttatca ctcatggtta   9540

tggcagcact gcataattct cttactgtca tgccatccgt aagatgcttt tctgtgactg   9600

gtgagtactc aaccaagtca ttctgagaat agtgtatgcg gcgaccgagt tgctcttgcc   9660

cggcgtcaat acgggataat accgcgccac atagcagaac tttaaaagtg ctcatcattg   9720

gaaaacgttc ttcggggcga aaactctcaa ggatcttacc gctgttgaga tccagttcga   9780

tgtaacccac tcgtgcaccc aactgatctt cagcatcttt tactttcacc agcgtttctg   9840

ggtgagcaaa aacaggaagg caaaatgccg caaaaaaggg aataagggcg acacggaaat   9900

gttgaatact catactcttc ctttttcaat attattgaag catttatcag ggttattgtc   9960

tcatgagcgg atacatattt gaatgtattt agaaaaataa acaaataggg gttccgcgca  10020

catttccccg aaaagtgcca cctgacgtct aagaaaccat tattatcatg acattaacct  10080

ataaaaatag gcgtatcacg aggccctttc gtctcgcgcg tttcggtgat gacggtgaaa  10140

acctctgaca catgcagctc ccggagacgg tcacagcttg tctgtaagcg gatgccggga  10200

gcagacaagc ccgtcagggc gcgtcagcgg gtgttggcgg gtgtcggggc tggcttaact  10260

atgcggcatc agagcagatt gtactgagag tgcaccatat gcggtgtgaa ataccgcaca  10320

gatgcgtaag gagaaaatac cgcatcaggc gccattcgcc attcaggctg cgcaactgtt  10380

gggaagggcg atcggtgcgg gcctcttcgc tattacgcca gctggcgaaa gggggatgtg  10440

ctgcaaggcg attaagttgg gtaacgccag ggttttccca gtcacgacgt tgtaaaacga  10500

cggccagtgc c                                                        10511
```